US008242280B2

(12) United States Patent
Chen et al.

(10) Patent No.: US 8,242,280 B2
(45) Date of Patent: Aug. 14, 2012

(54) FUSED RING HETEROCYCLE KINASE MODULATORS

(75) Inventors: Chixu Chen, San Diego, CA (US); Brian Eastman, San Diego, CA (US); Andreas Gosberg, San Diego, CA (US); Stefan N. Gradl, San Diego, CA (US); Gavin Hirst, San Diego, CA (US); Stephanie Hopkins, San Diego, CA (US); Khanh Thi Tuong Nguyen, San Diego, CA (US); Richard Pracitto, San Diego, CA (US); Paul E. Sprengeler, San Diego, CA (US); Ruo W. Steensma, San Diego, CA (US)

(73) Assignee: SGX Pharmaceuticals, Inc., San Diego, CA (US)

( * ) Notice: Subject to any disclaimer, the term of this patent is extended or adjusted under 35 U.S.C. 154(b) by 1151 days.

(21) Appl. No.: 12/101,110

(22) Filed: Apr. 10, 2008

(65) Prior Publication Data
US 2008/0261921 A1 Oct. 23, 2008

Related U.S. Application Data

(60) Provisional application No. 60/911,060, filed on Apr. 10, 2007.

(51) Int. Cl.
*C07D 401/00* (2006.01)
(52) U.S. Cl. .................................................. 546/275.7
(58) Field of Classification Search ................ 546/275.7
See application file for complete search history.

(56) References Cited

U.S. PATENT DOCUMENTS

| | | | |
|---|---|---|---|
| 5,643,734 A | 7/1997 | Henderson | |
| 6,589,950 B1 | 7/2003 | Collingwood et al. | |
| 7,361,763 B2 | 4/2008 | Arnold | |
| 7,361,764 B2 | 4/2008 | Arnold | |
| 7,452,993 B2 | 11/2008 | Arnold | |
| 7,582,637 B2 | 9/2009 | Arnold | |
| 7,601,839 B2 | 10/2009 | Arnold | |
| 7,626,021 B2 | 12/2009 | Arnold | |
| 7,709,645 B2 | 5/2010 | Arnold | |
| 7,829,558 B2 | 11/2010 | Arnold | |
| 7,906,648 B2 | 3/2011 | Arnold | |
| 2006/0035898 A1 | 2/2006 | Arnold et al. | |
| 2009/0005356 A1 | 1/2009 | Blaney | |
| 2010/0036118 A1 | 2/2010 | Arnold | |

FOREIGN PATENT DOCUMENTS

| | | | |
|---|---|---|---|
| WO | WO-02-051837 | | 7/2002 |
| WO | WO-03-024969 | | 3/2003 |
| WO | WO-2004-014368 | | 2/2004 |
| WO | WO-2004-024895 A2 | | 3/2004 |
| WO | WO 2004/078756 | * | 9/2004 |
| WO | WO-2005-028475 | | 3/2005 |
| WO | WO-2005-095400 | | 10/2005 |
| WO | WO-2006-015123 | | 2/2006 |
| WO | WO-2006-015124 | | 2/2006 |
| WO | WO-2006-063167 | | 6/2006 |
| WO | WO-2006-124863 A2 | | 11/2006 |
| WO | WO 2007-106236 | | 9/2007 |
| WO | WO 2008-124849 | | 10/2008 |
| WO | WO 2008-124850 | | 10/2008 |
| WO | WO 2008-155000 | | 12/2008 |

OTHER PUBLICATIONS

PCT/US08/65150 Search Report dated Aug. 21, 2008.
Adamczyk et al., "Synthesis of 3,7-dihydroimidazo1[1,2a]pyrazine-3-ones and their chemiluminescent properties," Tetrahedron 59:8129-8143 (2003).
Altschul et al., "Gapped BLAST and PSI-BLAST: a new generation of protein database search programs," Nucl. Acids Res. 24:3389-3402 (1997).
Arduengo et al., "Adducts of Carbenes with Group II and XII Metallocenes," Organometallics 17:3375-3382 (1998).
Arduengo et al., "Low-Coordinate Carbene Complexes of Nickel(0)and Platinum(0)†," J. Am. Chem. Soc. 116:4391-4394 (1994).
Bach et al., "Synthesis of 2'-Substituted 4-Bromo-2,4'-bithiazoles by Regioselective Cross-Coupling Reactions," J. Org. Chem. 67:5789-5795 (2002).
Berge et al., "Pharmaceutical Salts," J. Pharma. Sci. 66:1-19 (1977).
Blaney, J.M. and Dixon, J.S., "A good ligand is hard to find: Automated docking methods," Perspectivesin Drug Discovery and Design 1:301-319 (1993).
Bolm et al., "Iron-Catalyzed Reactions in Organic Synthesis," Chem. Rev. 104:6217-6254 (2004).
Boudier et al., "New Applications of Polyfunctional Organometallic Compounds in Organic Synthesis," Angew. Chem. Int. Ed. 39: 4414-4435 (2000).
Brooks et al., "CHARMM: A program for macromolecular energy, minimization, and dynamics calculations," J. Comp. Chem. 4:187-217 (1983).
Bundgaard, H. Chapter 5: Design and application of prodrugs. A Textbook of Drug Design and Development. Krosgaard-Larsen, et al., eds., pp. 113-191, 1991.
Bundgaard, H., "Means to enhance penetration: Prodrugs as a means to improve the delivery of peptide drugs," Advanced Drug Delivery Reviews 8: 1-38, 1992.
Charifson et al., "Consensus Scoring: A Method for Obtaining Improved Hit Rates from Docking Databases of Three-Dimensional Structures into Proteins," J. Med. Chem. 42:5100-5109 (1999).
Christman, U. and Vilar,R., "Monoligated Palladium Species as Catalysts in Cross-Coupling Reactions," Angew. Chem. 117:366-374 (2005).
Crabtree, S. et al., "Facile and Gentle Method for Quantitative Lysis of *Escherichia coli* and *Salmonella typhimurium*," J. Bacteriol. 158(1):354-356 (1984).
Deininger, M. et al., "The development of imatinib as a therapeutic agent for chronic myeloid leukemia," Blood 105(7):2640-2653 (2005).

(Continued)

*Primary Examiner* — Janet Andres
*Assistant Examiner* — John Mabry
(74) *Attorney, Agent, or Firm* — Wilson, Sonsini, Goodrich & Rosati

(57) ABSTRACT

The present invention provides fused ring heterocycles as kinase modulators, pharmaceutical compositions containing these modulators, and methods of using these modulators to treat diseases mediated by kinase activity.

20 Claims, 2 Drawing Sheets

OTHER PUBLICATIONS

Fedorak et al., "A novel colon-specific steroid prodrug enhances sodium chloride absorption in rat colitis," Am J Physiol 269(2 Pt 1): G210-8, 1995.

Fleisher et al., "Improved oral drug delivery: solubility limitations overcome by the use of prodrugs," Advanced Drug Delivery Reviews 19(2): 115-30, 1996.

Fuerstner et al., "Iron-Catalyzed Cross-Coupling Reactions," J. A. Chem. Soc. 124:13856-13863 (2002).

Furukawa, J. et al., "Synthesis of Cyclopropanes by the Reaction of Olefins with Dialkylzinc and Methylene Iodide," Tetrahedron 24:53-58 (1968).

Goodsell & Olsen, "Automated Docking of Substrates to Proteins by Simulated Annealing," Proteins: Structure, Function and Genetics 8:195-202 (1990).

Gouet et al., "ESPript: analysis of multiple sequence alignments in PostScript," Bioinformatics 15:305-308 (1999).

Harrington et al., "VX-680, a potent and selective small-molecule inhibitor of the Aurora kinases, suppresses tumor growth in vivo," Nature Medicine Advance Online Publication Feb. 22, 2004, pp. 1-6.

Hartwig, Acc. "Carbon-Heteroatom Bond-Forming Reductive Eliminations of Amines, Ethers, and Sulfides," Chem. Res. 31:852-860 (1998).

Hochhaus et al. A selective HPLC/RIA for dexamethasone and its prodrug dexamethasone-21-sulphobenzoate sodium in biological fluids. Biomed Chromatogr. 1992; 6(6):283-286 (1992).

Ishiyama et al., "Paladium (0)-Catalyzed Cross-Coupling Reaction of Alkoxydiboron with Haloarenes: A Direct Procedure for Arylvoboronic Esters," J. Org. Chem. 60:7508-7510 (1995).

Ji et al., "Selective Amination of Polyhalopyridines Catalyzed by a Palladium-Xantphos Complex," Org. Lett. 5:4611-4614 (2003).

Jones et al., "Molecular Recognition of Receptor Sites using a Genetic Algorithm with a Description of Desolvation," J. Mol. Biol. 245:43-53 (1995).

Klapars, A. et al., "Mild and Practical Method for the α-Arylation of Nitriles with Heteroaryl Halides," Journal Org. Chem. 70:10186-10189 (2005).

Klemm, L.H. et al., "Chemistry of Thienopyridines. XLII. Three Novel Compounds Derived from Thienopyridine N-Oxides[1]," J. Heterocyclic Chem. 31:261-263 (1994).

Kuntz et al., "A Geometric Approach to Macromolecule-Ligand Interactions," J. Mol. Biol. 161:269-288 (1982).

Larsen, et al., "Prodrug forms for the sulfonamide group. I. Evaluation of N-acyl derivative, N-sulfonylamidines, N-sulfonylsulfilimines and sulfonylureas as possible prodrug derivatives," Int J Pharmaceutics 37(1-2): 87-95, 1987.

Larsen et al., "Prodrug forms for the sulfonamide group. II. Water-soluble amino acid derivatives of N-methylsulfonamides as possible prodrugs," Int J Pharmaceutics 47(1-3): 103-10, 1988.

Ley et al., "Modern Synthetic Methods for Copper-Mediated C(aryl)-O, C(aryl)-N, and C(aryl)-S Bond Formation," Angew Chem. 115:5400-5449 (2003).

Li, L. and Wu, Y., "An efficient method for synthesis of α-keto acid esters from terminal alkynes," Tetrahedron Lett. 43:2427-2430 (2002).

Littke et al., "Palladium-Catalyzed Coupling Reactions of Aryl Chlorides," Angew. Chem. 41:4176-4211 (2002).

Ma, L. et al., "An efficient synthesis of aryl α-keto esters," Tetrahedron Lett. 46:3927-3929 (2005).

Maligres, P.E. et al., "Stereocontrolled Preparation of a Nonpeptidal (–)- Spirobicyclic NK-1 Receptor Agonist," Journal Org. Chem. 67:1093-1101 (2002).

Maryanoff et al., "The Wittig Olefination Reaction and Modifications Involving Phosphoryl-Stabilized Carbanions. Stereochemistry, Mechanism, and Selected Synthetic Aspects," Chem. Rev. 89:863-927 (1989).

Matsui, T. et al., "Expression of Unphosphorylated Form of Human Double-Stranded RNA-Activated Protein Kinase in *Escherichia coli*," Biochem. Biophys. Res. Commun. 284:798-807 (2001).

Mcleod et al., "A glucocorticoid prodrug facilitates normal mucosal function in rat colitis without adrenal suppression," Gastroenterology 106(2): 405-13, 1994.

Meng et al., "Automated Docking with Grid-Based Energy Evaluation," J. Comp. Chem. 13:505-524 (1992).

Mittal, S. et al., "Synthesis and evaluation of S-4-(3-thienyl)phenyl-α-methylacetic acid," Bioorg. Med. Chem. Lett. 14:979-982 (2004).

Molander et al., "Palladium-Catalyzed Suzuki-Miyaura Cross-Coupling Reactions of Potassium Aryl-and Heteroarylatrifluoroborates," J. Org. Chem. 68:4302-4314 (2003).

Molander et al., "*B*-Alkyl Suzuki-Miyaura Cross-Coupling Reactions with Air-Stable Potassium Alkyltrifluoroborates," J. Org. Chem. 68:5534-5539 (2003).

Mongin et al., "Advances in the directed metallation of azines and diazines (pyridines, pyrmimidines, pyrazines, pyrizadines, quinolines, benzodiazines and carbolines). Part 1: Metallation of pyridines, quinolines and carbolines," Tetrahedron 57:4059-4090 (2001).

Nahm et al., "N-Methoxy-N-Methylamides as Effective Acylating Agents," Tetrahedron Lett. 22(39):3815-3818 (1981).

Navarro et al., "Cross-Coupling and Dehalogenation Reactions Catalyzed by (N-Heterocyclic carbene)Pd(allyl)C1 Complexes," J. Org. Chem. 69:3173-3180 (2004).

Rarey et al., "A Fast Flexible Docking Method using an Incremental Construction Algorithm," J. Mol. Biol. 261:470-489 (1996).

Robinson et al., "Discovery of the hemifumarate and (alpha-L-alanyloxy)methyl ether as prodrugs of an antirheumatic oxindole: prodrugs for the enolic OH group," J Med Chem 39(1): 10-8, 1996.

Sakamoto et al., "Condensed Heteroaromatic Ring Systems. XXII ₁Simple and General Synthesis of 1*H*-Pyrrolo-Pyridines," Heterocycles 34(12): 2379-84 (1992).

Sapoltntzis et al., "A New General Preparation of Polyfunctional Diarylamines by the Addition of Functionalized Arylmagnesium Compounds to Nitroarenes," J. Am Chem. Soc. 124:9390-9391 (2002).

Saulnier et al., "An efficient method for the synthesis of guanidino prodrugs," Bioorganic & Medicinal Chemistry Letters 4(16): 1985-90, 1994.

Simpson, W.G., "The Calcium Channel Blocker Verapamil and Cancer Therapy," Cell Calcium. 6:449-467 (1985).

Sinkula et al., "Rationale for design of biologically reversible drug derivatives: prodrugs," J Pharm Sci 64(2): 181-210, 1975.

Snieckus, V., "Directed Ortho Metalation. Tertiary Amide and O-Carbamate Directors in Synthetic Strategies for Polysubstituted Aromatics," Chem. Rev. 90(6):879-933 (1990).

Thasana, N. et al., "Synthesis of aryl α-keto esters via the rearrangement of aryl cyanohydrin carbonate esters," Tetrahedron Lett. 44:1019-1021 (2003).

Thompson et al. "DbClustal: rapid and reliable global multiple alignments of protein sequences detected by database searches," Nucl. Acids Res. 28:2919-2926 (2000).

Travis, J., "Proteins and Organic Solvents Make an Eye-Opening Mix," Science 262:1374 (1993).

Turck et al., Advances in the directed metallation of azines and diazines (pyridines, pyrimidines, pyrazines, pyridazines, quinolines, benzodiazines and carbolines). Part 2. Metallation of pyrimidines, pyrazines, pyridazines and benzodiazines,) Tetrahedron 57:4489-4905 (2001).

Wang, L. and Sharpless, K.B., "Catalytic Asymmetric Dihydroxylation of Cis-Disubstituted Olefins," J. Am. Chem. Soc. 114:7568-7570 (1992).

Weiner et al., "A New Force Field for Molecular Mechanical Simulation of Nucleic Acids and Proteins," J. Am. Chem. Soc. 106:765-784 (1984).

Widder, K. et al., Method in Enzymology vol. 42 (1985), pp. 309-396.

Wolfe et al., "Rational Development of Practical Catalysts for Aromatic Carbon—Nitrogen Bond Formation," Acc. Chem. Res. 31:805-818 (1998).

Wu, L. and Hartwig, J.F., "Mild Palladium-Catalyzed Selective Monoarylation of Nitriles," J. Am. Chem. Soc. 127:15824-15832 (2005).

Yang, Z. et al., "A Strategy for the Synthesis of Aryl α-Ketoamides Based Upon the Acylation of Anions Derived from Cyanomethylamines Followed by Oxidative Cleavage," Org. Lett. 4(7):1103-1105 (2002).

You, J. and Verkade, J.G., "P(i-BuNCH2CH2)3N: An Efficient Ligand for the Direct α-Arylation of Nitriles with Aryl Bromides," J. Org. Chem. 68:8003-8007 (2003).

Misra et al., "1H-Pyrazolo[3,4-b]pyridine inhibitors of Cyclin-Dependent Kinases: Highly Potent 2,6-Diffluorophenacyl Analogues," Bioorg. Med. Chem. Lett. 12(14):2405-2408 (2003).

PCT/US08/59962 Search Report dated Jul. 21, 2008.

EP08745550 Supplementary European Search Report mailed Sep. 21, 2011.

EP8745550 European Search Opinion mailed Sep. 21, 2011.

PCT/US2008/059962 IPRP mailed Oct. 13, 2009.

\* cited by examiner

FIGURE 1

```
MLEICLKLVGCKSKKGLSSSSSCYLEEALQRFVASDPHPQGLSEAARWNS
1                                                50
KENLLAGPSENDPNLFVALYDFVASGDNTLSITKGEKLRVLGYNHNGEWC
51                                               100
EAQTKNGQGWVPSNYITPVNSLEKHSWYHGPVSRNAAEYLLSSGINGSFL
101                                              150
VRESESSPGQRSISLRYEGRVYHYRINTASDGKLYVSSESRFNTLAELVH
151                                              200
HHSTVADGLITTLHYPAPKRNKPTVYGVSPNYDKNEMERTDITMKHKLGG
201                                              250
GQYGEVYEGVWKKYSLTVAVKTLKEDTMEVEEFLKEAAVMKEIKHPNLVQ
251                                              300
LLGVCTREPPFYIITEFMTYGNLLDYLRECNRQEVNAVVLLYMATQISSA
301                                              350
MEYLEKKNFIHRDLAARNCLVGENHLVKVADFGLSRLMTGDTYTAHAGAK
351                                              400
FPIKWTAPESLAYNKFSIKSDVWAFGVLLWEIATYGMSPYPGIDLSQVYE
401                                              450
LLEKDYRMERPEGCPEKVYELMRACWQWNPSDRPSFAEIHQAFETMFQES
451                                              500
SISDEVEKELGKQGVRGAVSTLLQAPELPTKTRTSRRAAEHRDTTDVPEM
501                                              550
PHSKGQGESDPLDHEPAVSPLLPRKERGPPEGGLNEDERLLPKDKKTNLF
551                                              600
SALIKKKKKTAPTPPKRSSSFREMDGQPERRGAGEEKGRDISNGALAFTP
601                                              650
LDTADPAKSPKPSNGAGVPNGALRESGGSGFRSPHLWKKSSTLTSSRLAT
651                                              700
GEEEGGGSSSKRPLRSCSASCVPHGAKDTEWRSVTLPRDLQSTGRQFDSS
701                                              750
```

FIGURE 1A

```
     TFGGHKSEKPALPRKRAGENRSDQVTRGTVTPPPRLVKKNEEAADEVFKD
751                                                800
     IMESSPGSSPPNLTPKPLREQVTVAPASGLPHKEEAEKGSALGTPAAAEP
801                                                850
     VTPTSKAGSQAPQGTSKGPAEESRVRRHKRSSESPGRDKGKLSRLKPAPP
851                                                900
     PPPAASAGKAGGKPSQSPSQEAAGEAVLGAKTKATSLVDAVNSDAAKPSQ
901                                                950
     PGEGLEKPVLPATPKPQSAKPSGTPISPAPVPSTLPSASSALAGDQPSST
951                                               1000
     AFIPLISTRVSLRKTRQPPERIASGAITKGVVLDSTEALCLAISRNSEQM
1001                                              1050
     ASHSAVLEAGKNLYTPCVSYVDSIQQMRNKFAFREAINKLENNLRELQIC
1051                                              1100
     PATAGSGPAATQDFSKLLSSVKEISDIVQR
1101                             1130
```

FUSED RING HETEROCYCLE KINASE MODULATORS

CROSS-REFERENCE

This application claims the benefit of U.S. Provisional Application No. 60/911,060, filed Apr. 10, 2007, which is incorporated herein by reference in its entirety.

INCORPORATION BY REFERENCE

This application contains references to amino acid sequences which have been submitted concurrently herewith as the sequence listing text file "20268-709.201 update_ST25.txt", file size 15.2 kilobytes (kb), created on Apr. 11, 2008. The aforementioned sequence listing is hereby incorporated by reference in its entirety pursuant to 37 CFR §1.52(e)(5).

BACKGROUND OF THE INVENTION

Mammalian protein kinases are important regulators of cellular functions. Because dysfunctions in protein kinase activity have been associated with several diseases and disorders, protein kinases are targets for drug development.

The tyrosine kinase receptor, FMS-like tyrosine kinase 3 (FLT3), is implicated in cancers, including leukemia, such as acute myeloid leukemia (AML), acute lymphoblastic leukemia (ALL), and myelodysplasia. About one-quarter to one-third of AML patients have FLT3 mutations that lead to constitutive activation of the kinase and downstream signaling pathways. Although in normal humans, FLT3 is expressed mainly by normal myeloid and lymphoid progenitor cells, FLT3 is expressed in the leukemic cells of 70-80% of patients with AML and ALL. Inhibitors that target FLT3 have been reported to be toxic to leukemic cells expressing mutated and/or constitutively-active FLT3. Thus, there is a need to develop potent FLT3 inhibitors that may be used to treat diseases and disorders such as leukemia.

The Abelson non-receptor tyrosine kinase (c-Abl) is involved in signal transduction, via phosphorylation of its substrate proteins. In the cell, c-Abl shuttles between the cytoplasm and nucleus, and its activity is normally tightly regulated through a number of diverse mechanisms. Abl has been implicated in the control of growth-factor and integrin signaling, cell cycle, cell differentiation and neurogenesis, apoptosis, cell adhesion, cytoskeletal structure, and response to DNA damage and oxidative stress.

The c-Abl protein contains approximately 1150 amino-acid residues, organized into a N-terminal cap region, an SH3 and an SH2 domain, a tyrosine kinase domain, a nuclear localization sequence, a DNA-binding domain, and an actin-binding domain.

Chronic myelogenous leukemia (CML) is associated with the Philadelphia chromosomal translocation, between chromosomes 9 and 22. This translocation generates an aberrant fusion between the bcr gene and the gene encoding c-Abl. The resultant Bcr-Abl fusion protein has constitutively active tyrosine-kinase activity. The elevated kinase activity is reported to be the primary causative factor of CML, and is responsible for cellular transformation, loss of growth-factor dependence, and cell proliferation.

The 2-phenylaminopyrimidine compound imatinib (also referred to as STI-571, CGP 57148, or Gleevec) has been identified as a specific and potent inhibitor of Bcr-Abl, as well as two other tyrosine kinases, c-kit and platelet-derived growth factor receptor. Imatinib blocks the tyrosine-kinase activity of these proteins. Imatinib has been reported to be an effective therapeutic agent for the treatment of all stages of CML. However, the majority of patients with advanced-stage or blast crisis CML suffer a relapse despite continued imatinib therapy, due to the development of resistance to the drug. Frequently, the molecular basis for this resistance is the emergence of imatinib-resistant variants of the kinase domain of Bcr-Abl. The most commonly observed underlying amino-acid substitutions include Glu255Lys, Thr315Ile, Tyr293Phe, and Met351Thr.

MET was first identified as a transforming DNA rearrangement (TPR-MET) in a human osteosarcoma cell line that had been treated with N-methyl-N'-nitro-nitrosoguanidine (Cooper et al. 1984). The MET receptor tyrosine kinase (also known as hepatocyte growth factor receptor, HGFR, MET or c-Met) and its ligand hepatocyte growth factor ("HGF") have numerous biological activities including the stimulation of proliferation, survival, differentiation and morphogenesis, branching tubulogenesis, cell motility and invasive growth. Pathologically, MET has been implicated in the growth, invasion and metastasis of many different forms of cancer including kidney cancer, lung cancer, ovarian cancer, liver cancer and breast cancer. Somatic, activating mutations in MET have been found in human carcinoma metastases and in sporadic cancers such as papillary renal cell carcinoma. The evidence is growing that MET is one of the long-sought oncogenes controlling progression to metastasis and therefore a very interesting target. In addition to cancer there is evidence that MET inhibition may have value in the treatment of various indications including: Listeria invasion, Osteolysis associated with multiple myeloma, Malaria infection, diabetic retinopathies, psoriasis, and arthritis.

The tyrosine kinase RON is the receptor for the macrophage stimulating protein and belongs to the MET family of receptor tyrosine kinases. Like MET, RON is implicated in growth, invasion and metastasis of several different forms of cancer including gastric cancer and bladder cancer.

The Aurora family of serine/theronine kinases is essential for mitotic progression. Expression and activity of the Arurora kinases are tightly regulated during the cell cycle. A variety of proteins having roles in cell division have been identified as Aurora kinase substrates. Based on the known function of the Aurora kinases, inhibition of their activity is believed to disrupt the cell cycle and block proliferation and therefore tumor cell viability. Harrington et al., *Nature Medicine* (2004).

3-phosphoinositide-dependent kinase 1 (PDK1) is a Ser/Thr protein kinase that can phosphorylate and activate a number of kinases in the AGC kinase super family, including Akt/PKB, protein kinase C (PKC), PKC-related kinases (PRK1 and PRK2), p70 ribobsomal S6-kinase (S6K1), and serum and glucocorticoid-regulated kinase (SGK). The first identified PDK1 substrate is the proto-oncogene Akt. Numerous studies have found a high level of activated Akt in a large percentage (30-60%) of common tumor types, including melanoma and breast, lung, gastric, prostate, hematological and ovarian cancers. The PDK1/Akt signaling pathway thus represents an attractive target for the development of small molecule inhibitors that may be useful in the treatment of cancer. Feldman et al., *JBC Papers in Press*, Mar. 16, 2005.

Because kinases have been implicated in numerous diseases and conditions, such as cancer, there is a need to develop new and potent protein kinase modulators that can be used for treatment. The present invention fulfills these and other needs in the art. Although certain protein kinases are specifically named herein, the present invention is not limited to modulators of these kinases, and, includes, within its scope, modulators of related protein kinases, and modulators of homologous proteins.

BRIEF SUMMARY OF THE INVENTION

It has been discovered that the fused ring heterocyclic compounds of the present invention may be used to modulate kinase activity and to treat diseases mediated by kinase activity and are described in detail below. In addition, inhibitory activities of selected compounds are disclosed herein.

In one aspect, the invention relates to compounds having Formula I:

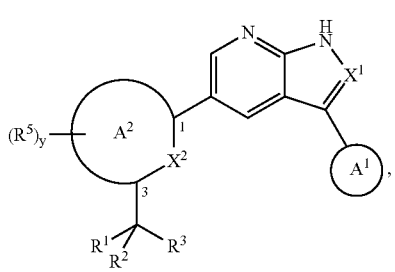

or an enantiomer, diastereomer, racemate, or pharmaceutically acceptable salt or solvate thereof, wherein:
$A^1$ is independently substituted or unsubstituted 6-membered aryl, substituted or unsubstituted 6-membered heteroaryl, substituted or unsubstituted 5-membered heteroaryl; substituted or unsubstituted cycloalkyl, or substituted or unsubstituted heterocycloalkyl;
$X^1$ is independently —$CR^4$=, or —N=;
$A^2$ is independently substituted or unsubstituted 6-membered aryl, substituted or unsubstituted 6-membered heteroaryl, or substituted or unsubstituted 5-membered heteroaryl;
$X^2$ is independently —$C(R^5)$=, —N=, —$NR^5$—, —O—, or —S—;
$R^1$ and $R^2$ are each independently hydrogen, halogen, cyano, nitro, trifluoromethyl, difluoromethyl, substituted or unsubstituted alkyl, —$NR^6R^7$, —$CONR^6R^7$, or —$OR^8$, or $R^1$ and $R^2$ together form oxo;
$R^3$ is independently hydrogen, substituted or unsubstituted alkyl, substituted or unsubstituted heteroalkyl, substituted or unsubstituted heterocycloalkyl, substituted or unsubstituted aryl, substituted or unsubstituted aralkyl, substituted or unsubstituted heteroaryl; substituted or unsubstituted heteroaralkyl, —$NR^9R^{10}$, —$CONR^9R^{10}$, or —$OR^{11}$; or
$R^2$ and $R^3$ are each independently joined together with the carbon atoms to which they are attached, to form substituted or unsubstituted heterocycloalkyl;
$R^4$ is independently hydrogen, halogen, cyano, nitro, trifluoromethyl, difluoromethyl, or substituted or unsubstituted alkyl;
each $R^5$ is independently hydrogen, halogen, cyano, nitro, trifluoromethyl, difluoromethyl, substituted or unsubstituted alkyl, —$NR^{11}R^{12}$, —$CONR^{11}R^{12}$, —$OR^3$, —$C(=Z)R^{14}$, —$S(O)_nR^{15}$, wherein n is independently an integer from 0 to 2;
y is independently an integer from 0 to 4;
Z is independently O, S or $N(R^{16})$;
$R^6$ and $R^7$, $R^9$ and $R^{10}$, and $R^{11}$ and $R^{12}$ are each independently hydrogen, substituted or unsubstituted alkyl, substituted or unsubstituted alkyl-$NR^{17}R^{18}$, substituted or unsubstituted alkyl-$CONR^{17}R^{18}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl, substituted or unsubstituted aralkyl, substituted or unsubstituted heteroaralkyl, or
$R^6$ and $R^7$, $R^9$ and $R^{10}$, and $R^{11}$ and $R^{12}$ are each independently joined together with the nitrogen to which they are attached, to form substituted or unsubstituted 3- to 7-membered heterocycloalkyl, or substituted or unsubstituted 5-membered heteroaryl;
$R^8$, $R^{11}$, and $R^{13}$ are each independently hydrogen, difluoromethyl, trifluoromethyl, substituted or unsubstituted alkyl; substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{14}$ is independently —$OR^{13}$, substituted or unsubstituted alkyl; substituted or unsubstituted heteroalkyl, substituted or unsubstituted cycloalkyl, substituted Or unsubstituted heterocycloalkyl, substituted or unsubstituted aryl, or substituted or unsubstituted heteroaryl;
$R^{15}$ is independently substituted or unsubstituted alkyl; substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein if n is 2, then $R^{15}$ is optionally —$NR^{19}R^{20}$ or —$OR^{13}$;
$R^{16}$ is independently hydrogen, substituted or unsubstituted alkyl, or substituted or unsubstituted heteroalkyl;
$R^{17}$ and $R^{18}$, and $R^{19}$ and $R^{20}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, substituted or unsubstituted aralkyl, substituted or unsubstituted heteroaralkyl, or
$R^{17}$ and $R^{18}$, and $R^{19}$ and $R^{20}$ are each independently joined together with the nitrogen to which they are attached, to form substituted or unsubstituted 3- to 7-membered heterocycloalkyl, or substituted or unsubstituted 5-membered heteroaryl; and
wherein any of the $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ groups are each optionally independently substituted with 1 to 3 groups, each group independently selected from halogen, hydroxyl, amino, aminomonoalkyl, aminodialkyl, cyano, nitro, difluoromethyl, trifluoromethyl, oxo, alkyl, —O-alkyl, and —S-alkyl.

In one aspect, the invention relates to compounds having Formula (A), or an enantiomer, diastereomer, racemate, tautomer or pharmaceutically acceptable salt, solvate, hydrate, polymorph or prodrug thereof:

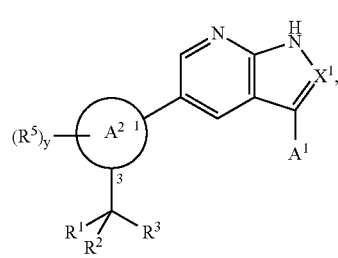

Formula (A)

wherein
- $A^1$ is substituted or unsubstituted aryl, substituted or unsubstituted heteroaryl, substituted or unsubstituted cycloalkyl, or substituted or unsubstituted heterocycloalkyl;
- $A^2$ is an aryl or heteroaryl group;
- $X^1$ is $CR^4$ or N; wherein
  - $R^4$ is hydrogen, halogen, cyano, nitro, haloalkyl, or substituted or unsubstituted alkyl;
- $R^1$ is hydrogen, lower alkyl or lower heteroalkyl;
- $R^2$ is hydrogen, lower alkyl, halogen, hydroxy, —$OR^8$, cyano, nitro, haloalkyl, —$NR^6R^7$;
- $R^3$ is hydrogen, substituted or unsubstituted alkyl, substituted or unsubstituted heteroalkyl, substituted or unsubstituted haloalkyl, substituted or unsubstituted heterocycloalkyl, substituted or unsubstituted aryl, substituted or unsubstituted (cycloalkyl)alkyl, substituted or unsubstituted (heterocycloalkyl)alkyl, substituted or unsubstituted arylalkyl, substituted or unsubstituted heteroaryl, substituted or unsubstituted heteroarylalkyl, —COOH, —$NR^9R^{10}$, —$CH_2NR^9R^{10}$, —$CONR^9R^{10}$, —$CH_2CONR^9R^{10}$ or —$OR^8$; or
- $R^2$ and $R^3$ together with the carbon atom to which they are attached, form a substituted or unsubstituted heterocycloalkyl, or a substituted or unsubstituted cycloalkyl;
- each $R^5$ is independently halogen, cyano, nitro, substituted or unsubstituted haloalkyl, substituted or unsubstituted alkyl, —$NR^{11}R^{12}$, —$CONR^{11}R^{12}$, —$OR^{13}$, —$C(=Z)R^{14}$, or —$S(O)_nR^{15}$, wherein n is independently an integer from 0 to 2;
- y is 0, 1, 2, 3 or 4;
- Z is independently O, S or $N(R^{16})$;
- $R^6$ and $R^7$, $R^9$ and $R^{10}$, and $R^{11}$ and $R^{12}$ are each independently hydrogen, substituted or unsubstituted alkyl, substituted or unsubstituted haloalkyl, substituted or unsubstituted alkyl-$NR^{17}R^{18}$, substituted or unsubstituted alkyl-$CONR^{17}R^{18}$, substituted or unsubstituted heteroalkyl, substituted or unsubstituted cycloalkyl, substituted or unsubstituted heterocycloalkyl, substituted or unsubstituted aryl or substituted or unsubstituted heteroaryl, substituted or unsubstituted (cycloalkyl)alkyl, substituted or unsubstituted (heterocycloalkyl)alkyl, substituted or unsubstituted arylalkyl substituted or unsubstituted heteroarylalkyl, or
- one or more of $R^6$ and $R^7$, $R^9$ and $R^{10}$, and $R^{11}$ and $R^{12}$ are each independently joined together with the nitrogen to which they are attached, to form substituted or unsubstituted 3- to 7-membered heterocycloalkyl, or substituted or unsubstituted heteroaryl;
- $R^8$ and $R^{13}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or
- a pair of $R^{13}$, taken together with the oxygens to which they are attached, form a heterocycle;
- $R^{14}$ is independently —$OR^{13}$, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^{15}$ is independently substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein if n is 2, then $R^{15}$ is optionally —$NR^{19}R^{20}$ or —$OR^{13}$;
- $R^{16}$ is independently hydrogen, substituted or unsubstituted alkyl, substituted or unsubstituted haloalkyl, or substituted or unsubstituted heteroalkyl;
- $R^{17}$ and $R^{18}$, and $R^{19}$ and $R^{20}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl substituted or unsubstituted heteroaryl, substituted or unsubstituted (cycloalkyl)alkyl, substituted or unsubstituted (heterocycloalkyl)alkyl, substituted or unsubstituted arylalkyl or substituted or unsubstituted heteroarylalkyl; or one or more of $R^{17}$ and $R^{18}$ and $R^{19}$ and $R^{20}$ are each independently joined together with the nitrogen to which they are attached, to form substituted or unsubstituted heterocycloalkyl, or substituted or unsubstituted heteroaryl; and
- wherein any of the groups listed for $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ are each optionally independently substituted with 1 to 3 groups, each group independently selected from halogen, hydroxyl, amino, aminomonoalkyl, aminomonoalkyl, aminodihaloalkyl, aminodialkyl, cyano, nitro, haloalkyl, alkyl, —O-alkyl, O-haloalkyl, S-haloalkyl and —S-alkyl with the proviso that when $R^1$ and $R^2$ are both hydrogen, $R^3$ is not hydrogen, $NR^9R^{10}$, $CONR^9R^{10}$, or $CHNH_2CONR^9R^{10}$ and with the proviso that when $R^1$ and $R^3$ are both hydrogen, $R^2$ is not $NR^6R^7$.

In some embodiments of this aspect of the invention, $A^2$ is substituted or unsubstituted 6-membered aryl, substituted or unsubstituted 5-membered heteroaryl, or substituted or unsubstituted 6-membered heteroaryl. In other embodiments, $A^2$ is substituted or unsubstituted phenyl, substituted or unsubstituted pyridinyl, substituted or unsubstituted pyridinyl N-oxide, or substituted or unsubstituted pyrimidinyl. In some embodiments, $A^2$ has the formula:

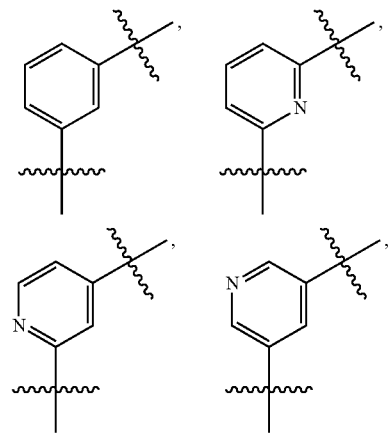

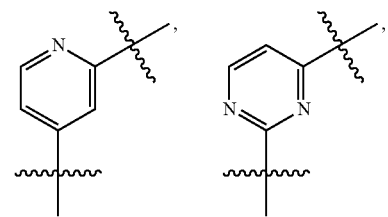
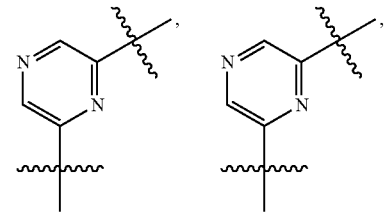
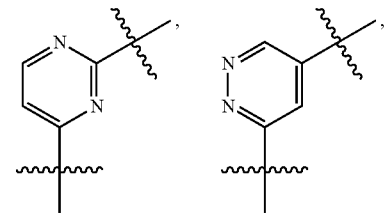
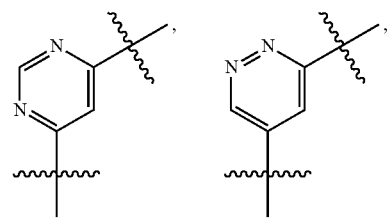
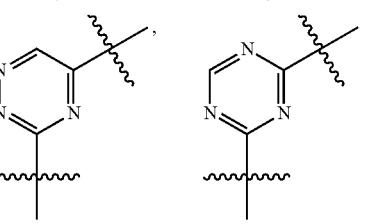
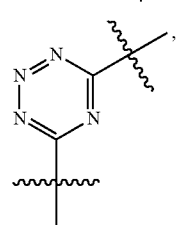
wherein any of the above groups are each independently optionally substituted with 1 to 4 R⁵ groups. In some embodiments, A² has the formula:
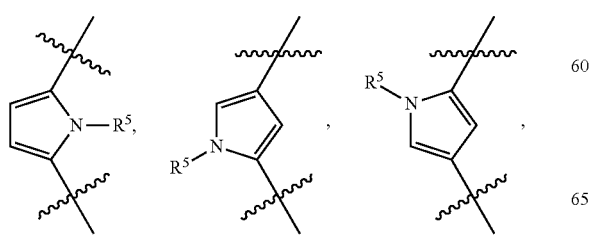
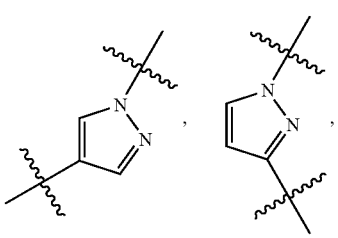
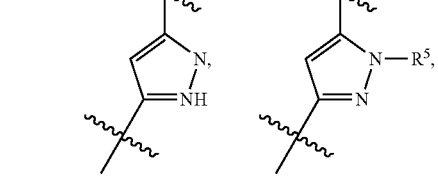
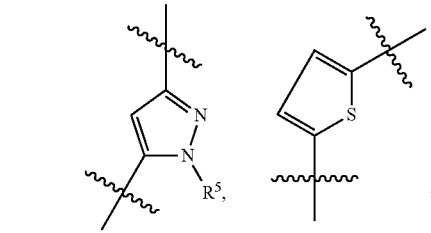
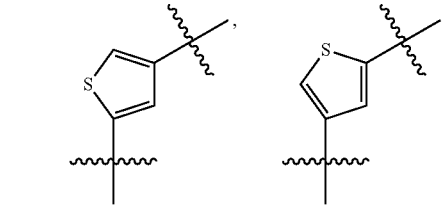
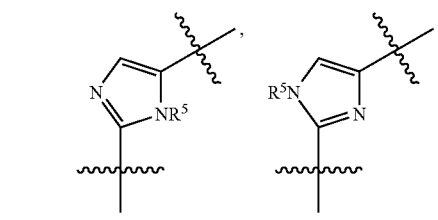
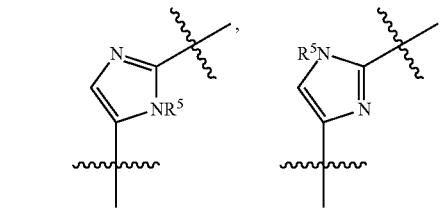
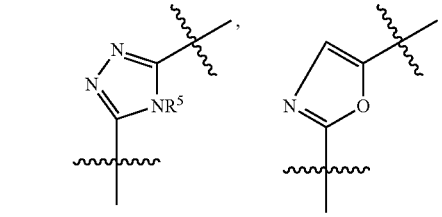

-continued

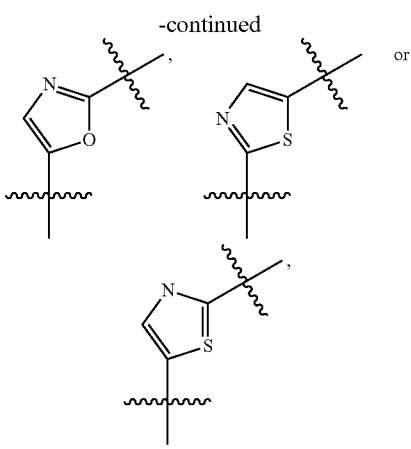

wherein any of the above groups are each independently optionally substituted with 1 to 3 $R^5$ groups.

In some embodiments of this aspect of the invention, $A^1$ is substituted or unsubstituted 6-membered aryl, substituted or unsubstituted 5-membered heteroaryl, or substituted or unsubstituted 6-membered heteroaryl. In some embodiments, $A^1$ is substituted with one or more halogen, cyano, nitro, trifluoromethyl, difluoromethyl, —$NR^{11}R^{12}$, —$N(R^{11})COR^{12}$, —$CONR^{11}R^{12}$, —$OR^{13}$, —$SR^{13}$, —$C(=Z)R^{14}$, —$S(O)_nR^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or combination thereof. In some embodiments, $A^1$ is substituted or unsubstituted phenyl, substituted or unsubstituted pyridinyl, substituted or unsubstituted pyridinyl N-oxide, substituted or unsubstituted pyrimidinyl, substituted or unsubstituted benzodioxolyl, substituted or unsubstituted benzimidazolyl, or substituted or unsubstituted indolyl. In some embodiments, $A^1$ is:

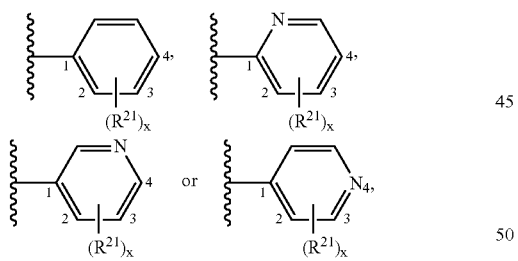

x is an integer from 1 to 5; and $R^{21}$ is independently halogen, cyano, nitro, trifluoromethyl, difluoromethyl, fluoromethyl, —$NR^{11}R^{12}$, —$CONR^{11}R^{12}$, —$OR^{13}$, —$SR^{13}$, —$C(=Z)R^{14}$, —$S(O)_nR^{15}$, substituted or unsubstituted alkyl, substituted or unsubstituted haloalkyl substituted or unsubstituted heteroalkyl, substituted or unsubstituted cycloalkyl, substituted or unsubstituted heterocycloalkyl, substituted or unsubstituted aryl, or substituted or unsubstituted heteroaryl; or two adjacent $R^{21}$ groups together with the carbon atoms to which they are attached are combined to form a substituted or unsubstituted ring.

In some embodiments of this aspect of the invention, $R^1$ is hydrogen or methyl.

In some embodiments of this aspect of the invention, $R^2$ is hydroxy or methoxy.

In some embodiments of this aspect of the invention, $R^3$ is —$CH_2CONR^9R^{10}$ or —$CONR^9R^{10}$.

In some embodiments of this aspect of the invention, the compound has the formula:

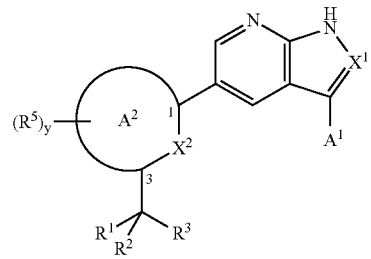

wherein $X^2$ is —$C(R^5)=$, —CH=, —N=, —$NR^5$—, —NH—, —O—, or —S—.

In some embodiments of this aspect of the invention, $A^1$ is 2-methoxyphenyl; $X^1$ is $CR^4$; and $A^2$ is phenyl.

In some embodiments of this aspect of the invention, $A^1$ is 2-methoxyphenyl; $X^1$ is $CR^4$; and $A^2$ is pyridinyl.

In some embodiments of this aspect of the invention, $A^1$ is 2-methoxyphenyl; $X^1$ is N; and $A^2$ is phenyl.

In some embodiments of this aspect of the invention, $A^1$ is 2-methoxyphenyl; $X^1$ is N; and $A^2$ is pyridinyl.

In some embodiments of this aspect of the invention, the compound has the formula:

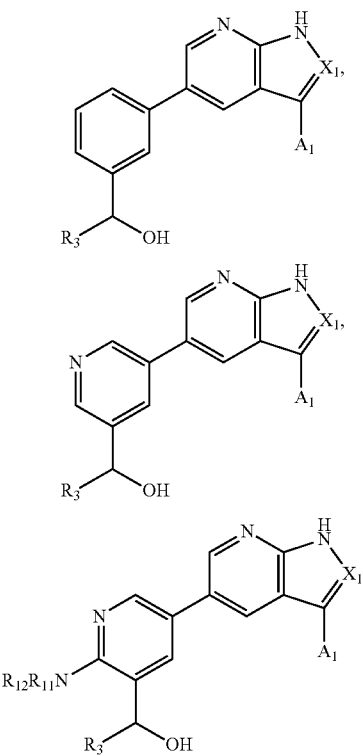

-continued
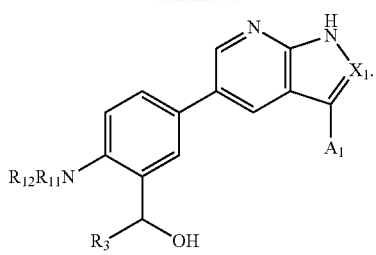
In some embodiments of this aspect of the invention, $R^3$ is —$CONR^9R^{10}$.
In some embodiments of this aspect of the invention, $R^1$ is hydrogen; $R^2$ is —OH, —$NH_2$, —$NHCH_3$, —$N(CH_3)_2$, —$CH_3$, —F, —CN, —$CF_3$, —$OCH_3$, thiomorpholinyl sulfone, or piperazinyl; and $R^3$ is
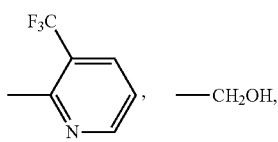
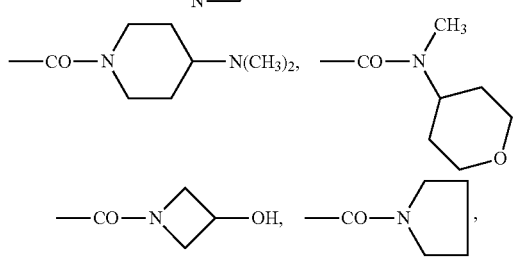
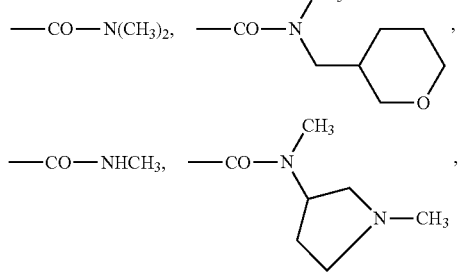
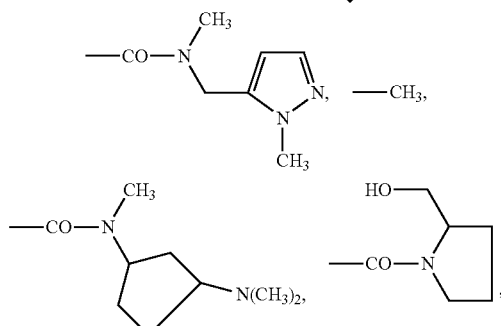
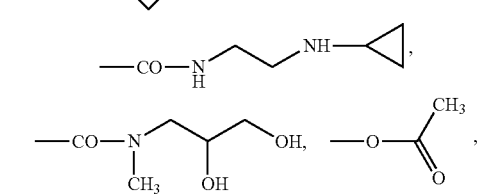
-continued
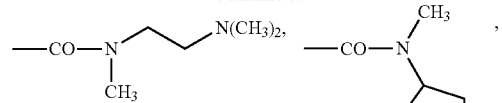
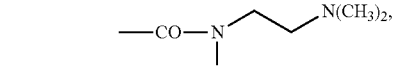
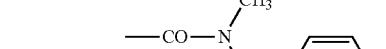
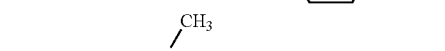
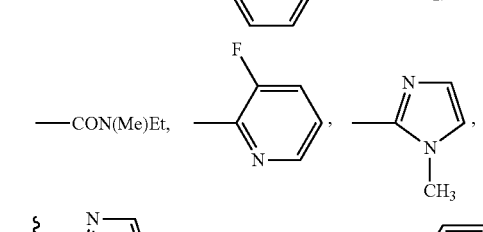
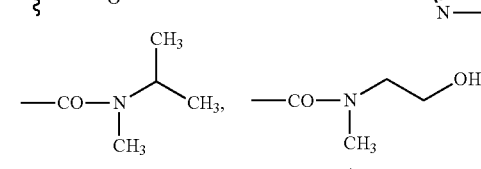
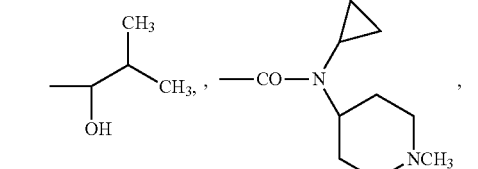
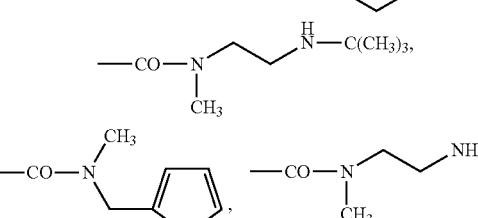
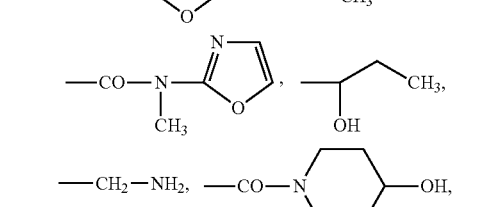
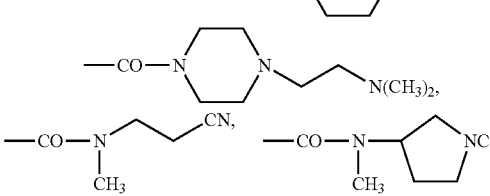

-continued

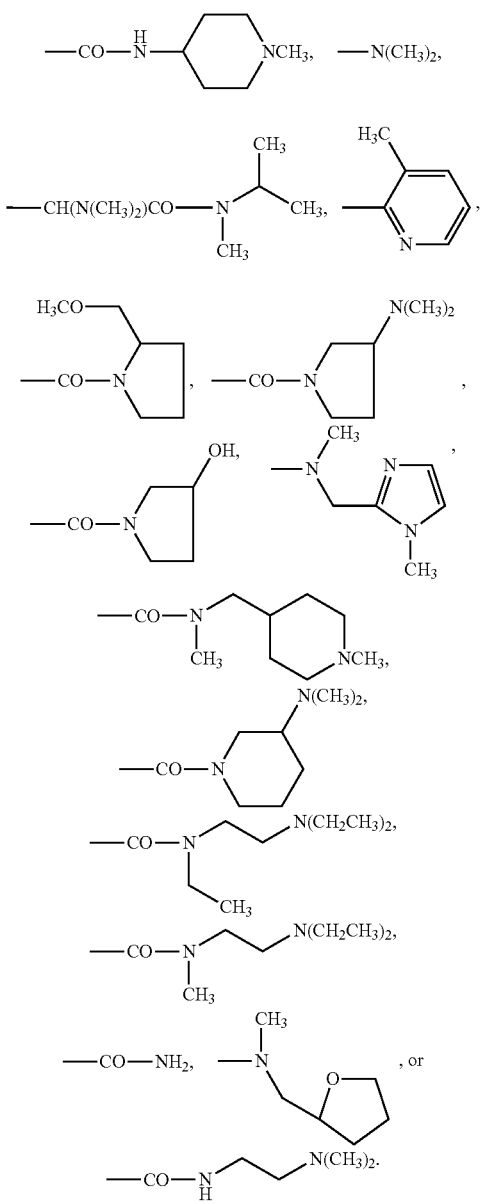

In some embodiments of this aspect of the invention, $R^1$ is hydrogen; $R^2$ is hydroxy; and $R^3$ is —CONR$^9$R$^{10}$.

In one aspect, the invention relates to compounds having Formula (B), or an enantiomer, diastereomer, racemate, tautomer or pharmaceutically acceptable salt, solvate, hydrate, polymorph or prodrug thereof:

Formula (B)

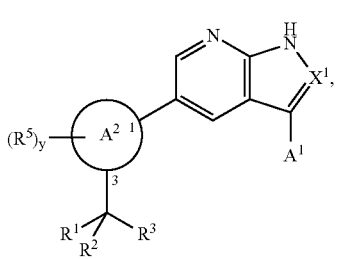

wherein
$A^1$ is substituted or unsubstituted aryl, substituted or unsubstituted heteroaryl, substituted or unsubstituted cycloalkyl, or substituted or unsubstituted heterocycloalkyl;
$A^2$ is an aryl or heteroaryl group;
$X^1$ is CR$^4$ or N; wherein
    $R^4$ is hydrogen, halogen, cyano, nitro, haloalkyl, or substituted or unsubstituted alkyl;
$R^1$ is hydrogen, lower alkyl or lower heteroalkyl;
$R^2$ is lower alkyl, halogen, hydroxy, —OR$^8$, cyano, nitro, haloalkyl, —NR$^6$R$^7$;
$R^3$ is substituted or unsubstituted alkyl, substituted or unsubstituted heteroalkyl, substituted or unsubstituted haloalkyl, substituted or unsubstituted heterocycloalkyl, substituted or unsubstituted aryl, substituted or unsubstituted (cycloalkyl)alkyl, substituted or unsubstituted (heterocycloalkyl)alkyl, substituted or unsubstituted arylalkyl, substituted or unsubstituted heteroaryl, substituted or unsubstituted heteroarylalkyl, —COOH, —NR$^9$R$^{10}$, —CH$_2$NR$^9$R$^{10}$, —CONR$^9$R$^{10}$, —CH$_2$CONR$^9$R$^{10}$ or —OR$^8$; or
$R^2$ and $R^3$ together with the carbon atom to which they are attached, form a substituted or unsubstituted heterocycloalkyl, or a substituted or unsubstituted cycloalkyl; or
each $R^5$ is independently halogen, cyano, nitro, substituted or unsubstituted haloalkyl, substituted or unsubstituted alkyl, —NR$^{11}$R$^{12}$, —CONR$^{11}$R$^{12}$, —OR$^{13}$, —C(=Z)R$^{14}$, or —S(O)$_n$R$^{15}$, wherein n is independently an integer from 0 to 2;
y is 0, 1, 2, 3 or 4;
Z is independently O, S or N(R$^{16}$);
$R^6$ and $R^7$, $R^9$ and $R^{10}$, and $R^{11}$ and $R^{12}$ are each independently hydrogen, substituted or unsubstituted alkyl, substituted or unsubstituted haloalkyl, substituted or unsubstituted alkyl-NR$^{17}$R$^{18}$, substituted or unsubstituted alkyl-CONR$^{17}$R$^{18}$, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted (cycloalkyl)alkyl, substituted or unsubstituted (heterocycloalkyl)alkyl, substituted or unsubstituted arylalkyl or substituted or unsubstituted heteroarylalkyl, or
one or more of $R^6$ and $R^7$, $R^9$ and $R^{10}$, and $R^{11}$ and $R^{12}$ are each independently joined together with the nitrogen to which they are attached, to form substituted or unsubstituted 3- to 7-membered heterocycloalkyl, or substituted or unsubstituted heteroaryl;
$R^8$ and $R^{13}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or
a pair of $R^{13}$, taken together with the oxygens to which they are attached, form a heterocycle;
$R^{14}$ is independently —OR$^{13}$, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{15}$ is independently substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein if n is 2, then $R^{15}$ is optionally $-NR^{19}R^{20}$ or $-OR^{13}$;

$R^{16}$ is independently hydrogen, substituted or unsubstituted alkyl, substituted or unsubstituted haloalkyl, or substituted or unsubstituted heteroalkyl;

$R^{17}$ and $R^{18}$, and $R^{19}$ and $R^{20}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted (cycloalkyl)alkyl, substituted or unsubstituted (heterocycloalkyl)alkyl, substituted or unsubstituted arylalkyl, or substituted or unsubstituted heteroarylalkyl; or one or more of $R^{17}$ and $R^{18}$ or $R^{19}$ and $R^{20}$ are each independently joined together with the nitrogen to which they are attached, to form substituted or unsubstituted heterocycloalkyl, or substituted or unsubstituted heteroaryl; and wherein any of the groups listed for $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ are each optionally independently substituted with 1 to 3 groups, each group independently selected from halogen, hydroxyl, amino, aminomonoalkyl, aminomonohaloalkyl, aminodihaloalkyl, aminodialkyl, cyano, nitro, haloalkyl, alkyl, —O-alkyl, O-haloalkyl, S-haloalkyl and —S-alkyl.

In some embodiments of this aspect of the invention, $A^1$ is 2-methoxyphenyl; $X^1$ is $CR^4$; and $A^2$ is phenyl.

In some embodiments of this aspect of the invention, $A^1$ is 2-methoxyphenyl; $X^1$ is $CR^4$; and $A^2$ is pyridinyl.

In some embodiments of this aspect of the invention, $A^1$ is 2-methoxyphenyl; $X^1$ is N; and $A^2$ is phenyl.

In some embodiments of this aspect of the invention, $A^1$ is 2-methoxyphenyl; $X^1$ is N; and $A^2$ is pyridinyl.

In some embodiments of this aspect of the invention, $R^1$ is hydrogen; $R^2$ is —OH, —NH$_2$, —NHCH$_3$, —N(CH$_3$)$_2$, —CH$_3$, —F, —CN, —CF$_3$, —OCH$_3$, thiomorpholinyl sulfone, or piperazinyl; and $R^3$ is substituted or unsubstituted alkyl, substituted or unsubstituted heteroalkyl, substituted or unsubstituted haloalkyl, substituted or unsubstituted heterocycloalkyl, substituted or unsubstituted aryl, substituted or unsubstituted heteroaryl, —COOH, —NR$^9$R$^{10}$, —CH$_2$NR$^9$R$^{10}$, —CONR$^9$R$^{10}$, —CH$_2$CONR$^9$R$^{10}$ or —OR$^8$.

In some embodiments of this aspect of the invention, $R^3$ is

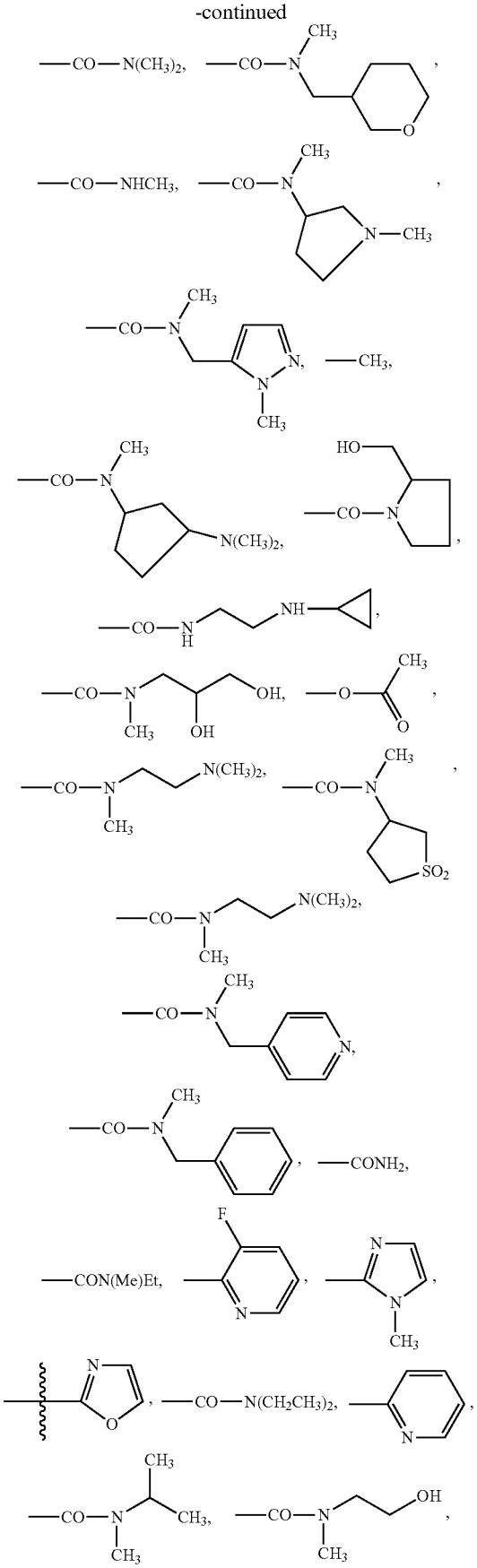

-continued

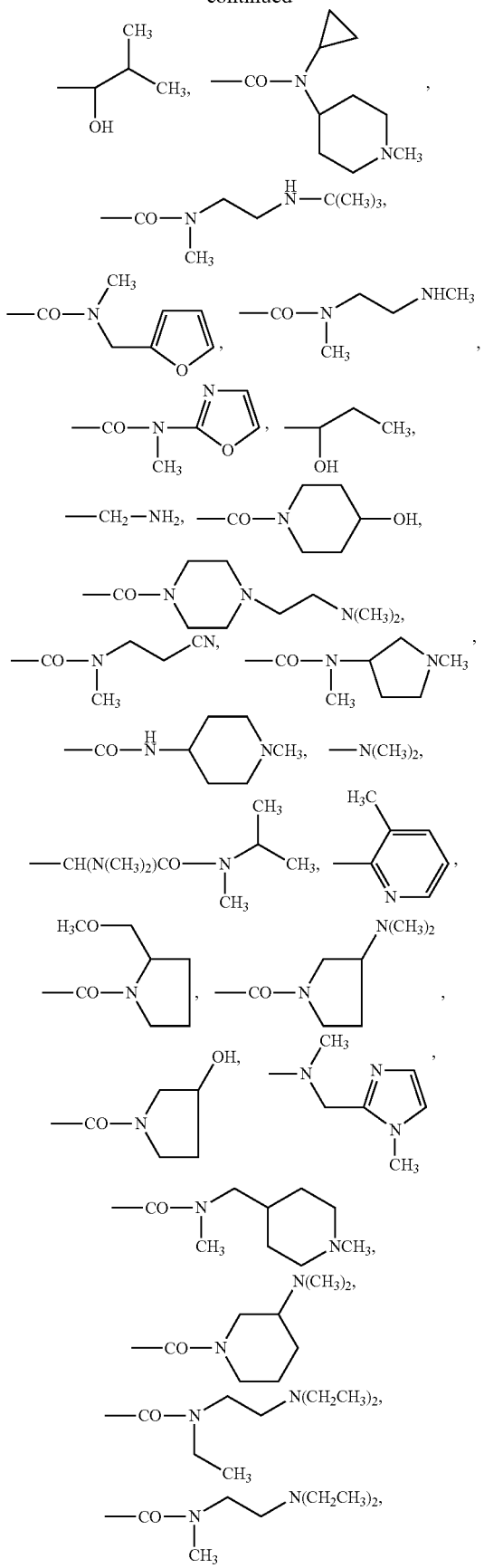

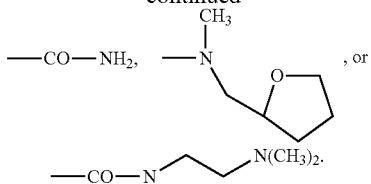

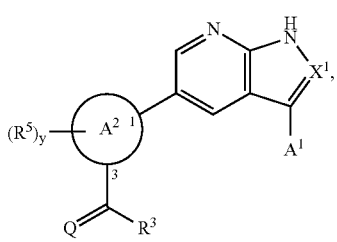

In one aspect, the invention relates to compounds having Formula (C), or an enantiomer, diastereomer, racemate, tautomer or pharmaceutically acceptable salt, solvate, hydrate, polymorph or prodrug thereof:

Formula (C)

wherein
$A^1$ is substituted or unsubstituted aryl, substituted or unsubstituted heteroaryl, substituted or unsubstituted cycloalkyl, or substituted or unsubstituted heterocycloalkyl;
$A^2$ is an aryl or heteroaryl group;
$X^1$ is $CR^4$ or N; wherein $R^4$ is hydrogen, halogen, cyano, nitro, haloalkyl, or substituted or unsubstituted alkyl;
Q is O;
$R^3$ is substituted or unsubstituted C-attached heteroalkyl, substituted or unsubstituted C-attached heterocycloalkyl, substituted or unsubstituted aryl, substituted or unsubstituted C-attached heteroaryl, —$COOR^8$, —$CH_2NR^9R^{10}$, —$CONR^9R^{10}$, or —$CH_2CONR^9R^{10}$;
each $R^5$ is independently halogen, cyano, nitro, substituted or unsubstituted haloalkyl, substituted or unsubstituted alkyl, —$NR^{11}R^{12}$, —$CONR^{11}R^{12}$, —$OR^{13}$, —$C(=Z)R^{14}$, or —$S(O)_nR^{15}$, wherein n is independently an integer from 0 to 2;
y is 0, 1, 2, 3 or 4;
Z is independently O, S or $N(R^{16})$;
$R^9$ and $R^{10}$, and $R^{11}$ and $R^{12}$ are each independently hydrogen, substituted or unsubstituted alkyl, substituted or unsubstituted haloalkyl, substituted or unsubstituted alkyl-$NR^{17}R^{18}$, substituted or unsubstituted alkyl-$CONR^{17}R^{18}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or
one or more of $R^9$ and $R^{10}$, and $R^{11}$ and $R^{12}$ are each independently joined together with the nitrogen to which they are attached, to form substituted or unsubstituted 3- to 7-membered heterocycloalkyl, or substituted or unsubstituted heteroaryl;
$R^8$ and $R^{13}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a pair of $R^{13}$, taken together with the oxygens to which they are attached, form a heterocycle;

$R^{14}$ is independently —$OR^{13}$, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is independently substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein if n is 2, then $R^{15}$ is optionally —$NR^{19}R^{20}$ or —$OR^{13}$;

$R^{16}$ is independently hydrogen, substituted or unsubstituted alkyl, substituted or unsubstituted haloalkyl, or substituted or unsubstituted heteroalkyl;

$R^{17}$ and $R^{18}$, and $R^{19}$ and $R^{20}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or one or more of $R^{17}$ and $R^{18}$ or $R^{19}$ and $R^{20}$ are each independently joined together with the nitrogen to which they are attached, to form substituted or unsubstituted heterocycloalkyl, or substituted or unsubstituted heteroaryl; and wherein any of the groups listed for $R^3$, $R^4$, $R^5$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ are each optionally independently substituted with 1 to 3 groups, each group independently selected from halogen, hydroxyl, amino, aminomonoalkyl, aminomonoalkyl, aminodihaloalkyl, aminodialkyl, cyano, nitro, haloalkyl, alkyl, —O-alkyl, O-haloalkyl, S-haloalkyl and —S-alkyl.

In some embodiments of this aspect of the invention, $A^1$ is 2-methoxyphenyl; $X^1$ is $CR^4$; and $A^2$ is phenyl.

In some embodiments of this aspect of the invention, $A^1$ is 2-methoxyphenyl; $X^1$ is $CR^4$; and $A^2$ is pyridinyl.

In some embodiments of this aspect of the invention, $A^1$ is 2-methoxyphenyl; $X^1$ is N; and $A^2$ is phenyl.

In some embodiments of this aspect of the invention, $A^1$ is 2-methoxyphenyl; $X^1$ is N; and $A^2$ is pyridinyl.

In some embodiments of this aspect of the invention, $R^3$ is —$CH_2NR^9R^{10}$, —$CONR^9R^{10}$, —$CH_2CONR^9R^{10}$.

In some embodiments of this aspect of the invention, $R^3$ is

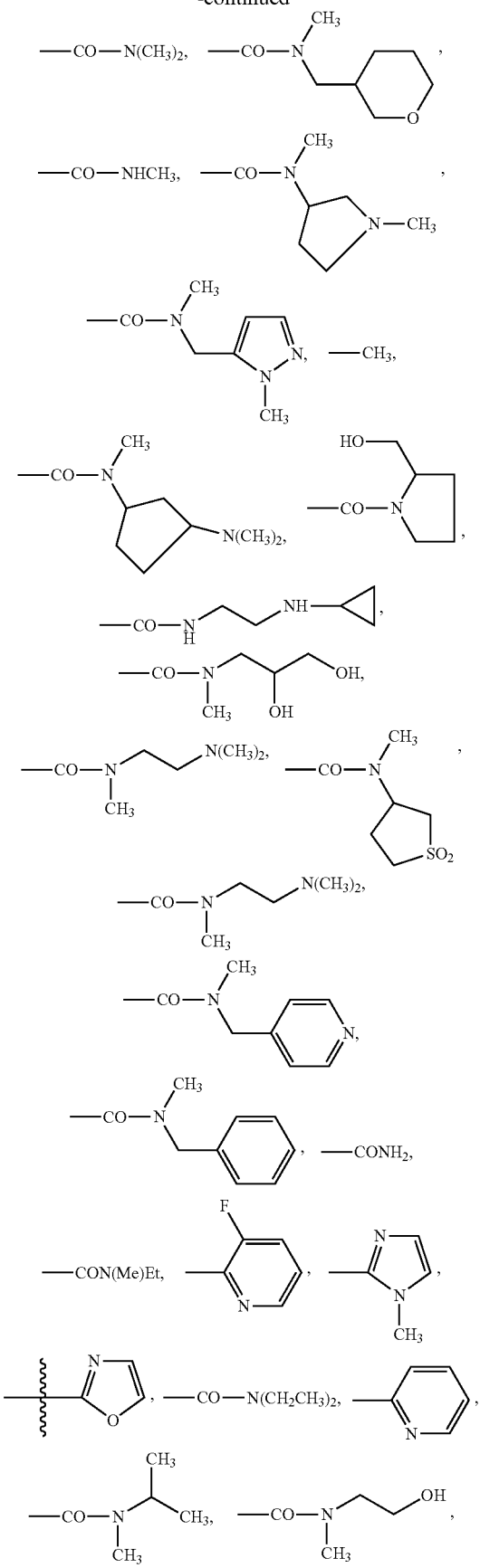

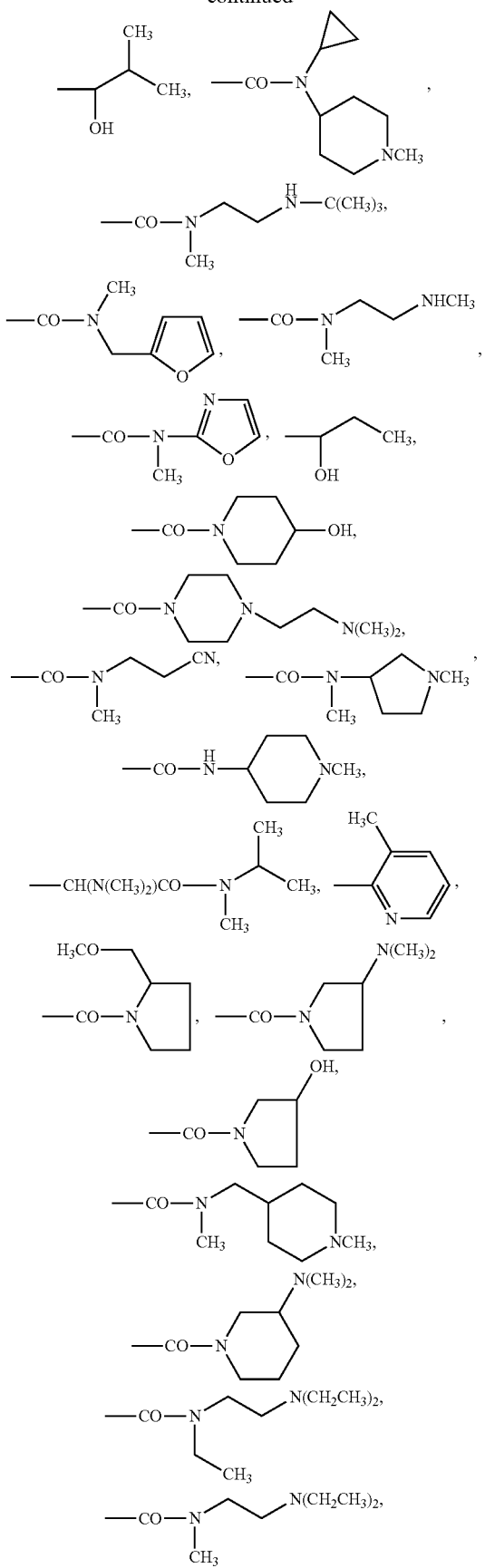

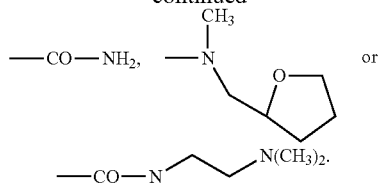

In one aspect of the invention, methods for modulating the activity of a protein kinase comprising contacting the protein kinase with a compound of Formula (A), Formula (B), Formula (C), or Formula (I), or an enantiomer, diastereomer, racemate, tautomer or pharmaceutically acceptable salt, solvate, hydrate, polymorph or prodrug thereof are provided.

In embodiment of this aspect of the invention, the protein kinase is Abelson tyrosine kinase, Ron receptor tyrosine kinase, Met receptor tyrosine kinase, Fms-like tyrosine kinase-3, Aurora kinases, p21-activated kinase-4 or 3-phosphoinositide-dependent kinase-1. In some embodiments of this aspect of the invention the protein kinase is a Bcr-Abl kinase having one or more mutations selected from the group consisting of M244V, L248V, G250E, G250A, Q252H, Q252R, Y253F, Y253H, E255K, E255V, D276G, F311L, T315I, T315N, T315A, F317V, F317L, M343T, M351T, E355G, F359A, F359V, V379I, F382L, L387M, H396P, H396R, S417Y, E459K and F486S. In one embodiment, the protein kinase has a T315I mutation.

In one aspect of the invention, methods for treating cancer, allergy, asthma, inflammation, obstructive airway disease, autoimmune diseases, metabolic disease, infection, CNS disease, brain tumor, obesity, asthma, hematological disorder, degenerative neural disease, cardiovascular disease, or disease associated with angiogenesis, neovascularization, or vasculogenesis in a subject in need of such treatment, the method comprising administering to the subject a therapeutically effective amount of a compound of Formula (A), Formula (B), Formula (C), or Formula (I), or an enantiomer, diastereomer, racemate, tautomer or pharmaceutically acceptable salt, solvate, hydrate, polymorph or prodrug thereof are provided. In one embodiment of this aspect of the invention, the cancer is leukemia or myeloproliferative disorder.

BRIEF DESCRIPTION OF THE DRAWINGS

FIG. 1 (SEQ ID NO: 23) shows the wild-type ABL numbering according to ABL exon Ia.

DETAILED DESCRIPTION OF THE INVENTION

Definitions

Abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH₂O— is equivalent to —OCH₂—.

The term "alkyl," by itself or as part of another substituent, means, unless otherwise stated, a straight (i.e., unbranched) or branched chain, or cyclic hydrocarbon radical, or combinations thereof, which may be fully saturated, mono- or poly-unsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, N-propyl, isopropyl, N-butyl, sec-butyl, tert-butyl, isobutyl, cyclobutyl, pentyl, cyclopentyl, hexyl, cyclohexyl, (cyclohexyl)methyl, cyclopropylmethyl, homologs and isomers of, for example, N-pentyl, N-hexyl, N-heptyl, N-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkyl, as exemplified, but not limited, by $-CH_2CH_2CH_2CH_2-$, $-CH_2CH=CHCH_2-$, $-CH_2C\equiv CCH_2-$, $-CH_2CH_2CH(CH_2CH_2CH_3)CH_2-$. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

As used herein, the terms "alkyl" and "alkylene" are interchangeable depending on the placement of the "alkyl" or "alkylene" group within the molecule.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2-$, $-S(O)-CH_3$, $-CH_2-CH_2-S(O)_2-CH_3$, $-CH=CH-O-CH_3$, $-Si(CH_3)_3$, $-CH_2-CH=N-OCH_3$, $-CH=CH-N(CH_3)-CH_3$, $O-CH_3$, $-O-CH_2-CH_3$, and $-CN$. Up to two or three heteroatoms may be consecutive, such as, for example, $-CH_2-NH-OCH_3$ and $-CH_2-O-Si(CH_3)_3$. Similarly, the term "heteroalkylene" by itself or as part of another substituent means a divalent radical derived from heteroalkyl, as exemplified, but not limited by, $-CH_2-CH_2-S-CH_2-CH_2-$ and $-CH_2-S-CH_2-CH_2-NH-CH_2-$. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula $-C(O)OR'-$ represents both $-C(O)OR'-$ and $-R'OC(O)-$. As described above, heteroalkyl groups, as used herein, include those groups that are attached to the remainder of the molecule through a heteroatom, such as $-C(O)R'$, $-C(O)NR'$, $-NR'R''$, $-OR'$, $-SR'$, and/or $-SO_2R'$. Where "heteroalkyl" is recited, followed by recitations of specific heteroalkyl groups, such as $-NR'R''$ or the like, it will be understood that the terms heteroalkyl and $-NR'R''$ are not redundant or mutually exclusive. Rather, the specific heteroalkyl groups are recited to add clarity. Thus, the term "heteroalkyl" should not be interpreted herein as excluding specific heteroalkyl groups, such as $-NR'R''$ or the like. As used herein, the terms "heteroalkyl" and "heteroalkylene" are interchangeable depending on the placement of the "heteroalkyl" or "heteroalkylene" group within the molecule.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively. As used herein, the terms "cycloalkyl" and "cycloalkylene" are interchangeable depending on the placement of the "cycloalkyl" or "cycloalkylene" group within the molecule. As used herein, the terms "heterocycloalkyl" and "heterocycloalkylene" are interchangeable depending on the placement of the "heterocycloalkyl" or "heterocycloalkylene" group within the molecule.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like. As used herein, the terms "haloalkyl" and "haloalkylene" are interchangeable depending on the placement of the "haloalkyl" or "haloalkylene" group within the molecule.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. For example, pyridine N-oxide moieties are included within the description of "heteroaryl." A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent radicals of aryl and heteroaryl, respectively. As used herein, the terms "aryl" and "arylene" are interchangeable depending on the placement of the "aryl" and "arylene" group within the molecule. As used herein, the terms "heteroaryl" and "heteroarylene" are interchangeable depending on the placement of the "heteroaryl" and "heteroarylene" group within the molecule.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g., "3 to 7 membered"), the term "member" referrers to a carbon or heteroatom.

The term "oxo" as used herein means an oxygen that is double bonded to a carbon atom.

Each of the above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical. Preferred substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R''' and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

An "aminoalkyl" as used herein refers to an amino group covalently bound to an alkylene linker. The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from at least the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from: (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

The compounds of the present invention may exist as salts. The present invention includes such salts. Non-limiting examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogen-phosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

The term "pharmaceutically acceptable salts" is meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science,* 66:1-19 (1977)). Certain specific compounds of the present invention contain both basic and acidic functionalities that allow the compounds to be converted into either base or acid addition salts.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" in reference to a particular disease includes prevention of the disease.

The symbol ⌇⌇ denotes the point of attachment of a moiety to the remainder of the molecule.

Fused Ring Heterocycles as Kinase Modulators

In one aspect, the invention relates to compounds having formula I:

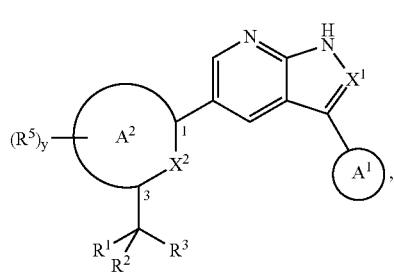

(I)

or an enantiomer, diastereomer, racemate, or pharmaceutically acceptable salt or solvate thereof, wherein:

$A^1$ is independently substituted or unsubstituted 6-membered aryl, substituted or unsubstituted 6-membered heteroaryl, substituted or unsubstituted 5-membered heteroaryl substituted or unsubstituted cycloalkyl, or substituted or unsubstituted heterocycloalkyl;

$X^1$ is independently —$CR^4$= or —N=;

$A^2$ is independently substituted or unsubstituted 6-membered aryl, substituted or unsubstituted 6-membered heteroaryl, or substituted or unsubstituted 5-membered heteroaryl;

$X^2$ is independently —$C(R^5)$=, —N=, —$NR^5$, —O—, or —S—;

$R^1$ and $R^2$ are each independently hydrogen, halogen, cyano, nitro, trifluoromethyl, difluoromethyl, substituted or unsubstituted alkyl, —$NR^6R^7$, —$CONR^6R^7$, or —$OR^8$, or $R^1$ and $R^2$ together form oxo;

$R^3$ is independently hydrogen, substituted or unsubstituted alkyl, substituted or unsubstituted heteroalkyl, substituted or unsubstituted heterocycloalkyl, substituted or unsubstituted aryl, substituted or unsubstituted aralkyl, substituted or unsubstituted heteroaryl; substituted or unsubstituted heteroaralkyl, —$NR^9R^{10}$, —$CONR^9R^{10}$, or —$OR^{11}$; or $R^2$ and $R^3$ are each independently joined together with the carbon atoms to which they are attached, to form substituted or unsubstituted heterocycloalkyl;

$R^4$ is independently hydrogen, halogen, cyano, nitro, trifluoromethyl, difluoromethyl, or substituted or unsubstituted alkyl;

each $R^5$ is independently hydrogen, halogen, cyano, nitro, trifluoromethyl, difluoromethyl, substituted or unsubstituted alkyl, —$NR^{11}R^{12}$, —$CONR^{11}R^{12}$, —$OR^{13}$, —$C(=Z)R^{14}$, —$S(O)_nR^{15}$, wherein n is independently an integer from 0 to 2;

y is independently an integer from 0 to 4;

Z is independently O, S or $N(R^{16})$;

$R^6$ and $R^7$, $R^9$ and $R^{10}$, and $R^{11}$ and $R^{12}$ are each independently hydrogen, substituted or unsubstituted alkyl, substituted or unsubstituted alkyl-$NR^{17}R^{18}$, substituted or unsubstituted alkyl-$CONR^{17}R^{18}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl, substituted or unsubstituted aralkyl, substituted or unsubstituted heteroaralkyl, or $R^6$ and $R^7$, $R^9$ and $R^{10}$, and $R^{11}$ and $R^{12}$ are each independently joined together with the nitrogen to which they are attached, to form substituted or unsubstituted 3- to 7-membered heterocycloalkyl, or substituted or unsubstituted 5-membered heteroaryl;

$R^8$, $R^{11}$, and $R^{13}$ are each independently hydrogen, difluoromethyl, trifluoromethyl, substituted or unsubstituted alkyl; substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{14}$ is independently —$OR^{13}$, substituted or unsubstituted alkyl; substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is independently substituted or unsubstituted alkyl; substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein if n is 2, then $R^{15}$ is optionally —$NR^{19}R^{20}$ or —$OR^{13}$;

R16 is independently hydrogen, substituted or unsubstituted alkyl, or substituted or unsubstituted heteroalkyl;

$R^{17}$ and $R^{18}$, and $R^{19}$ and $R^{20}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, substituted or unsubstituted aralkyl, substituted or unsubstituted heteroaralkyl, or $R^{17}$ and $R^{18}$, and $R^{19}$ and $R^{20}$ are each independently joined together with the nitrogen to which they are attached, to form substituted or unsubstituted 3- to 7-membered heterocycloalkyl, or substituted or unsubstituted 5-membered heteroaryl; and wherein any of the $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ groups are each optionally independently substituted with 1 to 3 groups, each group independently selected from halogen, hydroxyl, amino, aminomonoalkyl, aminodialkyl, cyano, nitro, difluoromethyl, trifluoromethyl, oxo, alkyl, —O-alkyl, and —S-alkyl.

In another aspect, the invention relates to compounds having formula I, wherein $A^1$ is substituted 6-membered aryl, substituted 5-membered heteroaryl, or substituted 6-membered heteroaryl.

In another aspect, the invention relates to compounds having formula I, wherein $A^1$ is substituted or unsubstituted phenyl, substituted or unsubstituted pyridinyl, substituted or unsubstituted pyridinyl N-oxide, substituted or unsubstituted pyrimidinyl, substituted or unsubstituted benzodioxolyl, substituted or unsubstituted benzimidazolyl, or substituted or unsubstituted indolyl.

In another aspect, the invention relates to compounds having formula I, wherein $A^1$ is substituted with halogen or $(C_1-C_6)$alkyl.

In another aspect, the invention relates to compounds having formula I, wherein $A^1$ is substituted phenyl.

In another aspect, the invention relates to compounds having formula I, wherein $A^1$ has anyone of formulae:

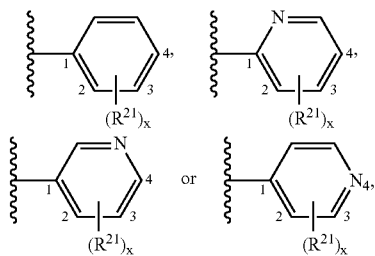

wherein x is an integer from 1 to 5; and $R^{21}$ is independently hydrogen, halogen, cyano, nitro, trifluoromethyl, difluoromethyl, substituted or unsubstituted alkyl, —$NR^{11}R^{12}$, —$CONR^{11}R^{12}$, —$OR^{13}$, —$C(=Z)R^{14}$, —$S(O)_nR^{15}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or wherein two $R^{21}$ groups are optionally combined to form a substituted or unsubstituted ring with the carbons to which they are attached.

In another aspect, the invention relates to compounds having formula I, wherein an $R^{21}$ attached at position 2 is combined with an $R^{21}$ attached at position 3 to form a substituted or unsubstituted ring.

In another aspect, the invention relates to compounds having formula I, wherein an $R^{21}$ attached at position 3 is combined with an $R^{21}$ attached at position 4 to form a substituted or unsubstituted ring.

In another aspect, the invention relates to compounds having formula I, wherein two $R^{21}$ groups are optionally combined to form a substituted or unsubstituted ring with the carbons to which they are attached, wherein the substituted or unsubstituted ring is substituted or unsubstituted heterocycloalkyl or substituted or unsubstituted heteroaryl.

In another aspect, the invention relates to compounds having formula I, wherein $R^{21}$ is independently halogen, —$OR^{13}$, —$NR^{11}R^{12}$, or substituted or unsubstituted alkyl.

In another aspect, the invention relates to compounds having formula I, wherein $R^{11}$, $R^{12}$ and $R^{13}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or wherein $R^{11}$ and $R^{12}$ are optionally joined with nitrogen to which they are attached to form substituted or unsubstituted heterocycloalkyl, or substituted or unsubstituted 5-membered heteroaryl.

In another aspect, the invention relates to compounds having formula I, wherein R11, $R^{12}$ and $R^{13}$ are each independently hydrogen, or substituted or unsubstituted alkyl.

In another aspect, the invention relates to compounds having formula I, wherein $R^{11}$, $R^{12}$ and $R^{13}$ are each independently hydrogen, or substituted or unsubstituted $(C_1-C_6)$ alkyl.

In another aspect, the invention relates to compounds having formula I, wherein x is 1 and $R^{21}$ is attached at position 2.

In another aspect, the invention relates to compounds having formula I, wherein x is 1 and $R^{21}$ is attached at position 3.

In another aspect, the invention relates to compounds having formula I, wherein x is an integer from 2 to 5 and at least one $R^{21}$ is attached at position 2.

In another aspect, the invention relates to compounds having formula I, wherein x is an integer from 2 to 5 and at least one $R^{21}$ is attached at position 3.

In another aspect, the invention relates to compounds having formula I, wherein $A^2$ is substituted or unsubstituted phenyl, substituted or unsubstituted pyridinyl, substituted or unsubstituted pyridinyl N-oxide, or substituted or unsubstituted pyrimidinyl.

In another aspect, the invention relates to compounds having formula I, wherein $A^2$ has formulae:

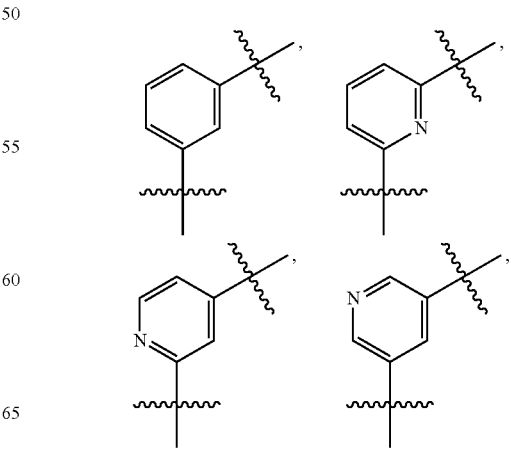

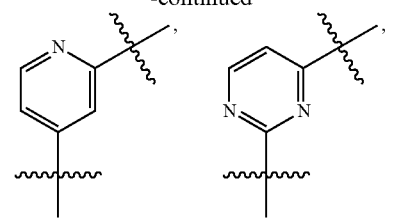
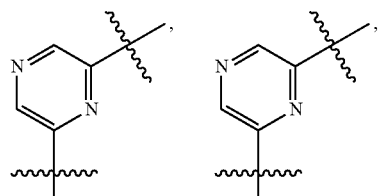
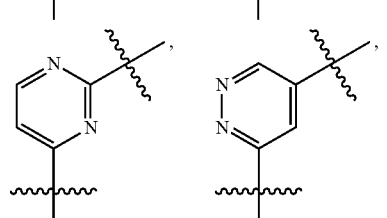
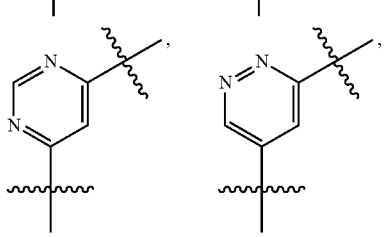
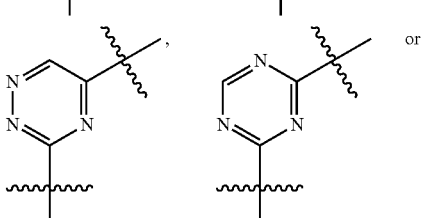
or
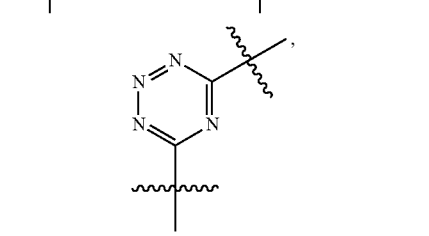
wherein any of the above groups are each independently optionally substituted with 1 to 4 $R^5$ groups.
In another aspect, the invention relates to compounds having formula I, wherein $A^2$ has formulae:
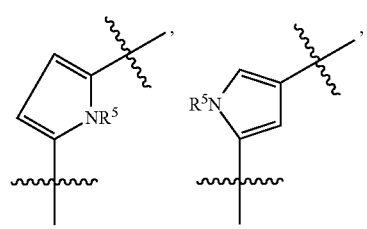
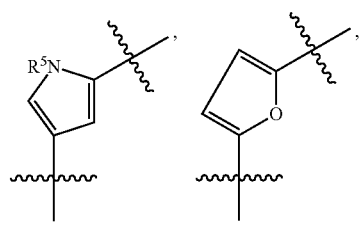
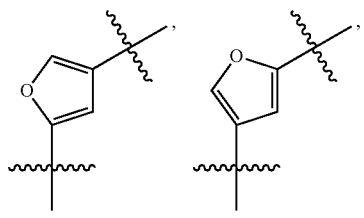
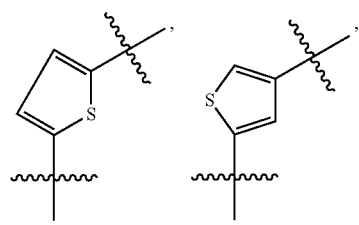
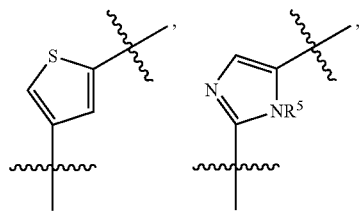
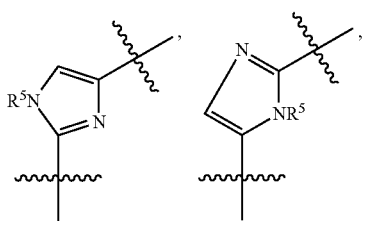
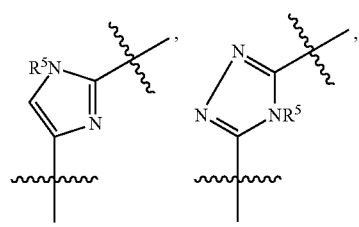

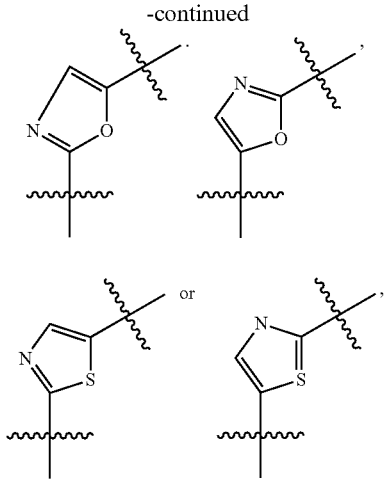

wherein any of the above groups are each independently optionally substituted with 1 to 3 R⁵ groups.

In another aspect, the invention relates to compounds having formula I, wherein A¹ is independently ortho —OCH₃ substituted phenyl; X¹ is independently —CR⁴=; R⁴ is independently hydrogen; and A² is independently phenyl.

In another aspect, the invention relates to compounds having formula I, wherein A¹ is independently ortho —OCH₃ substituted phenyl; X¹ is independently —CR⁴=; R⁴ is independently hydrogen; and A² is independently pyridinyl.

In another aspect, the invention relates to compounds having formula I, wherein A¹ is independently ortho —OCH₃ substituted phenyl; X¹ is independently —N=; R⁴ is independently hydrogen; and A² is independently phenyl.

In another aspect, the invention relates to compounds having formula I, wherein A¹ is independently ortho —OCH₃ substituted phenyl; X¹ is independently —N=; R⁴ is independently hydrogen; and A² is independently pyridinyl.

In another aspect, the invention relates to compounds having formula I, wherein R⁵ is independently hydrogen, halogen, cyano, nitro, trifluoromethyl, difluoromethyl, substituted or unsubstituted alkyl, —NR¹¹R¹², —CONR¹¹R¹², —OR¹³, —C(=Z)R¹⁴, —S(O)ₙR¹⁵, wherein n is independently an integer from 0 to 2, and wherein R¹¹ and R¹² are each independently hydrogen or (C₁-C₆)alkyl; R¹³ is hydrogen or (C₁-C₆)alkyl; Z is O; R¹⁴ is —OR¹³ or (C₁-C₆)alkyl; R¹⁵ is (C₁-C₆)alkyl or —NR¹⁹R²⁰; and R¹⁹ and R²⁰ are each independently hydrogen or (C₁-C₆)alkyl.

In another aspect, the invention relates to compounds having formula I, wherein R¹ and R² are each independently hydrogen, halogen, cyano, nitro, trifluoromethyl, difluoromethyl, substituted or unsubstituted alkyl, —NR⁶R⁷, —CONR⁶R⁷, —OR⁸, wherein R⁶ and R⁷ are each independently hydrogen or (C₁-C₆)alkyl; and R⁸ is independently hydrogen or (C₁-C₆)alkyl.

In another aspect, the invention relates to compounds having formula I, wherein R¹ and R² are each independently hydrogen, —NR⁶R⁷ or —CONR⁶R⁷, wherein R⁶ and R⁷ are each independently joined together with the nitrogen to which they are attached, to form substituted or unsubstituted 3- to 7-membered heterocycloalkyl, or substituted or unsubstituted 5-membered heteroaryl.

In another aspect, the invention relates to compounds having formula I, wherein R¹ and R² are each independently hydrogen, —NR⁶R⁷ or —CONR⁶R⁷, wherein R⁶ and R⁷ are each independently joined together with the nitrogen to which they are attached, to form substituted or unsubstituted 3- to 7-membered heterocycloalkyl, wherein the substituted or unsubstituted 3- to 7-membered heterocycloalkyl is substituted or unsubstituted pyrrolidinyl, substituted or unsubstituted imidazolidinyl, substituted or unsubstituted pyrazolidinyl, substituted or unsubstituted piperidinyl, substituted or unsubstituted morpholinyl, substituted or unsubstituted thiomorpholinyl, substituted or unsubstituted thiomorpholinyl sulfone, or substituted or unsubstituted piperazinyl.

In another aspect, the invention relates to compounds having formula I, wherein R¹ and R² are each independently hydrogen, —NR⁶R⁷ or —CONR⁶R⁷, wherein R⁶ and R⁷ are each independently joined together with the nitrogen to which they are attached, to form substituted or unsubstituted 5-membered heteroaryl, wherein the substituted or unsubstituted 5-membered heteroaryl is substituted or unsubstituted pyrrolyl, substituted or unsubstituted imidazolyl, substituted or unsubstituted pyrazolyl.

In another aspect, the invention relates to compounds having formula I, wherein R¹ is hydrogen; R² is —OR⁸; and R⁸ is hydrogen.

In another aspect, the invention relates to compounds having formula I, wherein R³ is independently hydrogen, substituted or unsubstituted alkyl, substituted or unsubstituted heteroalkyl, substituted or unsubstituted heterocycloalkyl, substituted or unsubstituted aryl, substituted or unsubstituted aralkyl, substituted or unsubstituted heteroaryl; substituted or unsubstituted heteroaralkyl, —NR⁹R¹⁰, —CONR⁹R¹⁰, or —OR¹¹, wherein R⁹ and R¹⁰ are each independently hydrogen, substituted or unsubstituted alkyl, substituted or unsubstituted alkyl-NR¹⁷R¹⁸, substituted or unsubstituted alkyl-CONR¹⁷R¹⁸; and R¹⁷ and R¹⁸; R¹⁹ and R²⁰ are each independently hydrogen, or substituted or unsubstituted alkyl; and R¹¹ is hydrogen, or substituted or unsubstituted alkyl.

In another aspect, the invention relates to compounds having formula I, wherein R³ is independently —NR⁹R¹⁰ or —CONR⁹R¹⁰, wherein R⁹ and R¹⁰ are each independently joined together with the nitrogen to which they are attached, to form substituted or unsubstituted 3- to 7-membered heterocycloalkyl, or substituted or unsubstituted 5-membered heteroaryl.

In another aspect, the invention relates to compounds having formula I, wherein R³ is independently —NR⁹R¹⁰ or —CONR⁹R¹⁰, wherein R⁹ and R¹⁰ are each independently joined together with the nitrogen to which they are attached, to form substituted or unsubstituted 3- to 7-membered heterocycloalkyl, wherein the substituted or unsubstituted 3- to 7-membered heterocycloalkyl is substituted or unsubstituted pyrrolidinyl, substituted or unsubstituted imidazolidinyl, substituted or unsubstituted pyrazolidinyl, substituted or unsubstituted piperidinyl, substituted or unsubstituted morpholinyl, substituted or unsubstituted thiomorpholinyl, substituted or unsubstituted thiomorpholinyl sulfone, or substituted or unsubstituted piperazinyl.

In another aspect, the invention relates to compounds having formula I, wherein R³ is independently —NR⁹R¹⁰ or —CONR⁹R¹⁰, wherein R⁹ and R¹⁰ are each independently joined together with the nitrogen to which they are attached, to form substituted or unsubstituted 5-membered heteroaryl, wherein the substituted or unsubstituted 5-membered heteroaryl is substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted isoxazolyl, substituted or unsubstituted isothiazolyl.

In another aspect, the invention relates to compounds having formula I, wherein $R^3$ is independently substituted or unsubstituted heterocycloalkyl, substituted or unsubstituted aryl, substituted or unsubstituted aralkyl, substituted or unsubstituted heteroaryl; or substituted or unsubstituted heteroaralkyl.

In another aspect, the invention relates to compounds having formula I, wherein $R^3$ is independently substituted or unsubstituted heterocycloalkyl, wherein the substituted or unsubstituted heterocycloalkyl is substituted or unsubstituted pyrrolidinyl, substituted or unsubstituted dioxolanyl, substituted or unsubstituted imidazolidinyl, substituted or unsubstituted pyrazolidinyl, substituted or unsubstituted piperidinyl, substituted or unsubstituted morpholinyl, substituted or unsubstituted dithianyl, substituted or unsubstituted thiomorpholinyl, substituted or unsubstituted thiomorpholinyl sulfone, or substituted or unsubstituted piperazinyl.

In another aspect, the invention relates to compounds having formula I, wherein $R^3$ is independently substituted or unsubstituted aryl, substituted or unsubstituted aralkyl, wherein the substituted or unsubstituted aryl is substituted or unsubstituted phenyl, and the substituted or unsubstituted aralkyl is substituted or unsubstituted benzyl.

In another aspect, the invention relates to compounds having formula I, wherein $R^3$ is substituted or unsubstituted heteroaryl, wherein the substituted or unsubstituted heteroaryl is substituted or unsubstituted furyl, substituted or unsubstituted thiophenyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted isoxazolyl, substituted or unsubstituted isothiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolizinyl, substituted or unsubstituted indolyl, substituted or unsubstituted isoindolyl, substituted or unsubstituted indolinyl, substituted or unsubstituted benzo[b]furanyl, substituted or unsubstituted benzo[b]thiophenyl, substituted or unsubstituted indazolyl, substituted or unsubstituted benzimidazolyl, substituted or unsubstituted benzothiazolyl, substituted or unsubstituted purinyl, substituted or unsubstituted quinolizinyl, substituted or unsubstituted quinolinyl, substituted or unsubstituted isoquinolinyl, substituted or unsubstituted cinnolinyl, substituted or unsubstituted phthalazinyl, substituted or unsubstituted quinazolinyl, substituted or unsubstituted quinoxalinyl, substituted or unsubstituted naphthyridinyl, or substituted or unsubstituted pteridinyl.

In another aspect, the invention relates to compounds having formula I, wherein $R^2$ and $R^3$ are each independently joined together with the carbon atoms to which they are attached, to form substituted or unsubstituted heterocycloalkyl.

In another aspect, the invention relates to compounds having formula I, wherein $R^2$ and $R^3$ are each independently joined together with the carbon atoms to which they are attached, to form substituted or unsubstituted dioxolanyl or substituted or unsubstituted pyrimidone.

In another aspect, the invention relates to compounds of formula I, having formulae:

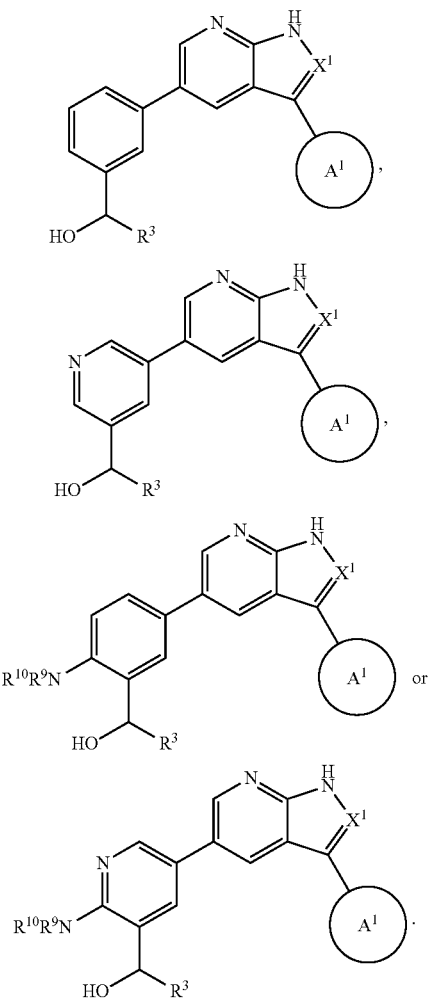

In another aspect, the invention relates to compounds of formula I, having formulae:

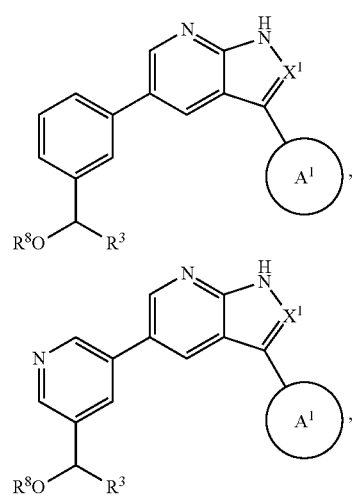

-continued
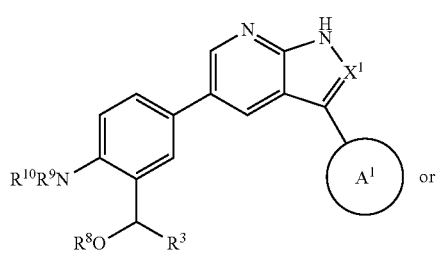
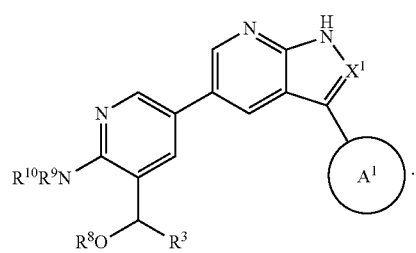
In another aspect, the invention relates to compounds of formula I, having formulae:
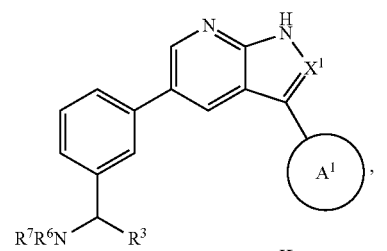
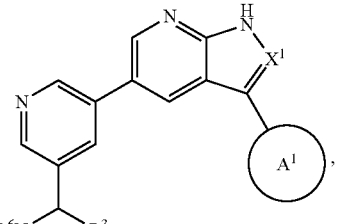
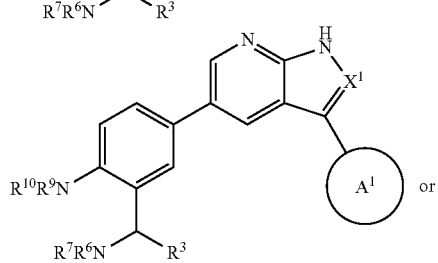
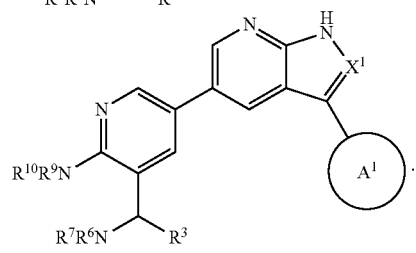
In another aspect, the invention relates to compounds of formula I, having formulae:
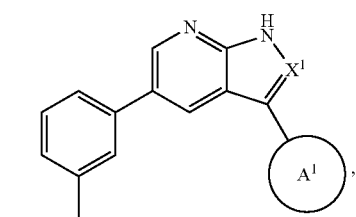
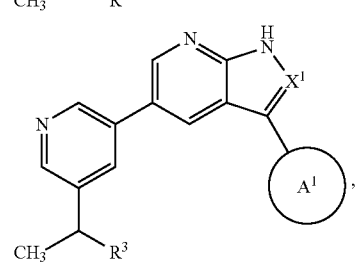
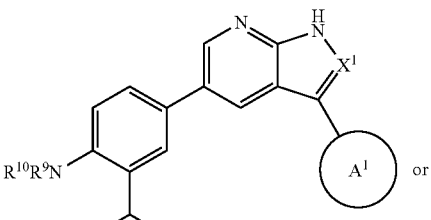
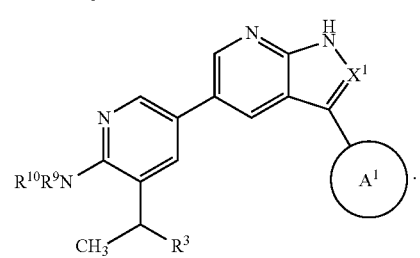
In another aspect, the invention relates to compounds of formula I, having formulae:
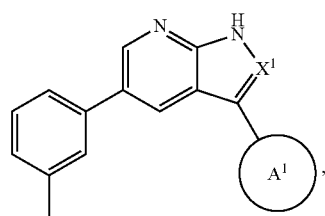
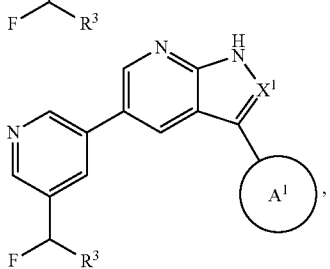

-continued
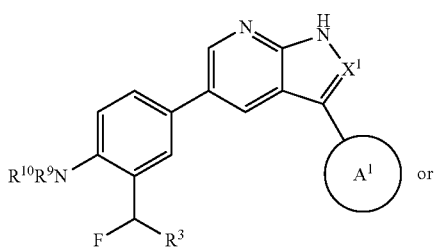
or
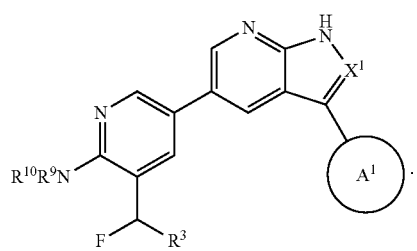
In another aspect, the invention relates to compounds of formula I, having formulae:
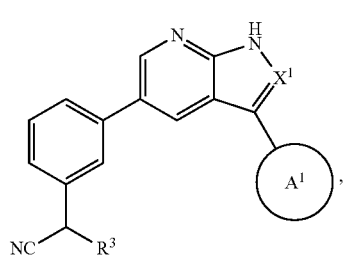
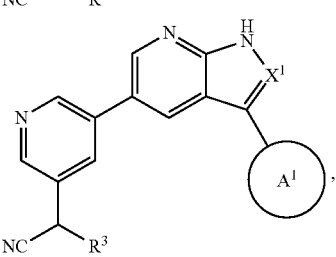
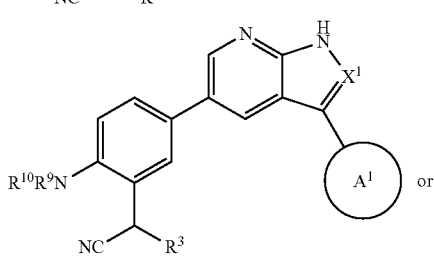
or
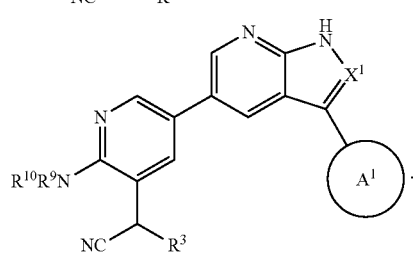
In another aspect, the invention relates to compounds of formula I, having formulae:
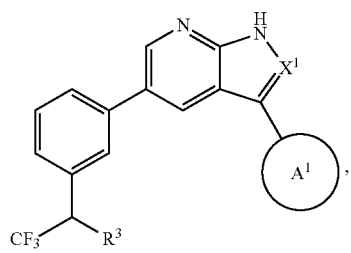
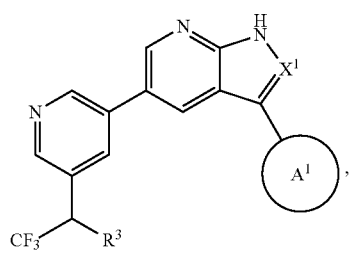
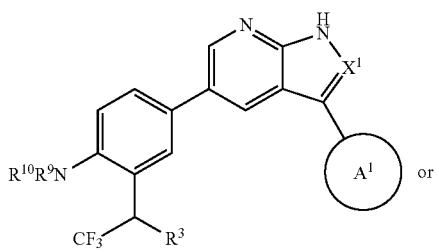
or
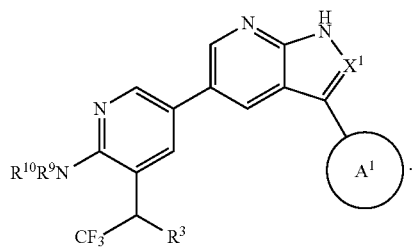
In another aspect, the invention relates to compounds of formula I, having formulae:
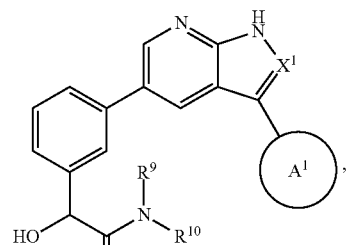
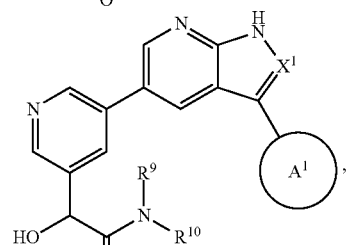

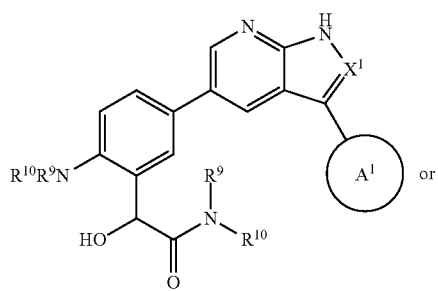
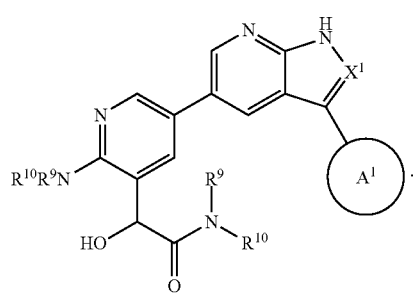
In another aspect, the invention relates to compounds of formula I, having formulae:
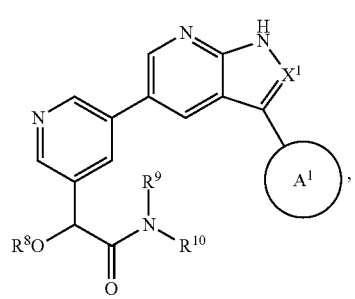
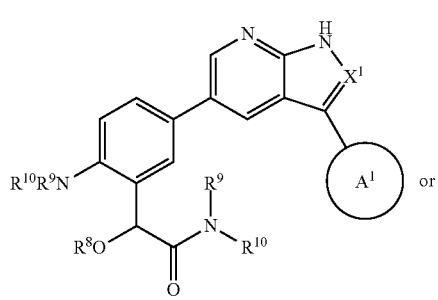
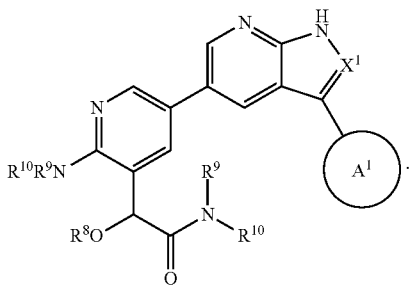
In another aspect, the invention relates to compounds of formula I, having formulae:
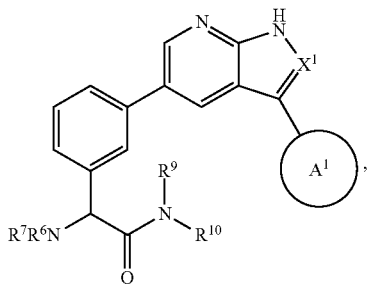
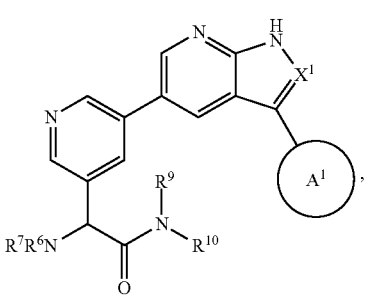
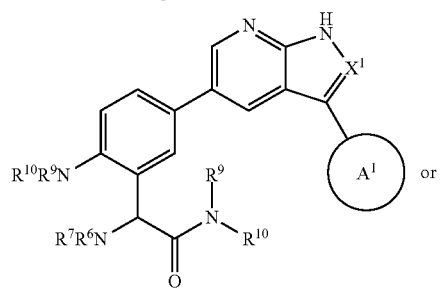
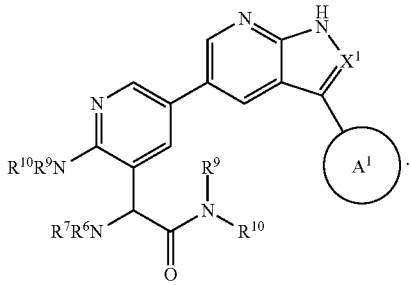
In another aspect, the invention relates to compounds of formula I, having formulae:

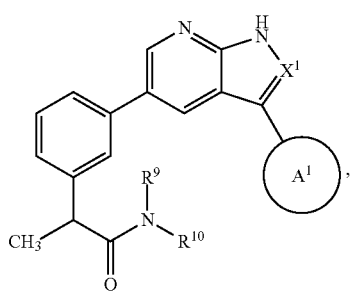
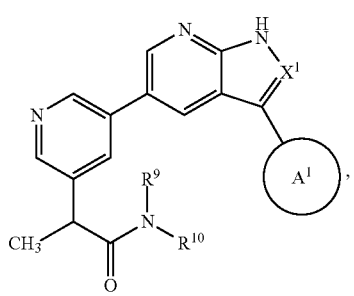
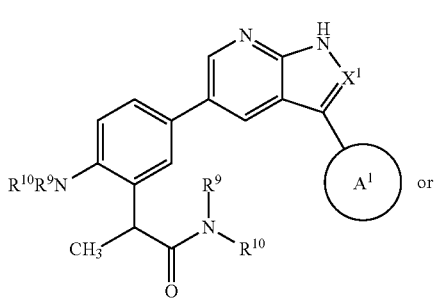 or
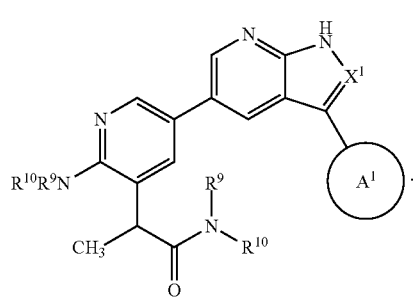.
In another aspect, the invention relates to compounds of formula I, having formulae:
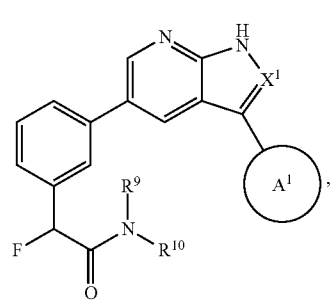,
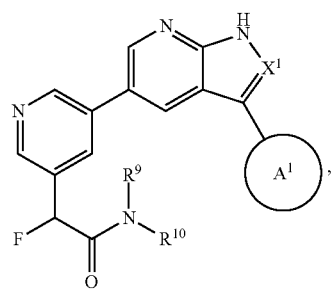,
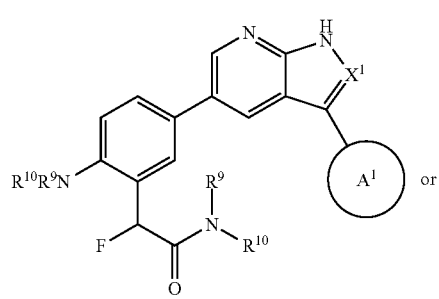 or
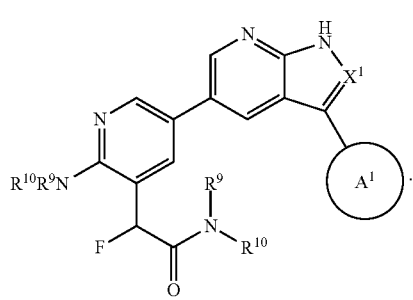.
In another aspect, the invention relates to compounds of formula I, having formulae:
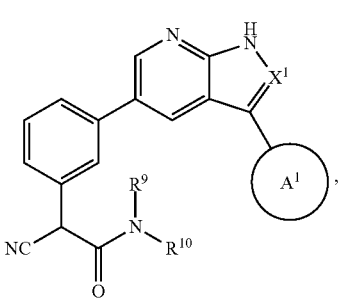,
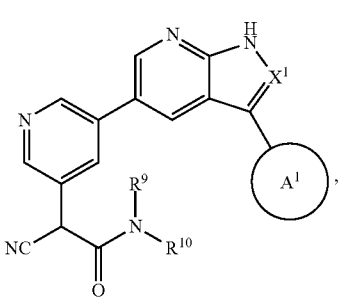, -continued

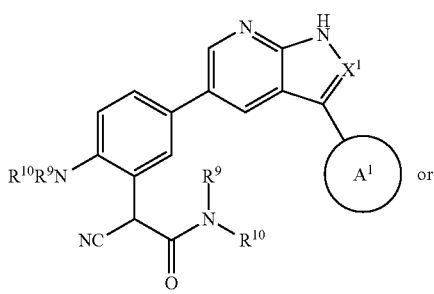 or

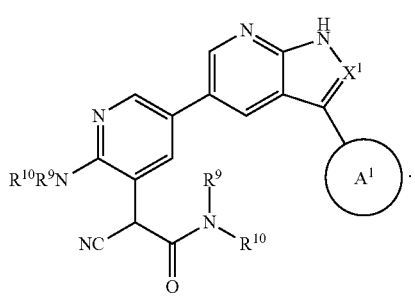

In another aspect, the invention relates to compounds of formula I, having formulae:

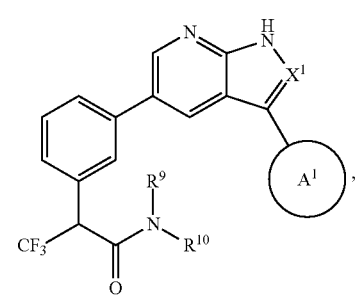,

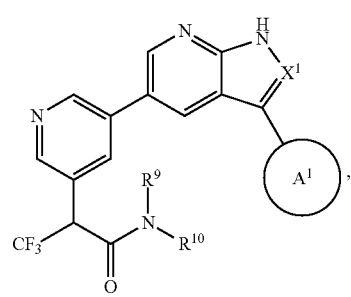,

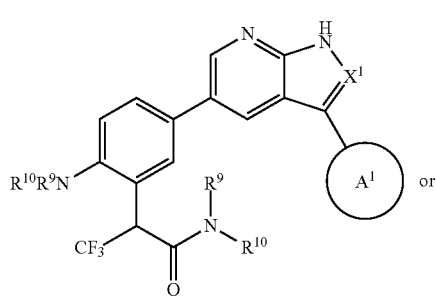 or

-continued

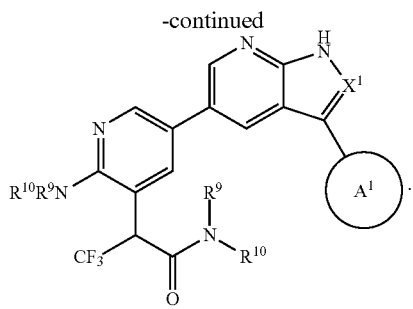

In another aspect, the invention relates to compounds of formula I, having formulae:

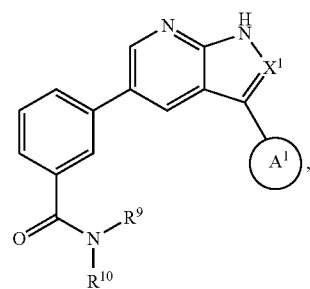,

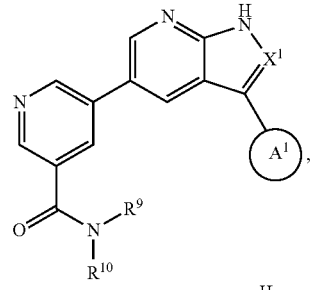,

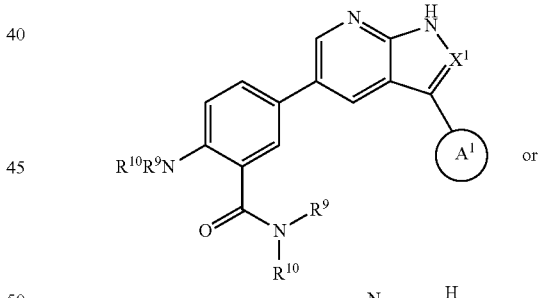 or

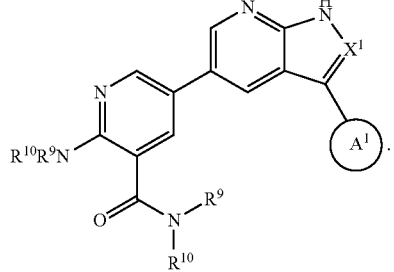.

In another aspect, the invention relates to compounds having formula I, wherein:
$R^1$ is hydrogen;
$R^2$ is —OH, —$NH_2$, $NHCH_3$, $N(CH_3)_2$, —$CH_3$, —F, —CN, —$CF_3$, —$OCH_3$, thiomorpholinyl sulfone, or piperazinyl;

$R^3$ is —C(=O)$NR^9R^{10}$; and $R^9$ and $R^{10}$ are each independently hydrogen, substituted or unsubstituted alkyl, substituted or unsubstituted alkyl-$NR^{17}R^{18}$, substituted or unsubstituted alkyl-$CONR^{17}R^{18}$, or $R^{17}$ and $R^{18}$ are each independently joined together with the nitrogen to which they are attached, to form substituted or unsubstituted pyrrolidinyl, substituted or unsubstituted piperidinyl, substituted or unsubstituted morpholinyl, substituted or unsubstituted thiomorpholinyl, substituted or unsubstituted thiomorpholinyl sulfone, or substituted or unsubstituted piperazinyl.

In another aspect, the invention relates to compounds having formula I, wherein $A^1$ is substituted phenyl or substituted pyridinyl.

In another aspect, the invention relates to compounds having formula I, wherein $R^1$ is hydrogen;

$R^2$ is —OH, —$NH_2$, $NHCH_3$, $N(CH_3)_2$, —$CH_3$, —F, —CN, —$CF_3$, —$OCH_3$, thiomorpholinyl sulfone, or piperazinyl; and

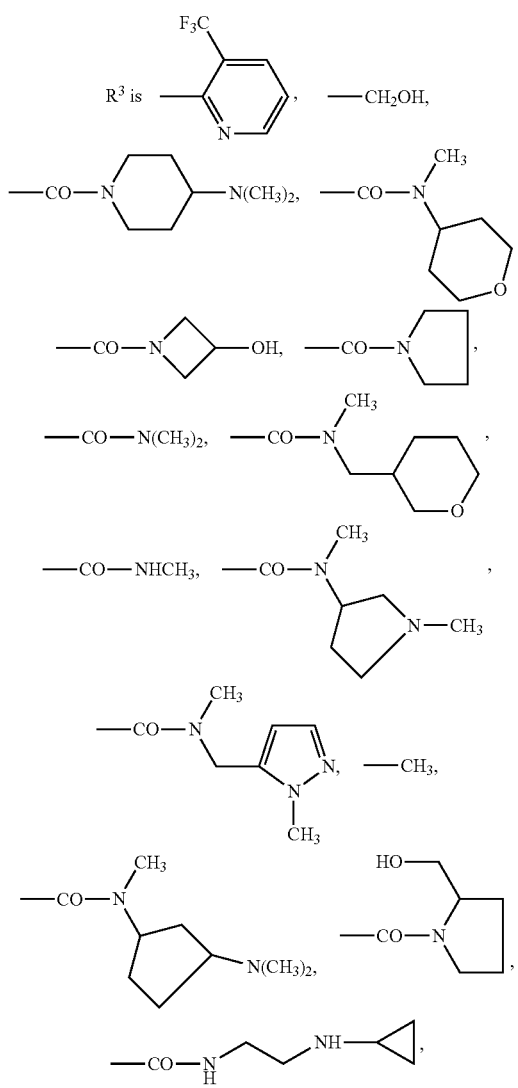

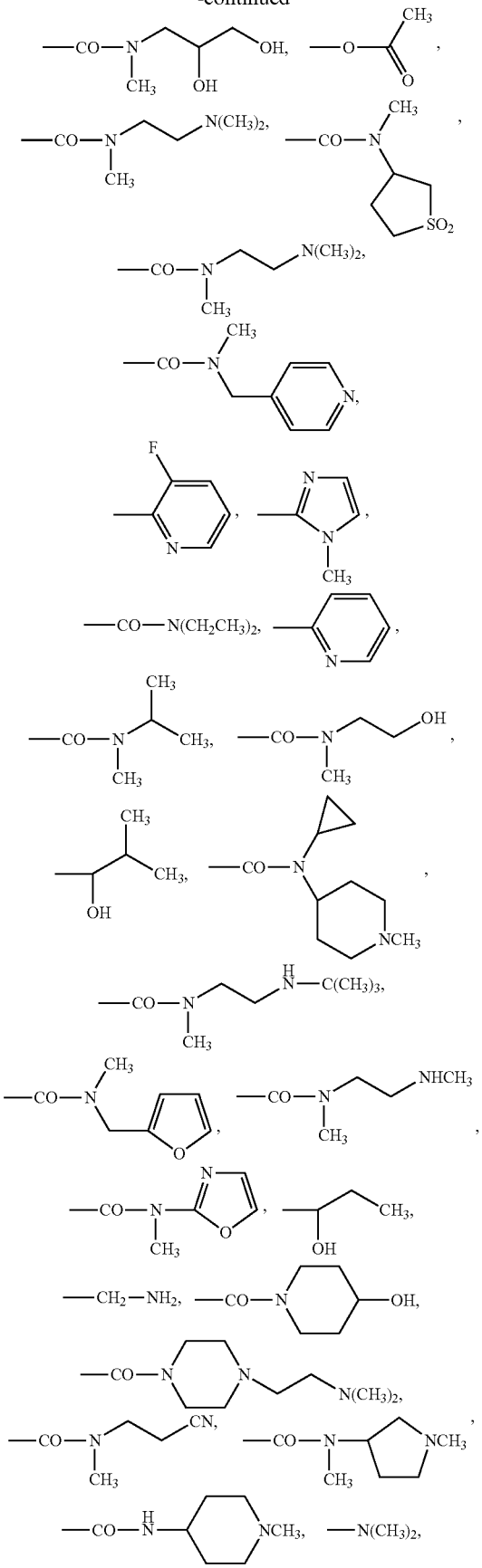

-continued

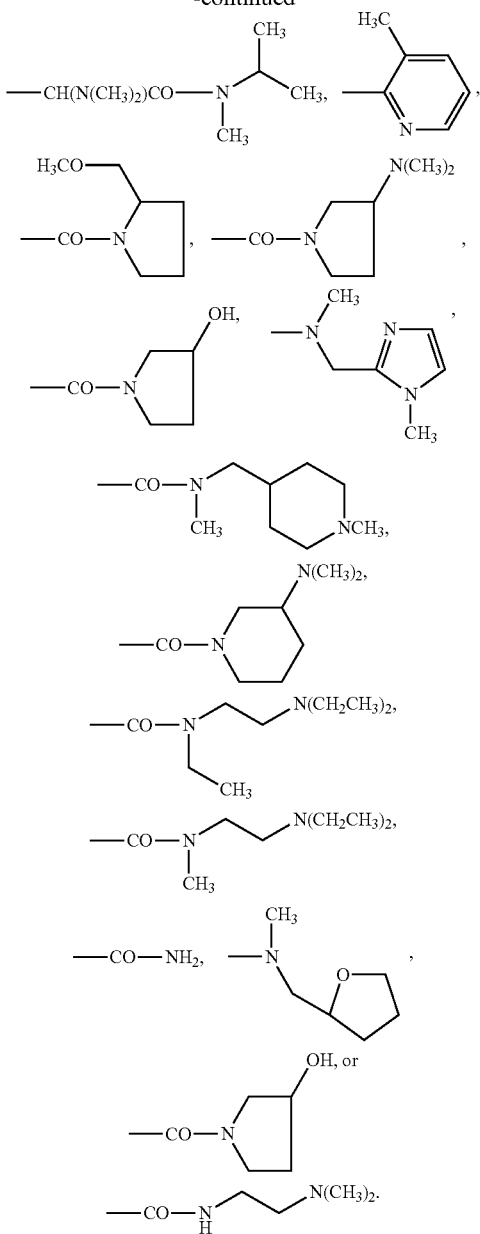

In one aspect, the invention relates to compounds having Formula (A), or an enantiomer, diastereomer, racemate, tautomer of pharmaceutically acceptable salt, solvate, hydrate, polymorph or prodrug thereof:

Formula (A)

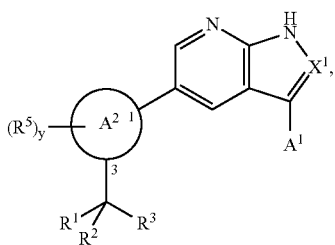

wherein
$A^1$ is substituted or unsubstituted aryl, substituted or unsubstituted heteroaryl, substituted or unsubstituted cycloalkyl, or substituted or unsubstituted heterocycloalkyl;
$A^2$ is an aryl or heteroaryl group;
$X^1$ is $CR^4$ or N; wherein
$R^4$ is hydrogen, halogen, cyano, nitro, haloalkyl, or substituted or unsubstituted alkyl;
$R^1$ is hydrogen, lower alkyl or lower heteroalkyl;
$R^2$ is hydrogen, lower alkyl, halogen, hydroxy, —$OR^8$, cyano, nitro, haloalkyl, —$NR^6R^7$;
$R^3$ is hydrogen, substituted or unsubstituted alkyl, substituted or unsubstituted heteroalkyl, substituted or unsubstituted haloalkyl, substituted or unsubstituted heterocycloalkyl, substituted or unsubstituted aryl, substituted or unsubstituted (cycloalkyl)alkyl, substituted or unsubstituted (heterocycloalkyl)alkyl, substituted or unsubstituted arylalkyl, substituted or unsubstituted heteroaryl, substituted or unsubstituted heteroarylalkyl, —COOH, —$NR^9R^{10}$, —$CH_2NR^9R^{10}$, —$CONR^9R^{10}$, —$CH_2CONR^9R^{10}$ or —$OR^8$; or
$R^2$ and $R^3$ together with the carbon atom to which they are attached, form a substituted or unsubstituted heterocycloalkyl, or a substituted or unsubstituted cycloalkyl;
each $R^5$ is independently halogen, cyano, nitro, substituted or unsubstituted haloalkyl, substituted or unsubstituted alkyl, —$NR^{11}R^{12}$, —$CONR^{11}R^{12}$, —$OR^{13}$, —$C(=Z)R^4$, or —$S(O)_nR^{15}$, wherein n is independently an integer from 0 to 2;
y is 0, 1, 2, 3 or 4;
Z is independently O, S or $N(R^{16})$;
$R^6$ and $R^7$, $R^9$ and $R^{10}$, and $R^{11}$ and $R^{12}$ are each independently hydrogen, substituted or unsubstituted alkyl, substituted or unsubstituted haloalkyl, substituted or unsubstituted alkyl-$NR^{17}R^{18}$, substituted or unsubstituted alkyl-$CONR^{17}R^{18}$, substituted or unsubstituted heteroalkyl, substituted or unsubstituted cycloalkyl, substituted or unsubstituted heterocycloalkyl, substituted or unsubstituted aryl substituted or unsubstituted heteroaryl, substituted or unsubstituted (cycloalkyl)alkyl, substituted or unsubstituted (heterocycloalkyl)alkyl, substituted or unsubstituted arylalkyl, or substituted or unsubstituted heteroarylalkyl, or
one or more of $R^6$ and $R^7$, $R^9$ and $R^{10}$, and $R^{11}$ and $R^{12}$ are each independently joined together with the nitrogen to which they are attached, to form substituted or unsubstituted 3- to 7-membered heterocycloalkyl, or substituted or unsubstituted heteroaryl;
$R^8$ and $R^{13}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or
a pair of $R^{13}$, taken together with the oxygens to which they are attached, form a heterocycle;
$R^{14}$ is independently —$OR^3$, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{15}$ is independently substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein if n is 2, then $R^{15}$ is optionally —$NR^{19}R^{20}$ or —$OR^{13}$;

$R^{16}$ is independently hydrogen, substituted or unsubstituted alkyl, substituted or unsubstituted haloalkyl, or substituted or unsubstituted heteroalkyl;

$R^{17}$ and $R^{18}$, and $R^{19}$ and $R^{20}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, substituted or unsubstituted (cycloalkyl)alkyl, substituted or unsubstituted (heterocycloalkyl)alkyl, substituted or unsubstituted arylalkyl, or substituted or unsubstituted heteroarylalkyl; or one or more of $R^{17}$ and $R^{18}$ and $R^{19}$ and $R^{20}$ are each independently joined together with the nitrogen to which they are attached, to form substituted or unsubstituted heterocycloalkyl, or substituted or unsubstituted heteroaryl; and wherein any of the groups listed for $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ are each optionally independently substituted with 1 to 3 groups, each group independently selected from halogen, hydroxyl, amino, aminomonoalkyl, aminomonohaloalkyl, aminodihaloalkyl, aminodialkyl, cyano, nitro, haloalkyl, alkyl, —O-alkyl, O-haloalkyl, S-haloalkyl and —S-alkyl with the proviso that when $R^1$ and $R^2$ are both hydrogen, $R^3$ is not hydrogen, $NR^9R^{10}$, $CONR^9R^{10}$, or $CHNH_2CONR^9R^{10}$ and with the proviso that when $R^1$ and $R^3$ are both hydrogen, $R^2$ is not $NR^6R^7$.

In some embodiments of this aspect of the invention, $A^2$ is substituted or unsubstituted 6-membered aryl, substituted or unsubstituted 5-membered heteroaryl, or substituted or unsubstituted 6-membered heteroaryl. In other embodiments, $A^2$ is substituted or unsubstituted phenyl, substituted or unsubstituted pyridinyl, substituted or unsubstituted pyridinyl N-oxide, or substituted or unsubstituted pyrimidinyl. In some embodiments, $A^2$ has the formula:

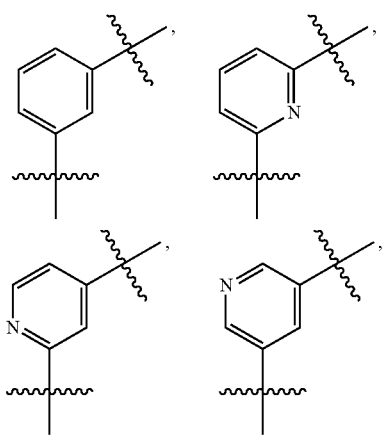

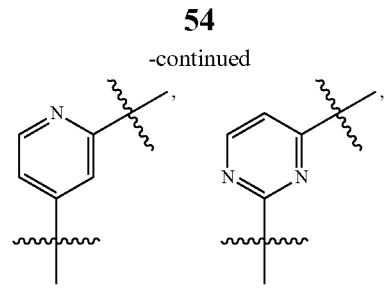

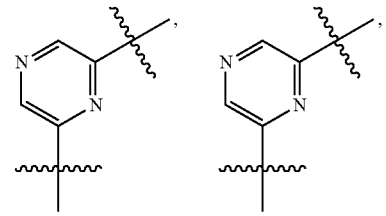

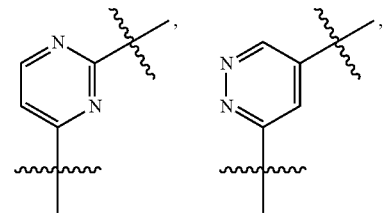

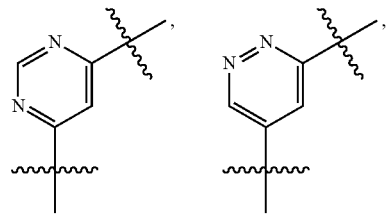

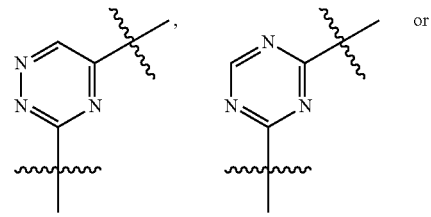

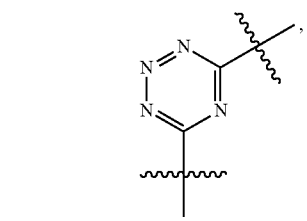

wherein any of the above groups are each independently optionally substituted with 1 to 4 $R^5$ groups. In some embodiments, $A^2$ has the formula:

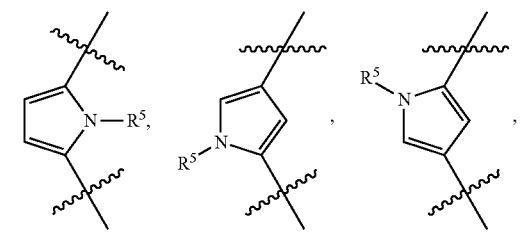

-continued

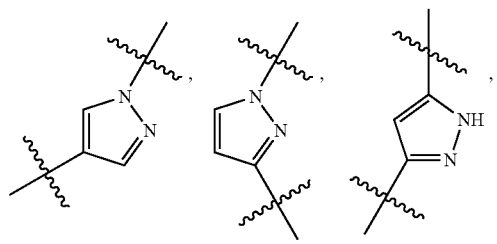
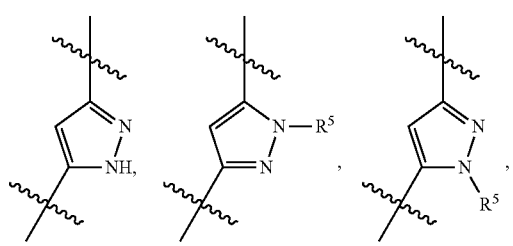
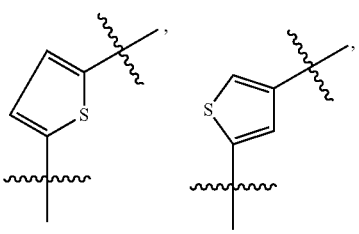
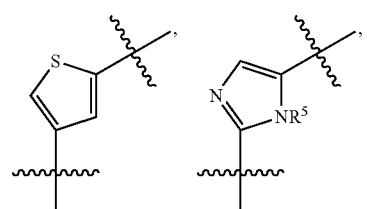
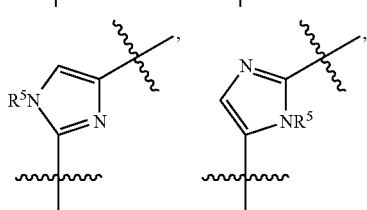
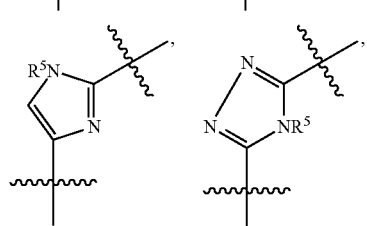
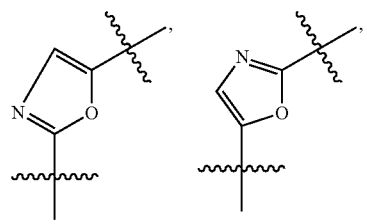

-continued

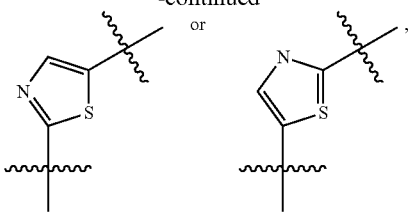

wherein any of the above groups are each independently optionally substituted with 1 to 3 $R^5$ groups.

In some embodiments of this aspect of the invention, $A^1$ is substituted or unsubstituted 6-membered aryl, substituted or unsubstituted 5-membered heteroaryl, or substituted or unsubstituted 6-membered heteroaryl. In some embodiments, $A^1$ is substituted with one or more halogen, cyano, nitro, trifluoromethyl, difluoromethyl, —$NR^{11}R^{12}$, —$N(R^{11})COR^{12}$, —$CONR^{11}R^{12}$, —$OR^{13}$, —$SR^{13}$, —$C(=Z)R^{14}$, —$S(O)_nR^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or combination thereof In some embodiments, $A^1$ is substituted or unsubstituted phenyl, substituted or unsubstituted pyridinyl, substituted or unsubstituted pyridinyl N-oxide, substituted or unsubstituted pyrimidinyl, substituted or unsubstituted benzodioxolyl, substituted or unsubstituted benzimidazolyl, or substituted or unsubstituted indolyl. In some embodiments, $A^1$ is:

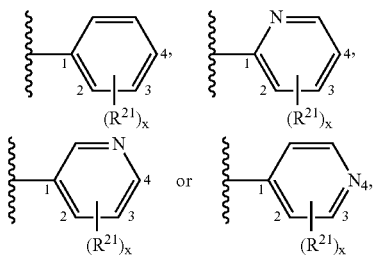

wherein:
x is an integer from 1 to 5; and
$R^{21}$ is independently halogen, cyano, nitro, trifluoromethyl, difluoromethyl, fluoromethyl, —$NR^{11}R^{12}$, —$CONR^{11}R^{12}$, —$OR^{13}$, —$SR^{13}$, —$C(=Z)R^{14}$, —$S(O)_nR^{15}$, substituted or unsubstituted alkyl, substituted or unsubstituted haloalkyl substituted or unsubstituted heteroalkyl, substituted or unsubstituted cycloalkyl, substituted or unsubstituted heterocycloalkyl, substituted or unsubstituted aryl, or substituted or unsubstituted heteroaryl; or
two adjacent $R^{21}$ groups together with the carbon atoms to which they are attached are combined to form a substituted or unsubstituted ring.

In some embodiments of this aspect of the invention, $R^1$ is hydrogen or methyl.

In some embodiments of this aspect of the invention, $R^2$ is hydroxy or methoxy.

In some embodiments of this aspect of the invention, $R^3$ is —$CH_2CONR^9R^{10}$ or —$CONR^9R^{10}$.

In some embodiments of this aspect of the invention, the compound has the formula:

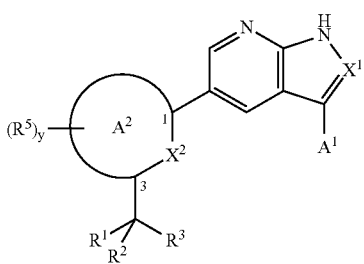

wherein $X^2$ is $—C(R^5)=$, $—CH=$, $—N=$, $—NR^5—$, $—NH—$, $—O—$, or $—S—$.

In some embodiments of this aspect of the invention, $A^1$ is 2-methoxyphenyl; $X^1$ is $CR^4$; and $A^2$ is phenyl.

In some embodiments of this aspect of the invention, $A^1$ is 2-methoxyphenyl; $X^1$ is $CR^4$; and $A^2$ is pyridinyl.

In some embodiments of this aspect of the invention, $A^1$ is 2-methoxyphenyl; $X^1$ is N; and $A^2$ is phenyl.

In some embodiments of this aspect of the invention, $A^1$ is 2-methoxyphenyl; $X^1$ is N; and $A^2$ is pyridinyl.

In some embodiments of this aspect of the invention, the compound has the formula:

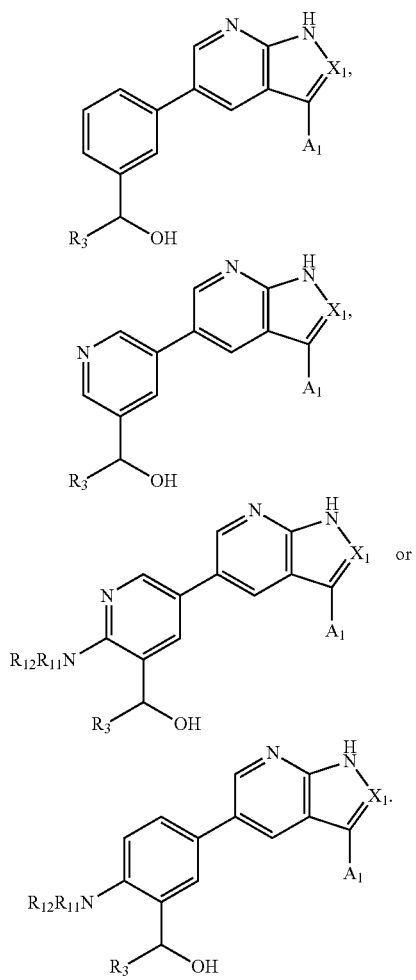

In some embodiments of this aspect of the invention, $R^3$ is $—CONR^9R^{10}$.

In some embodiments of this aspect of the invention, $R^1$ is hydrogen; $R^2$ is $—OH$, $—NH_2$, $—NHCH_3$, $—N(CH_3)_2$, $—CH_3$, $—F$, $—CN$, $—CF_3$, $—OCH_3$, thiomorpholinyl sulfone, or piperazinyl; and $R^3$ is

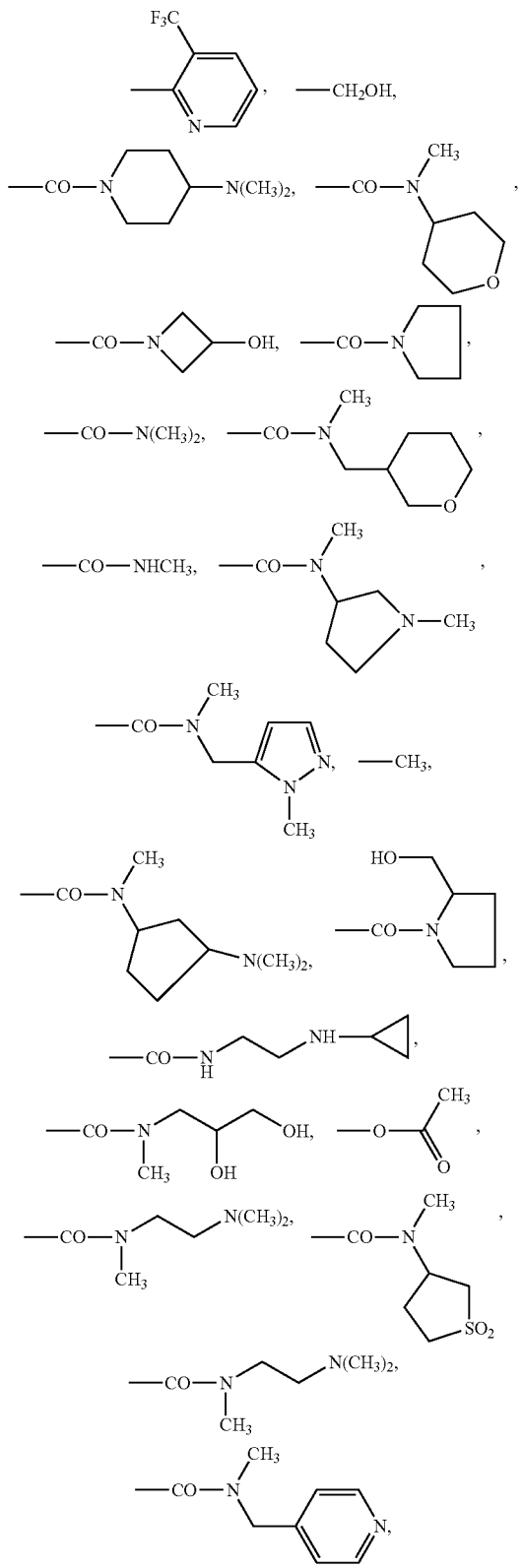

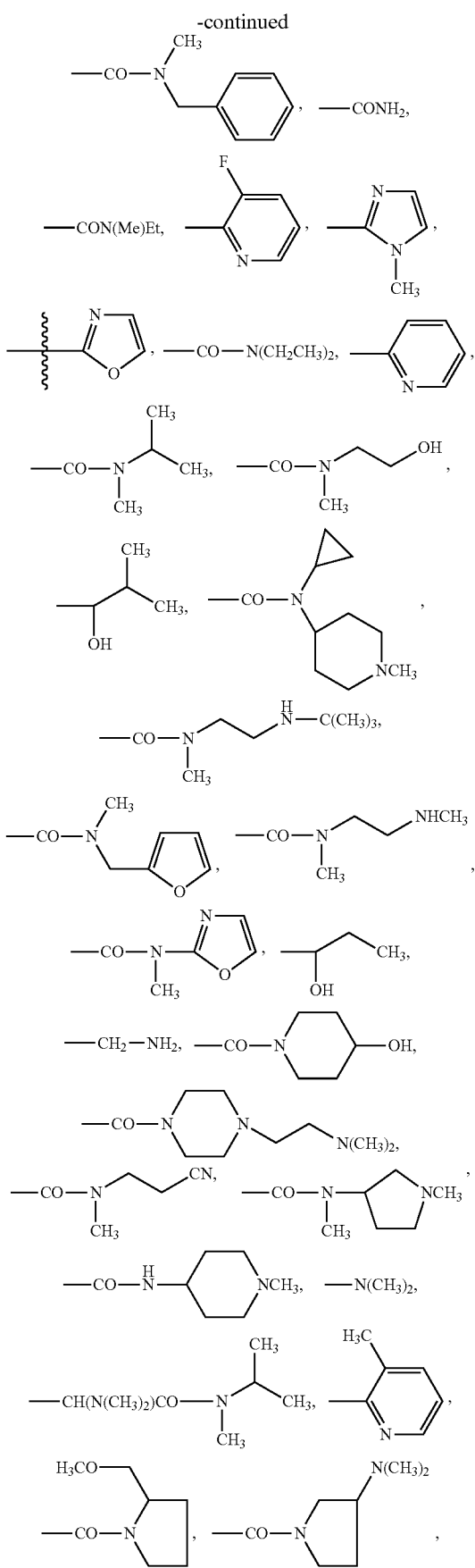
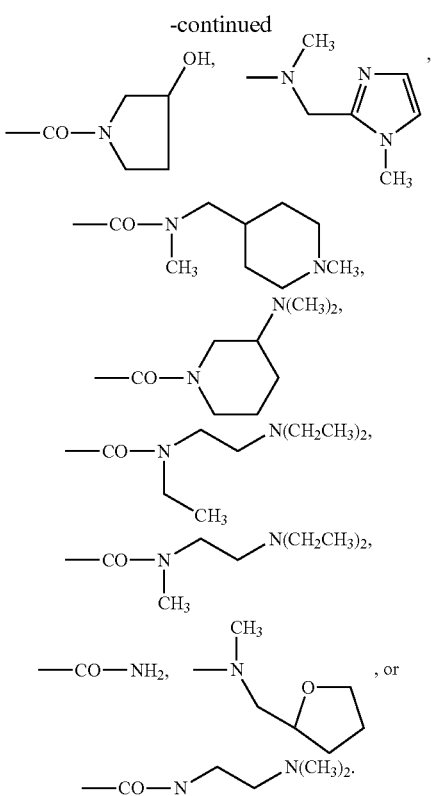

In some embodiments of this aspect of the invention, $R^1$ is hydrogen; $R^2$ is hydroxy; and $R^3$ is —CONR$^9$R$^{10}$.

In one aspect, the invention relates to compounds having Formula (B), or an enantiomer, diastereomer, racemate, tautomer or pharmaceutically acceptable salt, solvate, hydrate, polymorph or prodrug thereof:

Formula (B)

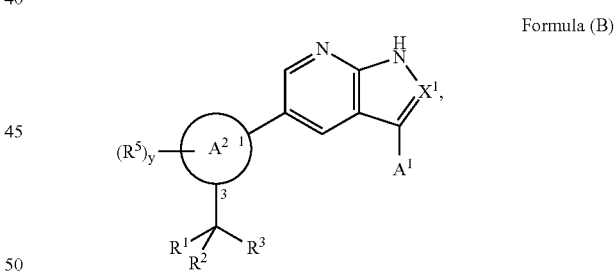

wherein
A$^1$ is substituted or unsubstituted aryl, substituted or unsubstituted heteroaryl, substituted or unsubstituted cycloalkyl, or substituted or unsubstituted heterocycloalkyl;
A$^2$ is an aryl or heteroaryl group;
X$^1$ is CR$^4$ or N; wherein
  R$^4$ is hydrogen, halogen, cyano, nitro, haloalkyl, or substituted or unsubstituted alkyl;
R$^1$ is hydrogen, lower alkyl or lower heteroalkyl;
R$^2$ is lower alkyl, halogen, hydroxy, —OR$^8$, cyano, nitro, haloalkyl, —NR$^6$R$^7$;
R$^3$ is substituted or unsubstituted alkyl, substituted or unsubstituted heteroalkyl, substituted or unsubstituted haloalkyl, substituted or unsubstituted heterocycloalkyl, substituted or unsubstituted aryl, substituted or unsubstituted (cycloalkyl)alkyl, substituted or unsubstituted (heterocycloalkyl)alkyl, substituted or unsubstituted arylalkyl, substituted or unsubstituted heteroaryl, substituted or unsubstituted heteroarylalkyl, —COOH, —$NR^9R^{10}$, —$CH_2NR^9R^{10}$, —$CONR^9R^{10}$, —$CH_2CONR^9R^{10}$ or —$OR^8$; or $R^2$ and $R^3$ together with the carbon atom to which they are attached, form a substituted or unsubstituted heterocycloalkyl, or a substituted or unsubstituted cycloalkyl; or each $R^5$ is independently halogen, cyano, nitro, substituted or unsubstituted haloalkyl, substituted or unsubstituted alkyl, —$NR^{11}R^{12}$, —$CONR^{11}R^{12}$, —$OR^{13}$, —$C(=Z)R^{14}$, or —$S(O)_nR^{15}$, wherein n is independently an integer from 0 to 2;

y is 0, 1, 2, 3 or 4;

Z is independently O, S or $N(R^{16})$;

$R^6$ and $R^7$, $R^9$ and $R^{10}$, and $R^{11}$ and $R^{12}$ are each independently hydrogen, substituted or unsubstituted alkyl, substituted or unsubstituted haloalkyl, substituted or unsubstituted alkyl-$NR^{17}R^{18}$, substituted or unsubstituted alkyl-$CONR^{17}R^{18}$, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted (cycloalkyl)alkyl, substituted or unsubstituted (heterocycloalkyl)alkyl, substituted or unsubstituted arylalkyl or substituted or unsubstituted heteroarylalkyl, or one or more of $R^6$ and $R^7$, $R^9$ and $R^{10}$, and $R^{11}$ and $R^{12}$ are each independently joined together with the nitrogen to which they are attached, to form substituted or unsubstituted 3- to 7-membered heterocycloalkyl, or substituted or unsubstituted heteroaryl;

$R^8$ and $R^{13}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a pair of $R^{13}$, taken together with the oxygens to which they are attached, form a heterocycle;

$R^{14}$ is independently —$OR^{13}$, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is independently substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein if n is 2, then $R^{15}$ is optionally —$NR^{19}R^{20}$ or —$OR^{13}$;

$R^{16}$ is independently hydrogen, substituted or unsubstituted alkyl, substituted or unsubstituted haloalkyl, or substituted or unsubstituted heteroalkyl;

$R^{17}$ and $R^{18}$, and $R^{19}$ and $R^{20}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted (cycloalkyl)alkyl, substituted or unsubstituted (heterocycloalkyl)alkyl, substituted or unsubstituted arylalkyl, or substituted or unsubstituted heteroarylalkyl; or one or more of $R^{17}$ and $R^{18}$ or $R^{19}$ and $R^{20}$ are each independently joined together with the nitrogen to which they are attached, to form substituted or unsubstituted heterocycloalkyl, or substituted or unsubstituted heteroaryl; and wherein any of the groups listed for $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ are each optionally independently substituted with 1 to 3 groups, each group independently selected from halogen, hydroxyl, amino, aminomonoalkyl, aminomonohaloalkyl, aminodihaloalkyl, aminodialkyl, cyano, nitro, haloalkyl, alkyl, —O-alkyl, O-haloalkyl, S-haloalkyl and —S-alkyl.

In some embodiments of this aspect of the invention, $A^1$ is 2-methoxyphenyl; $X^1$ is $CR^4$; and $A^2$ is phenyl.

In some embodiments of this aspect of the invention, $A^1$ is 2-methoxyphenyl; $X^1$ is $CR^4$; and $A^2$ is pyridinyl.

In some embodiments of this aspect of the invention, $A^1$ is 2-methoxyphenyl; $X^1$ is N; and $A^2$ is phenyl.

In some embodiments of this aspect of the invention, $A^1$ is 2-methoxyphenyl; $X^1$ is N; and $A^2$ is pyridinyl.

In some embodiments of this aspect of the invention, $R^1$ is hydrogen; $R^2$ is —OH, —$NH_2$, —$NHCH_3$, —$N(CH_3)_2$, —$CH_3$, —F, —CN, —$CF_3$, —$OCH_3$, thiomorpholinyl sulfone, or piperazinyl; and $R^3$ is substituted or unsubstituted alkyl, substituted or unsubstituted heteroalkyl, substituted or unsubstituted haloalkyl, substituted or unsubstituted heterocycloalkyl, substituted or unsubstituted aryl, substituted or unsubstituted heteroaryl, —COOH, —$NR^9R^{10}$, —$CH_2NR^9R^{10}$, —$CONR^9R^{10}$, —$CH_2CONR^9R^{10}$ or —$OR^8$.

In some embodiments of this aspect of the invention, $R^3$ is

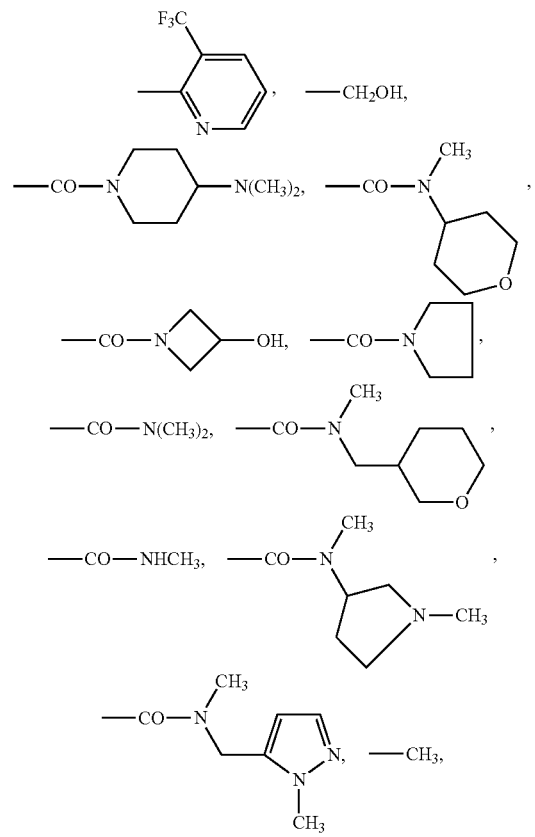

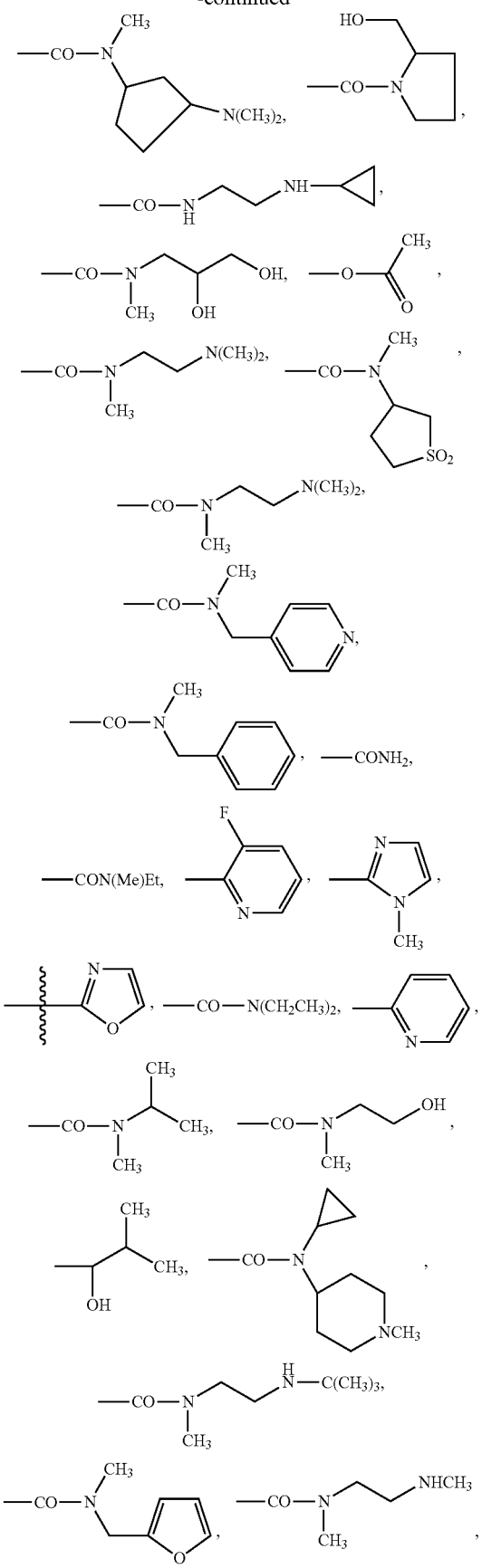
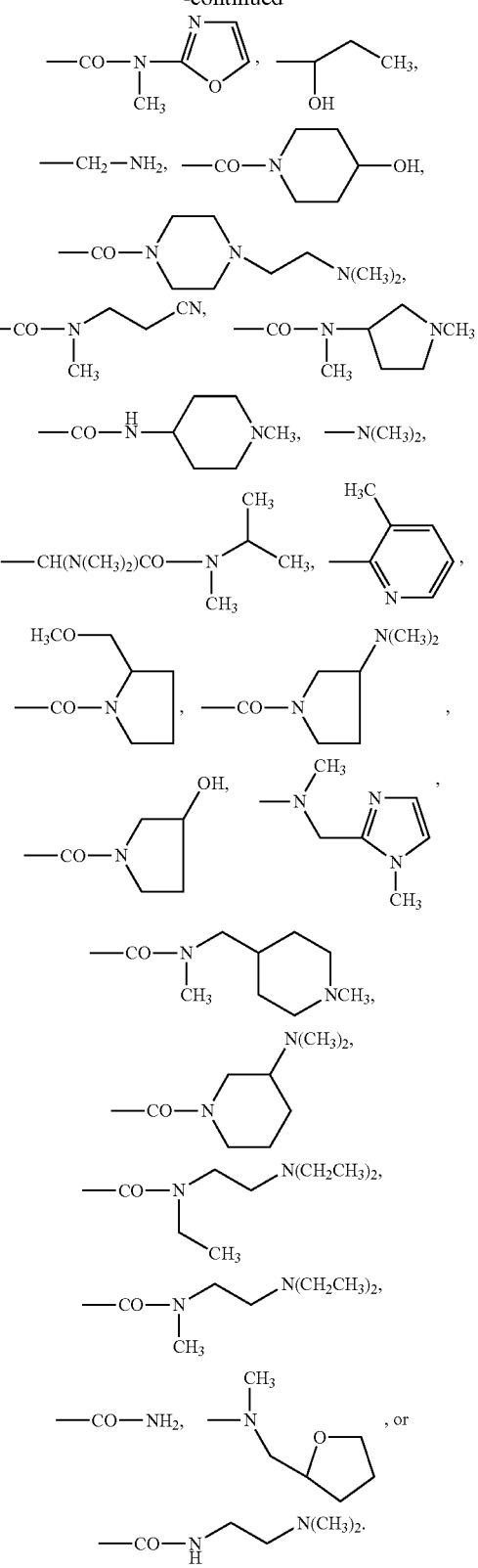
In one aspect, the invention relates to compounds having Formula (C), or an enantiomer, diastereomer, racemate, tautomer or pharmaceutically acceptable salt, solvate, hydrate, polymorph or prodrug thereof:

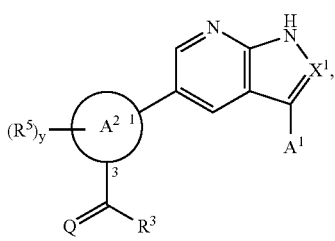

Formula (C)

wherein
- $A^1$ is substituted or unsubstituted aryl, substituted or unsubstituted heteroaryl, substituted or unsubstituted cycloalkyl, or substituted or unsubstituted heterocycloalkyl;
- $A^2$ is an aryl or heteroaryl group;
- $X^1$ is $CR^4$ or N; wherein $R^4$ is hydrogen, halogen, cyano, nitro, haloalkyl, or substituted or unsubstituted alkyl;
- Q is O;
- $R^3$ is substituted or unsubstituted C-attached heteroalkyl, substituted or unsubstituted C-attached heterocycloalkyl, substituted or unsubstituted aryl, substituted or unsubstituted C-attached heteroaryl, —$COOR^8$, —$CH_2NR^9R^{10}$, —$CONR^9R^{10}$, —$CH_2CONR^9R^{10}$;
- each $R^5$ is independently halogen, cyano, nitro, substituted or unsubstituted haloalkyl, substituted or unsubstituted alkyl, —$NR^{11}R^{12}$, —$CONR^{11}R^{12}$, —$OR^{13}$, —$C(=Z)R^{14}$, or —$S(O)_nR^{15}$, wherein n is independently an integer from 0 to 2;
- y is 0, 1, 2, 3 or 4;
- Z is independently O, S or $N(R^{16})$;
- $R^9$ and $R^{10}$, and $R^{11}$ and $R^{12}$ are each independently hydrogen, substituted or unsubstituted alkyl, substituted or unsubstituted haloalkyl, substituted or unsubstituted alkyl-$NR^{17}R^{18}$, substituted or unsubstituted alkyl-$CONR^{17}R^{18}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or one or more of $R^9$ and $R^{10}$, and $R^{11}$ and $R^{12}$ are each independently joined together with the nitrogen to which they are attached, to form substituted or unsubstituted 3- to 7-membered heterocycloalkyl, or substituted or unsubstituted heteroaryl;
- $R^8$ and $R^{13}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a pair of $R^{13}$, taken together with the oxygens to which they are attached, form a heterocycle;
- $R^{14}$ is independently —$OR^{13}$, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or unsubstituted heteroaryl;
- $R^{15}$ is independently substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein if n is 2, then $R^{15}$ is optionally —$NR^{19}R^{20}$ or —$OR^{13}$;
- $R^{16}$ is independently hydrogen, substituted or unsubstituted alkyl, substituted or unsubstituted haloalkyl, or substituted or unsubstituted heteroalkyl;
- $R^{17}$ and $R^{18}$, and $R^{19}$ and $R^{20}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or one or more of $R^{17}$ and $R^{18}$ or $R^{19}$ and $R^{20}$ are each independently joined together with the nitrogen to which they are attached, to form substituted or unsubstituted heterocycloalkyl, or substituted or unsubstituted heteroaryl; and
- wherein any of the groups listed for $R^3$, $R^4$, $R^5$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ are each optionally independently substituted with 1 to 3 groups, each group independently selected from halogen, hydroxyl, amino, aminomonoalkyl, aminomonohaloalkyl, aminodihaloalkyl, aminodialkyl, cyano, nitro, haloalkyl, alkyl, —O-alkyl, O-haloalkyl, S-haloalkyl and —S-alkyl.

In some embodiments of this aspect of the invention, $A^1$ is 2-methoxyphenyl; $X^1$ is $CR^4$; and $A^2$ is phenyl.

In some embodiments of this aspect of the invention, $A^1$ is 2-methoxyphenyl; $X^1$ is $CR^4$; and $A^2$ is pyridinyl.

In some embodiments of this aspect of the invention, $A^1$ is 2-methoxyphenyl; $X^1$ is N; and $A^2$ is phenyl.

In some embodiments of this aspect of the invention, $A^1$ is 2-methoxyphenyl; $X^1$ is N; and $A^2$ is pyridinyl.

In some embodiments of this aspect of the invention, $R^3$ is —$CH_2NR^9R^{10}$, —$CONR^9R^{10}$, —$CH_2CONR^9R^{10}$.

In some embodiments of this aspect of the invention, $R^3$ is

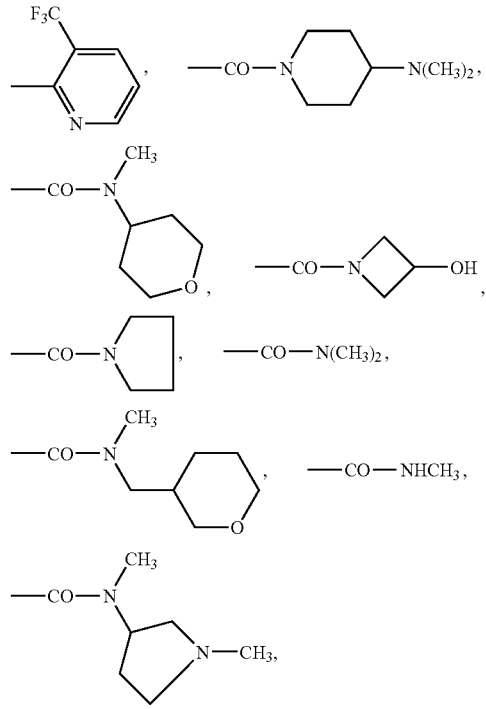

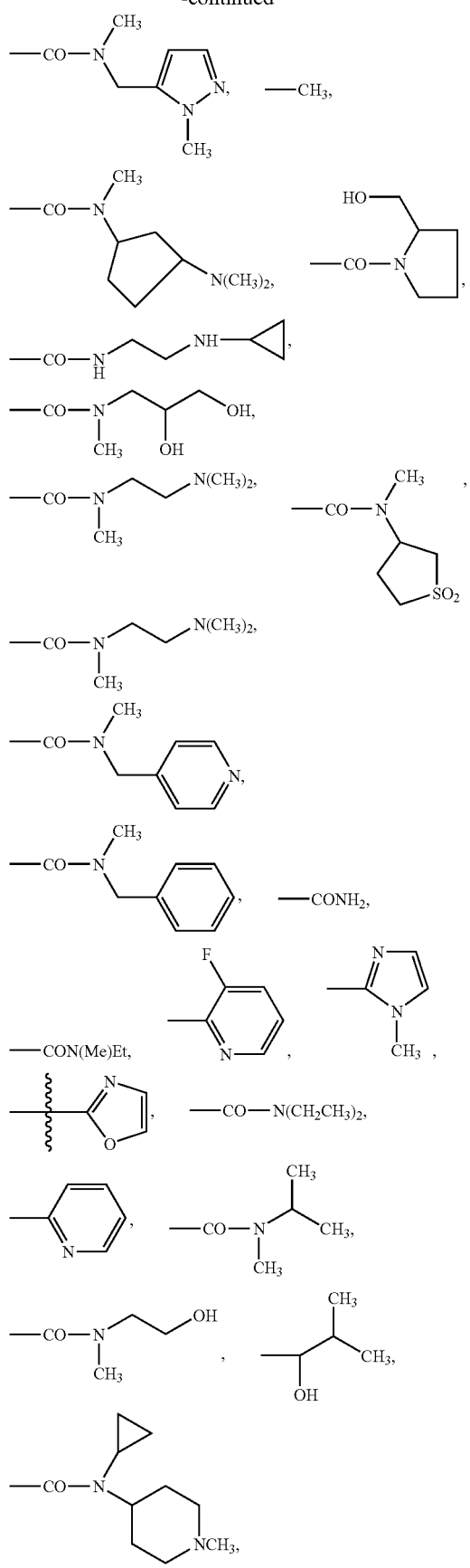
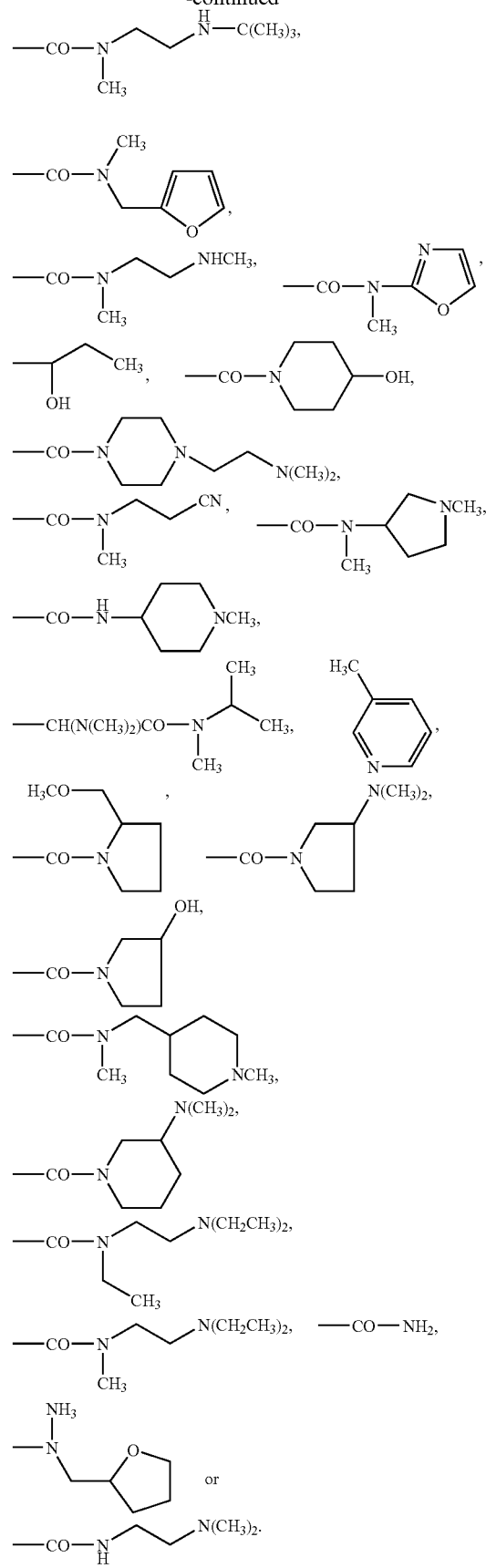

In one embodiment of this aspect of the invention, the cancer is leukemia or myeloproliferative disorder.

In another aspect, the invention relates to methods for modulating the activity of a protein kinase comprising contacting the protein kinase with a compound of a formula described herein.

In another aspect, the invention relates to methods for modulating the activity of a protein kinase comprising contacting the protein kinase with a compound of a formula described herein, wherein the protein kinase is Abelson tyrosine kinase, Ron receptor tyrosine kinase, Met receptor tyrosine kinase, Fms-like tyrosine kinase-3, Aurora kinases, p21-activated kinase-4 or 3-phosphoinositide-dependent kinase-1.

In another aspect, the invention relates to methods for modulating the activity of a protein kinase comprising contacting the protein kinase with a compound of a formula described herein, wherein the protein kinase is a Bcr-Abl kinase having a mutation selected from the group consisting of M244V, L248V, G250E, G250A, Q252H, Q252R, Y253F, Y253H, E255K, E255V, D276G, F311L, T315I, T315N, T315A, F317V, F317L, M343T, M351T, E355G, F359A, F359V, V379I, F382L, L387M, H396P, H396R, S417Y, E459K and F486S.

In another aspect, the invention relates to methods for modulating the activity of a protein kinase comprising contacting the protein kinase with a compound of a formula described herein, wherein the protein kinase has a T315I mutation.

In another aspect, the invention relates to methods for treating cancer, allergy, asthma, inflammation, obstructive airway disease, autoimmune diseases, metabolic disease, infection, CNS disease, brain tumor, obesity, asthma, hematological disorder, degenerative neural disease, cardiovascular disease, or disease associated with angiogenesis, neovascularization, or vasculogenesis in a subject in need of such treatment, the method comprising administering to the subject a therapeutically effective amount of a compound described herein.

In another aspect, the invention relates to methods for treating cancer in a subject in need of such treatment, the method comprising administering to the subject a therapeutically effective amount of a compound of a formula described herein, wherein the cancer is leukemia or myeloproliferative disorder.

In another aspect, the invention relates to methods for treating cancer, in a subject in need of such treatment, the method comprising administering to the subject a therapeutically effective amount of a compound of a formula described herein.

In another aspect, the invention relates to methods for treating cancer, in a subject in need of such treatment, the method comprising administering to the subject a therapeutically effective amount of a compound of a formula described herein, wherein the cancer is leukemia or myeloproliferative disorder.

In another aspect, the invention relates pharmaceutical compositions comprising a pharmaceutically acceptable excipient and a compound of a formula described herein.

Exemplary Syntheses

The compounds of the invention are synthesized by an appropriate combination of generally well known synthetic methods. Techniques useful in synthesizing the compounds of the invention are both readily apparent and accessible to those of skill in the relevant art.

The discussion below is offered to illustrate how, in principle, to gain access to the compounds claimed under this invention and to give details on certain of the diverse methods available for use in assembling the compounds of the invention, However, the discussion is not intended to define or limit the scope of reactions or reaction sequences that are useful in preparing the compounds of the present invention. The compounds of this invention may be made by the procedures and techniques disclosed in the Examples section below, as well as by known organic synthesis techniques.

1H-Pyrrolo[2,3-b]pyridine Analogs

The synthesis of certain compounds of the present invention is outlined in Exemplary Scheme 1 below.

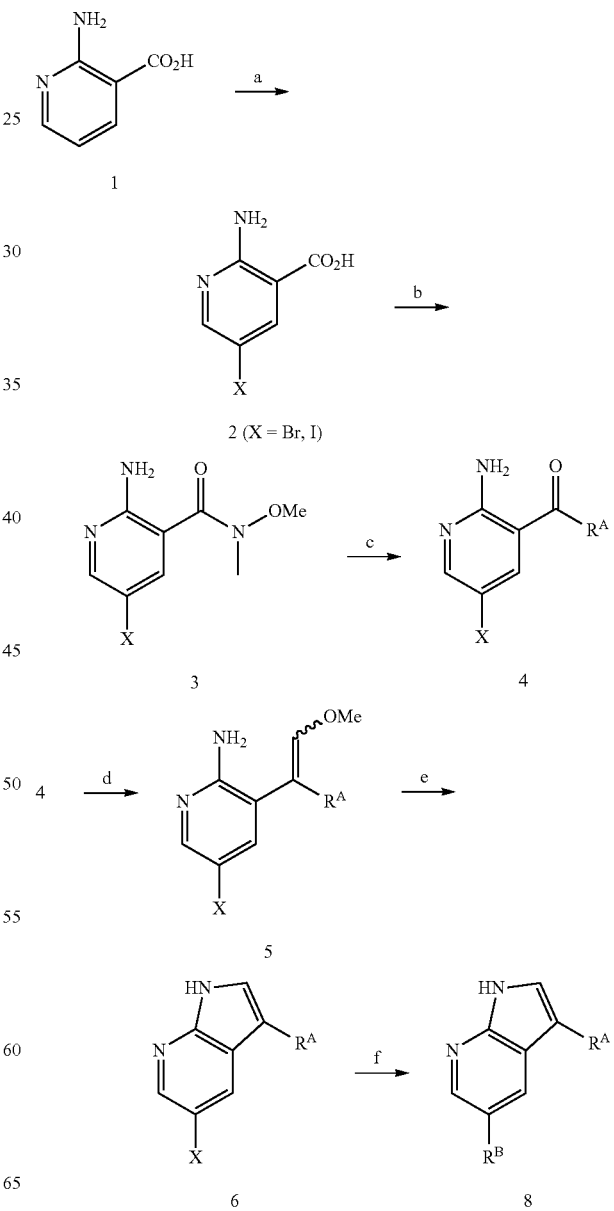

-continued

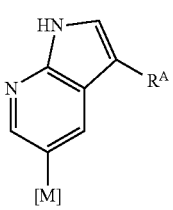

[M] = e.g. BR$_2$, SnR$_3$, MgX, ZnX, Li

Many of these compounds can be synthesized conveniently from commercially available 2-amino-nicotinic acid (1). Starting from compound 1 in Exemplary Scheme 1, bromination at the 5-position provides compound 2 (X=Br). This is easily achieved by various methods well known in the chemical literature, such as, but not limited to reactions using elemental bromine or N-bromosuccinimide (step a).

Synthesis of the intermediate ketone having general formula 4 (X=Br) can be achieved by treating the corresponding Weinreb amide 3 or its hydrochloride salt with a suitable organometallic species, for example, using an organomagnesium or organolithium compound (step c) (for examples of the use of N-methoxy-N-methylamides (Weinreb amides) in ketone synthesis, see S. Nam, S. M. Weinreb—*Tetrahedron Lett.* 1981, 22, 3815.) The Weinreb amide 3 (X=Br) is accessible by condensation of the parent acid 2 (X=Br, X$^2$=CH) with N,O-dimethylhydroxylamine using standard methods for amide-formation, either by prior activation of the acid or in situ or via a direct condensation. Methods and reagents for both transformations are described in the chemical literature and are well known to those skilled in the art (step b), for example, amide formation is achieved by direct methods using suitable coupling reagents such as, but not limited to, PyBOP, HBTU or HATU.

The organometallic reagents required for the introduction of a ketone residue R$^A$ in 4 (X=Br) (step c) in Exemplary Scheme 1 can be obtained either commercially or synthesized by various methods described in the literature, such as, but not limited to the Grignard-reaction of organic chlorides, bromides, or iodides, with magnesium (cf. J. March—*Advanced Organic Chemistry*, 3rd ed., John Wiley & Sons, 1992), metal-halogen exchange reactions of organic bromides or iodides using suitable organolithium or organomagnesium compounds such as, but not limited to, n-butyllithium, tert-butyllithium or iso-propylmagnesium chloride or bromide (e.g. J. Clayden—*Organolithiums: Selectivity for Synthesis*, Pergamon, 2002; A. Boudier, L. O. Bromm, M. Lotz, P. Knochel—*Angew. Chem. Int. Ed.* (2000) 39, 4414.) or deprotonation of sufficiently acidic compounds, such as for example pyrimidines, pyrazines, 2-chloro- or 2-fluoropyridines using a suitable base, such as for example lithium N,N-diisopropylamide or lithium 2,2,6,6-tetramethylpiperidide (cf. J. Clayden—*Organolithiums: Selectivity for Synthesis*, Pergamon, 2002; A. Turck, N. Plé, F. Mongin, G. Quéguiner—*Tetrahedron* (2001) 57, 4489; F. Mongin, G. Quéguiner—*Tetrahedron* (2001) 57, 4059). The aforementioned group R$^A$ can be substituted with one or more functional groups, in which acidic protons such as, for example, the hydrogen atoms attached to nitrogen or oxygen may, as needed, be protected by a suitable protecting group by methods well known in the chemical literature (cf. T. W. Greene, P. G. M. Wuts—*Protective Groups in Organic Synthesis*, 3rd ed., John Wiley & Sons, 1999). Such functional groups will allow for the elaboration of the products obtained in such fashion to various compounds claimed under this invention by generally well known methods.

Olefination of the resulting ketone 4 (X=Br) (step d) in Exemplary Scheme 1 can be achieved by several methods known to those skilled in the art but is most conveniently carried out via a Wittig-reaction (cf. B. E. Maryanoff, A. B. Reitz—*Chem. Rev.* (1989) 89, 863) using an ylide generated from commercially available methoxymethyltriphenylphosphonium chloride and a suitable base, for example, but not limited to, a strong organometallic base such as, but not limited to, a non-nucleophilic amide such as the lithium, sodium or potassium salt of bis(trimethylsilyl)amine. Such olefinations can also be conveniently carried out without purification of the respective ketone 4 (X=Br), using the crude material obtained from the reaction of the Weinreb amide 3 (X=Br) with an organometallic reagent as described above.

Subsequent cyclization of the resulting olefin 5 (X=Br), (step e) in Exemplary Scheme 1 which can be utilized in either the E- or Z-form or a mixture of these both forms, can be achieved under general acid catalysis conditions using strong inorganic or organic acids, such as, but not limited to sulfuric acid, perchloric acid, hydrochloric acid, trifluoromethane-sulfonic acid or trifluoroacetic acid in suitable solvents such as, but not limited to THF, dioxane, diethyl ether, dimethoxyethane, diglyme, dichloromethane, dichloroethane or chloroform, water, methanol, or ethanol, or mixtures thereof. A similar cyclization has been described by Sakamoto et al., *Heterocycles* (1992), 34(12), 2379-84. There the authors describe the conversion of 2-nitro-3-(2-ethoxyvinyl)pyridine to the parent pyrrolo[2,3-b]pyridine. Formation of the vinyl group is achieved via a Stille-coupling of the 3-bromo analog with tributyl-2-ethoxyvinylstannane.

Introduction of aromatic, olefin, alkyne, or an aliphatic substituents at the 5-position of bromide 6 to afford compounds of the general formula 8 (X=Br) (step f) in Exemplary Scheme 1 can be achieved via standard halogen cross-coupling methodologies (cf. F. Diederich, P. J. Stang (eds.)—*Metal-catalyzed Cross-coupling Reactions*, Wiley-VCH, 1998; J. Tsuji—*Palladium Reagents and Catalysts*, John Wiley & Sons, 1995). Couplings of the bromide 6 (X=Br) with suitable reagents such as, but not limited to, boronic acids and boronates, organoboranes, trifluoroborate salts (e.g. G. A. Molander, G.-S. Yun, M. Ribagorda, B. Biolatto—*J. Org. Chem.* (2003) 68, 5534; G. A. Molander, B. Biolatto—*J. Org. Chem.* (2003) 68, 4302), organo-stannanes, organozinc compounds, organomagnesium compounds, olefins or terminal alkynes, either purchased or obtained via protocols well known in the chemical literature, are carried out in the presence of a suitable transition metal catalyst, for example, but not limited to, suitable palladium compounds, either in the presence of ligands such as, but not limited to, phosphines, diphosphines or arsines or without and, as necessary, organic or inorganic bases, such as tertiary or secondary amines, alkaline carbonates, bicarbonates or phosphates and, as needed, other additives that are known in the chemical literature to assist or accelerate such transformations, such as lithium chloride, copper halides or silver salts. These cross coupling reactions are carried out in suitable solvents such as, but not limited to, THF, dioxane, dimethoxyethane, diglyme, dichloromethane, dichloroethane, acetonitrile, DMF, N-methylpyrrolidone, ethanol, or water, or mixtures of these at temperatures ranging from 25° C. to 200° C. using either no heating, conventional heating or microwave irradiation.

This methodology may be extended to the incorporation of non-carbon based nucleophiles such as, but not limited to alcohols, thiols, primary or secondary amines, heterocyclic rings containing hydrogen attached to a nitrogen atom, that may or may not contain groups which are known in the chemical literature to be suitable protecting groups (examples of such groups can be found in T. W. Greene, P. G. M. Wuts—*Protective Groups in Organic Synthesis*, 3rd ed., John Wiley & Sons, 1999) of alcohols, thiols or amines by methods well known in the chemical literature such as, by way of example, those mentioned in S. V. Ley, A. W. Thomas—*Angew. Chem.* (2003) 115, 5558; J. P. Wolfe, S. Wagaw, J.-F. Marcoux, S. L. Buchwald—*Acc. Chem. Res.* (1998) 31, 805 and J. F. Hartwig—*Acc. Chem. Res.* (1998) 31, 852. The compounds obtained by such methods can be further elaborated by methods well known in the chemical literature to other compounds claimed under this invention.

In one embodiment of the invention, a halide 6 (X=Br) in Exemplary Scheme 1 is treated with a boronic acid in the presence of a suitable palladium catalyst, for example, but not limited to tetrakis(triphenylphosphino)palladium(0), dichlorobis(triphenylphosphino)palladium(II) or dichloro[1,1'-bis(diphenylphosphino)ferrocene]palladium(II), and a suitable base (e.g. sodium carbonate, cesium carbonate or cesium fluoride) in aqueous solvent mixtures such as, acetonitrile/water or dimethoxyethane/water at temperatures between 110° C. and 200° C. either using conventional heating or microwave irradiation.

In some cases it may be advantageous to achieve cross-couplings to carbon or non-carbon atoms such as all those mentioned above, by first converting a halide 6 into an organometallic derivative 7 such as a boronic acid or ester, trifluoroborate salt, organomagnesium, organozinc, or organotin compound. Such compounds are accessible by means of substituting the bromide moiety with an appropriate metal or metalloid in which case any functional group present in derivative 6, most notably the ring nitrogen in position 1 of the pyrrolo[2,3-b]pyridine, may be protected by a suitable protecting group (examples of such groups can be found in T. W. Greene, P. G. M. Wuts—*Protective Groups in Organic Synthesis,* 3rd ed., John Wiley & Sons, 1999). Introduction of such metals or metalloids can be achieved in a number of ways, such as via reductive metallation using metals such alkaline or alkaline earth metals or activated forms of such metals such as lithium, magnesium or lithium naphthalide or via a metal-halogen exchange reactions using suitable organolithium or organomagnesium compounds (e.g. n-butyl-lithium, tert-butyllithium or iso-propyl-magnesium chloride or bromide) and, as needed, subsequent transmetalation reactions of the organometallic intermediate with a suitable soluble and reactive metal compound (e.g. magnesium chloride, magnesium bromide, tri-n-butyltin chloride, trimethyltin chloride, trimethyl borate, triethyl borate, tri-iso-propyl borate, zinc triflate or zinc chloride). Introduction of a boronic acid pinacol ester may be conveniently achieved by reacting derivative 6 directly with bis(pinacolato)diboron in the presence of dichloro[1,1'-bis(diphenylphos-phino)-ferrocene]palladium(II) and suitable bases (e.g. potassium or sodium acetate) in solvents such as DMSO, DMF, DMA or N-methylpyrrolidone at temperatures ranging from 80-160° C. either using conventional heating or microwave irradiation (literature precedent for similar transformations can be found in T. Ishiyama, M. Murata, N. Miyaura—*J. Org. Chem.* (1995) 60, 7508). Methods for conversion of the boronic acid pinacol ester obtained by this method into other boronic acid derivatives such as boronic acids, boronates, or trifluoroborate salts are well described in the chemical literature.

Cross-couplings of metallated derivatives 7 in Exemplary Scheme 1 with suitable reagents such as aromatic, heteroaromatic or olefinic chlorides, bromides, iodides, triflates or acyl halides either purchased or obtained via protocols well known in the chemical literature, are carried out in the presence of a suitable transition metal catalyst (e.g. suitable palladium compounds, either in the presence of ligands such as phosphines, diphosphines or arsines or without and, as necessary, organic or inorganic bases, such as tertiary or secondary amines, alkaline carbonates, bicarbonates or phosphates and, as needed, other additives that are known in the chemical literature to assist or accelerate such transformations, such as copper halides or silver salts). These cross coupling reactions are carried out in suitable solvents (e.g. THF, dioxane, dimethoxyethane, diglyme, dichloromethane, dichloroethane, acetonitrile, DMF, N-methylpyrrolidone, or mixtures of these) at temperatures ranging from 25° C. to 200° C. using either no heating, conventional heating or microwave irradiation. The compounds obtained by such methods, particularly those containing suitable functional groups (e.g. carboxylic acids or esters, nitriles, amines, aldehydes or olefins) can be further elaborated by methods well known in the chemical literature to other compounds claimed under this invention.

More reactive organic nucleophiles such as organometallic compounds 7 in Exemplary Scheme 1 containing alkaline, or alkaline earth or certain transition metals (e.g. organolithium, organomagnesium or organozinc compounds) can also be coupled to a range of other electrophilic coupling partners such as activated olefins (Michael acceptors), aldehydes, nitriles, aromatic nitro compounds (see for example I. Sapountzis, P. Knochel—*J. Am. Chem. Soc.* (2002) 124, 9390), carboxylic acid derivatives, carbon dioxide, organic disulfides or organic halides. Such couplings can be achieved using either no catalyst or a suitable transition metal catalyst, such as a suitable copper, cobalt or iron compound in suitable solvents (e.g. ether, THF, dioxane, dimethoxyethane, or diglyme, or mixtures of these) at temperatures ranging from −100° C. to 100° C. either in the presence of other additives that are known in the chemical literature to assist or accelerate such transformations, such as, for example, lithium halides, amines or diamines or their derivatives, or without. As will be apparent to someone with skill in the art, the compounds obtained by such methods, particularly such compounds containing suitable functional groups, such as carboxylic acids or esters, nitriles, amines, aldehydes or olefins, can be further elaborated by methods well known in the chemical literature to other compounds claimed under this invention.

Exemplary Scheme 2

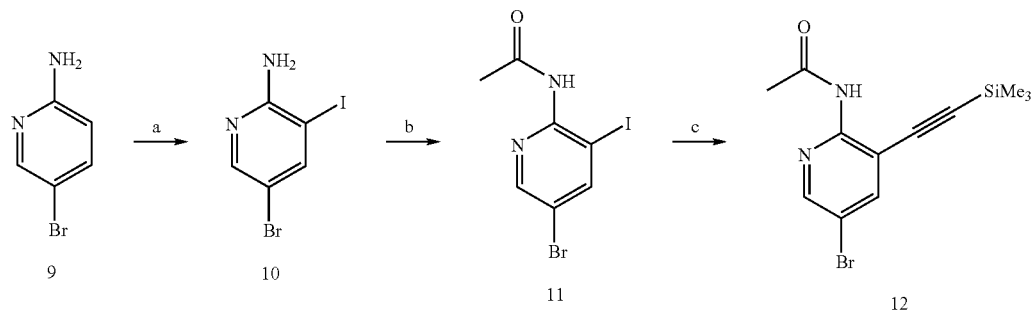

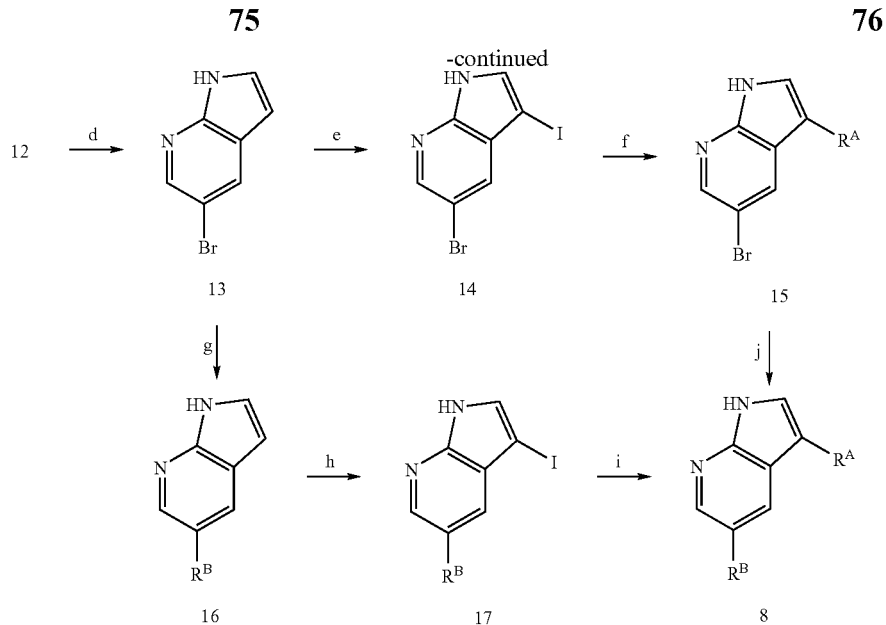

3,5-disubstituted pyrrolo[2,3-b]pyridines can also be accessed via another method outlined in Scheme 2 (see also WO 2004/032874). Iodination of 2-amino-5-bromopyridine (9) in Exemplary Scheme 2 above can be achieved by reacting it with iodine and sodium periodate in a suitable solvent such as DMF, DMA or N-methylpyrrolidone at elevated temperatures of 100-200° C. to afford the iodo intermediate 10. Intermediate 10 in Exemplary Scheme 2 can be acylated under standard conditions, such as reacting it with acetyl chloride in a suitable solvent such as pyridine at 25-100° C. to provide the N-acetylated intermediate 11. Coupling of bromide 11 with ethynyltrimethylsilane to afford alkyne 12 can be achieved via standard halogen cross-coupling methodologies (cf. F. Diederich, P. J. Stang (eds.), *Metal-catalyzed Cross-coupling Reactions*, Wiley-VCH, 1998; J. Tsuji, *Palladium Reagents and Catalysts*, John Wiley & Sons, 1995) such as using suitable palladium compounds, such as dichlorobis(triphenylphosphino)palladium(II) or dichloro[1,1'-bis(diphenylphosphino)-ferrocene]palladium(II) as a catalyst in the presence of copper(I)-salts, such as cuprous iodide in the presence of organic bases, such as triethyl amine, in suitable solvents, such as dichloromethane at temperatures of 25° C. or above. Cyclization of the resulting alkynylpyridine 12 can be conveniently achieved by exposure to soluble fluorides, such as tetrabutylammonium fluoride, in suitable solvents such as THF or dioxane at temperatures of 25-110° C. to afford the 5-bromo-pyrrolo[2,3-b]pyridine (13).

Elaboration of halides 13, 14, 15 and 17 (steps g, f, j and i) in Exemplary Scheme 2 can be readily accomplished by generally well known methods. For example, metal catalyzed cross coupling reactions may be employed using various known transition metal compounds (e.g. compounds derived from palladium, iron or nickel). Examples of such transformations can be found in the following references: Diederich, F., Stang, P. J.—*Metal-catalyzed Cross-coupling Reactions*, Wiley-VCH, 1998; Beller, M., *Transition Metals for Organic Synthesis*, Wiley-VCH, 1998; Tsuji, J., *Palladium Reagents and Catalysts*, Wiley-VCH, $1^{st}$. & $2^{nd}$ ed.s, 1995, 2004; Fuerstner, A., et al., *J. Am. Chem. Soc.* (2002) 124, 13856; and Bolm, C., et al., *Chem. Rev.* (2004) 104, 6217. Other useful methods involve the conversion of a bromine or iodine substituent into a metal or metalloid substituent (e.g. organoboron, organolithium, organotin, organosilicon, organozinc, organocopper or organomagnesium compound) using generally well known methods (e.g. metal halogen exchange and, as appropriate or required, subsequent transmetallation using soluble and reactive compounds of boron, magnesium, zinc, tin, silicon or copper; for representative examples of such methodology see: Schlosser, M., *Organometallics in Synthesis*, 2nd. ed., Wiley-VCH, 2002). Organometallic derivatives obtained in such fashion may itself be of use in transition metal catalyzed coupling reactions with aromatic or olefinic halides or triflates, or, if sufficiently reactive, be reacted directly with suitable electrophiles, such as, for example, certain organic halides, Michael-acceptors, oxiranes, aziridines, aldehydes, acyl halides, or nitrites.

Selective functionalization at either the 3- or 5-position of the pyrrolo[3,4-b]pyridine ring, may require different strategies depending on the nature of the trans-formations utilized to introduce functionalities at either position, especially the sequence of functionalization at either position. Thus, it may be advantageous or necessary to achieve functionalization at the 3-position prior to functionalization of the 5-position in some cases while the opposite approach may be required in other cases, depending on the nature of the specific groups to be introduced, the methods required to accomplish such transformations, or the inherent selectivity of the methods utilized. For example, some reactants, such as for example some boronic acids or their esters that are electron deficient (i.e. contain one or more electron withdrawing substituents or that represent derivatives of certain heterocyclic systems) and/or contain one or more substituents ortho to the boron-carbon bond may require the use of highly active palladium catalysts (such as, for example, those mentioned in Vilar, R., Christman, U. *Angew. Chem.* (2005) 117, 370; Littke, A. F., Fu, G.—*Angew. Chem.* (2002) 114, 4350.) and more forcing conditions, such as for example higher temperatures and/or longer reaction times. Such conditions may not be conducive to achieving appreciable selectivities in reactions of 5-bromo-3-iodo-1H-pyrrolo[3,4-b]pyridine. Hence, in such cases, it will be advantageous to avoid selectivity issues altogether by sequential substitution of bromine in 5-bromo-1H-pyrrolo[3,4-b]pyridine, iodination at the 3-position and subsequent introduction of the second substituent at position 3 utilizing the methods detailed above. Generally speaking, whenever substitution of the halogen atom at either position may require conditions that involve highly reactive catalysts or reagents under conditions that generally do not favor high levels of selectivity between the two halogen atoms present in 5-bromo-3-iodo-1H-pyrrolo[3,4-b]pyridine it will be advantageous to resort to this sequential approach.

It will also be appreciated that protection of reactive groups within $R^A$ and/or $R^B$ as well as the pyrrolo[3,4-b]pyridine scaffold, (e.g. the proton at position 1), with a suitable protecting group may be advantageous or required. For example it was found to be advantageous in some cross-coupling reactions to protect the nitrogen at position 1 of the 1H-pyrrolo [3,4-b]pyridine scaffold by introduction of, for example, a 4-toluoylsulfonyl, tri-iso-propylsilyl or tetrahydro-1H-pyranyl group at that position. Introduction and removal of these protecting groups could be conveniently accomplished by methods well known in the chemical literature. As will be apparent to someone with skill in the art, the compounds obtained by any of the aforementioned methods may contain functional groups, either free or protected, that can be further elaborated by generally well known methods.

suitable transition metal catalyst (e.g. palladium compounds). The coupling may optionally be performed in the presence of ligands such as, but not limited to, phosphines, diphosphines, Arduengo-type heterocyclic carbenes (cf. A. J. Arduengo III et al.—*Organometallics* (1998) 17, 3375; A. J. Arduengo III et al.—*J. Am. Chem. Soc*. (1994) 116, 4391) or arsines. Organic or inorganic bases (e.g. tertiary or secondary amines, alkaline carbonates, bicarbonates, fluorides or phosphates) and/or other well known additives (e.g. lithium chloride, copper halides or silver salts) may be utilized to effect, assist or accelerate such transformations.

These cross coupling reactions may be carried out in suitable solvents such as THF, dioxane, dimethoxyethane, diglyme, dichloromethane, dichloroethane, acetonitrile, DMF, N-methylpyrrolidone, water, or mixtures of thereof at temperatures ranging from 25° C. to 200° C. using. The temperature may optionally be maintained with heating, conventional heating or microwave irradiation. In the case of the 3-iodo-5-bromo-1H-pyrrolo[3,4-b]pyridine, the selective or preferential substitution of the iodo substituent over the bromo substituent is possible under generally less forcing conditions, such as lower temperature and shorter reaction times Exemplary Scheme 3

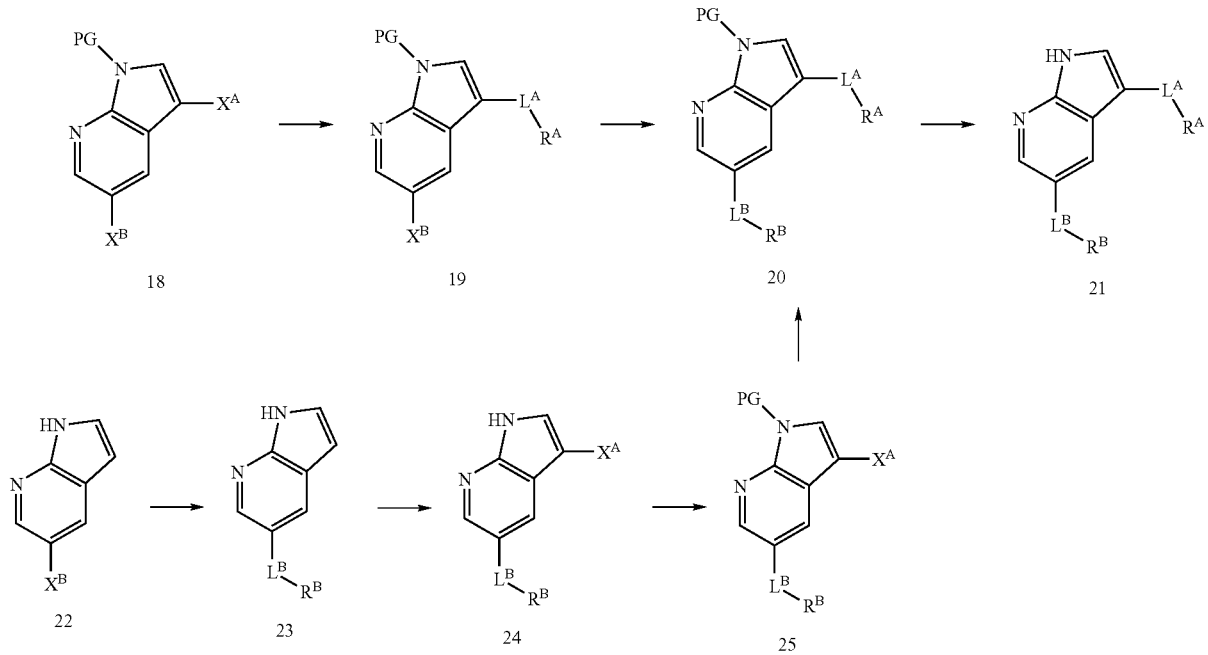

A more detailed description of the utilization of cross-coupling procedures in the synthesis of the compounds claimed under this invention is illustrated in Scheme 3 above: $X^1$ and $X^2$ are selected from, but not limited to, halogen, boronic acid or ester, trifluoroborate salt, organomagnesium, organozinc, or organotin. With respect to the introduction of individual residues $L^1R^1$ or $L^2R^2$ such transformations, as outlined above, can be achieved via standard halogen cross-coupling methodologies.

Couplings of the corresponding bromide or iodide ($X^A$, $X^B$=Br, I) with suitable reagents such as boronic acids and boronates, organoboranes, organostannanes, organozinc compounds, organomagnesium compounds, olefins or terminal alkynes (either purchased or obtained via generally well known protocols) can be carried out in the presence of a using a suitable transition metal catalyst. Selective functionalizations of di- or oligohalogen compounds by means of transition metal catalyzed transformations are well precedented in the chemical literature: see for example Ji, J., et al.—*Org. Lett* (2003) 5, 4611; Bach, T. et al.—*J. Org. Chem* (2002) 67, 5789, Adamczyk, M. et al.—*Tetrahedron* (2003) 59, 8129.

This methodology may be extended to the incorporation of non-carbon based nucleophiles (e.g. alcohols, thiols, primary or secondary amines) that may optionally contain suitable protecting groups of alcohols, thiols or amines. Examples of such groups can be found in Greene, T., et al., *Protective Groups in Organic Synthesis,* 3rd ed., John Wiley & Sons, 1999. Exemplary methods of such utilization of non-carbon nucleophiles in related cross-coupling reactions may be found in Ley, S., et al., *Angew. Chem.* (2003) 115, 5558; Wolfe, J., et al., *Acc. Chem. Res.* (1998) 31, 805; Hartwig, *Acc. Chem. Res.* (1998) 31, 852; Navarro, O., et al., *J. Org. Chem.* (2004) 69, 3173, Ji, J., et al., *Org. Lett* (2003) 5, 4611. The skilled artisan will recognize that the compounds obtained by such methods can be further elaborated by generally well known methods to obtain other compounds of the present invention.

In some cases it may be advantageous to achieve cross-couplings to carbon or non-carbon atoms by first converting the respective halogen derivative into the corresponding organometallic derivative (e.g., a boronic acid or ester, trifluoroborate salt, organomagnesium, organozinc or organotin compound). Such compounds are accessible by means of substituting the halide moiety with an appropriate metal or metalloid. Any functional groups present (e.g. the ring nitrogen in position 1 of the pyrrolo[3,4-b]pyridine), may need to be protected by a suitable protecting group ("PG", c.f. Greene, T., et al., *Protective Groups in Organic Synthesis*, 3rd ed., John Wiley & Sons, 1999).

Introduction of such metals or metalloids can be achieved by generally well-known methods, such as metallation using metals or a metal-halogen exchange reaction. Useful metals for metallation include alkaline or alkaline earth metals or activated forms of such metals. Suitable reagents for use in metal-halogen exchange reactions include organolithium or organomagnesium compounds (e.g. n-butyllithium, tert-butyllithium or iso-propylmagnesium chloride or bromide). Subsequent transmetalation reactions of the organometallic intermediate may be performed as needed with a suitable soluble and reactive metal compound such as magnesium chloride, magnesium bromide, tri-n-butyltin chloride, trimethyltin chloride, trimethyl borate, triethyl borate, tri-isopropyl borate, zinc triflate or zinc chloride. Introduction of a boronic acid pinacol ester can be conveniently achieved by reacting the halogen derivative directly with bis(pinacolato) diboron in the presence of dichloro[1,1'-bis(diphenylphosphino)ferrocene]palladium(II) and suitable bases (e.g. potassium or sodium acetate) in solvents such as DMSO, DMF, DMA or N-methylpyrrolidone at temperatures ranging from 80-160° C. Conventional heating or microwave irradiation may be employed to maintain the appropriate temperature (for literature precedent of similar transformations, see Ishiyama, T. et al.—*J. Org. Chem.* (1995) 60, 7508).

Methods for conversion of the boronic acid pinacol ester obtained by this method into other boronic acid derivatives such as boronic acids, boronates, or trifluoroborate salts are generally well known. As will be apparent to the skilled artisan, such organometallic derivatives may be utilized in cross-coupling reactions similar to those described above in the case of halogen containing derivatives of pyrrolo[3,4-b] pyridine. Such couplings can be effected utilizing suitable coupling partners, such as aromatic, heteroaromatic halides or olefinic reagents under conditions identical or evidently similar and/or related to the methods described above.

Other methods may utilize the reactivity of organometallic derivatives generated from halogen containing derivatives of pyrrolo[3,4-b]pyridine by any of the methods described above. For example, derivatives containing alkaline or alkaline earth metals (e.g. organolithium, organomagnesium or organozinc compounds) may be employed in direct couplings to a range of other electrophilic coupling partners such as, for example, activated olefins (Michael-acceptors), aldehydes, nitriles, aromatic nitro compounds, carboxylic acid derivatives, oxiranes, aziridines, organic disulfides or organic halides. Such transformations are generally well known in the art (for reactions with aromatic nitro compounds, see for example Sapountzis, I., et al., *J. Am. Chem. Soc.* (2002) 124, 9390).

1H-Pyrazolo[3,4-b]pyridine

One intermediate for the synthesis of 3,5-disubstituted 1H-pyrazolo[3,4-b]pyridine derivatives are 5-bromo-1H-pyrazolo[3,4-b]pyridine and 5-bromo-3-iodo-1H-pyrazolo [3,4-b]pyridine. The iodine and/or bromine substituents on $sp^2$-hybridized, aromatic carbon atoms present in these building blocks offer numerous synthetic possibilities for functionalization of either position. A great variety of such synthetic methods exists and these procedures are generally well known and familiar to someone with skill in the art and include, by means of example and not limitation: transition metal catalyzed processes, most notably processes utilizing palladium, iron, nickel or copper catalysts, as well as metal-halogen exchange reactions, most notably such procedures introducing lithium or magnesium, and subsequent reaction of the transient or isolated organometallic derivative with an electrophile of suitable reactivity either directly or via transmetallation to fine tune the reactivity of the organometallic species.

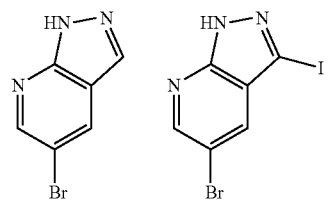

Using such methods, introduction of different substituents on the 3- and 5-position of the 1H-pyrazolo[3,4-b]pyridine core can be accomplished by introducing a chosen substituent at the 5-position starting from 5-bromo-1H-pyrazolo[3,4-b] pyridine and subsequent halogenation, especially iodination, at position 3 of the 1H-pyrazolo[3,4-b]pyridine core to enable the use of the aforementioned methods to introduce another substituent of choice at that position. Alternatively, some of the methods outlined above may be utilized to selectively functionalize 5-bromo-3-iodo-1H-pyrazolo[3,4-b]pyridine at the 3-position by selectively reacting with the iodo substituent over the bromo substituent. It is generally well known and familiar to someone with skill in the art, that a variety of palladium catalysts are known and readily available or accessible which will exhibit higher reaction rates with aromatic iodo substituents as compared to aromatic bromo substituents and such catalysts may be utilized under suitable conditions to effect selective iodine substitution.

5-bromo-1H-pyrazolo[3,4-b]pyridine or a derivative containing an appropriate protecting group may also be functionalized at the 3-position via various electrophilic aromatic substitution reactions that are generally well known and familiar to someone with skill in the art, such as Friedel-Crafts acylation.

The substituents introduced on either position in such fashion may either represent fully elaborated compounds, such as those claimed under this invention, or they may contain functional groups, such as, for example and without limitation, amines, carboxylic acids or esters, nitriles, olefins or halogens, either free or bearing suitable protecting groups, which in turn may be utilized as starting material in generally well known synthetic transformations to synthesize compounds that are claimed under this invention.

Suitably functionalized pyrazolo[3,4-b]pyridine derivatives, particularly 5-bromo-1H-pyrazolo[3,4-b]pyridine and 5-bromo-3-iodo-1H-pyrazolo[3,4-b]pyridine, useful in synthesizing compounds of the present invention can be prepared as outlined in Scheme 4 from commercially available 5-bromo-2-fluoropyridine. 5-Bromo-2-fluoropyridine can be selectively functionalized at the 3-position by the generally well known selective metallation of 2-fluoropyridines in a manner resembling general methods described in Schlosser, M., *Organometallics in Synthesis,* 2nd. ed., Wiley-VCH, 2002; Clayden, J., *Organolithiums: Selectivity for Synthesis,* Pergamon, 2002; and Mongin et al., *Tetrahedron* (2001) 57, 4059-4090. Thus, metallation may be accomplished by treatment with a suitable, non-nucleophilic strong base (e.g. lithium di-iso-propylamide or lithium 2,2,6,6-tertramethylpiperidide) in an aprotic solvent (e.g. THF, hexanes, ether or mixtures thereof) at low temperature, typically –78° C. or below.

The unpurified metallated intermediate can be converted to the corresponding 3-carbaldehyde 2 by treatment with a formylating reagent such as DMF, N-formyl-N-methylaniline, N-formylmorpholine, N-formylpiperidine or ethyl formate. Reaction of the carbaldehyde with hydrazine or a suitable hydrazine derivative (e.g. hydrazine-tert-butylcarbazate, or a soluble organic or inorganic salt derived from hydrazine such as hydrazine hydrochloride) either directly or upon protection of the aldehyde using a suitable protecting group (e.g. acetal) will provide access to 5-bromo-1H-pyrazolo[3,4-b]pyridine. Introduction of a suitable group at the 3-position for further elaboration can be accomplished via methods generally well known in the art, such as an electrophilic aromatic substitution (e.g. bromination or iodination). Thus, the iodide 4 is accessible from 3 by treatment with suitable reagents, such as N-iodosuccinimide, iodine monochloride or iodine, under conditions facilitating such transformation. Other examples of functionalization via electrophilic aromatic substitution are, by means of example and not limitation, FRIEDEL-CRAFTS-acylation using functionalized acyl halides such as, for example, bromoacetyl chloride, acryloyl chloride or trichloroacetyl chloride in the presence of aluminum trichloride in dichloromethane at ambient temperature or below. As will be appreciated by the skilled artisan, the products of such reactions may be utilized as starting materials for the synthesis of certain heterocyclic compounds.

shutz, B., *Organometallics in Synthesis,* 2nd. ed., Wiley-VCH, 2002). Reaction of the cuprate generated in such fashion with an acyl halide gives access to ketones of the general structure 30, which can be cyclized by reaction with hydrazine or a soluble organic or inorganic salt derived from hydrazine (e.g. hydrazine hydrochloride) to afford the corresponding 3-substituted 5-bromo-1H-pyrazolo[3,4-b]pyridines of the general structure 31.

Elaboration of halides 28, 29 and 30 in Exemplary Scheme 4 can be readily accomplished by generally well known methods, such as those outlined in Scheme 5 below. For example, metal catalyzed cross coupling reactions may be employed using various known transition metal compounds (e.g. compounds derived from palladium, iron or nickel). Examples of such transformations can be found in the following references: Diederich, F., Stang, P. J.—*Metal-catalyzed Cross-coupling Reactions,* Wiley-VCH, 1998; Beller, M., *Transition Metals for Organic Synthesis,* Wiley-VCH, 1998; Tsuji, J., *Palladium Reagents and Catalysts,* Wiley-VCH, 1$^{st}$. & 2$^{nd}$ eds., 1995, 2004; Fuerstner, A., et al., *J. Am. Chem. Soc.* (2002) 124, 13856; and Bolm, C., et al., *Chem. Rev.* (2004) 104, 6217. Other useful methods involve the conversion of a bromine or iodine substituent into a metal or metalloid substituent (e.g. organoboron, organolithium, organotin, organosilicon, organozinc, organocopper or organomagnesium compound) using generally well known methods (e.g. metal halogen exchange and, as appropriate or required, subsequent transmetallation using soluble and reactive compounds of boron, magnesium, zinc, tin, silicon or copper; for representative examples of such methodology see: Schlosser, M., *Organometallics in Synthesis,* 2nd. ed., Wiley-VCH, 2002). Organometallic derivatives obtained in such fashion may itself be of use in transition metal catalyzed coupling reactions with aromatic or olefinic halides or triflates, or, if sufficiently reactive, be reacted directly with suitable electrophiles, such as, for example, certain organic halides, MICHAEL-acceptors, oxiranes, aziridines, aldehydes, acyl halides, or nitriles.

Exemplary Scheme 4

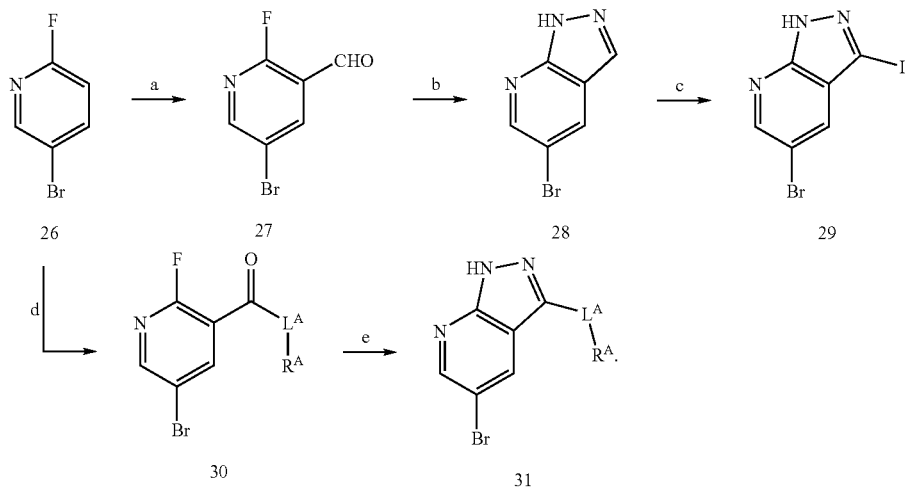

Alternatively, the metallated intermediate derived from deprotonation of 5-bromo-2-fluoropyridine can be transmetallated under suitable conditions to form an organocuprate reagent as depicted above in Exemplary Scheme 4 (c.f. Lip- Selective functionalization at either the 3- or 5-position may require different strategies depending on the nature of the transformations utilized to introduce functionalities at either position, especially the sequence of functionalization at either position. Thus, it may be advantageous or necessary to achieve functionalization at the 3-position prior to functionalization of the 5-position in some cases while the opposite approach may be required in other cases, depending on the nature of the specific groups to be introduced, the methods required to accomplish such transformations, or the inherent selectivity of the methods utilized. For example, some reactants, such as for example some boronic acids or their esters that are electron deficient (e.g. contain one or more electron withdrawing substituents or that represent derivatives of certain heterocyclic systems) and/or contain one or more substituents ortho to the boron-carbon bond may require the use of highly active palladium catalysts (such as those mentioned in Vilar, R., Christman, U.—*Angew. Chem.* (2005) 117, 370; Littke, A. F., Fu, G.—*Angew. Chem.* (2002) 114, 4350.) and more forcing conditions, such as higher temperatures and/or longer reaction times. Such conditions may not be conducive to achieving appreciable selectivities in reactions of 5-bromo-3-iodo-1H-pyrazolo[3,4-b]pyridine. Hence, in such cases, it may be advantageous to avoid selectivity issues altogether by sequential substitution of bromine in 5-bromo-1H-pyrazolo[3,4-b]pyridine, iodination at the 3-position and subsequent introduction of the second substituent at position 3 utilizing the methods detailed above. Generally, when substitution of the halogen atom at either position require conditions that involve highly reactive catalysts or reagents under conditions that generally do not favor high levels of selectivity between the two halogen atoms present in 5-bromo-3-iodo-1H-pyrazolo[3,4-b]pyridine, it may be advantageous to resort to this sequential approach.

It will also be appreciated that protection of reactive groups within $L^A$, $L^B$, $R^A$ and/or $R^B$ as well as the pyrazolo[3,4-b]pyridine scaffold, (e.g. the proton at position 1), with a suitable protecting group may be advantageous or required. For example it was found to be advantageous in some cross-coupling reactions to protect the nitrogen at position 1 of the 1H-pyrazolo[3,4-b]pyridine scaffold by introduction of either a (2-trimethylsilylethoxy)-methyl or (2-methoxyethoxy)methyl group at that position. Introduction and removal of these protecting groups could be conveniently accomplished by methods well known in the chemical literature. The compounds obtained by any of the aforementioned methods may contain functional groups, either free or protected, that can be further elaborated by generally well known methods.

A more detailed description of the utilization of cross-coupling procedures in the synthesis of the compounds claimed under this invention is illustrated in Scheme 5: $X^1$ and $X^2$ are selected from, but not limited to, halogen, boronic acid or ester, trifluoroborate salt, organomagnesium, organozinc, or organotin. With respect to the introduction of individual residues -$L^1$-$R^1$ or -$L^2$-$R^2$ such transformations, as outlined above, can be achieved via standard halogen cross-coupling methodologies.

Exemplary Scheme 5

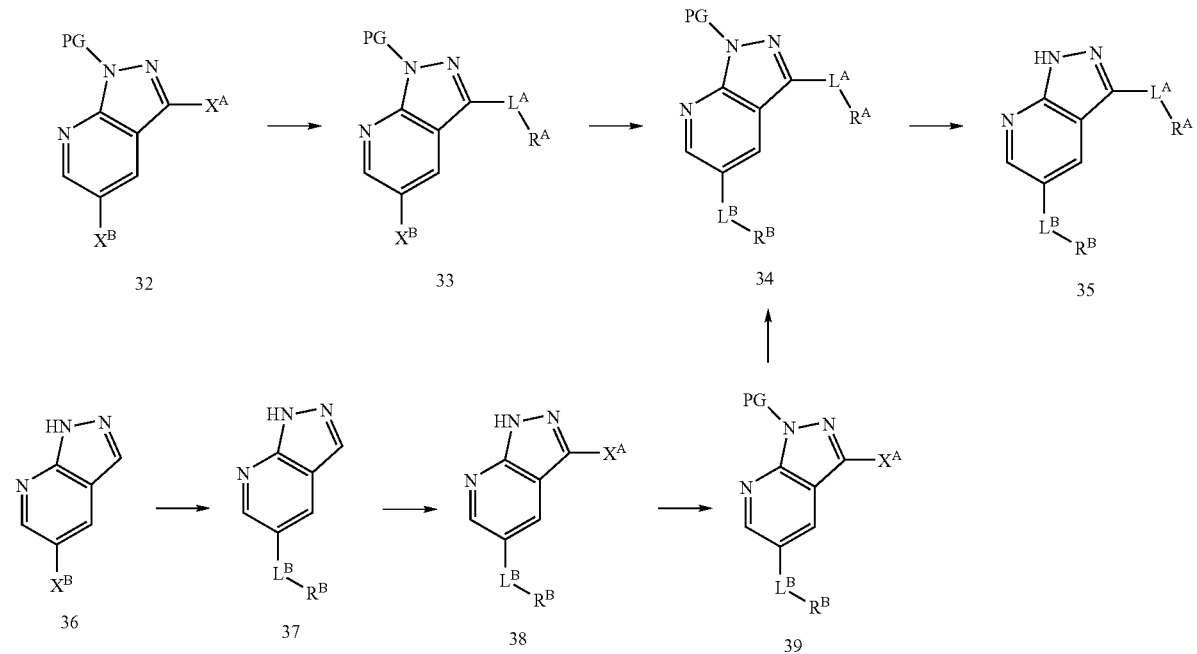

Coupling of the corresponding bromide or iodide ($X^1$, $X^2$=Br, I) with suitable reagents such as boronic acids and boronates, organoboranes, organostannanes, organozinc compounds, organomagnesium compounds, olefins or terminal alkynes (either purchased or obtained via generally well known protocols) can be carried out in the presence of a suitable transition metal catalyst (e.g. palladium compounds). The coupling may optionally be performed in the presence of ligands such as phosphines, diphosphines, Arduengo-type heterocyclic carbenes or arsines. Organic or inorganic bases (e.g. tertiary or secondary amines, alkaline carbonates, bicarbonates or phosphate) and/or other well known additives (e.g. lithium chloride, copper halides or silver salts) may be utilized to assist or accelerate such transformations.

These cross coupling reactions may be carried out in suitable solvents such as THF, dioxane, dimethoxyethane, diglyme, dichloromethane, dichloroethane, acetonitrile, DMF, N-methylpyrrolidone, water, or mixtures of thereof at temperatures ranging from 25° C. to 200° C. using. The temperature may optionally be maintained with heating, conventional heating or microwave irradiation. In the case of the 3-iodo-5-bromo-1H-pyrazolo[3,4-b]pyridine, the selective or preferential substitution of the iodo substituent over the bromo substituent is possible under generally less forcing conditions, such as lower temperature and shorter reaction times using a suitable transition metal catalyst. Selective functionalizations of di- or oligohalogen compounds by means of transition metal catalyzed transformations are well precedented in the chemical literature: see for example Ji, J., et al. *Org. Lett* (2003) 5, 4611; Bach, T., et al., *J. Org. Chem* (2002) 67, 5789, Adamczyk, M. et. al., *Tetrahedron* (2003) 59, 8129.

This methodology may be extended to the incorporation of non-carbon based nucleophiles (e.g. alcohols, thiols, primary or secondary amines) that may optionally contain suitable protecting groups of alcohols, thiols or amines. Examples of such groups can be found in Greene, T., et al., *Protective Groups in Organic Synthesis,* 3rd ed., John Wiley & Sons, 1999. Exemplary methods of protection are described in Ley, S., et al., *Angew. Chem.* (2003) 115, 5558; Wolfe, J., et al., *Acc. Chem. Res.* (1998) 31, 805; Hartwig, *Acc. Chem. Res.* (1998) 31, 852; Navarro, O., et al., *J. Org. Chem.* (2004) 69, 3173, Ji, J., et al., *Org. Lett* (2003) 5, 4611. The compounds obtained by such methods can be further elaborated by well known methods to obtain other compounds of the present invention.

In some cases it may be advantageous to achieve cross-couplings to carbon or non-carbon atoms by first converting the respective halogen derivative into the corresponding organometallic derivative (e.g., a boronic acid or ester, trifluoroborate salt, organomagnesium, organozinc or organotin compound). Such compounds are accessible by means of substituting the halide moiety with an appropriate metal or metalloid. Any functional groups present (e.g. the ring nitrogen in position 1 of the pyrazolo[3,4-b]pyridine), may need to be protected by a suitable protecting group ("PG"). See Greene, et al, 1999.

Introduction of such metals or metalloids can be achieved by generally well-known methods, such as metallation using metals or a metal-halogen exchange reaction. Useful metals for metallation include alkaline or alkaline earth metals or activated forms of such metals. Suitable reagents for use in metal-halogen exchange reactions include organolithium or organomagnesium compounds (e.g. n-butyllithium, tert-butyllithium or iso-propylmagnesium chloride or bromide). Subsequent transmetalation reactions of the organometallic intermediate may be performed as needed with a suitable soluble and reactive metal compound such as magnesium chloride, magnesium bromide, tri-n-butyltin chloride, trimethyltin chloride, trimethyl borate, triethyl borate, tri-iso-propyl borate, zinc triflate or zinc chloride. Introduction of a boronic acid pinacol ester can be conveniently achieved by reacting the halogen derivative directly with bis(pinacolato)diboron in the presence of dichloro[1,1'-bis(diphenylphosphino)ferrocene]palladium(II) and suitable bases (e.g. potassium or sodium acetate) in solvents such as DMSO, DMF, DMA or N-methylpyrrolidone at temperatures ranging from 80-160° C. Conventional heating or microwave irradiation may be employed to maintain the appropriate temperature (for literature precedent of similar transformations, see Ishiyama, T., et al., *J. Org. Chem.* (1995) 60, 7508).

Methods for conversion of the boronic acid pinacol ester obtained by this method into other boronic acid derivatives such as boronic acids, boronates, or trifluoroborate salts are generally well known. As will be apparent to the skilled artisan, such organometallic derivatives may be utilized in cross-coupling reactions similar to those described above in the case of halogen containing derivatives of pyrazolo[3,4-b] pyridine. Such couplings can be effected utilizing suitable coupling partners, such as aromatic, heteroaromatic halides or olefinic reagents under conditions identical or evidently similar and/or related to the methods described above.

Other methods may utilize the reactivity of organometallic derivatives generated from halogen containing derivatives of pyrazolo[3,4-b]pyridine by any of the methods described above. For example, derivatives containing alkaline or alkaline earth metals (e.g. organolithium, organomagnesium or organozinc compounds) may be employed in direct couplings to a range of other electrophilic coupling partners such as, for example, activated olefins (Michael-acceptors), aldehydes, nitriles, aromatic nitro compounds, carboxylic acid derivatives, oxiranes, aziridines, organic disulfides or organic halides. Such transformations are generally well known in the art (for reactions with aromatic nitro compounds, see for example Sapountzis, I., et al., *J. Am. Chem. Soc.* (2002) 124, 9390).

Alpha-hydroxy-arylacetic acid Derivatives

Numerous methods exist in the literature for the synthesis of α-hydroxy-arylacetic acid derivatives, many of which either have been or conceivably can be extended to the synthesis of the corresponding α-hydroxy-heteroarylacetic acids. Some of the more general synthetic strategies pertaining to the synthesis of intermediates useful in the synthesis of compounds claimed under this invention are summarized in Scheme 6. The one-carbon extension of an appropriately substituted aryl- or heteraryl-carbaldehyde is accomplished via a Strecker-reaction (hydrocyanation) or silylcyanation (a), amide hydrolysis (b) and subsequent amide formation (c) (Route 1); enolate formation (a) and subsequent oxidation (b) starting from an appropriately substituted aryl- or heteraryl-acetic acid derivative (Route 2), or one-carbon extension of an appropriately substituted aryl- or heteraryl-carboxylic acid ester by nucleophilic addition of a carbanion generated from a suitably substituted cyanomethylamine and subsequent oxidation of the resulting β-ketonitrile (Route 3).

Exemplary Scheme 6

Route 1

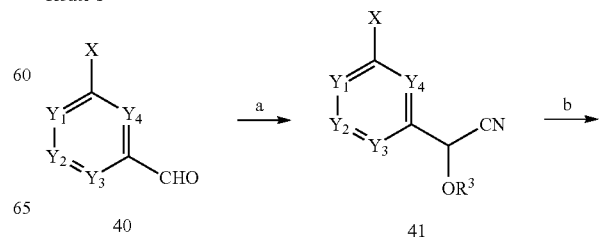

Route 2

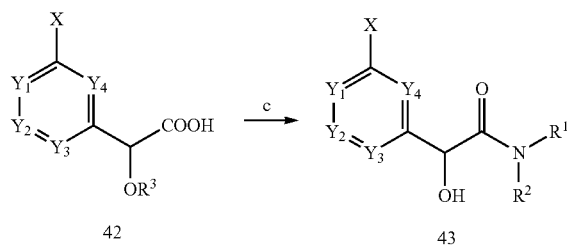

R³ = H, SiR₃ (R = C₁-C₄ alkyl, Ph), C(O)OᵗBu,
C(O)OCH₂Ph, CH₂Ph, CH₂Ph(OMe)ₙ (n = 1-3)

Route 3

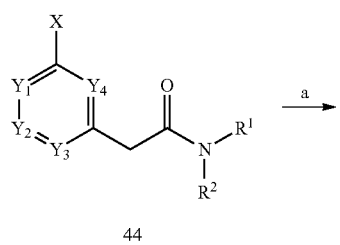

44

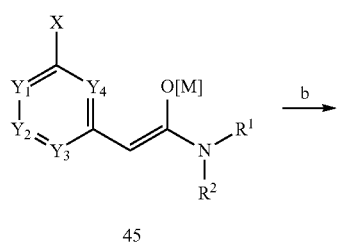

45

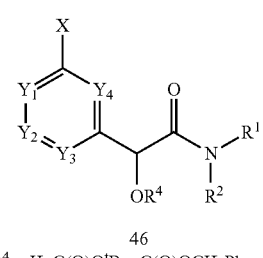

46
R⁴ = H, C(O)OᵗBu, C(O)OCH₂Ph
[M] = Li, Na, K

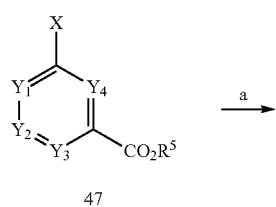

47
R⁵ = lower alkyl

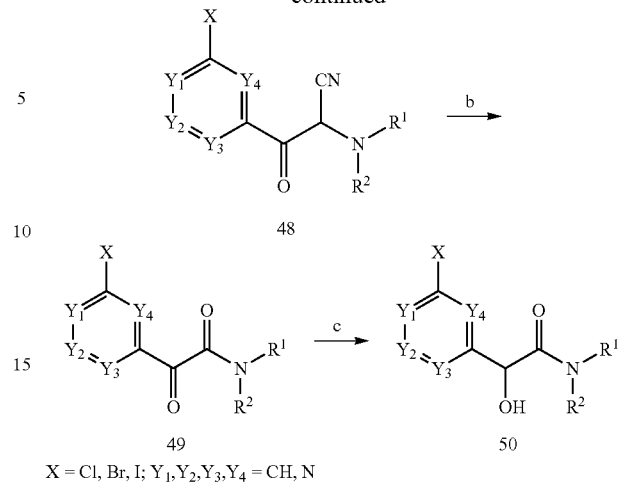

X = Cl, Br, I; Y₁,Y₂,Y₃,Y₄ = CH, N

Appropriately substituted aryl- or heteraryl-acetic acids or derivatives thereof can either be purchased or they can be prepared by methods known in the chemical literature. For example, sufficiently reactive heterocyclic halides may be converted directly into the corresponding aryl- or heteraryl-acetic acid derivatives via a nucleophilic aromatic substitution reaction using suitable nucleophiles such as, for example, carbanions derived from malonitrile, malonates, suitably substituted acetates or acetamides. The derivatives obtained in such ways may either be of direct used in methods described below or may be conveniently converted into such compounds by methods known and familiar to someone with ordinary skill in the art, such as hydrolysis, esterification, saponification, amide formation and decarboxylation of malonic acid derivatives.

Another method to access appropriately substituted aryl- or heteraryl-acetic acids derivatives is the palladium catalyzed reaction between an aryl halide and an alpha-silyl nitrile, such as trimethylsilylacetonitrile, which is then converted to the corresponding amide or acid as described above (Hartwig et al.—*J. Am. Chem. Soc.,* 2005, 15824).

Similarly, appropriately substituted aryl- or heteraryl-carboxylic acids or derivatives thereof or appropriately substituted aryl- or heteraryl-carbaldehydes can either be purchased or they can be prepared by methods known in the chemical literature. Most conveniently such compounds may be accessed either via direct metallation of sufficiently acidic heterocyclic compounds, such as for example derivatives of pyrimidines, or pyrazines, using a suitable base, such as for example lithium N,N-diisopropylamide or lithium 2,2,6,6-tetramethylpiperidide (cf. J. Clayden—*Organolithiums: Selectivity for Synthesis*, Pergamon, 2002; A. Turck, N. Plé, F. Mongin, G. Quéguiner—*Tetrahedron* (2001) 57, 4489; F. Mongin, G. Quéguiner—*Tetrahedron* (2001) 57, 4059) and subsequent reaction with either carbon dioxide to afford the corresponding carboxylic acid or with a suitable formylating reagent, such as, for example DMF, N-formylmorpholine, ethyl formiate or N-formylpiperidine, to give the corresponding carbaldehyde.

Alternatively, especially for starting materials with very low acidity, such as substituted phenyl derivatives, metal-halogen exchange reactions of suitably substituted and bromides or iodides using suitable organolithium or organomagnesium compounds such as, but not limited to, n-butyllithium, tert-butyllithium or iso-propylmagnesium chloride or bromide (e.g. J. Clayden—*Organolithiums: Selectivity for Synthesis*, Pergamon, 2002; A. Boudier, L. O. Bromm, M. Lotz, P. Knochel—*Angew. Chem. Int. Ed.* (2000) 39, 4414.) will provide metallated intermediates that can be utilized in the same fashion and subsequent reaction with either carbon dioxide to afford the corresponding carboxylic acid or with a suitable formylating reagent, such as, for example DMF, N-formylmorpholine, ethyl formiate or N-formylpiperidine, to give the corresponding carbaldehyde.

Furthermore, it will be appreciated by the skilled artisan that metallated intermediates obtained in a manner described above can also be reacted with other electrophiles, such as, but not limited to, ketones, aldehydes, nitriles, imines, activated organic halides, organic azides, such as toluenesulfonyl azide or 4-acetamidophenylsulfonyl azide) or disulfides to give other intermediates that are useful, either directly or upon further modifications, such as, for example, reduction or hydrolysis, in the synthesis of compounds claimed under this invention. It will also be apparent to the skilled artisan that certain functional groups, including in particular known protective groups of amino and hydroxyl groups, such as some of those mentioned in Peter G. M. Wutts, Theodora W. Greene—*Protective Groups in Organic Synthesis*, $4^{th}$. Ed., Wiley-Interscience (2007), contained in the substituted aryl or heteroaryl compounds utilized in the methods described above may provide useful in directing the position of metallation (directed ortho metallation, see for example Snieckus—*Chem. Rev.* (1990) 90, 879.) and may be used to favorably influence the selectivity of such reactions.

It will be readily apparent that the reaction of an organometallic reagent obtained by methods similar or identical to the ones described above can also be reacted with an appropriately substituted or unsubstituted aryl or heteroaryl carbaldehyde to obtain intermediates useful for the synthesis of compounds claimed under this invention.

It is well known in the chemical literature and readily apparent to someone with skill in the art, that an appropriately substituted α-hydroxy-aryl acetic acid or α-hydroxy-heteroaryl acetic acid or derivatives of either class of compounds are useful starting materials for the synthesis of other compounds claimed under this invention. Several methods have been described in the chemical literature and are familiar to someone with skill in the art, that allow for the activation of an α-hydroxy acid or derivative thereof and subsequent substitution with a suitable nucleophile, such as nucleophiles in which the reacting atom is, for example, sulfur, oxygen or nitrogen. Examples of such nucleophiles are amines, alcohols and thiols. Examples of methods that allow for activation of the hydroxy group in α-hydroxy acids or derivatives thereof are reaction with sulfonyl chlorides or anhydrides, such as, for example, toluene sulfonyl chloride, methane sulfonyl chloride, methane sulfonic anhydride, trifluoromethane sulfonic anhydride, in the presence of a suitable base, such as, for example, pyridine, 2,6-lutidine, sodium carbonate, sodium bicarbonate or sodium hydride, in suitable aprotic solvents, such as, for example, pyridine, DMF, THF, 1,4-dioxane, toluene or acetonitrile.

Other methods useful for the synthesis of such intermediates useful for the synthesis of compounds claimed under this invention are other reactions familiar to someone skilled in the art, such as, for example, one of several methods available for the introduction of an α-halogen atom, especially the reaction of an enolate derived from an appropriately substituted aryl or heteroaryl acetic acid or one of its derivatives with a suitable halogen source, such as, for example, tetrabromomethane, tetraiodomethane, 1,2-diiodotetrafluoroethylene, 1,2-dibromotetrafluoroethylene, N-bromosuccinimide, N-iodosuccinimide or iodine or the reaction of an appropriately substituted aryl or heteroaryl acetic acid with bromine in the presence of phosphorus or phosphorus tribromide. The enolates derived from an appropriately substituted aryl or heteroaryl acetic acid or one of its derivatives that are useful for such transformations may be obtained by well known methods in the chemical literature, such as, for example, by reaction with a suitable base, such as for example lithium N,N-diisopropylamide or lithium 2,2,6,6-tetramethylpiperidide. As will be apparent to someone skilled in the art, such enolates may readily be converted into other intermediates useful for the synthesis of compounds claimed under this invention, such as, for example, by reaction with a suitable organic azide, such as, for example, 4-acetamidophenylsulfonyl azide or 4-toluenesulfonyl azide.

It will also be readily apparent to someone with skill in the art that an appropriately substituted α-ketoaryl acetic acid or α-ketoheteroaryl acetic acid or a derivative of either class of compounds is useful for the synthesis of intermediates useful for the synthesis of other compounds claimed under this invention. By means of example, such reactions include the addition of organometallic reagents, such as organomagnesium or organolithium reagents, olefination reactions, such as, for example, the reaction with triphenylphosphonium ylides (W$_{\text{ITTIG}}$-reaction) or carbanions derived from suitable phosphonic acid esters (Homer-Wadsworth-Emmons reaction), reaction with an amine in the presence of a reducing agent such as, for example, sodium borohydride, sodium cyanoborohydride or sodium triacetoxyborohydride (reductive amination). Intermediates obtained by any of the methods described above may themselves be further elaborated into compounds useful for the synthesis of other compounds useful for the synthesis of compounds claimed under this invention by other methods well known in the chemical literature and familiar to someone with ordinary skill in the art.

The methods described above could also be used in the synthesis of halogen containing building blocks that can be utilized in the synthesis of compounds claimed under this invention by cross coupling methods described herein with appropriately functionalized pyrrolo[2,3-b]pyridine- or pyrazolo[3,4-b]pyridine derivatives described herein. The sequence of such cross couplings and the elaboration of an appropriately substituted aryl or heteroaryl halide can either follow a linear route, which means that cross coupling of said aromatic halide with an appropriately functionalized pyrrolo[2,3-b]pyridine- or pyrazolo[3,4-b]pyridine derivative precedes the elaboration to compounds claimed under this invention or it may follow a convergent route, in which the elaboration as outlined in Scheme 7 itself may be accomplished prior to cross coupling of such aromatic or heteroaromatic halides with an appropriately functionalized pyrrolo[2,3-b]pyridine- or pyrazolo[3,4-b]pyridine derivative. This concept is described in Scheme 8. A skilled artisan will appreciate that any stable intermediate in the synthesis of α-functionalized aryl- or heteroaryl acetic acids or derivatives thereof that was described above may in itself be useful in such cross coupling reactions and be further elaborated to compounds claimed under this invention, especially tetramethylpiperidide. α-keto-aryl acetic acid or α-keto-heteroaryl acetic acids or derivatives thereof. It is apparent that such methods may readily be extended to a more general set of appropriately substituted and optionally protected aryl or heteroaryl derivatives that contain α-branched substituents, the synthesis of which was described above and that may be useful for the synthesis of compounds claimed under this invention.

Exemplary Scheme 7

Linear Route

Convergent Route

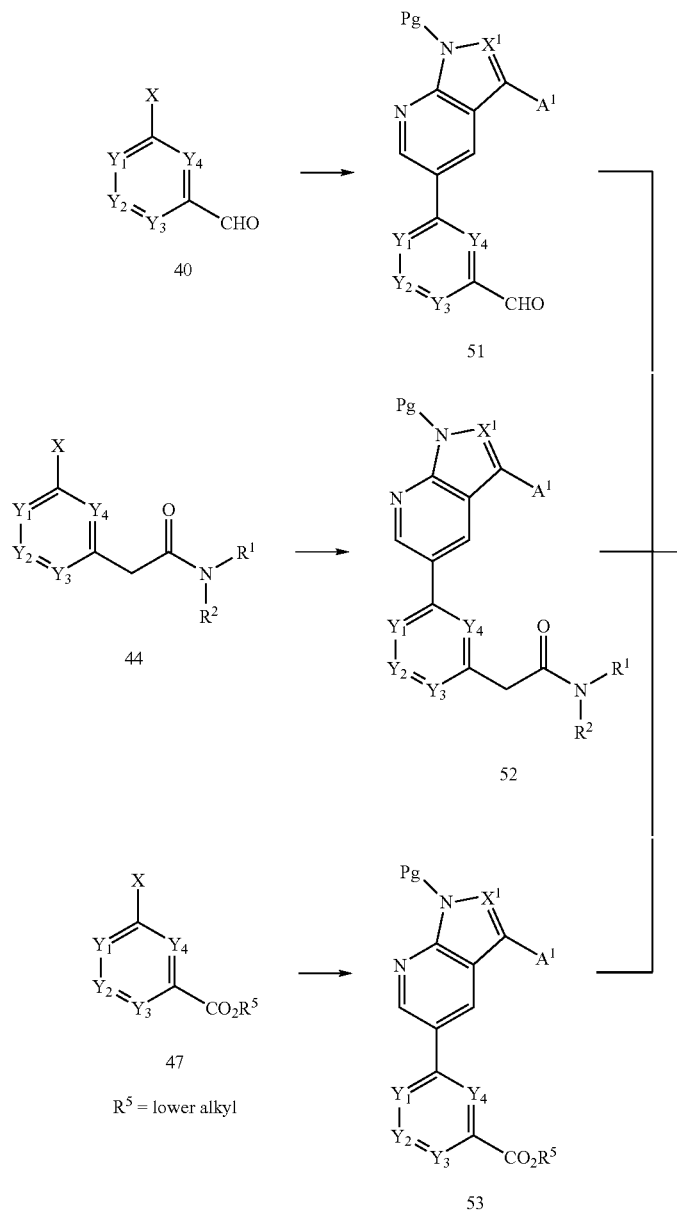

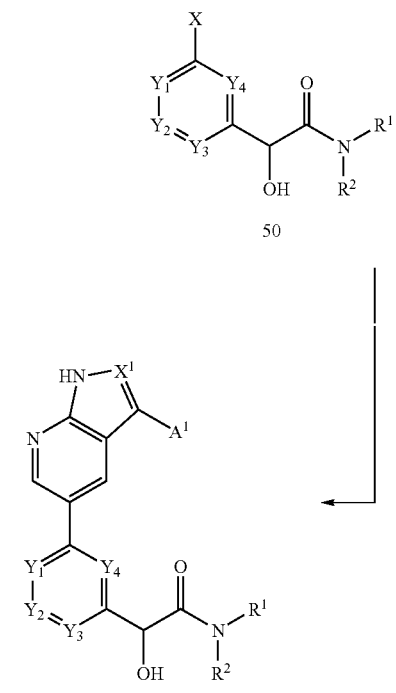

X = Cl, Br, I; $Y_1, Y_2, Y_3, Y_4$ = CH, N

A subset of the compounds claimed under this invention contain at least one element of chirality, for example, the chiral center present in α-hydroxyaryl- or α-hydroxyheteroaryl acetic acids or their derivatives. Numerous methods exist and have been described in the chemical literature detailing procedures that are useful in the separation or selective synthesis of such molecules. These include, for example, methods relying on physical separation (eg. crystallization or chromatography using chiral stationary phases), or methods relying on stereoselective transformations. Numerous biocatalytic methods, that is methods relying either on isolated enzyme catalysts or preparations thereof or methods using whole cell incubations, have been described for the preparation of single enantiomers of α-hydroxyaryl- or α-hydroxyheteroaryl acetic acids or their derivatives, whereby such methods may either lead to preferential formation of one of two possible enantiomers (enantioselective methods), preferential transformation of on one of either enantiomers present (kinetic resolution), or preferential transformation of on one of either enantiomers with concomitant interconversion of either enantiomer into the other (dynamic kinetic resolution). Several purely chemical transformations have been described in the chemical literature as well, leading to the preferential formation of either one of the two possible enantiomers. Such methods include, but are not limited to, enantioselective variants of the Strecker reaction using chiral transition metal or other suitable catalysts or enantioselective reduction of an α-keto-aryl- or α-keto-heteroaryl acetic acid or derivative thereof by either a suitable transition metal catalyst or chiral reducing reagent, such as, chiral borane reagents including isopinocampheyl-9-borabicyclo[3.3.1]nonane or chloro diiso-pinocampheylbrorane. Chiral α-hydroxyaryl or α-hydroxyheteroaryl acetic acids or derivatives thereof are useful intermediates in the synthesis of other chiral compounds accessible by methods described above. In addition to such enantioselective methods, diastereoselective methods are known where an existing element of chirality determines the selectivity for the preferential formation of one epimer over the other in reactions leading to the formation of diastereomeric products, such as, the utilization of amides derived from chiral amines and chiral α-hydroxyaryl or α-hydroxyheteroaryl acetic acids in transformations proceding via an enolate in a fashion similar to methods described above. Such transformations have also been described for the diastereoselective synthesis of other α-substituted aryl- or heteroaryl acetic acid amides containing α-substituents other than a hydroxyl group or those linked via an oxygen atom.

Other methods useful for the synthesis of intermediates in the synthesis of compounds claimed under this invention include, for example, the epoxidation, dihydroxylation, or aminohydroxylation of olefins, which are conveniently accessible via well known olefination reactions starting from suitably functionalized aromatic or heteroaromatic aldehydes or via transition metal catalyzed transformations of a corresponding aromatic or heteroaromatic halide or trifluoromethanoe sulfonate. Such methods are familiar to a person with skill in the art and described in the chemical literature, including stereoselective variants thereof.

As described above, the synthesis of compounds claimed under this invention by methods detailed above, may proceed in a linear or convergent fashion. For reasons of simplicity and not limitation, the methods described above may be illustrated subsequently for either strategy. It will be appreciated by those skilled in the art that any such method can be readily extended to the other respective strategy, utilizing intermediates that can be synthesized by methods described throughout this invention.

The syntheses of mandelic amide analogs and heteroaryl alpha-hydroxyamides in the current invention are described in the schemes below. In Scheme 8 ($Y_1$—$Y_4$=C or N), a suitably substituted aldehyde is converted to a cyanohydrin using known conditions such as, but not limited to, trimethylsilyl cyanide, tert-butyldimethylsilyl cyanide or tert-butyldiphenylsilyl cyanide and a suitable catalyst such as a LEWIS-acid, such as, for example, $ZnI_2$ or KCN in an aprotic solvent, such as, for example DCM, with or without an additive, such as 18-crown-6 or dicyclohexyl-18-crown-6 (Bioorg, Med. Chem. Lett., 2004, 979) (step a). The nitrile obtained in such fashion may be converted to the corresponding acid using an acid, such as, for example, concentrated hydrochloric acid (step b). Amide formation is achieved using conditions well known in the chemical literature and familiar to someone with ordinary skill in the art, such as, for example, reaction with HATU, HBTU, DCC, CDI or EDCI in the presence of a base such as, for example, triethyl amine, diisopropyl ethyl amine or pyridine and a desired amine in an aprotic solvent such as DCM, DMF, THF, NMP, DMA, ACN or mixtures thereof. Alternatively the amide may be accessible through aminolysis of a mixed anhydride, formed in a reaction between the acid and a hindered acid halide or carbamoyl halide such as, for example, pivaloyl chloride, isopropylcarbonyl chloride or iso-butyl chloroformate in the presence of a suitable base such as, for example, triethyl amine, diisopropyl ethyl amine or pyridine in THF or DCM (step c). The final compound is deprotected in the final step following standard literature protocols, such as, for example, those referenced in mentioned in Peter G. M. Wutts, Theodora W. Greene, Protective Groups in Organic Synthesis, 4th. Ed., Wiley-Interscience (2007).

Alternatively, a suitably functionalized aldehyde can be converted directly and stereoselectively, to the corresponding α-hydroxy amide using conditions described by Denmark et al. in J. Am. Chem. Soc., 2003, 7825, wherein an isonitrile is reacted with the aldehyde in the presence of a chiral lewis base (enantioselective PASSERINI-type reaction).

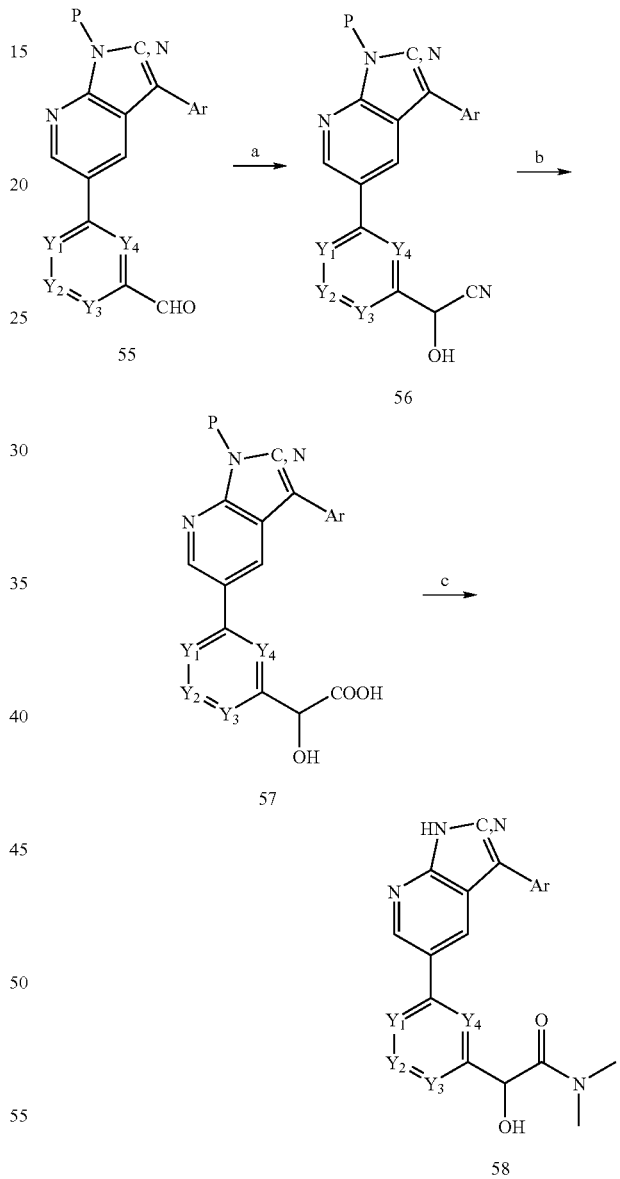

Exemplary Scheme 8

An additional route to the desired alpha-hydroxy amide is by alpha hydroxylation of the enolate of an activated methylene (ie. cyanomethyl, acetyl) (Exemplary Scheme 9, step a below). This transformation can be carried out with oxidizing reagents such as, but not limited to, molecular oxygen, molybdenum peroxide-pyridine-hexamethylphosphoramide (MoOPH), 3-chloroperbenzoic acid (RUBOTTOM conditions), tert-butyl hydrogen peroxide, or 2-sulfonyl oxaziridines such as, for example (R)- or (R)-camphorsulfonyloxaziridine (*J. Org. Chem.*, 1984, 3241) and base such as, for example LiHMDS, NaH, KHMDS, NaHMDS, or LDA in a suitable aprotic solvent (step b). Alternatively, an acetic amide or ester can be converted to the diazo intermediate and oxidized to the hydroxy amide or ester as described by Ma, et al. in *Tetrahedron Letters*, 2005, 3927. Many phenyl or heteroaryl acetic acids can be purchased or they can be prepared by a palladium (ie. $Pd_2(dba)_3$) catalyzed reaction between an aryl halide and an alpha-silyl nitrile which is then converted to the amide as described above (Hartwig et al.—*J. Am. Chem. Soc.*, 2005, 15824). The final compound is deprotected in the final step following standard literature protocols, such as, for example, those referenced in mentioned in Peter G. M. Wutts, Theodora W. Greene—*Protective Groups in Organic Synthesis*, 4th. Ed., Wiley-Interscience (2007).

ing an aryl cyanohydrin carbonate ester followed by rearrangement upon treatment with LDA. Finally, Li and Wu describe the preparation of α-ketoacids from terminal alkynes (X=CCH) by a bromination-oxidation sequence (*Tetrahedron Letters*, 2002, 2427-2430). Once obtained, the ketoamide is reduced to the hydroxy amide by hydrides such as, but not limited to, $NaBH_4$, $LiAlH(OMe)_3$, or chiral borane reagents, such as, for example including isopinocampheyl-9-borabicyclo[3.3.1]nonane or chloro di-iso-pinocampheyl-brorane (step c). The The final compound is deprotected in the final step following standard literature protocols, such as, for example, those referenced in mentioned in Peter G. M. Wutts, Theodora W. Greene—*Protective Groups in Organic Synthesis*, 4th. Ed., Wiley-Interscience (2007).

Exemplary Scheme 9

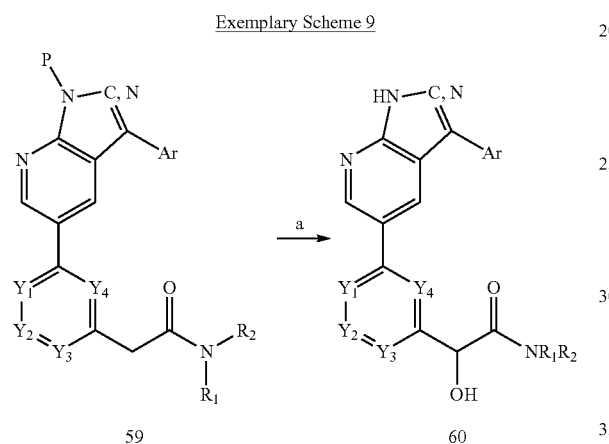

Another alternative method for the preparation of α-hydroxy amides utilizes the reduction of a suitably functionalized α-ketoamide. One method useful in obtaining such α-ketoamides is a palladium catalyzed α-arylation of a nitrile followed by oxidation of the nitrile to a ketone. For example, arylation of ethyl cyanoacetate by ArX (X=halide) can be achieved as described by You and Verkade in *J. Org. Chem.*, 2003, 8003, utilizing a catalyst such as, but not limited to those generated in situ from $Pd_2(dba)_3$, $Pd(OAc)_2$ or $[Pd(allyl)Cl]_2$, a triaminophoshine, tert-butoxide and toluene (Exemplary Scheme 10 below). Alternatively, a heteroaryl alpha-cyanoamide is readily prepared from the nucleophilic aromatic substitution of an appropriately substituted heteroaryl halide (X=halide) by an active methylene group such as, but not limited to, ethyl or amido cyanoacetate (*Tetrahedron letters*, 2005, 3587; *J. Org. Chem.*, 2005, 10186; *J. Heterocyclic Chem.*, 1994, 261.). The ethyl or amido cyanoacetate anion is generated upon deprotonation of the methylene by base such as, for example, NaH, KHMDS, or LDA in a polar aprotic solvent such as, but not limited to, THF, NMP, DMA or DMF. Oxidation of the nitrile by oxidizing agents such as, but not limited to, peracetic acid, 3-chloroperbenzoic acid, potassium peroxosulfate or bleach readily affords the ketone (step b). Yet another route to a ketoamide includes the substitution of a heteroaryl ester (X=$CO_2R$) by a dialkylaminoacetonitrile anion followed by simple oxidation by bleach, as described by Yang, et al. in *Org. Lett.* 2002, 1103-1105. Ketoesters can also be synthesized according to a method described by Thasana et al. (*Tetrahedron Letters*, 2003, 1019-1021) (X=CHO) by form- Exemplary Scheme 10

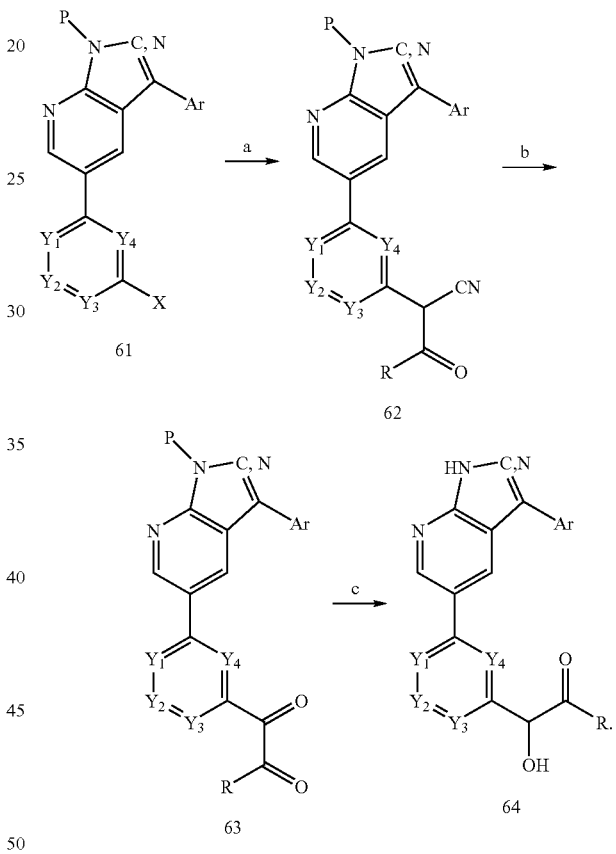

Protecting Groups

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups are known in the art and include, but are not limited to the following moieties:

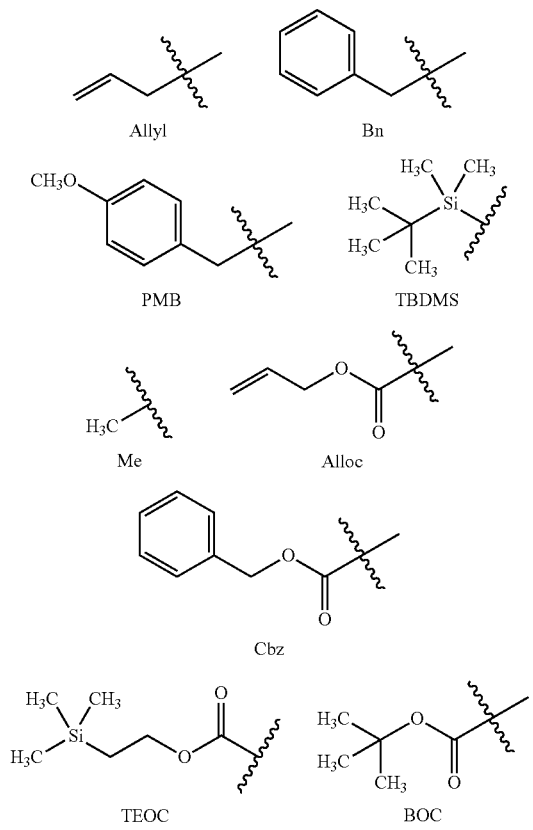

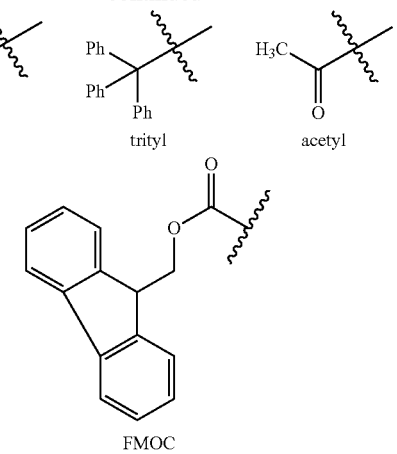

Methods of Inhibiting Kinases

In another aspect, the present invention provides methods of modulating protein kinase activity using the kinase modulators described herein. The term "modulating kinase activity," as used herein, means that the activity of the protein kinase is increased or decreased when contacted with a kinase modulator described herein relative to the activity in the absence of the kinase modulator. Therefore, the present invention provides a method of modulating protein kinase activity by contacting the protein kinase with a kinase modulator as described herein. In some embodiments, the kinase modulator described herein inhibits kinase activity. The term "inhibit," as used herein in reference to kinase activity, means that the kinase activity is decreased when contacted with a kinase modulator described herein relative to the activity in the absence of the kinase modulator. Therefore, the present invention further provides a method of inhibiting protein kinase activity by contacting the protein kinase with a kinase modulator described herein.

In certain embodiments, the protein kinase is a protein tyrosine kinase. A protein tyrosine kinase, as used herein, refers to an enzyme that catalyzes the phosphorylation of tyrosine residues in proteins with a phosphate donors (e.g. a nucleotide phosphate donor such as ATP). Protein tyrosine kinases include, for example, Abelson tyrosine kinases ("Abl") (e.g. c-Abl and v-Abl), Ron receptor tyrosine kinases ("RON"), Met receptor tyrosine kinases ("MET"), Fms-like tyrosine kinases ("FLT") (e.g. FLT3), src-family tyrosine kinases (e.g. lyn, CSK), and p21-activated kinase-4 ("PAK"), FLT3, aurora kinases, B-lymphoid tyrosine kinases ("Blk"), cyclin-dependent kinases ("CDK") (e.g. CDK1 and CDK5), src-family related protein tyrosine kinases (e.g. Fyn kinase), glycogen synthase kinases ("GSK") (e.g. GSK3α and GSK3β), lymphocyte protein tyrosine kinases ("Lck"), ribosomal S6 kinases (e.g. Rsk1, Rsk2, and Rsk3), sperm tyrosine kinases (e.g. Yes), and subtypes and homologs thereof exhibiting tyrosine kinase activity. In certain embodiments, the protein tyrosine kinase is Abl, RON, MET, PAK, or FLT3. In other embodiments, the protein tyrosine kinase is a FLT3 or Abl family member.

In another embodiment, the kinase is a mutant kinase, such as a mutant Bcr-Abl kinase, FLT3 kinase or aurora kinases. Useful mutant Bcr-Abl kinases include those having at least one of the following clinically isolated mutations: M244V, L248V, G250E, G250A, Q252H, Q252R, Y253F, Y253H, E255K, E255V, D276G, F311L, T315I, T315N, T315A, F317V, F317L, M343T, M351T, E355G, F359A, F359V, V379I, F382L, L387M, H396P, H396R, S417Y, E459K and F486S. In some embodiments, the mutant Abl kinase has a T315I mutation. The numbering system denoting the position of the amino acid mutation above is the well known wild-type ABL numbering according to ABL exon Ia. See Deininger, M., et al., Blood 105(7), 2640 (2005). The numbering system is reproduced in FIG. 1. In some embodiments, the mutant Bcr-Abl kinase includes at least one of the mutations listed above and has at least 80%, 85%, 90%, 95%, 96%, 97%, 98%, 99%, or 100% sequence identity to the sequence of FIG. 1 (SEQ ID NO: 23). In some embodiments, the mutant Bcr-Abl kinase includes at least one of the mutations listed above, has a sequence identity to FIG. 1 as discussed above, and includes at least 50, 100, 150, 200, 250, 300, 350, 400, 450, 500, 550, 600, 650, 700, 750, 800, 850, 900, 950, 1000, 1050, or 1100 amino acids.

In some embodiments, the kinase is selected from Abelson tyrosine kinase, Ron receptor tyrosine kinase, Met receptor tyrosine kinase, Fms-like tyrosine kinase-3, Aurora kinases, p21-activated kinase-4, and 3-phosphoinositide-dependent kinase-1. In some embodiments, the compounds described herein are contacted with the kinase.

In some embodiments, the kinase is homologous to a known kinase (also referred to herein as a "homologous kinase"). Compounds and compositions useful for inhibiting the biological activity of homologous kinases may be initially screened, for example, in binding assays. Homologous enzymes comprise an amino acid sequence of the same length that is at least 50%, at least 60%, at least 70%, at least 80%, or at least 90% identical to the amino acid sequence of full length known kinase, or 70%, 80%, or 90% homology to the known kinase active domains. Homology may be determined using, for example, a PSI BLAST search, such as, but not limited to that described in Altschul, et al., *Nuc. Acids Rec.* 25:3389-3402 (1997). In certain embodiments, at least 50%, or at least 70% of the sequence is aligned in this analysis. Other tools for performing the alignment include, for example, DbClustal and ESPript, which may be used to generate the PostScript version of the alignment. See Thompson et al., *Nucleic Acids Research*, 28:2919-26, 2000; Gouet, et al., *Bioinformatics*, 15:305-08 (1999). Homologs may, for example, have a BLAST E-value of $1 \times 10^{-6}$ over at least 100 amino acids (Altschul et al., *Nucleic Acids Res.*, 25:3389-402 (1997) with FLT3, Abl, or another known kinase, or any functional domain of FLT3, Abl, or another known kinase.

Homology may also be determined by comparing the active site binding pocket of the enzyme with the active site binding pockets of a known kinase. For example, in homologous enzymes, at least 50%, 60%, 70%, 80%, or 90% of the amino acids of the molecule or homolog have amino acid structural coordinates of a domain comparable in size to the kinase domain that have a root mean square deviation of the alpha carbon atoms of up to about 1.5 Å, about 1.25 Å, about 1 Å, about 0.75 Å, about 0.5 Å, and or about 0.25 Å.

The compounds and compositions of the present invention are useful for inhibiting kinase activity and also for inhibiting other enzymes that bind ATP. They are thus useful for the treatment of diseases and disorders that may be alleviated by inhibiting such ATP-binding enzyme activity. Methods of determining such ATP binding enzymes include those known to those of skill in the art, those discussed herein relating to selecting homologous enzymes, and by the use of the database PROSITE, where enzymes containing signatures, sequence patterns, motifs, or profiles of protein families or domains may be identified.

The compounds of the present invention, and their derivatives, may also be used as kinase-binding agents. As binding agents, such compounds and derivatives may be bound to a stable resin as a tethered substrate for affinity chromatography applications. The compounds of this invention, and their derivatives, may also be modified (e.g., radiolabelled or affinity labeled, etc.) in order to utilize them in the investigation of enzyme or polypeptide characterization, structure, and/or function.

In an exemplary embodiment, the kinase modulator described herein is a kinase inhibitor. In some embodiments, the kinase inhibitor has an $IC_{50}$ or inhibition constant ($K_i$) of 10 picomolar to 1 micromolar. In another embodiment, the kinase inhibitor has an $IC_{50}$ or inhibition constant ($K_i$) of 10 to 500 micromolar. In another embodiment, the kinase inhibitor has an $IC_{50}$ or $K_i$ of 1 to 10 micromolar. In another embodiment, the kinase inhibitor has an $IC_{50}$ or $K_i$ of 0.5 to 1 micromolar. In another embodiment, the kinase inhibitor has an $IC_{50}$ or $K_i$ of 10 to 500 nanomolar. In another embodiment, the kinase inhibitor has an $IC_{50}$ or $K_i$ of 1 to 10 nanomolar. In another embodiment, the kinase inhibitor has an $IC_{50}$ or $K_i$ of 50 picomolar to 1 nanomolar.

Methods of Treatment

In another aspect, the present invention provides methods of treating a disease mediated by kinase activity (kinase-mediated disease or disorder) in a subject (e.g. mammals, such as humans) in need of such treatment. By "kinase-mediated" or "kinase-associated" diseases is meant diseases in which the disease or symptom can be alleviated by inhibiting kinase activity (e.g. where the kinase is involved in signaling, mediation, modulation, or regulation of the disease process). By "diseases" is meant diseases, or disease symptoms. The method includes administering to the subject an effective amount of a kinase modulator as described herein.

Examples of kinase associated diseases include cancer (e.g. leukemia, tumors, and metastases), allergy, asthma, obesity, inflammation (e.g. inflammatory diseases such as inflammatory airways disease), hematological disorders, obstructive airways disease, asthma, autoimmune diseases, metabolic diseases, infection (e.g. bacterial, viral, yeast, fungal), CNS diseases, brain tumors, degenerative neural diseases, cardiovascular diseases, and diseases associated with angiogenesis, neovascularization, and vasculogenesis. In an exemplary embodiment, the compounds are useful for treating cancer, including leukemia, and other diseases or disorders involving abnormal cell proliferation, such as myeloproliferative disorders. In some embodiments, the compounds described herein are administered to the subject.

More specific examples of cancers treated with the compounds of the present invention include breast cancer, lung cancer, melanoma, colorectal cancer, bladder cancer, ovarian cancer, prostate cancer, renal cancer, squamous cell cancer, glioblastoma, pancreatic cancer, Kaposi's sarcoma, multiple myeloma, and leukemia (e.g. myeloid, chronic myeloid, acute lymphoblastic, chronic lymphoblastic, Hodgkins, and other leukemias and hematological cancers).

Other specific examples of diseases or disorders for which treatment by the compounds or compositions of the invention are useful for treatment or prevention include, but are not limited to transplant rejection (for example, kidney, liver, heart, lung, islet cells, pancreas, bone marrow, cornea, small bowel, skin allografts or xenografts and other transplants), graft vs. host disease, osteoarthritis, rheumatoid arthritis, multiple sclerosis, diabetes, diabetic retinopathy, inflammatory bowel disease (for example, Crohn's disease, ulcerative colitis, and other bowel diseases), renal disease, cachexia, septic shock, lupus, myasthenia gravis, psoriasis, dermatitis, eczema, seborrhea, Alzheimer's disease, Parkinson's disease, stem cell protection during chemotherapy, ex vivo selection or ex vivo purging for autologous or allogeneic bone marrow transplantation, ocular disease, retinopathies (for example, macular degeneration, diabetic retinopathy, and other retinopathies), corneal disease, glaucoma, infections (for example bacterial, viral, or fungal), heart disease, including, but not limited to, restenosis.

Assays

The compounds of the present invention may be easily assayed to determine their ability to modulate protein kinases, bind protein kinases, and/or prevent cell growth or proliferation. Some examples of useful assays are presented below.

Kinase Inhibition and Binding Assays

Inhibition of various kinases is measured by methods known to those of ordinary skill in the art, such as the various methods presented herein, and those discussed in the Upstate KinaseProfiler Assay Protocols June 2003 publication.

For example, where in vitro assays are performed, the kinase is typically diluted to the appropriate concentration to form a kinase solution. A kinase substrate and phosphate donor, such as ATP, is added to the kinase solution. The kinase is allowed to transfer a phosphate to the kinase substrate to form a phosphorylated substrate. The formation of a phosphorylated substrate may be detected directly by any appropriate means, such as radioactivity (e.g. [$\gamma$-$^{32}$P-ATP]), or the use of detectable secondary antibodies (e.g. ELISA). Alternatively, the formation of a phosphorylated substrate may be detected using any appropriate technique, such as the detection of ATP concentration (e.g. Kinase-Glo® assay system (Promega)). Kinase inhibitors are identified by detecting the formation of a phosphorylated substrate in the presence and absence of a test compound (see Examples section below).

The ability of the compound to inhibit a kinase in a cell may also be assayed using methods well known in the art. For example, cells containing a kinase may be contacted with an activating agent (such as a growth factor) that activates the kinase. The amount of intracellular phosphorylated substrate formed in the absence and the presence of the test compound may be determined by lysing the cells and detecting the presence phosphorylated substrate by any appropriate method (e.g. ELISA). Where the amount of phosphorylated substrate produced in the presence of the test compound is decreased relative to the amount produced in the absence of the test compound, kinase inhibition is indicated. More detailed cellular kinase assays are discussed in the Examples section below.

To measure the binding of a compound to a kinase, any method known to those of ordinary skill in the art may be used. For example, a test kit manufactured by Discoverx (Fremont, Calif.), ED-Staurosporine NSIP™ Enzyme Binding Assay Kit (see U.S. Pat. No. 5,643,734) may be used. Kinase activity may also be assayed as in U.S. Pat. No. 6,589,950, issued Jul. 8, 2003.

Suitable kinase inhibitors may be selected from the compounds of the invention through protein crystallographic screening, as disclosed in, for example Antonysamy, et al., PCT Publication No. WO03087816A1, which is incorporate herein by reference in its entirety for all purposes.

The compounds of the present invention may be computationally screened to assay and visualize their ability to bind to and/or inhibit various kinases. The structure may be computationally screened with a plurality of compounds of the present invention to determine their ability to bind to a kinase at various sites. Such compounds can be used as targets or leads in medicinal chemistry efforts to identify, for example, inhibitors of potential therapeutic importance (Travis, Science, 262:1374, 1993). The three dimensional structures of such compounds may be superimposed on a three dimensional representation of kinases or an active site or binding pocket thereof to assess whether the compound fits spatially into the representation and hence the protein. In this screening, the quality of fit of such entities or compounds to the binding pocket may be judged either by shape complementarity or by estimated interaction energy (Meng, et al., J. Comp. Chem. 13:505-24, 1992).

The screening of compounds of the present invention that bind to and/or modulate kinases (e.g. inhibit or activate kinases) according to this invention generally involves consideration of two factors. First, the compound must be capable of physically and structurally associating, either covalently or non-covalently with kinases. For example, covalent interactions may be important for designing irreversible or suicide inhibitors of a protein. Non-covalent molecular interactions important in the association of kinases with the compound include hydrogen bonding, ionic interactions, van der Waals, and hydrophobic interactions. Second, the compound must be able to assume a conformation and orientation in relation to the binding pocket that allows it to associate with kinases. Although certain portions of the compound will not directly participate in this association with kinases, those portions may still influence the overall conformation of the molecule and may have a significant impact on potency. Conformational requirements include the overall three-dimensional structure and orientation of the chemical group or compound in relation to all or a portion of the binding pocket, or the spacing between functional groups of a compound comprising several chemical groups that directly interact with kinases.

Docking programs described herein, such as, for example, DOCK, or GOLD, are used to identify compounds that bind to the active site and/or binding pocket. Compounds may be screened against more than one binding pocket of the protein structure, or more than one set of coordinates for the same protein, taking into account different molecular dynamic conformations of the protein. Consensus scoring may then be used to identify the compounds that are the best fit for the protein (Charifson, P. S. et al., J. Med. Chem. 42:5100-9 (1999)). Data obtained from more than one protein molecule structure may also be scored according to the methods described in Klingler et al., U.S. Utility Application, filed May 3, 2002, entitled "Computer Systems and Methods for Virtual Screening of Compounds." Compounds having the best fit are then obtained from the producer of the chemical library, or synthesized, and used in binding assays and bioassays.

Computer modeling techniques may be used to assess the potential modulating or binding effect of a chemical compound on kinases. If computer modeling indicates a strong interaction, the molecule may then be synthesized and tested for its ability to bind to kinases and affect (by inhibiting or activating) its activity.

Modulating or other binding compounds of kinases may be computationally evaluated by means of a series of steps in which chemical groups or fragments are screened and selected for their ability to associate with the individual binding pockets or other areas of kinases. This process may begin by visual inspection of, for example, the active site on the computer screen based on the kinases coordinates. Selected fragments or chemical groups may then be positioned in a variety of orientations, or docked, within an individual binding pocket of kinases (Blaney, J. M. and Dixon, J. S., Perspectives in Drug Discovery and Design, 1:301, 1993). Manual docking may be accomplished using software such as Insight II (Accelrys, San Diego, Calif.) MOE (Chemical Computing Group, Inc., Montreal, Quebec, Canada); and SYBYL (Tripos, Inc., St. Louis, Mo., 1992), followed by energy minimization and/or molecular dynamics with standard molecular mechanics force fields, such as CHARMM (Brooks, et al., *J. Comp. Chem.* 4:187-217, 1983), AMBER (Weiner, et al., *J. Am. Chem. Soc.* 106:765-84, 1984) and C$^2$MMFF (Merck Molecular Force Field; Accelrys, San Diego, Calif.). More automated docking may be accomplished by using programs such as DOCK (Kuntz et al., *J. Mol. Biol.,* 161:269-88, 1982; DOCK is available from University of California, San Francisco, Calif.); AUTODOCK (Goodsell & Olsen, Proteins: Structure, Function, and Genetics 8:195-202, 1990; AUTODOCK is available from Scripps Research Institute, La Jolla, Calif.); GOLD (Cambridge Crystallographic Data Centre (CCDC); Jones et al., *J. Mol. Biol.* 245:43-53, 1995); and FLEXX (Tripos, St. Louis, Mo.; Rarey, M., et al., *J. Mol. Biol.* 261:470-89, 1996). Other appropriate programs are described in, for example, Halperin, et al.

During selection of compounds by the above methods, the efficiency with which that compound may bind to kinases may be tested and optimized by computational evaluation. For example, a compound that has been designed or selected to function as a kinases inhibitor may occupy a volume not overlapping the volume occupied by the active site residues when the native substrate is bound, however, those of ordinary skill in the art will recognize that there is some flexibility, allowing for rearrangement of the main chains and the side chains. In addition, one of ordinary skill may design compounds that could exploit protein rearrangement upon binding, such as, for example, resulting in an induced fit. An effective kinase inhibitor may demonstrate a relatively small difference in energy between its bound and free states (i.e., it must have a small deformation energy of binding and/or low conformational strain upon binding). Thus, the most efficient kinase inhibitors should, for example, be designed with a deformation energy of binding of not greater than 10 kcal/mol, not greater than 7 kcal/mol, not greater than 5 kcal/mol, or not greater than 2 kcal/mol. Kinase inhibitors may interact with the protein in more than one conformation that is similar in overall binding energy. In those cases, the deformation energy of binding is taken to be the difference between the energy of the free compound and the average energy of the conformations observed when the inhibitor binds to the enzyme.

Specific computer software is available in the art to evaluate compound deformation energy and electrostatic interaction. Examples of programs designed for such uses include: Gaussian 94, revision C (Frisch, Gaussian, Inc., Pittsburgh, Pa. 01995); AMBER, version 7. (Kollman, University of California at San Francisco, ®2002); QUANTA/CHARMM (Accelrys, Inc., San Diego, Calif., ®1995); Insight II/Discover (Accelrys, Inc., San Diego, Calif., ®1995); DelPhi (Accelrys, Inc., San Diego, Calif., ®1995); and AMSOL (University of Minnesota) (Quantum Chemistry Program Exchange, Indiana University). These programs may be implemented, for instance, using a computer workstation, as are well known in the art, for example, a LINUX, SGI or Sun workstation. Other hardware systems and software packages will be known to those skilled in the art.

Those of ordinary skill in the art may express kinase protein using methods known in the art, and the methods disclosed herein. The native and mutated kinase polypeptides described herein may be chemically synthesized in whole or part using techniques that are well known in the art (see, e.g., Creighton, Proteins: Structures and Molecular Principles, W.H. Freeman & Co., NY, 1983).

Gene expression systems may be used for the synthesis of native and mutated polypeptides. Expression vectors containing the native or mutated polypeptide coding sequence and appropriate transcriptional/translational control signals, that are known to those skilled in the art may be constructed. These methods include in vitro recombinant DNA techniques, synthetic techniques and in vivo recombination/genetic recombination. See, for example, the techniques described in Sambrook et al., Molecular Cloning: A Laboratory Manual, Cold Spring Harbor Laboratory, NY, 2001, and Ausubel et al., Current Protocols in Molecular Biology, Greene Publishing Associates and Wiley Interscience, NY, 1989.

Host-expression vector systems may be used to express kinase. These include, but are not limited to, microorganisms such as bacteria transformed with recombinant bacteriophage DNA, plasmid DNA or cosmid DNA expression vectors containing the coding sequence; yeast transformed with recombinant yeast expression vectors containing the coding sequence; insect cell systems infected with recombinant virus expression vectors (e.g., baculovirus) containing the coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence; or animal cell systems. The protein may also be expressed in human gene therapy systems, including, for example, expressing the protein to augment the amount of the protein in an individual, or to express an engineered therapeutic protein. The expression elements of these systems vary in their strength and specificities.

Specifically designed vectors allow the shuttling of DNA between hosts such as bacteria-yeast or bacteria-animal cells. An appropriately constructed expression vector may contain: an origin of replication for autonomous replication in host cells, one or more selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency.

The expression vector may also comprise various elements that affect transcription and translation, including, for example, constitutive and inducible promoters. These elements are often host and/or vector dependent. For example, when cloning in bacterial systems, inducible promoters such as the T7 promoter, pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, mammalian promoters (e.g., metallothionein promoter) or mammalian viral promoters, (e.g., adenovirus late promoter; vaccinia virus 7.5 K promoter; SV40 promoter; bovine papilloma virus promoter; and Epstein-Barr virus promoter) may be used.

Various methods may be used to introduce the vector into host cells, for example, transformation, transfection, infection, protoplast fusion, and electroporation. The expression vector-containing cells are clonally propagated and individually analyzed to determine whether they produce the appropriate polypeptides. Various selection methods, including, for example, antibiotic resistance, may be used to identify host cells that have been transformed. Identification of polypeptide expressing host cell clones may be done by several means, including but not limited to immunological reactivity with anti-kinase antibodies, and the presence of host cell-associated activity.

Expression of cDNA may also be performed using in vitro produced synthetic mRNA. Synthetic mRNA can be efficiently translated in various cell-free systems, including but not limited to wheat germ extracts and reticulocyte extracts, as well as efficiently translated in cell-based systems, including, but not limited, to microinjection into frog oocytes.

To determine the cDNA sequence(s) that yields optimal levels of activity and/or protein, modified cDNA molecules are constructed. A non-limiting example of a modified cDNA is where the codon usage in the cDNA has been optimized for the host cell in which the cDNA will be expressed. Host cells are transformed with the cDNA molecules and the levels of kinase RNA and/or protein are measured.

Levels of kinase protein in host cells are quantitated by a variety of methods such as immunoaffinity and/or ligand affinity techniques, kinase-specific affinity beads or specific antibodies are used to isolate $^{35}$S-methionine labeled or unlabeled protein. Labeled or unlabeled protein is analyzed by SDS-PAGE. Unlabeled protein is detected by Western blotting, ELISA or RIA employing specific antibodies.

Following expression of kinase in a recombinant host cell, polypeptides may be recovered to provide the protein in active form. Several purification procedures are available and suitable for use. Recombinant kinase may be purified from cell lysates or from conditioned culture media, by various combinations of, or individual application of, fractionation, or chromatography steps that are known in the art.

In addition, recombinant kinase can be separated from other cellular proteins by use of an immuno-affinity column made with monoclonal or polyclonal antibodies specific for full length nascent protein or polypeptide fragments thereof. Other affinity based purification techniques known in the art may also be used.

Alternatively, the polypeptides may be recovered from a host cell in an unfolded, inactive form, e.g., from inclusion bodies of bacteria. Proteins recovered in this form may be solubilized using a denaturant, e.g., guanidinium hydrochloride, and then refolded into an active form using methods known to those skilled in the art, such as dialysis.

Cell Growth Assays

A variety of cell growth assays are known in the art and are useful in identifying compounds (i.e. "test compounds") capable of inhibiting (e.g. reducing) cell growth and/or proliferation.

For example, a variety of cells are known to require specific kinases for growth and/or proliferation. The ability of such a cell to grow in the presence of a test compound may be assessed and compared to the growth in the absence of the test compound thereby identifying the anti-proliferative properties of the test compound. One common method of this type is to measure the degree of incorporation of label, such as tritiated thymidine, into the DNA of dividing cells. Alternatively, inhibition of cell proliferation may be assayed by determining the total metabolic activity of cells with a surrogate marker that correlates with cell number. Cells may be treated with a metabolic indicator in the presence and absence of the test compound. Viable cells metabolize the metabolic indicator thereby forming a detectable metabolic product. Where detectable metabolic product levels are decreased in the presence of the test compound relative to the absence of the test compound, inhibition of cell growth and/or proliferation is indicated. Exemplary metabolic indicators include, for example tetrazolium salts and AlamorBlue® (see Examples section below).

Pharmaceutical Compositions and Administration

In another aspect, the present invention provides a pharmaceutical composition including a kinase modulator described herein in admixture with a pharmaceutically acceptable excipient. One of skill in the art will recognize that the pharmaceutical compositions include the pharmaceutically acceptable salts of the kinase modulators described herein.

In therapeutic and/or diagnostic applications, the compounds of the invention can be formulated for a variety of modes of administration, including systemic and topical or localized administration. Techniques and formulations generally may be found in Remington: The Science and Practice of Pharmacy (20$^{th}$ ed.) Lippincott, Williams & Wilkins (2000).

Provided herein are pharmaceutical compositions comprising a compound as described herein or a pharmaceutically acceptable salt, prodrug, solvate, polymorph, tautomer or isomer thereof. In various embodiments, the pharmaceutical composition comprises at least one pharmaceutically acceptable carrier.

In a one embodiment, the disclosure provides for compounds described herein and their pharmaceutically acceptable salts. In further or additional embodiments, the disclosure provides for compounds described herein and their pharmaceutically acceptable solvates. In further or additional embodiments, the disclosure provides for compounds disclosed herein and their pharmaceutically acceptable polymorphs. In further or additional embodiments, the disclosure provides for compounds described herein and their pharmaceutically acceptable esters. In further or additional embodiments, the disclosure provides for compounds described herein and their pharmaceutically acceptable tautomers. In further or additional embodiments, the disclosure provides for compounds described herein and their pharmaceutically acceptable prodrugs.

Salts

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

In some embodiments, the compounds described herein also exist as their pharmaceutically acceptable salts, which in other embodiments are useful for treating disorders. For example, the disclosure provides for methods of treating diseases, by administering pharmaceutically acceptable salts of the compounds described herein. In some embodiments, the pharmaceutically acceptable salts are administered as pharmaceutical compositions.

Thus, in some embodiments, the compounds described herein are prepared as pharmaceutically acceptable salts formed when an acidic proton present in the parent compound either is replaced by a metal ion, for example an alkali metal ion, an alkaline earth ion, or an aluminum ion; or coordinates with an organic base. In other embodiments, base addition salts are also prepared by reacting the free acid form of the compounds described herein with a pharmaceutically acceptable inorganic or organic base, including, but not limited to organic bases such as ethanolamine, diethanolamine, triethanolamine, N-methylglucamine, and the like and inorganic bases such as aluminum hydroxide, calcium hydroxide, potassium hydroxide, sodium carbonate, sodium hydroxide, and the like. In addition, in further embodiments, the salt forms of the disclosed compounds are prepared using salts of the starting materials or intermediates.

Further, in some embodiments, the compounds described herein are prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

Solvates

In other embodiments, the compounds described herein also exist in various solvated forms, which in further embodiments are useful for treating disorders. For example, the disclosure provides for methods of treating diseases, by administering solvates of the compounds described herein. In some embodiments, the solvates are administered as pharmaceutical compositions. In other embodiments, the solvates are pharmaceutically acceptable solvates.

Solvates contain either stoichiometric or non-stoichiometric amounts of a solvent, and in further embodiments are formed during the process of crystallization with pharmaceutically acceptable solvents such as water, ethanol, and the like. Hydrates are formed when the solvent is water, or alcoholates are formed when the solvent is alcohol. In some embodiments, solvates of the compounds described herein are conveniently prepared or formed during the processes described herein. By way of example only, in some embodiments, hydrates of the compounds described herein are conveniently prepared by recrystallization from an aqueous/organic solvent mixture, using organic solvents including, but not limited to, dioxane, tetrahydrofuran or methanol. In addition, in other embodiments, the compounds provided herein exist in unsolvated as well as solvated forms. In general, the solvated forms are considered equivalent to the unsolvated forms for the purposes of the compounds and methods provided herein.

Polymorphs

In some embodiments, the compounds described herein also exist in various polymorphic states, all of which are herein contemplated, and in other embodiments, are useful for treating disorders. For example, the disclosure provides for methods of treating diseases, by administering polymorphs of the compounds described herein. In some embodiments, the various polymorphs are administered as pharmaceutical compositions.

Thus, the compounds described herein include all their crystalline forms, known as polymorphs. Polymorphs include the different crystal packing arrangements of the same elemental composition of the compound. In some embodiments, polymorphs have different x-ray diffraction patterns, infrared spectra, melting points, density, hardness, crystal shape, optical and electrical properties, stability, solvates and solubility. In other embodiments, various factors such as the recrystallization solvent, rate of crystallization, and storage temperature cause a single crystal form to dominate.

Prodrugs

In some embodiments, the compounds described herein also exist in prodrug form, which in other embodiments, are useful for treating disorders. For example, the disclosure provides for methods of treating diseases, by administering prodrugs of the compounds described herein. In some embodiments, the prodrugs are administered as pharmaceutical compositions.

Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some embodiments, they are easier to administer than the parent drug. In further embodiments, they are bioavailable by oral administration whereas the parent is not. In some embodiments, the prodrug has improved solubility in pharmaceutical compositions over the parent drug. An example, without limitation, of a prodrug would be the compound as described herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. In some embodiments, the prodrug is a short peptide (polyamino acid) bonded to an acid group where the peptide is metabolized to reveal the active moiety.

In other embodiments, prodrugs are designed as reversible drug derivatives, for use as modifiers to enhance drug transport to site-specific tissues. The design of prodrugs to date has been to increase the effective water solubility of the therapeutic compound for targeting to regions where water is the principal solvent. See, e.g., Fedorak et al., Am. J. Physiol., 269:g210-218 (1995); McLoed et al., Gastroenterol, 106: 405-413 (1994); Hochhaus et al., Biomed. Chrom., 6:283-286 (1992); J. Larsen and H. Bundgaard, Int. J. Pharmaceutics, 37, 87 (1987); J. Larsen et al., Int. J. Pharmaceutics, 47, 103 (1988); Sinkula et al., J. Pharm. Sci., 64:181-210 (1975); T. Higuchi and V. Stella, Pro-drugs as Novel Delivery Systems, Vol. 14 of the A.C.S. Symposium Series; and Edward B. Roche, Bioreversible Carriers in Drug Design, American Pharmaceutical Association and Pergamon Press, 1987, all incorporated herein in their entirety.

Pharmaceutically acceptable prodrugs of the compounds described herein include, but are not limited to, esters, carbonates, thiocarbonates, N-acyl derivatives, N-acyloxyalkyl derivatives, quaternary derivatives of tertiary amines, N-mannich bases, schiff bases, amino acid conjugates, phosphate esters, metal salts and sulfonate esters. Various forms of prodrugs are known. See for example design of prodrugs, Bundgaard, A. Ed., Elseview, 1985 and Method in Enzymology, Widder, K. Et al., ed.; Academic, 1985, Vol. 42, p. 309-396; Bundgaard, H. "Design and Application of Prodrugs" in A Textbook of Drug Design and Development, Krosgaard-Larsen and H. Bundgaard, ed., 1991, chapter 5, p. 113-191; and Bundgaard, H., Advanced Drug Delivery Review, 1992, 8, 1-38, each of which is incorporated herein by reference. The prodrugs described herein include, but are not limited to, the following groups and combinations of these groups; amine derived prodrugs:

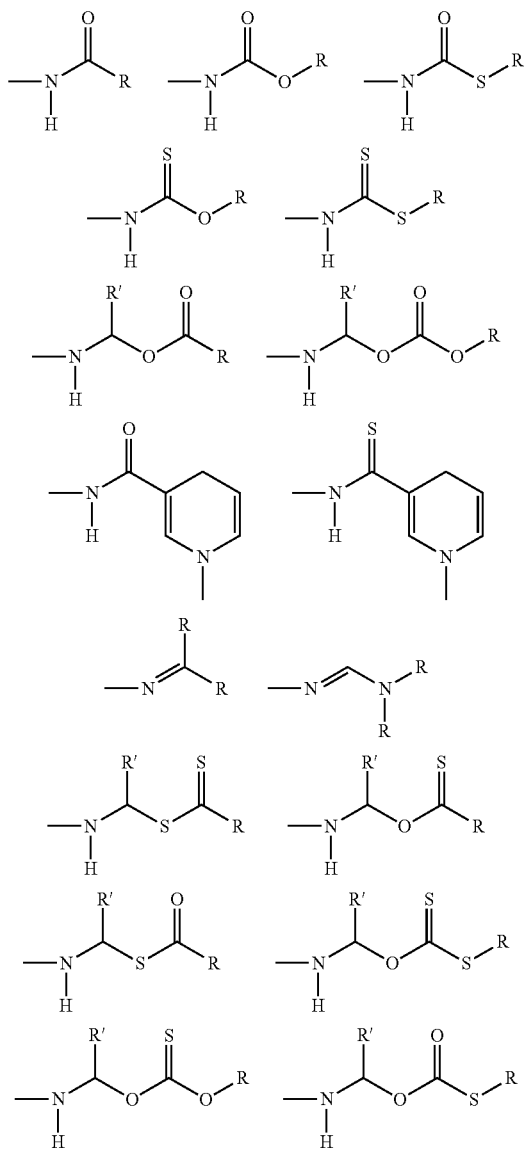

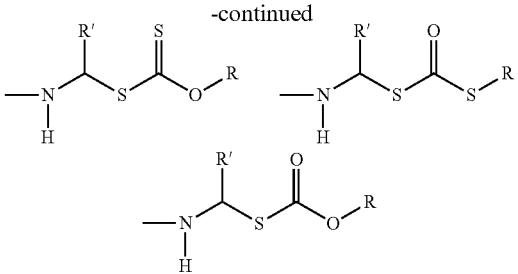

Hydroxy prodrugs include, but are not limited to acyloxyalkyl esters, alkoxycarbonyloxyalkyl esters, alkyl esters, aryl esters and disulfide containing esters.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present disclosure. The amino acid residues include but are not limited to the 20 naturally occurring amino acids commonly designated by three letter symbols and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. Additional types of prodrugs are also encompassed.

Prodrug derivatives of compounds described herein can be prepared by methods described herein (e.g., for further details see Saulnier et al., (1994), Bioorganic and Medicinal Chemistry Letters, Vol. 4, p. 1985). By way of example only, in some embodiments, appropriate prodrugs are prepared by reacting a non-derivatized compound as described herein with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, in some embodiments, some of the herein-described compounds are a prodrug for another derivative or active compound.

In some embodiments, compounds as described herein having free amino, amido, hydroxy or carboxylic groups are converted into prodrugs. For instance, in some embodiments, free carboxyl groups are derivatized as amides or alkyl esters. In other embodiments, free hydroxy groups are derivatized using groups including but not limited to hemisuccinates, phosphate esters, dimethylaminoacetates, and phosphoryloxymethyloxycarbonyls, as outlined in Advanced Drug Delivery Reviews 1996, 19, 115. Carbamate prodrugs of hydroxy and amino groups are also included, as are carbonate prodrugs, sulfonate esters and sulfate esters of hydroxy groups.

Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. In some embodiments, free amines are derivatized as amides, sulfonamides or phosphonamides. In some embodiments, all of these prodrug moieties incorporate groups including but not limited to ether, amine and carboxylic acid functionalities. In other embodiments, phosphate ester functionalities are used as prodrug moieties.

In some other embodiments, sites on the aromatic ring portions of the compounds described herein are susceptible to various metabolic reactions, therefore incorporation of appropriate substitutes on the aromatic ring structures, reduces, minimizes or eliminates this metabolic pathway.

Pharmaceutical Compositions and Administration

In some embodiments, administration of the compounds and compositions described herein are effected by any method that enables delivery of the compounds to the site of action. These methods include oral routes, intraduodenal routes, parenteral injection (including intravenous, subcutaneous, intraperitoneal, intramuscular, intravascular or infusion), topical, intrapulmonary, rectal administration, by implant, by a vascular stent impregnated with the compound, and other suitable methods commonly known in the art. For example, in other embodiments, compounds described herein are administered locally to the area in need of treatment. In some other embodiments, this is achieved by, for example, but not limited to, local infusion during surgery, topical application, e.g., cream, ointment, injection, catheter, or implant, said implant made, e.g., out of a porous, non-porous, or gelatinous material, including membranes, such as sialastic membranes, or fibers. In some embodiments, the administration is by direct injection at the site (or former site) of a tumor or neoplastic or pre-neoplastic tissue. Those of ordinary skill in the art are familiar with formulation and administration techniques that can be employed with the compounds and methods of the present disclosure, e.g., as discussed in Goodman and Gilman, The Pharmacological Basis of Therapeutics, current ed.; Pergamon; and Remington's, Pharmaceutical Sciences (current edition), Mack publishing co., Easton, Pa.

In some embodiments, the formulations include those suitable for oral, parenteral (including subcutaneous, intradermal, intramuscular, intravenous, intraarticular, intramedullary, intracardiac, intrathecal, intraspinal, intracapsular, subcapsular, intraorbital, intratracheal, subcuticular, intraarticular, subarachnoid, and intrastemal), intraperitoneal, transmucosal, transdermal, rectal and topical (including dermal, buccal, sublingual, intranasal, intraocular, and vaginal) administration although in other embodiments the most suitable route depends upon for example the condition and disorder of the recipient. In yet other embodiments, the formulations are conveniently presented in unit dosage form and may be prepared by any of the methods well known in the art of pharmacy. All methods include the step of bringing into association the compound of the subject disclosure or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

In some embodiments, in therapeutic and/or diagnostic applications, the compounds of the disclosure are formulated for a variety of modes of administration, including systemic and topical or localized administration. In further embodiments, techniques and formulations generally are found in Remington: The Science and Practice of Pharmacy (20th ed.) Lippincott, Williams & Wilkins (2000).

According to another aspect, the disclosure provides pharmaceutical compositions including compounds of the formulas described herein, and a pharmaceutically acceptable carrier, adjuvant, or vehicle. The amount of compound in the compositions of the disclosure is such that is effective to detectably inhibit a protein kinase in a biological sample or in a patient.

Pharmaceutically acceptable salts are generally known, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, famarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20th ed.) Lippincott, Williams & Wilkins (2000). In some embodiments, pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, the agents of the invention may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a subject (e.g. patient) to be treated.

For nasal or inhalation delivery, the agents of the invention may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

In some embodiments, depending on the specific conditions being treated, such agents are formulated into liquid or solid dosage forms and administered systemically or locally. In further embodiments, the agents are delivered, for example, in a timed- or sustained-low release forms is known to those skilled in the art. In further embodiments, techniques for formulation and administration are found in Remington: The Science and Practice of Pharmacy (20th ed.) Lippincott, Williams & Wilkins (2000). In other embodiments, suitable routes include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

In other embodiments, for injection, the agents of the disclosure are formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, in other embodiments, the compositions of the present disclosure, in particular, those formulated as solutions, are administered parenterally, such as by intravenous injection. In yet other embodiments, the compounds are formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a patient to be treated.

In other embodiments, for nasal or inhalation delivery, the agents of the disclosure are also formulated by methods known to those of skill in the art, and include, for example, but not limited to, examples of solubilizing, diluting, or dispersing substances such as, saline, preservatives, such as benzyl alcohol, absorption promoters, and fluorocarbons.

Pharmaceutical compositions suitable for use in the present disclosure include compositions wherein active ingredients are contained in an effective amount to achieve its intended purpose. Determination of the effective amounts is well within the capability of those skilled in the art, especially in light of the detailed disclosure provided herein.

In addition to the active ingredients, in other embodiments, these pharmaceutical compositions contain suitable pharmaceutically acceptable carriers comprising excipients and auxiliaries which facilitate processing of the active compounds into preparations which are used pharmaceutically. In some embodiments, the preparations formulated for oral administration are in the form of tablets, dragees, capsules, or solutions.

In other embodiments, pharmaceutical preparations for oral use are obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, in some other embodiments, disintegrating agents are added, such as the cross-linked polyvinylpyrrolidone, agar, or alginic acid or a salt thereof such as sodium alginate.

Dragee cores are provided with suitable coatings. For this purpose, concentrated sugar solutions may be used, which in some embodiments optionally contain gum arabic, talc, polyvinylpyrrolidone, carbopol gel, polyethylene glycol (peg), and/or titanium dioxide, lacquer solutions, and suitable organic solvents or solvent mixtures. In further embodiments, dye-stuffs or pigments are added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

In yet other embodiments, pharmaceutical preparations that are used orally include push-fit capsules made of gelatin, as well as soft, sealed capsules made of gelatin, and a plasticizer, such as glycerol or sorbitol. In some other embodiments, push-fit capsules contain the active ingredients in admixture with filler such as lactose, binders such as starches, and/or lubricants such as talc or magnesium stearate and, optionally, stabilizers. In other embodiments, with soft capsules, the active compounds are dissolved or suspended in suitable liquids, such as fatty oils, liquid paraffin, or liquid polyethylene glycols (PEGs). In addition, stabilizers may be added.

In some embodiments, pharmaceutical preparations are formulated as a depot preparation. In other embodiments, such long acting formulations are administered by implantation (for example, subcutaneously or intramuscularly) or by intramuscular injection. Thus, for example in further embodiments, the compounds are formulated with suitable polymeric or hydrophobic materials (for example, as an emulsion in an acceptable oil) or ion exchange resins, or as sparingly soluble derivatives, for example, as a sparingly soluble salt.

In some other embodiments, for buccal or sublingual administration, the compositions take the form of tablets, lozenges, pastilles, or gels formulated in conventional manner. In further embodiments, such compositions comprise the active ingredient in a flavored basis such as sucrose and acacia or tragacanth.

In yet other embodiments, pharmaceutical preparations are formulated in rectal compositions such as suppositories or retention enemas, e.g., containing conventional suppository bases such as cocoa butter, polyethylene glycol, or other glycerides.

In some other embodiments, pharmaceutical preparations are administered topically, that is by non-systemic administration. This includes the application of the compound of the present disclosure externally to the epidermis or the buccal cavity and the instillation of such the compound into the ear, eye and nose, such that the compound does not significantly enter the blood stream. In contrast, systemic administration refers to oral, intravenous, intraperitoneal and intramuscular administration.

Pharmaceutical preparations suitable for topical administration include liquid or semi-liquid preparations suitable for penetration through the skin to the site of inflammation such as gels, liniments, lotions, creams, ointments or pastes, suspensions, powders, solutions, spray, aerosol, oil, and drops suitable for administration to the eye, ear or nose. Alternatively, a formulation may comprise a patch or a dressing such as a bandage or adhesive plaster impregnated with active ingredients and optionally one or more excipients or diluents. The amount of active ingredient present in the topical formulation may vary widely. The active ingredient may comprise, for topical administration, from about 0.001% to about 10% w/w, for instance from about 1% to about 2% by weight of the formulation. It may however comprise as much as about 10% w/w but in other embodiments will comprise less than about 5% w/w, in yet other embodiments from about 0.1% to about 1% w/w of the formulation.

Formulations suitable for topical administration in the mouth include losenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations suitable for topical administration to the eye also include eye drops wherein the active ingredient is dissolved or suspended in a suitable carrier, especially an aqueous solvent for the active ingredient.

Pharmaceutical preparations for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Depending upon the particular condition, or disease state, to be treated or prevented, additional therapeutic agents, which are normally administered to treat or prevent that condition, in other embodiments are administered together with the inhibitors of this disclosure.

The present disclosure is not to be limited in scope by the exemplified embodiments, which are intended as illustrations of single aspects of the disclosure. Indeed, various modifications of the disclosure in addition to those described herein will become apparent to those having skill in the art from the foregoing description. Such modifications are intended to fall within the scope of the disclosure. Moreover, any one or more features of any embodiment of the disclosure may be combined with any one or more other features of any other embodiment of the disclosure, without departing from the scope of the disclosure. References cited throughout this application are examples of the level of skill in the art and are hereby incorporated by reference herein in their entirety for all purposes, whether previously specifically incorporated or not.

Dosing

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A most preferable dosage is 10 to 30 mg per day. The exact dosage will depend upon the route of administration, the form in which the compound is administered, the subject to be treated, the body weight of the subject to be treated, and the preference and experience of the attending physician.

In some embodiments, continuously or discontinuously dosages are administered, for example once, twice or more per cycle or course of treatment, which in other embodiments are repeated for example every 7, 14, 21 or 28 days.

In other embodiments, the compounds of the present disclosure are continuously or discontinuously administered to a subject systemically, for example, intravenously, orally, subcutaneously, intramuscular, intradermal, or parenterally. In other embodiments, the compounds of the present disclosure are continuously or discontinuously administered to a subject locally. Non-limiting examples of local delivery systems include the use of intraluminal medical devices that include intravascular drug delivery catheters, wires, pharmacological stents and endoluminal paving.

In other embodiments the compounds of the present disclosure are further continuously or discontinuously administered to a subject in combination with a targeting agent to achieve high local concentration of the compound at the target site. In some embodiments, the compounds of the present disclosure are formulated for fast-release or slow-release with the objective of maintaining the drugs or agents in contact with target tissues for a period ranging from hours to weeks.

In other embodiments the optimum method and order of continuously or discontinuously dosing or administration and the dosage amounts and regime are readily determined using conventional methods and in view of the information set out herein.

In various embodiments, the compounds disclosed herein are administered continuously or discontinuously.

In one embodiment, the compound is administered once or twice daily for 28 days with patients then being evaluated for continuation of treatment. In another embodiment, the compound is administered once or twice daily dosing on a 14 days on, 7 days off therapy schedule, cycling every 21 days. In various embodiments, the therapy can last up to 12 months. In some embodiments, the therapy lasts for at least two months, at least three months, at least four months, at least five months, at least six months, at least seven months, at least eight months, at least nine months, or at least eleven months.

In some embodiments, the compound is administered in a dosage of about 1 mg/kg/day to about 120 mg/kg/day, for example about 10 to about 100 mg/kg/day, in other embodiments, in a dosage of about 60 mg/kg/day. In some embodiments, the compound is administered in a dosage of about 2 to about 10 mg/kg. In some embodiments the compound is administered in a dosage of about 5 mg/kg. In some embodiments the compound is administered in an amount of about 10 mg/kg. In some embodiments the compound is administered in an amount of about 20 mg/kg. In some embodiments the compound is administered in an amount of about 30 mg/kg. In some embodiments the compound is administered in an amount of about 40 mg/kg. In some embodiments the compound is administered in an amount of about 50 mg/kg. In some embodiments the compound is administered in an amount of about 60 mg/kg. In various embodiments, the compounds administered daily or twice daily.

In some embodiments, the compound is discontinuously administered in a dosage of about 1 mg/kg/day to about 120 mg/kg/day, for example about 10 to about 100 mg/kg/day. In some embodiments, the administered dosage is about 60 mg/kg/day. In various embodiments, the compound is administered once or twice daily.

In some embodiments, the compound is continuously administered dosage of about 1 mg/kg/day to about 120 mg/kg/day, for example about 10 to about 100 mg/kg/day. In some embodiments, the administered dosage is about 60 mg/kg/day. In some embodiments, the administered dosage is about 120 mg/kg/day. In various embodiments, the compound can be administered once or twice daily.

In some embodiments, the compound is administered orally in a dosage of about 10 to about 100 mg/kg twice a day. In another embodiment, the compound is administered once a day in a dosage of about 60 mg/kg. In various embodiments, treatment is continued for 14 consecutive days.

In some embodiments, the compound is advantageously administered in a dosage of about 1 to about 30 mg/kg. In some embodiments, the compound is administered at about 1, about 3, about 10, or about 30 mg/kg. In various embodiments, the compound is administered once or twice daily. In some embodiments, the compound is administered for 13 consecutive days.

In various embodiments, treatment with a compound disclosed herein is continued for 13 to 28 days. In various embodiments, the compound is administered continuously or discontinuously. In various embodiments, the compound is administered once or twice daily.

In some embodiments, the compound is administered in an amount effective to inhibit tumor growth to less than about 10% during the first 10 days of administration. In some embodiments, the compound is administered in an amount effective to inhibit tumor growth to less than about 8% during the first 10 days of administration. In some embodiments, the compound is administered in an amount effective to inhibit tumor growth to less than about 6% during the first 10 days of administration. In some embodiments, the compound is administered continuously over ten days. In other embodiments, the compound is administered discontinuously over ten days.

In various embodiments, the compound is administered in an amount effective to inhibit tumor growth to about 0.5% to about 10% during the first 10 days of administration. In some embodiments, the compound is administered in an amount effective to inhibit tumor growth to about 5% to about 10% during the first 10 days of administration. In some embodiments, the compound is administered in an amount effective to inhibit tumor growth to about 2% to about 6% during the first 10 days of administration. In some embodiments, the compound is administered continuously over ten days. In other embodiments, the compound is administered discontinuously over ten days.

In various embodiments, the compound is administered in an amount effective to inhibit tumor growth to about 0.01% to about 10% during the first 20 days of administration. In some embodiments, the compound is administered in an amount effective to inhibit tumor growth to about 0.01% to about 5% during the first 20 days of administration. In some embodiments, the compound is administered in an amount effective to inhibit tumor growth to about 0.01% to about 2% during the first 20 days of administration. In some embodiments, the compound is administered continuously over twenty days. In other embodiments, the compound is administered discontinuously over twenty days.

In some embodiments, the compound is administered in an amount effective to decrease tumor size after 10 day of administration. In some embodiments, the compound is administered in an amount effective to decrease tumor size after 15 days of administration. In some embodiments, the compound is administered in an amount effective to decrease tumor size after 20 days of administration. In some embodiments, the compound is administered in an amount effective to decrease tumor size after 25 days of administration. In some embodiments, the compound is administered in an amount effective to decrease tumor size after 30 days of administration. In some embodiments, the compound is administered continuously. In other embodiments, the compound is administered discontinuously.

In some embodiments, the compound is administered in an amount effective to decrease tumor size by about 0.1% to about 10% after 10 day of administration. In some embodiments, the compound is administered in an amount effective to decrease tumor size by about 0.1% to about 10% after 15 days of administration. In some embodiments, the compound is administered in an amount effective to decrease tumor size by about 0.1% to about 10% after 20 days of administration. In some embodiments, the compound is administered in an amount effective to decrease tumor size by about 0.1% to about 10% after 25 days of administration. In some embodiments, the compound is administered in an amount effective to decrease tumor size by about 0.1% to about 10% after 30 days of administration. In some embodiments, the compound is administered continuously. In other embodiments, the compound is administered discontinuously.

In some embodiments, the compound is administered in an amount effective to decrease tumor size by about 0.5% to about 5% after 10 day of administration. In some embodiments, the compound is administered in an amount effective to decrease tumor size by about 0.5% to about 5% after 15 days of administration. In some embodiments, the compound is administered in an amount effective to decrease tumor size by about 0.5% to about 5% after 20 days of administration. In some embodiments, the compound is administered in an amount effective to decrease tumor size by about 0.5% to about 5% after 25 days of administration. In some embodiments, the compound is administered in an amount effective to decrease tumor size by about 0.5% to about 5% after 30 days of administration. In some embodiments, the compound is administered continuously. In other embodiments, the compound is administered discontinuously.

In some embodiments, the compound is administered in an amount effective to decrease tumor size by about 1% to about 5% after 10 day of administration. In some embodiments, the compound is administered in an amount effective to decrease tumor size by about 1% to about 5% after 15 days of administration. In some embodiments, the compound is administered in an amount effective to decrease tumor size by about 1% to about 5% after 20 days of administration. In some embodiments, the compound is administered in an amount effective to decrease tumor size by about 1% to about 5% after 25 days of administration. In some embodiments, the compound is administered in an amount effective to decrease tumor size by about 1% to about 5% after 30 days of administration. In some embodiments, the compound is administered continuously. In other embodiments, the compound is administered discontinuously.

In addition to the aforementioned examples and embodiments of dosages, cycles, and schedules of cycles, numerous permutations of the aforementioned dosages, cycles, and schedules of cycles for the co-administration of a compound with a second chemotherapeutic compound, radiotherapy, or surgery are contemplated herein and in some embodiments are administered according to the patient, type of cancer, and/or appropriate treatment schedule as determined by qualified medical professionals.

The compounds according to the disclosure are effective over a wide dosage range. For example, in the treatment of adult humans, dosages from about 0.01 to about 10,000 mg, from about 0.5 to about 1000 mg, from about 1 to about 500 mg per day, and from about 5 to about 100 mg per day are examples of dosages that in some embodiments are used. The exact dosage will depend upon the route of administration, the form in which the compound is administered, the subject to be treated, the body weight of the subject to be treated, and the preference and experience of the attending physician.

It should be understood that in addition to the ingredients particularly mentioned above, the compounds and compositions described herein may include other agents conventional in the art having regard to the type of formulation in question, for example those suitable for oral administration may include flavoring agents.

Combination Therapy

Depending upon the particular condition, or disease state, to be treated or prevented, additional therapeutic agents, which are normally administered to treat or prevent that condition, may be administered together with the inhibitors of this invention. For example, chemotherapeutic agents or other anti-proliferative agents may be combined with the inhibitors of this invention to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents the inhibitors of this invention may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and antiviral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition. The present invention is not to be limited in scope by the exemplified embodiments, which are intended as illustrations of single aspects of the invention. Indeed, various modifications of the invention in addition to those described herein will become apparent to those having skill in the art from the foregoing description. Such modifications are intended to fall within the scope of the invention. Moreover, any one or more features of any embodiment of the invention may be combined with any one or more other features of any other embodiment of the invention, without departing from the scope of the invention. For example, the kinase modulators described in the Fused Ring Heterocycles as Kinase Modulators section are equally applicable to the methods of treatment and methods of inhibiting kinases described herein. References cited throughout this application are examples of the level of skill in the art and are hereby incorporated by reference herein in their entirety for all purposes, whether previously specifically incorporated or not.

In another aspect, the disclosure provides combination therapies for treating or inhibiting the onset of a cell proliferative disorder or a disorder related to kinase signaling in a subject. The combination therapy comprises continuously or discontinuously dosing or administering to the subject a therapeutically or prophylactically effective amount of a compound of the formulas described herein, and one or more other anti-cell proliferation therapy including chemotherapy, radiation therapy, gene therapy and immunotherapy.

In another aspect, the compounds of the disclosure are continuously or discontinuously administered in combination with chemotherapy. As used herein, chemotherapy refers to a therapy involving a chemotherapeutic agent. In some embodiments, a variety of chemotherapeutic agents are used in the combined treatment methods disclosed herein. Chemotherapeutic agents contemplated as exemplary, include, but are not limited to: platinum compounds (e.g., cisplatin, carboplatin, oxaliplatin); taxane compounds (e.g., paclitaxcel, docetaxol); campotothecin compounds (irinotecan, topotecan); vinca alkaloids (e.g., vincristine, vinblastine, vinorelbine); anti-tumor nucleoside derivatives (e.g., 5-fluorouracil, leucovorin, gemcitabine, capecitabine) alkylating agents (e.g., cyclophosphamide, carmustine, lomustine, thiotepa); epipodophyllotoxins/podophyllotoxins (e.g. Etoposide, teniposide); aromatase inhibitors (e.g., anastrozole, letrozole, exemestane); anti-estrogen compounds (e.g., tamoxifen, fulvestrant), antifolates (e.g., premetrexed disodium); hypomethylating agents (e.g., azacitidine); biologics (e.g., gemtuzamab, cetuximab, rituximab, pertuzumab, trastuzumab, bevacizumab); antibiotics/anthracylines (e.g. Idarubicin, actinomycin D, bleomycin, daunorubicin, doxorubicin, mitomycin C, dactinomycin, carminomycin, daunomycin); antimetabolites (e.g., clofarabine, aminopterin, cytosine arabinoside, methotrexate); tubulin-binding agents (e.g. Combretastatin, colchicine, nocodazole); topoisomerase inhibitors (e.g., camptothecin); differentiating agents (e.g., retinoids, vitamin D and retinoic acid); retinoic acid metabolism blocking agents (RAMBA) (e.g., accutane); kinase inhibitors (e.g., flavoperidol, imatinib mesylate, gefitinib, erlotinib, sunitinib, lapatinib, sorafinib, temsirolimus, dasatinib); farnesyltransferase inhibitors (e.g., tipifarnib); histone deacetylase inhibitors; inhibitors of the ubiquitin-proteasome pathway (e.g., bortezomib, yondelis).

Further useful agents include verapamil, a calcium antagonist found to be useful in combination with antineoplastic agents to establish chemosensitivity in tumor cells resistant to accepted chemotherapeutic agents and to potentiate the efficacy of such compounds in drug-sensitive malignancies. See Simpson W. G., The Calcium Channel Blocker Verapamil and Cancer Chemotherapy. Cell Calcium. December 1985; 6(6): 449-67. Additionally, yet to emerge chemotherapeutic agents are contemplated as being useful in combination with the compound of the present disclosure.

In further embodiments, specific, non-limiting examples of combination therapies include use of the compounds of the present disclosure with agents found in the following pharmacotherapeutic classifications as indicated below. These lists should not be construed to be closed, but should instead serve as illustrative examples common to the relevant therapeutic area at present. Moreover, in other embodiments, combination regimens include a variety of routes of administration and should include oral, intravenous, intraocular, subcutaneous, dermal, and inhaled topical.

In some embodiments, therapeutic agents include chemotherapeutic agents, but are not limited to, anticancer agents, alkylating agents, cytotoxic agents, antimetabolic agents, hormonal agents, plant-derived agents, and biologic agents.

Examples of anti-tumor substances, for example those selected from, mitotic inhibitors, for example vinblastine; alkylating agents, for example cis-platin, carboplatin and cyclophosphamide; anti-metabolites, for example 5-fluorouracil, cytosine arabinside and hydroxyurea, or, for example, one of the preferred anti-metabolites disclosed in European Patent application No. 239362 such as N-(5-[N-(3,4-dihydro-2-methyl-4-oxoquinazolin-6-yhnethyl)-n-methylamino]-2-thenoyl)-L-glutamic acid; growth factor inhibitors; cell cycle inhibitors; intercalating antibiotics, for example adriamycin and bleomycin; enzymes, for example, interferon; and anti-hormones, for example anti-estrogens such as nolvadextm (tamoxifen) or, for example anti-androgens such as casodextm (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of treatment.

Alkylating agents are polyfunctional compounds that have the ability to substitute alkyl groups for hydrogen ions. Examples of alkylating agents include, but are not limited to, bischloroethylamines (nitrogen mustards, e.g. Chlorambucil, cyclophosphamide, ifosfamide, mechlorethamine, melphalan, uracil mustard), aziridines (e.g. Thiotepa), alkyl alkone sulfonates (e.g. Busulfan), nitrosoureas (e.g. Carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups. Under physiological conditions, these drugs ionize and produce positively charged ion that attach to susceptible nucleic acids and proteins, leading to cell cycle arrest and/or cell death. In some embodiments, combination therapy including a kinase modulator as described herein and an alkylating agent has therapeutic synergistic effects on cancer and reduces side effects associated with these chemotherapeutic agents.

Cytotoxic agents are a group of drugs that produced in a manner similar to antibiotics as a modification of natural products. Examples of cytotoxic agents include, but are not limited to, anthracyclines (e.g. Doxorubicin, daunorubicin, epirubicin, idarubicin and anthracenedione), mitomycin C, bleomycin, dactinomycin, plicatomycin. These cytotoxic agents interfere with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and forms an activated complex, which then binds to bases of DNA, causing strand scissions and cell death. In some embodiments, combination therapy including a kinase modulator as described herein and a cytotoxic agent has therapeutic synergistic effects on cancer and reduces side effects associated with these chemotherapeutic agents.

Antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUDR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. In other embodiments, combination therapy including a kinase modulator as described herein and an antimetabolic agent has therapeutic synergistic effects on cancer and reduces side effects associated with these chemotherapeutic agents.

Hormonal agents are a group of drug that regulate the growth and development of their target organs. Most of the hormonal agents are sex steroids and their derivatives and analogs thereof, such as estrogens, androgens, and progestins. These hormonal agents may serve as antagonists of receptors for the sex steroids to down regulate receptor expression and transcription of vital genes. Examples of such hormonal agents are synthetic estrogens (e.g. Diethylstibestrol), antiestrogens (e.g. Tamoxifen, toremifene, fluoxymesterol and raloxifene), antiandrogens (bicalutamide, nilutamide, flutamide), aromatase inhibitors (e.g., aminoglutethimide, anastrozole and letrazole), ketoconazole, goserelin acetate, leuprolide, megestrol acetate and mifepristone. In other embodiments, combination therapy including a kinase modulator as described herein and a hormonal agent has therapeutic synergistic effects on cancer and reduces side effects associated with these chemotherapeutic agents.

Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine and vinorelbine), podophyllotoxins (e.g., etoposide (vp-16) and teniposide (vm-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. In other embodiments, combination therapy including a kinase modulator as described herein and a plant-derived agent having therapeutic synergistic effects on cancer and reducing side effects associated with these chemotherapeutic agents.

Biologic agents are a group of biomolecules that elicit cancer/tumor regression when used alone or in combination with chemotherapy and/or radiotherapy. Examples of biologic agents include, but are not limited to, immuno-modulating proteins such as cytokines, monoclonal antibodies against tumor antigens, tumor suppressor genes, and cancer vaccines. In another embodiment is a combination therapy including a kinase modulator as described herein and a biologic agent having therapeutic synergistic effects on cancer, enhance the patient's immune responses to tumorigenic signals, and reduce potential side effects associated with this chemotherapeutic agent.

For the treatment of oncologic diseases, proliferative disorders, and cancers, compounds according to the present disclosure may be administered with an agent selected from the group comprising: aromatase inhibitors, antiestrogen, anti-androgen, corticosteroids, gonadorelin agonists, topoisomerase I and II inhibitors, microtubule active agents, alkylating agents, nitrosoureas, antineoplastic antimetabolites, platinum containing compounds, lipid or protein kinase targeting agents, imids, protein or lipid phosphatase targeting agents, anti-angiogenic agents, AKT inhibitors, IGF-I inhibitors, FGF3 modulators, mTOR inhibitors, smac mimetics, hdac inhibitors, agents that induce cell differentiation, bradykinin 1 receptor antagonists, angiotensin II antagonists, cyclooxygenase inhibitors, heparanase inhibitors, lymphokine inhibitors, cytokine inhibitors, IKK inhibitors, p38 MAP kinase inhibitors, hsp90 inhibitors, multi-kinase inhibitors, bisphosphanates, rapamycin derivatives, anti-apoptotic pathway inhibitors, apoptotic pathway agonists, PPAR agonists, inhibitors of ras isoforms, telomerase inhibitors, protease inhibitors, metalloproteinase inhibitors, aminopeptidase inhibitors, dacarbazine (dtic), actinomycins C2, C3, D, and F1, cyclophosphamide, melphalan, estramustine, maytansinol, rifamycin, streptovaricin, doxorubicin, daunorubicin, epirubicin, idarubicin, detorubicin, carminomycin, idarubicin, epirubicin, esorubicin, mitoxantrone, bleomycins A, A2, and B, camptothecin, Irinotecan®, Topotecan®, 9-aminocamptothecin, 10,11-methylenedioxycamptothecin, 9-nitrocamptothecin, bortezomib, temozolomide, TAS103, NP10052, combretastatin, combretastatin A-2, combretastatin A-4, calicheamicins, neocarcinostatins, epothilones A, B, or C, and semi-synthetic variants, Herceptin®, Rituxan®, cd40 antibodies, asparaginase, interleukins, interferons, leuprolide, and pegaspargase, 5-fluorouracil, fluorodeoxyuridine, ptorafur, 5'-deoxyfluorouridine, uft, mitc, s-1 capecitabine, diethylstilbestrol, tamoxifen, toremefine, tolmudex, thymitaq, flutamide, fluoxymesterone, bicalutamide, finasteride, estradiol, trioxifene, dexamethasone, leuproelin acetate, estramustine, droloxifene, medroxyprogesterone, megesterol acetate, aminoglutethimide, testolactone, testosterone, diethylstilbestrol, hydroxyprogesterone, mitomycins A, B and C, porfiromycin, cisplatin, carboplatin, oxaliplatin, tetraplatin, platinum-dach, ormaplatin, thalidomide, lenalidomide, CI-973, telomestatin, CHIR258, rad 001, saha, tubacin, 17-aag, sorafenib, JM-216, podophyllotoxin, epipodophyllotoxin, etoposide, teniposide, Tarceva®, Iressa®, Imatinib®, Miltefosine®, Perifosine®, aminopterin, methotrexate, methopterin, dichloro-methotrexate, 6-mercaptopurine, thioguanine, azattuoprine, allopurinol, cladribine, fludarabine, pentostatin, 2-chloroadenosine, deoxycytidine, cytosine arabinoside, cytarabine, azacitidine, 5-azacytosine, gencitabine, 5-azacytosine-arabinoside, vincristine, vinblastine, vinorelbine, leurosine, leurosidine and vindesine, paclitaxel, taxotere and docetaxel.

Cytokines possess profound immunomodulatory activity. Some cytokines such as interleukin-2 (IL-2, aldesleukin) and interferon have demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. In some embodiments, examples of interleukins that are used in conjunction with a RON receptor tyrosine kinase or an abl tyrosine kinase modulator include, but are not limited to, interleukin 2 (IL-2), and interleukin 4 (IL-4), interleukin 12 (IL-12).

Interferons include more than 23 related subtypes with overlapping activities, all of the IFN subtypes within the scope of the present disclosure. IFN has demonstrated activity against many solid and hematologic malignancies, the later appearing to be particularly sensitive.

In further embodiments, other cytokines that are used in conjunction with a kinase modulator as described herein include those cytokines that exert profound effects on hematopoiesis and immune functions. Examples of such cytokines include, but are not limited to erythropoietin, granulocyte-csf (filgrastin), and granulocyte, macrophage-csf (sargramostim). In further embodiments, these cytokines are used in conjunction with a kinase modulator as described herein to reduce chemotherapy-induced myelopoietic toxicity.

In yet other embodiments, other immuno-modulating agents other than cytokines are used in conjunction with a kinase modulator as described herein to inhibit abnormal cell growth. Examples of such immuno-modulating agents include, but are not limited to *bacillus* calmette-guerin, levamisole, and octreotide, a long-acting octapeptide that mimics the effects of the naturally occurring hormone somatostatin.

Monoclonal antibodies against tumor antigens are antibodies elicited against antigens expressed by tumors, preferably tumor-specific antigens. For example, monoclonal antibody Herceptin® (trastruzumab) is raised against human epidermal growth factor receptor-2 (her2) that is overexpressed in some breast tumors including metastatic breast cancer. Overexpression of her2 protein is associated with more aggressive disease and poorer prognosis in the clinic. Herceptin® is used as a single agent for the treatment of patients with metastatic breast cancer whose tumors over express the her2 protein. In some embodiments are combination therapy including a kinase modulator as described herein and Herceptin® having therapeutic synergistic effects on tumors, especially on metastatic cancers.

Another example of monoclonal antibodies against tumor antigens is Rituxan® (rituximab) that is raised against cd20 on lymphoma cells and selectively deplete normal and malignant cd20+pre-b and mature b cells. Rituxan® is used as single agent for the treatment of patients with relapsed or refractory low-grade or follicular, cd20+, b cell non-hodgkin's lymphoma. In another embodiment is a combination therapy including a kinase modulator as described herein and Rituxan® having therapeutic synergistic effects not only on lymphoma, but also on other forms or types of malignant tumors.

Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth-cancer. Examples of the tumor suppressor genes include, but are not limited to, dpc-4, nf-1, nf-2, rb, p53, wt1, brca1 and brca2.

Dpc-4 is involved in pancreatic cancer and participates in a cytoplasmic pathway that inhibits cell division. Nf-1 codes for a protein that inhibits ras, a cytoplasmic inhibitory protein. Nf-1 is involved in neurofibroma and pheochromocytomas of the nervous system and myeloid leukemia. Nf-2 encodes a nuclear protein that is involved in meningioma, schwanoma, and ependymoma of the nervous system. Rb codes for the prb protein, a nuclear protein that is a major inhibitor of cell cycle. Rb is involved in retinoblastoma as well as bone, bladder, small cell lung and breast cancer. P53 codes for p53 protein that regulates cell division and can induce apoptosis. Mutation and/or inaction of p53 is found in a wide ranges of cancers. Wt1 is involved in Wilms tumor of the kidneys. Brca1 is involved in breast and ovarian cancer, and brca2 is involved in breast cancer. The tumor suppressor gene can be transferred into the tumor cells where it exerts its tumor suppressing functions. In another embodiment is a combination therapy including a kinase modulator as described herein and a tumor suppressor having therapeutic synergistic effects on patients suffering from various forms of cancer.

Cancer vaccines are a group of agents that induce the body's specific immune response to tumors. Most of cancer vaccines under research and development and clinical trials are tumor-associated antigens (TAAs). TAAs are structures (i.e. proteins, enzymes or carbohydrates) which are present on tumor cells and relatively absent or diminished on normal cells. By virtue of being fairly unique to the tumor cell, taas provide targets for the immune system to recognize and cause their destruction. Example of TAAs include, but are not limited to gangliosides (gm2), prostate specific antigen (psa), alpha-fetoprotein (afp), carcinoembryonic antigen (cea) (produced by colon cancers and other adenocarcinomas, e.g. Breast, lung, gastric, and pancreas cancer s), melanoma associated antigens (mart-1, gp 100, mage 1,3 tyrosinase), papillomavirus e6 and e7 fragments, whole cells or portions/lysates of antologous tumor cells and allogeneic tumor cells.

In some embodiments, an additional component is used in the combination to augment the immune response to TAAs. Examples of adjuvants include, but are not limited to, *bacillus* calmette-guerin (bcg), endotoxin lipopolysaccharides, keyhole limpet hemocyanin (gklh), interleukin-2 (IL-2), granulocyte-macrophage colony-stimulating factor (gm-csf) and cytoxan, a chemotherapeutic agent which is believe to reduce tumor-induced suppression when given in low doses.

In another aspect, the disclosure provides compounds which are continuously or discontinuously administered in combination with radiation therapy. As used herein, "radiation therapy" refers to a therapy comprising exposing the subject in need thereof to radiation. Such therapy is known to those skilled in the art. In other embodiments, the appropriate scheme of radiation therapy is similar to those already employed in clinical therapies wherein the radiation therapy is used alone or in combination with other chemotherapeutics.

In another aspect, the disclosure provides compounds which are continuously or discontinuously administered in combination with a gene therapy. As used herein, "gene therapy" refers to a therapy targeting on particular genes involved in tumor development. Possible gene therapy strategies include the restoration of defective cancer-inhibitory genes, cell transduction or transfection with antisense dna corresponding to genes coding for growth factors and their receptors, RNA-based strategies such as ribozymes, RNA decoys, antisense messenger RNAs and small interfering RNA (sirna) molecules and the so-called 'suicide genes'.

In other aspect, the disclosure provides compounds which are continuously or discontinuously administered in combination with an immunotherapy. As used herein, "immunotherapy" refers to a therapy targeting particular protein involved in tumor development via antibodies specific to such protein. For example, monoclonal antibodies against vascular endothelial growth factor have been used in treating cancers.

In other embodiments, where a second pharmaceutical is used in addition to a compound of the disclosure, the two pharmaceuticals are continuously or discontinuously administered simultaneously (e.g. In separate or unitary compositions) sequentially in either order, at approximately the same time, or on separate dosing schedules. In further embodiments, the two compounds are continuously or discontinuously administered within a period and in an amount and manner that is sufficient to ensure that an advantageous or synergistic effect is achieved. It will be appreciated that in some embodiments, the method and order of administration and the respective dosage amounts and regimes for each component of the combination will depend on the particular chemotherapeutic agent being administered in conjunction with the compound of the present disclosure, their route of administration, the particular tumor being treated and the particular host being treated.

In certain embodiments, the kinase modulators as described herein are taken alone or in combination with other compounds. In one embodiment, a mixture of two or more kinase modulating compounds are administered to a subject in need thereof.

In yet another embodiment, one or more kinase modulators as described herein are administered with one or more therapeutic agents for the treatment or prevention of various diseases, including, for example, cancer, diabetes, neurodegenerative diseases, cardiovascular disease, blood clotting, inflammation, flushing, obesity, ageing, stress, etc. In various embodiments, combination therapies comprising a kinase modulating compound refer to (1) pharmaceutical compositions that comprise one or more kinase modulating compounds in combination with one or more therapeutic agents (e.g., one or more therapeutic agents described herein); and (2) co-administration of one or more kinase modulating compounds with one or more therapeutic agents wherein the kinase modulating compound and therapeutic agent have not been formulated in the same compositions (but in some embodiments, are present within the same kit or package, such as a blister pack or other multi-chamber package; connected, separately sealed containers (e.g., foil pouches) that in further embodiments are separated by the user; or a kit where the kinase modulating compound(s) and other therapeutic agent(s) are in separate vessels). In further embodiments, when using separate formulations, the kinase modulator as described herein is administered at the same, intermittent, staggered, prior to, subsequent to, or combinations thereof, with the administration of another therapeutic agent.

In certain embodiments, the compounds described herein, their pharmaceutically acceptable salts, prodrug, solvates, polymorphs, tautomers or isomers are administered in combination with another cancer therapy or therapies. In other embodiments, these additional cancer therapies are for example, surgery, and the methods described herein and combinations of any or all of these methods. In further embodiments, combination treatments occur sequentially or concurrently and the combination therapies are neoadjuvant therapies or adjuvant therapies.

In some embodiments, the compounds described herein are administered with an additional therapeutic agent. In these embodiments, the compounds described herein are in a fixed combination with the additional therapeutic agent or a non-fixed combination with the additional therapeutic agent.

By way of example only, if one of the side effects experienced by a patient upon receiving one of the compounds described herein is hypertension, then in some embodiments, it is appropriate to administer an anti-hypertensive agent in combination with the compound. Or, by way of example only, the therapeutic effectiveness of one of the compounds described herein is enhanced by administration of another therapeutic agent, the overall therapeutic benefit to the patient is enhanced. Or, by way of example only, in other embodiments, the benefit experienced by a patient is increased by administering one of the compounds described herein with another therapeutic agent (which also includes a therapeutic regimen) that also has therapeutic benefit. In any case, in some embodiments, regardless of the disease, disorder or condition being treated, the overall benefit experienced by the patient is simply additive of the two therapeutic agents or in further embodiments, the patient experiences a synergistic benefit.

In some embodiments, the appropriate doses of chemotherapeutic agents is generally similar to or less than those already employed in clinical therapies wherein the chemotherapeutics are administered alone or in combination with other chemotherapeutics.

By way of example only, platinum compounds are advantageously administered in a dosage of about 1 to about 500 mg per square meter ($mg/m^2$) of body surface area, for example about 50 to about 400 $mg/m^2$, particularly for cisplatin in a dosage of about 75 $mg/m^2$ and for carboplatin in about 300 $mg/m^2$ per course of treatment. Cisplatin is not absorbed orally and must therefore be delivered via injection intravenously, subcutaneously, intratumorally or intraperitoneally.

By way of example only, taxane compounds are advantageously continuously or discontinuously administered in a dosage of about 50 to about 400 mg per square meter ($mg/m^2$) of body surface area, for example about 75 to about 250 $mg/m^2$, particularly for paclitaxel in a dosage of about 175 to about 250 $mg/m^2$ and for docetaxel in about 75 to about 150 $mg/m^2$ per course of treatment.

By way of example only, camptothecin compounds are advantageously continuously or discontinuously administered in a dosage of about 0.1 to about 400 mg per square meter ($mg/m^2$) of body surface area, for example about 1 to about 300 $mg/m^2$, particularly for irinotecan in a dosage of about 100 to about 350 $mg/m^2$ and for topotecan in about 1 to about 2 $mg/m^2$ per course of treatment.

By way of example only, in some embodiments, vinca alkaloids are advantageously continuously or discontinuously administered in a dosage of about 2 to about 30 mg per square meter ($mg/m^2$) of body surface area, particularly for vinblastine in a dosage of about 3 to about 12 $mg/m^2$, for vincristine in a dosage of about 1 to about 2 $mg/m^2$, and for vinorelbine in dosage of about 10 to about 30 $mg/m^2$ per course of treatment.

By way of example only, in further embodiments, anti-tumor nucleoside derivatives are advantageously continuously or discontinuously administered in a dosage of about 200 to about 2500 mg per square meter ($mg/m^2$) of body surface area, for example about 700 to about 1500 $mg/m^2$. 5-fluorouracil (5-FU) is commonly used via intravenous administration with doses ranging from about 200 to about 500 $mg/m^2$ (in some embodiments from about 3 to about 15 mg/kg/day). Gemcitabine is advantageously continuously or discontinuously administered in a dosage of about 800 to about 1200 $mg/m^2$ and capecitabine is advantageously continuously or discontinuously administered in about 1000 to about 2500 $mg/m^2$ per course of treatment.

By way of example only, in other embodiments, alkylating agents are advantageously continuously or discontinuously administered in a dosage of about 100 to about 500 mg per square meter ($mg/m^2$) of body surface area, for example about 120 to about 200 $mg/m^2$, in other embodiments for cyclophosphamide in a dosage of about 100 to about 500 $mg/m^2$, for chlorambucil in a dosage of about 0.1 to about 0.2 mg/kg of body weight, for carmustine in a dosage of about 150 to about 200 $mg/m^2$, and for lomustine in a dosage of about 100 to about 150 $mg/m^2$ per course of treatment.

By way of example only, in yet other embodiments podophyllotoxin derivatives are advantageously continuously or discontinuously administered in a dosage of about 30 to about 300 mg per square meter ($mg/m^2$) of body surface area, for example about 50 to about 250 $mg/m^2$, particularly for etoposide in a dosage of about 35 to about 100 $mg/m^2$ and for teniposide in about 50 to about 250 $mg/m^2$ per course of treatment.

By way of example only, in other embodiments, anthracycline derivatives are advantageously continuously or discontinuously administered in a dosage of about 10 to about 75 mg per square meter ($mg/m^2$) of body surface area, for example about 15 to about 60 $mg/m^2$, particularly for doxorubicin in a dosage of about 40 to about 75 $mg/m^2$, for daunorubicin in a dosage of about 25 to about 45 $mg/m^2$, and for idarubicin in a dosage of about 10 to about 15 $mg/m^2$ per course of treatment.

By way of example only, in further embodiments, anti-estrogen compounds are advantageously continuously or discontinuously administered in a dosage of about 1 to about 100 mg daily depending on the particular agent and the condition being treated. Tamoxifen is advantageously administered orally in a dosage of about 5 to about 50 mg, about 10 to about 20 mg twice a day, continuing the therapy for sufficient time to achieve and maintain a therapeutic effect. Toremifene is advantageously continuously or discontinuously administered orally in a dosage of about 60 mg once a day, continuing the therapy for sufficient time to achieve and maintain a therapeutic effect. Anastrozole is advantageously continuously or discontinuously administered orally in a dosage of about 1 mg once a day. Droloxifene is advantageously continuously or discontinuously administered orally in a dosage of about 20-100 mg once a day. Raloxifene is advantageously continuously or discontinuously administered orally in a dosage of about 60 mg once a day. Exemestane is advantageously continuously or discontinuously administered orally in a dosage of about 25 mg once a day.

By way of example only, in further embodiments, biologics are advantageously continuously or discontinuously administered in a dosage of about 1 to about 5 mg per square meter ($mg/m^2$) of body surface area, or as known in the art, if different. For example, trastuzumab is advantageously administered in a dosage of 1 to about 5 mg/m², in other embodiments, from about 2 to about 4 mg/m² per course of treatment.

In other embodiments, when a compound is administered with an additional treatment such as radiotherapy, the radiotherapy is administered at 1 day, 2 days, 3 days, 4 days, 5 days, 6 days, 7 days, 14 days, 21 days, or 28 days after administration of at least one cycle of a compound. In some embodiments, the radiotherapy is administered at 1 day, 2 days, 3 days, 4 days, 5 days, 6 days, 7 days, 14 days, 21 days, or 28 days before administration of at least one cycle of a compound. In additional embodiments, the radiotherapy is administered in any variation of timing with any variation of the aforementioned cycles for a compound. In other embodiments, additional schedules for co-administration of radiotherapy with cycles of a compound are further determined by appropriate testing, clinical trials, or in some embodiments are determined by qualified medical professionals.

When a compound is administered with an additional treatment such as surgery, the compound is administered 1, 2, 3, 4, 5, 6, 7, 14, 21, or 28 days prior to surgery. In additional embodiments, at least one cycle of the compound is administered 1, 2, 3, 4, 5, 6, 7, 14, 21, or 28 days after surgery. In yet further embodiments, additional variations of administering compound cycles in anticipation of surgery, or after the occurrence of surgery, are further determined by appropriate testing and/or clinical trials, or in some embodiments are determined by assessment of qualified medical professionals.

Other therapies include, but are not limited to administration of other therapeutic agents, radiation therapy or both. In the instances where the compounds described herein are administered with other therapeutic agents, the compounds described herein need not be administered in the same pharmaceutical composition as other therapeutic agents, and may, because of different physical and chemical characteristics, be administered by a different route. For example, in some embodiments, the compounds/compositions are administered orally to generate and maintain good blood levels thereof, while the other therapeutic agent is administered intravenously. The determination of the mode of administration and the advisability of administration, where possible, in the same pharmaceutical composition, is within the knowledge of the skilled clinician with the teachings described herein. In some embodiments, the initial administration is made according to established protocols, and then, based upon the observed effects, the dosage, modes of administration and times of administration in other embodiments, is modified by the skilled clinician. The particular choice of compound (and where appropriate, other therapeutic agent and/or radiation) will depend upon the diagnosis of the attending physicians and their judgment of the condition of the patient and the appropriate treatment protocol.

In other embodiments, the compounds and compositions described herein (and where appropriate chemotherapeutic agent and/or radiation) is administered concurrently (e.g., simultaneously, essentially simultaneously or within the same treatment protocol) or sequentially, depending upon the nature of the disease, the condition of the patient, and the actual choice of chemotherapeutic agent and/or radiation to be administered in conjunction (i.e., within a single treatment protocol) with the compound/composition.

In combinational applications and uses, the compound/composition and the chemotherapeutic agent and/or radiation need not be administered simultaneously or essentially simultaneously, and the initial order of administration of the compound/composition, and in other embodiments, the chemotherapeutic agent and/or radiation, is not important. Thus, in some embodiments, the compounds/compositions of the present disclosure are administered first followed by the administration of the chemotherapeutic agent and/or radiation; or the chemotherapeutic agent and/or radiation is administered first followed by the administration of the compounds/compositions described herein. In further embodiments, this alternate administration is repeated during a single treatment protocol. With the teachings described herein, the determination of the order of administration, and the number of repetitions of administration of each therapeutic agent during a treatment protocol, would be within the knowledge of the skilled physician after evaluation of the disease being treated and the condition of the patient. For example, in some embodiments, the chemotherapeutic agent and/or radiation is administered first, especially if it is a cytotoxic agent, and then the treatment continued with the administration of the compounds/compositions of the present disclosure followed, where determined advantageous, by the administration of the chemotherapeutic agent and/or radiation, and so on until the treatment protocol is complete. Thus, in other embodiments and in accordance with experience and knowledge, the practicing physician modifies each protocol for the administration of the compound/composition for treatment according to the individual patient's needs, as the treatment proceeds. The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. In further embodiments, relief of disease-related symptoms such as pain, and improvement in overall condition is used to help judge effectiveness of treatment.

In some embodiments, a composition described herein is administered before the administration of one or more chemotherapeutic agents. As non-limiting examples of this embodiment, the chemotherapeutic agent is administered hours (e.g. one, five, ten, etc.) or days (e.g., one, two, three, etc.) After administration of the composition described herein. In some embodiments, the subsequent administration is shortly after (e.g., within an hour) administration of the compound described herein.

Anti-emetic agents are a group of drugs effective for treatment of nausea and emesis (vomiting). Cancer therapies frequently cause urges to vomit and/or nausea. Many anti-emetic drugs target the 5-HT3 seratonin receptor which is involved in transmitting signals for emesis sensations. These 5-HT3 antagonists include, but are not limited to, dolasetron (Anzemet®), granisetron (Kytril®), ondansetron (Zofran®), palonosetron and tropisetron. Other anti-emetic agents include, but are not limited to, the dopamine receptor antagonists such as chlorpromazine, domperidone, droperidol, haloperidol, metaclopramide, promethazine, and prochlorperazine; antihistamines such as cyclizine, diphenhydramine, dimenhydrinate, meclizine, promethazinie, and hydroxyzine; lorazepram, scopolamine, dexamethasone, Emetrol®, propofol, and trimethobenzamide. Administration of these anti-emetic agents in addition to the above described combination treatment will manage the potential nausea and emesis side effects caused by the combination treatment.

Immuno-restorative agents are a group of drugs that counter the immuno-suppressive effects of many cancer therapies. The therapies often cause myelosuppression, a substantial decrease in the production of leukocytes (white blood cells). The decreases subject the patient to a higher risk of infections. Neutropenia is a condition where the concentration of neutrophils, the major leukocyte, is severely depressed. Immuno-restorative agents are synthetic analogs of the hormone, granulocyte colony stimulating factor (g-csf), and act by stimulating neutrophil production in the bone marrow. These include, but are not limited to, filgrastim (Neupogen®), peg-filgrastim (Neulasta®) and lenograstim. Administration of these immuno-restorative agents in addition to the above described combination treatment will manage the potential myelosupression effects caused by the combination treatment.

Antibiotic agents are a group of drugs that have anti-bacterial, anti-fungal, and anti-parasite properties. Antibiotics inhibit growth or causes death of the infectious microorganisms by various mechanisms such as inhibiting cell wall production, preventing DNA replication, or deterring cell proliferation. Potentially lethal infections occur from the myelosupression side effects due to cancer therapies. The infections can lead to sepsis where fever, widespread inflammation, and organ dysfunction arise. Antibiotics manage and abolish infection and sepsis and include, but are not limited to, amikacin, gentamicin, kanamycin, neomycin, netilmicin, streptomycin, tobramycin, loracarbef, ertapenem, cilastatin, meropenem, cefadroxil, cefazolin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, teicoplanin, vancomycin, azithromycin, clarithromycin, dirithromycin, erthromycin, roxithromycin, troleandomycin, aztreonam, amoxicillin, ampicillin, azlocillin, carbenicillin, cloxacillin, dicloxacillin, flucloxacillin, mezlocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, benzolamide, bumetanide, chlorthalidone, clopamide, dichlorphenamide, ethoxzolamide, indapamide, mafenide, mefruside, metolazone, probenecid, sulfanilamides, sulfamethoxazole, sulfasalazine, sumatriptan, xipamide, democlocycline, doxycycline, minocycline, oxytetracycline, tetracycline, chloramphenical, clindamycin, ethambutol, fosfomycin, fusidic acid, furazolidone, isoniazid, linezolid, metronidazole, mupirocin, nitrofurantoin, platesimycin, pyrazinamide, dalfopristin, rifampin, spectinomycin, and telithromycin. Administration of these antibiotic agents in addition to the above described combination treatment will manage the potential infection and sepsis side effects caused by the combination treatment.

Anemia treatment agents are compounds directed toward treatment of low red blood cell and platelet production. In addition to myelosuppression, many cancer therapies also cause anemias, deficiencies in concentrations and production of red blood cells and related factors. Anemia treatment agents are recombinant analogs of the glycoprotein, erythropoeitin, and function to stimulate erythropoesis, the formation of red blood cells. Anemia treatment agents include, but are not limited to, recombinant erythropoietin (Epogen®, Dynopro®) and darbepoetin alfa (Aranesp®). Administration of these anemia treatment agents in addition to the above described combination treatment will manage the potential anemia side effects caused by the combination treatment.

In some embodiments, pain and inflammation side effects arising from the described herein combination treatment are treated with compounds selected from the group comprising: corticosteroids, non-steroidal anti-inflammatories, muscle relaxants and combinations thereof with other agents, anesthetics and combinations thereof with other agents, expectorants and combinations thereof with other agents, antidepressants, anticonvulsants and combinations thereof, antihypertensives, opioids, topical cannabinoids, and other agents, such as capsaicin.

In some embodiments, for the treatment of pain and inflammation side effects, compounds according to the present disclosure are administered with an agent selected from the group comprising: betamethasone dipropionate (augmented and nonaugmented), betamethasone valerate, clobetasol propionate, prednisone, methyl prednisolone, diflorasone diacetate, halobetasol propionate, amcinonide, dexamethasone, dexosimethasone, fluocinolone acetononide, fluocinonide, halocinonide, clocortalone pivalate, dexosimetasone, flurandrenalide, salicylates, ibuprofen, ketoprofen, etodolac, diclofenac, meclofenamate sodium, naproxen, piroxicam, celecoxib, cyclobenzaprine, baclofen, cyclobenzaprine/lidocaine, baclofen/cyclobenzaprine, cyclobenzaprine/lidocaine/ketoprofen, lidocaine, lidocaine/deoxy-d-glucose, prilocaine, emla cream (eutectic mixture of local anesthetics (lidocaine 2.5% and prilocaine 2.5%), guaifenesin, guaifenesin/ketoprofen/cyclobenzaprine, amitryptiline, doxepin, desipramine, imipramine, amoxapine, clomipramine, nortriptyline, protriptyline, duloxetine, mirtazepine, nisoxetine, maprotiline, reboxetine, fluoxetine, fluvoxamine, carbamazepine, felbamate, lamotrigine, topiramate, tiagabine, oxcarbazepine, carbamezipine, zonisamide, mexiletine, gabapentin/clonidine, gabapentin/carbamazepine, carbamazepine/cyclobenzaprine, antihypertensives including clonidine, codeine, loperamide, tramadol, morphine, fentanyl, oxycodone, hydrocodone, levorphanol, butorphanol, menthol, oil of wintergreen, camphor, eucalyptus oil, turpentine oil; CB1/CB2 ligands, acetaminophen, infliximab) nitric oxide synthase inhibitors, particularly inhibitors of inducible nitric oxide synthase; and other agents, such as capsaicin. Administration of these pain and inflammation analgesic agents in addition to the above described combination treatment will manage the potential pain and inflammation side effects caused by the combination treatment.

EXAMPLES

Example 1

Synthesis of the Compounds

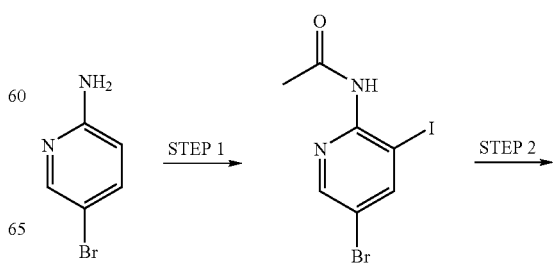

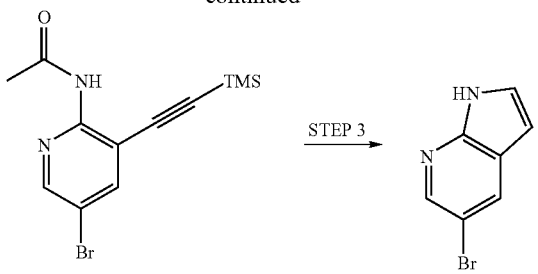

Step 1: Synthesis of N-(5-bromo-3-iodo-pyridin-2-yl)-acetamide

To a solution of 2-amino-5-bromopyridine (12.7 g, 73.4 mmol) in DMF (150 ml) was added iodine (14.9 g, 58.7 mmol) and sodium periodate (6.3 g, 29.4 mmol). The reaction mixture was stirred at 90° C. for 20 hours, then diluted with water and extracted with ethyl acetate. The combined organic extracts were washed twice with a 1 M aqueous solution of sodium thiosulfate, dried over anhydrous magnesium sulfate, and filtered over a pad of silica gel. Solvent was evaporated to give 16.5 g of a brown solid. The solid was dissolved in THF (150 ml) and cooled to 0° C. Pyridine (6.7 ml, 71.7 mmol) was added, followed by dropwise addition of acetyl chloride (5.1 ml, 71.7 mmol). The reaction mixture was stirred at room temperature for 20 hours then at 60° C. for 4 hours. Solvent was evaporated and the residue was partitioned between water (200 ml) and dichloromethane (250 ml). The aqueous layer was extracted three times with dichloromethane and the combined organic layers were dried over anhydrous magnesium sulfate and filtered off. Purification by flash chromotography on silica gel with a gradient of ethyl acetate/hexanes afforded the title compound as an orange solid (7.76 g, 41% yield). $^1$H NMR (DMSO-$d_6$): δ 10.17 (s, 1H), 8.55 (d, J=2.0 Hz, 1H), 8.54 (d, J=2.0 Hz, 1H), 2.01 (s, 3H); HPLC/MS m/z: 340.8, 342.8 [MH]$^+$. Diacetylated material was also isolated as a light orange solid (7.0 g, 33% yield). $^1$H NMR (DMSO-$d_6$): δ 8.78 (d, J=2.5 Hz, 1H), 8.74 (d, J=2.5 Hz, 1H), 2.17 (s, 6H); HPLC/MS m/z: 402.8, 404.8 [Ma]$^+$.

The diacetylated material (7 g, 18.27 mmol) was dissolved in dichloromethane (180 ml) and treated with PS-trisamine (26 g, 3.53 mmol/g loading, Argonaut Technologies) for 17 hours. The resin was filtered off, washed with, dichloromethane and the solvent was evaporated to give 5.95 g of the title compound, contaminated with 10% of 2-amino-3-iodo-5-bromopyridine.

Step 2: Synthesis of N-(5-bromo-3-trimethylsilanyl-ethynyl-pyridin-2-yl)-acetamide To a suspension of N-(5-bromo-3-iodo-pyridin-2-yl)-acetamide (6.42 g, 18.83 mmol) in dichloromethane (90 ml) was added triethyl amine (3.15 ml, 22.6 mmol), then the mixture was cooled to 0° C. and dichlorobis(triphenylphosphino)palladium (II) (66 mg, 0.094 mmol) and copper(I) iodide (36 mg, 0.188 mmol) were added sequentially. Finally trimethylsilylacetylene (2.93 ml, 20.71 mmol) was added dropwise, and the ice bath was removed. After stirring at room temperature for 17 hours, the crude mixture was directly adsorbed on silica gel. Purification by flash chromatography on silica gel with a gradient of ethyl acetate/hexane afforded the title compound as light yellow solid (4.75 g, 81% yield). $^1$H NMR (DMSO-$d_6$): δ 9.99 (s, 1H), 8.31 (d, J=2.5 Hz, 1H), 7.95 (d, J=2.5 Hz, 1H), 1.82 (s, 3H), 0.00 (s, 9H); HPLC/MS m/z: 311, 313 [MH]$^+$.

Step 3: Synthesis of 5-bromo-1H-pyrrolo[2,3-b]pyridine

To a solution of N-(5-bromo-3-trimethylsilanylethynyl-pyridin-2-yl)-acetamide (4.75 g, 15.26 mmol) in THF (90 ml) was added dropwise a 1 M solution of tetra-n-butyl ammonium fluoride in THF (30.5 ml, 30.5 mmol). After stirring at reflux for 15 hours, the reaction mixture was concentrated in vacuo and water was added. The aqueous layer was extracted three times with dichloromethane with, and the combined extracts were directly adsorbed on silica gel. Purification by flash chromotography on silica gel with a gradient of ethyl acetate/hexanes afforded 2.29 g of a beige solid. Recrystallization from ethyl acetate/hexanes provided the title compound as light beige flakes (1.33 g). Further purification of the filtrate on silica gel with a gradient of ethyl acetate/hexanes afforded more of the title compound as a crystalline powder (675 mg) for a combined yield of 2.01 g; 67%. $^1$H NMR (DMSO-$d_6$): δ 11.89 (s, 1H), 8.24 (d, J=2.0 Hz, 1H), 8.17 (d, J=2.5 Hz, 1H), 7.53 (t, J=3.0 Hz, 1H), 6.42 (dd, J=1.0, 3.0 Hz, 1H); HPLC/MS m/z: 197 [MH]$^+$.

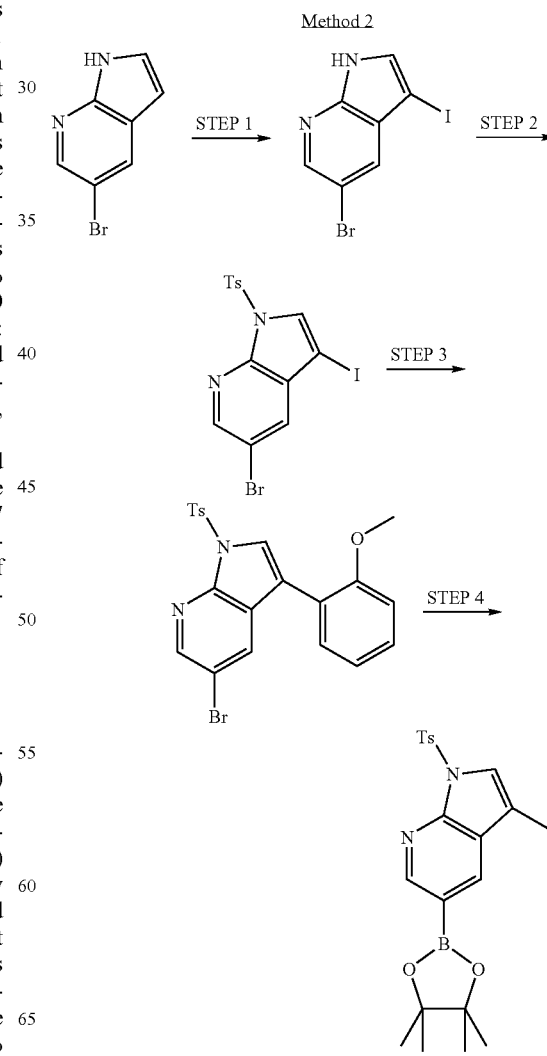

Method 2

Step 1: Synthesis of 5-bromo-3-iodo-1H-pyrrolo[2,3-b]pyridine

Into a 500 mL round bottomed flask were added 5-bromo-1H-pyrrolo[2,3-b]pyridine (10.11 g, 51.3 mmol) and 250 ml acetone. N-iodosuccinimide (NIS, 12.7 g, 56.4 mmol) was added, and the reaction mixture was stirred at room temperature for 1 hour. The precipitate was collected and washed with cold acetone to afford 12. 2 g (74%) of the title compound as a tan powder. $^1$H-NMR (500 MHz, d$_6$-DMSO) δ=12.35 (br.s, 1H), 8.29 (d, J=2.0 Hz, 1H), 7.84 (d, J=2.0 Hz 1H), 7.79 (s, 1H); MS: m/z 322.8/324.8 [MH$^+$].

Step 2: Synthesis of 5-Bromo-3-iodo-1-(toluene-4-sulfonyl)-1H-pyrrolo[2,3-b]pyridine Into a 250 mL round bottomed flask were added 5-bromo-3-iodo-1H-pyrrolo[2,3-b]pyridine (8.00 g, 40.6 mmol) and 120 mL dry THF. The solution was cooled in an ice bath at 0° C. and NaH (2.40 g, 60.0 mmol) was added in three portions. After 20 min, p-toluenesulfonyl chloride (8.70 g, 45.63 mmol) was added, and the reaction mixture was allowed to warm to rt over 30 min. The reaction mixture was concentrated and hexanes was added to obtain a precipitate, which was collected and washed with ice cold 2M NaOH. The crude product was recrystallized from EtOAc/hexanes to afford 17.8 g (92%) of the title compound as a light tan powder. $^1$H-NMR (500 MHz, d$_6$-DMSO) δ 8.49 (d, J=2.5 Hz, 1H), 8.21 (s, 1H), 7.99 (d, J=2.0 Hz, 1H), 7.98 (d, J=8.5 Hz, 2H), 7.42 (d, J=8.5 Hz, 2H), 2.32 (s, 3H); MS: m/z 476.8/478.8 [MH$^+$].

Step 3: Synthesis of 5-Bromo-3-(2-methoxy-phenyl)-1-(toluene-4-sulfonyl)-1H-pyrrolo[2,3-b]pyridine Into a 500 mL round bottomed flask were added 5-Bromo-3-iodo-1-(toluene-4-sulfonyl)-1H-pyrrolo[2,3-b]pyridine (11.80 g, 20.96 mmol), 2-methoxyphenyl boronic acid (3.76 g, 24.74 mmol), dichlorobis(triphenylphosphine)palladium(II) (0.756 g, 1.08 mmol), acetonitrile (100 mL) and 100 mL of 2M Na$_2$CO$_3$ (aq). The flask was fitted with a reflux condenser and heated at 60° C. with rapid stirring under N$_2$ for 8 h. The reaction mixture was filtered to obtain a grey-tan precipitate, which was dissolved in EtOAc and washed with water followed by brine. Concentration of this solution afforded 7.70 g (80%) of the title compound as a tan powder. $^1$H-NMR (500 MHz, d$_6$-DMSO) δ 8.50 (d, J=2.0 Hz, 1H), 8.14 (d, J=2.5 Hz, 1H), 8.07 (s, 1H), 8.03 (d, J=8.0 Hz, 2H), 7.54 (dd, J=1.5, 7.5 Hz, 1H), 7.43 (d, J=8.0 Hz, 2H), 7.39 (m, 1H), 7.15 (d, J=7.5 Hz, 1H), 7.05 (t, J=7.0 Hz, 1H), 3.80 (s. 3H), 2.34 (s, 3H); MS: m/z 456.9/458.9 [MH$^+$].

Step 4: Synthesis of 3-(2-Methoxy-phenyl)-5-(4,4,5,5-tetramethyl-[1,3,2]dioxaborolan-2-yl)-1-(toluene-4-sulfonyl)-1H-pyrrolo[2,3-b]pyridine Into a 5 mL Personal Chemistry microwave reaction vial were added 5-Bromo-3-(2-methoxy-phenyl)-1-(toluene-4-sulfonyl)-1H-pyrrolo[2,3-b]pyridine (0.102 g, 0.220 mmol), Bis(pinacolato)diboron (0.123 g, 0.483 mmol), 1,1′-bis(diphenylphosphino)ferrocenepalladium(II)-dichloride dichloromethane adduct (9.1 mg, 0.01 mmol) and anhydrous sodium acetate (55 mg, 0.67 mmol) and anhydrous DMF (1 mL). The resulting mixture was irradiated in a Personal Chemistry Optimizer at 140° C. for 60 min and then diluted with EtOAc and extracted 4× with water. The organic phase was treated with brine, dried (Na$_2$SO$_4$), filtered and concentrated. The crude product was purified by flash silica gel chromatography using a gradient of ethyl acetate in hexanes to afford 90.9 mg (81%) of the title compound a white powder. $^1$H-NMR (500 MHz, CDCl$_3$) δ 8.79 (d, J=1.0 Hz, 1H), 8.32 (d, J=1.0 Hz, 1H), 8.11 (d, J=5.5 Hz, 2H), 7.94 (d, J=3.0 Hz, 1H), 7.50 (m, 1H), 7.35 (t, J=7.5 Hz, 1H), 7.25 (d, J=7.5 Hz, 2H), 7.05 (t, J=7.2 Hz, 1H), 7.01 (d, J=7.2 Hz, 1H), 3.85 (s, 3H), 2.35 (s, 3H), 1.31 (s, 12H); MS: m/z 505.1 [MH$^+$].

Other compounds prepared by Method 2 are shown in Table 1:

TABLE 1

| Structure |
| --- |
| 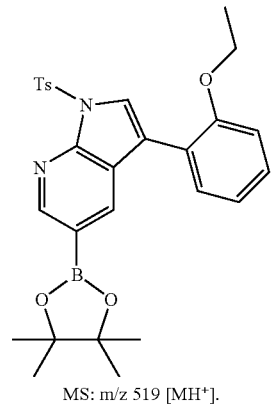<br>MS: m/z 519 [MH$^+$]. |
| 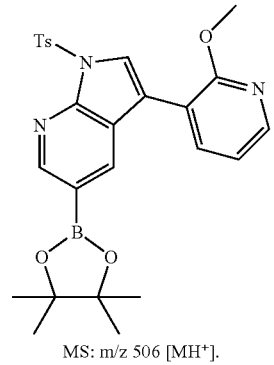<br>MS: m/z 506 [MH$^+$]. |
| 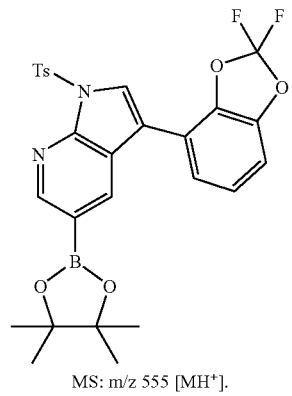<br>MS: m/z 555 [MH$^+$]. |

TABLE 1-continued
Structure
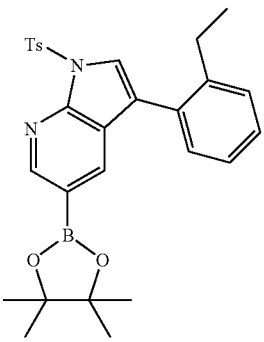
MS: m/z 503 [MH+].
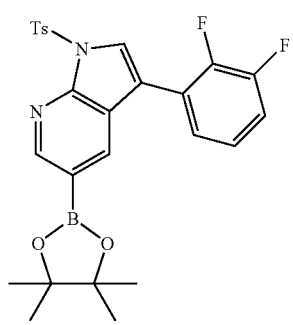
MS: m/z 511 [MH+].
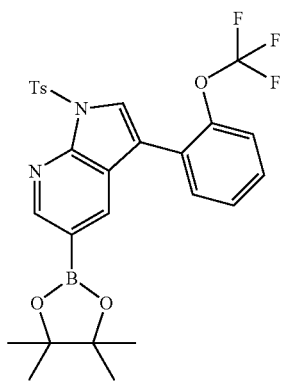
MS: m/z 559 [MH+].
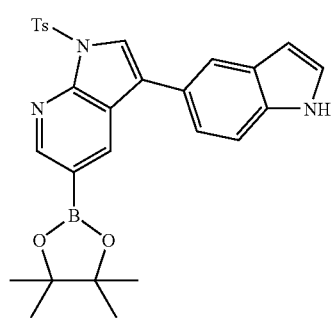
MS: m/z 514 [MH+].
TABLE 1-continued
Structure
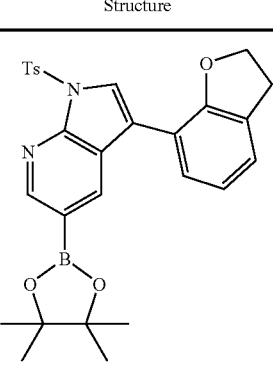
MS: m/z 517 [MH+].
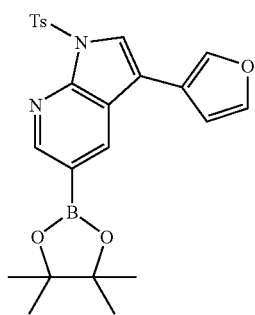
MS: m/z 465 [MH+].
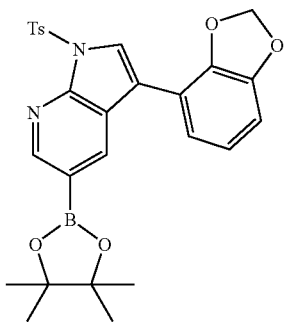
MS: m/z 519 [MH+].
Method 3
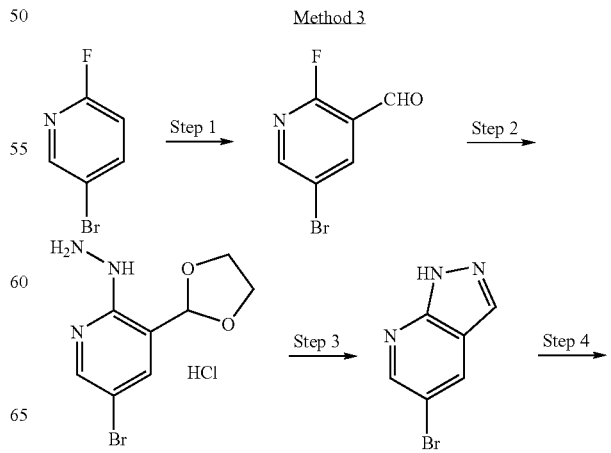

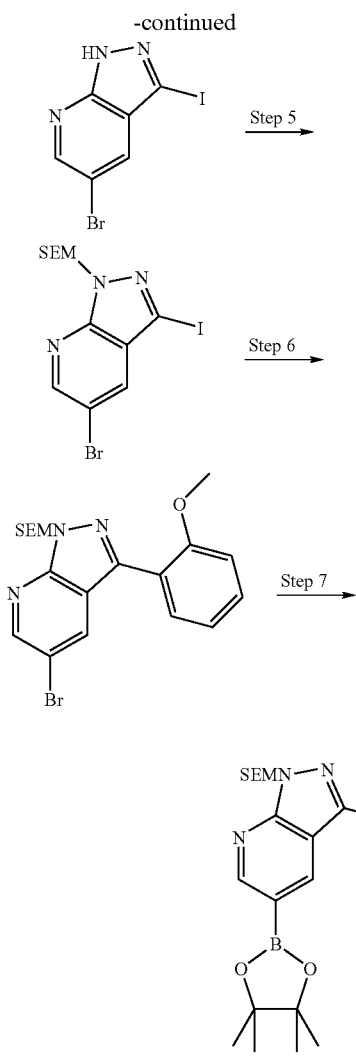

Step 1: Synthesis of
5-bromo-2-fluoro-pyridine-3-carbaldehyde

A solution of lithium di-iso-propylamine (5 mL, 35 mmol) in anhydrous THF (40 mL) was cooled to −78° C. under nitrogen and n-butyl lithium (2.5 M in hexanes, 12 mL, 30 mmol) was added. The mixture was then stirred at −78° C. for 15 min before 5-bromo-2-fluoro-pyridine (5 g, 28 mmol) was added. The resulting mixture was then stirred at −78° C. for 90 min. N-formylpiperidine (4 mL, 36 mmol) was added very rapidly to the suspension at −78° C. and the mixture stirred vigorously for 60 sec. The reaction was immediately quenched by the addition of a 10% (w/v) aqueous solution of citric acid. The mixture was warmed to room temperature and distributed between water and dichloromethane. The aqueous phase was extracted three times with dichloromethane and the organic phases were combined, dried over sodium sulfate, filtered and concentrated. Crystallization of the crude product from cyclohexane afforded 5-bromo-2-fluoro-pyridine-3-carbaldehyde (2.993 g, 52% yield) as pale beige flaky crystals. $^1$H-NMR (500 MHz, $d_6$-DMSO) δ 10.07 (s, 1H), 8.70 (dd, 1H), 8.55 (dd, 1H). MS: m/z 236, 238 [MNa$^+$], 204, 206 [MH$^+$], 176, 178 [MH—CO$^+$].

Steps 2 and 3: Synthesis of
5-bromo-1H-pyrazolo[3,4-b]pyridine 5-bromo-2-fluoro-pyridine-3-carbaldehyde (13.66 g, 66.96 mmol), pinacol (8.75 g, 74.0 mmol) and para-toluenesulfonic acid monohydrate (1.50 g, 7.89 mmol) were placed in a flask equipped with a DEAN-STARK-condenser and dissolved in anhydrous benzene (400 mL). The mixture was heated to reflux and solvent distilled off until the distillate remains clear and the remaining volume was approximately 200 ml. The mixture was diluted with ethyl acetate (300 mL) and washed with a saturated aqueous solution of sodium bicarbonate and brine, then dried over sodium sulfate, filtered and concentrated. The resulting residue was dissolved in a mixture of ethanol (400 mL) and di-iso-propyl-ethyl-amine (25 mL). Anhydrous hydrazine (15 ml, 0.48 mol) was then added and the resulting mixture was stirred under reflux conditions for 4 h. The mixture was then concentrated to dryness and the resulting residue was distributed between water and toluene. The organic phase was washed with brine twice, dried over sodium sulfate, filtered and concentrated. The residue was dissolved in anhydrous ether (700 mL) and hydrogen chloride in anhydrous ether (2M, 70 mL) was added slowly to the vigorously stirred solution. The precipitate was filtered off, washed with ether and hexane and then dried in vacuum. $^1$H-NMR (500 MHz, $d_6$-DMSO) δ 10.31 (s,br, 1H), 8.86 (s, 1H), 8.37 (d, 1H), 7.88 (d, 1H), 6.08 (s, 1H), 3.56 (s,br), 1.27 (s, 6H), 1.19 (s, 6H). MS: m/z 198, 200 [MH$^+$].

The above solid was dissolved in a mixture of water (500 mL), ethanol (200 mL) and concentrated aqueous hydrochloric acid (50 mL) at 50-65° C. The mixture was then stirred at room temperature for 16 h before being neutralized to pH=8 with sodium bicarbonate. The resulting precipitate was filtered off and the aqueous phase extracted three times with ethyl acetate. The combined organic phases are washed with brine, dried over sodium sulfate, filtered and concentrated. The resulting residue and the precipitate obtained are crystallized from ethanol to afford 5-bromo-1H-pyrazolo[3,4-b]pyridine (6.615 g, 50% yield) as a crystalline beige to pale olive-green solid. $^1$H-NMR (500 MHz, $d_6$-DMSO) δ 13.91 (s, 1H), 8.60 (d, 1H), 8.54 (d, 1H), 8.16 (s, br, 1H). MS: m/z 198, 200 [MH$^+$].

Step 4. Synthesis of
5-bromo-3-iodo-1H-pyrazolo[3,4-b]pyridine 5-bromo-1H-pyrazolo[3,4-b]pyridine (3.00 g, 15.2 mmol) and N-iodosuccinimide (3.60 g, 16.0 mmol) were dissolved in anhydrous dichloroethane (100 mL). The resulting mixture was stirred under reflux conditions for 6 h, cooled to room temperature and diluted with THF (300 mL). The resulting solution was washed with a saturated aqueous solution of sodium thiosulfate (100 mL) and brine, then dried over magnesium sulfate, filtered and concentrated. The residue was titurated with a 1:1 mixture of dichloromethane and ether and then ether before being dried in vacuum to afford 5-bromo-3-iodo-1H-pyrazolo[3,4-b]pyridine (3.795 g, 77% yield) as a beige-brown solid. $^1$H-NMR (500 MHz, $d_6$-DMSO) δ 14.31 (s, 1H), 8.65 (d, 1H), 8.20 (d, 1H). MS: m/z 323, 325 [MH$^+$].

Step 5: Synthesis of 5-bromo-3-iodo-1-(2-trimethylsilanyl-ethoxymethyl)-1H-pyrazolo[3,4-b]pyridine Under nitrogen 5-bromo-3-iodo-1H-pyrazolo[3,4-b]pyridine (2.68 g, 8.27 mmol) was dissolved in anhydrous DMF (40 mL). The solution was cooled to 0-5° C. and an excess of dry sodium hydride added until further addition does not result in hydrogen formation. To the resulting suspension was added 2-trimethylsilanyl-ethoxymethylchloride (2.5 ml, 14 mmol) drop wise at 0-5° C. The resulting mixture was stirred at 0° C. for 1 h and thereafter quenched by addition of methanol and subsequently of a saturated aqueous solution of ammonium chloride. The mixture was then concentrated to dryness at 50° C. under reduced pressure. The resulting residue was distributed between water, brine and dichloromethane. The aqueous phase was then extracted with dichloromethane and the combined organic phases were dried over sodium sulfate, filtered and concentrated. The crude product was purified by flash silica gel chromatography using a gradient of ethyl acetate in hexanes to afford 5-bromo-3-iodo-1-(2-trimethylsilanyl-ethoxymethyl)-1H-pyrazolo[3,4-b]pyridine (2.929 g, 78% yield) as a beige to brown solid. $^1$H-NMR (500 MHz, d$_6$-DMSO) δ 8.85 (d, 1H), 8.40 (d, 1H), 5.85 (s, 2H), 3.69 (t, 2H), 0.92 (t, 2H), 0.11 (s, 9H).

Step 6: Synthesis of 5-bromo-3-(2-methoxy-phenyl)-1-(2-trimethylsilanyl-ethoxymethyl)-1H-pyrazolo[3,4-b]pyridine A mixture of 5-bromo-3-iodo-1-(2-trimethylsilanyl-ethoxymethyl)-1H-pyrazolo[3,4-b]pyridine (1.606 g, 3.537 mmol), 2-methoxy-phenyl-boronic acid (575 mg, 3.78 mmol) and of 1,1'-bis(diphenylphosphino)ferrocenepalladium(II)-dichloride dichloromethane adduct (145 mg, 0.178 mmol) in acetonitrile (8 mL) and aqueous solution of sodium carbonate (2M, 8 mL) was stirred in a closed vial at 85° C. for 100 min. The resulting mixture was then distributed between a saturated aqueous solution of sodium bicarbonate and dichloromethane and the aqueous phase extracted three times with dichloromethane. The combined organic phases were dried over sodium sulfate, filtered and concentrated. The crude product was purified by flash silica gel chromatography using a gradient of ethyl acetate in hexanes to afford 5-bromo-3-(2-methoxy-phenyl)-1-(2-trimethylsilanyl-ethoxymethyl)-1H-pyrazolo[3,4-b]pyridine (1.002 g, 65% yield) as an off-white oil. $^1$H-NMR (500 MHz, d$_6$-DMSO) δ 8.70 (d, 1H), 8.40 (d, 1H), 7.61 (d, 1H), 7.50 (ddd, 1H), 7.23 (dd, 1H), 7.10 (ddd, 1H), 5.81 (s, 2H), 3.85 (s, 3H), 3.66 (t, 2H), 0.84 (t, 2H), −0.10 (s, 9H). MS: m/z 456, 458 [MNa$^+$].

Step 7: Synthesis of 3-(2-methoxy-phenyl)-5-(4,4,5,5-tetramethyl-[1,3,2]dioxaborolan-2-yl)-1-(2-trimethylsilanyl-ethoxymethyl)-1H-pyrazolo[3,4-b]pyridine Bis(pinacolato)diboron (1.20 g, 4.73 mmol), 1,1'-bis(diphenylphosphino)ferrocene-palladium(II)-dichloride dichlormethane adduct (100 mg, 0.122 mmol) and anhydrous sodium acetate (625 mg, 7.62 mmol) were placed in a nitrogen flushed vial. To this was added a solution of 5-bromo-3-(2-methoxy-phenyl)-1-(2-trimethylsilanyl-ethoxymethyl)-1H-pyrazolo[3,4-b]pyridine (1.002 g, 2.307 mmol) in anhydrous DMF (15 mL). The resulting mixture was irradiated in a Personal Chemistry Optimizer at 130° C. for 60 min and then concentrated at 50° C. under reduced pressure. The resulting residue was distributed between ether and brine and the aqueous phase was extracted with ether. The organic phases were combined, dried over sodium sulfate, filtered and concentrated. The crude product was then purified by flash silica gel chromatography using a gradient of ethyl acetate in hexanes to afford 3-(2-methoxy-phenyl)-5-(4,4,5,5-tetramethyl-[1,3,2]dioxaborolan-2-yl)-1-(2-trimethylsilanyl-ethoxymethyl)-1H-pyrazolo[3,4-b]pyridine (1.370 g, 123% yield) as a pale olive-green solid. $^1$H-NMR (500 MHz, d$_6$-DMSO) δ 8.76 (d, 1H), 8.40 (d, 1H), 7.59 (dd, 1H), 7.51 (ddd, 1H), 7.25 (m, 1H), 7.12 (ddd, 1H), 5.84 (s, 2H), 3.82 (s, 3H), 3.67 (t, 2H), 1.33 (s, 12H), 0.84 (t, 2H), −0.10 (s, 9H).

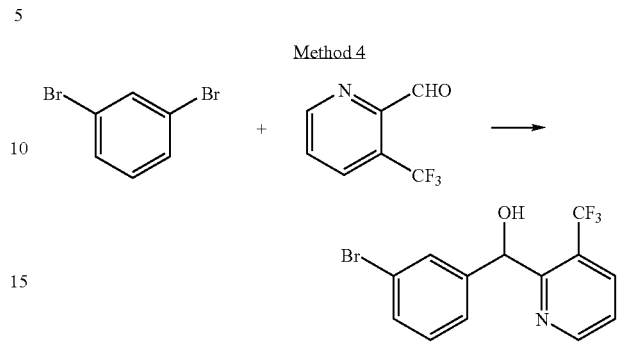

Synthesis of (3-bromo-phenyl)-(3-trifluoromethyl-pyridin-2-yl)-methanol 25 mL of anhydrous THF was placed under nitrogen and cooled to −78° C. 2.2 ml (5.5 mmol) of a 2.5 M solution of n-butyl lithium in hexanes were added. To the resulting solution was slowly added 0.7 mL (1.4 g, 5.8 mmol) of 1,3-dibromobenzene. Upon complete addition the resulting solution was stirred at −78° C. for 90 min. 1.00 g (5.71 mmol) of 3-trifluoromethyl-pyridine-2-carbaldehyde was added rapidly. The dark solution was warmed to −20° C. and stirred for 20 min at that temperature. The resulting mixture was distributed between 10% aqueous citric acid and dichloromethane. The phases were separated and the aqueous layer extracted three times with dichloromethane. The combined organic phases were dried over sodium sulfate and the solvent completely evaporated. The resulting residue was purified by flash chromatography on silica gel using a gradient of ethyl acetate in hexanes to afford 1.053 g (3.171 mmol, 58%) of (3-bromo-phenyl)-(3-trifluoromethyl-pyridin-2-yl)-methanol as a yellow oil. $^1$H NMR (500 MHz, DMSO-d$_6$) δ 8.84 (m, 1H), 8.18 (dd, 1H), 7.63 (m, 1H), 7.53 (dd, 1H), 7.42 (m, 1H), 7.26-7.24 (m, 2H), 6.31 (d, 1H), 6.02 (d, 1H); MS: m/z 332.0+334.0 (M+H$^+$).

Other intermediates prepared by Method 4 are shown in Table 2:

TABLE 2

| Structure | MS: m/z (M + H$^+$) |
|---|---|
| Br—⬡—CH(OH)—pyridin-2-yl | 264.0 + 266.0 |
| Br—⬡—CH(OH)—(1-methyl-imidazol-2-yl) | 266.9 + 269.0 |

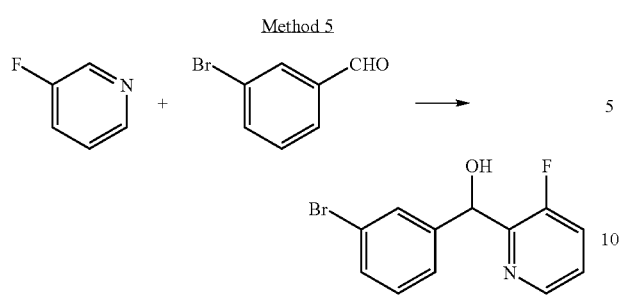

Method 5

Synthesis of (3-bromo-phenyl)-(3-fluoro-pyridin-2-yl)-methanol

Under nitrogen 4.27 g (38.1 mmol) of 1,4-diazabicyclo[2.2.2]octane was dispersed in 100 mL of anhydrous diethyl ether at room temperature. The resulting suspension was cooled to −78° C. and 15 mL (37.5 mmol) of a 2.5 M solution of n-butyl lithium in hexanes was added. Upon stirring at −78° C. for 15 min, 3.36 g (34.6 mmol) of 3-fluoropyridine was added dropwise at that temperature. The resulting reaction mixture was stirred at −78° C. for 1 h. To the resulting yellow suspension was added 5 mL (8 g, 43 mmol) of 3-bromobenzaldehyde and the resulting solution stirred at −78° C. to −20° C. for 2 h. The reaction was then quenched by addition of 10% aqueous citric acid and distributed between dichloromethane and water. The aqueous layer showed a pH of about 3 and was extracted with dichloromethane. The combined organic phases were dried over sodium sulfate and evaporated. The resulting residue was purified by flash chromatography on silica gel using a gradient of ethyl acetate in hexanes to afford 3.775 (13.38 mmol, 39%) of (3-bromo-phenyl)-(3-fluoro-pyridin-2-yl)-methanol as a tan oil. $^1$H NMR (500 MHz, DMSO-$d_6$) δ 8.40 (dt, 1H), 7.69 (ddd, 1H), 7.63 (m, br., 1H), 7.44 (dm, 1H), 7.42 (dd, 1H), 7.35 (d(m), 1H), 7.23 (t, 1H), 6.25 (d, 1H), 6.01 (d, 1H); MS: m/z 282.0+284.0 (M+H$^+$).

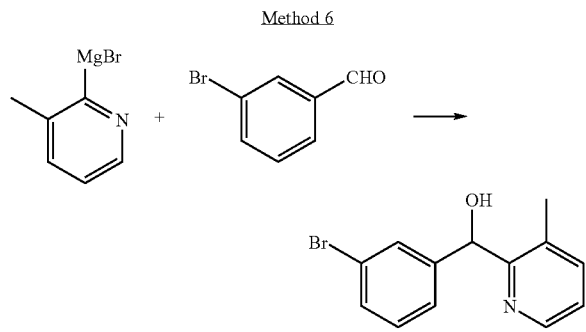

Method 6

Synthesis of (3-bromo-phenyl)-(3-methyl-pyridin-2-yl)-methanol

Under nitrogen 0.5 mL (794 mg, 4.3 mmol) of 3-bromobenzaldehyde was was added to 30 mL (7.5 mmol) of a 0.25 M solution of 3-methyl-2-pyridylmagnesium bromide in THF (obtained commercially from Rieke Metals, Inc.) at room temperature. The resulting mixture was heated to reflux for 18 h. The resulting mixture was distributed between 10% aqueous citric acid and dichloromethane. The phases were separated and the aqueous layer extracted three times with dichloromethane. The combined organic phases were washed with a saturated aqueous solution of sodium bromide, dried over sodium sulfate and completely evaporated. The resulting residue was purified by flash chromatography on silica gel using a gradient of ethyl acetate in hexanes to afford 244 mg (0.88 mmol, 12%) of 3-bromo-phenyl)-(3-methyl-pyridin-2-yl)-methanol as a yellow oil. $^1$H NMR (500 MHz, DMSO-$d_6$) δ 8.39 (dd, 1H), 7.57 (d(m), 1H), 7.52 (d(m), 1H), 7.41 (m, 1H), 7.30 (m, 1H), 7.27 (t, 1H), 7.24 (dd, 1H), 6.07 (d, 1H), 5.91 (d, 1H), 2.24 (s, 3H); MS: m/z 278.0+280.0 (M+H$^+$).

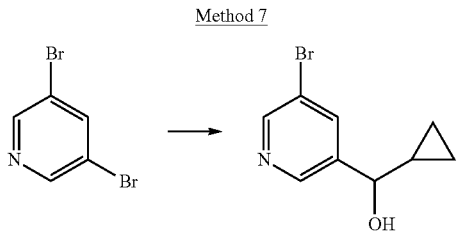

Method 7

Synthesis of (5-Bromo-pyridin-3-yl)-cyclopropyl-methanol intermediate 3,5-Dibromo-pyridine (1 g, 4.22 mmol) was dissolved in 5 mL of tetrahydrofuran and cooled to 0° C. A solution of isopropyl magnesium lithium chloride (15% in tetrahydrofuran, 5.07 mL, 5.06 mmol) was added dropwise and the solution was stirred for 15 min at 0° C. The resulting solution was added to a solution of cyclopropyl aldehyde (0.31 mL, 4.22 mmol) in 2 mL of tetrahydrofuran at 0° C. and the mixture was stirred for another 30 min at 0° C. The reaction was quenched with a saturated solution of ammonium chloride (10 mL) and water (10 mL). The crude mixture was passed through a Varian Chemelut cartridge (ethyl acetate as eluent) and concentrated to afford 623 mg of (5-Bromo-pyridin-3-yl)-cyclopropyl-methanol as an oil (2.73 mmol, 65% yield). $^1$H NMR (500 MHz, DMSO-$d_6$) δ 8.57 (m, 2H), 7.99 (t, J=2 Hz, 1H), 5.49 (d, J=5 Hz, 1H), 4.02 (m, 1H), 1.04 (m, 1H), 0.47 (m, 1H), 0.4 (m, 3H). MS: m/z 228.0/230.0 (M+H$^+$).

The following intermediate was synthesized in a manner analogous to the synthesis of (5-Bromo-pyridin-3-yl)-cyclopropyl-methanol, described above.

| Structure | MS: m/z (M + H$^+$) |
|---|---|
|  Br, pyridine with CH(OH)CH2CH(CH3)2 | 244.0 + 246.0 |

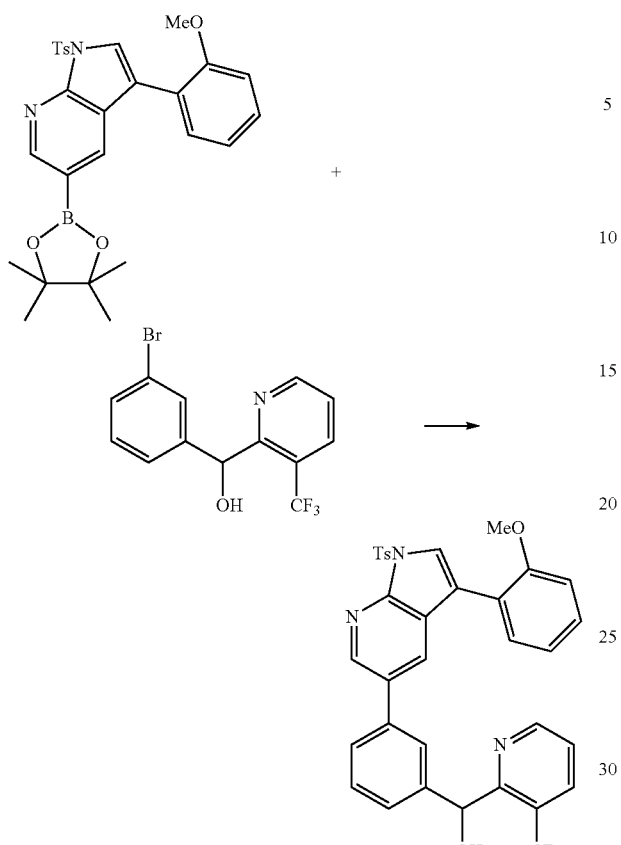

Synthesis of {3-[3-(2-methoxy-phenyl)-1-(toluene-4-sulfonyl)-1H-pyrrolo[2,3-b]pyridin-5-yl]-phenyl}-(3-trifluoromethyl-pyridin-2-yl)-methanol 504 mg (1.00 mmol) of 3-(2-methoxy-phenyl)-5-(4,4,5,5-tetramethyl-[1,3,2]dioxaborolan-2-yl)-1-(toluene-4-sulfonyl)-1H-pyrrolo[2,3-b]pyridine, 50 mg (61 μmol) of dichloro [1,1'-bis(diphenylphoshino)ferrocene]-palladium(II) dichloromethane adduct and 337 mg (1.01 mmol) of (3-bromo-phenyl)-(3-trifluoromethyl-pyridin-2-yl)-methanol were place in a microwave vial. 8 mL of acetonitrile, 3 mL of toluene and 8 mL of a saturated aqueous solution of sodium bicarbonate were added. The vial was sealed and irradiated in a Personal Chemistry® Optimizer to 125° C. for 20 min. The resulting mixture was distributed between dichloromethane and a saturated aqueous solution of sodium bicarbonate. The aqueous layer was extracted twice with dichloromethane and the combined organic phases were dried over sodium sulfate and evaporated. The resulting residue was purified by flash chromatography on silica gel using a gradient of ethyl acetate in hexanes to afford 397 mg (0.63 mmol, 63%) of {3-[3-(2-methoxy-phenyl)-1-(toluene-4-sulfonyl)-1H-pyrrolo[2,3-b]pyridin-5-yl]-phenyl}-(3-trifluoromethyl-pyridin-2-yl)-methanol as an ivory solid. $^1$H NMR (500 MHz, DMSO-$d_6$) δ 8.45 (d, 1H), 8.65 (d, 1H), 8.19 (dd, 1H), 8.09 (d, 2H), 8.07 (d, 1H), 8.06 (s, 1H), 7.75 (s, br., 1H), 7.61-7.58 (m, 1H), 7.53 (dd, 1H), 7.45 (d, 2H), 7.43-7.40 (m, 2H), 7.35 (d(m), 1H), 7.21 (d, 1H), 7.09 (dd(d), 1H), 6.24 (d, 1H), 6.09 (d, 1H), 3.83 (s, 3H), 2.36 (s, 3H); MS: m/z 630.1 (M+H$^+$).

Other intermediates prepared by Method 7 are shown in Table 3:

TABLE 3

| Structure | MS: m/z (M + H$^+$) |
|---|---|
| 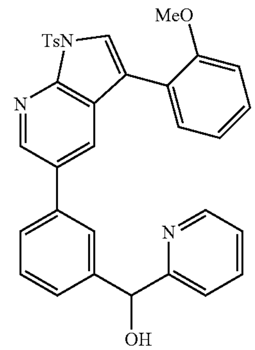 | 562 |
| | 565 (microwave heating to 125-140° for 50 min) |
| 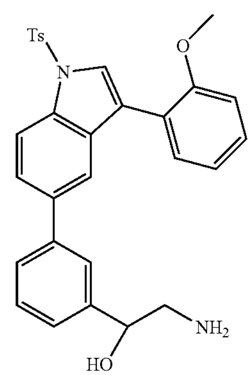 | 513 |
| 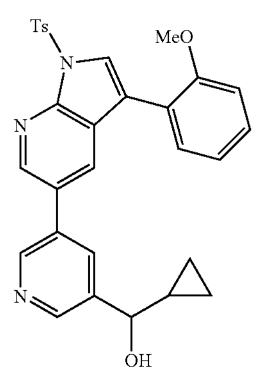 | 526.2 |

TABLE 3-continued

| Structure | MS: m/z (M + H+) |
|---|---|
| 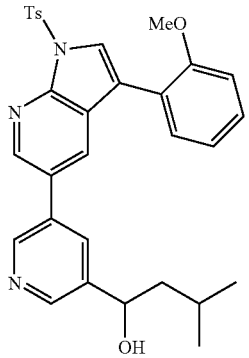 | 542.2 |

Method 8

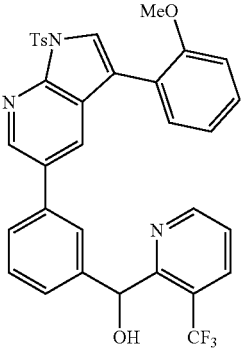

Synthesis of {3-[3-(2-methoxy-phenyl)-1H-pyrrolo[2,3-b]pyridin-5-yl]-phenyl}-(3-trifluoromethyl-pyridin-2-yl)-methanol 390 mg (0.62 mmol) of {3-[3-(2-methoxy-phenyl)-1-(toluene-4-sulfonyl)-1H-pyrrolo[2,3-b]pyridin-5-yl]-phenyl}-(3-trifluoromethyl-pyridin-2-yl)-methanol was dissolved in ethanol under gentle warming. The resulting solution was diluted with 2 M aqueous sodium hydroxide (16-30% v/v) and the resulting mixture was left at room temperature for 16 h. The pH was adjusted to 8 by addition of concentrated aqueous hydrochloric acid and the resulting solution was extracted three times with chloroform. The combined organic phases were dried over sodium sulfate and evaporated to afford 144 mg (0.30 mmol, 49%) of {3-[3-(2-methoxy-phenyl)-1H-pyrrolo[2,3-b]pyridin-5-yl]-phenyl}-(3-trifluoromethyl-pyridin-2-yl)-methanol as a yellow solid. $^1$H NMR (500 MHz, DMSO-$d_6$) δ 11.93 (d, 1H), 8.86 (d, 1H), 8.49 (d, 1H), 8.20 (dd, 1H), 8.11 (d, 1H), 7.75 (s, br., 1H), 7.73 (d, 1H), 7.58 (d(m), 1H), 7.56 (d, 1H), 7.54 (dd, 1H), 7.40 (t, 1H), 7.32-7.29 (m, 2H), 7.15 (dd, 1H), 7.05 (dd, 1H), 6.23 (d, 1H), 6.09 (d, 1H), 3.82 (s, 3H); MS: m/z 476.1 (M+H+).

Other compounds prepared by method 8 are shown in Tables 4A and 4B:

TABLE 4A

| Structure | MS: m/z (M + H+) |
|---|---|
| 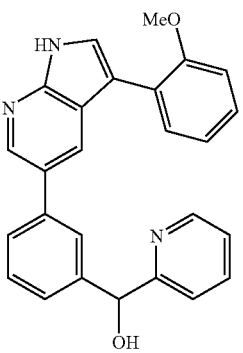 | 408.1 |
| 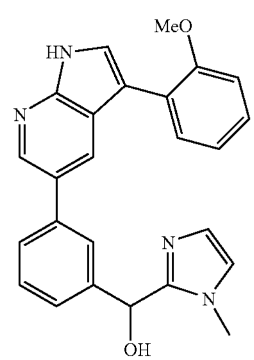 | 411.1 |
| 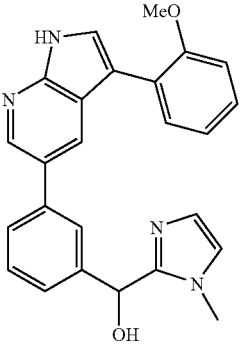 | 360.4 |

TABLE 4B

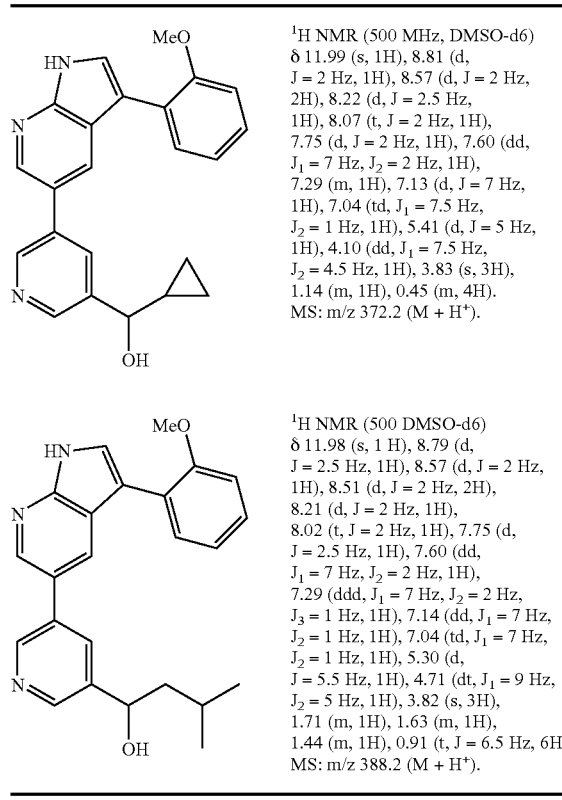

¹H NMR (500 MHz, DMSO-d6) δ 11.99 (s, 1H), 8.81 (d, J = 2 Hz, 1H), 8.57 (d, J = 2 Hz, 2H), 8.22 (d, J = 2.5 Hz, 1H), 8.07 (t, J = 2 Hz, 1H), 7.75 (d, J = 2 Hz, 1H), 7.60 (dd, $J_1$ = 7 Hz, $J_2$ = 2 Hz, 1H), 7.29 (m, 1H), 7.13 (d, J = 7 Hz, 1H), 7.04 (td, $J_1$ = 7.5 Hz, $J_2$ = 1 Hz, 1H), 5.41 (d, J = 5 Hz, 1H), 4.10 (dd, $J_1$ = 7.5 Hz, $J_2$ = 4.5 Hz, 1H), 3.83 (s, 3H), 1.14 (m, 1H), 0.45 (m, 4H). MS: m/z 372.2 (M + H⁺).

¹H NMR (500 DMSO-d6) δ 11.98 (s, 1 H), 8.79 (d, J = 2.5 Hz, 1H), 8.57 (d, J = 2 Hz, 1H), 8.51 (d, J = 2 Hz, 2H), 8.21 (d, J = 2 Hz, 1H), 8.02 (t, J = 2 Hz, 1H), 7.75 (d, J = 2.5 Hz, 1H), 7.60 (dd, $J_1$ = 7 Hz, $J_2$ = 2 Hz, 1H), 7.29 (ddd, $J_1$ = 7 Hz, $J_2$ = 2 Hz, $J_3$ = 1 Hz, 1H), 7.14 (dd, $J_1$ = 7 Hz, $J_2$ = 1 Hz, 1H), 7.04 (td, $J_1$ = 7 Hz, $J_2$ = 1 Hz, 1H), 5.30 (d, J = 5.5 Hz, 1H), 4.71 (dt, $J_1$ = 9 Hz, $J_2$ = 5 Hz, 1H), 3.82 (s, 3H), 1.71 (m, 1H), 1.63 (m, 1H), 1.44 (m, 1H), 0.91 (t, J = 6.5 Hz, 6H). MS: m/z 388.2 (M + H⁺).

Method 9

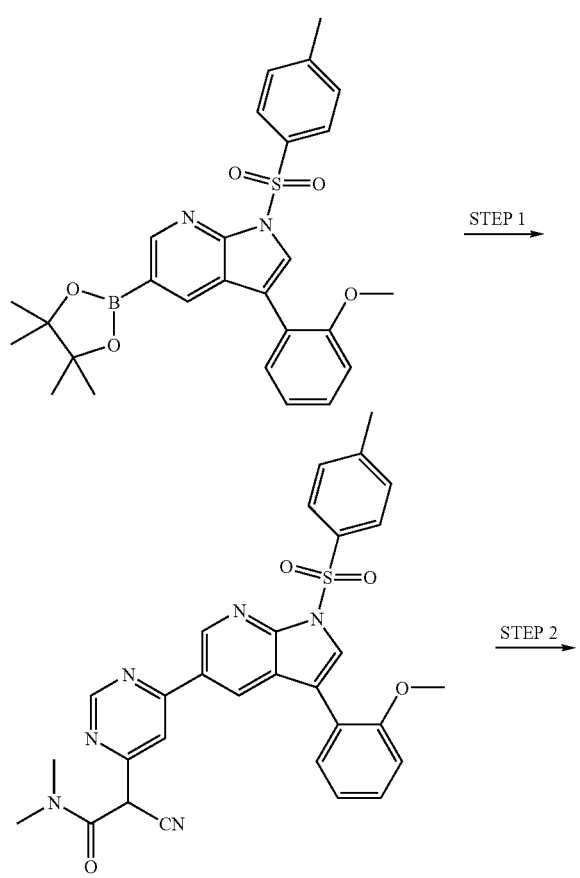

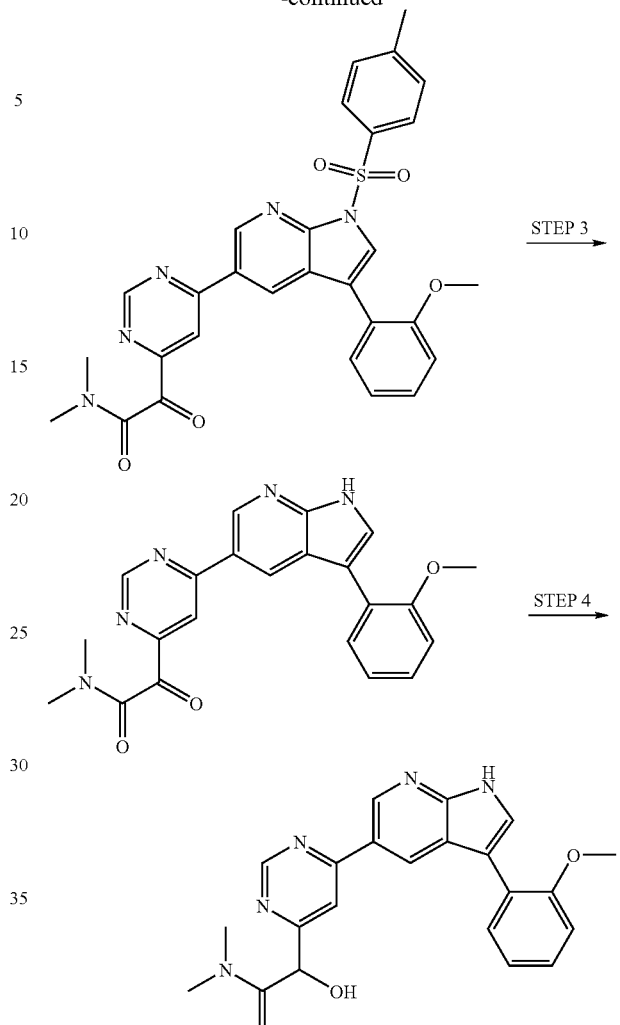

Synthesis of 2-Hydroxy-2-{6-[3-(2-methoxy-phenyl)-1H-pyrrolo[2,3-b]pyridin-5-yl]-pyrimidin-4-yl}-N,N-dimethyl-acetamide Step 1: Synthesis of 2-Cyano-2-{6-[3-(2-methoxy-phenyl)-1-(toluene-4-sulfonyl)-1H-pyrrolo[2,3-b]pyridin-5-yl]-pyrimidin-4-yl}-N,N-dimethyl-acetamide A mixture of 3-(2-Methoxy-phenyl)-5-(4,4,5,5-tetramethyl-[1,3,2]dioxaborolan-2-yl)-1-(toluene-4-sulfonyl)-1H-pyrrolo[2,3-b]pyridine (1.0 g, 2.0 mmole), 2-(6-Chloro-pyrimidin-4-yl)-2-cyano-N,N-dimethyl-acetamide (prepared according to the method published in *Tetrahedron Letters* (2005) 46, 3587-3589) (670 mg, 3.0 mmole), sodium bicarbonate, (2M aq, 4.9 mmole), acetonitrile (13.2 mL), and dichloro[1,1'-bis(diphenylphosphino)ferrocene]palladium (II) dichloromethane adduct (97 mg, 0.12 mmole) was heated in a microwave reactor at 120° C. for 45 min. The crude mixture was concentrated to dryness, suspended in water (50 mL), and stirred for 30 min. The resulting precipitate was filtered off, suspended in ethyl acetate (15 mL), and stirred for 15 h. The precipitate was filtered off, rinsed with ethyl acetate (3×5 mL), and air dried. Recrystallization from ethylacetate/ methanol afforded 2-cyano-2-{6-[3-(2-methoxy-phenyl)-1-(toluene-4-sulfonyl)-1H-pyrrolo[2,3-b]pyridin-5-yl]-pyrimidin-4-yl}-N,N-dimethyl-acetamide (762 mg, 68% yield) as a bright yellow solid. MS: m/z 567.1 (M+H$^+$).

Step 2: Synthesis of 2-{6-[3-(2-Methoxy-phenyl)-1-(toluene-4-sulfonyl)-1H-pyrrolo[2,3-b]pyridin-5-yl]-pyrimidin-4-yl}-N,N-dimethyl-2-oxo-acetamide 2-Cyano-2-{6-[3-(2-methoxy-phenyl)-1-(toluene-4-sulfonyl)-1H-pyrrolo[2,3-b]pyridin-5-yl]-pyrimidin-4-yl}-N,N-dimethyl-acetamide (500 mg, 0.88 mmole) was suspended in tetrahydrofuran (11 mL) and cooled to 0° C. in an ice bath. Peroxy acetic acid (32% in acetic acid, 174 mg, 2.29 mmole) was added and after 10 min, the heterogeneous solution was removed from the ice bath and maintained at ambient temperature for 6 h. Sodium bisulfite (918 mg, 8.83 mmole) in water (10 mL) was added, followed by saturated aqueous sodium bicarbonate (20 mL) and the mixture extracted with ethyl acetate (3×30 mL). The combined organic portions were dried over magnesium sulfate, filtered, and concentrated to dryness. Silica gel chromatography of the crude residue afforded 2-{6-[3-(2-methoxy-phenyl)-1-(toluene-4-sulfonyl)-1H-pyrrolo[2,3-b]pyridin-5-yl]-pyrimidin-4-yl}-N,N-dimethyl-2-oxo-acetamide (315 mg, 89% yield) as a clear residue. MS: m/z 402.2 (M+H$^+$).

Step 3: Synthesis of 2-{6-[3-(2-Methoxy-phenyl)-1H-pyrrolo[2,3-b]pyridin-5-yl]-pyrimidin-4-yl}-N,N-dimethyl-2-oxo-acetamide 2-{6-[3-(2-Methoxy-phenyl)-1-(toluene-4-sulfonyl)-1H-pyrrolo[2,3-b]pyridin-5-yl]-pyrimidin-4-yl}-N,N-dimethyl-2-oxo-acetamide (100 mg, 0.179 mmole) in methanol (3.6 mL) was cooled to 0° C. in an ice bath. Potassium hydroxide (aqueous 50% w/v, 0.06 mL) was added, the solution removed from the ice bath, maintained at ambient temperature for 15 hrs, and quenched with acetic acid (0.06 mL). The resulting solution was concentrated to remove all volatile organics, dissolved in ethyl acetate (10 mL), washed with sodium bicarbonate (5 mL), then with water (5 mL), then with brine (5 mL), and dried over magnesium sulfate. The solution was filtered and concentrated to dryness to afford 2-{6-[3-(2-methoxy-phenyl)-1H-pyrrolo[2,3-b]pyridin-5-yl]-pyrimidin-4-yl}-N,N-dimethyl-2-oxo-acetamide (63 mg, 72%) as a yellow solid which was used without further purification. MS: m/z 402.2 (M+H$^+$).

Step 4: Synthesis of 2-Hydroxy-2-{6-[3-(2-methoxy-phenyl)-1H-pyrrolo[2,3-b]pyridin-5-yl]-pyrimidin-4-yl}-N,N-dimethyl-acetamide A solution of 2-{6-[3-(2-Methoxy-phenyl)-1H-pyrrolo[2,3-b]pyridin-5-yl]-pyrimidin-4-yl}-N,N-dimethyl-2-oxo-acetamide (25 mg, 0.062 mmole), in ethanol (0.4 mL), was cooled to 0° C. in an ice bath and sodium borohydride (7 mg, 0.186 mmole) added in one portion. The solution was removed from the cooling bath, maintained at ambient temperature for 15 min, heated to 50° C., and maintained for an additional 15 min. After cooling to ambient temperature, water (0.2 mL) was added followed by saturated ammonium chloride (0.2 mL). The reaction mixture was concentrated to remove most of the ethanol, diluted with ethyl acetate (10 mL), and the organic layer washed with saturated sodium bicarbonate (5 mL). The resulting organic layer was dried over magnesium sulfate, filtered, and concentrated. The crude product was dissolved in DMSO and purified by mass triggered reverse phase HPLC to afford pure 2-hydroxy-2-{6-[3-(2-methoxy-phenyl)-1H-pyrrolo[2,3-b]pyridin-5-yl]-pyrimidin-4-yl}-N,N-dimethyl-acetamide as a white solid. (2.3 mg, 9.2%). MS: m/z 404.2 (M+H$^+$). $^1$H NMR (500 MHz, DMSO-d6) δ 2.87 (s, 3H), 3.13 (s, 3H), 3.83 (s, 3H), 5.57 (d, J=8.0 Hz, 1H), 6.08 (s, J=8.5 Hz, 1H), 7.09 (t, 1H), 7.17 (d, J=8.5 Hz, 1H), 7.34 (t, 1H), 7.58 (d, J=7.5 Hz. 1H), 7.79 (s, 1H), 8.24 (s, 1H), 8.74 (s, 1H), 9.08 (s, 1H), 9.12 (s, 1H), 12.17 (s, 1H).

Other compounds prepared by Method 9 are shown in Table 5:

TABLE 5

| Structure | MS: m/z (M + H$^+$) |
|---|---|
| 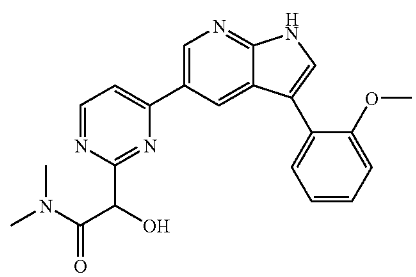 | 404 |
| 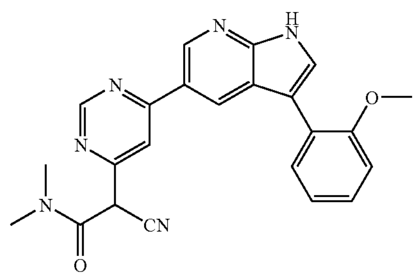 | 413 |
| 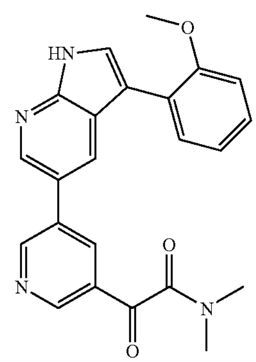 | 401 |

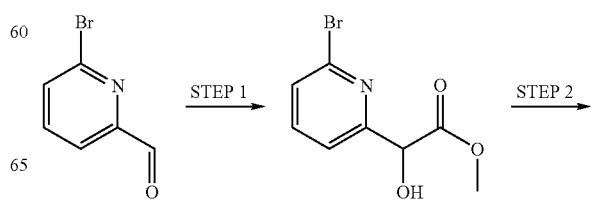

Method 10

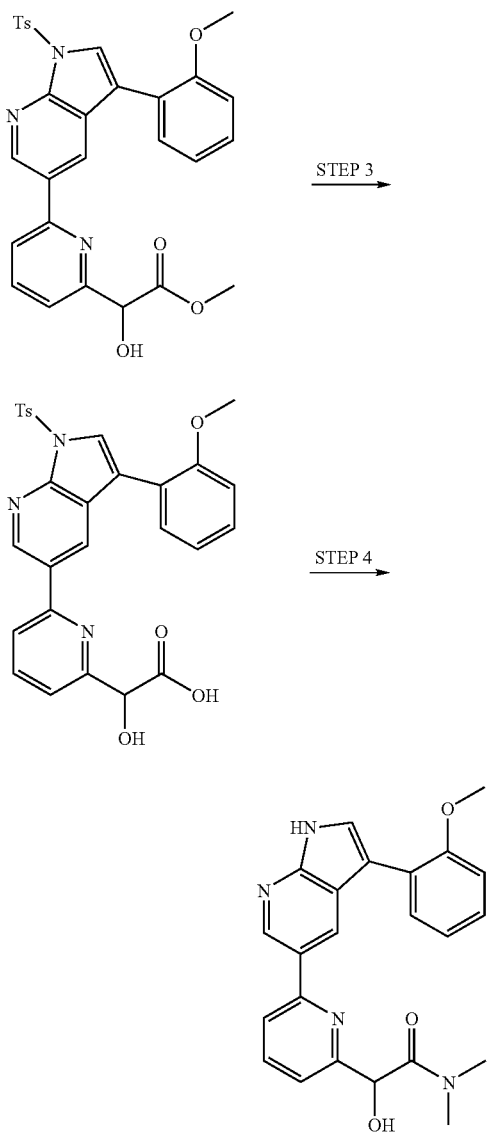

Step 1: Synthesis of (6-bromo-pyridin-2-yl)-hydroxy-acetic acid methyl ester

To a mixture of 6-bromo-pyridine-2-carbaldehyde 1.00 g, 5.38 mmol) in dichloromethane (50 ml) was added trimethylsilyl cyanide (1.58 ml, 11.83 mmol) and zinc(II)-iodide (1.72 g, 5.38 mmol). This mixture was stirred for 2 hours the solvent was removed under reduced pressure. Methanol/Sulfuric Acid was then added and the mixture was stirred at 50° C. for 16 hours. The reaction was then neutralized with 4 N aqueous sodium hydroxide and extracted with ethyl acetate (3×), the combined organic layers were then dried over magnesium sulfate. The solid obtained was then purified by silica gel chromatography to yield (6-bromo-pyridin-2-yl)-hydroxy-acetic acid methyl ester as a white solid. (0.96 g, 72%). MS: m/z 246.1 (M+H$^+$).

Step 2: Synthesis of 5-hydroxy-{6-[3-2-methoxyphenyl)-1-(toluene-4-sulfonyl)-1H-pyrrolo[2,3-b]pyridin-5-yl]-pyridin-2-yl}-acetic acid methyl ester In a microwave vial (6-bromo-pyridin-2-yl)-hydroxy-acetic acid methyl ester (430.9 mg, 1.75 mmol), 3-(2-methoxyphenyl)-5-(4,4,5,5-tetramethyl-[1,3,2]dioxaborolan-2-yl)-1-(toluene-4-sulfonyl)-1H-pyrrolo[2,3-b]pyridine (1.00 g, 1.75 mmol) in tetrahydrofuran/acetonitrile/1 N aqueous sodium bicarbonate (20 ml) was degassed with nitrogen and 1,1'-bis(diphenylphosphino)ferrocenepalladium(II)-dichloride dichloromethane adduct (143.0 mg, 0.18 mmol) was added and the vial sealed. This reaction mixture was heated to 80° C. for 30 minutes in a microwave reactor. 100 ml water was added and this mixture was extracted with ethyl acetate (3×) the combined organic layers were dried over magnesium sulfate and purified by silica gel chromatography to yield hydroxy-{6-[3-(2-methoxy-phenyl)-1-(toluene-4-sulfonyl)-1H-pyrrolo[2,3-b]pyridin-5-yl]-pyridin-2-yl}-acetic acid methyl ester as a white solid (312 mg, 32% yield). MS: m/z 544.5 (M+H$^+$).

Step 3: Synthesis of Hydroxy-{6-[3-(2-methoxyphenyl)-1-(toluene-4-sulfonyl)-1H-pyrrolo[2,3-b]pyridin-5-yl]-pyridin-2-yl}-acetic acid 4 N aqueous lithium hydroxide (17 μl, 0.66 mmol) was added to 5-[3-(2-methoxy-phenyl)-1-(2-trimethylsilanyl-ethoxymethyl)-1H-pyrazolo[3,4-b]pyridin-5-yl]-N,N-dimethyl-isophthalamic acid methyl ester (300 mg, 0.55 mmol) in water/methanol(3:1) (5 ml) and stirred at room temperature for 3 days, water was added and the mixture was extracted with ethyl acetate (3×), the combined organic layers were dried over magnesium sulfate and purified by silica gel chromatography to give hydroxy-{6-[3-(2-methoxy-phenyl)-1-(toluene-4-sulfonyl)-1H-pyrrolo[2,3-b]pyridin-5-yl]-pyridin-2-yl}-acetic acid (156 mg, 54% yield) as an off white powder. MS: m/z 530.5 (M+H$^+$).

Step 4: Synthesis of 2-hydroxy-2-{6-[3-(2-methoxyphenyl)-1H-pyrrolo[2,3-b]pyridin-5-yl]-pyridin-2-yl}-N,N-dimethyl-acetamide In a microwave vial O-(7-azabenzotriazol-1-yl)-N,N,N'N'-tetramethyluronium hexafluorophosphate 53.9 mg, 0.14 mmol) was added to a solution of hydroxy-{6-[3-(2-methoxy-phenyl)-1-(toluene-4-sulfonyl)-1H-pyrrolo[2,3-b]pyridin-5-yl]-pyridin-2-yl}-acetic acid (75 mg, 0.14 mmol), dimethyl amine (2 M solution in THF, 65 μl, 0.14 mmol) and di-iso-propyl ethyl amine (75 μl, 0.43 mmol) in tetrahydrofuran (1 ml). The vial was sealed and the solution irradiated to 70° C. for 10 min in a microwave reactor. Methanol (2 ml) was then added to the solution followed by 50% w/v aqueous sodium hydroxide (200 μl) and stirred at room temperature for 2 hours. The reaction was then neutralized with acetic acid and purified by preparative high pressure liquid chromatography, to give 2-hydroxy-2-{6-[3-(2-methoxy-phenyl)-1H-pyrrolo[2,3-b]pyridin-5-yl]-pyridin-2-yl}-N,N-dimethyl-acetamide (9.2 mg, 16% yield). $^1$H NMR (500 MHz, Dimethyl sulfoxide-d6) δ 2.86 (s, 3H) 3.32 (s, 3H); 3.82 (s, 3H)); 5.61 (m, 2H); 7.06 (t, J=8 Hz 1H); 7.15 (d, J=8 Hz, 1H) 7.31 (t, J=8 Hz, 1H); 7.44 (d, J=7.5 Hz 1H); 7.58 (d, J=8 Hz 1H); 7.73 (s, 1H); 7.58 (t, J=7.5 Hz 1H); 7.95 (d, J=7.5 Hz 1H); 7.94 (s, 1H); 8.60 (s, 1H); 8.95 (s, 1H); 11.98 (s, br, 1H) MS: m/z 403.4 (M+H$^+$).

Other compounds prepared by Method 10 are shown in Table 6:

TABLE 6

| Structure | MS: m/z (M + H⁺) |
|---|---|
| 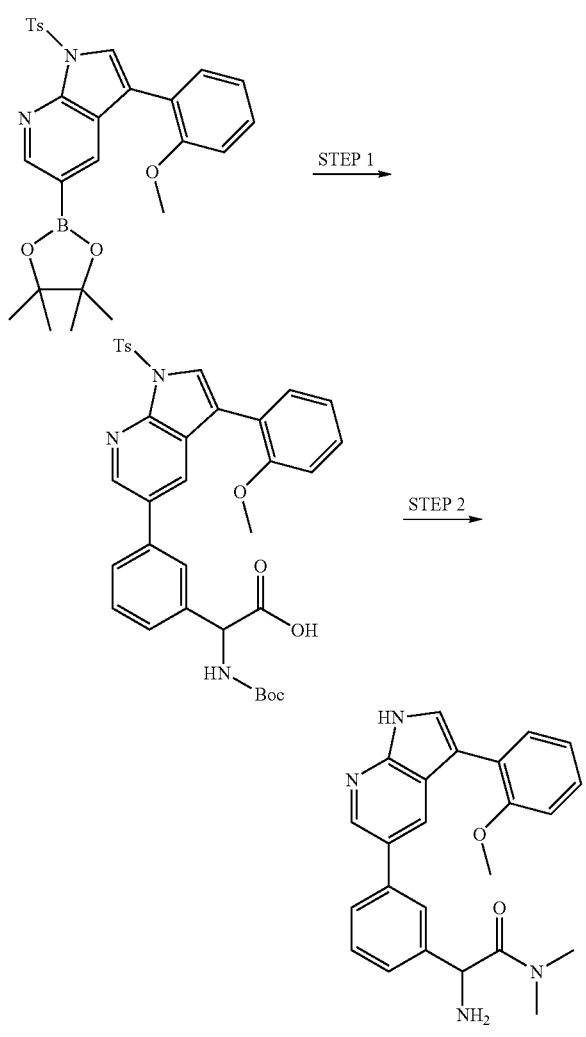 | 460.6 |

Method 11

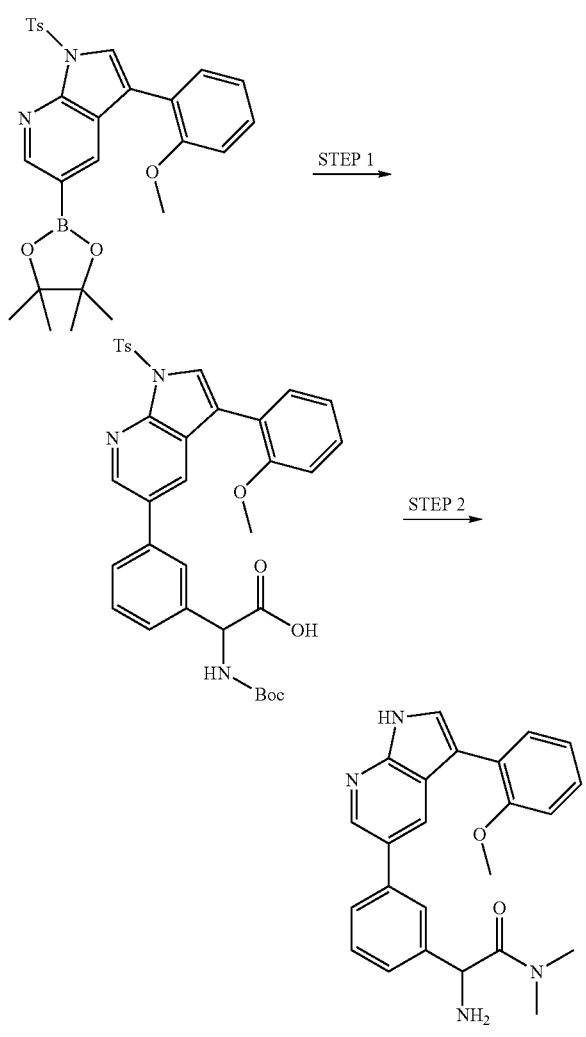

Step 1: Synthesis of tert-Butoxycarbonylamino-{3-[3-(2-methoxy-phenyl)-1-(toluene-4-sulfonyl)-1H-pyrrolo[2,3-b]pyridin-5-yl]-phenyl}-acetic acid To a mixture of 3-(2-Methoxy-phenyl)-5-(4,4,5,5-tetram-ethyl-[1,3,2]dioxaborolan-2-yl)-1-(toluene-4-sulfonyl)-1H-pyrrolo[2,3-b]pyridine (500 mg, 0.99 mmol) and 3-(3-Bromo-phenyl)-2-tert-butoxycarbonylamino-propionic acid (344 mg, 1.0 mmol) in a 20 mL microwave reaction flask was added THF (3 mL), acetonitrile (3 mL) and sodium carbonate (3 mL, 1 N aqueous solution, 3 mmol). The mixture was bubbled with $N_2$ for 1 minute. Dichloro[1,1'-bis(diphe-nylphoshino)ferrocene]palladium(II) (82 mg, 0.1 mmol) was added and the bubbling continued for another minute. The flask was sealed and irradiated with microwave in Emrys Optimizer at 120° C. for 20 min. Saturated sodium chloride (10 mL) was added and the pH was adjusted to 5 using HCl (1 N). The resulting mixture was extracted with ethyl acetate (10 mL×3). The combined organic layers were dried over sodium sulfate, filtered, and concentrated. The residue was purified with flash chromatography on silica gel using a gradient of methanol in dichloromethane to afford tert-Butoxycarbony-lamino-{3-[3-(2-methoxy-phenyl)-1-(toluene-4-sulfonyl)-1H-pyrrolo[2,3-b]pyridin-5-yl]-phenyl}-acetic acid as a yellow solid (370 mg, 58% yield). MS: m/z 628 (M+H⁺).

Step 2: Synthesis of 2-Amino-2-{3-[3-(2-methoxy-phenyl)-1H-pyrrolo[2,3-b]pyridin-5-yl]-phenyl}-N,N-dimethyl-acetamide To a solution of tert-Butoxycarbonylamino-{3-[3-(2-methoxy-phenyl)-1-(toluene-4-sulfonyl)-1H-pyrrolo[2,3-b]pyridin-5-yl]-phenyl}-acetic acid (100 mg, 0.16 mmol), dimethylamine (2 N solution in THF, 0.16 mL, 0.32 mmol), diisopropylethylamine (24 mg, 0.19 mmol) in DMF (1 mL) was added O-(7-azabenzotriazol-1-yl)-N,N,N',N',-tetram-ethyluromiumhexafluorophosphate (73 mg, 0.19 mmol). The resulting solution was stirred at room temperature for 1 hour. Methanol (1 mL) and potassium hydroxide (50% in water, 0.2 mL) were added and the resulting mixture was stirred for 30 minutes. The mixture was concentrated in GeneVac at 60° C. for 2 hours. To the residue was added trifluoroacetic acid (1 mL) and the resulting mixture was sonicated till the residue is completely dissolved. The solution was concentrated and the residue was taken up in DMSO (2 mL) and purified with reverse phase preparative LCMS to afford 2-Amino-2-{3-[3-(2-methoxy-phenyl)-1H-pyrrolo[2,3-b]pyridin-5-yl]-phenyl}-N,N-dimethyl-acetamide as a pale yellow solid (23 mg, 35%). MS: m/z 401 (M+H⁺). ¹H NMR (500 MHz, DMSO-d6) δ 2.86 (s, 3H), 2.93 (s, 3H), 3.84 (s, 3H), 5.14 (s, 1H), 7.05 (t, 1H), 7.15 (d, 1H), 7.31 (dt, 1H), 7.35 (d, 1H), 7.48 (t, 1H), 7.58 (dd, 1H), 7.68 (d, 1H), 7.73 (s, 1H), 7.74 (s, 1H), 8.16 (d, 1H), 8.54 (d, 1H), 11.95 (s, 1H).

Other compounds prepared by Method 11 are shown in Table 7:

TABLE 7

| Structure | MS: m/z (M + H⁺) |
|---|---|
| 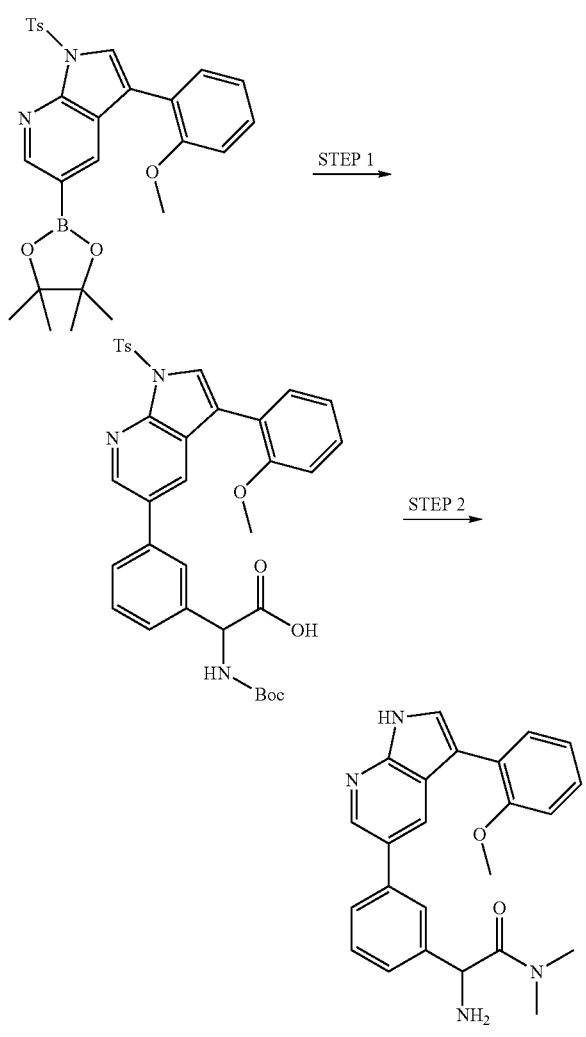 | 415 |

TABLE 7-continued

| Structure | MS: m/z (M + H+) |
|---|---|
| (structure) | 472 |
| (structure) | 471 |
| (structure) | 458 |
| (structure) | 444 |

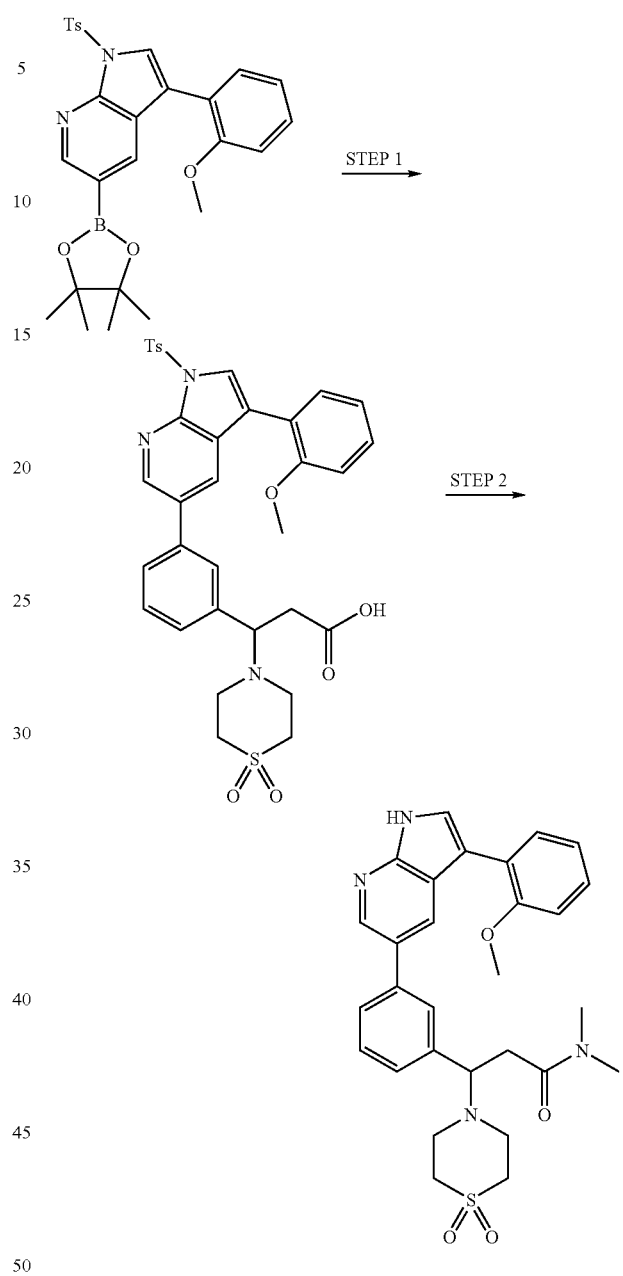

Method 12

Step 1: Synthesis of 3-(1,1-Dioxothiomorpholin-4-yl)-3-{3-[3-(2-methoxy-phenyl)-1-(toluene-4-sulfonyl)-1H-pyrrolo[2,3-b]pyridin-5-yl]-phenyl}-propionic acid To a mixture of 3-(2-methoxy-phenyl)-5-(4,4,5,5-tetramethyl-[1,3,2]dioxaborolan-2-yl)-1-(toluene-4-sulfonyl)-1H-pyrrolo[2,3-b]pyridine (504 mg, 1 mmol) and 3-(3-bromophenyl)-3-(1,1-dioxothiomorpholin-4-yl)-propionic acid (362 mg, 1.0 mmol) in a 20 mL microwave reaction flask was added THF (3 mL), acetonitrile (3 mL) and sodium carbonate (3 mL, 1 N aqueous solution, 3 mmol). The mixture was purged with nitrogen for 1 minute. Dichloro[1,1'-bis(diphenylphoshino)ferrocene]palladium(II) dichloromethane adduct (82 mg, 0.1 mol) was added and the purging continued for another minute. The flask was sealed and irradiated in a microwave reactor to 135° C. for 20 minutes. Saturated sodium chloride (10 mL) was added and the pH was adjusted to 5 using hydrochloric acid (1 N). The resulting mixture was extracted with ethyl acetate (10 mL×3). The combined organic layers were dried over sodium sulfate, filtered, and concentrated. The residue was purified by flash chromatography on silica gel using a gradient of methanol in dichloromethane to afford 3-(1,1-dioxothiomorpholin-4-yl)-3-{3-[3-(2-methoxy-phenyl)-1-(toluene-4-sulfonyl)-1H-pyrrolo[2,3-b]pyridin-5-yl]-phenyl}-propionic acid as a yellow solid (353 mg, 53% yield). MS: m/z 660 (M+H$^+$).

Step 2: Synthesis of 3-(1,1-dioxothiomorpholin-4-yl)-3-{3-[3-(2-methoxy-phenyl)-1H-pyrrolo[2,3-b]pyridin-5-yl]-phenyl}-N,N-dimethyl-propionamide To a solution of 3-(1,1-dioxothiomorpholin-4-yl)-3-{3-[3-(2-methoxy-phenyl)-1-(toluene-4-sulfonyl)-1H-pyrrolo[2,3-b]pyridin-5-yl]-phenyl}-propionic acid (100 mg, 0.15 mmol), dimethylamine (2 N solution in THF, 0.15 mL, 0.30 mmol), diisopropylethylamine (23 mg, 0.18 mmol) in DMF (1 mL) was added O-(7-azabenzotriazol-1-yl)-N,N,N',N'-tetramethyluronium hexafluorophosphate (68 mg, 0.18 mmol). The resulting solution was stirred at room temperature for 1 hour. Methanol (1 mL) and potassium hydroxide (50% w/v in water, 0.2 mL) were added and the resulting mixture was stirred for 30 minutes. The mixture was directly purified by mass-triggered reverse-phase HPLC to afford 3-(1,1-dioxothiomorpholin-4-yl)-3-{3-[3-(2-methoxy-phenyl)-1H-pyrrolo[2,3-b]pyridin-5-yl]-phenyl}-N,N-dimethyl-propionamide as a white solid (31 mg, 39%). MS: m/z 533 (M+H$^+$). $^1$H NMR (500 MHz, DMSO-d6) δ 2.75 (s, 3H), 2.82 (br, 2H), 2.88 (dd, 1H), 2.96 (br, 2H), 3.02 (s, 3H), 3.07 (br, 4H), 3.105 (dd, 1H), 3.83 (s, 3H), 4.41 (br, 1H), 7.05 (t, 1H), 7.15 (d, 1H), 7.30 (t, 1H), 7.30 (dt, 1H), 7.31 (d, 1H), 7.44 (t, 1H), 7.61 (d, 1H), 7.65 (s, 1H), 7.74 (d, 1H), 8.18 (d, 1H), 8.57 (d, 1H), 11.93 (s, 1H).

Other compounds prepared by Method 12 are shown in Table 8:

TABLE 8

| Structure | MS: m/z (M + H$^+$) |
|---|---|
|  | 590 |
| 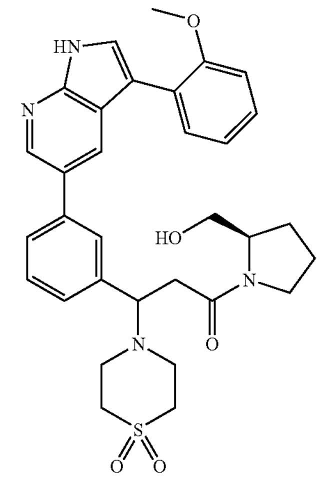 | 589 |
| 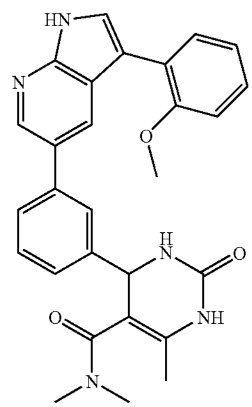 | 482 |
| 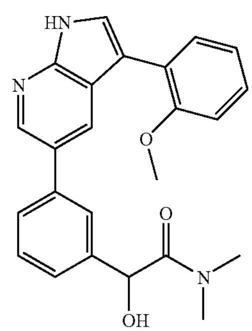 | 402 |
| 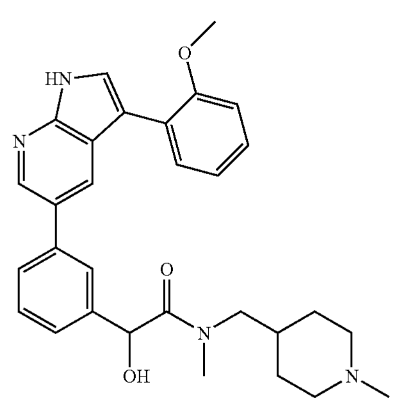 | 499 |

TABLE 8-continued
| Structure | MS: m/z (M + H⁺) |
|---|---|
| 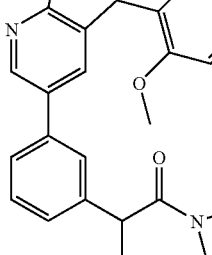 | 486 |
| 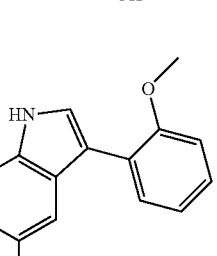 | 471 |
| 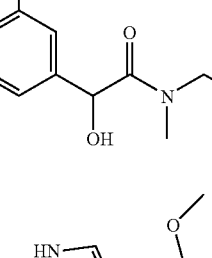 | 482 |
| 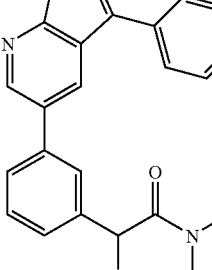 | 459 |
TABLE 8-continued
| Structure | MS: m/z (M + H⁺) |
|---|---|
| 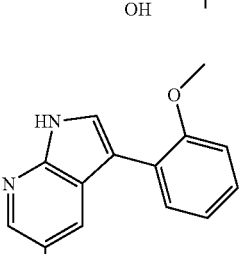 | 430 |
| 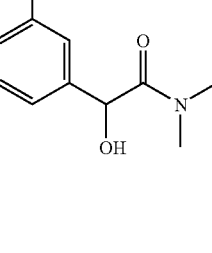 | 462 |
|  | 472 |
| | 472 |

TABLE 8-continued

| Structure | MS: m/z (M + H⁺) |
|---|---|
| (structure) | |
| (structure) | 472 |
| (structure) | 526 |


Method 13

Step 1: Synthesis of 5-{3-[3-(2-methoxy-phenyl)-1-(toluene-4-sulfonyl)-1H-pyrrolo[2,3-b]pyridin-5-yl]-phenyl}-5-methyl-imidazolidine-2,4-dione To a mixture of 3-(2-Methoxy-phenyl)-5-(4,4,5,5-tetramethyl-[1,3,2]dioxaborolan-2-yl)-1-(toluene-4-sulfonyl)-1H-pyrrolo[2,3-b]pyridine (100 mg, 0.2 mmol) and 5-(3-Bromo-phenyl)-5-methyl-imidazolidine-2,4-dione (54 mg, 0.2 mmol) in a 5 mL microwave reaction flask was added THF (1 mL), acetonitrile (1 mL) and sodium carbonate (1 mL, 1 N aqueous solution, 1 mmol). The mixture was purged with nitrogen for 30 seconds. Dichloro[1,1'-bis(diphenylphoshino)ferrocene]palladium(II) dichloromethane adduct (16 mg, 0.02 mmol) was added and the purging continued for another 30 seconds. The flask was sealed and irradiated in a microwave reactor to 150° C. for 40 min. Saturated sodium chloride (5 mL) was added and the pH was adjusted to 7 using hydrochloric acid (1 N). The resulting mixture was extracted with ethyl acetate (5 mL×3). The combined organic layers were dried over sodium sulfate, filtered, and concentrated. The residue was purified by flash chromatography on silica gel using a gradient of ethyl acetate in hexane to afford 5-{3-[3-(2-methoxy-phenyl)-1-(toluene-4- sulfonyl)-1H-pyrrolo[2,3-b]pyridin-5-yl]-phenyl}-5-methyl-imidazolidine-2,4-dione as a pale yellow solid (57 mg, 50% yield).

MS: m/z 567 (M+H$^+$).

Step 2: Synthesis of 5-{3-[3-(2-methoxy-phenyl)-1H-pyrrolo[2,3-b]pyridin-5-yl]-phenyl}-5-methyl-imidazolidine-2,4-dione To a solution of 5-{3-[3-(2-methoxy-phenyl)-1-(toluene-4-sulfonyl)-1H-pyrrolo[2,3-b]pyridin-5-yl]-phenyl}-5-methyl-imidazolidine-2,4-dione (57 mg, 0.1 mmol) in methanol (2 mL) was added potassium hydroxide (50% w/v in water, 0.4 mL) and the resulting mixture was stirred at room temperature for 1 hour. The reaction solution was purified directly by mass-triggered reverse-phase HPLC to afford 5-{3-[3-(2-methoxy-phenyl)-1H-pyrrolo[2,3-b]pyridin-5-yl]-phenyl}-5-methyl-imidazolidine-2,4-dione as a white powder (21 mg, 51%). MS: m/z 413 (M+H$^+$). $^1$H NMR (500 MHz, DMSO-d6) δ 1.72 (s, 3H), 3.85 (s, 3H), 7.05 (t, 1H), 7.15 (d, 1H), 7.31 (dt, 1H), 7.49 (d, 1H), 7.51 (t, 1H), 7.57 (dd, 1H), 7.70 (d, 1H), 7.73 (d, 1H) 7.76 (s, 1H), 8.14 (d, 1H), 8.53 (d, 1H), 8.73 (s, 1H), 10.82 (s, 1H), 11.95 (s, 1H).

Other compounds prepared by Method 13 are shown in Table 9:

TABLE 9

| Structure | MS: m/z (M + H$^+$) |
|---|---|
| 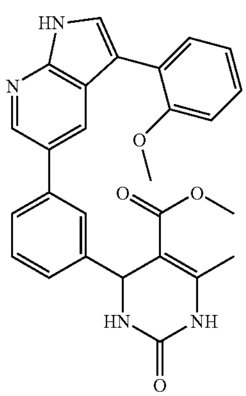 | 469 |

Method 14

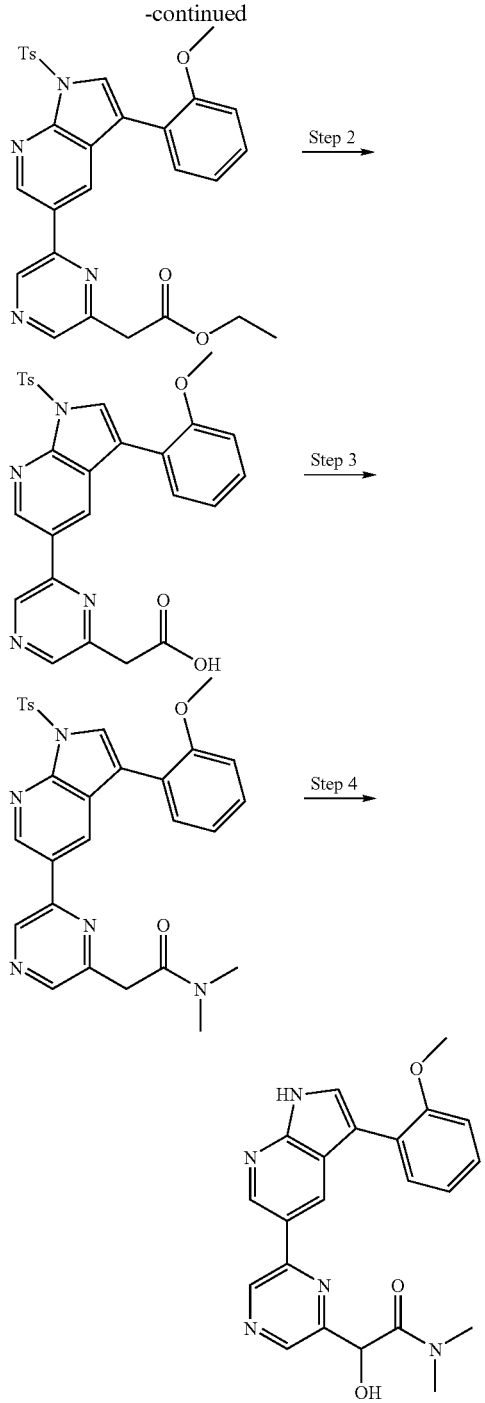

Synthesis of 2-hydroxy-2-{6-[3-(2-methoxy-phenyl)-1H-pyrrolo[2,3-b]pyridin-5-yl]-pyrazin-2-yl}-N,N-dimethyl-acetamide Step 1: Synthesis of {6-[3-(2-methoxyphenyl)-1-(toluene-4-sulfonyl)-1H-pyrrolo[2,3-b]pyridine-5-yl-acetic acid ethyl ester 3-(2-Methoxy-phenyl)-5-(4,4,5,5-tetramethyl-[1,3,2]dioxaborolan-2-yl)-1-(toluene-4-sulfonyl)-1H-pyrrolo[2,3-b]pyridine (938 mg, 3.02 mmol), (6-Chloro-pyrazin-2-yl)-acetic acid ethyl ester (605 mg, 3.02 mmol), palladium acetate (20.8 mg, 0.093 mmol) and 2-dicyclohexylphosphino-2',6'-dimethoxybiphenyl (S-Phos) (76.3 mg, 0.186 mmol) were combined under nitrogen. Acetonitrile (10 mL) and 1 M potassium carbonate (5.5 mL, 5.5 mmol) were added and the vial was flushed with nitrogen, capped and heated at 80° C. for 15 h. The layers were separated. The organics were diluted with ethyl acetate and washed with brine (1×), dried over sodium sulfate and adsorbed onto silica gel. The material was purified by flash chromatography on silica gel using a gradient of ethyl acetate in hexanes to afford {6-[3-(2-methoxyphenyl)-1-(toluene-4-sulfonyl)-1H-pyrrolo[2,3-b]pyridine-5-yl-acetic acid ethyl ester (1.05 g, 64%). MS: m/z 453 (M+H$^+$).

Step 2: Synthesis of {6-[3-(2-methoxy-phenyl)-1-(toluene-4-sulfonyl)-1H-pyrrolo[2,3-b]pyridin-5-yl]-pyrazin-2-yl}-acetic acid Dissolved {6-[3-(2-methoxyphenyl)-1-(toluene-4-sulfonyl)-1H-pyrrolo[2,3-b]pyridine-5-yl-acetic acid ethyl ester (300 mg, 0.55 mmol) in tetrahydrofuran (1.5 mL) and treated with 4 N aqueous lithium hydroxide (138 μL) for 9 h. The reaction was quenched by addition of 6 N hydrochloric acid (91.6 μL), dried over sodium sulfate, filtered and concentrated in vacuo to afford a yellow foam. The crude material was used directly in the next step.

Step 3: Synthesis of 2-{6-[3-(2-methoxy-phenyl)-1-(toluene-4-sulfonyl)-1H-pyrrolo[2,3-b]pyridin-5-yl]-pyrazin-2-yl}-N,N-dimethyl-acetamide Crude {6-[3-(2-Methoxy-phenyl)-1-(toluene-4-sulfonyl)-1H-pyrrolo[2,3-b]pyridin-5-yl]-pyrazin-2-yl}-acetic acid (0.55 mmol), O-(7-azabenzotriazol-1-yl)-N,N,N',N'-tetramethyluronium hexafluorophosphate (HATU) (251 mg, 0.66 mmol), and di-iso-propylamine (114.9 μL, 0.66 mmol) were dissolved in tetrahydrofuran (5 mL) and 2 M dimethylamine (412 μL, 0.825 mmol) was added. The mixture was heated to 60° C. in a capped vial for 30 minutes, cooled, diluted with ethyl acetate and washed with saturated sodium bicarbonate (1×), saturated ammonium chloride (1×) and brine (1×). The organics were dried over sodium sulfate, filtered and concentrated to yield a yellow foam (305 mg, >100%). The crude material was used without further purification in the next step. MS: m/z 542 (M+H$^+$).

Step 4: Synthesis of 2-hydroxy-2-{6-[3-(2-methoxy-phenyl)-1H-pyrrolo[2,3-b]pyridin-5-yl]-pyrazin-2-yl}-N,N-dimethyl-acetamide Crude 2-{6-[3-(2-Methoxy-phenyl)-1-(toluene-4-sulfonyl)-1H-pyrrolo[2,3-b]pyridin-5-yl]-pyrazin-2-yl}-N,N-dimethyl-acetamide (0.271 mmol) was dissolved in methanol (1 mL) and dimethylformamide (1 mL) and 50% w/v aqueous potassium hydroxide (0.5 mL) was added. After 30 minutes, the reaction was quenched by addition of acetic acid (0.5 mL). The mixture was carefully poured into saturated sodium bicarbonate and extracted with ethyl acetate. The organics were dried over sodium sulfate, filtered and dried to a residue which was purified by preparative HPLC to afford 2-hydroxy-2-{6-[3-(2-methoxy-phenyl)-1H-pyrrolo[2,3-b]pyridin-5-yl]-pyrazin-2-yl}-N,N-dimethyl-acetamide (25 mg, 22.8%, 3 steps). $^1$H-NMR (500 MHz, dimethylsulfoxide-d6) δ 2.32 (s, 3H), 2.78 (s, 3H), 3.79 (s, 3H), 5.37 (m, 1H), 5.61 (m, 1H), 7.03 (dt, J=7.0 Hz, 1H), 7.12 (br d, J=8.5 Hz, 1H), 7.29 (br dt, J=7.5 Hz, 1H), 7.57 (dd, J=7.5 Hz, 1H), 7.79 (br t, 1H), 8.47 (d, 1H), 8.61 (d, 1H), 8.65 (d, 1H), 8.75 (d, 1H). MS: m/z 404 (M+H$^+$).

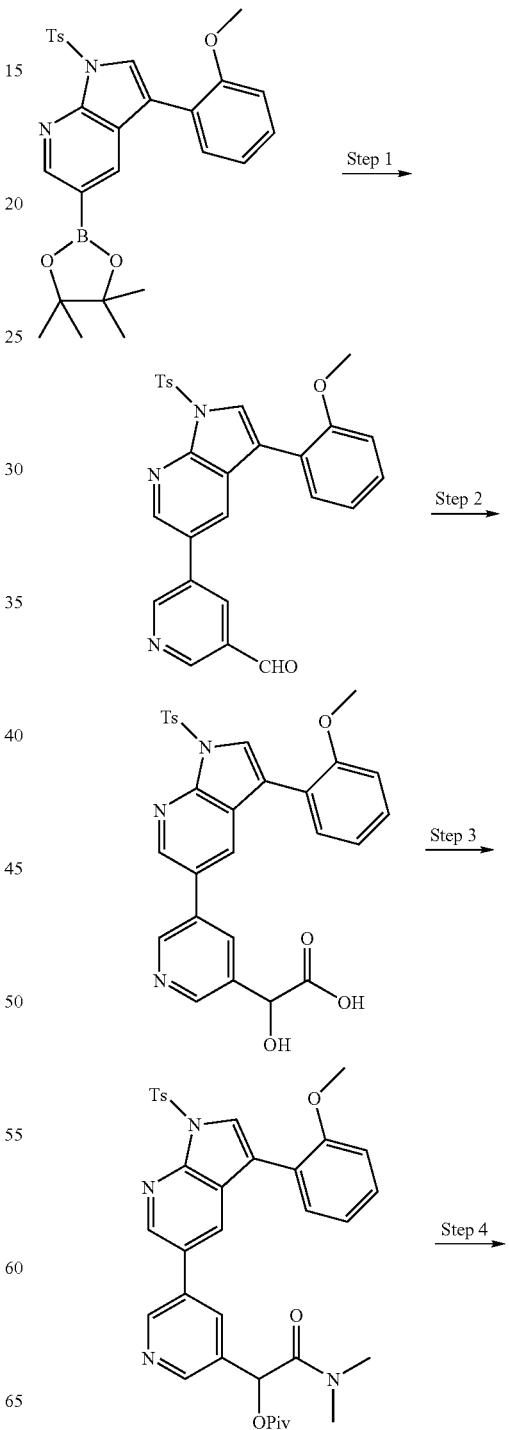

Method 15

-continued

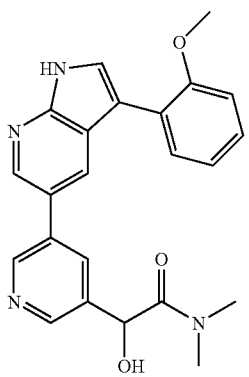

Synthesis of 2-hydroxy-2-{5-[3-(2-methoxy-phenyl)-1H-pyrrolo[2,3-b]pyridin-5-yl]-pyridin-3-yl}-N,N-dimethyl-acetamide Step 1: Synthesis of 5-[3-(2-methoxy-phenyl)-1-(toluene-4-sulfonyl)-1H-pyrrolo[2,3-b]pyridin-5-yl]-pyridine-3-carbaldehyde 3-(2-Methoxy-phenyl)-5-(4,4,5,5-tetramethyl-[1,3,2]dioxaborolan-2-yl)-1-(toluene-4-sulfonyl)-1H-pyrrolo[2,3-b]pyridine (5.0 g, 9.91 mmol), commercial 5-bromo-pyridine-3-carbaldehyde 1.84 g, 9.91 mmol) and 1,1'-bis(diphenylphosphino)ferrocenepalladium(II)-dichloride dichloromethane adduct (405 mg, 0.495 mmol) were combined in a vial under nitrogen and dissolved in acetonitrile (25 mL) and tetrahydrofuran (25 mL). Saturated sodium bicarbonate (25 mL) was added and the system was purged with nitrogen gas. The reaction mixture was capped and heated for 15 h at 80° C. The cooled mixture was diluted with ethyl acetate and washed with brine. The combined organic layers were dried over sodium sulfate and purified by flash chromatography on silica gel using a gradient of ethyl acetate in hexanes to afford 5-[3-(2-methoxy-phenyl)-1-(toluene-4-sulfonyl)-1H-pyrrolo[2,3-b]pyridin-5-yl]-pyridine-3-carbaldehyde (2.66 g, 55.7%). MS: m/z 484 (M+H+).

Step 2: Synthesis of hydroxy-{5-[3-(2-methoxy-phenyl)-1-(toluene-4-sulfonyl)-1H-pyrrolo[2,3-b]pyridin-5-yl]-pyridin-3-yl}-acetic acid Hydroxy-{5-[3-(2-methoxy-phenyl)-1-(toluene-4-sulfonyl)-1H-pyrrolo[2,3-b]pyridin-5-yl]-pyridin-3-yl}-acetic acid was prepared as described by Schenck et al. (in *Bioorg. Med. Chem. Lett.* (2004), 979).

Step 3: Synthesis of 2,2-dimethyl-propionic acid dimethylcarbamoyl-{5-[3-(2-methoxy-phenyl)-1-(toluene-4-sulfonyl)-1H-pyrrolo[2,3-b]pyridin-5-yl]-pyridin-3-yl}-methyl ester Hydroxy-{5-[3-(2-methoxy-phenyl)-1-(toluene-4-sulfonyl)-1H-pyrrolo[2,3-b]pyridin-5-yl]-pyridin-3-yl}-acetic acid (208 mg, 0.393 mmol) was dissolved in dichloromethane (3.0 mL) and cooled in an ice water bath. Di-iso-propylethylamine (137 µL, 0.786 mmol) and pivaloyl chloride (48.3 µL, 0.393 mmol) were added. After 10 minutes, dimethylamine solution (2 M tetrahydrofuran) was added (393 µL, 0.786 mmol) and the mixture was stirred for 15 h. The mixture was then diluted with dichloromethane and washed with saturated sodium bicarbonate (1×) and brine (1×), dried over sodium sulfate, filtered and concentrated to a foam (quantitative). The material was used as is in the next step. MS: m/z 641 (M+H+).

Step 4: Synthesis of 2-hydroxy-2-{5-[3-(2-methoxy-phenyl)-1H-pyrrolo[2,3-b]pyridin-5-yl]-pyridin-3-yl}-N,N-dimethyl-acetamide 2-Hydroxy-2-{5-[3-(2-methoxy-phenyl)-1H-pyrrolo[2,3-b]pyridin-5-yl]-pyridin-3-yl}-N,N-dimethyl-acetamide was (0.189 mmol) was dissolved in methanol (0.5 mL) and dimethylformamide (0.5 mL) and 50% w/v aqueous potassium hydroxide (0.2 mL) was added. After 60 minutes, the reaction was quenched by addition of acetic acid (0.2 mL). The mixture was carefully poured into saturated sodium bicarbonate and extracted with ethyl acetate. The organic layers were dried over sodium sulfate, filtered and dried to a residue which was purified by preparative HPLC (5.5 mg, 7.2%). $^1$H-NMR (500 MHz, dimethylsulfoxide-d6) δ 2.79 (s, 3H), 2.91 (s, 3H), 3.76 (s, 3H), 5.12 (d, J=7 Hz, 1H), 5.76 (d, J=7 Hz, 1H), 6.98 (dt, J=7.0, J=1.0 Hz, 1H), 7.07 (d, J=7.5 Hz, 1H), 7.23 (dt, J=2.0, J=7.0 Hz, 1H), 7.52 (dd, J=1.0, J=7.0 Hz 1H), 7.69 (d, J=2.5 Hz, 1H), 8.00 (t, J=2.5 Hz, 1H), 8.14 (d, J=2.0 Hz, 1H), 8.48 (d, J=1.5 Hz, 1H), 8.50 (d, J=2.5 Hz, 1H), 8.13 (d, J=2.0 Hz, 1H). MS: m/z 403 (M+H+).

The racemic material from step 5 was separated on a CHIRALCEL OD column using Hexane/Ethanol (76/24) as eluant. The absolute configuration of the isomers was determined by co-crystalliztion with Ab1 protein.

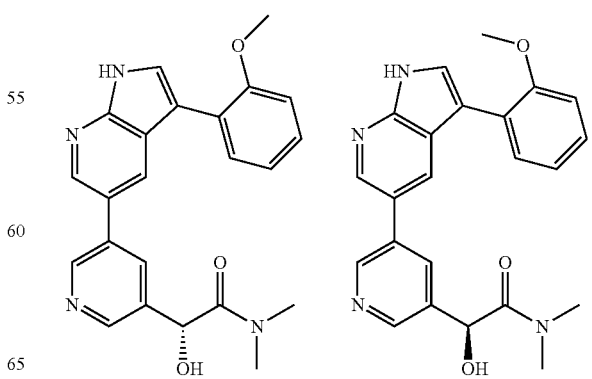

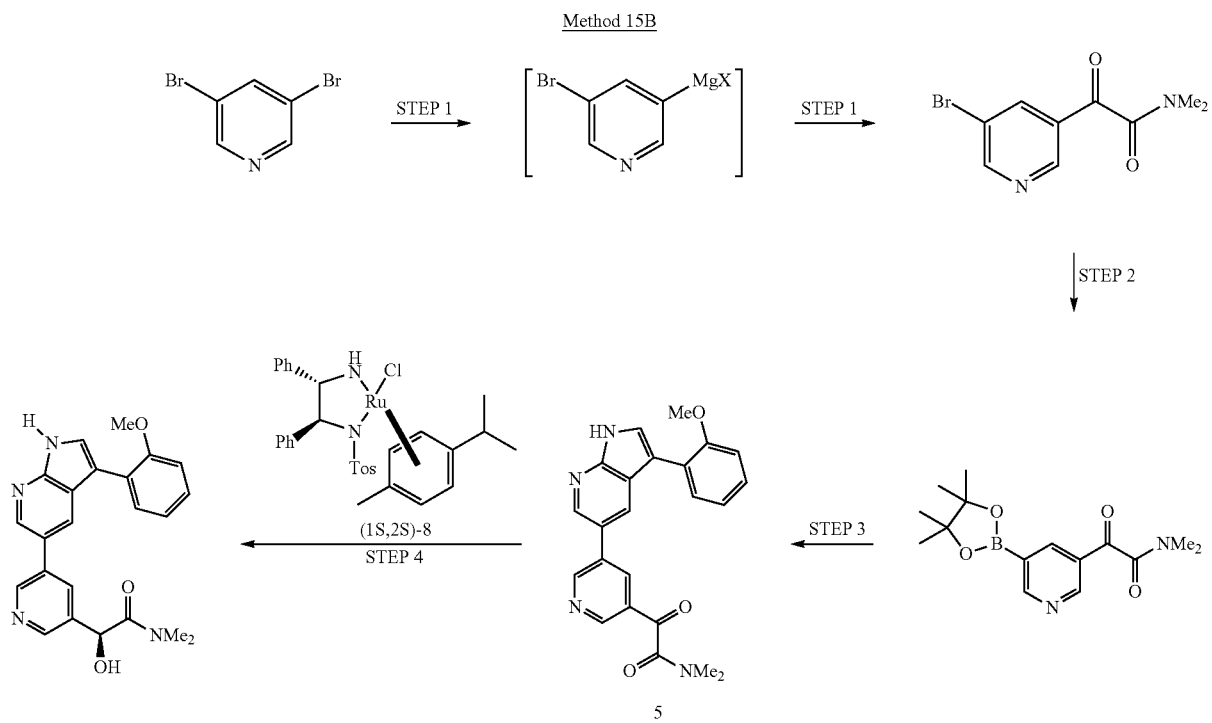

Method 15B

Step 1: Synthesis of 2-(5-bromopyridin-3-yl)-N,N-dimethyl-2-oxoacetamide

Isopropylmagnesium chloride.LiCl (2.0 L, 1 M in THF (2.5×800 mL, 14% in THF), 2 mol, pre-cooled in an ice bath ±30 min) was added via a dropping funnel (1 L) over 30 minutes to a suspension of 3,5-dibromopyridine 1 (437 g, 1.84 mol) in THF (1.1 L) in a 5 L three-necked roundbottomed flask while cooling with a large ice-bath (T<20° C.) while stirring with a magnetic stirring bar and under inert nitrogen atmosphere. After the addition was complete (solution was dark/black) stirring and cooling was continued for 30 minutes.

A second 5 L three-necked roundbottomed flask was filled with ethyl N,N-dimethyloxamate (290 g, 2 mol) in THF (combined total (oxamate+THF) 375 mL) and was cooled with an ice-bath to ~0° C. while stirring with a magnetic stirring bar.

The Grignard solution of 1 in THF from the first 5 L flask was transferred in 30 minutes to the second vessel (T<20° C.), which contained the cooled oxamate in THF by using a Teflon tube (Ø 4 mm) and reduced pressure in the second flask, under continued stirring and cooling of the second vessel. After addition the reaction mixture was stirred for an additional half hour at 0° C. The ice bath was removed and the solution was stirred and allowed to warm up to RT during one hour.

After the solution was cooled to ~5° C. using an ice bath and 2M HCl(aq) (1.25 L) was slowly added (T<20° C., fast T increase at the start of addition). After this EtOAc (625 mL) was added and stirring was continued for 10 min. The layers were separated and the aqueous layer was extracted with EtOAc (3×500 mL). The organic layers were combined and dried over $Na_2SO_4$ followed by filtration. Then the solvent was concentrated in vacuo, tert-butylmethylether (1 L) was added to the residue and the suspension was stirred with a magnetic stirring bar while cooling with an ice bath (T=0° C.). The precipitate was filtered off using a glass filter (P2) and dried in vacuo to give 2-(5-bromopyridin-3-yl)-N,N-dimethyl-2-oxoacetamide (249.4 g, 970 mmol) as a light-yellow solid in 53% isolated yield.

Step 2: N,N-dimethyl-2-oxo-2-(5-(4,4,5,5-tetramethyl-1,3,2-dioxaborolan-2-yl)pyridin-3-yl)acetamide Acetamide (340 g, 1.32 mol) and bis(pinacolato)diboron (336 g, 1.32 mol) were dissolved in 1,4-dioxane (6.8 L) in a 20 L reaction flask. The solution was stirred and purged with $N_2$ for 30 min. After which dichloro[1,1'-bis(diphenylphosphino)ferrocene]palladium (II) dichloromethane adduct (34 g, 0.41 mol) and potassium acetate (400 g, 2.45 mol) were added. Stirring and purging with $N_2$ was continued for 30 min. Thereafter the solution was heated to 80° C. and stirred under $N_2$ overnight. After the conversion is confirmed to be complete by NMR (evaporate solvent of sample and take up residue into $CDCl_3$) heating was stopped and the reaction mixture was filtered over a pad of Celite®. The Celite® pad was washed with 2000 ml of acetonitrile. The combined organic layers were concentrated in vacuo and used as is in the Suzuki reaction.

Step 3: 2-(5-(3-(2-methoxyphenyl)-1H-pyrrolo[2,3-b]pyridin-5-yl)pyridin-3-yl)-N,N-dimethyl-2-oxoacetamide Crude N,N-dimethyl-2-oxo-2-(5-(4,4,5,5-tetramethyl-1,3,2-dioxaborolan-2-yl)pyridin-3-yl)acetamide (592 g, 1.32 mol) from the boronic ester synthesis and 5-bromo-3-(2- methoxyphenyl)-1H-pyrrolo[2,3-b]pyridine 7 (398.5 g, 1.32 mol) were stirred in acetonitrile (5 L) in 10 L reaction vessel. The solution was stirred and purged with N₂ for 30 min. Dichloro[1,1'-bis(diphenylphosphino)ferrocene]palladium (II)dichloromethane adduct (34 g, 40.8 mmol) and Na₂CO₃ (aq) (312.8 g dissolved in 1.36 L H₂O) were added. Stirring and purging with N₂ continued for 30 min. Thereafter, the solution was heated to 75° C. and stirred under N₂ for two days. After the conversion was confirmed to be complete by NMR, H₂O (1700 ml) was added and stirring was continued for 10 min. Then heating was stopped and the reaction mixture was filtered over a pad of Celite®. The Celite® pad was washed with a 1:1 mixture of acetonitrile/H₂O (3×1000 ml). The filtrate was concentrated until almost acetonitrile had evaporated and a brownish precipitate formed. The concentrated mixture was then extracted with CH₂Cl₂ (1×3.6 L, 2×1000 ml). The organic layers were combined and dried over Na₂SO₄, after which the solvent was evaporated in vacuo. The residue was treated with 1800 ml MeOH and sonicated for 15 minutes. The yellowish solid is filtered off and dried in vacuo. This solid is dissolved in a mixture of 10% MeOH in CH₂Cl₂ and filtered over a SiO₂ plug, and washed off using 10% MeOH in CH₂Cl₂ (±15 L). Yielding after evaporation of the solvent in vacuo ketoamide (380 g, 0.95 mol, 72% over two steps).

Step 4: (2S)-2-hydroxy-2-(5-(3-(2-methoxyphenyl)-1H-pyrrolo[2,3-b]pyridin-5-yl)pyridin-3-yl)-N,N-dimethylacetamide Preparation of HCOOH/Et₃N (=5/2, molar ration) solution: Triethylamine (2.22 L, 1.6 mol) was cooled to 0° C. using an ice-bath and formic acid (1.51 L, 4.00 mol) was added dropwise. The mixture was stirred for 15 minutes at 0° C. and an additional 15 minutes at room temperature. The solution was used as such.

Ruthenium catalyst preparation: di-μ-chlorobis[(p-cymene)chlororuthenium(II)] (12.2 g, 20.0 mmol) and (1S,2S)-(+)-N-p-tosyl-1,2-diphenylethylenediamine (15.4 g, 42 mmol) were suspended in isopropanol (500 mL). In addition, triethylamine (8.01 g, 80 mmol) was added and the mixture was heated to 75° C. for 1 hour (using a rotavap and waterbath at 75° C., no reduced pressure), and then evaporated to dryness under reduced pressure yielding a light brown solid that was used without any further purification.

Transfer hydrogenation: The ketoamide (424 g, 1.06 mol) was dissolved in DMSO (3 L, newly opened bottles), some heating was necessary in order to dissolve all of compound 5 (using a rotavap with 40° C. waterbath). The earlier prepared HCOOH/Et₃N (=5/2) solution (2.9 L) was added, the mixture was purged with nitrogen (15 min.) and the mixture was cooled to −5° C. The ruthenium catalyst (00551) dissolved in dry DMSO (170 mL) was added and the mixture was stirred for 3 days at −5° C. under reduced pressure (p=200 mbar). The reaction was monitored by NMR (sample was neutralized using NaHCO₃(aq), extracted with EtOAc, dried over Na₂SO₄ and the solvent evaporated, NMR in DMSO-d6). After completion the reaction mixture was divided in two equal portions. Each portion was slowly poured on a stirred NaHCO₃ (aq.) solution (17 L, (8.5 L conc. NaHCO₃(aq) diluted with 8.5 L H₂O) in order to neutralize the reaction mixture (solution must remain basic, solid NaHCO₃ was carefully added when necessary). An orange brown solid precipitated that was filtered off (P2 filter) and was washed with water. The solids were dissolved in a mixture of 10% MeOH in CH₂Cl₂ (3.5 L) and were washed with 5% NaHCO₃ (aq) (1.75 L). The aqueous washing layer was extracted with CH₂Cl₂ (3×750 mL). The combined organic layers were dried over Na₂SO₄ and the solvent was evaporated in vacuo giving a black foam. The black foam was dissolved in EtOAc (3.5 L) and the solvent was evaporated in vacuo giving a brown solid. The solid was sonicated with MeOH (2.7 L), filtered off and dried. The product was subjected to ruthenium scavenging experiments using Quadrapure MPA, (which is a bead covered with a Mercaptophenylaminobut-2-enoate): conditions product was dissolved in IPA/CH₂Cl₂ (4 L) and refluxed with the quadrapure MPA (50 g) overnight and filtered over celite (2 scavenging runs) yielding (2S)-2-hydroxy-2-(5-(3-(2-methoxyphenyl)-1H-pyrrolo[2,3-b]pyridin-5-yl)pyridin-3-yl)-N,N-dimethylacetamide (263 g, 0.654 mol, 61.7%, e.e.=98.3%, purity>98%). %). ¹H-NMR (500 MHz, dimethylsulfoxide-d6) δ 2.79 (s, 3H), 2.91 (s, 3H), 3.76 (s, 3H), 5.12 (d, J=7 Hz, 1H), 5.76 (d, J=7 Hz, 1H), 6.98 (dt, J=7.0, J=1.0 Hz, 1H), 7.07 (d, J=7.5 Hz, 1H), 7.23 (dt, J=2.0, J=7.0 Hz, 1H), 7.52 (dd, J=1.0, J=7.0 Hz 1H), 7.69 (d, J=2.5 Hz, 1H), 8.00 (t, J=2.5 Hz, 1H), 8.14 (d, J=2.0 Hz, 1H), 8.48 (d, J=1.5 Hz, 1H), 8.50 (d, J=2.5 Hz, 1H), 8.13 (d, J=2.0 Hz, 1H). MS: m/z 403 (M+H⁺).

Other compounds prepared by Method 15 are shown in Table 10:

TABLE 10

| Structure | MS: m/z (M + H⁺) |
|---|---|
| 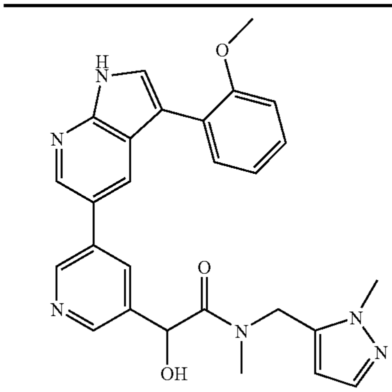 | 484 |
| 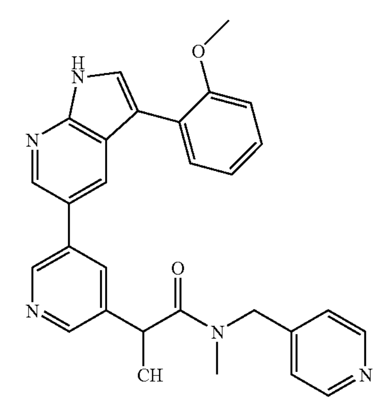 | 481 |

TABLE 10-continued

| Structure | MS: m/z (M + H+) |
|---|---|
| 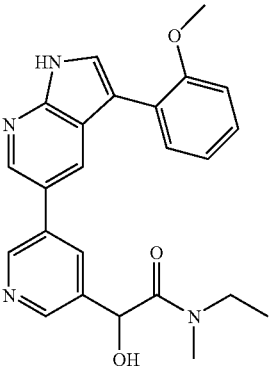 | 417 |
| 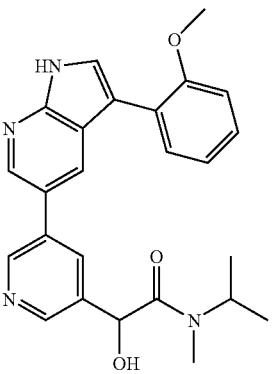 | 431 |

Method 16

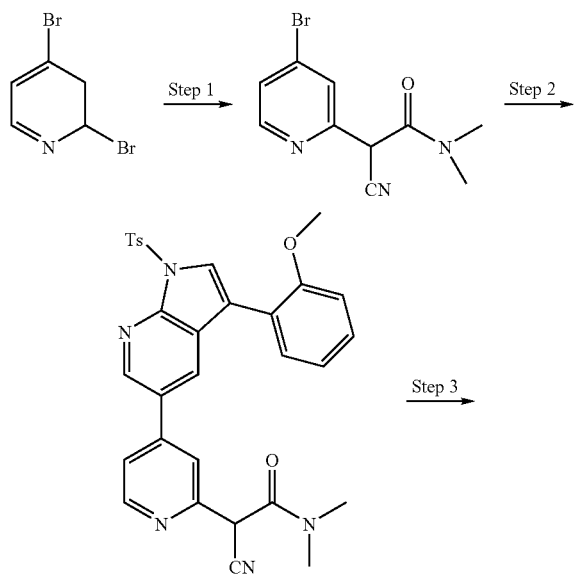

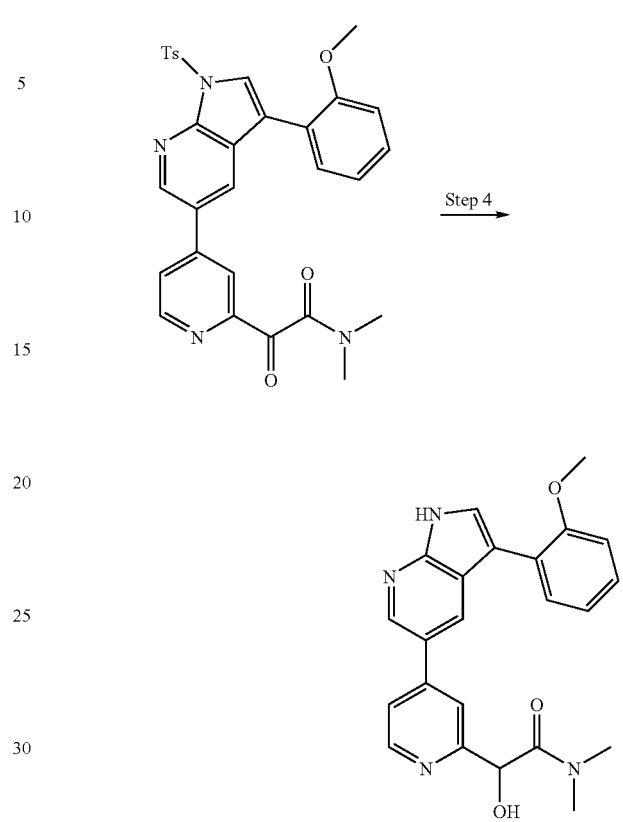

Synthesis of 2-{4-[3-(2-methoxy-phenyl)-1H-pyrrolo[2,3-b]pyridin-5-yl]-pyridin-2-yl}-N,N-dimethyl-2-oxo-acetamide Step 1: Synthesis of 2-(4-bromo-pyridin-2-yl)-2-cyano-N,N-dimethyl-acetamide Sodium hydride (186.2 mg, 4.65 mmol, 60% dispersion in oil) was added to a solution of 2-cyano-N,N-dimethyl-acetamide (373.7 mg, 3.33 mmol) in dimethylformamide (10 mL) at 0° C. The mixture was removed from the ice bath for 20 min, and a solution of 2,4-dibromopyridine (300 mg, 1.33 mmol) in dimethylformamide (3 mL) was quickly added. The mixture was heated at 60° C. for 16 h. The reaction was cooled to room temperature, quenched by addition of 200 µL saturated ammonium chloride and concentrated to a residue. The compound was purified by flash chromatography on silica gel using a gradient of ethyl acetate in hexanes to afford 2-(4-bromo-pyridin-2-yl)-2-cyano-N,N-dimethyl-acetamide and 2-(3-bromo-pyridin-4-yl)-2-cyano-N,N-dimethyl-acetamide.

MS: m/z 268 (M+H+).

Step 2: Synthesis of 2-cyano-2-{4-[3-(2-methoxy-phenyl)-1-(toluene-4-sulfonyl)-1H-pyrrolo[2,3-b]pyridin-5-yl]-pyridin-2-yl}-N,N-dimethyl-acetamide 2-{4-[3-(2-Methoxy-phenyl)-1-(toluene-4-sulfonyl)-1H-pyrrolo[2,3-b]pyridin-5-yl]-pyridin-2-yl}-N,N-dimethyl-2-oxo-acetamide was 3-(2-methoxy-phenyl)-5-(4,4,5,5-tetramethyl-[1,3,2]dioxaborolan-2-yl)-1-(toluene-4-sulfonyl)-1H-pyrrolo[2,3-b]pyridine (493 mg, 0.977 mmol), 2-(4-bromo-pyridin-2-yl)-2-cyano-N,N-dimethyl-acetamide (80%, 391 mg, 1.46 mmol) and 1,1'-bis(diphenylphosphino) ferrocenepalladium(II)-dichloride dichloromethane adduct (39.8 mg, 0.048 mmol) were combined in a vial under nitrogen and dissolved in acetonitrile (2.5 mL) and toluene (2.5 mL). Saturated sodium bicarbonate (5 mL) was added and the system was purged with nitrogen gas. The reaction mixture was capped and heated for 15 h at 80° C. The cooled mixture was diluted with ethyl acetate and washed with brine. The combined organic layers were dried over sodium sulfate and purified by flash chromatography on silica gel using a gradient of ethyl acetate in hexanes to afford 2-cyano-2-{4-[3-(2-methoxy-phenyl)-1-(toluene-4-sulfonyl)-1H-pyrrolo[2,3-b]pyridin-5-yl]-pyridin-2-yl}-N,N-dimethyl-acetamide.

MS: m/z 566 (M+H$^+$).

Step 3: Synthesis of 2-{4-[3-(2-methoxy-phenyl)-1-(toluene-4-sulfonyl)-1H-pyrrolo[2,3-b]pyridin-5-yl]-pyridin-2-yl}-N,N-dimethyl-2-oxo-acetamide Crude 2-{4-[3-(2-methoxy-phenyl)-1-(toluene-4-sulfonyl)-1H-pyrrolo[2,3-b]pyridin-5-yl]-pyridin-2-yl}-N,N-dimethyl-2-oxo-acetamide (0.977 mmol) was dissolved in dimethylformamide (10 mL) and cooled to 0° C. Peracetic acid (226 µL, 1.07 mmol, 32% solution in acetic acid) was added dropwise. The reaction was allowed to warm to room temperature and after 16 h it was poured into 50 mL of water. The solids were collected by filtration and dried in vacuo to afford crude 2-{4-[3-(2-methoxy-phenyl)-1-(toluene-4-sulfonyl)-1H-pyrrolo[2,3-b]pyridin-5-yl]-pyridin-2-yl}-N,N-dimethyl-2-oxo-acetamide (481 mg, 87.8%, 2 steps). MS: m/z 555 (M+H$^+$).

Step 4: Synthesis of 2-{4-[3-(2-methoxy-phenyl)-1H-pyrrolo[2,3-b]pyridin-5-yl]-pyridin-2-yl}-N,N-dimethyl-2-hydroxy-acetamide 2-{4-[3-(2-Methoxy-phenyl)-1-(toluene-4-sulfonyl)-1H-pyrrolo[2,3-b]pyridin-5-yl]-pyridin-2-yl}-N,N-dimethyl-2-oxo-acetamide (100 mg, 0.18 mmol) was dissolved in ethanol (2.0 mL) and treated with 4 N aqueous sodium hydroxide (49.6 µL, 0.198 mmol). After 4 h, an additional 22.5 µL (0.09 mmol) 4 N aqueous sodium hydroxide was added. After 19 h, sodium borohydride (7.5 mg, 0.198 mmol) was added to the mixture at 0° C. After 55 min., the mixture was concentrated in vacuo and purified by preparative HPLC to afford 2-{4-[3-(2-methoxy-phenyl)-1H-pyrrolo[2,3-b]pyridin-5-yl]-pyridin-2-yl}-N,N-dimethyl-2-hydroxy-acetamide (10.2 mg, 14.1%). $^1$H-NMR (500 MHz, dimethylsulfoxide-d6) δ 2.85 (s, 3H), 3.00 (s, 3H), 3.82 (s, 3H), 5.53 (d, J=7.5 Hz, 1H), 5.95 (d, J=7.5 Hz, 1H), 7.06 (dt, J=7.0, J=1.0 Hz, 1H), 7.15 (br d, J=8.5 Hz, 1H), 7.27 (dd, J=1.0, J=5.0 Hz, 1H), 7.32 (dt, J=2.0, J=7.0 Hz, 1H), 7.56 (dd, J=1.0, J=8.0 Hz, 1H), 7.73 (d, J=3.0 Hz, 1H), 7.99 (br s, 1H), 8.58 (d, J=2.0 Hz, 1H), 8.62 (d, J=5.0 Hz, 1H), 8.94 (d, J=2.0 Hz, 1H), 11.99 (s, 1H). MS: m/z 403 (M+H$^+$).

Synthesis of 2-{3-[3-(2-methoxy-phenyl)-1H-pyrrolo[2,3-b]pyridin-5-yl]-pyridin-4-yl}-N,N-dimethyl-2-hydroxy-acetamide

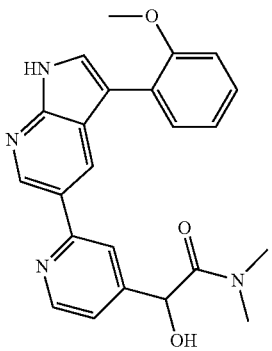

The 2-(3-bromo-pyridin-4-yl)-2-cyano-N,N-dimethyl-acetamide obtained above was processed to 2-{3-[3-(2-methoxy-phenyl)-1H-pyrrolo[2,3-b]pyridin-5-yl]-pyridin-4-yl}-N,N-dimethyl-2-hydroxy-acetamide following the procedure described above.

Method 17

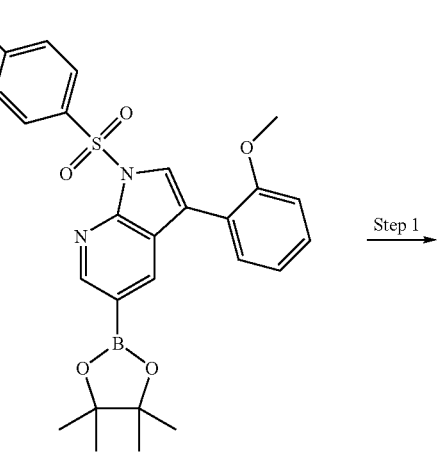

Step 1

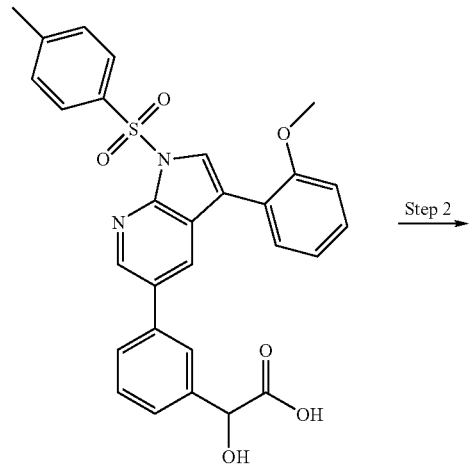

Step 2

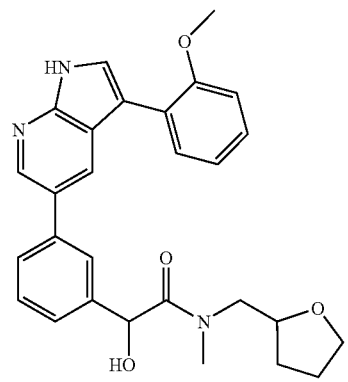

Step 1: Synthesis of hydroxyl-{3-[3-(2-methoxy-phenyl)-1-(toluene-4-sulfonyl)-1H-pyrrolo[2,3-b]pyridine-5-yl]-phenyl}-acetic acid A mixture of 3-(2-methoxy-phenyl)-5-(boronic ester)-1-(toluene-4-sulfonyl)-1H-pyrrolo[2,3-b]pyridine (10 g, 19.8 mmol), 3-bromomandelic acid (4.6 g, 19.8 mmol), and dichloro[1,1'-bis(diphenylphosphino)ferrocene]palladium (II) dichloromethane adduct 0.7 g, 1 mmol) in THF/Acetonitrile/saturated NaHCO₃ (35 ml/35 ml/70 ml) was stirred at 100° C. for 4 hours. The mixture was allowed to cool down to room temperature and then extracted with ethyl acetate (3×). The combined organic layers were extracted with brine, dried with Na₂SO₄, decanted, and concentrated to dryness. Silica gel chromatography of the crude using a gradient of ethyl acetate and hexane afforded hydroxyl-{3-[3-(2-methoxy-phenyl)-1-(toluene-4-sulfonyl)-1H-pyrrolo[2,3-b]pyridine-5-yl]-phenyl}acetic acid (7.1 g, 67% yield). ¹H NMR (500 MHz, DMSO-d6) δ 2.35 (s, 3H), 3.82 (s, 3H), 4.87 (2, 1H), 7.14 (m, 1H), 7.20 (d, 1H), 7.48 (m, 5H), 7.60 (m, 1H), 7.76 (s, 1H), 8.08 (m, 4H), 8.68 (s, 1H). MS: m/z 529.2 (M+H⁺).

Step 2: Synthesis of 2-hydroxyl-2{3-[3-(2-methoxy-phenyl)-1H-pyrrolo[2,3-b]pyridin-5-yl]-phenyl}-N-methyl-N-(tetrahydro-furan-2-ylmethyl)-acetamide A mixture of hydroxyl-{3-[3-(2-methoxy-phenyl)-1-(toluene-4-sulfonyl)-1H-pyrrolo[2,3-b]pyridine-5-yl]-phenyl}-acetic acid (0.2 g, 0.38 mmol), methyl-(tetrahydro-furan-2-ylmethyl)-amine (0.7 g, 0.57 mmol), diisopropylethylamine (DIEA, 200 µl, 1.14 mmol), N,N,N'N'-Tetramethyl-O-(7-azabenzotriazol-1-yl)uronium hexafluorophosphate (HATU, 216 mg, 0.57 mmol) in THF (5 ml) was stirred at 60° C. until no solid remained. The reaction mixture was taken up in 10 ml ethyl acetate and subsequently extracted with 1N HCl, saturated NaHCO₃, brine, dried with Na₂SO₄, concentrated to dryness. The crude was purified by silica chromatography. The resulting material was dissolved in 3 ml of methanol and aqueous NaOH (1 ml, 2 N in H₂O) was added and the mixture stirred overnight at room temperature. The solvent was removed under reduced pressure and the residue neutralized with 500 µl of 1N HCl. The resulting crude was directly purified by mass-triggered reverse phase HPLC to afford 2-hydroxyl-2{3-[3-(2-methoxy-phenyl)-1H-pyrrolo[2,3-b]pyridin-5-yl]-phenyl}-N-methyl-N-(tetrahydro-furan-2-yl-methyl-acetamide as an off-white powder (51 mg, 28% yield). ¹H NMR (500 MHz, DMSO-d6) δ 1.35-1.45 (m, 1H), 1.61-1.79 (m, 3H), 2.89-2.92 (d, 3H), 3.14-3.68 (m, 4H), 3.84 (s, 3H), 3.92-3.98 (m, 1H), 5.47 (d, 1H), 7.05 (m, 1H, 7.15 (d, 1H), 7.31 (m, 1H), 7.36 (m, 1H), 7.45-7.48 (m, 1H), 7.56-7.59 (m, 1H), 7.63-7.70 (m, 2H), 7.73 (m, 1H), 8.14 (m, 1H), 8.52 (m, 1H). MS: m/z 472.2 (M+H⁺).

Other compounds prepared by method 17 are shown in Table 11:

TABLE 11

| Structure | MS: m/z (M + H⁺) |
|---|---|
| 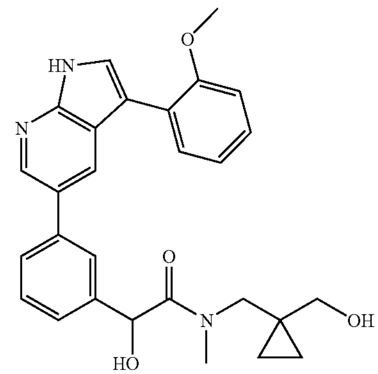 | 462 |
| 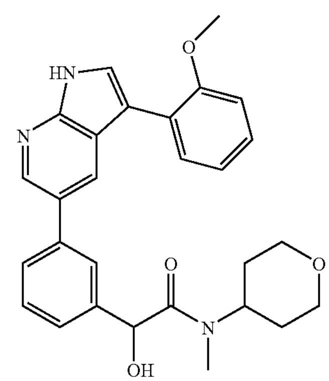 | 472 |
| 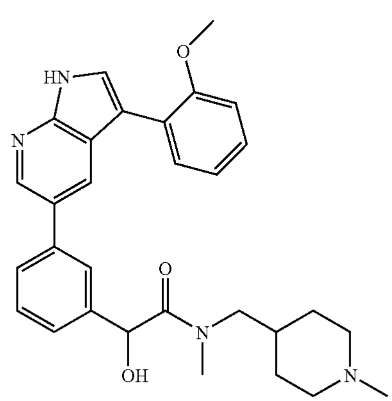 | 499 |

TABLE 11-continued

| Structure | MS: m/z (M + H+) |
|---|---|
| 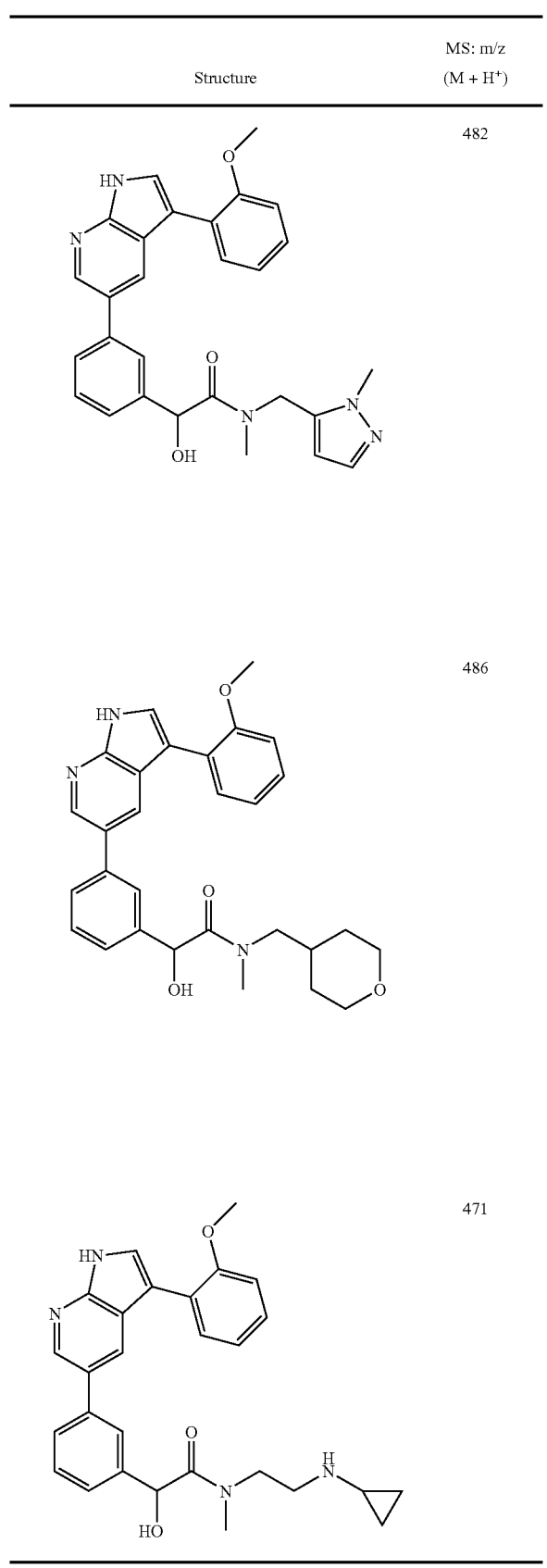 | 482 |
| 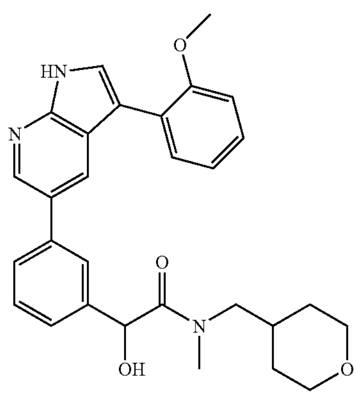 | 486 |
| 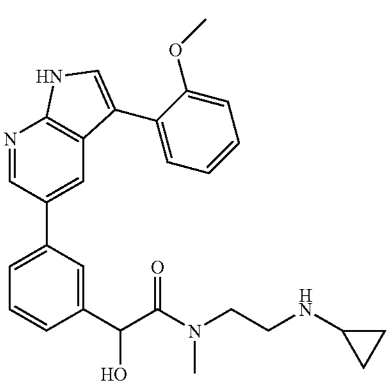 | 471 |

Method 18

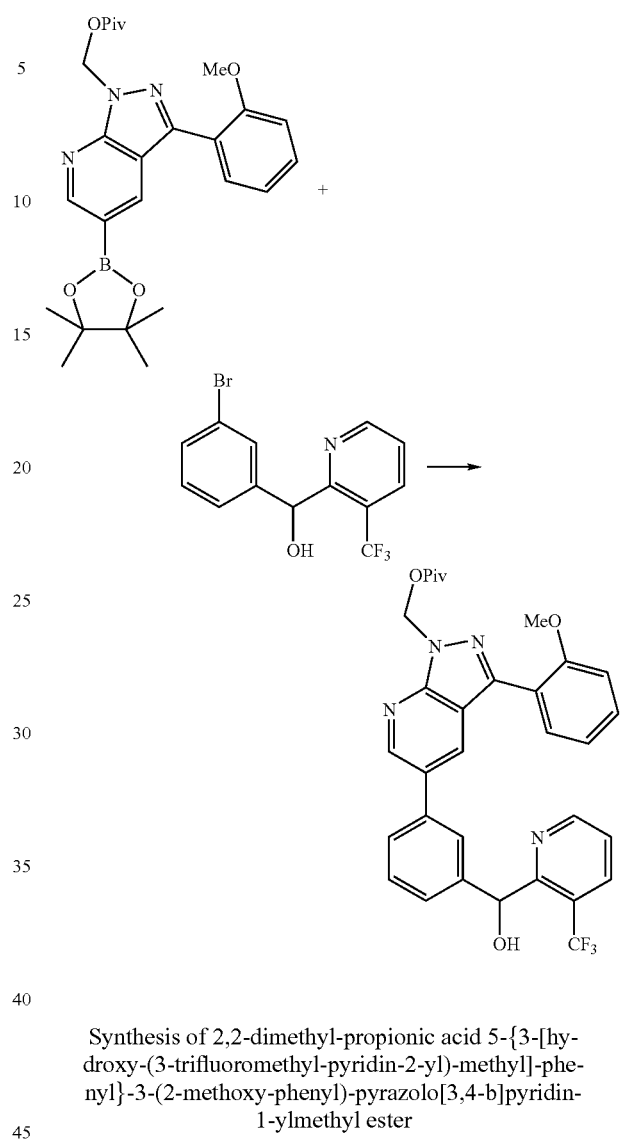

Synthesis of 2,2-dimethyl-propionic acid 5-{3-[hydroxy-(3-trifluoromethyl-pyridin-2-yl)-methyl]-phenyl}-3-(2-methoxy-phenyl)-pyrazolo[3,4-b]pyridin-1-ylmethyl ester 465 mg (1.00 mmol) of 2,2-dimethyl-propionic acid 3-(2-methoxy-phenyl)-5-(4,4,5,5-tetramethyl-[1,3,2]dioxaborolan-2-yl)-pyrazolo[3,4-b]pyridin-1-ylmethyl ester, 50 mg (61 μmol) of dichloro[1,1'-bis(diphenyl-phoshino)ferrocene]palladium(II) dichloromethane adduct and 340 mg (1.02 mmol) of (3-bromo-phenyl)-(3-trifluoromethyl-pyridin-2-yl)-methanol were place in a microwave vial. 8 mL of acetonitrile, 3 mL of toluene and 8 mL of a saturated aqueous solution of sodium bicarbonate were added. The vial was sealed and the resulting mixture heated in an oil bath to 65° C. for 22 h. The resulting mixture was distributed between dichloromethane and a saturated aqueous solution of sodium bicarbonate. The aqueous layer was extracted twice with dichloromethane and the combined organic phases were dried over sodium sulfate and evaporated. The resulting residue was purified by flash chromatography on silica gel using a gradient of ethyl acetate in hexanes to afford 388 mg (0.66 mmol, 66%) of 2,2-dimethyl-propionic acid 5-{3-[hydroxy-(3-trifluoromethyl-pyridin-2-yl)-methyl]-phenyl}-3-(2-methoxy-phenyl)-pyrazolo[3,4-b]pyridin-1-ylmethyl ester as a beige solid. $^1$H NMR (500 MHz, DMSO-d$_6$) α 8.90 (d, 1H), 8.86 (d, 1H), 8.34 (d, 1H), 8.20 (d(d), 1H), 7.81 (s, 1H), 7.67-7.64 (m, 2H), 7.56-7.50 (m, 2H), 7.45 (t, 1H), 7.39 (d, 1H), 7.27 (d, 1H), 7.13 (t, 1H), 6.51 (s, 2H), 6.26 (d, 1H), 6.11 (d, 1H), 3.86 (s, 3H), 1.12 (s, 9H); MS: m/z 591.1 (M+H$^+$), 613.1 (M+Na$^+$).

Other intermediates prepared by method 18 are shown in Table 12:

TABLE 12

| Structure | MS: m/z (M + H$^+$) |
|---|---|
| (OPiv, MeO pyrazolopyridine-pyridine structure) | 523.3, 545.2 (M + Na$^+$) |
| (OPiv, MeO pyrazolopyridine-fluoropyridine structure) | 563.2 (M + Na$^+$) |
| (OPiv, MeO pyrazolopyridine-methylimidazole structure) (microwave heating to 125-140° for 50 min) | 526.2 |

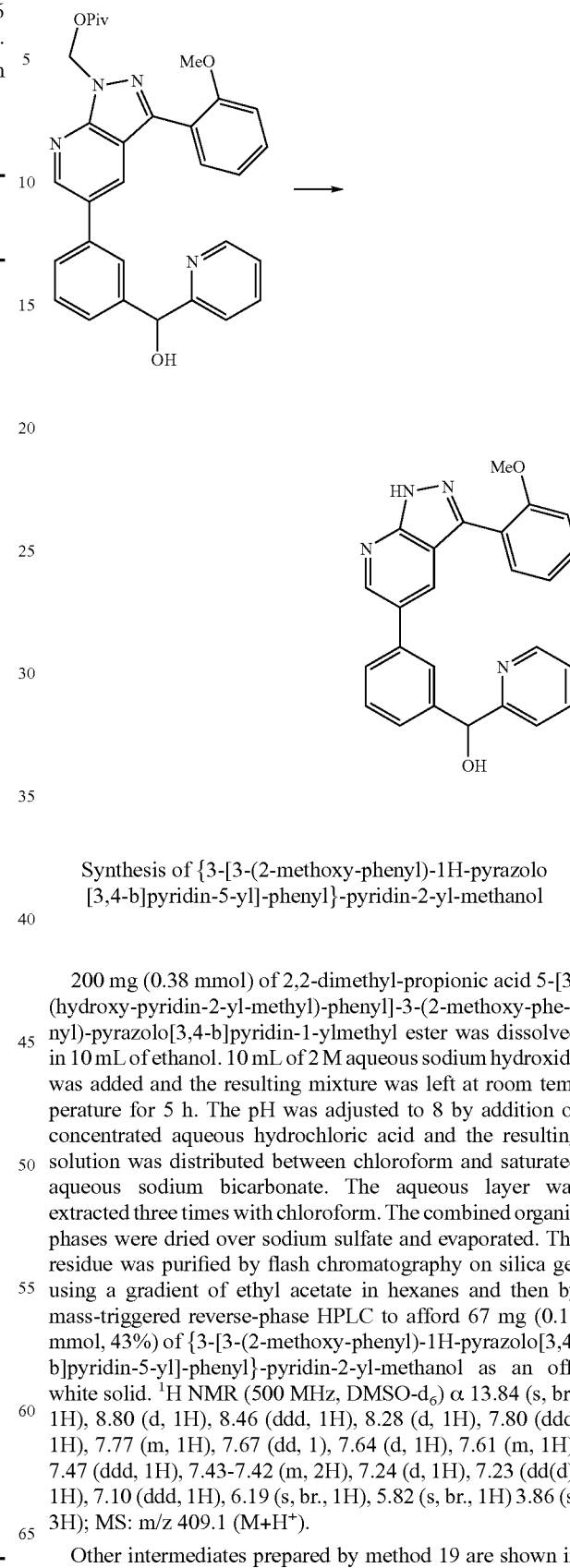

Method 19

Synthesis of {3-[3-(2-methoxy-phenyl)-1H-pyrazolo[3,4-b]pyridin-5-yl]-phenyl}-pyridin-2-yl-methanol 200 mg (0.38 mmol) of 2,2-dimethyl-propionic acid 5-[3-(hydroxy-pyridin-2-yl-methyl)-phenyl]-3-(2-methoxy-phenyl)-pyrazolo[3,4-b]pyridin-1-ylmethyl ester was dissolved in 10 mL of ethanol. 10 mL of 2 M aqueous sodium hydroxide was added and the resulting mixture was left at room temperature for 5 h. The pH was adjusted to 8 by addition of concentrated aqueous hydrochloric acid and the resulting solution was distributed between chloroform and saturated aqueous sodium bicarbonate. The aqueous layer was extracted three times with chloroform. The combined organic phases were dried over sodium sulfate and evaporated. The residue was purified by flash chromatography on silica gel using a gradient of ethyl acetate in hexanes and then by mass-triggered reverse-phase HPLC to afford 67 mg (0.16 mmol, 43%) of {3-[3-(2-methoxy-phenyl)-1H-pyrazolo[3,4-b]pyridin-5-yl]-phenyl}-pyridin-2-yl-methanol as an off-white solid. $^1$H NMR (500 MHz, DMSO-d$_6$) α 13.84 (s, br., 1H), 8.80 (d, 1H), 8.46 (ddd, 1H), 8.28 (d, 1H), 7.80 (ddd, 1H), 7.77 (m, 1H), 7.67 (dd, 1), 7.64 (d, 1H), 7.61 (m, 1H), 7.47 (ddd, 1H), 7.43-7.42 (m, 2H), 7.24 (d, 1H), 7.23 (dd(d), 1H), 7.10 (ddd, 1H), 6.19 (s, br., 1H), 5.82 (s, br., 1H) 3.86 (s, 3H); MS: m/z 409.1 (M+H$^+$).

Other intermediates prepared by method 19 are shown in Table 13:

TABLE 13

| Structure | MS: m/z (M + H⁺) |
|---|---|
| 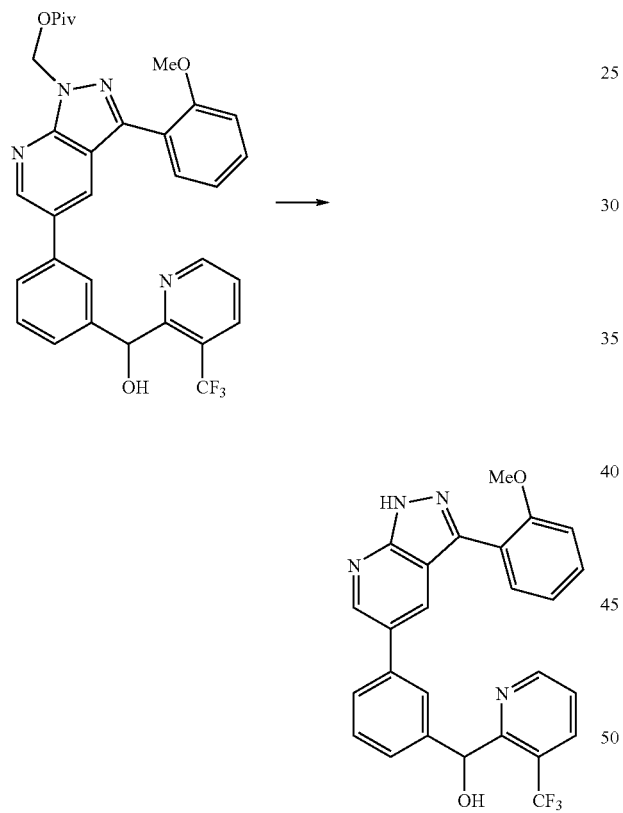 | 427.1 |

Method 20

Synthesis of {3-[3-(2-methoxy-phenyl)-1H-pyrazolo[3,4-b]pyridin-5-yl]-phenyl}-(3-trifluoromethyl-pyridin-2-yl)-methanol 380 mg (0.64 mmol) of 2,2-dimethyl-propionic acid 5-{3-[hydroxy-(3-trifluoromethyl-pyridin-2-yl)-methyl]-phenyl}-3-(2-methoxy-phenyl)-pyrazolo[3,4-b]pyridin-1-ylmethyl ester was dissolved in hot ethanol. 0.5 ml (450 mg, 7.5 mmol) of ethylene diamine was added and the mixture diluted with 2 M aqueous sodium hydroxide (30% v/v). The resulting mixture was gently heated until all material was dissolved and the solution left at room temperature for 16 h. The pH was adjusted to 8 by addition of concentrated aqueous hydrochloric acid and the resulting solution was distributed between chloroform and saturated aqueous sodium bicarbonate. The aqueous layer was extracted three times with chloroform. The combined organic phases were dried over sodium sulfate and evaporated. The residue was purified by mass-triggered reverse-phase HPLC to afford 12 mg (25 μmol, 4%) of {3-[3-(2-methoxy-phenyl)-1H-pyrazolo[3,4-b]pyridin-5-yl]-phenyl}-(3-trifluoromethyl-pyridin-2-yl)-methanol as a yellow solid. $^1$H NMR (500 MHz, DMSO-d$_6$) δ 13.83 (s, 1H), 8.86 (d, 1H), 8.79 (s, 1H), 8.28 (d, 1H), 7.79 (s, 1H), 7.66 (d, 1H), 7.62 (d, 1H), 7.54 (dd, 1H), 7.47 (t, 1H), 7.43 (t, 1H), 7.35 (d, 1H), 7.24 (d, 1H), 7.10 (t, 1H), 6.23 (d, 1H), 6.10 (d, 1H), 3.85 (s, 3H); MS: m/z 477.1 (M+H⁺).

Other intermediates prepared by method 20 are shown in Table 14:

TABLE 14

| Structure | MS: m/z (M + H⁺) |
|---|---|
| 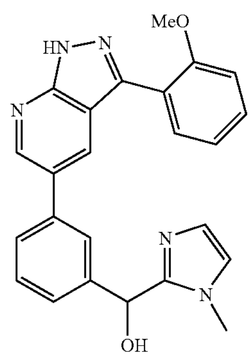 | 412.1 |

Method 21 step 1

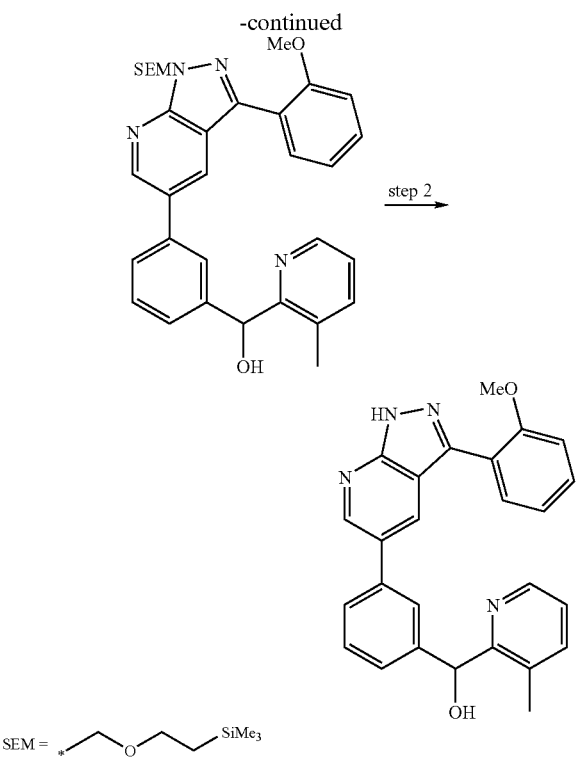

SEM = *\O\SiMe₃

* denotes point of attachment

Synthesis of {3-[3-(2-methoxy-phenyl)-1H-pyrazolo[3,4-b]pyridin-5-yl]-phenyl}-(3-methyl-pyridin-2-yl)-methanol Step 1: Synthesis of {3-[3-(2-methoxy-phenyl)-1-(2-trimethylsilanyl-ethoxymethyl)-1H-pyrazolo[3,4-b]pyridin-5-yl]-phenyl}-(3-methyl-pyridin-2-yl)-methanol 415 mg (0.87 mmol) of 3-(2-methoxy-phenyl)-5-(4,4,5,5-tetramethyl-[1,3,2]dioxaborolan-2-yl)-1-(2-trimethylsilanyl-ethoxymethyl)-1H-pyrazolo[3,4-b]pyridine, 40 mg (49 μmol) of dichloro[1,1'-bis(diphenyl-phoshino)ferrocene]palladium(II) dichloromethane adduct and 240 mg (0.86 mmol) of (3-bromo-phenyl)-(3-methyl-pyridin-2-yl)-methanol were place in a microwave vial. 6 mL of acetonitrile, 2 mL of toluene and 6 mL of a saturated aqueous solution of sodium carbonate were added. The vial was sealed and irradiated in a Personal Chemistry® Optimizer to 145° C. for 30 main. The resulting mixture was distributed between dichloromethane and a saturated aqueous solution of sodium bicarbonate. The aqueous layer was extracted twice with dichloromethane and the combined organic phases were dried over sodium sulfate and evaporated. The resulting residue was purified by flash chromatography on silica gel using a gradient of ethyl acetate in hexanes to afford a yellow oil. MS: m/z 553.0 (M+H⁺).

Step 2: Synthesis of {3-[3-(2-methoxy-phenyl)-1H-pyrazolo[3,4-b]pyridin-5-yl]-phenyl}-(3-methyl-pyridin-2-yl)-methanol The material from step 1 was dissolved in dichloromethane and 1 mL of trifluoroacetic acid was added. The resulting mixture was left at room temperature for 6 h. The solvent was then completely evaporated and the residue dissolved in dichloromethane. 0.5 mL (450 mg, 7.5 mmol) of ethylene diamine was added. After 2 h at room temperature the mixture was evaporated and the crude purified by mass-triggered reverse-phase HPLC to afford 52 mg (0.12 mmol, 14%) of {3-[3-(2-methoxy-phenyl)-1H-pyrazolo[3,4-b]pyridin-5-yl]-phenyl}-(3-methyl-pyridin-2-yl)-methanol as an off-white solid. ¹H-NMR (500 MHz, DMSO-d₆) a 8.80 (d, 1H), 8.42 (d(d), 1H), 8.27 (d, 1H), 7.71 ((t), br. 1H), 7.68 (dd, 1H), 7.62 (d(m), 1H), 7.57 (d(m), 1H), 7.47 (dd(d), 1H), 7.43 (t, 1H), 7.34 (d(m), 1H), 7.26-7.23 (m, 2H), 7.10 (ddd, 1H), 5.99 (s, 1H), 3.84 (s, 3H), 2.27 (s, 3H) (exchangeable protons not visible in ¹H-NMR); MS: m/z 423.2 (M+H⁺).

Other intermediates prepared by method 21 (Step 1 only) are shown in Table 15:

TABLE 15

| Structure | MS: m/z (M + H⁺) |
|---|---|
| 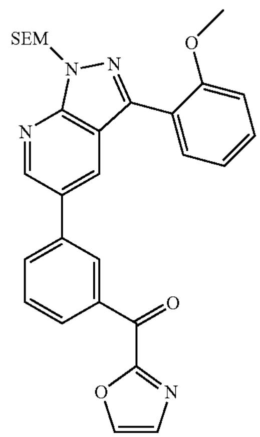 | 527 |
| 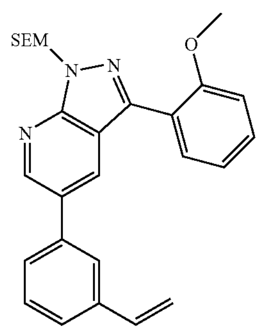 | 458 |
| 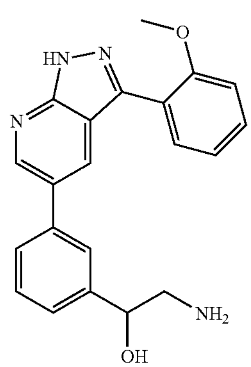 | 361 |

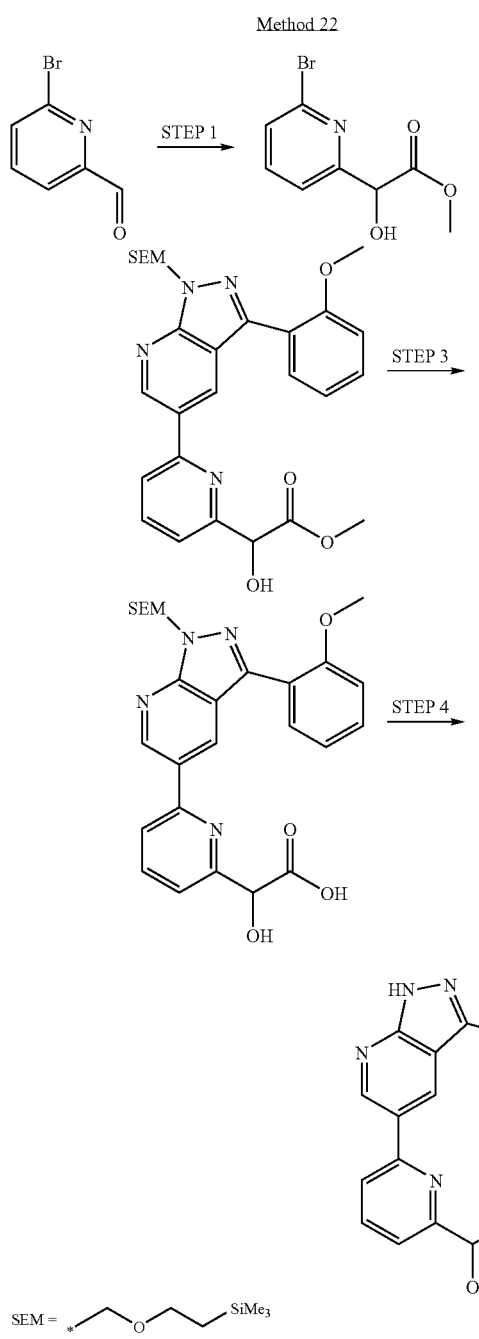

Method 22

SEM = *~O~SiMe₃
* denotes point of attachment

Synthesis of 2-hydroxy-2-{6-[3-(2-methoxy-phenyl)-1H-pyrazolo[3,4-b]pyridin-5-yl]-pyridin-2-yl}-N,N-dimethyl-acetamide Step 1: Synthesis of (6-bromo-pyridin-2-yl)-hydroxy-acetic acid methyl ester To a mixture of 6-bromo-pyridine-2-carbaldehyde 1.00 g, 5.38 mmol) in dichloromethane (50 ml) was added trimethylsilyl cyanide (1.58 ml, 11.83 mmol) and zinc(II)-iodide (1.72 g, 5.38 mmol). This mixture was stirred for 2 hours before the solvent was removed under reduced pressure. Methanol/sulfuric acid (3:1) (20 ml) was then added and the mixture was stirred at 50° C. for 16 hours. The reaction was then neutralized with 4 N aqueous sodium hydroxide and extracted with ethyl acetate (3×), the combined organic layers were then dried over magnesium sulfate. The solid obtained was then purified by silica gel chromatography to yield (6-bromo-pyridin-2-yl)-hydroxy-acetic acid methyl ester as a white solid. (0.96 g, 72%). MS: m/z 246.1 (M+H⁺).

Step 2: Synthesis of 5-hydroxy-{6-[3-(2-methoxy-phenyl)-1-(2-trimethylsilanyl-ethoxymethyl)-1H-pyrazolo[3,4-b]pyridin-5-yl]-pyridin-2-yl}-acetic acid methyl ester In a microwave vial (6-bromo-pyridin-2-yl)-hydroxy-acetic acid methyl ester (430.9 mg, 1.75 mmol), 3-(2-Methoxy-phenyl)-5-(4,4,5,5-tetramethyl-[1,3,2]dioxaborolan-2-yl)-1-(2-trimethylsilanyl-ethoxymethyl)-1H-pyrazolo[3,4-b]pyridine (842.3 mg, 1.75 mmol) in tetrahydrofuran/acetonitrile/1 N aqueous sodium bicarbonate (20 ml) was degassed with nitrogen and 1,1'-bis(diphenylphosphino)ferrocenepalladium(II)-dichloride dichloromethane adduct (143.0 mg, 0.18 mmol) was added and the vial sealed. This reaction mixture was irradiated to 80° C. for 30 minutes in a microwave reactor. 100 ml water was added and this mixture was extracted with ethyl acetate (3×). The combined organic layers were dried over magnesium sulfate and purified by silica gel chromatography to yield 5-hydroxy-{6-[3-(2-methoxy-phenyl)-1-(2-trimethylsilanyl-ethoxymethyl)-1H-pyrazolo[3,4-b]pyridin-5-yl]-pyridin-2-yl}-acetic acid methyl ester as a white solid (319 mg, 35% yield). MS: m/z 521.6 (M+H⁺).

Step 3: Synthesis of 5-hydroxy-{6-[3-(2-methoxy-phenyl)-1-(2-trimethylsilanyl-ethoxymethyl)-1H-pyrazolo[3,4-b]pyridin-5-yl]-pyridin-2-yl}-acetic acid 4 N aqueous lithium hydroxide (17 μl, 0.66 mmol) was added to hydroxy-{6-[3-(2-methoxy-phenyl)-1-(2-trimethylsilanyl-ethoxymethyl)-1H-pyrazolo[3,4-b]pyridin-5-yl]-pyridin-2-yl}-acetic acid methyl ester (286 mg, 0.55 mmol) in water/methanol(3:1) (5 ml) and stirred at room temperature for 3 days. Water was added and the mixture was extracted with ethyl acetate (3×), the combined organic layers were dried over magnesium sulfate and purified by silica gel chromatography to give 5-hydroxy-{6-[3-(2-methoxy-phenyl)-1-(2-trimethylsilanyl-ethoxymethyl)-1H-pyrazolo[3,4-b]pyridin-5-yl]-pyridin-2-yl}-acetic acid (174 mg, 61% yield) as an off white powder. MS: m/z 507.6 (M+H⁺).

Step 4: Synthesis of 2-hydroxy-2-{6-[3-(2-methoxy-phenyl)-1H-pyrazolo[3,4-]pyridin-5-yl-pyridin-2-yl}-N,N-dimethyl-acetamide In a microwave vial O-(7-azabenzotriazol-1-yl)-N,N,N',N'-tetramethyluronium hexafluorophosphate (53.9 mg, 0.14 mmol) was added to a solution of 5-hydroxy-{6-[3-(2-methoxy-phenyl)-1-(2-trimethylsilanyl-ethoxylethyl)-1H-pyrazolo[3,4-b]pyridin-5-yl]-pyridin-2-yl}-acetic acid (71 mg, 0.14 mmol), dimethyl amine (2 M in THF, 65 μl, 0.14 mmol) and di-iso-propyl ethyl amine (75 μl, 0.43 mmol) in tetrahydrofuran (1 ml). The vial was sealed and the solution irradiated to 70° C. for 10 min in a microwave reactor. The solvent was then removed under reduced pressure and 1 ml of trifluoroacetic acid was added this reaction was stirred for 16 hours and the solvent evaporated under reduced pressure, and purified by preparative mass-triggered reverse-phase HPLC to afford 2-hydroxy-2-{6-[3-(2-methoxy-phenyl)-1H-pyrazolo[3,4-b]pyridin-5-yl]-pyridin-2-yl}-N,N-dimethyl-acetamide (13.6 mg, 24% yield). ¹H NMR (500 MHz, Dimethyl sulfoxide-d6) δ 2.85 (s, 3H) 3.30 (s, 3H); 3.85 (s, 3H)); 5.63 (m, 2H); 7.10 (t, J=8 Hz 1H); 7.4 (d, J=8 Hz 1H); 7.44 (m, 2H); 7.63 (d, J=8 Hz 1H); 7.87 (m, 2H) 8.88 (s, 1H); 9.22 (s, 1H); 13.84 (s, br, 1H) MS: m/z 404.3 (M+H⁺).

Other compounds prepared by Method 22 are shown in Table 16:

TABLE 16

| Structure | MS: m/z (M + H⁺) |
|---|---|
| 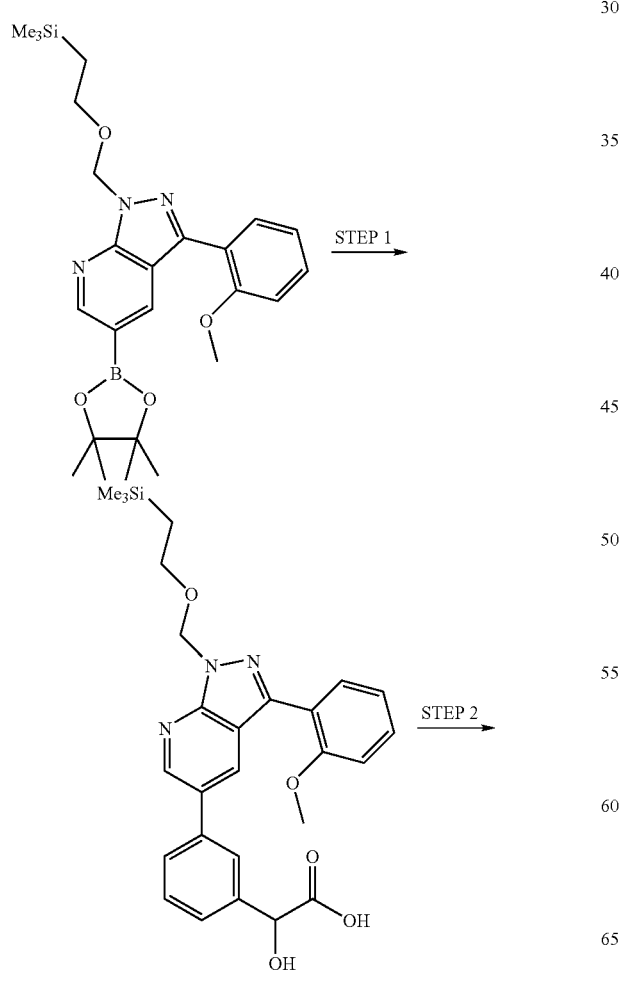 | 461.5 |

Method 23

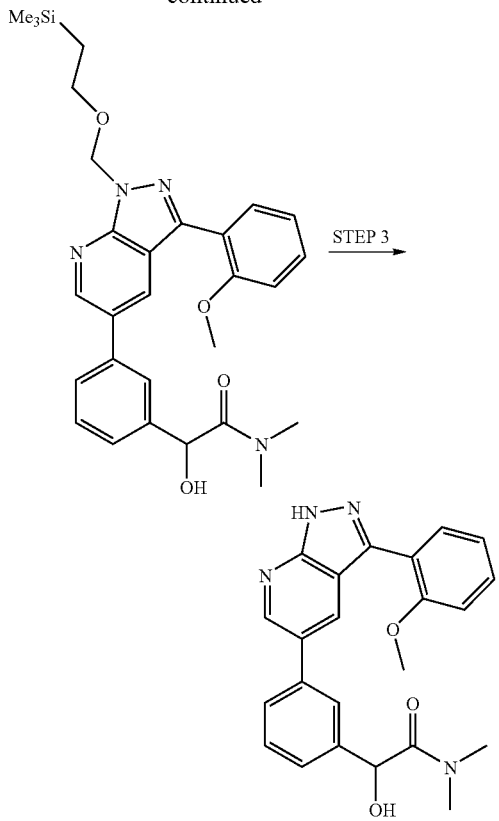

Synthesis of 2-hydroxy-2-{3-[3-(2-methoxy-phenyl)-1H-pyrazolo[3,4-b]pyridin-5-yl]-phenyl}-N,N-dimethyl-acetamide Step 1: Synthesis of hydroxy-{3-[3-(2-methoxyphenyl)-1-(2-trimethylsilanyl-ethoxymethyl)-1H-pyrazolo[3,4-b]pyridin-5-yl]-phenyl}-acetic acid To a mixture of 3-(2-Methoxy-phenyl)-5-(4,4,5,5-tetramethyl-[1,3,2]dioxaborolan-2-yl)-1-(2-trimethylsilanyl-ethoxymethyl)-1H-pyrazolo[3,4-b]pyridine (500 mg, 1.04 mmol) and 3-bromomandelic acid (288 mg, 1.25 mmol) in a 20 mL microwave reaction flask was added THF (3 mL), acetonitrile (3 mL) and sodium carbonate (3 mL, 1 N aqueous solution, 3 mmol). The mixture was purged with nitrogen for 1 min. dichloro[1,1'-bis(diphenylphoshino)ferrocene]palladium(II) dichloromethane adduct (73 mg, 89 μmol) was added and the purging continued for another minute. The flask was sealed and irradiated in a microwave reactor to 120° C. for 20 min. The reaction mixture was partitioned between aqueous saturated sodium chloride and ethyl acetate (15 mL:15 mL). The aqueous layer was extracted with ethyl acetate (10 mL×2). The combined organic layers were washed with brine, dried over sodium sulfate and evaporated. The resulting crude was purified by flash chromatography on silica gel using a gradient of methanol in dichloromethane to afford hydroxy-{3-[3-(2-methoxy-phenyl)-1-(2-trimethylsilanyl-ethoxymethyl)-1H-pyrazolo[3,4-b]pyridin-5-yl]-phenyl}-acetic acid as a yellow solid (370 mg, 67% yield). MS: m/z 506 (M+H⁺).

Step 2: Synthesis of 2-hydroxy-2-{3-[3-(2-methoxy-phenyl)-1-(2-trimethylsilanylethoxymethyl)-1H-pyrazolo[3,4-b]pyridin-5-yl]-phenyl}-N,N-dimethyl-acetamide To a solution of hydroxy-{3-[3-(2-methoxy-phenyl)-1-(2-trimethylsilanyl-ethoxymethyl)-1H-pyrazolo[3,4-b]pyridin-5-yl]-phenyl}-acetic acid (100 mg, 0.19 mmol), dimethylamine (2 N solution in THF, 0.19 mL, 0.38 mmol), diisopropylethylamine (49 mg, 0.38 mmol) in THF was added O-(7-azabenzotriazol-1-yl)-N,N,N',N,-tetramethyluronium hexafluorophosphate (110 mg, 0.29 mmol). The resulting suspension was heated to 60° C. with stirring until all was dissolved dissolved. The solvent was evaporated and the residue was used in the next step reaction without further purification. MS: m/z 533 (M+H$^+$).

Step 3: Synthesis of 2-hydroxy-2-{3-[3-(2-methoxy-phenyl)-1H-pyrazolo[3,4-b]pyridin-5-yl]-phenyl}-N,N-dimethyl-acetamide To the crude 2-hydroxy-2-{3-[3-(2-methoxy-phenyl)-1-(2-trimethylsilanylethoxymethyl)-1H-pyrazolo[3,4-b]pyridin-5-yl]-phenyl}-N,N-dimethyl-acetamide obtained in last step was added trifluoroacetic acid (2 mL) and the resulting mixture was sonicated until the residue was completely dissolved. The trifluoroacetic acid was evaporated and the residue treated with ethylene diamine (0.2 mL). The resulting mixture was purified via mass-triggered reverse-phase HPLC to yield 2-hydroxy-2-{3-[3-(2-methoxy-phenyl)-1H-pyrazolo[3,4-b]pyridin-5-yl]-phenyl}-N,N-dimethyl-acetamide as a white solid (25 mg, 33% over two steps). MS: m/z 403 (M+H$^+$). $^1$H NMR (500 MHz, DMSO-d6) δ 2.89 (d, 6H), 3.87 (s, 3H), 5.48 (d, 1H), 5.57 (d, 1H), 7.10 (t, 1H), 7.24 (d, 1H), 7.38 (d, 1H), 7.47 (dt, 1H), 7.48 (t, 1H), 7.67 (dd, 1H), 7.70 (d, 1H), 7.75 (s, 1H), 8.32 (d, 1H), 8.84 (d, 1H), 13.84 (s, 1H).

Other compounds prepared by Method 23 are shown in Table 17:

TABLE 17

| Structure | MS: m/z (M + H$^+$) |
|---|---|
| (structure) | 460 |
| (structure) | 446 |
| (structure) | 502 |
| (structure) | 445 |

TABLE 17-continued
| Structure | MS: m/z (M + H+) |
|---|---|
| 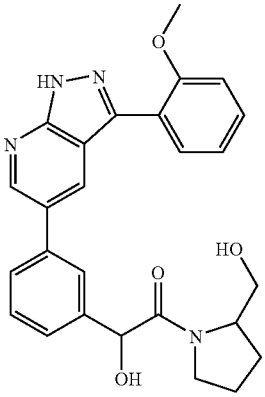 | 459 |
| 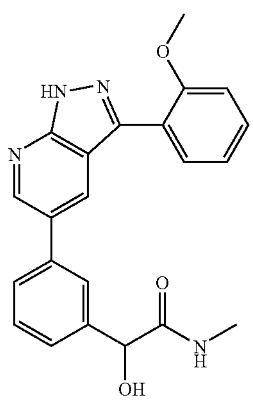 | 389 |
| | 459 |
TABLE 17-continued
| Structure | MS: m/z (M + H+) |
|---|---|
| 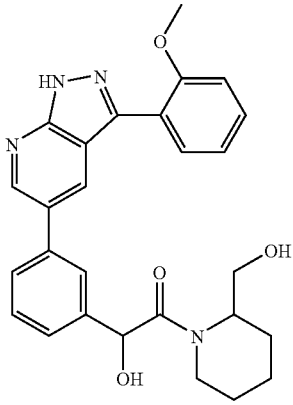 | 473 |
| 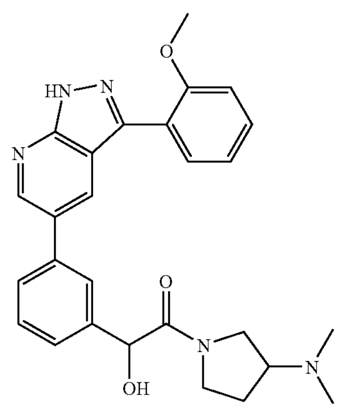 | 472 |
| | 473 |

TABLE 17-continued

| Structure | MS: m/z (M + H+) |
|---|---|
| 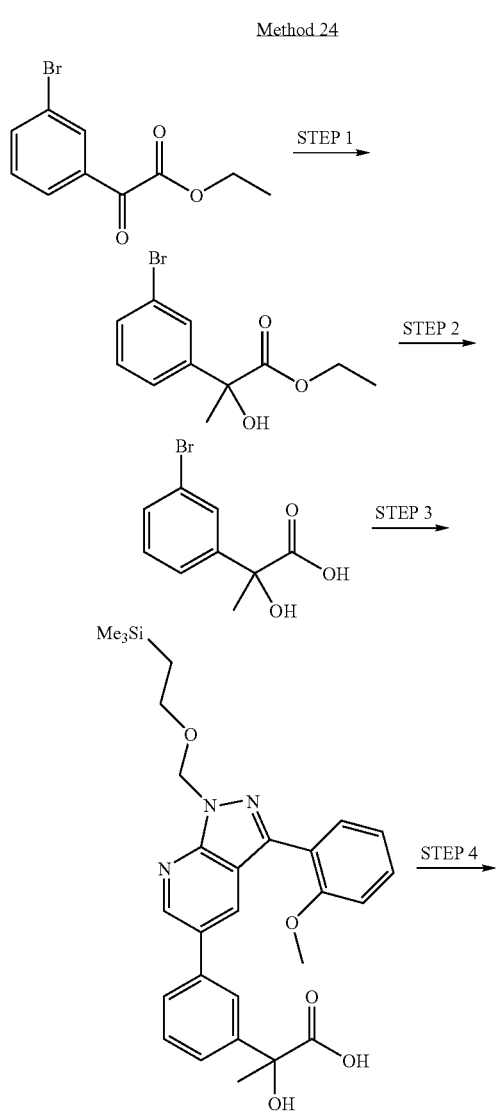 | 431 |

Method 24

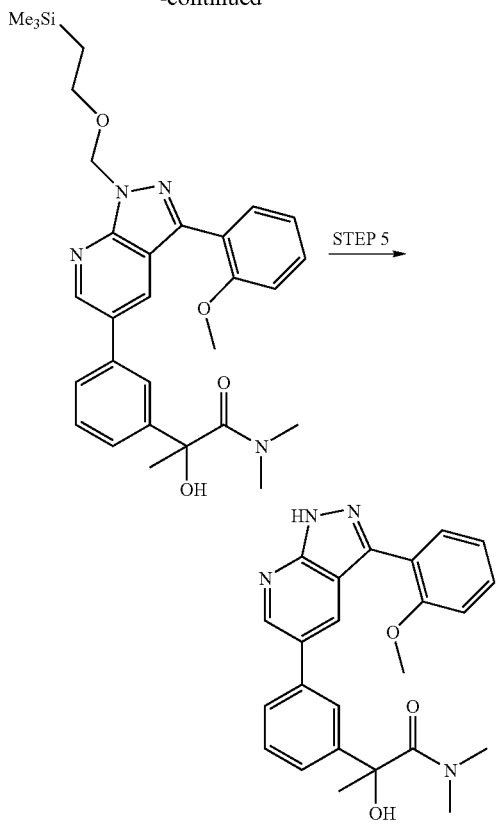

Synthesis of 2-hydroxy-2-{3-[3-(2-methoxy-phenyl)-1H-pyrazolo[3,4-b]pyridin-5-yl]-phenyl}-N,N-dimethyl-propionamide

Step 1: Synthesis of 2-(3-bromo-phenyl)-2-hydroxy-propionic acid ethyl ester To a solution of (3-Bromo-phenyl)-oxo-acetic acid ethyl ester (2.5 g, 9.8 mmol) in ether (20 mL) at 0° C. was added methyl magnesium bromide (10.8 mmol, 3 M in ether, 3.6 mL) with stirring. The reaction was stirred at 0° C. for 15 min. Water was added and the crude partitioned between ethyl acetate and water. The aqueous layer was extracted three times with ethyl acetate and the combined organic layers were washed with brine, dried over sodium sulfate and evaporated. The resulting crude was purified by flash chromatography on silica gel using a gradient of ethyl acetate in hexane to afford 2-(3-bromo-phenyl)-2-hydroxy-propionic acid ethyl ester as a colorless liquid. (1.87 g, 70% yield). MS: m/z 273 (M+H+).

Step 2: Synthesis of 2-(3-bromo-phenyl)-2-hydroxy-propionic acid

To a solution of 2-(3-Bromo-phenyl)-2-hydroxy-propionic acid ethyl ester (1.87 g, 6.7 mmol) in methanol (10 mL) was added potassium hydroxide (50% in water, 2 mL) and the solution was stirred at room temperature for 15 minutes. Hydrochloric acid (1 N) was added to adjust the pH to 4. The resulting mixture was extracted with ethyl acetate (10 ml×3). The combined organic layers were dried over sodium sulfate, filtered, and concentrated to afford the crude 2-(3-bromophenyl)-2-hydroxy-propionic acid as a white solid (1.6 g, 97%). MS: m/z 245 (M+H⁺).

Step 3: Synthesis 2-hydroxy-2-{3-[3-(2-methoxy-phenyl)-1-(2-trimethylsilanyl-ethoxymethyl)-1H-pyrazolo[3,4-b]pyridin-5-yl]-phenyl}-propionic acid To a mixture of 3-(2-Methoxy-phenyl)-5-(4,4,5,5-tetramethyl-[1,3,2]dioxaborolan-2-yl)-1-(2-trimethylsilanyl-ethoxymethyl)-1H-pyrazolo[3,4-b]pyridine (1.0 g, 2.0 mmol) and the crude 2-(3-bromo-phenyl)-2-hydroxy-propionic acid obtained in last step (0.49 g, 2.0 mmol) in a 20 mL microwave reaction flask was added THF (6 mL), acetonitrile (6 mL), and sodium carbonate (1 N in water, 6 mL, 6 mmol). The resulting suspension was purged with nitrogen for 1 minute. Dichloro[1,1'-bis(diphenylphoshino)ferrocene]palladium(II) dichloromethane adduct (73 mg, 89 µmol) was added and purging was continued for another minute. The flask was sealed and was irradiated in a microwave reactor to 100° C. for 10 minutes. The reaction mixture was neutralized to pH 4 using 1 N hydrochloric acid, extracted with ethyl acetate (10 mL×3). The combine organic layers were dried over sodium sulfate, filtered, and concentrated. The residue was purified by flash chromatography on silica gel using a gradient of methanol in dichloromethane to afford 2-hydroxy-2-{3-[3-(2-methoxy-phenyl)-1-(2-trimethylsilanyl-ethoxymethyl)-1H-pyrazolo[3,4-b]pyridin-5-yl]-phenyl}-propionic acid as a off white solid (469 mg, 45%). MS: m/z 520 (M+H⁺).

Step 4: Synthesis of 2-hydroxy-2-{3-[3-(2-methoxy-phenyl)-1-(2-trimethylsilanyl-ethoxymethyl)-1H-pyrazolo[3,4-b]pyridin-5-yl]-phenyl}-N,N-dimethyl-propionamide To a solution of 2-hydroxy-2-{3-[3-(2-methoxy-phenyl)-1-(2-trimethylsilanyl-ethoxymethyl)-1H-pyrazolo[3,4-b]pyridin-5-yl]-phenyl}-propionic acid (100 mg, 0.19 mmol), dimethylamine (2 N in THF, 0.143 mL, 0.29 mmol), and diisopropylethylamine (37 mg, 0.29 mmol) in THF (2 mL) was added O-(7-azabenzotriazol-1-yl)-N,N,N',N'-tetramethyluronium hexafluorophosphate (110 mg, 0.29 mmol.). The resulting suspension was heated to 60° C. with stirring until all was dissolved. The solvent was evaporated and the residue was used in next step without purification. MS: m/z 547 (M+H⁺).

Step 5: Synthesis of 2-hydroxy-2-{3-[3-(2-methoxy-phenyl)-1H-pyrazolo[3,4-b]pyridin-5-yl]-phenyl}-N,N-dimethyl-propionamide To the crude product obtained from last step was added trifluoroacetic acid (2 mL) and the resulting mixture was sonicated until the residue was completely dissolved. The volatiles were removed under reduced pressure and the residue treated with ethylene diamine (0.2 mL). The crude was directly purified by mass-triggered reverse-phase HPLC to afford 2-hydroxy-2-{3-[3-(2-methoxy-phenyl)-1H-pyrazolo[3,4-b]pyridin-5-yl]-phenyl}-N,N-dimethyl-propionamide as a white solid (23 mg, 29% over two steps). MS: m/z 517 (M+H⁺). ¹H NMR (500 MHz, DMSO-d6) δ 1.59 (s, 3H), 2.80 (d, 6H), 3.89 (s, 3H), 6.24 (s, 1H), 7.10 (t, 1H), 7.25 (d, 1H), 7.35 (d, 1H), 7.47 (m, 2H), 7.65 (s, 1H), 7.66 (d, 1H), 7.69 (d, 1H), 8.30 (s, 1H), 8.82 (s, 1H), 13.83 (s, br 1H).

Other compounds prepared by Method 24 are shown in Table 18:

TABLE 18

| Structure | MS: m/z (M + H⁺) |
|---|---|
| 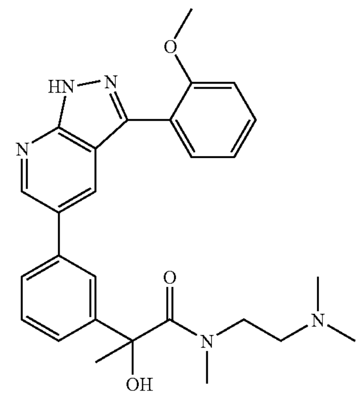 | 474 |
| 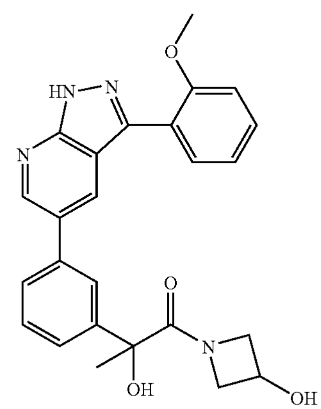 | 446 |

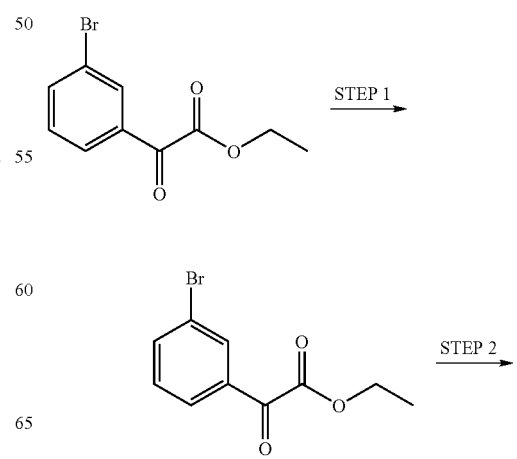

Method 25

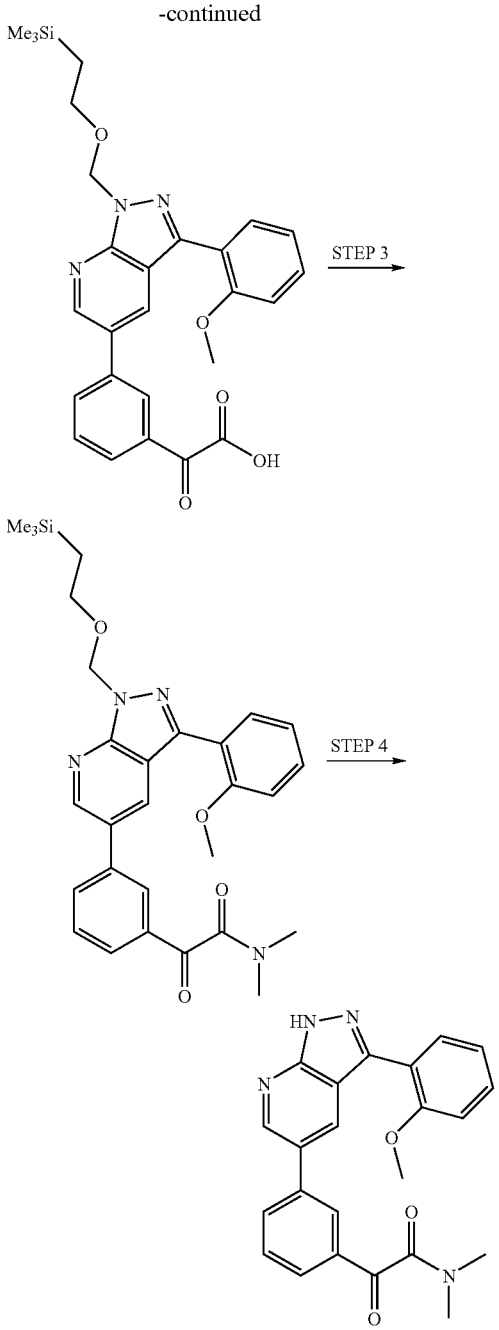

Synthesis of 2-{3-[3-(2-methoxy-phenyl)-1H-pyrazolo[3,4-b]pyridin-5-yl]-phenyl}-N,N-dimethyl-2-oxo-acetamide Step 1: Synthesis of (3-bromo-phenyl)-oxo-acetic acid To a solution of (3-Bromo-phenyl)-oxo-acetic acid ethyl ester (1 g, 3.9 mmol) in methanol (10 mL) was added potassium hydroxide (2 mL, 50% w/v in water) and the resulting mixture was stirred at room temperature for 30 minutes. Hydrochloric acid (1 N) was added to adjust to pH 4. The mixture was extracted with ethyl acetate (5 mL×4) and the combined organic extracts were dried over sodium sulfate, filtered, and concentrated. The residue was used in next step without further purification (0.8 g, 89% yield). MS: m/z 230 (M−H⁺).

Step 2: Synthesis of {3-[3-(2-methoxy-phenyl)-1-(2-trimethylsilanyl-ethoxymethyl)-1H-pyrazolo[3,4-b]pyridin-5-yl]-phenyl}-oxo-acetic acid To a mixture of 3-(2-Methoxy-phenyl)-5-(4,4,5,5-tetramethyl-[1,3,2]dioxaborolan-2-yl)-1-(2-trimethylsilanyl-ethoxymethyl)-1H-pyrazolo[3,4-b]pyridine (1.0 g, 2.1 mmol) and the crude (3-Bromo-phenyl)-oxo-acetic acid obtained in last step (0.49 g, 2.1 mmol) in a 20 mL microwave reaction flask was added THF (6 mL), acetonitrile (6 mL), and sodium carbonate (1 N in water, 6 mL, 6 mmol). The resulting suspension was purged with nitrogen for 1 minute. Dichloro[1,1'-bis(diphenylphoshino)ferrocene]palladium(II) dichloromethane adduct (73 mg, 89 µmol) was added and the purging was continued for another minute. The flask was sealed and was irradiated in a microwave reactor to 90° C. for 10 minutes. The reaction mixture was adjusted to pH 4 by addition of 1 N hydrochloric acid, extracted with ethyl acetate (10 mL×3). The combine organic layers were dried over sodium sulfate, filtered, and concentrated. The residue was purified by flash chromatography on silica gel using a gradient of methanol in dichloromethane to afford {3-[3-(2-methoxy-phenyl)-1-(2-trimethylsilanyl-ethoxymethyl)-1H-pyrazolo[3,4-b]pyridin-5-yl]-phenyl}-oxo-acetic acid as a off white solid (490 mg, 46%). MS: m/z 504 (M+H⁺).

Step 3: Synthesis of 2-{3-[3-(2-methoxy-phenyl)-1-(2-trimethylsilanylethoxymethyl)-1H-pyrazolo[3,4-b]pyridin-5-yl]-phenyl}-N,N-dimethyl-2-oxo-acetamide To a solution of {3-[3-(2-methoxy-phenyl)-1-(2-trimethylsilanyl-ethoxymethyl)-1H-pyrazolo[3,4-b]pyridin-5-yl]-phenyl}-oxo-acetic acid. (100 mg, 0.20 mmol), dimethylamine (2 N in THF, 0.143 mL, 0.29 mmol), and diisopropylethylamine (37 mg, 0.29 mmol) in THF (2 mL) was added O-(7-azabenzotriazol-1-yl)-N,N,N',N'-tetramethyluronium hexafluorophosphate (110 mg, 0.29 mmol.). The resulting suspension was heated to 60° C. with stirring until all was dissolved. The solvent was evaporated and the residue was used in next step without purification. MS: m/z 531 (M+H⁺).

Step 4: Synthesis of 2-{3-[3-(2-Methoxy-phenyl)-1H-pyrazolo [3,4-b]pyridin-5-yl]-phenyl}-N,N-dimethyl-2-oxo-acetamide To the crude product obtained from last step was added trifluoroacetic acid (2 mL) and the resulting mixture was sonicate until the residue was completely dissolved. The trifluoroacetic acid was completely evaporated and the residue was treated with ethylene diamine (0.2 mL). The crude was directly purified by mass-triggered reverse-phase HPLC to afford 2-{3-[3-(2-Methoxy-phenyl)-1H-pyrazolo[3,4-b]pyridin-5-yl]-phenyl}-N,N-dimethyl-2-oxo-acetamide as a white solid (20 mg, 25% over two steps). MS: m/z 401 (M+H⁺). ¹H NMR (500 MHz, DMSO-d6) δ 2.93 (s, 3H), 3.03 (s, 3H), 3.89 (s, 3H), 7.10 (t, 1H), 7.24 (d, 1H), 7.48 (t, 1H), 7.68 (d, 1H), 7.75 (t, 1H), 7.89 (d, 1H), 8.16 (s, 1H), 8.165 (d, 1H), 8.40 (d, 1H), 8.89 (d, 1H), 13.86 (s, br 1H).

Other compounds prepared by Method 25 are shown in Table 19:

TABLE 19

| Structure | MS: m/z (M + H+) |
|---|---|
| (structure) | 458 |
| (structure) | 429 |

Method 26

Synthesis of 2-Methoxy-2-{3-[3-(2-methoxy-phenyl)-1H-pyrazolo[3,4-b]pyridin-5-yl]-phenyl}-N,N-dimethyl-acetamide

Step 1: Synthesis of (3-Bromo-phenyl)-methoxy-acetic acid

To a solution of 3-Bromomandelic acid ethyl ester (0.5 g, 2.2 mmol) in THF (5 mL) at 0° C. was added sodium hydride (352 mg, 60% in mineral oil, 8.8 mmol) and the resulting mixture was stirred at 0° C. for 15 minutes. Methyl iodide (1.9 g, 13.2 mmol) was added and the resulting mixture was stirred at 0° C. for 10 minutes and warmed to room temperature for 15 minutes. Saturated sodium chloride (10 mL) was added and 1 N hydrochloric acid was added to adjust the pH to 4. The resulting mixture was extracted with ethyl acetate (5 mL×4) and the combined organic extracts were dried over sodium sulfate, filtered, and concentrated. The residue (0.43 g, 80%) was used in next step without further purification. MS: m/z 245 (M+H⁺).

Step 2: Synthesis of methoxy-{3-[3-(2-methoxy-phenyl)-1-(2-trimethylsilanyl-ethoxymethyl)-1H-pyrazolo[3,4-b]pyridin-5-yl]-phenyl}-acetic acid To a mixture of 3-(2-methoxy-phenyl)-5-(4,4,5,5-tetramethyl-[1,3,2]dioxaborolan-2-yl)-1-(2-trimethylsilanyl-ethoxymethyl)-1H-pyrazolo[3,4-b]pyridine (0.84 g, 1.7 mmol) and the crude (3-bromo-phenyl)-methoxy-acetic acid obtained in last step (0.43 g, 1.7 mmol) in a 20 mL microwave reaction flask was added THF (6 mL), acetonitrile (6 mL), and sodium carbonate (1 N in water, 6 mL, 6 mmol). The resulting suspension was purged with nitrogen for 1 minute. Dichloro[1,1'-bis(diphenylphoshino)ferrocene]palladium(II) dichloromethane adduct (62 mg, 76 μmol) was added and the purging was continued for another minute. The flask was sealed and was irradiated in a microwave reactor to 90° C. for 10 minutes. The reaction mixture was adjusted to pH 4 using 1 N hydrochloric acid, extracted with ethyl acetate (10 mL×3). The combine organic layers were dried over sodium sulfate, filtered, and concentrated. The residue was purified by flash chromatography on silica gel using a gradient of methanol in dichloromethane to afford methoxy-{3-[3-(2-methoxy-phenyl)-1-(2-trimethylsilanyl-ethoxymethyl)-1H-pyrazolo-[3,4-b]pyridin-5-yl]-phenyl}-acetic acid as an off white solid (300 mg, 34%). MS: m/z 520 (M+H⁺).

Step 3: Synthesis of 2-methoxy-2-{3-[3-(2-methoxy-phenyl)-1-(2-trimethylsilanyl-ethoxymethyl)-1H-pyrazolo[3,4-b]pyridin-5-yl]-phenyl}-N,N-dimethyl-acetamide To a solution of methoxy-{3-[3-(2-methoxy-phenyl)-1-(2-trimethylsilanyl-ethoxymethyl)-1H-pyrazolo[3,4-b]pyridin-5-yl]-phenyl}-acetic acid, (100 mg, 0.19 mmol), dimethylamine (2 N in THF, 0.143 mL, 0.29 mmol), and diisopropylethylamine (37 mg, 0.29 mmol) in THF (2 mL) was added O-(7-azabenzotriazol-1-yl)-N,N,N',N',-tetramethyluronium hexafluorophosphate (110 mg, 0.29 mmol.). The resulting suspension was heated to 60° C. with stirring until all was dissolved. The solvent was evaporated and the residue was used in next step without purification. MS: m/z 547 (M+H⁺).

Step 4: Synthesis of 2-Methoxy-2-{3-[3-(2-methoxy-phenyl)-1H-pyrazolo[3,4-b]pyridin-5-yl]-phenyl}-N,N-dimethyl-acetamide To the crude product obtained from last step was added trifluoroacetic acid (2 mL) and the resulting mixture was sonicate until the residue was completely dissolved. The trifluoroacetic acid was completely evaporated and the residue was treated with ethylene diamine (0.2 mL). The crude was directly purified by mass-triggered reverse-phase HPLC to afford 2-methoxy-2-{3-[3-(2-methoxy-phenyl)-1H-pyrazolo[3,4-b]pyridin-5-yl]-phenyl}-N,N-dimethyl-acetamide as a white solid (19 mg, 24% over two steps). MS: m/z 417 (M+H⁺). ¹H NMR (500 MHz, DMSO-d6) δ 2.84 (s, 3H), 2.98 (s, 3H), 3.31 (s, 3H), 3.87 (s, 3H), 5.28 (s, 1H), 7.10 (t, 1H), 7.24 (d, 1H), 7.40 (d, 1H), 7.47 (dt, 1H), 7.50 (t, 1H), 7.68 (dd, 1H), 7.73 (d, 1H), 7.75 (s, 1H), 8.31 (d, 1H), 8.83 (d, 1H), 13.83 (s, br 1H).

Other compounds prepared by Method 26 are shown in Table 20:

TABLE 20

| Structure | MS: m/z (M + H⁺) |
|---|---|
| 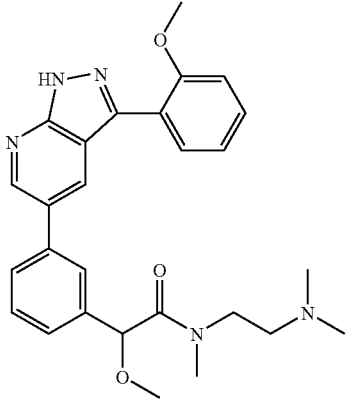 | 474 |
| 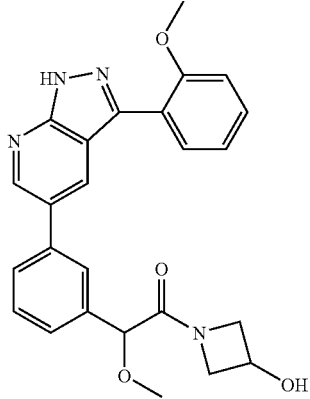 | 445 |

Method 27

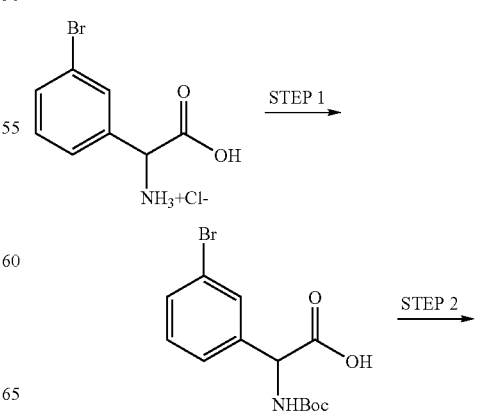

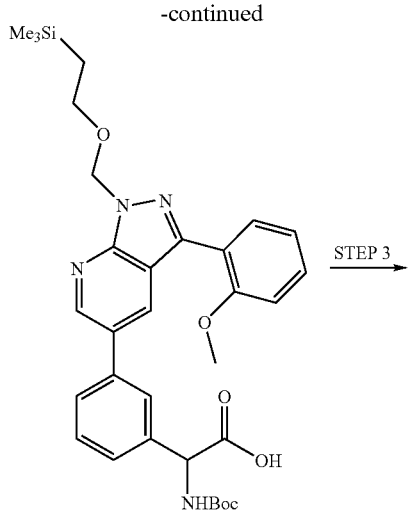

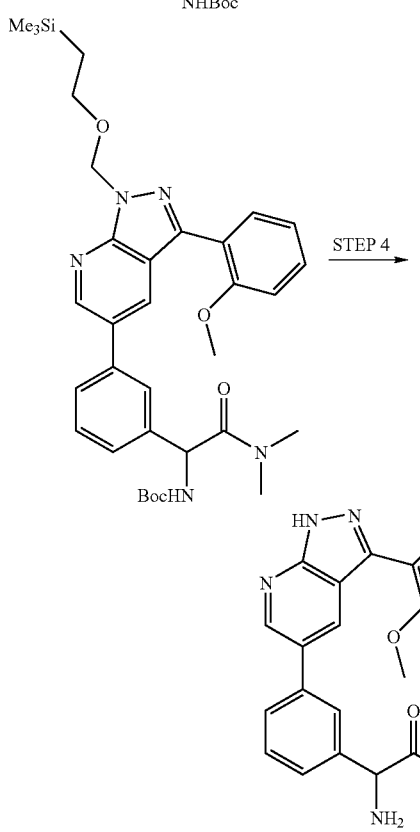

Synthesis of 2-amino-2-{3-[3-(2-methoxy-phenyl)-1H-pyrazolo[3,4-b]pyridin-5-yl]-phenyl}-N,N-dimethyl-acetamide Step 1: Synthesis of (3-Bromo-phenyl)-tert-butoxycarbonylamino-acetic acid To a solution of amino-(3-bromo-phenyl)-acetic acid hydrochloride (2 g, 7.6 mmol) and potassium carbonate (1.58 g, 11.4 mmol) in water (40 mL) was added a solution of di-tert-butyl dicarbonate (1.82 g, 8.4 mmol) in THF (40 mL). The resulting mixture stirred at room temperature for 16 hours. The pH was adjusted to 4 by addition of hydrochloric acid (16 N) and the mixture extracted with ethyl acetate (30 mL×3). The combined organic layers were dried over sodium sulfate, filtered, and concentrated. The residue (2.4 g, 96%) was used in next step without further purification. MS: m/z 330 (M+H$^+$).

Step 2: Synthesis of tert-butoxycarbonylamino-{3-[3-(2-methoxy-phenyl)-1-(2-trimethylsilanyl-ethoxymethyl)-1H-pyrazolo[3,4-b]pyridin-5-yl]-phenyl}-acetic acid To a mixture of 3-(2-Methoxy-phenyl)-5-(4,4,5,5-tetramethyl-[1,3,2]dioxaborolan-2-yl)-1-(2-trimethylsilanyl-ethoxymethyl)-1H-pyrazolo[3,4-b]pyridine (0.9 g, 0.19 mmol) and the crude (3-bromo-phenyl)-tert-butoxycarbonylamino-acetic acid (0.69 g, 2.1 mmol) in a 20 mL microwave reaction flask was added THF (6 mL), acetonitrile (6 mL), and sodium carbonate (1 N in water, 6 mL, 6 mmol). The resulting suspension was purged with nitrogen for 1 minute. Dichloro [1,1'-bis(diphenylphoshino)ferrocene]palladium(II) dichloromethane adduct (62 mg, 76 μmol) was added and the purging was continued for another minute. The flask was sealed and was irradiated in a microwave reactor to 90° C. for 10 minutes. The reaction mixture was adjusted to pH 4 using 1 N hydrochloric acid, extracted with ethyl acetate (10 mL×3). The combined organic layers were dried over sodium sulfate, filtered, and concentrated. The residue was purified by flash chromatography on silica gel using a gradient of methanol in dichloromethane to afford tert-butoxycarbonylamino-{3-[3-(2-methoxy-phenyl)-1-(2-trimethylsilanylethoxymethyl)-1H-pyrazolo[3,4-b]pyridin-5-yl]-phenyl}-acetic acid as a pale yellow solid (520 mg, 50%). MS: m/z 605 (M+H$^+$).

Step 3: Synthesis of (dimethylcarbamoyl-{3-[3-(2-methoxy-phenyl)-1-(2-trimethylsilanyl-ethoxymethyl)-1H-pyrazolo[3,4-b]pyridin-5-yl]-phenyl}-methyl)-carbamic acid tert-butyl ester To a solution of tert-Butoxycarbonylamino-{3-[3-(2-methoxy-phenyl)-1-(2-trimethyl-silanylethoxymethyl)-1H-pyrazolo[3,4-b]pyridin-5-yl]-phenyl}-acetic acid. (100 mg, 0.17 mmol), dimethylamine (2 N in THF, 0.13 mL, 0.26 mmol), and diisopropylethylamine (33 mg, 0.26 mmol) in THF (2 mL) was added O-(7-azabenzotriazol-1-yl)-N,N,N',N'-tetramethyluronium hexafluorophosphate (99 mg, 0.26 mmol.). The resulting suspension was heated to 60° C. with stirring until all was dissolved. The solvent was evaporated and the residue was used in next step without purification. MS: m/z 632 (M+H$^+$).

Step 4: Synthesis of 2-amino-2-{3-[3-(2-methoxy-phenyl)-1H-pyrazolo[3,4-b]pyridin-5-yl]-phenyl}-N,N-dimethyl-acetamide To the crude product obtained from last step was added trifluoroacetic acid (2 mL) and the resulting mixture was sonicate until the residue was completely dissolved. The trifluoroacetic acid was completely evaporated and the residue was treated with ethylene diamine (0.2 mL). The crude was directly purified by mass-triggered reverse phase HPLC to afford 2-amino-2-{3-[3-(2-methoxy-phenyl)-1H-pyrazolo[3,4-b]pyridin-5-yl]-phenyl}-N,N-dimethyl-acetamide as a white solid (19 mg, 24% over two steps). MS: m/z 402 (M+H$^+$). $^1$H NMR (500 MHz, DMSO-d6) δ 2.86 (s, 3H), 2.94 (s, 3H), 3.87 (s, 3H), 5.09 (s, 1H), 7.10 (t, 1H), 7.24 (d, 1H), 7.38 (d, 1H), 7.48 (dt, 1H), 7.49 (t, 1H), 7.67 (dd, 1H), 7.71 (d, 1H), 7.77 (s, 1H), 8.34 (d, 1H), 8.85 (d, 1H), 13.83 (s, br 1H).

Other compounds prepared by Method 27 are shown in Table 21:

TABLE 21

| Structure | MS: m/z (M + H+) |
|---|---|
| 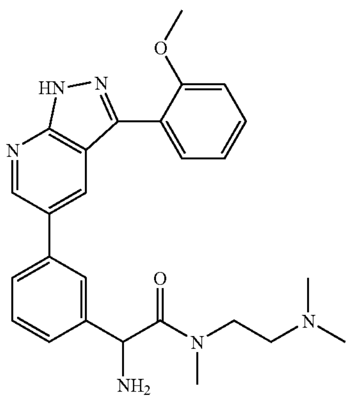 | 459 |
| 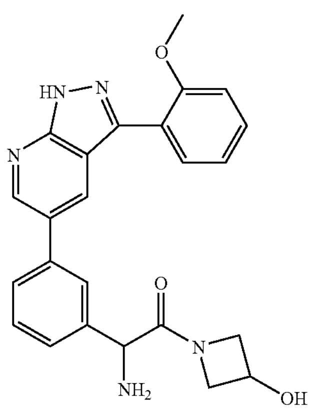 | 430 |

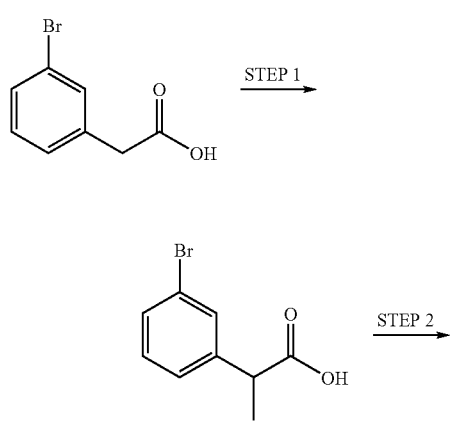

Method 28

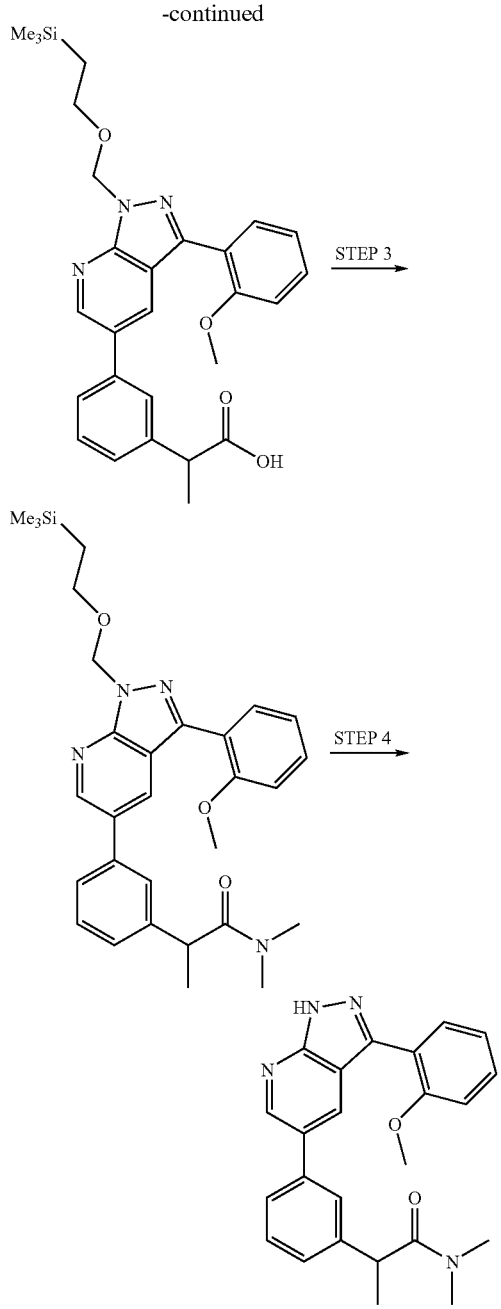

Synthesis of 2-{3-[3-(2-methoxy-phenyl)-1H-pyrazolo[3,4-b]pyridin-5-yl]-phenyl}-N,N-dimethyl-propionamide Step 1: Synthesis of 2-(3-bromo-phenyl)-propionic acid To a solution of diisopropylamine (0.97 g, 9.6 mmol) in THF (20 mL) at room temperature was added n-butyl lithium (2.5 N in hexane, 4 mL, 10 mmol) and the resulting solution was stirred at room temperature for 15 minutes. To above solution was added a solution of 3-bromophenylacetic acid (1.0 g, 4.6 mmol) in THF (10 mL) dropwise at room temperature and the stirring was continued for another 15 minutes. Methyl iodide (1.49 g, 10.5 mmol) was added and the resulting mixture was stirred at room temperature for 15 minutes. Satuated sodium chloride (30 mL) was added and the aqueous phase was adjusted to pH 5 by addition of hydrochloric acid (1 N). The resulting mixture was extracted with ethyl acetate (20 mL×3) and the combined organic extracts were dried over sodium sulfate, filtered, and concentrated. The residue was purified by flash chromatography on silica gel using a gradient of formic acid and methanol in dichloromethane to afford 2-(3-bromo-phenyl)-propionic acid (890 mg, 84%) as a white solid. MS: m/z 229 (M+H+).

Step 2: Synthesis of 2-{3-[3-(2-methoxy-phenyl)-1-(2-trimethylsilanyl-ethoxymethyl)-1H-pyrazolo[3,4-b]pyridin-5-yl]-phenyl}-propionic acid To a mixture of 3-(2-methoxy-phenyl)-5-(4,4,5,5-tetramethyl-[1,3,2]dioxaborolan-2-yl)-1-(2-trimethylsilanyl-ethoxymethyl)-1H-pyrazolo[3,4-b]pyridine (0.84 g, 1.7 mmol) and 2-(3-Bromo-phenyl)-propionic acid (0.39 g, 1.7 mmol) in a 20 mL microwave reaction flask was added THF (6 mL), acetonitrile (6 mL), and sodium carbonate (1 N in water, 6 mL, 6 mmol). The resulting suspension was purged with nitrogen for 1 minute. Dichloro[1,1'-bis(diphenylphoshino)ferrocene]palladium(II) dichloromethane adduct (62 mg, 76 mmol) was added and the purging was continued for another minute. The flask was sealed and was irradiated in a microwave reactor to 90° C. for 10 minutes. The reaction mixture was adjusted to pH 4 using 1 N hydrochloric acid, extracted with ethyl acetate (10 mL×3). The combine organic layers were dried over sodium sulfate, filtered, and concentrated. The residue was purified by flash chromatography on silica gel using a gradient of methanol in dichloromethane to afford 2-{3-[3-(2-methoxy-phenyl)-1-(2-trimethylsilanyl-ethoxymethyl)-1H-pyrazolo[3,4-b]pyridin-5-yl]-phenyl}-propionic acid as a off white solid (497 mg, 58%). MS: m/z 504 (M+H+).

Step 3: Synthesis of 2-{3-[3-(2-methoxy-phenyl)-1-(2-trimethylsilanyl-ethoxymethyl)-1H-pyrazolo[3,4-b]pyridin-5-yl]-phenyl}-N,N-dimethyl-propionamide To a solution of 2-{3-[3-(2-methoxy-phenyl)-1-(2-trimethylsilanyl-ethoxymethyl)-1H-pyrazolo[3,4-b]pyridin-5-yl]-phenyl}-propionic acid, (100 mg, 0.20 mmol), dimethylamine (2 N in THF, 0.143 mL, 0.29 mmol), and diisopropylethylamine (37 mg, 0.29 mmol) in THF (2 mL) was added O-(7-azabenzotriazol-1-yl)-N,N,N',N'-tetramethyluronium hexafluorophosphate (110 mg, 0.29 mmol.). The resulting suspension was heated to 60° C. with stirring until all was dissolved. The solvent was evaporated and the residue was used in next step without purification. MS: m/z 547 (M+H+).

Step 4: Synthesis of 2-{3-[3-(2-methoxy-phenyl)-1H-pyrazolo[3,4-b]pyridin-5-yl]-phenyl}-N,N-dimethyl-propionamide To the crude product obtained from last step was added trifluoroacetic acid (2 mL) and the resulting mixture was sonicate until the residue was completely dissolved. The trifluoroacetic acid was completely evaporated and the residue was treated with ethylene diamine (0.2 mL). The crude was directly purified by mass-triggered reverse-phase HPLC to afford 2-{3-[3-(2-methoxy-phenyl)-1H-pyrazolo[3,4-b]pyridin-5-yl]-phenyl}-N,N-dimethyl-propionamide as a white solid (28 mg, 35% over two steps). MS: m/z 401 (M+H+). 1H NMR (500 MHz, CD3OD-d4) δ 1.41 (s, 3H), 2.93 (s, 3H), 2.98 (s, 3H), 3.89 (s, 3H), 4.16 (q, 1H), 7.08 (t, 1H), 7.18 (d, 1H), 7.29 (d, 1H), 7.34 (t, 1H), 7.45 (t, 1H), 7.53 (d, 1H), 7.56 (s, 1H), 7.64 (d, 1H), 8.32 (d, 1H), 8.75 (d, 1H).

Other compounds prepared by Method 28 are shown in Table 22:

TABLE 22

| Structure | MS: m/z (M + H+) |
|---|---|
| 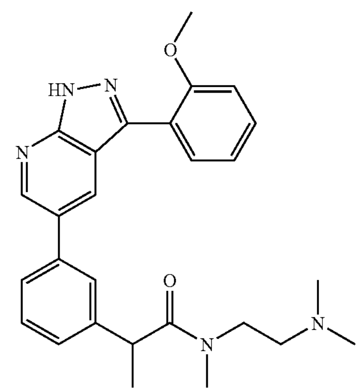 | 458 |
| 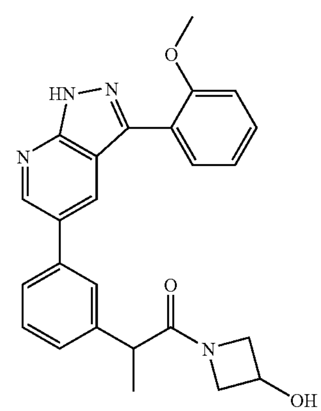 | 429 |
| 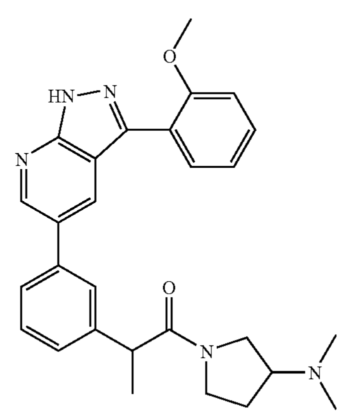 | 470 |

TABLE 22-continued
| Structure | MS: m/z (M + H⁺) |
|---|---|
| 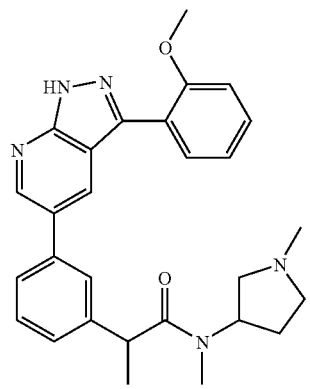 | 470 |
| 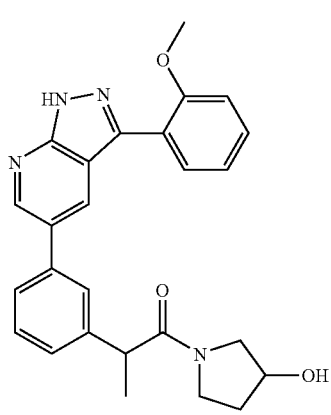 | 443 |
| 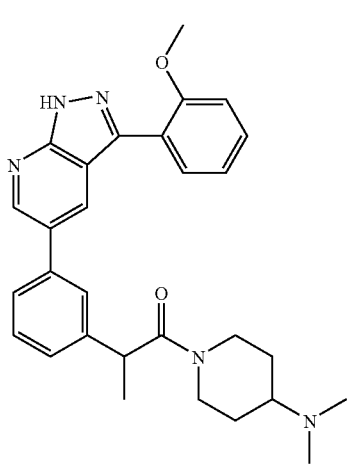 | 484 |
TABLE 22-continued
| Structure | MS: m/z (M + H⁺) |
|---|---|
| 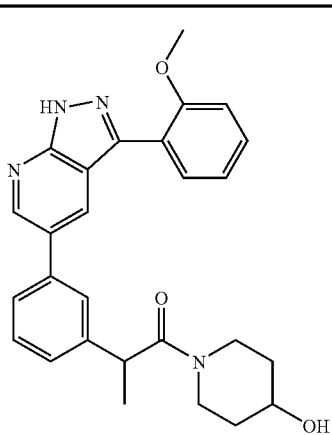 | 457 |
Method 29
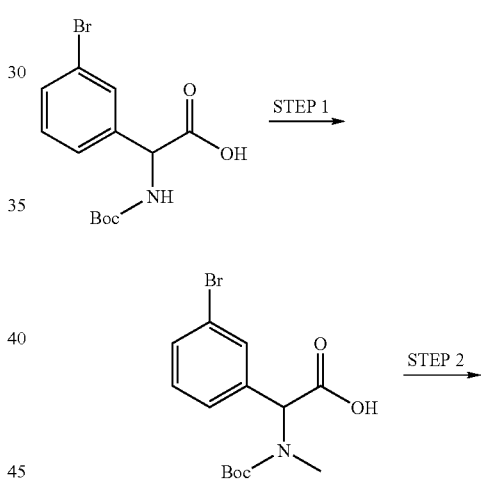
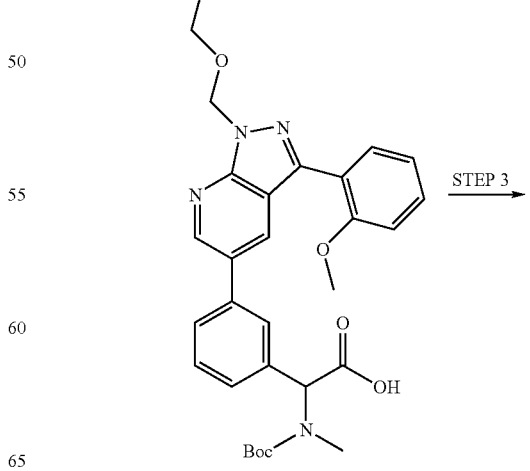

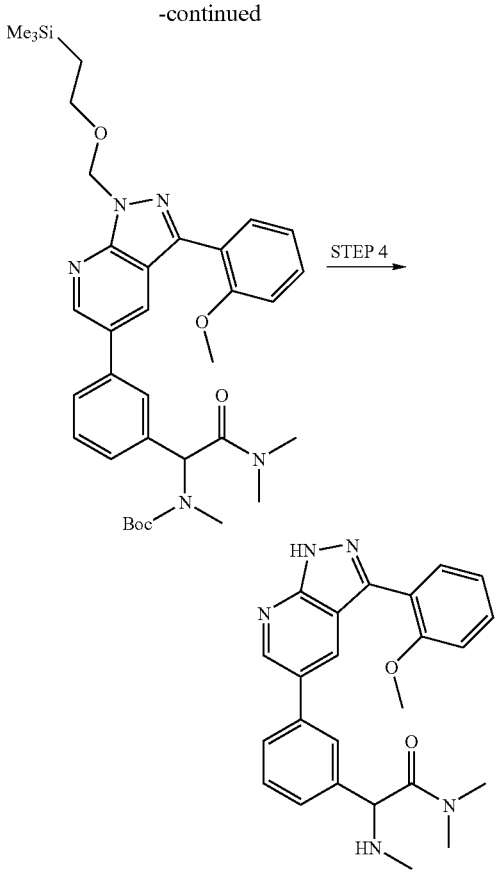

Synthesis of 2-{3-[3-(2-methoxy-phenyl)-1H-pyrazolo[3,4-b]pyridin-5-yl]-phenyl}-N,N-dimethyl-2-methylamino-acetamide Step 1: Synthesis of (3-bromo-phenyl)-(tert-butoxycarbonyl-methyl-amino)-acetic acid To a solution of (3-bromo-phenyl)-tert-butoxycarbonylamino-acetic acid (490 mg, 1.49 mmol) in THF (10 mL) at room temperature was added sodium hydride (125 mg, 60% in mineral oil, 3.1 mmol) and the resulting pale yellow suspension was stirred at room temperature for 3 hours. Methyl iodide (528 mg, 3.7 mmol) was added and the resulting mixture was stirred overnight. Satuated sodium chloride (10 mL) was added and the aqueous phase pH was adjusted to 5 by addition of 1 N hydrochloric acid. The resulting mixture was extracted with ethyl acetate (10 mL×3) and the combined organic extracts were dried over sodium sulfate, filtered, and concentrated. The residue was purified using a gradient of methanol in dichloromethane to afford (3-bromo-phenyl)-(tert-butoxy-carbonyl-methyl-amino)-acetic acid (390 mg, 76%) as an oil. MS: m/z 344 (M+H$^+$).

Step 2: Synthesis of (tert-butoxycarbonyl-methyl-amino)-{3-[3-(2-methoxy-phenyl)-1-(2-trimethylsilanyl-ethoxymethyl)-1H-pyrazolo[3,4-b]pyridin-5-yl]-phenyl}-acetic acid To a mixture of 3-(2-methoxy-phenyl)-5-(4,4,5,5-tetramethyl-[1,3,2]dioxaborolan-2-yl)-1-(2-trimethylsilanyl-ethoxymethyl)-1H-pyrazolo[3,4-b]pyridine (0.545 g, 1.1 mmol) and (3-Bromo-phenyl)-(tert-butoxycarbonyl-methyl-amino)-acetic acid (0.39 g, 1.1 mmol) in a 20 mL microwave reaction flask was added THF (3 mL), acetonitrile (3 mL), and sodium carbonate (1 N in water, 3 mL, 6 mmol). The resulting suspension was purged with nitrogen for 1 minute. Dichloro[1,1'-bis(diphenylphoshino)ferrocene]palladium(II) dichloromethane adduct (39 mg, 48 µmol) was added and the purging was continued for another minute. The flask was sealed and was irradiated in a microwave reactor to 90° C. for 10 minutes. The reaction mixture was adjusted to pH 4 by addition of 1 N hydrochloric acid, extracted with ethyl acetate (10 mL×3). The combine organic layers were dried over sodium sulfate, filtered, and concentrated. The residue was purified by flash chromatography on silica gel using a gradient of methanol in dichloromethane to afford (tert-butoxycarbonyl-methyl-amino)-{3-[3-(2-methoxy-phenyl)-1-(2-trimethylsilanyl-ethoxymethyl)-1H-pyrazolo[3,4-b]pyridin-5-yl]-phenyl}-acetic acid as a off white solid (490 mg, 72%). MS: m/z 619 (M+H$^+$).

Step 3: Synthesis of (dimethylcarbamoyl-{3-[3-(2-methoxy-phenyl)-1-(2-trimethylsilanyl-ethoxymethyl)-1H-pyrazolo[3,4-b]pyridin-5-yl]-phenyl}-methyl)-methyl-carbamic acid tert-butyl ester To a solution of (tert-butoxycarbonyl-methyl-amino)-{3-[3-(2-methoxy-phenyl)-1-(2-trimethylsilanyl-ethoxymethyl)-1H-pyrazolo[3,4-b]pyridin-5-yl]-phenyl}-acetic acid, (100 mg, 0.16 mmol), dimethylamine (2 N in THF, 0.12 mL, 0.24 mmol), and diisopropylethylamine (31 mg, 0.24 mmol) in THF (2 mL) was added O-(7-azabenzotriazol-1-yl)-N,N,N',N-tetramethyluronium hexafluorophosphate (91 mg, 0.24 mmol.). The resulting suspension was heated to 60° C. with stirring until all was dissolved. The solvent was evaporated and the residue was used in next step without purification. MS: m/z 646 (M+H$^+$).

Step 4: Synthesis of 2-{3-[3-(2-methoxy-phenyl)-1H-pyrazolo[3,4-b]pyridin-5-yl]-phenyl}-N,N-dimethyl-2-methylamino-acetamide To the crude product obtained from last step was added trifluoroacetic acid (2 mL) and the resulting mixture was sonicated until the residue was completely dissolved. The trifluoroacetic acid was completely evaporated and the residue was treated with ethylene diamine (0.2 mL). The crude was directly purified by mass-triggered reverse-phase HPLC to afford 2-{3-[3-(2-methoxy-phenyl)-1H-pyrazolo[3,4-b]pyridin-5-yl]-phenyl}-N,N-dimethyl-2-methylamino-acetamide as a yellow solid (23 mg, 35% over two steps). MS: m/z 416 (M+H$^+$). $^1$H NMR (500 MHz, CD$_3$OD-d4) δ 2.56 (s, 3H), 2.97 (s, 3H), 3.01 (s, 3H), 3.91 (s, 3H), 5.24 (s, 1H), 7.13 (t, 1H), 7.23 (d, 1H), 7.50 (dt, 1H), 7.53 (d, 1H), 7.64 (t, 1H), 7.68 (dd, 1H), 7.82 (s, 1H), 7.83 (d, 1H), 8.41 (d, 1H), 8.84 (d, 1H).

Other compounds prepared by Method 29 are shown in Table 23:

TABLE 23

| Structure | MS: m/z (M + H+) |
|---|---|
| [structure] | 473 |
| [structure] | 458 |
| [structure] | 485 |

TABLE 23-continued

| Structure | MS: m/z (M + H+) |
|---|---|
| [structure] | 444 |

Method 30

[Reaction scheme showing STEP 1, STEP 2, STEP 3, STEP 4]

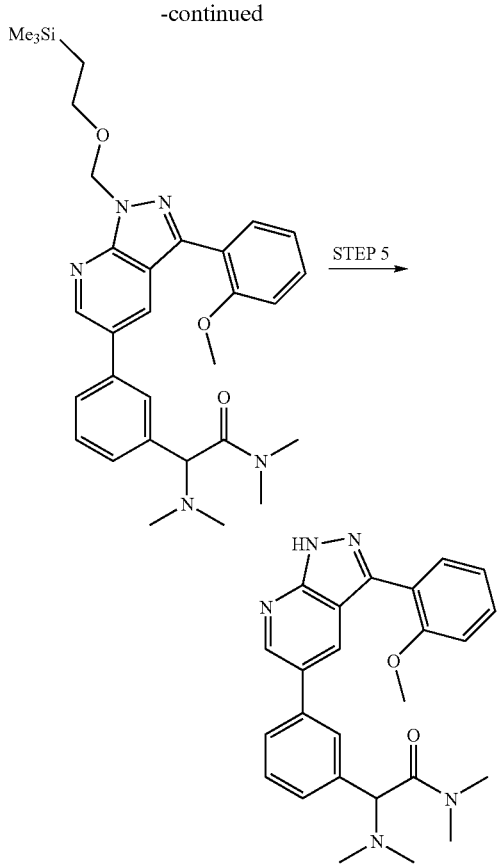

Synthesis of 2-Dimethylamino-2-{3-[3-(2-methoxy-phenyl)-1H-pyrazolo[3,4-b]pyridin-5-yl]-phenyl}-N,N-dimethyl-acetamide

Step 1: Synthesis of (3-bromo-phenyl)-dimethylamino-acetic acid ethyl ester

A suspension of (3-bromo-phenyl)-oxo-acetic acid ethyl ester (2.0 g, 7.8 mmol), dimethylamine (19.5 mL, 2 N in THF, 39 mmol), and sodium triacetoxyborohydride (4.95 g, 23.4 mmol) in 1,2-dichloroethane (40 mL) was stirred at room temperature for 36 hours. Satuated sodium bicarbonate (50 mL) was added and the resulting mixture was extracted with ethyl acetate. The combined organic extracts were dried over sodium sulfate, filtered, and concentrated. The residue was purified by flash chromatography on silica gel using a gradient of methanol in dichloromethane to afford (3-bromo-phenyl)-dimethylamino-acetic acid ethyl ester (350 mg, 16%) as an oil. MS: m/z 286 (M+H+).

Step 2: Synthesis of (3-bromo-phenyl)-dimethylamino-acetic acid

To a solution of (3-bromo-phenyl)-dimethylamino-acetic acid ethyl ester (350 mg, 1.2 mmol) in DMF was added potassium hydroxide (4 mL, 50% in water) and water (50 mL). The resulting mixture was refluxed for 25 hours. The mixture was neutralized to pH 7 with concentrated hydrochloric acid and extracted with ethyl acetate (50 mL×4). The combined organic extracts were dried over sodium sulfate, filtered, and concentrated to afford (3-Bromo-phenyl)-dimethylamino-acetic acid (290 mg, 94%). MS: m/z 258 (M+H+).

Step 3: Synthesis of dimethylamino-{3-[3-(2-methoxy-phenyl)-1-(2-trimethylsilanyl-ethoxymethyl)-1H-pyrazolo[3,4-b]pyridin-5-yl]-phenyl}-acetic acid To a mixture of 3-(2-methoxy-phenyl)-5-(4,4,5,5-tetramethyl-[1,3,2]dioxaborolan-2-yl)-1-(2-trimethylsilanyl-ethoxymethyl)-1H-pyrazolo[3,4-b]pyridine (0.545 g, 1.1 mmol) and (3-bromo-phenyl)-(tert-butoxycarbonyl-methyl-amino)-acetic acid (0.29 g, 1.1 mmol) in a 20 mL microwave reaction flask was added THF (3 mL), acetonitrile (3 mL), and sodium carbonate (1 N in water, 3 mL, 6 mmol). The resulting suspension was purged with nitrogen for 1 minute. Dichloro[1,1'-bis(diphenylphoshino)ferrocene]palladium(II) dichloromethane adduct (39 mg, 48 µmol) was added and the purging was continued for another minute. The flask was sealed and was irradiated in a microwave reactor to 90° C. for 10 minutes. The reaction mixture was adjusted to pH 4 using 1 N hydrochloric acid, extracted with ethyl acetate (10 mL×3). The combine organic layers were dried over sodium sulfate, filtered, and concentrated. The residue was purified by flash chromatography on silica gel using a gradient of methanol in dichloromethane to afford dimethylamino-{3-[3-(2-methoxy-phenyl)-1-(2-trimethylsilanyl-ethoxymethyl)-1H-pyrazolo[3,4-b]pyridin-5-yl]-phenyl}-acetic acid as a off white solid (280 mg, 48%). MS: m/z 533 (M+H+).

Step 4: Synthesis of 2-Dimethylamino-2-{3-[3-(2-methoxy-phenyl)-1-(2-trimethylsilanyl-ethoxymethyl)-1H-pyrazolo[3,4-b]pyridin-5-yl]-phenyl}-N,N-dimethyl-acetamide To a solution of dimethylamino-{3-[3-(2-methoxy-phenyl)-1-(2-trimethylsilanyl-ethoxymethyl)-1H-pyrazolo[3,4-b]pyridin-5-yl]-phenyl}-acetic acid (56 mg, 0.11 mmol), dimethylamine (2 N in THF, 0.08 mL, 0.16 mmol), and diisopropylethylamine (21 mg, 0.16 mmol) in THF (1.5 mL) was added O-(7-azabenzotriazol-1-yl)-N,N,N',N'-tetramethyluronium hexafluorophosphate (61 mg, 0.16 mmol.). The resulting suspension was heated to 60° C. with stirring until all was dissolved. The solvent was evaporated and the residue was used in next step without purification. MS: m/z 560 (M+H+).

Step 5: Synthesis of 2-Dimethylamino-2-{3-[3-(2-methoxy-phenyl)-1H-pyrazolo[3,4-b]pyridin-5-yl]-phenyl}-N,N-dimethyl-acetamide To the crude product obtained from last step was added trifluoroacetic acid (1.5 mL) and the resulting mixture was sonicate until the residue was completely dissolved. The trifluoroacetic acid was completely evaporated and the residue was treated with ethylene diamine (0.15 mL). The crude was directly purified by mass-triggered reverse-phase HPLC to afford 2-dimethylamino-2-{3-[3-(2-methoxy-phenyl)-1H-pyrazolo[3,4-b]pyridin-5-yl]-phenyl}-N,N-dimethyl-acetamide as a yellow solid (23 mg, 35% over two steps). MS: m/z 430 (M+H+). $^1$H NMR (500 MHz, CD$_3$OD-d4) δ 2.31 (s, 6H), 2.94 (s, 3H), 3.08 (s, 3H), 3.91 (s, 3H), 4.61 (s, 1H), 7.12 (t, 1H), 7.22 (d, 1H), 7.49 (t, 1H), 7.51 (d, 1H), 7.54 (t, 1H), 7.67 (d, 1H), 7.72 (d, 1H), 7.87 (s, 1H), 8.41 (d, 1H), 8.84 (d, 1H).

Other compounds prepared by Method 30 are shown in Table 24:
TABLE 24
| Structure | MS: m/z (M + H+) |
|---|---|
| 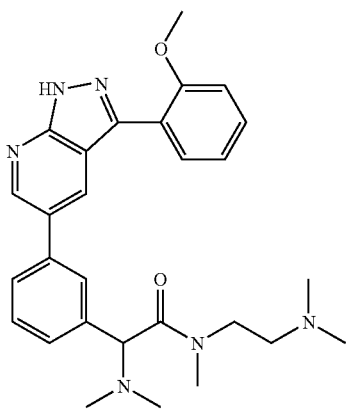 | 487 |
| 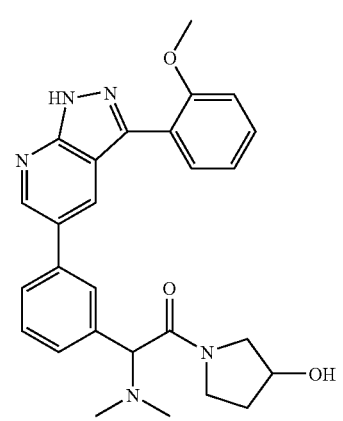 | 472 |
| 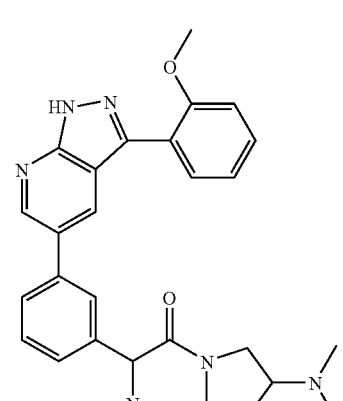 | 499 |
TABLE 24-continued
| Structure | MS: m/z (M + H+) |
|---|---|
| 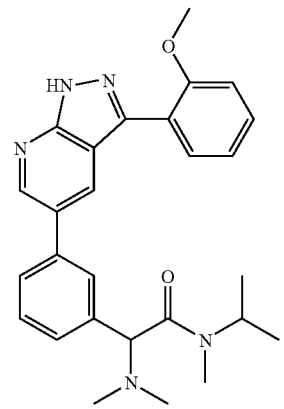 | 458 |
Method 31
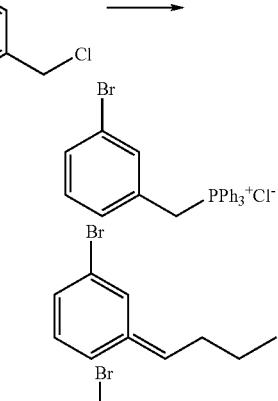 STEP 1 →
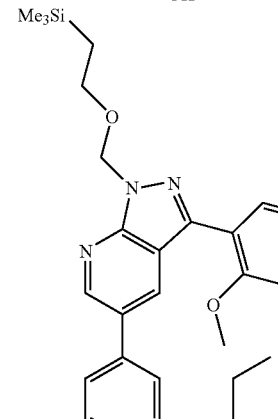 STEP 2 →
 STEP 3 →
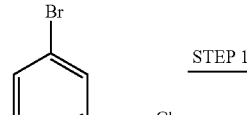 STEP 4 →
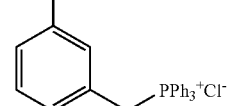 STEP 5 →

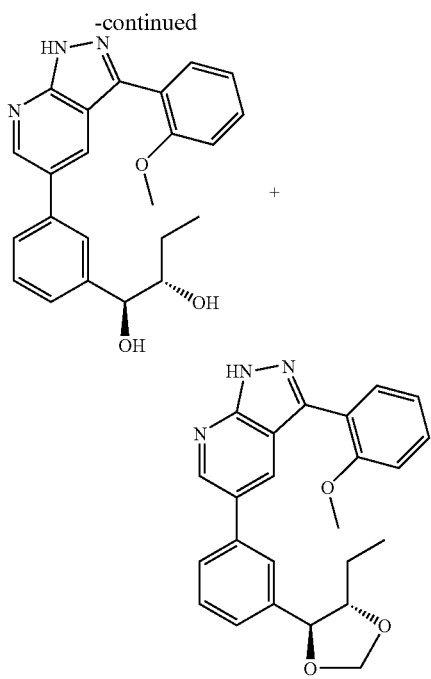

Synthesis of 1-{3-[3-(2-methoxy-phenyl)-1H-pyrazolo[3,4-b]pyridin-5-yl]-phenyl}-butane-(1S),(2)-diol and 5-[3-(5S)-ethyl-[1,3]dioxolan-(4S)-yl]-phenyl]-3-(2-methoxy-phenyl)-1H-pyrazolo[3,4-b]pyridine Step 1: Synthesis of (3-bromo-benzyl)-triphenyl-phosphonium chloride A solution of 3-bromobenzyl chloride (20 g, 97 mmol) and triphenylphosphine (25.5 g, 97 mmol) in o-xylene (200 mL) was heated to 140° C. with stirring for 48 hours. The white precipitate was filtered, washed with hexane, and air dried to afford (3-bromo-benzyl)-triphenyl-phosphonium chloride (36.8 g, 95%) as a white crystalline solid. The crude was used in next step without farther purification. MS: m/z 431 (M+H$^+$).

Step 2: Synthesis of 1-bromo-3-but-1-enyl-benzene

To a suspension of (3-bromo-benzyl)-triphenyl-phosphonium chloride (10 g, 23.2 mmol) in THF (100 mL) at 0° C. was added n-butyl lithium (10.2 mL, 2.5 N in hexane, 25.5 mmol) dropwise. The resulting orange suspension was stirred for 30 minutes. Propanal (1.61 g, 28 mmol) was added and the resulting mixture was stirred at room temperature for 2 hours. The mixture was cooled to 0° C. and cold hexane (500 mL) was added. The white precipitate was filtered, and the filtrate was concentrated. The residue was purified with flash chromatography using hexane to afford 1-bromo-3-but-1-enyl-benzene (4.4 g, 90%) as a mixture of 3:1 (E):(Z) isomers. MS: m/z 211 (M+H$^+$). The mixture was distillled under vacuum to afford the (E) isomer (1 g, >95% E) and the (Z) isomer (200 mg, 75% Z).

Step 3: Synthesis of 1-(3-bromo-phenyl)-butane-(1S),(2S)-diol

A 40 mL tall vial, equipped with a magnetic stirrer, was charged with of t-butanol (5 mL), water (5 mL) and AD-mix-α (1.4 g, containing 0.2 mol % potassium osmate(VI), and 1 mol % (DHQ)$_2$-PHAL)). The resulting mixture was stirred at room temperature until all was dissolved. Methanesulfonamide (95 mg, 1 mmol) was added and the mixture cooled to 0° C. (E)-1-Bromo-3-but-1-enyl-benzene (211 mg, 1 mmol) was added in one portion, and the heterogeneous slurry was stirred vigorously at 0° C. overnight. Additional AD-mix-α (1.4 g) and methane sulfonamide (95 mg) were added and the reaction left stirred at room temperature for 8 hours. Solid sodium sulfite (1.5 g, 12 mmol) was added and the mixture was stirred for 30 minutes. The mixture was partitioned between water and ethyl acetate (10 mL each). The aqueous phase was extracted with ethyl acetate (10 mL×4). The combined organic extracts were washed with aqueous potassium hydroxide (2 N, 50 ml), dried over sodium sulfate and concentrated. The residue was purified by flash chromatography using a gradient of methanol in dichloromethane to afford 1-(3-bromo-phenyl)-butane-(1S),(2S)-diol (152 mg, 62%) as a colorless oil. MS: m/z 245 (M+H$^+$).

Step 4: Synthesis of 1-{3-[3-(2-methoxy-phenyl)-1-(2-trimethylsilanyl-ethoxymethyl)-1H-pyrazolo[3,4-b]pyridin-5-yl]-phenyl}-butane-1(S),2(S)-diol To a mixture of 3-(2-methoxy-phenyl)-5-(4,4,5,5-tetramethyl-[1,3,2]dioxaborolan-2-yl)-1-(2-trimethylsilanyl-ethoxymethyl)-1H-pyrazolo[3,4-b]pyridine (0.3 g, 0.62 n mmol) and 1-(3-bromo-phenyl)-butane-1(S),2(S)-diol (0.152 g, 0.62 mmol) in a 20 mL microwave reaction flask was added THF (3 mL), acetonitrile (3 mL), and sodium carbonate (1 N in water, 3 mL, 6 n mmol). The resulting suspension was purged with nitrogen for 1 minute. Dichloro[1,1'-bis(diphenylphoshino)ferrocene]palladium(II) dichloromethane adduct (22 mg, 27 μmol) was added and the purging was continued for another minute. The flask was sealed and irradiated in a microwave reactor to 90° C. for 10 minutes. The reaction mixture was neutralized to pH 7 using 1 N hydrochloric acid, extracted with ethyl acetate (10 mL×3). The combine organic layers were dried over sodium sulfate, filtered, and concentrated. The residue was purified by flash chromatography on silica gel using a gradient of ethyl acetate in hexane to afford 1-{3-[3-(2-methoxy-phenyl)-1-(2-trimethylsilanyl-ethoxymethyl)-1H-pyrazolo[3,4-b]pyridin-5-yl]-phenyl}-butane-1,2-diol as a off white solid (171 mg, 53%). MS: m/z 520 (M+H$^+$).

Step 5: Synthesis of 1-{3-[3-2-methoxy-phenyl)-1H-pyrazolo[3,4-b]pyridin-5-yl]-phenyl}-butane-(1S),(2S)-diol and 5-[3-(5S)-ethyl-[1,3]dioxolan-(4S)-yl)-phenyl]-3-(2-methoxy-phenyl)-1H-pyrazolo[3,4-b]pyridine To 1-{3-[3-(2-methoxy-phenyl)-1-(2-trimethylsilanyl-ethoxymethyl)-1H-pyrazolo[3,4-b]pyridin-5-yl]-phenyl}-butane-1(S),2(S)-diol (171 mg, 0.33 mmol), was added trifluoro acetate acid (3 mL) and the resulting solution was concentrated. Ethylene diamine (0.3 mL) was added. The resulting crude was directly purified by mass-triggered reverse-phase HPLC to afford 1-{3-[3-(2-methoxy-phenyl)-1H-pyrazolo[3,4-b]pyridin-5-yl]-phenyl}-butane-1(S),2(S)-diol (32 mg, 25%) as a white solid. The chirality of the products was assigned as described by Wang and Sharpless in *J. Am. Chem. Soc.,* 1992, 114, 7568 and were verified by co-crystal structures of selected compounds. MS: m/z 390 (M+H$^+$). $^1$H NMR (500 MHz, CD$_3$CN-d3) δ 0.95 (t, 3H), 1.38 (m, 1H), 1.44 (m, 1H), 3.26 (s, br, 1H), 3.59 (m, 1H), 3.62 (s, br, 1H), 3.93 (s, 3H), 7.14 (t, 1H), 7.23 (d, 1H), 7.42

(d, 1H), 7.50 (t, 1H), 7.52 (t, 1H), 7.65 (d, 1H), 7.71 (s, 1H), 7.74 (dd, 1H), 8.41 (d, 1H), 8.86 (d, 1H).

5-[3-((5S)-ethyl-[1,3]dioxolan-(4S)-yl)-phenyl]-3-(2-methoxy-phenyl)-1H-pyrazolo[3,4-b]pyridine was isolated as a by product (19 mg, 14%). MS: m/z 402 (M+H$^+$). $^1$H NMR (500 MHz, CD$_3$CN-d3) δ 0.95 (t, 3H), 1.67 (m, 2H), 3.73 (m, 1H), 3.86 (s, 3H), 4.62 (d, 1H), 5.15 (s, 1H), 5.22 (s, 1H), 7.10 (t, 1H), 7.23 (d, 1H), 7.42 (d, 1H), 7.47 (dt, 1H), 7.51 (t, 1H), 7.66 (dd, 1H), 7.71 (d, 1H), 7.74 (s, 1H), 8.35 (d, 1H), 8.86 (d, 1H), 13.82 (s, br, 1H).

Other compounds prepared by Method 31 are shown in Table 25:

TABLE 25

| Structure | MS: m/z (M + H$^+$) |
|---|---|
| | 404 |
| 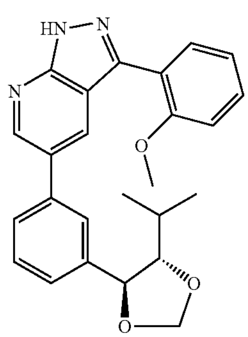 | 416 |
| | 404 |

TABLE 25-continued

| Structure | MS: m/z (M + H$^+$) |
|---|---|
| | 416 |
| 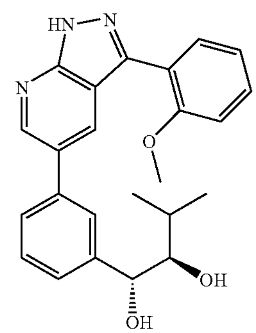 | 404 |
| | 416 |
| 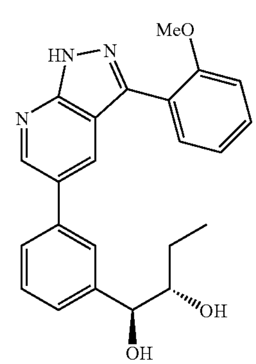 | 389 |

Method 32

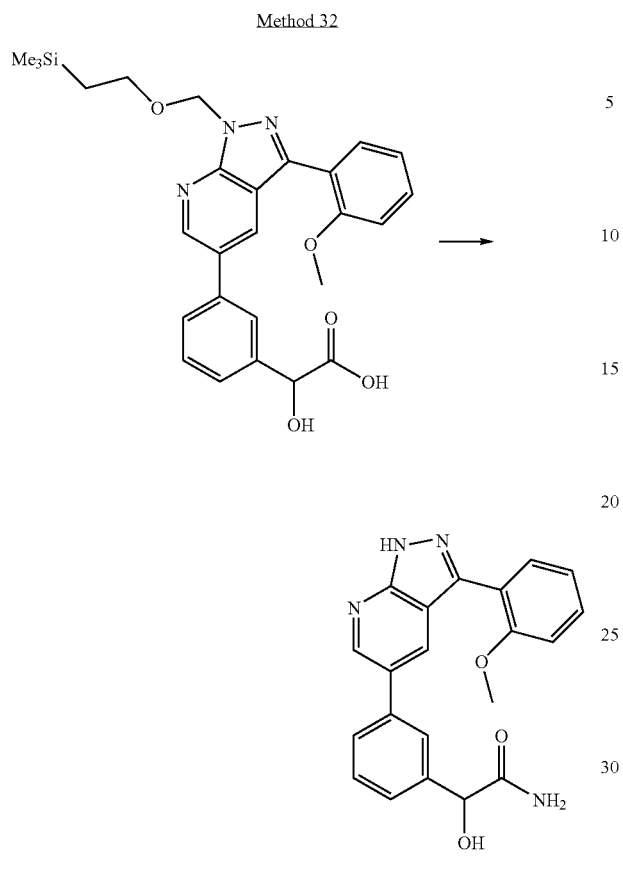

Synthesis of 2-hydroxy-2-{3-[3-(2-methoxy-phenyl)-1H-pyrrolo[2,3-b]pyridin-5-yl]-phenyl}-acetamide Hydroxy-{3-[3-(2-methoxy-phenyl)-1-(2-trimethylsilanyl-ethoxymethyl)-1H-pyrazolo[3,4-b]pyridin-5-yl]-phenyl}-acetic acid (92 mg, 0.19 mmol) was dissolved in dichloromethane (1 mL) and oxalyl chloride (145 mg, 1.14 mmol) and DMF (10 µL) were added. The resulting solution was heated to 60° C. with stirring overnight. The mixture was concentrated and ammonium hydroxide (30% w/v in water, 1 mL) was added and the stirring was continued for 15 minutes. The mixture was neutralized to pH 7 and extracted with ethyl acetate (5 mL×5). The combined organic extracts were dried over sodium sulfate, filtered, and concentrated. To the residue was added trifluoroacetic acid (2 mL) and the resulting mixture was sonicated until the residue was completely dissolved. The volatiles were evaporated and the residue was treated with ethylene diamine (0.2 mL). The resulting mixture was directly purified by mass-triggered reverse-phase HPLC to afford 2-hydroxy-2-{3-[3-(2-methoxy-phenyl)-1H-pyrrolo[2,3-b]pyridin-5-yl]-phenyl}-acetamide as a white solid (32 mg, 45%). MS: m/z 374 (M+H$^+$). $^1$H NMR (500 MHz, DMSO-d6) δ 3.86 (s, 3H), 4.95 (s, 1H), 6.09 (s, 1H), 7.11 (t, 1H), 7.21 (s, br, 1H), 7.23 (d, 1H), 7.47 (m, 4H), 7.67 (d, 2H), 7.81 (s, 1H), 8.31 (d, 1H), 8.83 (d, 1H), 8.73 (s, 1H), 13.82 (s, 1H).

Method 33

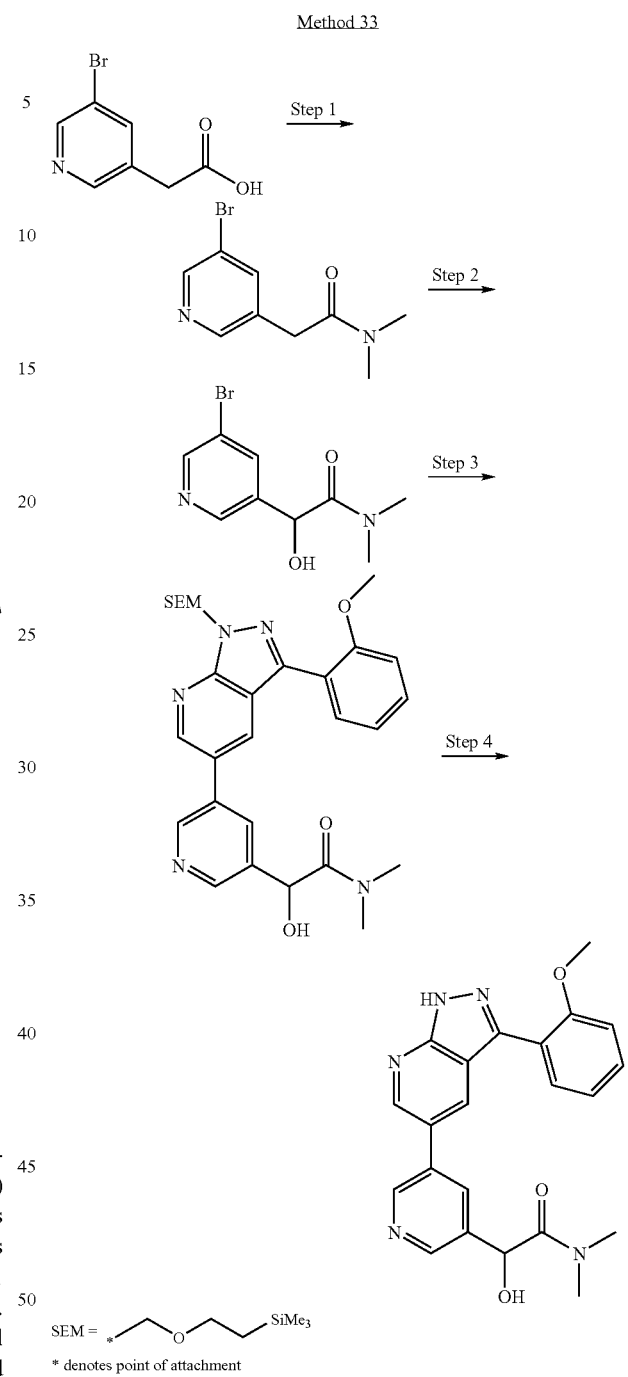

Synthesis of 2-hydroxy-2-{5-[3-(2-methoxyphenyl)-1H-pyrazolo[3,4-]pyridin5-yl]-pyridin-3-yl}-N,N-dimethylacetamide

Step 1: Synthesis of 2-(5-bromopyridin-3-yl)-N,N-dimethylacetamide (5-Bromopyridin-3-yl)acetic acid (500 mg, 2.31 mmol) was dissolved in dichloromethane (5 mL), treated with di-iso-propylamine (402.4 µL, 2.31 mmol) and cooled in an ice water bath. Pivaloyl chloride (284.7 µL, 2.31 mmol) was added and the mixture was stirred for 25 minutes. 2 M dimethylamine (1.73 mL, 3.46 mmol) was added and the reaction was stirred 15 h. The mixture was washed with saturated ammonium chloride (1×), saturated sodium bicarbonate (1×), and dried over sodium sulfate to yield 2-(5-bromopyridin-3-yl)-N,N-dimethylacetamide as a brown oil (445 mg, 79%). MS: m/z 562 (M+H$^+$).

Step 2: Synthesis of 2-(5-bromopyridin-3-yl)-2-hydroxy-N,N-dimethylacetamide 2-(5-Bromopyridin-3-yl)-N,N-dimethylacetamide (198.8 mg, 0.366 mmol) was oxidized using conditions reported by Davis et al (in *J. Org. Chem.*, 1984, 3241) to afford 2-(5-bromopyridin-3-yl)-2-hydroxy-N,N-dimethylacetamide (152.9 mg, 74.9%). MS: m/z 559 (M+H$^+$).

Step 3: Synthesis of 2-hydroxy-2-{5-[3-(2-methoxyphenyl)-1-(2-trimethylsilanylethoxymethyl)-1H-pyrazolo[3,4-b]pyridin5-yl]-pyridin-3-yl}-N,N-dimethylacetamide 3-(2-Methoxyphenyl)-5-(4,4,5,5-tetramethyl-[1,3,2]dioxaborolan-2-yl)-1-(2-trimethyl-silanylethoxymethyl)-1H-pyrazolo[3,4-b]pyridine (520.5 mg, 1.08 mmol) and 2-(5-bromopyridin-3-yl)-2-hydroxy-N,N-dimethylacetamide (280 mg, 1.08 mmol) and 1,1'-bis(diphenylphosphino)ferrocenepalladium(II)-dichloride dichloromethane adduct (44.1 mg, 0.054 mmol) were combined in a Smith microwave vial under nitrogen and dissolved in dimethylformamide (3.5 mL). Saturated sodium carbonate was added and the system was purged with nitrogen gas. The reaction mixture was irradiated in a microwave reactor for 900 s at 165° C. The cooled mixture was poured into 25 mL deionized water and extracted into ethyl acetate (3×). The combined organic layers were dried over sodium sulfate, adsorbed onto silica gel and purified by silica gel chromatography using a gradient methanol in dichloromethane. The moderately pure material was used in the next step (433 mg, 75.2%). MS: m/z 534 (M+H$^+$).

Step 4: Synthesis of 2-hydroxy-2-{5-[3-(2-methoxyphenyl)-1H-pyrazolo[3,4-b]pyridin5-yl]-pyridin-3-yl}-N,N-dimethylacetamide 2-Hydroxy-2-{5-[3-(2-methoxyphenyl)-1-(2-trimethylsilanylethoxymethyl)-1H-pyrazolo[3,4-b]pyridin5-yl]-pyridin-3-yl}-N,N-dimethylacetamide (374 mg, 0.702 mmol) was treated with 5% v/v of 70% perchloric acid in glacial acetic acid (5 mL) for 2 h. The solids were collected by filtration and were dissolved in ethyl acetate upon shaking with saturated sodium bicarbonate. The layers were separated and the organics were dried over sodium sulfate and concentrated in vacuo. The material was dissolved in dichloromethane (1 mL) and treated with N,N-dimethylethylenediamine (154 μL) for 2.5 h. The mixture was concentrated and the residue was dissolved in dimethylsulfoxide and purified by preparative HPLC to afford 2-hydroxy-2-{5-[3-(2-methoxyphenyl)-1H-pyrazolo[3,4-b]pyridin5-yl]-pyridin-3-yl}-N,N-dimethylacetamide (10 mg, 0.025 mmol). $^1$H-NMR (500 MHz, dimethylsulfoxide-d6) δ 2.79 (s, 3H), 2.92 (s, 3H), 3.79 (s, 3H), 5.52 (m, 1H), 5.78 (m, 1H), 7.03 (t, J=7.0 Hz, 1H), 7.17 (d, J=8 Hz, 1H), 7.40 (dt, J=1, J=6.5 Hz, 1H), 7.59 (dd, J=1.5, J=7.5 Hz, 1H), 8.04 (t, J=2.5 Hz, 1H), 8.33 (d, J=2.5 Hz, 1H), 8.52 (d, J=2.0 Hz, 1H), 8.81 (d, J=2.0 Hz, 1H), 8.85 (d, J=2.5 Hz, 1H). MS: m/z 404 (M+H$^+$).

Other compounds prepared by Method 33 are shown in Table 26:

TABLE 26

| Structure | MS: m/z (M + H$^+$) |
|---|---|
| *structure* | 333 |
| *structure* | 332 |
| *structure* | 346 |
| *structure* | 346 |

Method 34

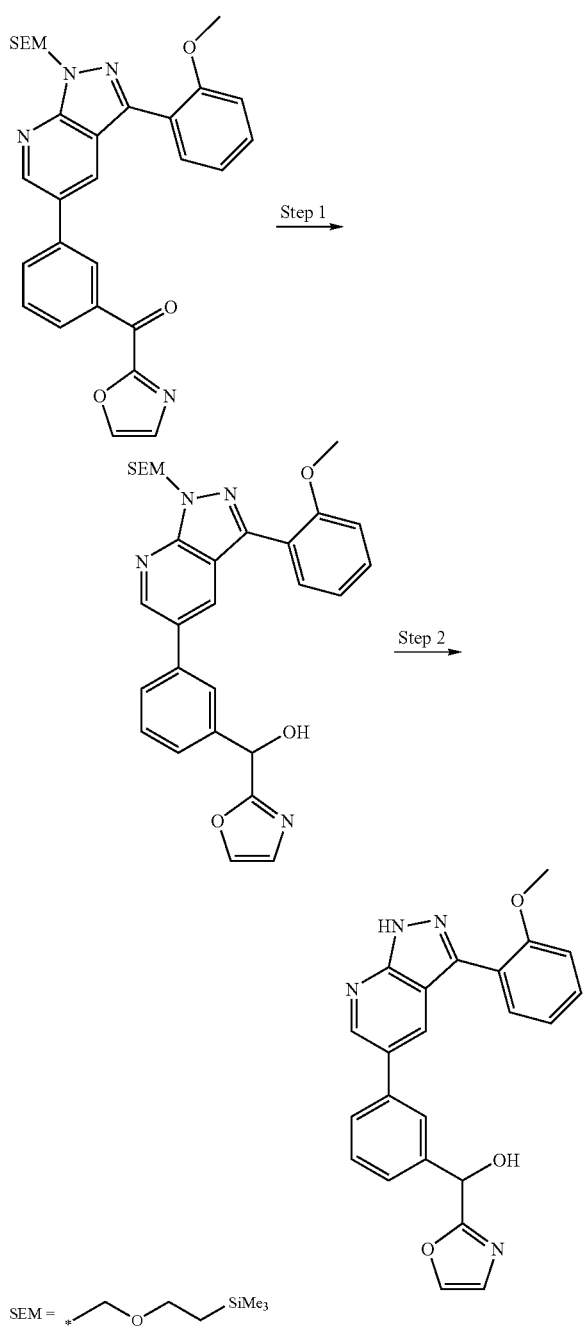

SEM = *\~\~O\~\~SiMe₃
* denotes point of attachment

Synthesis of {3-[3-(2-methoxy-phenyl)-1H-pyrazolo[3,4-b]pyridin-5-yl]-phenyl}-oxazol-2-yl-methanol Step 1: Synthesis of {3-[3-(2-methoxy-phenyl)-1-(2-trimethylsilanyl-ethoxymethyl)-1H-pyrazolo[3,4-b]pyridin-5-yl]-phenyl}-oxazol-2-yl-methanol {3-[3-(2-Methoxy-phenyl)-1-(2-trimethylsilanyl-ethoxymethyl)-1H-pyrazolo[3,4-b]pyridin-5-yl]-phenyl}-oxazol-2-yl-methanone (100 mg, 0.189 mmol) was dissolved in methanol (10 mL) and cooled in an ice bath. The mixture was treated with sodium borohydride (7.2 mg, 0.189 mmol). After 15 min., the reaction was quenched by addition of saturated ammonium chloride and concentrated. The residue was dissolved in ethyl acetate, washed with saturated ammonium chloride, dried over sodium sulfate and purified by flash chromatography on silica gel using a gradient of ethyl acetate in hexanes to afford 3-[3-(2-methoxy-phenyl)-1-(2-trimethylsilanyl-ethoxymethyl)-1H-pyrazolo[3,4-b]pyridin-5-yl]-phenyl}-oxazol-2-yl-methanol (65 mg, 65%). MS: m/z 530 (M+H⁺).

Step 2: Synthesis of {3-[3-(2-methoxy-phenyl)-1H-pyrazolo[3,4-b]pyridin-5-yl]-phenyl}-oxazol-2-yl-methanol 3-[3-(2-Methoxy-phenyl)-1-(2-trimethylsilanyl-ethoxymethyl)-1H-pyrazolo[3,4-b]pyridin-5-yl]-phenyl}-oxazol-2-yl-methanol (64.2 mg, 0.121 mmol) was treated with 2 mL trifluoroacetic acid for 5 h. The solution was concentrated and co-evaporated with tetrahydrofuran (2×), then dissolved in ethyl acetate, washed with saturated sodium bicarbonate (1×), brine (1×), and dried over sodium sulfate. The organics were concentrated in vacuo and then lyophilized from acetonitrile/water to afford 13.7 mg. The material was then treated with 100 mg PS-trisamine (Argonaut Technologies, Inc.) in tetrahydrofuran at 50° C. for 15 h., filtered and the resin was washed with tetrahydrofuran/methanol and concentrated to afford {3-[3-(2-methoxy-phenyl)-1H-pyrazolo[3,4-b]pyridin-5-yl]-phenyl}-oxazol-2-yl-methanol (9.9 mg, 20.5%). ¹H-NMR (500 MHz, dimethylsulfoxide-d6) δ 3.79 (s, 3H), 5.85 (d, J=5.5 Hz, 1H), 6.42 (d, J=5.5 Hz, 1H), 7.03 (t, J=6.5 Hz, 1H), 7.10 (s, 1H), 7.16 (d, J=8 Hz, 1H), 7.40 (m, 3H), 7.61 (m, 2H), 7.72 (br s, 1H), 7.99 (s, 1H), 8.23 (d, J=2.0 Hz, 1H), 8.75 (d, J=2.0 Hz, 1H). MS: m/z 399 (M+H⁺).

Method 35

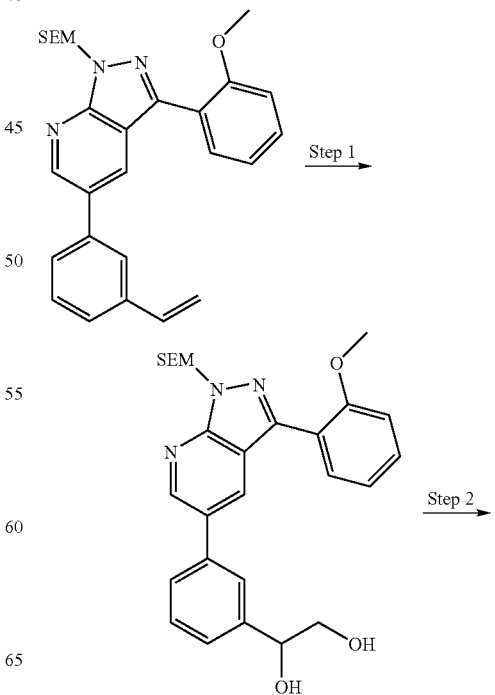

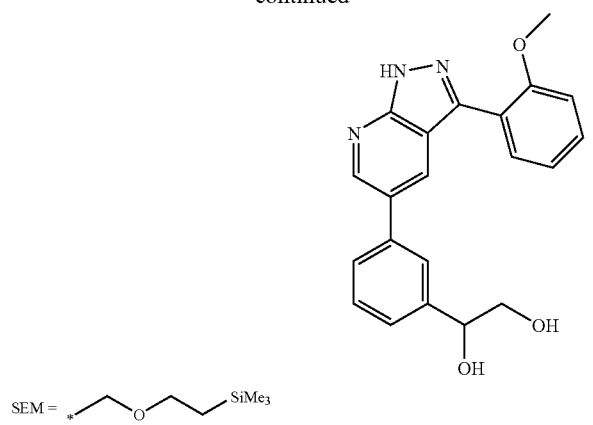

SEM = *~O~SiMe₃

* denotes point of attachment

Synthesis of 1-{3-[3-(2-methoxy-phenyl)-1H-pyrazolo[3,4-b]pyridin-5-yl]-phenyl}-ethane-1,2-diol Step 1: Synthesis of 1-{3-[3-(2-methoxy-phenyl)-1-(2-trimethylsilanyl-ethoxymethyl)-1H-pyrazolo[3,4-b]pyridin-5-yl]-phenyl}-ethane-1,2-diol 3-(2-Methoxy-phenyl)-1-(2-trimethylsilanyl-ethoxymethyl)-5-(3-vinyl-phenyl)-1H-pyrazolo[3,4-b]pyridine (1.5 g, 3.28 mmol) was dihydroxylated following a procedure described by Sharpless at al. (in *J. Org. Chem.* 1992, 57, 2768) to afford 1-{3-[3-(2-methoxy-phenyl)-1-(2-trimethylsilanyl-ethoxymethyl)-1H-pyrazolo[3,4-b]pyridin-5-yl]-phenyl}-ethane-1,2-diol (513 mg, 31.8%). MS: m/z 492 (M+H⁺).

Step 2: Synthesis of 1-{3-[3-(2-methoxy-phenyl)-1H-pyrazolo[3,4-b]pyridin-5-yl]-phenyl}-ethane-1,2-diol 1-{3-[3-(2-methoxy-phenyl)-1-(2-trimethylsilanyl-ethoxymethyl)-1H-pyrazolo[3,4-b]pyridin-5-yl]-phenyl}-ethane-1,2-diol (114 mg, 0.232 mmol) was treated with 2 mL trifluoroacetic acid for 5 h. The solution was concentrated and co-evaporated with tetrahydrofuran (2×), then dissolved in ethyl acetate, washed with saturated sodium bicarbonate (1×), brine (1×), and dried over sodium sulfate. The material was purified by preparative HPLC and shown to contain hydroxymethyl attached to the product (28 mg). Therefore, the material was treated with 100 mg PS-trisamine (Argonaut Technologies, Inc.) in tetrahydrofuran at 50° C. for 15 h., filtered and the resin was washed with tetrahydrofuran/methanol and concentrated to afford 1-{3-[3-(2-methoxy-phenyl)-1H-pyrazolo[3,4-b]pyridin-5-yl]-phenyl}-ethane-1, 2-diol (10.5 mg, 12.5%). ¹H-NMR (500 MHz, dimethylsulfoxide-d6) δ 3.45 (t, J=6.0 Hz, 2H), 3.79 (s, 3H), 4.56 (q, J=5 Hz, 1H), 4.67 (t, J=6 Hz, 1H), 5.23 (d, J=4 Hz, 1H), 7.03 (t, J=7.0 Hz, 1H), 7.15 (d, J=8 Hz, 1H), 7.40 (d, J=8.0 Hz, 1H), 7.37 (t, J=7.5 Hz, 1H), 7.40 (t, J=8.5 Hz, 1H), 7.53 (d, J=8.0 Hz, 1H), 7.58 (dd, J=7.5 Hz, J=2.0 Hz, 1H), 7.62 (s, 1H), 8.24 (d, J=2.5 Hz, 1H), 8.75 (d, J=2.5 Hz, 1H). MS: m/z 362 (M+H⁺).

Method 36

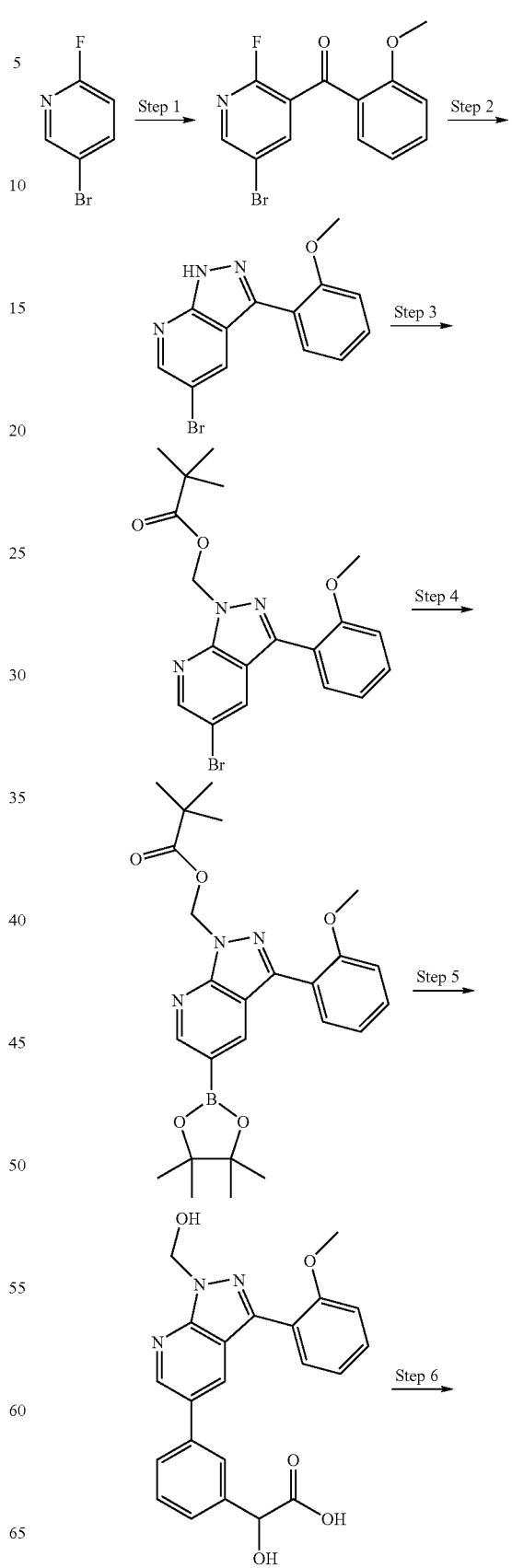

-continued

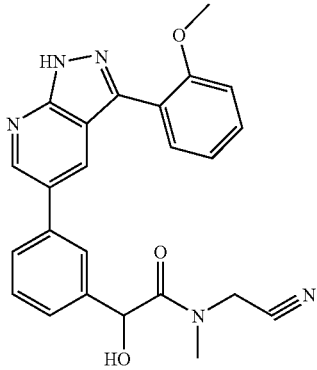

Synthesis of N-cyanomethyl-2-hydroxy-2-{3-[3-(2-methoxy-phenyl)-1H-pyrazolo[3,4-b]pyridin-5-yl]-phenyl}-N-methyl-acetamide Step 1: Synthesis of (5-bromo2-fluoro-pyridin-3-yl)-(2-methoxy-phenyl)-methanone To a round bottom flask were added di-iso-propylamine (5 ml, 35 mmol), and anhydrous THF (40 ml). The solution was stirred at −78° C. for 5 minutes under nitrogen. Then a 2.5 M solution of n-butyl lithium in hexane (12 ml, 30 mmol) was added slowly and the resulting solution was allowed to stir at −78° C. for another 30 minutes. At this time 5-bromo-2-fluoro-pyridine (5 g, 28 mmol) was added dropwise and the solution was allowed to sir at −40° C. for 2 hours. Then 2,N-dimethoxy-N-methyl-benzamide (7.2 g, 37 mmol) in THF (10 ml) was added and the resulting mixture was stirred at −40° C. for another 2 hours. The reaction was then quenched with 10% citric acid (40 ml) and worked up with ethyl acetate, brine, dried with $Na_2SO_4$. Silica chromatography of the crude using a gradient of ethyl acetate and hexane afforded (5-bromo-2-fluoro-pyridin-3-yl)-(2-methoxy-phenyl)-methanone (1.9 g, 21% yield). $^1$H NMR (500 MHz, DMSO-d6) δ 3.64 (s, 3H), 7.14 (m, 1H), 7.18 (d, 1H), 7.65 (m, 2H), 8.38 (d, 1H), 8.58 (s, 1H).). MS: m/z 310+312 (M+H$^+$).

Step 2: Synthesis of 5-bromo-3-(2-methoxy-phenyl)-1H-pyrazolo[3,4-b]pyridine

To a solution of (5-bromo-2-fluoro-pyridin-3-yl)-(2-methoxy-phenyl)-methanone (1.9 g, 6.1 mmol) in ethanol (125 ml), hydrazine monohydrate (691 μl, 12.2 mmol) was added and the resulting solution was allowed to stir at room temperature overnight. Solvent was removed under reduced pressure and the product was precipitated out by addition of water to afford 5-bromo-3-(2-methoxy-phenyl)-1H-pyrazolo[3,4-b]pyridine (1.1 g, 58% yield). $^1$H NMR (500 MHz, DMSO-d$_6$) δ 3.84 (s, 3H), 7.07 (m, 1H), 7.20 (d, 1H), 7.45 (m, 1H), 7.62 9d, 1H), 8.34 (s, 1H), 8.60 (s, 1H). MS: m/z 304+306 (M+H$^+$).

Step 3: Synthesis of 2,2-dimethyl-propionic acid 5-bromo-3-(2-methoxy-phenyl)-pyrazolo[3,4-b]pyridin-1-ylmethyl ester To a solution of 5-bromo-3-(2-methoxy-phenyl)-1H-pyrazolo[3,4-b]pyridine (4.8 g, 15.8 mmol) in DMF (60 ml) at −40° C. under nitrogen, sodium hydride (1.1 g, 47.3 mmol) was added. The mixture was stirred at −40° C. for 1 hour. Then 2,2-dimethyl-propionic acid chloromethyl ester (6.9 ml, 47.3 mmol; chloromethyl pivalate) in DMF (20 ml) was added dropwise and the resulting mixture was allowed to stir at 40° C. for another 2 hours. The reaction was quenched with saturated aqueous NH$_4$Cl (40 ml) and worked up with ethyl acetate, brine, dried with $Na_2SO_4$ and evaporated. Silica gel chromatography of the crude using a gradient of ethyl acetate and hexane afforded 2,2-dimethyl-propionic acid 5-bromo-3-(2-methoxy-phenyl)-pyrazolo[3,4-b]pyridine-1-ylmethyl ester (4.1 g, 62% yield). $^1$H NMR (500 MHz, DMSO-d$_6$) δ 1.11 (s, 9H), 3.85 (s, 3H), 6.46 (s, 2H), 7.09 (m, 1H), 7.24 (d, 1H), 7.51 (m, 1H), 7.60 (d, 1H), 8.43 (s, 1H), 8.74 (s, 1H).

Step 4: Synthesis of 2,2-dimethyl-propionic acid 3-(2-methoxy-phenyl)-5-(4,4,5,5-tetramethyl-[1,3,2]dioxaborolan-2-yl)-pyrazolo[3,4-b]pyridin-1-ylmethyl ester A mixture of 22,2-dimethyl-propionic acid 5-bromo-3-(2-methoxy-phenyl)-pyrazolo[3,4-b]pyridine-1-ylmethyl ester (4.1 g, 9.8 mmol), bis(pinacolato)diboron (5.0 g, 19.7 mmol), dichloro[1,1'-bis(diphenylphosphino)ferrocene]palladium (II) dichloromethane adduct (360 mg, 0.5 mmol), and sodium acetate (2.4 g, 29.5 mmol) in DMF (20 ml) was stirred at 100° C. overnight. The mixture was allowed to cool down to room temperature and then extracted with ethyl acetate (3×). The combined organic layers were extracted with brine, dried with $Na_2SO_4$, decanted, and concentrated to dryness. Silica gel chromatography of the crude using a gradient of ethyl acetate and hexane afforded 2,2-dimethyl-propionic acid 3-(2-methoxy-phenyl)-5-(4,4,5,5-tetramethyl-[1,3,2]dioxaborolan-2-yl)-pyrazolo[3,4-b]pyridin-1-ylmethyl ester (4.5 g, 98% yield). $^1$H NMR (500 MHz, DMSO-d6) δ 1.11 (m, 12H), 1.31 (s, 9H), 3.83 (s, 3H), 6.51 (s, 2H), 7.12 (m, 1H), 7.25 (d, 1H), 7.52 (m, 1H), 7.56 (d, 1H), 8.40 (s, 1H), 8.79 (s, 1H). MS: m/z 466.3 (M+H$^+$).

Step 5: Synthesis of hydroxy-{3-[1-hydroxymethyl-3-(2-methoxy-phenyl)-1H-pyrazolo[3,4-b]pyridin-5-yl]-phenyl}-acetic acid A mixture of 2,2-dimethyl-propionic acid 3-(2-methoxyphenyl)-5-(4,4,5,5-tetramethyl-[1,3,2]dioxaborolan-2-yl)-pyrazolo[3,4-b]pyridin-1-ylmethyl ester (4.5 g, 9.7 mmol), (±)-(3-bromo-phenyl)-hydroxy-acetic acid (2.7 g, 11.6 mmol), and dichloro[1,1'-bis(diphenylphosphino)ferrocene] palladium(II) dichloromethane adduct (355 mg, 0.5 mmol) in THF/Acetonitrile/saturated NaHCO$_3$ (20 ml/20 ml/50 ml) was stirred at 100° C. for 4 hours. The mixture was allowed to cool down to room temperature and then extracted with ethyl acetate (3×). The combined organic layers were extracted with brine, dried with $Na_2SO_4$, decanted, and concentrated to dryness. The crude was purified by reverse phase HPLC afforded hydroxy-{3-[1-hydroxymethyl-3-(2-methoxy-phenyl)-1H-pyrazolo[3,4-b]pyridin-5-yl]-phenyl}-acetic acid (1.7 g, 35% yield). $^1$H NMR (500 MHz, DMSO-d$_6$) δ 3.86 (s, 3H), 5.05 (s, 1H), 5.14 (s, 2H), 7.10 (m, 1H), 7.21 (d, 1H), 7.40-7.50 (m, 3H), 7.67 (d, 1H), 7.79 (s, 1H).
MS: m/z 406.1 (M+H$^+$).

Step 6: Synthesis of N-cyanomethyl-2-hydroxy-2-{3-[3-(2-methoxy-phenyl)-1H-pyrazolo[3,4-b]pyridine-5-yl]-phenyl}-N-methyl-acetamide A mixture of hydroxy-{3-[1-hydroxymethyl-3-(2-methoxy-phenyl)-1H-pyrazolo[3,4-b]pyridin-5-yl]-phenyl}-acetic acid (0.1 g, 0.25 mmol), methylaminoacetonitrile (20 μl, 0.27 mmol), diisopropylethylamine (DIEA, 87 μl, 0.48 mmol), N,N,N',N',-Tetramethyl-O-(7-azabenotriazol-1-yl) uronium hexafluorophosphate (HATU, 101 mg, 0.27 mmol) in DMF (3 ml) was stirred at room temperature overnight. The reaction mixture was dissolved in 10 ml ethyl acetate and subsequently extracted with 1N HCl, saturated NaHCO$_3$, brine, dried with Na$_2$SO$_4$, concentrated to dryness. The crude was purified by silica gel chromatography. The resulting material was dissolved in 3 ml of methanol, aqueous NaOH was added (1 ml, 2 N in H$_2$O) and the mixture stirred overnight at room temperature. The solvent was removed under reduced pressure and the crude was neutralized with 500 μl of 1N HCl and purified by mass-triggered reverse phase HPLC to afford N-cyanomethyl-2-hydroxy-2-{3-[3-(2-methoxy-phenyl)-1H-pyrazolo[3,4-b]pyridine-5-yl]-phenyl}-N-methyl-acetamide as a yellow powder (56 mg, 53% yield). $^1$H NMR (500 MHz, DMSO-d6) δ 3.02 (s, 3H), 3.87 (s, 3H), 4.14 (s, 2H), 5.55 (s, 1H), 7.10 (m, 1H), 7.23 (d, 1H), 7.40 (d, 1H), 7.45-7.52 (m, 2H), 7.66 (d, 1H), 7.72 (m, 2H), 8.32 (s, 1H), 8.33 (s, 1H). MS: m/z 427.5 (M+H$^+$).

Other compounds prepared by method 36 are shown in Table 27:

TABLE 27

| Structure | MS: m/z (M + H$^+$) |
|---|---|
| 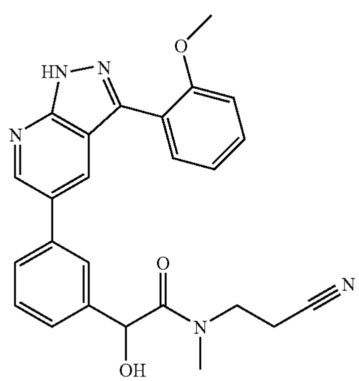 | 442.2 |
| 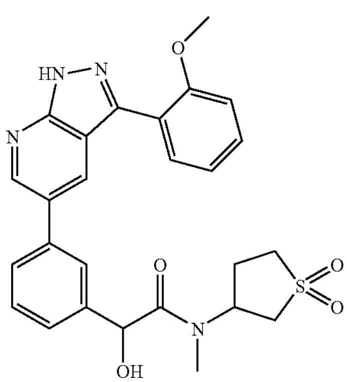 | 507.2 |

TABLE 27-continued

| Structure | MS: m/z (M + H$^+$) |
|---|---|
| 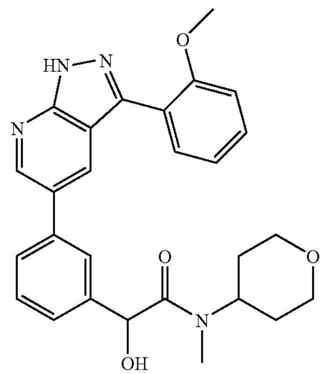 | 473.2 |
| 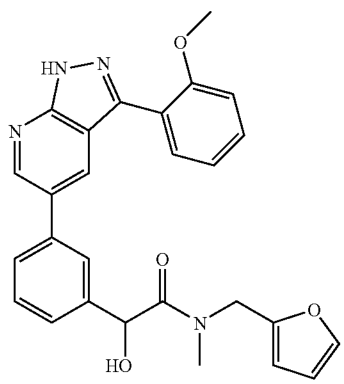 | 469.2 |
| 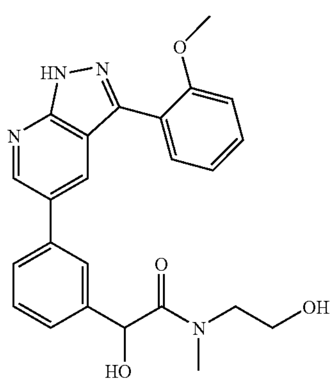 | 433.2 |
| 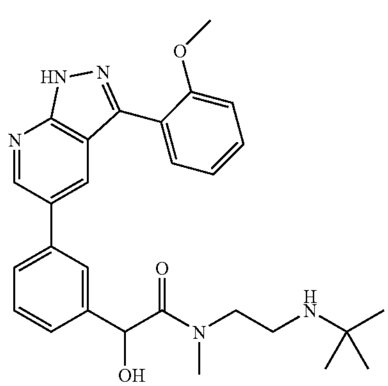 | 488.2 |

TABLE 27-continued
| Structure | MS: m/z (M + H⁺) |
|---|---|
| 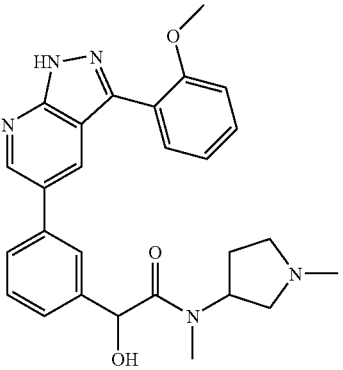 | 472.2 |
| 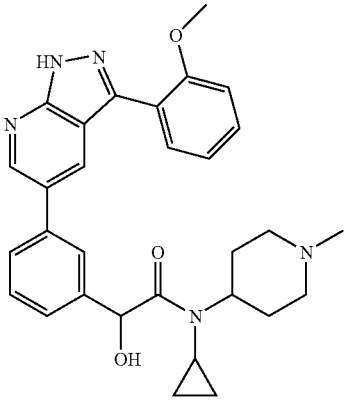 | 512.2 |
Method 37
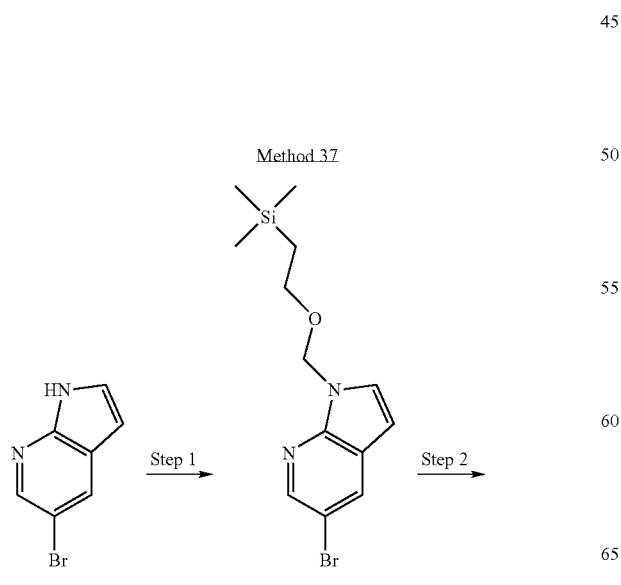
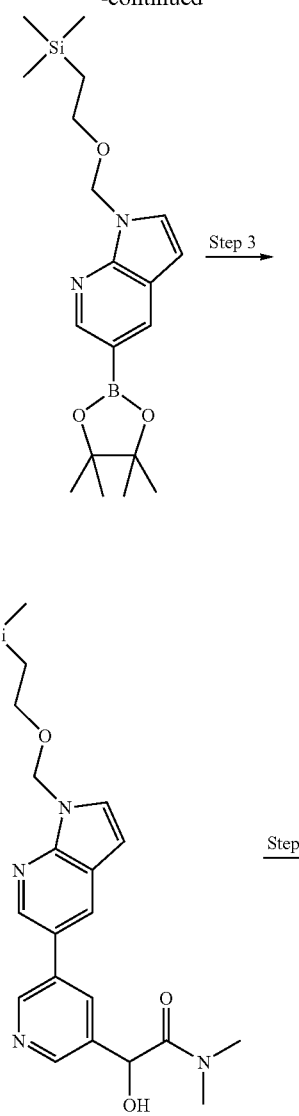
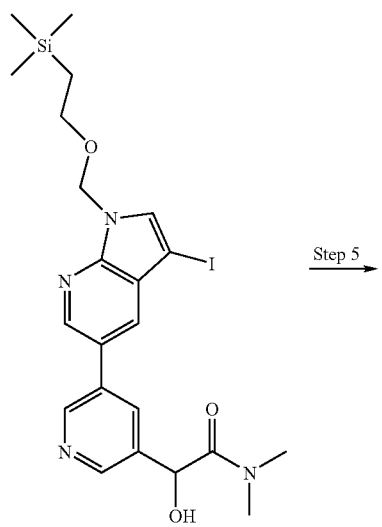

-continued

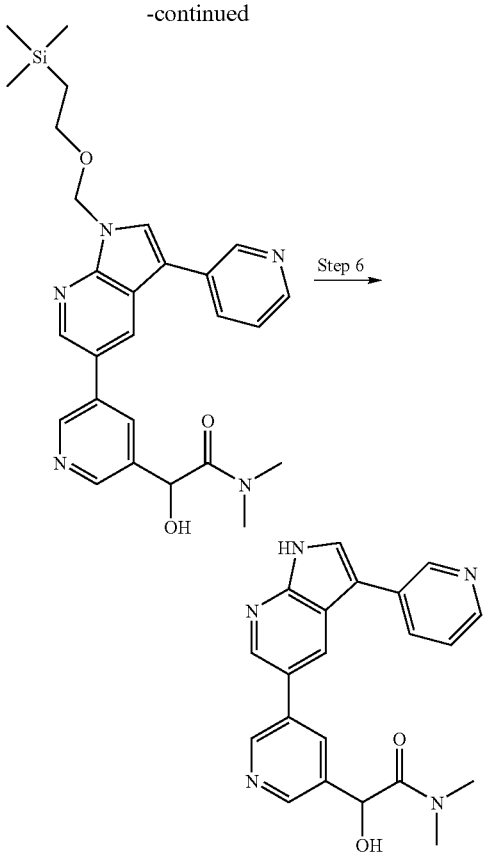

Step 1: Synthesis of 5-bromo-1-(2-trimethylsilanyl-ethoxymethyl)-1H-pyrrolo[2,3-b]pyridine To a 250 ml 3-neck flask, 5-bromo-1H-pyrrolo[2,3-b]pyridine (10 g, 50.5 mmol) and DMF (80 ml) were added. The solution was cool to −40° C. under nitrogen, sodium hydride (1.5 g, 60.6 mmol) was added in 2 batches. The mixture was stirred at −40° C. for 1 hour. Then SEM-Cl (10.7 ml, 60.6 mmol) in DMF (20 ml) was added dropwise and the resulting mixture was allowed to stir at −40° C. for another 2 hours. The reaction was quenched with saturated NH$_4$Cl (40 ml) and worked up with ethyl acetate, brine, dried with Na$_2$SO$_4$. Silica chromatography of the crude using a gradient of ethyl acetate and hexane afforded 5-bromo-1-(2-trimethylsilanyl-ethoxymethyl)-1H-pyrrolo[2,3-b]pyridine (14.4 g, 87% yield). $^1$H NMR (500 MHz, DMSO-d6) δ 0.02 (s, 9H), 0.92 (m, 2H), 3.59 (m, 2H), 5.72 (s, 2H), 6.65 (s, 1H), 7.84 (s, 1H), 8.37 (2, 1H), 8.45 (s, 1H). MS: m/z 327.0 (M+H$^+$).

Step 2: Synthesis of 5-(4,4,5,5)-tetramethyl-[1,3,2]dioxaborolan-2-yl)-1-(2-trimethylsilanyl-ethoxymethyl)-1H-pyrrolo[2,3-b]pyridine A mixture of (5-bromo-1-(2-trimethylsilanyl-ethoxymethyl)-1H-pyrrolo[2,3-b]pyridine 5.0 g, 15.3 mmol), bis(pinacolato)diboron (7.8 g, 30.6 mmol), dichloro[1,1'-bis(diphenylphosphino)ferrocene]palladium(II) dichloromethane adduct (559 mg, 0.8 mmol), and sodium acetate (3.8, 45.8 mmol) in DMF (20 ml) was stirred at 95° C. overnight. The mixture was allowed to cool down to room temperature and then extracted with ethyl acetate (3×). The combined organic layers were extracted with brine, dried with Na$_2$SO$_4$, decanted, and concentrated to dryness. Silica chromatography of the crude using a gradient of ethyl acetate and hexane afforded 5-(4,4,5,5)-tetramethyl[1,3,2]dioxaborolan-2-yl)-1-(2-trimethylsilanyl-ethoxymethyl)-1H-pyrrolo[2,3-b]pyridine (5.0 g, 88% yield). $^1$H NMR (500 MHz, DMSO-d6) δ 0.02 (s, 9H), 0.95 (, 2H), 1.45 (s, 2H), 3.65 (m, 2H), 5.75 (s, 2H), 6.70 (s, 1H), 7.75 (s, 1H), 8.40 (s, 1H), 8.60 (s, 1H). MS: m/z 375.2 (M+H$^+$).

Step 3: Synthesis of 2-hydroxy-N,N-dimethyl-2-{5-[1-(2-trimethylsilanyl-ethoxymethyl)-H-pyrrolo[2,3-b]pyridin-5-yl]-pyridin-3-yl}-acetamide A mixture of 5-(4,4,5,5)-tetramethyl[1,3,2]dioxa-borolan-2-yl)-1-(2-trimethylsilanyl-ethoxymethyl)-1H-pyrrolo[2,3-b]pyridine (1.6 g, 4.3 mmol), 2-(5-bromo-pyridin-3-yl)-2-hydroxy-N,N-dimethyl-acetamide (1.1 g, 4.3 mmol), and dichloro[1,1'-bis(diphenylphosphino)ferrocene]palladium(II) dichloromethane adduct (156 mg, 0.2 mmol) in THF/Acetonitrile/saturated NaHCO$_3$ (5 ml/5 ml/5 ml) was stirred at 100° C. in a microwave for 20 minutes. The mixture was allowed to cool down to room temperature and then extracted with ethyl acetate (2×). The combined organic layers were extracted with brine, dried with Na$_2$SO$_4$, decanted, and concentrated to dryness. Silica chromatography of the crude using a gradient of ethyl acetate and hexane afforded 2-hydroxy-N,N-dimethyl-2-{5-[1-(2-trimethylsilanyl-ethoxymethyl)-H-pyrrolo[2,3-b]pyridin-5-yl]-pyridin-3-yl}-acetamide (361 mg, 20% yield). $^1$H NMR (500 MHz, DMSO-d6) δ 0.05 (s, 9H), 0.92 (m, 2H), 3.63 (m, 2H), 5.75 (s, 2H), 6.73 (s, 1H), 7.82 (s, 1H), 8.17 (s, 1H), 8.41 (s, 1H), 8.66 (s, 1H), 8.70 (s, 1H), 8.97 (s, 1H). MS: m/z 427.2 (M+H$^+$).

Step 4: Synthesis of 2-hydroxy-2-{5-[3-iodo-1-(2-trimethylsilanyl-ethoxymethyl)-1H-pyrrolo[2,3-b]pyridin-5-yl]-pyridin-3-yl}-N,N-dimethyl-acetamide A mixture of 2-hydroxy-N,N-dimethyl-2-{5-[1-(2-trimethylsilanyl-ethoxymethyl)-H-pyrrolo[2,3-b]pyridin-5-yl]-pyridin-3-yl}-acetamide (795 mg, 1.86 mmol), N-iodosuccinimide (461 mg, 2.05 mmol) in dichloroethane (10 ml) was stirred at 100° C. in the microwave for 20 minutes. The reaction was allowed to cool down to room temperature and saturated NaS$_2$O$_3$ (5 ml) was added. The mixture was extracted with ethyl acetate (2×). The combine organic layers were extracted with brine, dried with Na2SO$_4$, decanted, and concentrated to dryness. Silica chromatography of the crude using a gradient of ethyl acetate and hexane afforded 2-hydroxy-2-{5-[3-iodo-1(2-trimethylsilanyl-ethoxymethyl)-1H-pyrrolo[2,3-b]pyridin-5-yl]-pyridin-3-yl}-N,N-dimethyl-acetamide (752 mg, 73% yield). $^1$H NMR (500 MHz, DMSO-d6) δ 0.05 (s, 9H), 0.9 (m, 2H), 3.62 (m, 2H), 5.74 (s, 2H), 8.05 (s, 1H), 8.10 (s, 1H), 8.22 (s, 1H), 8.67 (s, 1H), 8.75 (s, 1H), 9.01 (s, 1H). MS: m/z 553.1 (M+H$^+$).

Step 5: Synthesis of 2-hydroxy-N,N-dimethyl-2-{5-[3-pyridin-3-yl-1-(2-trimethyl-silanyl-ethoxymethyl)-1H-pyrrolo[2,3-b]pyridin-5-yl]-pyridin-3-yl-acetamide A mixture of 2-hydroxy-2-{5-[3-iodo-1(2-trimethylsilanyl-ethoxymethyl)-1H-pyrrolo[2,3-b]pyridin-5-yl]-pyridin-3-yl}-N,N-dimethyl-acetamide (150 mg, 0.3 mmol), pyridine-3-boronic acid (34 mg, 0.3 mmol), dichloro[1,1'bis(diphenyl-phosphino)ferrocene]palladium(II) dichloromethane adduct (10 mg, 0.02 mmol) in THF/Acetonitrile/saturated NaHCO₃ (2 ml/2 ml/30 ml) was stirred at 120° C. for 20 minutes. The mixture was allowed to cool down to room temperature and then extracted with ethyl acetate (2×). The combined organic layers were extracted with brine, dried with Na₂SO₄, decanted, and concentrated to dryness. Silica chromatography of the crude using a gradient of ethyl acetate and hexane afforded 2-hydroxy-N,N-dimethyl-2-{5-[3-pyridin-3-yl-1-(2-trimethyl-silanyl-ethoxymethyl)-1H-pyrrolo[2,3-b]pyridin-5-yl]-pyridin-3-yl-acetamide (100 mg, 73% yield).

Step 6: Synthesis of 2-hydroxy-N,N-dimethyl-2-{5-[3-pyridin-3-yl-1H-pyrrolo[2,3b]pyridin-5-yl]-pyridin-3-yl-acetamide 2-Hydroxy-N,N-dimethyl-2-{5-[3-pyridin-3-yl-1-(2-trimethyl-silanyl-ethoxymethyl)-1H-pyrrolo[2,3-b]pyridin-5-yl]-pyridin-3-yl-acetamide (100 mg, 0.2 mmol) was stirred in dichloromethane/trifluoroacetate acid (1 ml/1 ml) at room temperature for 2 hours. The solvents was removed under vacuum and the crude was stirred in dichloromethane/ethylenediamine (1 ml/n1 ml) for 2 hours at room temperature. Again the solvents was removed under vacuum and the crude was dissolved in DMSO, filtered and purified by reverse phase HPLC, lyophilized afforded 2-hydroxy-N,N-dimethyl-2-{5-[3-pyridin-3-yl-1H-pyrrolo[2,3, b]pyridin-5-yl]-pyridin-3-yl-acetamide (32 mg, 41% yield). ¹H NMR (500 MHz, DMSO-d6) δ 2.86 (s, 3H), 2.99 (s, 3H), 5.60 (s, 1H), 7.48 (m, 1H), 8.12, (s, 1H), 8.15 (m, 1H), 8.22 (m, 1H), 8.48 (m, 1H), 8.55-8.57 (m, 2H), 8.62 (m, 1H), 8.96 (m, 1H), 9.06 (m, 1H), 12.25 (s, 1H). MS: m/z 374.2 (M+H⁺).

Other compounds were prepared by the method 37 are shown in Table 28:

TABLE 28

| Structure | MS: m/z (M + H⁺) | ¹H NMR (500 MHz, DMSO-d6) δ |
|---|---|---|
| (4-chlorophenyl structure) | 407.1 | 2.84 (s, 3H), 3.01 (s, 3H), 5.60 (s, 1H), 5.84 (s, 1H), 7.50 (d, 2H), 7.85 (d, 2H), 8.03 (d, 1H), 8.14 (t, 1H), 8.52 (d, 1H), 8.56 (d, 1H), 8.59 (d, 1H), 8.94 (d, 1H), 12.20 (s, 1H). |
| (3,4-dichlorophenyl structure) | 441.1 | 2.84 (s, 3H), 3.00 (s, 3H), 5.60 (s, 1H), 5.84 (s, 1H), 7.68 (d, 1H), 7.86 (d, 1H), 8.05 (s, 1H), 8.14 (m, 2H), 8.52 (s, 1H), 8.58 (s, 1H), 8.60 (s, 1H), 8.95 (s, 1H). |
| (4-methylphenyl structure) | 387.2 | 2.40 (s, 3H), 2.84 (s, 3H), 3.0 (s, 3H), 5.60 (s, 1H), 7.28 (d, 2H), 7.68 (d, 2H), 7.90 (s, 1H), 8.12 (t, 1H), 8.46 (d, 1H), 8.56 (d, 1H), 8.58 (d, 1H), 8.92 (d, 1H), 12.01 (s, 1H). |

TABLE 28-continued

| Structure | MS: m/z (M + H⁺) | ¹H NMR (500 MHz, DMSO-d6) δ |
|---|---|---|
| 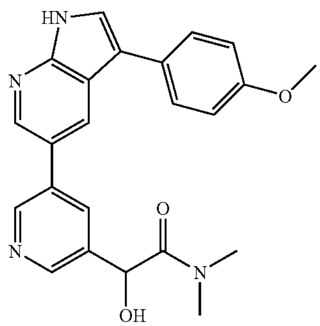 | 403.2 | 2.84 (s, 3H), 3.0 (s, 3H), 3.81 (s, 3H), 5.60 (d, 1H), 5.82 (d, 1H), 7.04 (d, 2H), 7.52 (d, 2H), 7.84 (s, 1H), 8.12 (t, 1H), 8.44 (d, 1H), 8.56 (d, 1H), 8.58 (d, 1H), 8.92 (d, 1H), 12.0 (s, 1H). |
| 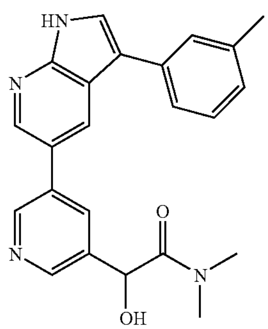 | 387.2 | 2.40 (s, 3H), 2.84 (s, 3H), 3.0 (s, 3H), 5.60 (s, 1H), 7.10 (d, 1H), 7.36 (t, 1H), 7.60 (m, 2H), 7.92 (s, 1H), 8.12 (t, 1H), 8.48 (d, 1H), 8.56 (d, 1H), 8.58 (d, 1H), 8.92 (d, 1H), 12.05 (s, 1H). |
| 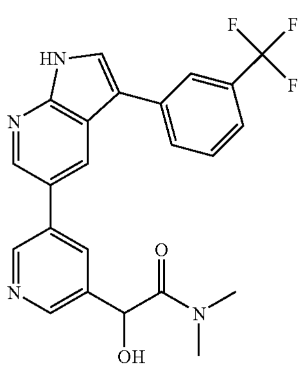 | 441.1 | 2.84 (s, 3H), 3.0 (s, 3H), 5.60 (s, 1H), 5.84 (s, 1H), 7.62 (d, 1H), 7.71 (t, 1H), 8.06 (s, 1H) 8.12 (t, 1H), 8.18 (m, 2H), 8.51 (d, 1H), 8.58 (d, 1H), 8.62 (d, 1H), 8.94 (d, 1H), 12.24 (s, 1H). |
| 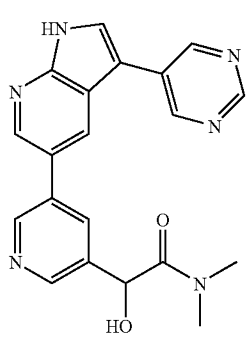 | 375.1 | 2.84 (s, 3H), 3.0 (s, 3H), 5.60 (s, 1H), 8.18 (t, 1H), 8.26 (s, 1H), 8.57 (d, 1H), 8.65 (m, 2H), 9.0 (d, 1H), 9.10 (s, 1H), 9.31 (s, 2H). |

TABLE 28-continued

| Structure | MS: m/z (M + H⁺) | ¹H NMR (500 MHz, DMSO-d6) δ |
|---|---|---|
| 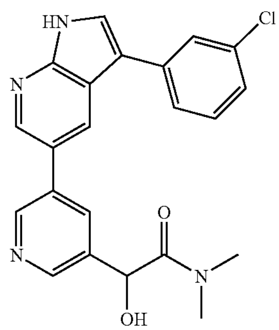 | 407.1 | 2.84 (s, 3H), 3.0 (s, 3H), 5.60 (s, 1H), 7.33 (d, 1H), 7.49 (t, 1H), 7.83 (m, 2H), 8.10 (d, 1H), 8.14 (t, 1H), 8.51 (d, 1H), 8.58 (d, 1H), 8.61 (d, 1H), 8.96 (d, 1H), 12.22 (s, 1H). |
| 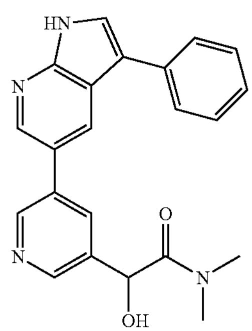 | 373.2 | 2.84 (s, 3H), 3.0 (s, 3H), 5.60 (s, 1H), 7.28 (t, 1H), 7.47 (t, 2H), 7.81 (d, 2H), 7.96 (d, 1H), 8.14 (t, 1H), 8.50 (d, 1H), 8.56 (d, 1H), 8.59 (d, 1H), 8.94 (d, 1H), 12.16 (s, 1H). |
| 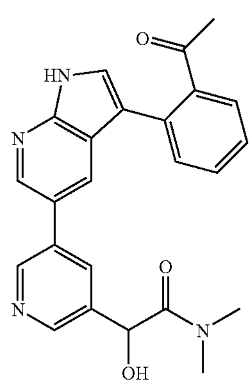 | 415.2 | 2.18 (s, 3H), 2.84 (s, 3H), 3.0 (s, 3H), 5.60 (s, 1H), 5.84 (s, 1H), 7.48 (t, 1H), 7.62 (m, 2H), 8.06 (m, 2H), 8.58 (s, 1H), 8.63 (s, 1H), 8.87 (s, 1H), 12.2 (s, 1H). |
| 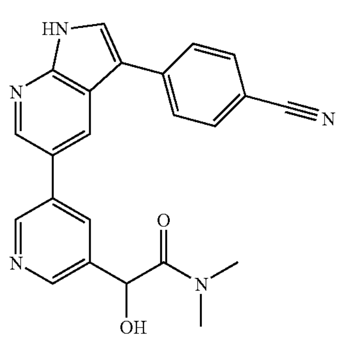 | 398.2 | 2.84 (s, 3H), 3.0 (s, 3H), 5.60 (s, 1H), 5.84 (s, 1H), 7.88 (d, 2H), 8.06 (d, 2H), 8.15 (t,H), 8.24 (s, 1H) 8.58 (d, 1H), 8.60 (d, 1H), 8.62 (d, 1H), 8.96 (d, 1H). |

TABLE 28-continued

| Structure | MS: m/z (M + H+) | ¹H NMR (500 MHz, DMSO-d6) δ |
|---|---|---|
| 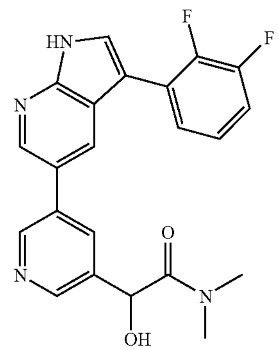 | 409.2 | 2.84 (s, 3H), 3.0 (s, 3H), 5.60 (s, 1H), 5.84 (s, 1H), 7.3-7.4 (m, 2H), 7.66 (t, 1H), 7.96 (s, 1H), 8.11 (t, 1H), 8.36 (s, 1H), 8.57 (d, 1H), 8.64 (d, 1H), 8.92 (d, 1H), 12.38 (s, 1H). |
| 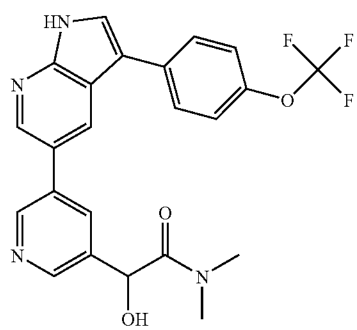 | 457.1 | 2.84 (s, 3H), 3.0 (s, 3H), 5.60 (s, 1H), 5.84 (s, 1H), 7.44 (d, 2H), 7.94 (d, 2H), 8.04 (s, 1H), 8.14 (t, 1H), 8.53 (d, 1H), 8.56 (d, 1H), 8.60 (d, 1H), 8.95 (d, 1H), 12.21 (s, 1H). |
| 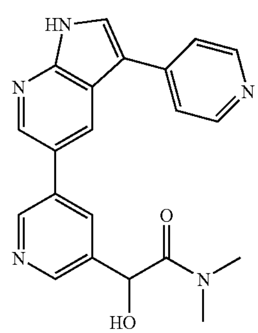 | 374.1 | 2.84 (s, 3H), 3.0 (s, 3H), 5.60 (s, 1H), 5.84 (s, 1H), 8.09 (d, 2H), 8.18 (t, 1H), 8.50 (s, 1H), 8.59 (d, 1H), 8.65 (m, 3H), 8.72 (s, 1H), 8.95 (d, 1H), 12.62 (s, 1H). |
| 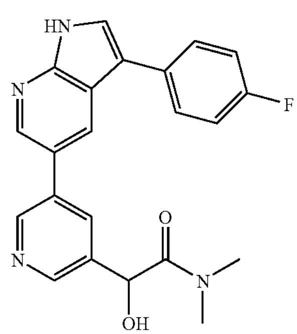 | 391.1 | 2.84 (s, 3H), 3.0 (s, 3H), 5.60 (s, 1H), 5.84 (s, 1H), 7.29 (t, 2H), 7.84 (t, 2H), 7.95 (d, 1H), 8.13 (t, 1H), 8.48 (d, 1H), 8.56 (d, 1H), 8.59 (d, 1H), 8.94 (d, 1H), 12.16 (s, 1H). |

TABLE 28-continued

| Structure | MS: m/z (M + H⁺) | ¹H NMR (500 MHz, DMSO-d6) δ |
|---|---|---|
| 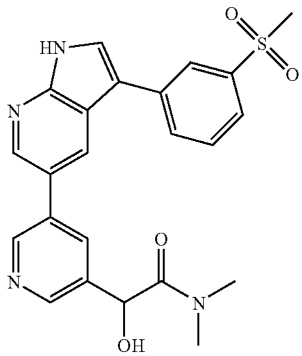 | 451.1 | 2.84 (s, 3H), 3.0 (s, 3H), 5.60 (s, 1H), 5.84 (s, 1H), 7.42 (t, 1H), 7.81 (d, 1H), 8.14 (t, 1H), 8.20 (t, 2H), 8.25 (t, 1H), 8.54 (d, 1H), 8.58 (d, 1H), 8.62 (d, 1H), 8.94 (d, 1H), 12.26 (s, 1H). |
| 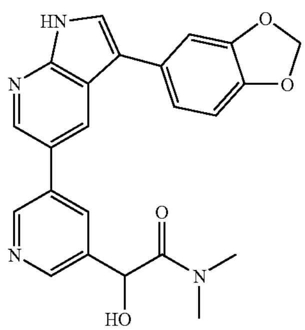 | 417.1 | 2.84 (s, 3H), 3.0 (s, 3H), 5.60 (s, 1H), 5.84 (s, 1H), 6.05 (s, 1H), 7.0 (d, 1H), 7.28 (d, 1H), 7.36 (d, 1H), 7.86 (d, 1H), 8.12 (t, 1H), 8.44 (d, 1H), 8.56 (d, 1H), 8.57 (d, 1H), 8.94 (d, 1H), 12.04 (s, 1H). |
| 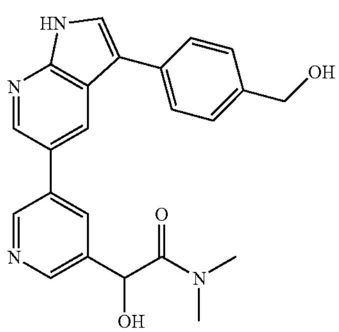 | 403.2 | 2.84 (s, 3H), 3.0 (s, 3H), 4.56 (s, 2H), 5.20 (s, 1H), 5.60 (s, 1H), 5.86 (s, 1H), 7.41 (d, 2H), 7.76 (d, 2H), 7.92 (d, 1H), 8.12 (t, 1H), 8.48 (d, 1H), 8.56 (d, 1H), 8.58 (d, 1H), 8.94 (d, 1H), 12.08 (s, 1H). |
| 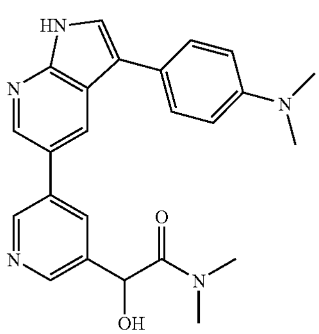 | 416.2 | 2.84 (s, 3H), 2.96 (s, 6H), 3.00 (s, 3H), 5.60 (s, 1H), 5.84 (s, 1H), 7.60 (d, 2H), 7.75 (s, 1H), 8.15 (t, 1H), 8.42 (d, 1H), 8.56 (m, 2H), 8.92 (d, 1H), 11.90 (s, 1H). |

TABLE 28-continued

| Structure | MS: m/z (M + H⁺) | ¹H NMR (500 MHz, DMSO-d6) δ |
|---|---|---|
| 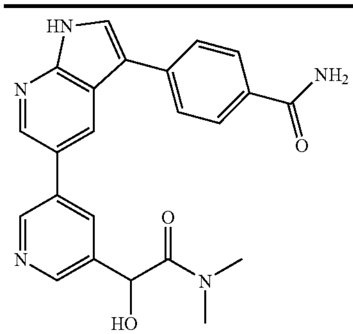 | 416.2 | 2.84 (s, 3H), 3.0 (s, 3H), 5.60 (s, 1H), 5.84 (s, 1H), 6.80 (s, 1H), 7.34 (s, 1H), 7.90 (d, 2H), 7.80 (m, 3H), 8.10 (d, 1H), 8.14 (t, 1H), 8.56 (m, 2H), 8.61 (d, 1H), 8.96 (d, 1H), 12.21 (s, 1H). |
| 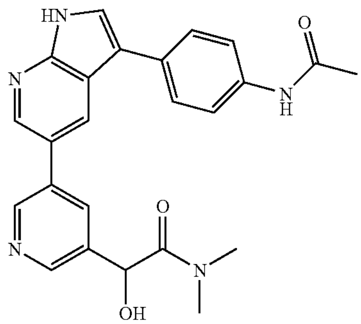 | 430.2 | 2.05 (s, 3H), 2.84 (s, 3H), 3.0 (s, 3H), 5.60 (s, 1H), 5.84 (s, 1H), 7.68 (d, 2H), 7.74 (d, 2H), 7.88 (s, 1H), 8.13 (t, 1H), 8.49 (d, 1H), 8.56 (d, 1H), 8.58 (d, 1H), 8.94 (d, 1H), 12.05 (s, 1H). |
| 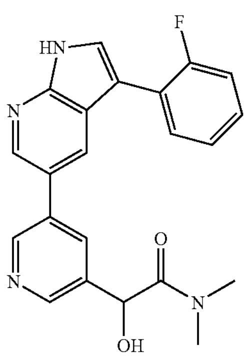 | 391.1 | 2.84 (s, 3H), 3.0 (s, 3H), 5.60 (d, 1H), 5.84 (d, 1H), 7.30-7.38 (m, 3H), 7.82 (t, 1H), 7.88 (s, 1H), 8.09 (t, 1H), 8.35 (m, 1H), 8.56 (d, 1H), 8.62 (d, 1H), 8.90 (d, 1H), 12.21 (s, 1H). |
| 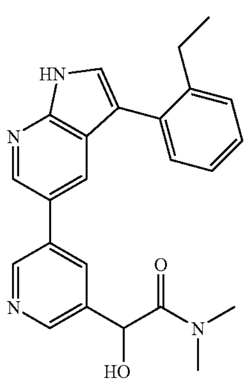 | 401.2 | 1.05 (t, 3H), 2.64 (m, 2H), 2.84 (s, 3H), 3.0 (s, 3H), 5.58 (s, 1H), 5.62 (s, 1H), 7.28 (t, 1H), 7.33 (t, 1H), 7.38 (m, 2H), 7.62 (d, 1H), 7.96 (d, 1H), 8.04 (t, 1H), 8.53 (d, 1H), 8.60 (d, 1H), 8.84 (d, 1H), 12.02 (s, 1H). |

TABLE 28-continued
| Structure | MS: m/z (M + H⁺) | ¹H NMR (500 MHz, DMSO-d6) δ |
|---|---|---|
| 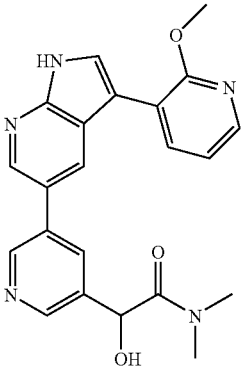 | 404.2 | 2.84 (s, 3H), 3.0 (s, 3H), 3.98 (s, 3H), 5.60 (s, 1H), 7.12 (s, 1H), 8.08 (d, 1H), 8.10 (m, 1H), 8.13 (d, 1H), 8.35 (d, 1H), 8.56 (d, 1H), 8.60 (d, 1H), 8.92 (d, 1H). |
| 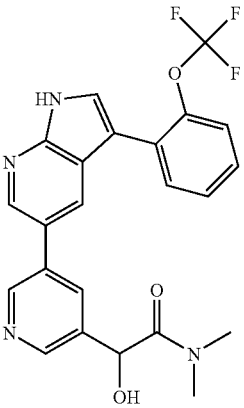 | 457.1 | 2.84 (s, 3H), 3.0 (s, 3H), 5.58 (s, 1H), 5.84 (s, 1H), 7.47 (m, 3H), 7.52 (m, 2H), 7.84 (m, 2H), 8.08 (t, 1H), 8.25 (d, 1H), 8.60 (d, 1H), 8.62 (d, 1H), 8.88 (d, 1H), 12.25 (s, 1H). |
| 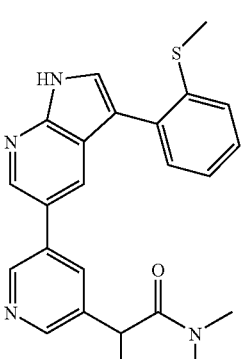 | 419.1 | 2.40 (s, 3H), 2.84 (s, 3H), 3.0 (s, 3H), 5.58 (s, 1H), 5.83 (s, 1H), 7.25 (t, 1H), 7.36-7.45 (m, 3H), 7.68 (s, 1H), 8.02 (d, 1H), 8.04 (t, 1H), 8.54 (d, 1H), 8.60 (d, 1H), 8.85 (d, 1H), 12.10 (s, 1H). |
| 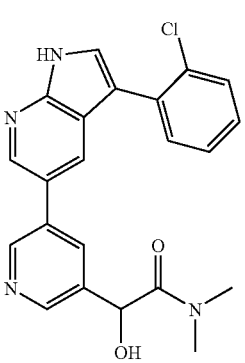 | 407.1 | 2.84 (s, 3H), 3.0 (s, 3H), 5.58 (s, 1H), 7.39 (t, 1H), 7.45 (t, 1H), 7.62 (d, 1H), 7.45 (d, 1H), 7.82 (s, 1H), 7.07 (t, 1H), 8.12 (d, 1H), 8.55 (d, 1H), 8.62 (d, 1H), 8.87 (d, 1H), 12.25 (s, 1H). |

TABLE 28-continued

| Structure | MS: m/z (M + H⁺) | ¹H NMR (500 MHz, DMSO-d6) δ |
|---|---|---|
| 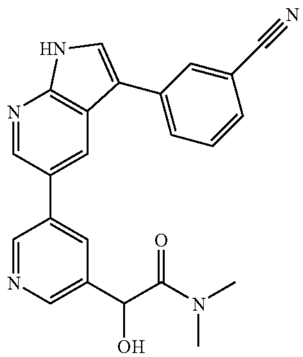 | 398.1 | 2.84 (s, 3H), 3.0 (s, 3H), 5.60 (d, 1H), 5.84 (d, 1H), 7.64 (t, 1H), 7.72 (d, 1H), 8.14 (t, 1H), 8.16 (s, 1H), 8.20 (d, 1H), 8.28 (t, 1H), 8.58 (d, 1H), 8.61 (m, 2H), 8.98 (d, 1H), 12.25 (s, 1H). |
| 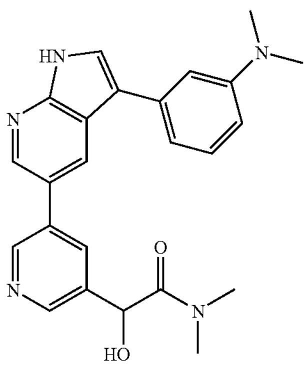 | 416.1 | 2.85 (s, 6H), 3.00 (d, 6H), 5.60 (s, 1H), 5.84 (s, 1H), 6.68 (d, 1H), 7.04 (m, 1H), 7.08 (d, 1H), 7.27 (t, 1H), 7.91 (s, 1H), 8.15 (t, 1H), 8.44 (d, 1H), 8.56 (d, 1H), 8.59 (d, 1H), 8.91 (d, 1H), 12.05 (s, 1H). |
| 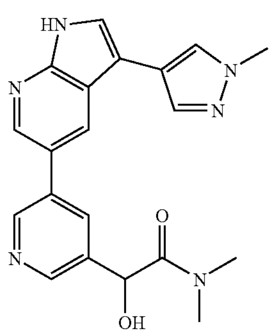 | 377.2 | 2.86 (s, 3 H 0, 3.05 (s, 3H), 3.90 (s, 3H), 5.60 (s, 1H), 5.84 (s, 1H), 7.78 (s, 1H), 7.91 (s, 1H), 8.14 (t, 1H), 8.26 (s, 1H), 8.45 (d, 1H), 8.55 (d, 1H), 8.65 (d, 1H), 8.96 (d, 1H), 11.85 (s, 1H). |
| 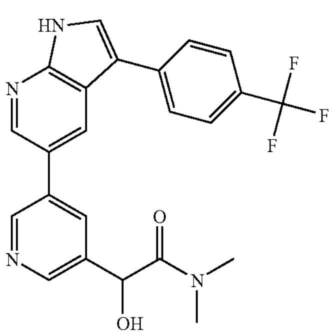 | 441.2 | 2.86 (s, 3H), 3.02 (s, 3H), 5.62 (s, 1H), 5.84 (s, 1H), 7.79 (d, 2H), 8.06 (d, 2H), 8.16 9 t, 1H), 8.17 (s, 1H), 8.58 (d, 1H), 8.59 (d, 1H), 8.63 (d, 1H), 8.96 (d, 1H), 12.36 (s, 1H). |

TABLE 28-continued

| Structure | MS: m/z (M + H⁺) | ¹H NMR (500 MHz, DMSO-d6) δ |
|---|---|---|
| (structure) | 407.1 | 2.86 (s, 3H), 3.02 (s, 3H), 5.62 (s, 1H), 5.84 (s, 1H), 7.33 (m, 1H), 7.49 (t, 1H), 7.83 (m, 2H), 8.09 (s, 1H), 8.14 (t, 1H), 8.51 (d, 1H), 8.58 (d, 1H), 8.60 (d, 1H), 8.95 (d, 1H), 12.22 (s, 1H). |
| (structure) | 392.2 | 2.20 (s, 3H), 2.38 (s, 3H), 2.86 (s, 3H), 2.94 (s, 3H), 5.58 (d, 1H), 5.82 (d, 1H), 7.21 (s, 1H), 8.08 (t, 1H), 8.14 (d, 1H), 8.54 (d, 1H), 8.62 (d, 1H), 8.88 (d, 1H), 12.18 (s, 1H). |
| (structure) | 453.1 | 2.84 (s, 3H), 3.00 (s, 3H), 5.58 (s, 1H), 5.84 (s, 1H), 7.53 (d, 2H), 7.75 (M, 1H), 8.02 (s, 1H), 8.13 (t, 1H), 8.50 (d, 1H), 8.58 (d, 1H), 8.66 (d, 1H), 8.93 (d, 1H), 12.42 (s, 1H). |
| (structure) | 363.1 | 2.84 (s, 3H), 3.02 (s, 3H), 5.62 (s, 1H), 5.86 (s, 1H), 6.74 (s, 1H), 7.73 (s, 1H), 7.97 (s, 1H), 8.18 (s, 1H), 8.57 (d, 1H), 8.60 (d, 1H), 8.68 (s, 1H), 8.92 (s, 1H), 12.01 (s, 1H) |

TABLE 28-continued
| Structure | MS: m/z (M + H+) | ¹H NMR (500 MHz, DMSO-d6) δ |
|---|---|---|
| 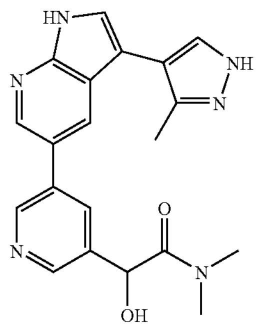 | 377.0 | 2.38 (s, 3H), 2.84 (s, 3H), 3.01 (s, 3H), 5.60 (s, 1H), 7.58 (s, 1H) 8.00 (s, 1H) 8.12 (m, 1H), 8.28 (d, 1H), 8.31 (s, 1H), 8.55 (d, 1H), 8.57 (d, 1H), 8.92 (d, 1H), 11.92 (s, 1H) |
| 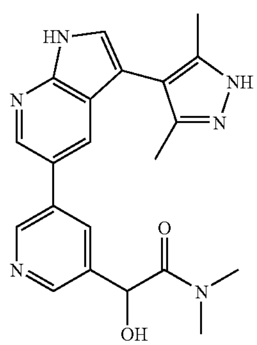 | 391.1 | 2.18 (s, 6H), 2.84 (s, 3H), 3.01 (s, 3H), 5.60 (s, 1H), 7.00 (d, 1H), 7.97 (d, 1H), 8.07 (t, 1H), 8.22 (s, 1H), 8.54 (d, 1H), 8.59 (d, 1H), 8.87 (d, 1H), 11.96 (s, 1H) |
| 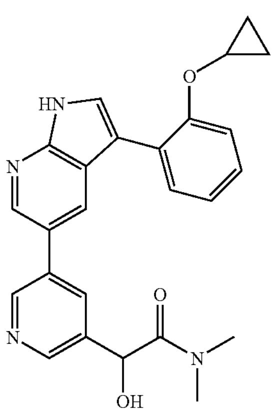 | 429 | |
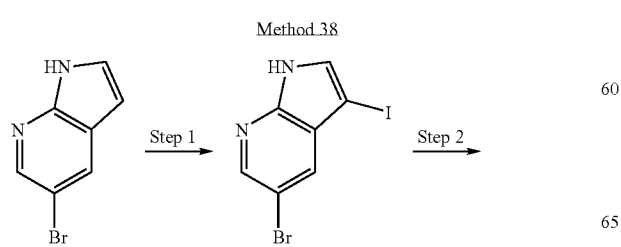
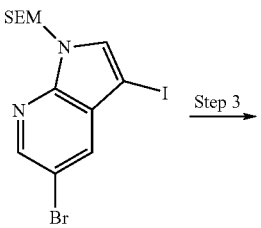

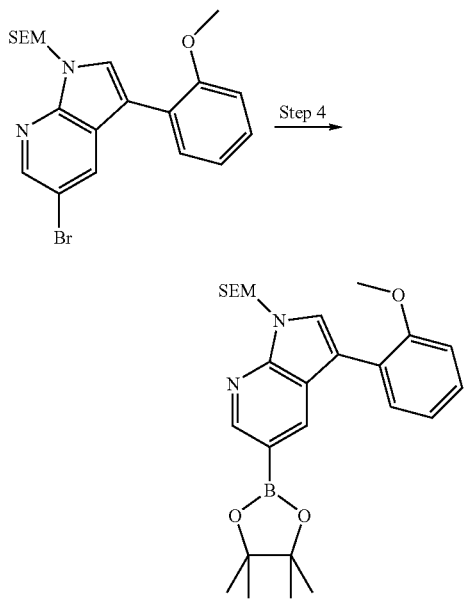

Step 1: Synthesis of 5-bromo-3-iodo-1H-pyrrolo[2,3-b]pyridine

A mixture of 5-Bromo-1H-pyrrolo[2,3-b]pyridine (50 g, 252.5 mmol) and N-iodosuccinimide (13.6 g, 60.6 mmol) in dichloroethane (200 ml) was stirred at 95° C. overnight. The reaction was allowed to cool to room temperature and saturated $Na_2H_2SO_4$ (200 ml) was added. The mixture was then extracted with ethyl acetate (400 ml×2). The combined organic layers were dried with $Na_2SO_4$, concentrated. Silica gel chromatography of the crude using a gradient of ethyl acetate and hexane afforded 5-bromo-3-iodo-1H-pyrrolo[2,3-b]pyridine (62.8 g, 77% yield).

Step 2: Synthesis of 5-bromo-3-iodo-1-(2-trimethylsilanyl-ethoxymethyl)-1H-pyrrolo[2,3-b]pyridine To a 500 ml 3-neck flask, 5-bromo-3-iodo-1H-pyrrolo[2,3-b]pyridine (32 g, 99.1 mmol) and DMF (300 ml) were added. The solution was cooled to −40° C. under nitrogen and sodium hydride (2.8 g, 118.9 mmol) was added in 2 batches. The mixture was stirred at −40° C. for 1 hour. Then SEM-Cl (21 ml, 118.9 mmol) in DMF (50 ml) was added drop wise and the resulting mixture was allowed to stir at −40° C. for another 2 hours. The reaction was quenched with saturated $NH_4Cl$ (40 ml) and worked up with ethyl acetate, brine, dried with $Na_2SO_4$, concentrated to dryness. Silica chromatography of the crude using a gradient of ethyl acetate and hexane afforded 5-bromo-3-iodo-1-(2-trimethylsilanyl-ethoxymethyl)-1H-pyrrolo[2,3-b]pyridine (32.8 g, 73% yield). NMR (500 MHz, DMSO-d6) δ 0.06 (s, 9H), 0.91 (m, 2H), 3.62 (m, 2H), 5.70 (s, 2H), 8.04 (m, 1H), 8.11 (s, 1H), 8.51 (m, 1H). MS: m/z 455.9 (M+H$^+$).

Step 3: Synthesis of 5-bromo-3-(2-methoxy-phenyl)-1-(2-trimethylsilanyl-ethoxymethyl)-1H-pyrrolo[2,3-b]pyridine A mixture of 5-bromo-3-iodo-1-(2-trimethylsilanyl-ethoxymethyl)-1H-pyrrolo[2,3-b]pyridine (8.0 g, 17.6 mmol), methoxyphenyl boronic acid (2.9 g, 19.4 mmol), dichloro[1,1'-bis(diphenyl-phosphino)ferrocene]palladium (II) dichloromethane adduct (646 mg, 0.9 mmol) in THF/Acetonitrile/saturated $NaHCO_3$ (50 ml/50 ml/50 ml) was stirred at 50° C. overnight under nitrogen. The mixture was allowed to cool to room temperature and was extracted with ethyl acetate (3×). The combined organic layers were extracted with brine, dried with $Na_2SO_4$, decanted, and concentrated to dryness. Silica chromatography of the crude using a gradient of ethyl acetate and hexane afforded 5-bromo-3-(2-methoxy-phenyl)-1-(2-trimethylsilanyl-ethoxymethyl)-1H-pyrrolo[2,3-b]pyridine (2.2 g, 29% yield). NMR (500 MHz, DMSO-d$_6$) δ 0.11 (s, 9H), 1.05 (m, 2H), 3.76 (m, 2H), 3.01 (s, 3H), 5.87 (s, 2H), 7.26 (m, 1H), 7.35 (m, 1H), 7.54 (m, 1H), 7.72 (m, 1H), 8.17 (s, 1H), 8.38 (m, 1H), 8.59 (m, 1H). MS: m/z 434.1 (M+H$^+$).

Step 4: Synthesis of 3-(2-methoxy-phenyl)-5-(4,4,5,5-tetramethyl-[1,3,2]dioxaborolan-2-yl)-1-(2-trimethylsilanyl-ethoxymethyl)-1H-pyrrolo[2,3-b]pyridine A mixture of 5-bromo-3-(2-methoxy-phenyl)-1-(2-trimethylsilanyl-ethoxymethyl)-1H-pyrrolo[2,3-b]pyridine (2.2 g, 5.2 mmol), bis(pinacolato)diboron (2.6 g, 10.4 mmol), dichloro[1,1'-bis(diphenylphosphino)ferrocene]palladium (II) dichloromethane adduct (190 mg, 0.3 mmol), and sodium acetate (1.3, 15.6 mmol) in DMF (20 ml) was stirred at 95° C. overnight. The mixture was allowed to cool down to room temperature and then extracted with ethyl acetate (3×). The combined organic layers were extracted with brine, dried with $Na_2SO_4$, decanted, and concentrated to dryness. Silica chromatography of the crude using a gradient of ethyl acetate and hexane afforded 3-(2-methoxy-phenyl)-5-(4,4,5,5-tetramethyl-[1,3,2]dioxaborolan-2-yl)-1-(2-trimethylsilanyl-ethoxymethyl)-1H-pyrrolo[2,3-b]pyridine (1.6 g, 63% yield). $^1$H NMR (500 MHz, DMSO-d6) δ 0.02 (s, 9H), 0.92 (m, 1H), 1.40 (s, 12H), 3.65 (m, 2H), 3.90 (s, 3H), 5.78 (s, 2H), 7.18 (m, 1H), 7.24 (m, 1H), 7.42 (m, 1H), 7.60 (m, 1H), 7.98 (s, 1H), 8.34 (m, 1H), 8.62 (m, 1H). MS: m/z 481.2 (M+H$^+$).

Method 39

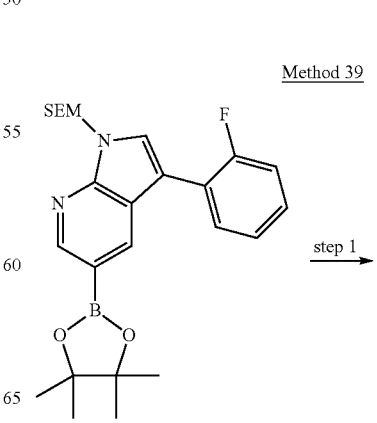

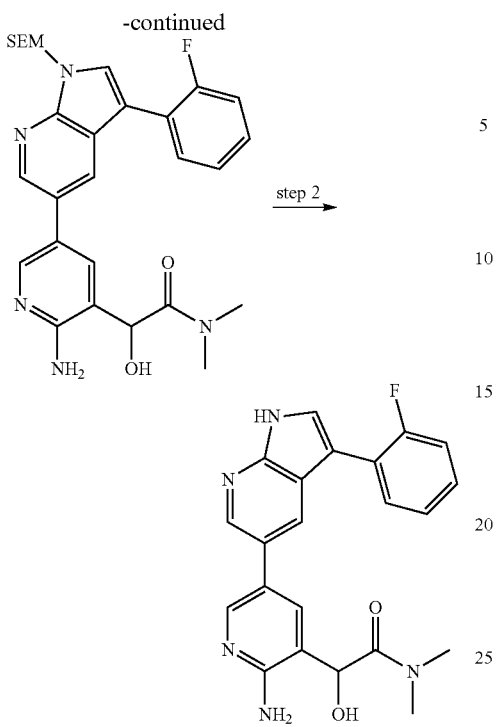

Step 1: Synthesis of 2-amino-5-[3-(2-fluorophenyl)-1-(2-trimethylsilanylethoxymethyl)-1H-pyrrolo[2,3-b]pyridin-5-yl]-N,N-dimethyl-nicotinamide 3-(2-Fluoro-phenyl)-5-(4,4,5,5-tetramethyl-[1,3,2]dioxaborolan-2-yl)-1-(2-trimethylsilanyl-ethoxymethyl)-1H-pyrrolo[2,3-b]pyridine (289 mg, 0.617 mmol), 2-(2-amino-5-bromo-pyridin-3-yl)-2-hydroxy-N,N-dimethyl-acetamide (168.5 mg, 0.617 mmol) and dichloro[1,1'-bis(diphenylphosphino)ferrocene]palladium(II) dichloromethane adduct (25 mg, 0.031 mmol) were combined in 1:1 acetonitrile/tetrahydrofuran (4 mL) under nitrogen. Saturated sodium bicarbonate was added (4 mL), also under nitrogen, and the mixture was capped and heated for 18 h at 80° C. After cooling, the aqueous layer was removed and the organic layer was purified by silica gel chromatography using DCM and MeoH as eluent to afford 2-{2-Amino-5-[3-(2-fluoro-phenyl)-1-(2-trimethylsilanyl-ethoxymethyl)-1H-pyrrolo[2,3-b]pyridin-5-yl]-pyridin-3-yl}-2-hydroxy-N,N-dimethyl-acetamide (130 mg, 39.3%). MS: m/z 536 (M+H+).

Step 2: Synthesis of 2-{2-amino-5-[3-(2-fluoro-phenyl)-1H-pyrrolo[2,3-b]pyridin-5-yl]-pyridin-3-yl}-2-hydroxy-N,N-dimethyl-acetamide 2-{2-Amino-5-[3-(2-fluoro-phenyl)-1H-pyrrolo[2,3-b]pyridin-5-yl]-pyridin-3-yl}-2-hydroxy-N,N-dimethyl-acetamide was prepared as described above (19.9%). 1H NMR (500 MHz, DMSO-d$_6$) δ 2.81 (d, 3H), 2.82 (s, 3H), 5.38 (s, 1H), 5.99 (s, 2H), 7.22-7.29 (m, 3H), 7.65 (d, 1H), 7.73 (dt, 1H), 7.74 (br t, 1H), 8.04 (t, 1H), 8.20 (d, 1H), 8.392 (d, 1H). MS: m/z 406 (M+H+).

Other compounds prepared by Method 39 are shown in Table 29

TABLE 29

| Compound | MS |
|---|---|
| (structure) | 421 |
| (structure) | 437 |
| (structure) | 418 |

Method 40

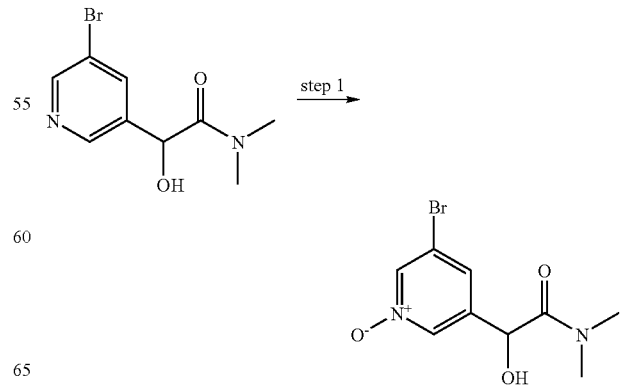

Step 1: Synthesis of 2-(5-bromo-pyridin-3-yl)-2-hydroxy-N,N-dimethyl-acetamide N-oxide A solution of 2-(5-bromo-pyridin-3-yl)-2-hydroxy-N,N-dimethyl-acetamide (100 mg, 0.387 mmol) in DCM (3.0 mL) was cooled in an ice water bath and treated with mCPBA (100.3 mg, 0.581 mmol). After stirring at room temperature for 4 h, the mixture was cooled and additional mCPBA was added (66.7 mg, 1 eq.). After stirring 18 h at room temperature, another 0.3 eq of mCPBA was added (13.3 mg). Finally after 4 h, the reaction was quenched by addition of 38% aqueous sodium bisulfite (100 uL) and the mixture was dried over $Na_2SO_4$. After filtration, $MP-CO_3$ (1.74 mmol) was added to scavenge the benzoic acid by-product. After 5 d (3 hours is sufficient), the mixture was filtered and the resin was rinsed with 10% MeOH in DCM. The product was concentrated in vacuo to afford 2-(5-bromo-pyridin-3-yl)-2-hydroxy-N,N-dimethyl-acetamide N-oxide (97.0 mg, 91.7%). MS: m/z 275 (M+H$^+$).

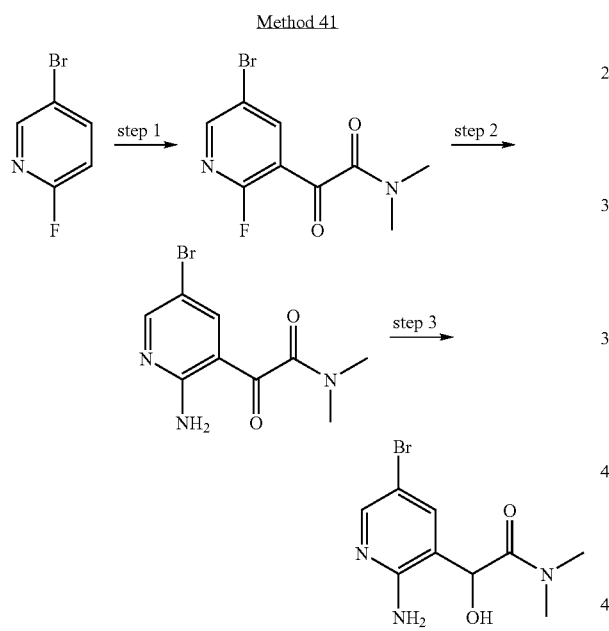

Method 41

Step 1: Synthesis of 2-(5-bromo-2-fluoro-pyridin-3-yl)-N,N-dimethyl-2-oxo-acetamide 5-Bromo-2-fluoro-pyridine (1 g, 5.68 mmol) in THF (1 mL) was added dropwise to a freshly prepared solution of lithium N,N-diisopropylamide (6.81 mmol) in THF at −78° C. The mixture was stirred 2 h at −78° C. The orange suspension was quickly added via cannula to a cold (−78° C.) solution of N,N-dimethyl-oxalamic acid ethyl ester (925.6 μL 6.81 mmol). After 1.5 h at −78° C., the reaction was quenched by addition of saturated $NH_4Cl$ solution and was allowed to warm to room temperature. The mixture was extracted with diethyl ether and the product was purified by silica gel chromoatography using hexanes and ethyl acetate (0-100% gradient) to afford 2-(5-bromo-2-fluoro-pyridin-3-yl)-N,N-dimethyl-2-oxo-acetamide (1.01 g, 65.1%). $^1$H NMR (500 MHz, DMSO-d6) δ 3.0 (d, 6H), 8.6 (dd, 1H), 8.78 (dd, 1H) MS: m/z 275 (M+H$^+$).

Step 2: Synthesis of 2-(2-amino-5-bromo-pyridin-3-yl)-N,N-dimethyl-2-oxo-acetamide 2-(5-Bromo-2-fluoro-pyridin-3-yl)-N,N-dimethyl-2-oxo-acetamide (948 mg, 3.45 mmol) was treated with saturated ammonia solution in ethyl alcohol (10 mL) in a sealed vial at 50° C. for 1 h. The reaction was complete and the mixture was dried in vacuo and used crude in the next step. MS: m/z 272 (M+H$^+$).

Step 3: Synthesis of 2-(2-amino-5-bromo-pyridin-3-yl)-2-hydroxy-N,N-dimethyl-acetamide Sodium borohydride (85.5 mg, 2.25 mmol) was added to methanol (5 mL) at 0° C. After 5 min., 2-(2-amino-5-bromo-pyridin-3-yl)-N,N-dimethyl-2-oxo-acetamide (408 mg, 1.50 mmol) in MeOH (15 mL) was added. After 1 h, the reaction was quenched by addition of saturated $NH_4Cl$ and the mixture was concentrated in vacuo. The residue was extracted with ethyl acetate, dried over $Na_2SO_4$ and purified by silica gel chromatography using DCM and MeOH to afford 2-(2-amino-5-bromo-pyridin-3-yl)-2-hydroxy-N,N-dimethyl-acetamide (234 mg, 57.1%) as a brown oily solid. The material was used in the next step. MS: m/z 274 (M+H$^+$).

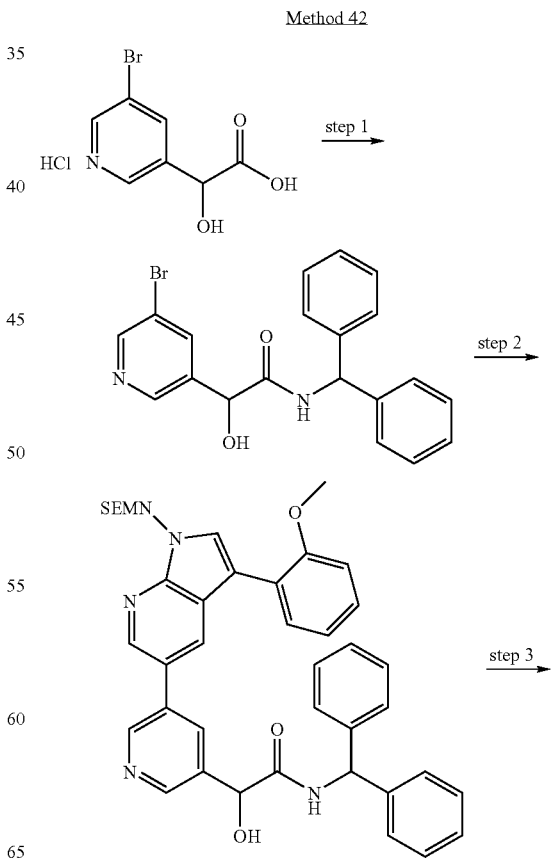

Method 42

269

-continued

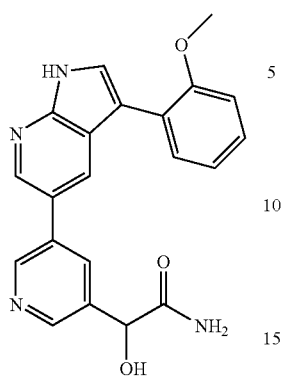

Step 1: Synthesis of N-benzhydryl-2-(5-bromo-pyridin-3-yl)-2-hydroxy-acetamide (5-Bromo-pyridin-3-yl)-hydroxy-acetic acid HCl salt (1.19 g, 4.47 mmol), C,C-Diphenyl-methylamine (1.3 g, 5.36 mmol), HOAT (2.0 g, 5.36 mmol) and DIEA (1.94 mL, 11.17 mmol) were all combined in THF (43.0 mL) and heated in a closed vial for 20 min. at 60° C. The solution was diluted with ethyl acetate and washed with saturated sodium bicarbonate (1×) and brine (1×). The material was purified by silica gel chromatography using a gradient of hexanes and ethyl acetate (0-100%) to afford N-benzhydryl-2-(5-bromo-pyridin-3-yl)-2-hydroxy-acetamide (1.5 g, 73.5%) as a waxy white solid. MS: m/z 397 (M+H+).

Step 2: Synthesis of N-benzhydryl-2-hydroxy-2-{5-[3-(2-methoxy-phenyl)-1-(2-trimethylsilanyl-ethoxymethyl)-1H-pyrrolo[2,3-b]pyridin-5-yl]-pyridin-3-yl}-acetamide Material was coupled as previously described.

Step 3: Synthesis of 2-hydroxy-2-{5-[3-(2-methoxy-phenyl)-1H-pyrrolo[2,3-b]pyridin-5-yl]-pyridin-3-yl}-acetamide 2-Hydroxy-2-{5-[3-(2-methoxy-phenyl)-1H-pyrrolo[2,3-b]pyridin-5-yl]-pyridin-3-yl}-acetamide (74.5 mg, 0.102 mmol) was treated with TFA (1 mL) and anisole (8.8 uL, 0.081 mmol). Additional anisole (8.8 uL, 0.081 mmol) and TFA (0.5 mL) were added after several hours, and the mixture was allowed to stir 18 h. The mixture was concentrated in vacuo and triturated with hexanes. The residue was treated with THF (1.0 mL) and ethylene diamine (0.5 mL) for 30 min. and was purified by preparative LCMS to afford 2-hydroxy-2-{5-[3-(2-methoxy-phenyl)-1H-pyrrolo[2,3-b]pyridin-5-yl]-pyridin-3-yl}-acetamide (12.1 mg, 31.7%). $^1$H NMR (500 MHz, DMSO-d6) δ 3.8 (s, 3H), 5.05 (s, 1H), 7.05 (m, 1H), 7.14 (d, 1H), 7.29-7.32 (m, 2H), 7.59-7.61 (m, 2H), 7.76 (s, 1H), 8.11 (t, 1H), 8.20 (d, 1H), 8.56 (d, 1H), 8.59 (d, 1H), 8.85 (d, 1H). MS: m/z 375 (M+H+).

270

Method 43

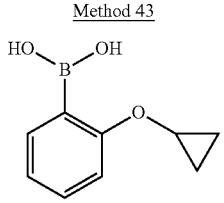

Perpared as described in *Tetrahedron* 1968, 24, 53-58 and *J. Org. Chem.*, 2002, 1093.

Method 44

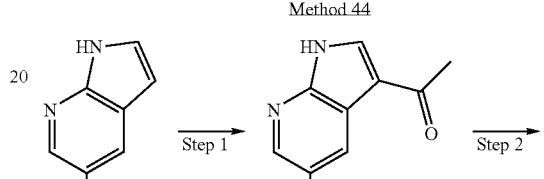

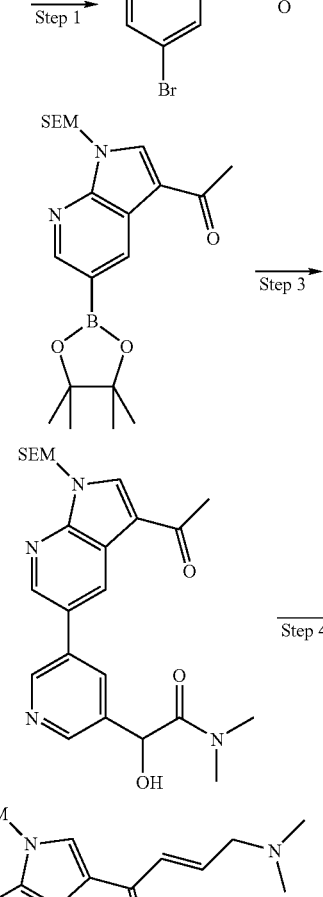

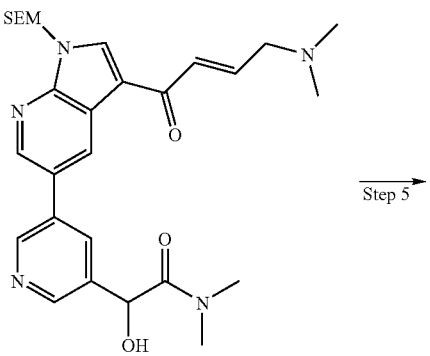

-continued

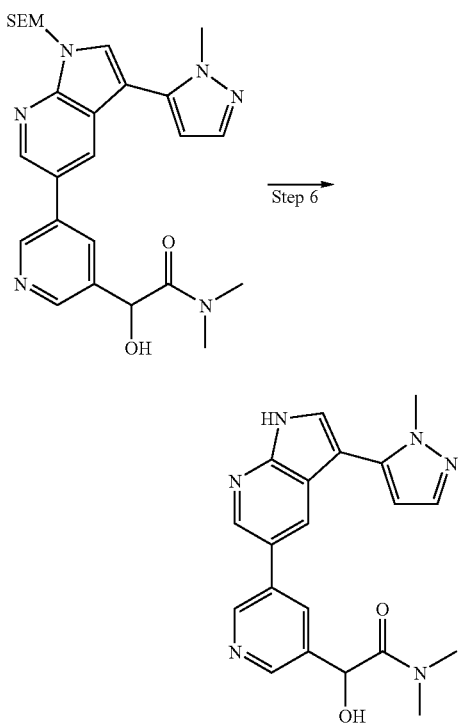

Step 1: Synthesis of 1-(5-bromo-1H-pyrrolo[2,3-b]pyridine-3-yl)-ethanone

5-Bromo-1H-pyrrolo[2,3-b]pyridine (5 g, 25.2 mmol) was added to aluminum chloride (16.8 g, 126.2 mmol) in dichloromethane (200 ml) under nitrogen. The mixture was allowed to stir at room temperature for 1 hour. Acetyl chloride (9 ml, 126.2 mmol) in dichloromethane was added drop wise and the reaction was allowed to proceed at room temperature overnight. Next day the reaction was cooled to 0° C. and quenched with methanol (~500 ml) until the reaction turned clear. The reaction was concentrated under vacuum and resuspended in water (300 ml). The pH was adjusted to 4 with 7N sodium hydroxide solution and then extracted with ethyl acetate (300 ml×3). The combined organic layers were extracted with saturated sodium potassium tartrate and brine and dried with $Na_2SO_4$. Silica chromatography of the crude using a gradient of ethyl acetate and hexane afforded 1-(5-bromo-1H-pyrrolo[2,3-b]pyridine-3-yl)-ethanone (5.2 g, 87% yield). $^1$H NMR (500 MHz, DMSO-d6) δ 2.48 (s, 3H), 8.41 (s, 1H), 8.57 (s, 1H), 8.58 (s, 1H). MS: m/z 241.0 (M+H$^+$).

Step 2: Synthesis of 1-[5-(4,4,5,5-tetramethyl-[1,3,2]dioxaborolan-2-yl-1-2(2-trimethylsilanyl-ethoxymethyl)-1H-pyrrolo[2,3-b]pyridin-3-yl)-ethanone To a 250 ml 3-neck flask, 1-(5-bromo-1H-pyrrolo[2,3-b]pyridine-3-yl)-ethanone (2.2 g, 9.3 mmol) and DMF (50 ml) were added. The solution was cool to −40° C. under nitrogen, and sodium hydride (0.3 g, 11.2 mmol) was added in 2 batches. The mixture was stirred at −40° C. for 1 hour. A solution of SEM-Cl (2 ml, 11.2 mmol) in DMF (10 ml) was added dropwise and the resulting mixture was allowed to stir at −40° C. for another 2 hours. The reaction was quenched with saturated $NH_4Cl$ (40 ml) and worked up with ethyl acetate, brine, dried with $Na_2SO_4$ and concentrated to dryness. The crude intermediate, bis(pinacolato)diboron (4.8 g, 18.6 mmol), dichloro[1,1'-bis(diphenylphosphino)ferrocene]palladium(II) dichloromethane adduct (341 mg, 0.5 mmol), and sodium acetate (2.3 g, 28 mmol) in DMF (20 ml) were stirred at 100° C. overnight. The mixture was allowed to cool to room temperature and was then extracted with ethyl acetate (3×). The combined organic layers were extracted with brine, dried with $Na_2SO_4$, decanted, and concentrated to dryness. Silica gel chromatography of the crude using a gradient of ethyl acetate and hexane afforded 1-[5-(4,4,5,5-tetramethyl-[1,3,2]dioxaborolan-2-yl-1-2(2-trimethylsilanyl-ethoxymethyl)-1H-pyrrolo[2,3-b]pyridine-3-yl)-ethanone (3.6 g, 92% yield). $^1$H NMR (500 MHz, DMSO-d6) δ 0.03 (s, 9H), 0.92 (m, 2H), 1.28 (s, 3H), 1.43 (s, 12H), 3.67 (m, 2H), 5.78 (s, 2H), 8.68, (m, 1H), 8.82 (s, 1H), 8.89 (m, 1H). MS: m/z 417.2 (M+H$^+$).

Step 3: Synthesis of 2-{5-[3-acetyl-1-(2-trimethylsilanyl-ethoxymethyl)-1H-pyrrolo[2,3-b]pyridin-5-yl]-pyridin-3-yl}-2-hydroxy-N,N-dimethyl-acetamide A mixture of 1-[5-(4,4,5,5-tetramethyl-[1,3,2]dioxaborolan-2-yl-1-2(2-trimethylsilanyl-ethoxymethyl)-1H-pyrrolo[2,3-b]pyridine-3-yl)-ethanone (2.0 g, 4.8 mmol), 2-(5-bromo-pyridin-3-yl)-2-hydroxy-N,N-dimethyl-acetamide (1.2 g, 4.8 mmol), and dichloro[1,1'-bis(diphenylphosphino)ferrocene]palladium(II) dichloromethane adduct (176 mg, 0.2 mmol) in THF/Acetonitrile/saturated $NaHCO_3$ (5 ml/5 ml/5 ml) was stirred at 100° C. in a microwave for 20 minutes. The mixture was allowed to cool down to room temperature and then extracted with ethyl acetate (2×). The combined organic layers were extracted with brine, dried with $Na_2SO_4$, decanted, and concentrated to dryness. Silica chromatography of the crude using a gradient of ethyl acetate and hexane afforded 2-{5-[3-acetyl-1-(2-trimethylsilanyl-ethoxymethyl)-1H-pyrrolo[2,3-b]pyridin-5-yl]-pyridin-3-yl}-2-hydroxy-N,N-dimethyl-acetamide (1.4 g, 63% yield). $^1$H NMR (500 MHz, DMSO-d6) δ 0.0 (s, 9H), 0.9 (m, 2H), 2.58 (s, 3H), 2.94 (s, 3H), 3.08 (s, 3H), 3.67 (m, 2H), 5.70 (s, 1H), 5.79 (s, 2H), 6.02 (s, 1H), 8.16 (s, 1H), 8.68 (n, 1H), 8.78 (m, 1H), 8.82 (m, 1H), 8.86 (s, 1H), 8.89 (m, 1H). MS: m/z 469.2 (M+H$^+$).

Step 4: Synthesis of 2-{5-[3-(4-dimethylamino-but-2-enoyl)-1-(2-trimethylsilanyl-ethoxymethyl)-1H-pyrrolo[2,3-b]pyridin-5-yl]-pyridin-3-yl}-2-hydroxy-N,N-dimethyl-acetamide A mixture of 2-{5-[3-acetyl-1-(2-trimethylsilanyl-ethoxymethyl)-1H-pyrrolo[2,3-b]pyridin-5-yl]-pyridin-3-yl}-2-hydroxy-N,N-dimethyl-acetamide (1.4 g, 3.0 mmol), t-butoxybis(dimethylamino)methane (1.9 ml, 9.1 mmol—Bredereck's reagent) was stirred at 100° C. for 7 hours. The reaction was allowed to cool to room temperature and product was triturated with ether afforded 2-{5-[3-(4-dimethylamino-but-2-enoyl)-1-(2trimethylsilanyl-ethoxymethyl)-1H-pyrrolo[2,3-b]pyridin-5-yl]-pyridin-3-yl}-2-hydroxy-N,N-dimethyl-acetamide (1.3 g, 80% yield). ¹H NMR (500 MHz, DMSO-d6) δ 0.02 (s, 9H), 0.92 (m, 1H), 2.58 (s, 6H), 2.94 (s, 3H), 3.08 (s, 3H), 3.67 (m, 1H), 5.70 (m, 1H), 5.79 (s, 2H), 5.91 (m, 1H), 6.02 (m, 1H), 7.70 (m, 1H), 8.15 (m, 1H), 8.68 (m, 1H), 8.75 (m, 1H), 8.90 (m, 1H), 8.95 (m, 1H). MS: m/z 524.3 (M+H⁺).

Step 5: Synthesis of 2-hydroxy-N,N-dimethyl-2-{5-[3-(2-methyl-2H-pyrazol-3-yl)-1-(2-trimethylsilanyl-ethoxymethyl)-1H-pyrrolo[2,3-b]pyridin-5-yl]-pyridin-3-yl}-acetamide A mixture of 2-{5-[3-(4-dimethylamino-but-2-enoyl)-1-(2-trimethylsilanyl-ethoxymethyl)-1ethoxymethyl)-1H-pyrrolo[2,3-b]pyridin-5-yl]-pyridin-3-yl}-2-hydroxy-N,N-dimethyl-acetamide (100 mg, 0.2 mmol), methyl hydrazine (12 μl, 0.2 mmol) in ethanol (10 ml) was stirred at 80° C. for 3 hours. Solvent was removed and silica chromatography of the crude using a gradient of ethyl acetate and hexane afforded 2-hydroxy-N,N-dimethyl-2-{5-[3-(2-methyl-2H-pyrazol-3-yl)-1-(2-trimethylsilanyl-ethoxymethyl)-1H-pyrrolo[2,3-b]pyridin-5-yl]-pyridin-3-yl}-acetamide (71 mg, 73% yield).

Step 6: Synthesis of 2-hydroxy-N,N-dimethyl-2-{5-[3-(2-methyl-2H-pyrazol-3-yl)-1H-pyrrolo[2,3-b]pyridin-5-yl]-pyridin-3-yl}-acetamide 2-Hydroxy-N,N-dimethyl-2-{5-[3-(2-methyl-2H-pyrazol-3-yl)-1-(2-trimethylsilanyl-ethoxymethyl)-1H-pyrrolo[2,3-b]pyridin-5-yl]-pyridin-3-yl}-acetamide (71 mg, 0.1 mmol) was stirred in dichloromethane/trifluoroacetate acid (1 ml/1 ml) at room temperature for 2 hours. The solvents were removed under vacuum and the crude material was stirred in dichloromethane/ethylenediamine (1 ml/1 ml) for 2 hours at room temperature. The solvents were removed in vacuo and the residue was dissolved in DMSO, filtered and purified by reverse phase HPLC and lyophilized to afford 2-hydroxy-N,N-dimethyl-2-{5-[3-(2-methyl-2H-pyrazol-3-yl)-1H-pyrrolo[2,3-b]pyridin-5-yl]-pyridin-3-yl}-acetamide (33 mg, 61% yield). ¹H NMR (500 MHz, DMSO-d6) δ 2.87 (s, 3H), 3.00 (s, 3H), 3.93 (s, 3H), 7.53 (m, 1H), 7.94 (s, 1H), 8.12 (m, 1H), 8.25 (m, 1H), 8.56 (m, 1H), 8.65 (m, 1H), 8.92 (m, 1H), 12.38 (s, 1H). MS: m/z 377.2 (M+H⁺).

Other compounds were prepared by the above Method 44 are shown in Table 30:

TABLE 30

| Structure | MS: m/z (M + H⁺) | ¹H NMR (500 MHz, DMSO-d6) δ |
|---|---|---|
| (structure) | 391.2 | 1.26 (t, 3H), 2.84 (s, 3H), 3.00 (s, 3H), 4.21 (m, 2H), 5.58 (s, 1H), 5.84 (s, 1H), 7.57 (d, 1H), 7.86 (s, 1H), 8.11 (t, 1H), 8.18 (d, 1H), 8.56 (d, 1H), 8.65 (d, 1H), 8.91 (d, 1H), 12.36 (s, 1H). |
| (structure) | 445.2 | 2.84 (s, 3H), 3.00 (s, 3H), 5.16 (m, 1H), 5.58 (s, 1H), 5.84 (s, 1H), 6.72 (s, 1H), 7.42 (d, 1H), 7.88 (s, 1H), 8.11 (t, 1H), 8.17 (d, 1H), 8.56 (d, 1H), 8.66 (d, 1H), 8.91 (d, 1H), 12.40 (s, 1H). |

TABLE 30-continued

| Structure | MS: m/z (M + H⁺) | ¹H NMR (500 MHz, DMSO-d6) δ |
|---|---|---|
| 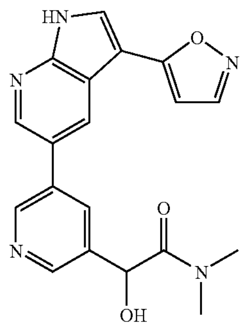 | 364.1 | 2.84 (s, 3H), 3.02 (s, 3H), 5.61 (s, 1H), 5.86 (s, 1H), 7.00 (s, 1H), 8.16 (t, 1H), 8.31 (s, 1H), 8.59 (t, 2H), 8.65 (d, 1H), 8.68 (d, 1H), 8.97 (d, 1H), 12.60 (s, 1H) |
| 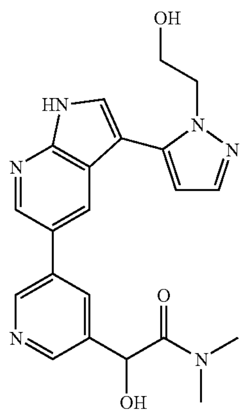 | 407.2 | 2.84 (s, 3H), 3.02 (s, 3H), 3.82 (t, 2H), 4.22 (t, 2H), 5.60 (s, 1H), 6.60 (s, 1H), 7.61 (d, 1H), 7.97 (s, 1H), 8.11 (t, 1H), 8.24 (d, 1H), 8.56 (d, 1H), 8.65 (d, 1H), 8.91 (d, 1H), 12.25 (s, 1H) |
| | 439.1 | 2.84 (s, 3H), 3.02 (s, 3H), 5.69 (s, 1H), 5.84 (s, 1H), 6.78 (d, 1H), 7.36 (m, 1H), 7.41 (m, 4H), 7.44 (s, 1H), 7.70 (d, 1H), 7.80 (d, 1H), 7.88 (t, 1H), 8.52 (d, 1H), 8.67 (d, 1H), 12.0 (s, 1H) |
| | 439.1 | 2.86 (s, 3H), 3.02 (s, 3H), 5.64 (d, 1H), 5.86 (d, 1H), 7.03 (d, 1H), 7.31 (t, 1H), 7.55 (t, 2H), 7.98 (d, 2H), 8.13 (s, 1H), 8.15 (t, 1H), 8.58 (d, 1H), 8.62 (d, 1H), 8.64 (d, 1H), 8.84 (d, 1H), 8.94 (d, 1H), 12.16 (s, 1H) |

Method 45

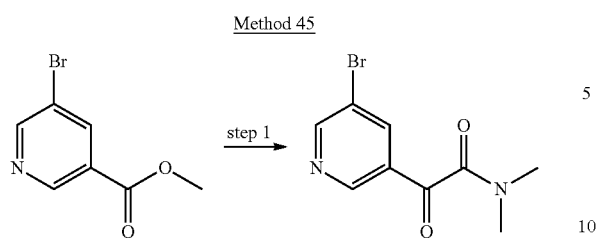

Synthesis 2-(5-bromo-pyridin-3-yl)-N,N-dimethyl-2-oxo-acetamide of was carried out according to Yang. et al., *Organic Letters,* 2002, 1103. This intermediate was then used in a procedure analogous to Method 44 to afford the following compound:

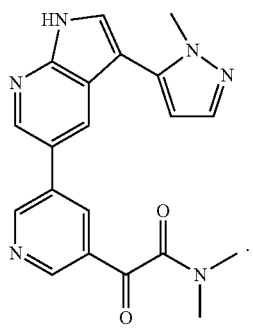

Method 46

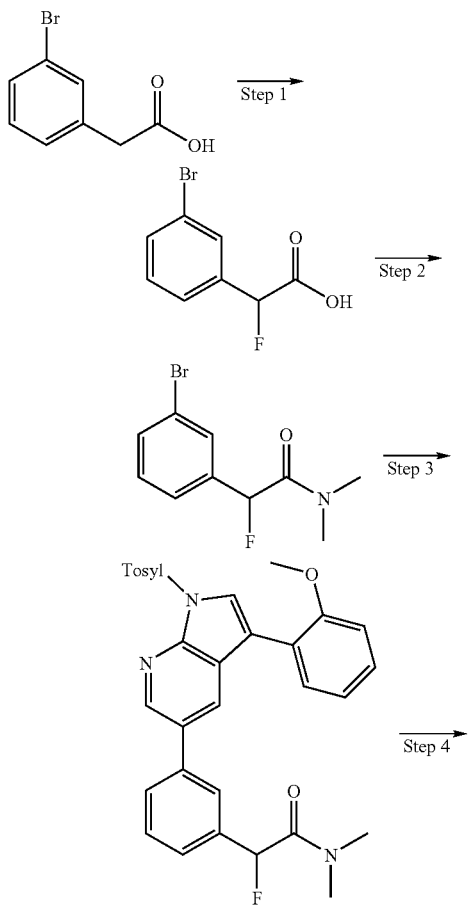

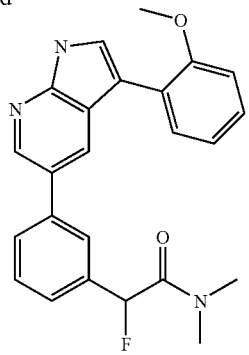

Step 1: Synthesis of (3-bromo-phenyl)-fluoro-acetic acid

A mixture of 3-bromophenyl acetic acid (1 g, 4.6 mmol), t-butyldimethylsilylchloride (1.6 g, 10.7 mmol) and THF (15 ml) were stirred at 0° C. under nitrogen. Lithium diisopropyl amide (5 ml-2M solution in heptane) was added to the mixture drop wise and the reaction was allowed to proceed first at 0° C., then at room temperature over night. The solvent was removed in vacuo and the crude material was redissolved in acetonitrile (20 ml). Selectfluor (2.1 g, 6.0 mmol) in acetonitrile (40 ml) was added drop wise and the reaction was allowed to stir at room temperature overnight. Solvent was removed under vacuum, redissolved in ethyl acetate and extracted with 1N HCl. The organic layer was dried with $Na_2SO_4$, decanted, and concentrated to dryness. Silica chromatography of the crude using a gradient of ethyl acetate and hexane afforded (3-bromo-phenyl)-fluoro-acetic acid (436 mg, 40% yield). $^1$H NMR (500 MHz, DMSO-d6) δ 6.0-6.1 (d, 1H), 7.44 (m, 2H), 7.62 (m, 2H).

Step 2: Synthesis of 2-(3-bromo-phenyl)-2-fluoro-N,N-dimethyl-acetamide

A mixture of (3-bromo-phenyl)-fluoro-acetic acid (436 mg, 1.9 mmol), dimethyl amine (1.9 ml, 3.7 mmol-2M solution in THF), HATU (1.1 g, 2.8 mmol), DIEA (0.7 ml, 3.7 mmol) in DMF were stirred at room temperature overnight. The reaction was diluted with ethyl acetate, washed with 1N HCl, saturated $Na_2HCO_3$, brine, dried with $Na_2SO_4$, decanted, and concentrated to dryness. Silica chromatography of the crude using a gradient of ethyl acetate and hexane afforded 2-(3-bromo-phenyl)-2-fluoro-N,N-dimethyl-acetamide (212 mg, 44% yield). $^1$H NMR (500 MHz, DMSO-d6) δ 2.86 (d, 6H), 6.40-6.44 (d, 1H), 7.41 (m, 1H), 7.45 (d, 1H), 7.642 (m, 2H). MS: m/z 261.1 (M+H$^+$).

Step 3: Synthesis of 2-fluoro-2-{3-[3-(2-methoxy-phenyl-1-(toluene-4-sulfonyl)-1H-pyrrolo[2,3-b]pyridin-5-yl]-phenyl}-N,N-dimethyl-acetamide A mixture of -(3-bromo-phenyl)-2-fluoro-N,N-dimethyl-acetamide (103 mg, 0.4 mmol), 3-(2-methoxy-phenyl)-5-(4,4,5,5-tetramethyl-[1,3,2]dioxaborolan-2-yl)-1-(toluene-4- sulfonyl)-1H-pyrrolo[2,3-b]pyridine (200 mg, 0.4 mmol), and dichloro[1,1'-bis(diphenylphosphino)ferrocene]palladium(II) dichloromethane adduct (15 mg, 0.02 mmol) in THF/Acetonitrile/saturated NaHCO$_3$ (5 ml/5 ml/5 ml) was stirred at 100° C. in a microwave for 20 minutes. The mixture was allowed to cool down to room temperature and then extracted with ethyl acetate (2×). The combined organic layers were extracted with brine, dried with Na$_2$SO$_4$, decanted, and concentrated to dryness. Silica chromatography of the crude using a gradient of ethyl acetate and hexane afforded 2-fluoro-2-{3-[3-(2-methoxy-phenyl-1-(toluene-4-sulfonyl)-1H-pyrrolo[2,3-b]pyridin-5-yl]-phenyl}-N,N-dimethyl-acetamide (119 mg, 54% yield). $^1$H NMR (500 MHz, DMSO-d6) δ 2.38 (s, 3H), 2.84 (d, 6H), 3.82 (s, 3H), 6.4-6.5 (d, 1H), 7.08 (t, 1H), 7.20 (d, 1H), 7.4-7.5 (m, 4H), 7.56 (t, 1H), 7.62 (d, 1H), 7.81 (m, 2H), 8.09 (t, 2H), 8.12 (d, 1H), 8.69 (d, 1H). MS: m/z 558.1 (M+H$^+$).

Step 4: Synthesis of 2-fluoro-2-{3-[3-(2-methoxy-phenyl)-1H-pyrrolo[2,3-b]pyridin-5-yl]-phenyl}-N,N-dimethyl-acetamide The tosyl group of 2-fluoro-2-{3-[3-(2-methoxy-phenyl-1-(toluene-4-sulfonyl)-1H-pyrrolo[2,3-b]pyridin-5-yl]-phenyl}-N,N-dimethyl-acetamide (119 mg, 0.2 mmol) was removed as described in previous experiment. The crude was purified by reverse phase HPLC, lyophilized afforded 2-fluoro-2-{3-[3-(2-methoxy-phenyl)-1H-pyrrolo[2,3-b]pyridin-5-yl]-phenyl}-N,N-dimethyl-acetamide (30 mg, 35% yield). $^1$H NMR (500 MHz, DMSO-d6) δ 2.85 (d, 6H), 3.82 (s, 3H), 6.42-6.74 (d, 1H), 7.06 (t, 1H), 7.16 (d, 1H), 7.32 (t, 1H), 7.46 (d, 1H), 7.56 (t, 1H), 7.59 (d, 1H), 7.75 (s, 1H), 7.82 (t, 2H), 8.17 (d, 1H), 8.55 (d, 1H), 12.0 (s, 1H). MS: m/z 404.1 (M+H$^+$).

Example 47

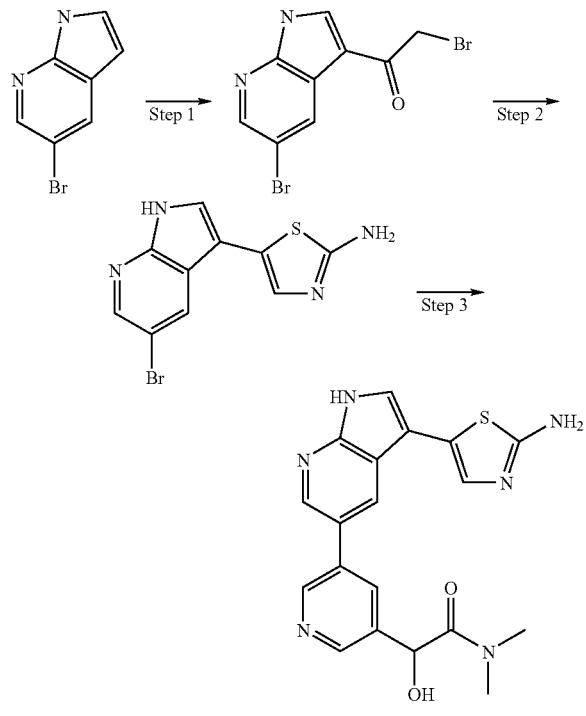

Step 1: Synthesis of 2-bromo-1-(5-bromo-1H-pyrrolo[2,3-b]pyridin-3-yl)-ethanone

5-Bromo-1H-pyrrolo[2,3-b]pyridine (5 g, 25.2 mmol) was added to aluminum chloride (16.8 g, 126.2 mmol) in dichloromethane (200 ml) under nitrogen. The mixture was allowed to stir at room temperature for 1 hour. Then bromoacetyl chloride (11 ml, 126.2 mmol) in dichloromethane was added drop wise and the reaction was allowed to proceed at room temperature overnight. The next day the reaction was cooled to 0° C. and was quenched with methanol (~30 ml) until the reaction turned clear. The reaction was concentrated under vacuum and resuspended in water (300 ml). The pH was adjusted to 7 with 7N sodium hydroxide solution and then extracted with ethyl acetate (300 ml×3). The combined organic layers were extracted with saturated sodium potassium tartrate, brine, dried with Na$_2$SO$_4$. Silica chromatography of the crude using a gradient of ethyl acetate and hexane afforded 2-bromo-1-(5-bromo-1H-pyrrolo[2,3-b]pyridin-3-yl)-ethanone (7.4 g, 92% yield). $^1$H NMR (500 MHz, DMSO-d6) δ 4.76 (s, 2H), 8.45 (s, 1H), 8.61 (s, 1H), 8.75 (s, 1H), 12.98 (s, 1H). MS: m/z 318.8 (M+H$^+$).

Step 2: Synthesis of 5-(5-bromo-1H-pyrrolo[2,3-b]pyridin-3-yl)-thiazol-2-ylamine A mixture of 2-bromo-1-(5-bromo-1H-pyrrolo[2,3-b]pyridin-3-yl)-ethanone (0.5 g, 1.6 mmol), thiourea (180 mg, 2.4 mmol) in ethanol (15 ml) were stirred at 100° C. under nitrogen overnight. Solvent was removed and the crude was titurated with DCM, filtered, and washed with more DCM afforded 5-(5-bromo-1H-pyrrolo[2,3-b]pyridin-3-yl)-thiazol-2-ylamine (114 mg, 24% yield). $^1$H NMR (500 MHz, DMSO-d6) δ 7.21 (s, 1H), 8.15 (s, 1H), 8.42 (s, 1H), 8.58 (s, 1H), 8.98 (s, 2H), 12.42 (s, 1H). MS: m/z 295.0 (M+H$^+$).

Step 3: Synthesis of 2-{5-[3-(2-amino-thiazol-5-yl)-1H-pyrrolo[2,3-b]pyridin-5-yl]-pyridine-3-yl}-2-hydroxy-N,N-dimethyl-acetamide A mixture of 5-(5-bromo-1H-pyrrolo[2,3-b]pyridin-3-yl)-thiazol-2-ylamine (114 mg, 0.4 mmol), 2-hydroxy-N,N-dimethyl-2-pyridin-3-yl-acetamide-5-boronic acid (173 mg, 0.8 mmol), dichloro[1,1'-bis(diphenylphosphino)ferrocene]palladium(II) dichloromethane adduct (28 mg, 0.04 mmol), Na$_2$CO$_3$ (1.2 ml of 2M solution) in acetonitrile (2 ml) were stirred at 120° C. in a microwave for 30 minutes. The solvent was removed and the crude material was resuspended in DMSO, filtered and purified by reverse phase HPLC and lyophilized to afford 2-{5-[3-(2-amino-thiazol-5-yl)-1H-pyrrolo[2,3-b]pyridin-5-yl]-pyridine-3-yl}-2-hydroxy-N,N-dimethyl-acetamide (6 mg, 4% yield). $^1$H NMR (500 MHz, DMSO-d6) δ 2.84 (s, 3H), 3.01 (s, 3H), 5.60 (s, 1H), 6.60 (s, 1H), 7.01 (s, 2H), 7.80 (s, 1H), 8.12 (t, 1H), 8.56 (m, 2H), 8.65 (d, 1H), 8.92 (d, 1H). MS: m/z 395.0 (M+H$^+$).

Example 48

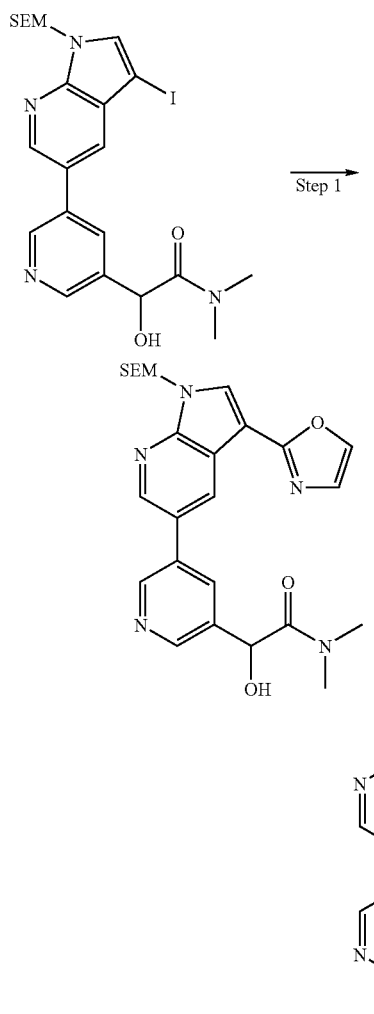

Step 1: Synthesis of 2-hydroxy-N,N-dimethyl-2-{5-[3-oxazol-2-yl-1(2-trimethyl-silanyl-ethoxymethyl)-1H-pyrrolo[2,3-b]pyridin-5-yl]-pyridin-3-yl}-acetamide A mixture of 2-hydroxy-2-{5-[3-iodo-1(2-trimethylsilanyl-ethoxymethyl)-1H-pyrrolo[2,3-b]pyridin-5-yl]-pyridin-3-yl}-N,N-dimethyl-acetamide (50 mg, 0.09 mmol), 2-tri-n-butylstannyloxazole (28 ul, 0.14 mmol), tetrakis(triphenylphosphine)palladium(0) (5 mg, 0.004 mmol), CuI (2 mg, 0.009 mmol) in DMA (1 ml) was stirred at 120° C. in a microwave for 20 minutes. The mixture was allowed to cool down to room temperature and then extracted with ethyl acetate (2X). The combined organic layers were extracted with brine, dried with Na₂SO₄, decanted, and concentrated to dryness. Silica gel chromatography of the crude using a gradient of ethyl acetate and hexane afforded 2-hydroxy-N,N-dimethyl-2-{5-[3-oxazol-2-yl-1(2-trimethylsilanyl-ethoxymethyl)-1H-pyrrolo[2,3-b]pyridin-5-yl]-pyridin-3-yl}-acetamide (10 mg, 22% yield).

Step 2: Synthesis of 2-hydroxy-N,N-dimethyl-2-{5-[3-oxazol-2-yl-1H-pyrrolo[2,3-b]pyridin-5-yl]-pyridin-3-yl}-acetamide 2-Hydroxy-N,N-dimethyl-2-{5-[3-oxazol-2-yl-1(2-trimethylsilanyl-ethoxymethyl)-1H-pyrrolo[2,3-b]pyridin-5-yl]-pyridin-3-yl}-acetamide (10 mg, 0.02 mmol) was stirred in dichloromethane/trifluoroacetate acid (1 ml/1 ml) at room temperature for 2 hours. The solvents were removed under vacuum and the crude was stirred in dichloromethane/ethylenediamine (1 ml/1 ml) for 2 hours at room temperature. Again the solvents was removed under vacuum and the crude was dissolved in DMSO, filtered and purified by reverse phase HPLC, lyophilized afforded 2-hydroxy-N,N-dimethyl-2-{5-[3-oxazol-2-yl-1H-pyrrolo[2,3-b]pyridin-5-yl]-pyridin-3-yl}-acetamide (2 mg, 31% yield). $^1$H NMR (500 MHz, DMSO-d6) δ 2.81 (s, 3H), 2.96 (s, 3H), 5.58 (s, 1H), 6.22 (s, 1H), 7.28 (s, 1H), 8.04 (t, 1H), 8.76 (s, 1H), 8.22 (s, 1H), 8.52 (d, 1H), 8.62 (s, 2H0, 8.83 (d, 1H). MS: m/z 364.0 (M+H$^+$).

Example 49

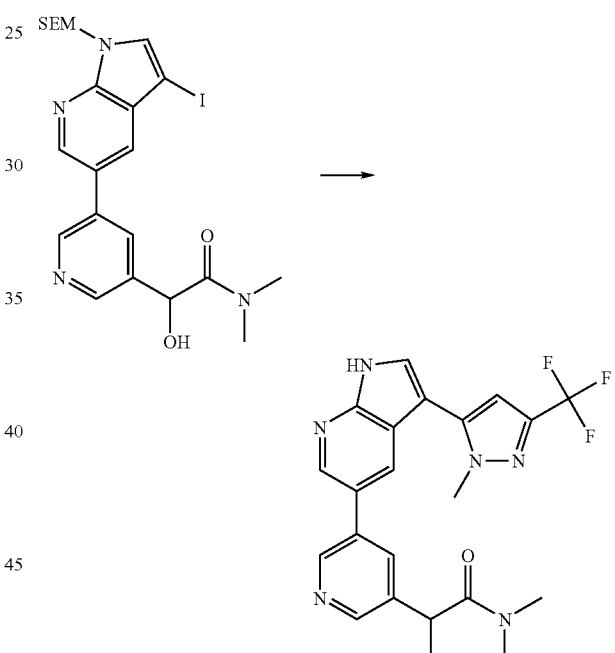

Synthesis of 2-hydroxy-N,N-dimethyl-2-{5-[3-(2-methyl-5-trifluoromethyl-2H-pyrazol-3-yl)-1H-pyrrolo[2,3-b]pyridine-5-yl]-pyridin-3-yl}-acetamide A mixture of 2-hydroxy-2-{5-[3-iodo-1(2-trimethylsilanyl-ethoxymethyl)-1H-pyrrolo[2,3-b]pyridin-5-yl]-pyridin-3-yl}-N,N-dimethyl-acetamide (194 mg, 0.4 mmol), 1-methyl-5(tributylstannyl)3-(trifluoromethyl)-1H-pyrazole (186 mg, 0.4 mmol), CuI (7 mg, 0.04 mmol), CsF (107 mg, 0.7 mmol), dichlorobis(benzonitrile)palladium (II) (7 mg, 0.02 mmol), tri-t-butylphosphine 10% w/v in hexanes (10 μl, 0.04 mmol) and DMF were stirred at 100° C. under nitrogen overnight. The mixture was allowed to cool to room temperature and then extracted with ethyl acetate (2X). The combined organic layers were extracted with brine, dried with Na₂SO₄, decanted, and concentrated to dryness. The material was purified using silica gel chromatography and a gradient of ethyl acetate and hexane. The purified product was treated with dichloromethane/trifluoroacetate acid (1 ml/1 ml) at room temperature for 2 hours. The solvents were removed under vacuum and the crude was stirred in dichloromethane/ethylenediamine (1 ml/1 ml) for 2 hours at room temperature. Again the solvents was removed under vacuum and the crude was dissolved in DMSO, filtered and purified by reverse phase HPLC, lyophilized afforded 2-hydroxy-N,N-dimethyl-2-{5-[3-(2-methyl-5-trifluoromethyl-2H-pyrazol-3-yl)-1H-pyrrolo[2,3-b]pyridine-5-yl]-pyridin-3-yl}-acetamide (13.2 mg, 8% yield). $^1$H NMR (500 MHz, DMSO-d6) δ 2.80 (s, 3H), 2.94 (s, 3H), 5.56 (s, 1H), 5.80 (s, 1H), 7.08 (s, 1H), 7.98 (s, 1H), 8.04 (t, 1H), 8.26 (d, 1H), 8.50 (d, 1H), 8.58 (d, 1H), 8.88 (d, 1H), 12.40 (s, 1H). MS: m/z 445.0 (M+H$^+$).

Example 2

Bioassays

Kinase assays known to those of skill in the art may be used to assay the inhibitory activities of the compounds and compositions of the present invention. Kinase assays include, but are not limited to, the following examples.

Although the first of these examples uses the kinase domain of a mutant form of Abl T315I ("Abl T315I KD"), the kinase assays may use various forms of mutant and wild type enzymes, including, for example, the entire protein, the kinase domain, or a portion thereof (e.g. Abl Y393F). The kinases used in the assays may also be of varying phosphorylation states. In the c-Abl example, a mutant kinase at a zero phosphorylation state was used. c-Abl Pyruvate Kinase/Lactate Dehydrogenase Coupled Enzyme Assay In the c-Abl Pyruvate Kinase (PK)/Lactate Dehydrogenase (LDH) Coupled Assay the protein kinase dependant phosphorylation of a substrate peptide was coupled to the oxidation of NADH. The oxidation of NADH to NAD+ was detected by monitoring a decrease in absorbance at 340 nm.

Materials: Abl substrate peptide=EAIYAAPFAKKK (SEQ ID NO: 1)—OH (Biopeptide, San Diego, Calif.); pNADH (Sigma Cat#N-8129, FW=709.4); 2M MgC12; 1M HEPES buffer, pH 7.5; Phosphoenolpyruvate (PEP) (Sigma Cat#P-7002, FW=234); Lactate dehydrogenase (LDH) (Worthington Biochemical Cat#2756); Pyruvate Kinase (PK) (Sigma Cat#P-9136); ATP (Sigma Cat#A-3377, FW=551); Greiner 384-well UV star plate; and purified and unphosphorylated T315I Abl kinase domain.

Stock Solutions: 10 mM NADH (7.09 mg/ml in miliQH$_2$O) made fresh daily; 10 mM Abl substrate peptide (13.4 mg/ml in miliQH$_2$O) stored at −20° C.; 100 mM HEPES buffer, pH 7.5 (5 ml 1M stock+45 ml miliQH$_2$O); 100 mM MgCl$_2$ (5 ml 2M MgCl$_2$+95 ml dH$_2$O); 100 MM PEP (23.4 mg/ml in dH$_2$O) stored at −20° C.; 10 mM ATP (5.51 mg/ml in dH$_2$O) stored at −20° C. (diluted 50 µl into total of 10 ml miliQH$_2$O daily=50 µM ATP working stock); 1000 U/ml PK (U/mg varies with lot) flash-frozen under liquid N$_2$ and stored at −80° C.; and 1000 U/ml LDH (U/mg varies with lot) flash-frozen under liquid N$_2$ and stored at −80° C.

Standard Assay Setup for 384-well format (50 µl reaction): 300 µM NADH; 10 mM MgCl$_2$; 2 mM PEP; 45U/ml PK; 60 U/ml LDH; 200 µM Abl substrate peptide; 2.5 µl test compound (in DMSO); 2 µg/ml Abl kinase domain; 10 µM ATP; 100 mM HEPES buffer. Positive controls contained DMSO with no test compound. Negative controls contained 5 µl of 0.5M EDTA (50 mM in the assay). The dephosphorylated form of the c-Abl T315I mutant was used in the biochemical screening assays. The kinase reaction was initiated at time t=0 by the addition of ATP.

Activity was measured by following the time-dependent loss of NADH by absorbance spectroscopy at 340 nm. The linear portion of the resulting progress curve was then analyzed by linear regression to get the activity in absorbance units/time, reported as the slope of that best fit line (moles/unit time can be calculated from using molar extinction coefficient for NADH at 340 nm, 6250M$^{-1}$ cm$^{-1}$).

Data was evaluated using the equation: $Z'=1-[3*(\sigma_++\sigma_-)/|\mu_+-\mu_-|]$(Zhang, et al., 1999 J Biomol Screening 4(2) 67-73), where µ denotes the mean and σ the standard deviation. The subscript designates positive or negative controls. The Z' score for a robust screening assay should be ≧0.50. The typical threshold=$\mu_+-3*\sigma_+$. Any value that falls below the threshold was designated a "hit".

Dose response was analyzed using the equation: $y=min+\{(max-min)/(1+10^{[compound]-logIC50})\}$, where y is the observed initial slope, max=the slope in the absence of inhibitor, min=the slope at infinite inhibitor, and the IC$_{50}$ is the [compound] that corresponds to ½ the total observed amplitude (Amplitude=max−min).

To measure modulation, activation, or inhibition of Abl KD, a test compound was added to the assay at a range of concentrations. Inhibitors may inhibit Abl KD activity at an IC$_{50}$ in the micromolar range, the nanomolar range, or, for example, in the subnanomolar range.

Additional Kinase Assays

In addition to the c-Abl PK/LDH coupled assay (above), homogeneous luminescence-based inhibitor screening assays were developed for c-Abl, MET, AurA, and PDK1 kinases (among others). Each of these assays made use of an ATP depletion assay (Kinase-Glo™, Promega Corporation, Madison, Wis.) to quantitate kinase activity. The Kinase-Glo™ format uses a thermostable luciferase to generate luminescent signal from ATP remaining in solution following the kinase reaction. The luminescent signal is inversely correlated with the amount of kinase activity.

cAbl Luminescence-Based Enzyme Assay

Materials: Abl substrate peptide=EAIYAAPFAKKK (SEQ ID NO: 1)—OH (Biopeptide, San Diego, Calif.), ATP (Sigma Cat#A-3377, FW=551), HEPES buffer, pH 7.5, Bovine serum albumin (BSA) (Roche 92423420), MgC12, Staurosporine (*Streptomyces* sp. Sigma Cat#85660-1MG), white Costar 384-well flat-bottom plate (VWR Cat#29444-088), Abl kinase (see below), Kinase-Glo™ (Promega Cat#V6712).

Stock Solutions: 10 mM Abl substrate peptide (13.4 mg/ml in miliQH$_2$O) stored at −20° C.; 100 mM HEPES buffer, pH 7.5 (5 ml 1M stock+45 ml miliQH$_2$O); 10 mM ATP (5.51 mg/ml in dH$_2$O) stored at −20° C. (diluted 50 µl into total of 10 ml miliQH$_2$O daily=50 µM ATP working stock); 1% BSA (1 g BSA in 100 ml 0.1 M HEPES, pH 7.5, stored at −20° C.), 100 mM MgCl$_2$; 200 µM Staurosporine, 2× Kinase-Glo™ reagent (made fresh or stored at −20° C.).

Standard Assay Setup for 384-well format (20 µl kinase reaction, 40 µl detection reaction): 10 mM MgCl$_2$; 100 µM Abl substrate peptide; 0.1% BSA; 1 µl test compound (in DMSO); 0.4 µg/ml Abl kinase domain; 10 µM ATP; 100 mM HEPES buffer. Positive controls contained DMSO with no test compound. Negative controls contained 10 µM staurosporine. The kinase reactions were initiated at time t=0 by the addition of ATP. Kinase reactions were incubated at 21° C. for 30 min, then 20 µl of Kinase-Glo™ reagent were added to each well to quench the kinase reaction and initiate the luminescence reaction. After a 20 min incubation at 21° C., the luminescence was detected in a plate-reading luminometer.

MET Luminescence-Based Enzyme Assay

Materials: Poly Glu-Tyr (4:1) substrate (Sigma Cat#P-0275), ATP (Sigma Cat#A-3377, FW=551), HEPES buffer, pH 7.5, Bovine serum albumin (BSA) (Roche 92423420), MgCl$_2$, Staurosporine (*Streptomyces* sp. Sigma Cat#85660-1MG), white Costar 384-well flat-bottom plate (VWR Cat#29444-088). MET kinase (see below), Kinase-Glo™ (Promega Cat#V6712).

Stock Solutions: 10 mg/ml poly Glu-Tyr in water, stored at −20° C.; 100 mM HEPES buffer, pH 7.5 (5 ml 1M stock+45 ml miliQH$_2$O); 10 mM ATP (5.51 mg/ml in dH$_2$O) stored at −20° C. (diluted 50 µl into total of 10 ml miliQH$_2$O daily=50 µM ATP working stock); 1% BSA (1 g BSA in 100 ml 0.1M HEPES, pH 7.5, stored at −20° C.), 100 mM MgCl$_2$; 200 µM Staurosporine, 2× Kinase-Glo™ reagent (made fresh or stored at −20° C.).

Standard Assay Setup for 384-well format (20 µl kinase reaction, 40 µl detection reaction): 10 mM MgCl$_2$; 0.3 mg/ml poly Glu-Tyr; 0.1% BSA; 1 µl test compound (in DMSO); 0.4 µg/ml MET kinase; 10 µM ATP; 100 mM HEPES buffer. Positive controls contained DMSO with no test compound. Negative controls contained 10 µM staurosporine. The kinase reactions were initiated at time t=0 by the addition of ATP. Kinase reactions were incubated at 21° C. for 60 min, then 20 µl of Kinase-Glo™ reagent were added to each well to quench the kinase reaction and initiate the luminescence reaction. After a 20 min incubation at 21° C., the luminescence was detected in a plate-reading luminometer.

AurA Luminescence-Based Enzyme Assay

Materials: Kemptide peptide substrate=LRRASLG (SEQ ID NO: 2) (Biopeptide, San Diego, Calif.), ATP (Sigma Cat#A-3377, FW=551), HEPES buffer, pH 7.5, 10% Brij 35 (Calbiochem Cat#203728), MgCl2, Staurosporine (*Streptomyces* sp. Sigma Cat#85660-1MG), white Costar 384-well flat-bottom plate (VWR Cat#29444-088), Autophosphorylated AurA kinase (see below), Kinase-Glo™ (Promega Cat#V6712).

Stock Solutions: 10 mM Kemptide peptide (7.72 mg/ml in water), stored at −20° C.; 100 mM HEPES buffer+0.015% Brij 35, pH 7.5 (5 ml 1M HEPES stock+75 µL 10% Brij 35+45 ml miliQH$_2$O); 10 mM ATP (5.51 mg/ml in dH$_2$O) stored at −20° C. (diluted 50 µl into total of 10 ml miliQH$_2$O daily=50 µM ATP working stock); 100 mM MgCl$_2$; 200 µM Staurosporine, 2× Kinase-Glo™ reagent (made fresh or stored at −20° C.).

AurA Autophosphorylation Reaction: ATP and MgCl$_2$ were added to 1-5 mg/ml AurA at final concentrations of 10 mM and 100 mM, respectively. The autophosphorylation reaction was incubated at 21° C. for 2-3 h. The reaction was stopped by the addition of EDTA to a final concentration of 50 mM, and samples were flash frozen with liquid N$_2$ and stored at −80° C.

Standard Assay Setup for 384-well format (20 µl kinase reaction, 40 µl detection reaction): 10 mM MgCl$_2$; 0.2 mM Kemptide peptide; 1 µl test compound (in DMSO); 0.3 µg/ml Autophosphorylated AurA kinase; 10 µM ATP; 100 mM HEPES+0.015% Brij buffer. Positive controls contained DMSO with no test compound. Negative controls contained 5 µM staurosporine. The kinase reactions were initiated at time t=0 by the addition of ATP. Kinase reactions were incubated at 21° C. for 45 min, then 20 µl of Kinase-Glo™ reagent were added to each well to quench the kinase reaction and initiate the luminescence reaction. After a 20 min incubation at 21° C., the luminescence was detected in a plate-reading luminometer.

PDK1 Luminescence-Based Enzyme Assay

Materials: PDKtide peptide substrate= KTFCGTPEYLA-PEVRREPRILSEEEQEMFRDFDYIADWC (SEQ ID NO: 3) (Upstate Cat#12-401), ATP (Sigma Cat#A-3377, FW=551), HEPES buffer, pH 7.5, 10% Brij 35 (Calbiochem Cat#203728), MgC12, Staurosporine (*Streptomyces* sp. Sigma Cat#85660-1MG), white Costar 384 well flat-bottom plate (VWR Cat#29444-088), PDK1 kinase (see below), Kinase-Glo™ (Promega Cat#V6712).

Stock Solutions: 1 mM PDKtide substrate (1 mg in 200 µl, as supplied by Upstate), stored at −20° C.; 100 mM HEPES buffer, pH 7.5 (5 ml 1M HEPES stock+45 ml miliQH$_2$O); 10 mM ATP (5.51 mg/ml in dH$_2$O) stored at −20° C. (diluted 25 µl into total of 10 ml miliQH$_2$O daily=25 µM ATP working stock); 100 mM MgCl$_2$; 10% Brij 35 stored at 2-8° C.; 200 µM Staurosporine, 2× Kinase-Glo™ reagent (made fresh or stored at −20° C.).

Standard Assay Setup for 384-well format (20 µl kinase reaction, 40 µl detection reaction): 10 mM MgCl$_2$; 0.01 mM PDKtide; 1 µl test compound (in DMSO); 0.1 µg/ml PDK1 kinase; 5 µM ATP; 10 mM MgCl$_2$; 100 mM HEPES+0.01% Brij buffer. Positive controls contained DMSO with no test compound. Negative controls contained 10 µM staurosporine. The kinase reactions were initiated at time t=0 by the addition of ATP. Kinase reactions were incubated at 21° C. for 40 min, then 20 µl of Kinase-Glo™ reagent were added to each well to quench the kinase reaction and initiate the luminescence reaction. After a 20 min incubation at 21° C., the luminescence was detected in a plate-reading luminometer.

Preparation of Co-Expression Plasmiid

A lambda phosphatase co-expression plasmid was constructed as follows.

An open-reading frame for Aurora kinase was amplified from a *Homo sapiens* (human) HepG2 cDNA library (ATCC HB-8065) by the polymerase chain reaction (PCR) using the following primers:

```
Forward primer:
TCAAAAAAGAGGCAGTGGGCTTTG           (SEQ ID NO: 4)

Reverse primer:
CTGAATTTGCTGTGATCCAGG.             (SEQ ID NO: 5)
```

The PCR product (795 base pairs expected) was gel purified as follows. The PCR product was purified by electrophoresis on a 1% agarose gel in TAE buffer and the appropriate size band was excised from the gel and eluted using a standard gel extraction kit. The eluted DNA was ligated for 5 minutes at room temperature with topoisomerase into pSB2-TOPO. The vector pSB2-TOPO is a topoisomerase-activated, modified version of pET26b (Novagen, Madison, Wis.) wherein the following sequence has been inserted into the NdeI site: CATAATGGGCCATCATCATCATCAT-CACGGT GGTCATATGTCCCTT (SEQ ID NO: 6) and the following sequence inserted into the BamHI site: AAGGGG-GATCCTAAACTGCAGAGATCC (SEQ ID NO: 7). The sequence of the resulting plasmid, from the Shine-Dalgarno sequence through the "original" NdeI site, the stop site and the "original" BamHI site is as follows: AAGGAG-GAGATATACATAATGGGCCATCATCAT-CATCATCACGGTGGTCATATGTCCCT T (SEQ ID NO: 8) [ORF] AAGGGGGATCCTAAACTGCAGAGATCC (SEQ ID NO: 9). The Aurora kinase expressed using this vector has 14 amino acids added to the N-terminus (MetGly-HisHisHisHisHisHisGlyGlyHisMetSerLeu) (SEQ ID NO: 10) and four amino acids added to the C-terminus (GluGlyGlySer) (SEQ ID NO: 11).

The phosphatase co-expression plasmid was then created by inserting the phosphatase gene from lambda bacteriophage into the above plasmid (Matsui T, et al., Biochem. Biophys. Res. Commun., 2001, 284:798-807). The phosphatase gene was amplified using PCR from template lambda bacteriophage DNA (HinD111 digest, New England Biolabs) using the following oligonucleotide primers:

```
Forward primer (PPfor):
GCAGAGATCCGAATTCGAGCTC            (SEQ ID NO: 12)

CGTCGACGGATGGAGTGAAAGAGATGCGC

Reverse primer (PPrev):
GGTGGTGGTGCTCGAGTGCGGCCGCAA       (SEQ ID NO: 13)

GCTTTCATCATGCGCCTTCTCCCTGTAC.
```

The PCR product (744 base pairs expected) was gel purified. The purified DNA and non-co-expression plasmid DNA were then digested with SacI and XhoI restriction enzymes. Both the digested plasmid and PCR product were then gel purified and ligated together for 8 h at 16° C. with T4 DNA ligase and transformed into Top10 cells using standard procedures. The presence of the phosphatase gene in the co-expression plasmid was confirmed by sequencing. For standard molecular biology protocols followed here, see also, for example, the techniques described in Sambrook et al., Molecular Cloning: A Laboratory Manual, Cold Spring Harbor Laboratory, NY, 2001, and Ausubel et al., Current Protocols in Molecular Biology, Greene Publishing Associates and Wiley Interscience, NY, 1989.

This co-expression plasmid contains both the Aurora kinase and lambda phosphatase genes under control of the lac promoter, each with its own ribosome binding site. By cloning the phosphatase into the middle of the multiple cloning site, downstream of the target gene, convenient restriction sites are available for subcloning the phosphatase into other plasmids. These sites include SacI, SalI and EcoRI between the kinase and phosphatase and HinDIII, NotI and XhoI downstream of the phosphatase.

Protein Kinase Expression

An open-reading frame for c-Abl was amplified from a *Mus musculus* (mouse) cDNA library prepared from freshly harvested mouse liver using a commercially available kit (invitrogen) by PCR using the following primers:

```
Forward primer:
GACAAGTGGGAAATGGAGC               (SEQ ID NO: 14)

Reverse primer:
CGCCTCGTTTCCCCAGCTC.              (SEQ ID NO: 15)
```

The PCR product (846 base pairs expected) was purified from the PCR reaction mixture using a PCR cleanup kit (Qiagen). The purified DNA was ligated for 5 minutes at room temperature with topoisomerase into pSGX3-TOPO. The vector pSGX3-TOPO is a topoisomerase-activated, modified version of pET26b (Novagen, Madison, Wis.) wherein the following sequence has been inserted into the NdeI site: CATATGTCCCTT (SEQ ID NO: 16) and the following sequence inserted into the BamHI site: AAGGGCATCATCACCATCACCACTGATCC (SEQ ID NO: 17). The sequence of the resulting plasmid, from the Shine-Dalgarno sequence through the stop site and the BamHI, site is as follows: AAGGAGGA GATATACATATGTCCCTT (SEQ ID NO: 18) [ORF]AAGGGCATCAT CACCA TGACCACTGATCC (SEQ ID NO: 19). The c-Abl expressed using this vector had three amino acids added to its N-terminus (Met Ser Leu) and 8 amino acids added to its C-terminus (GluGlyHis HisHisHisHisHis) (SEQ ID NO: 20).

A c-Abl/phosphatase co expression plasmid was then created by subcloning the phosphatase from the Aurora co-expression plasmid of Example 1 into the above plasmid. Both the Aurora co-expression plasmid and the Abl non-co-expression plasmid were digested 3 hrs with restriction enzymes EcoRI and NotI. The DNA fragments were gel purified and the phosphatase gene from the Aurora plasmid was ligated with the digested c-Abl plasmid for 8 h at 16° C. and transformed into Top10 cells. The presence of the phosphatase gene in the resulting construct was confirmed by restriction digestion analysis.

This plasmid codes for c-Abl and lambda phosphatase co expression. It has the additional advantage of two unique restriction sites, XbaI and NdeI, upstream of the target gene that can be used for subcloning of other target proteins into this phosphatase co-expressing plasmid.

The plasmid for Abl T315I was prepared by modifying the Abl plasmid using the Quick Change mutagenesis kit (Stratagene) with the manufacturer's suggested procedure and the following oligonucleotides:

```
Mm05582dS4                        (SEQ ID NO: 21)
5'-CCACCATTCTACATAATCATTGAGTTCATGACCTATGGG-3'

Mm05582dA4                        (SEQ ID NO: 22)
5'-CCCATAGGTCATGAACTCAATGATTATGTAGAATGGTGG-3'.
```

Protein from the phosphatase co-expression plasmids was purified as follows. The non-co-expression plasmid was transformed into chemically competent BL21(DE3)Codon+ RIL (Stratagene) cells and the co-expression plasmid was transformed into BL21(DE3) pSA0145 (a strain that expresses the lytic genes of lambda phage and lyses upon freezing and thawing (Crabtree S, Cronan J E Jr. J Bacteriol April 1984; 158(1):354-6)) and plated onto petri dishes containing LB agar with kanamycin. Isolated single colonies were grown to mid-log phase and stored at −80° C. in LB containing 15% glycerol. This glycerol stock was streaked on LB agar plates with kanamycin and a single colony was used to inoculate 10 ml cultures of LB with kanamycin and chloramphenicol, which was incubated at 30° C. overnight with shaking. This culture was used to inoculate a 2 L flask containing 500 ml of LB with kanamycin and chloramphenicol, which was grown to mid-log phase at 37° C. and induced by the addition of IPTG to 0.5 mM final concentration. After induction flasks were incubated at 21° C. for 18 h with shaking.

The c-Abl T315I KD (kinase domain) was purified as follows. Cells were collected by centrifugation, lysed in diluted cracking buffer (50 mM Tris HCl, pH 7.5, 500 mM KCl, 0.1% Tween 20, 20 mM Imidazole, with sonication, and centrifuged to remove cell debris. The soluble fraction was purified over an IMAC column charged with nickel (Pharmacia, Uppsala, Sweden), and eluted under native conditions with a gradient of 20 mM to 500 mM imidazole in 50 mM Tris, pH 7.8, 500 mM NaCl, 10 mM methionine, 10% glycerol. The protein was then further purified by gel filtration using a Superdex 75 preparative grade column equilibrated in GF5 buffer (10 mM HEPES, pH 7.5, 10 mM methionine, 500 mM NaCl, 5 mM DTT, and 10% glycerol). Fractions containing the purified c-Abl T315I KD kinase domain were pooled. The protein obtained was 98% pure as judged by electrophoresis on SDS polyacrylamide gels. Mass spectroscopic analysis of the purified protein showed that it was predominantly singly phosphorylated. The protein was then dephosphorylated with Shrimp Alkaline Phosphatase (MBI Fermentas, Burlington, Canada) under the following conditions: 100U Shrimp Alkaline Phosphatase/mg of c-Abl T315I KD, 100 mM $MgCl_2$, and 250 mM additional NaCl. The reaction was run overnight at 23° C. The protein was determined to be unphosphorylated by Mass spectroscopic analysis. Any precipitate was spun out and the soluble fraction was separated from reactants by gel filtration using a Superdex 75 preparative grade column equilibrated in GF4 buffer (10 mM HEPES, pH 7.5, 10 mM methionine, 150 mM NaCl, 5 mM DTT, and 10% glycerol).

Purification of Met

The cell pellets produced from half of a 12 L Sf9 insect cell culture expressing the kinase domain of human Met were resuspended in a buffer containing 50 mM Tris-HCl pH 7.7 and 250 mM NaCl, in a volume of approximately 40 ml per 1 L of original culture. One tablet of Roche Complete, EDTA-free protease inhibitor cocktail (Cat#1873580) was added per 1 L of original culture. The suspension was stirred for 1 hour at 4° C. Debris was removed by centrifugation for 30 minutes at 39,800×g at 4° C. The supernatant was decanted into a 500 ml beaker and 10 ml of 50% slurry of Qiagen Ni-NTA Agarose (Cat#30250) that had been pre-equilibrated in 50 mM Tris-HCl pH 7.8, 50 mM NaCl, 10% Glycerol, 10 mM Imidazole, and 10 mM Methionine, were added and stirred for 30 minutes at 4° C. The sample was then poured into a drip column at 4° C. and washed with 10 column volumes of 50 mM Tris-HCl pH 7.8, 500 mM NaCl, 10% Glycerol, 10 mM Imidazole, and 10 mM Methionine. The protein was eluted using a step gradient with two column volumes each of the same buffer containing 50 mM, 200 mM, and 500 mM Imidazole, sequentially. The 6× Histidine tag was cleaved overnight using 40 units of TEV protease (Invitrogen Cat#10127017) per 1 mg of protein while dialyzing in 50 mM Tris-HCl pH 7.8, 500 mM NaCl, 10% Glycerol, 10 mM Imidazole, and 10 mM Methionine at 4° C. The 6× Histidine tag was removed by passing the sample over a Pharmacia 5 ml IMAC column (Cat#17-0409-01) charged with Nickel and equilibrated in 50 mM Tris-HCl pH 7.8, 500 mM NaCl, 10% Glycerol, 10 mM Imidazole, and 10 mM Methionine. The cleaved protein bound to the Nickel column at a low affinity and was eluted with a step gradient. The step gradient was run with 15% and then 80% of the B-side (A-side=50 mM Tris-HCl pH 7.8, 500 mM NaCl, 10% Glycerol, 10 mM Imidazole, and 10 mM Methionine; B-side=50 mM Tris-HCl pH 7.8, 500 mM NaCl, 10% Glycerol, 500 mM Imidazole, and 10 mM Methionine) for 4 column volumes each. The Met protein eluted in the first step (15%), whereas the non-cleaved Met and the cleaved Histidine tag eluted in the 80% fractions. The 15% fractions were pooled after SDS-PAGE gel analysis confirmed the presence of cleaved Met; further purification was done by gel filtration chromatography on an Amersham Biosciences HiLoad 16/60 Superdex 200 prep grade (Cat#17-1069-01) equilibrated in 50 mM Tris-HCl pH 8.5, 150 mM NaCl, 10% Glycerol and 5 mM DTT. The cleanest fractions were combined and concentrated to ~10.4 mg/ml by centrifugation in an Amicon Ultra-15 10,000 Da MWCO centrifugal filter unit (Cat#UFC901024).

Purification of AurA

The Sf9 insect cell pellets (~18 g) produced from 6 L of cultured cells expressing human Aurora-2 were resuspended in 50 mM Na Phosphate pH 8.0, 500 mM NaCl, 10% glycerol, 0.2% n-octyl-β-D-glucopyranoside (BOG) and 3 mM β-Mercaptoethanol (BME). One tablet of Roche Complete, EDTA-free protease inhibitor cocktail (Cat#1873580) and 85 units Benzonase (Novagen Cat#70746-3)) were added per 1 L of original culture. Pellets were resuspended in approximately 50 ml per 1 L of original culture and were then sonicated on ice with two 30-45 sec bursts (100% duty cycle). Debris was removed by centrifugation and the supernatant was passed through a 0.8 μm syringe filter before being loaded onto a 5 ml $Ni^{2+}$ HiTrap column (Pharmacia). The column was washed with 6 column volumes of 50 mM Na Phosphate pH 8.0, 500 mM NaCl, 10% glycerol, 3 mM BME. The protein was eluted using a linear gradient of the same buffer containing 500 nM Imidazole. The eluant (24 ml) was cleaved overnight at 4° C. in a buffer containing 50 mM Na Phosphate pH 8.0, 500 mM NaCl, 10% glycerol, 3 mM BME and 10,000 units of TEV (Invitrogen Cat#10127-017). The protein was passed over a second nickel affinity column as described above; the flow-through was collected. The cleaved protein fractions were combined and concentrated using spin concentrators. Further purification was done by gel filtration chromatography on a S75 sizing column in 50 mM Na Phosphate (pH 8.0), 250 mM NaCl, 1 mM EDTA, 0.1 mM AMP-PNP or ATP buffer, and 5 mM DTT. The cleanest fractions were combined and concentrated to approximately 8-11 mg/ml, and were either flash frozen in liquid nitrogen in 120 μl aliquots and stored at −80° C., or stored at 4° C.

Purification of PDK1

Cell pellets produced from 6 L of Sf9 insect cells expressing human PDK1 were resuspended in a buffer containing 50 mM Tris-HCl pH 7.7 and 250 mM NaCl in a volume of approximately 40 mL per 1 L of original culture. One tablet of Roche Complete, EDTA-free protease inhibitor cocktail (Cat#1873580) and 85 units Benzonase (Novagen Cat#70746-3)) were added per 1 L of original culture. The suspension was stirred for 1 hour at 4° C. Debris was removed by centrifugation for 30 minutes at 39,800×g at 4° C. The supernatant was decanted into a 500 mL beaker and 10 ml of a 50% slurry of Qiagen Ni-NTA Agarose (Cat#30250) that had been pre-equilibrated in 50 mM Tris-HCl pH 7.8, 500 mM NaCl, 10% Glycerol, 10 mM Imidazole, and 10 mM Methionine, were added and stirred for 30 minutes at 4° C. The sample was then poured into a drip column at 4° C. and washed with 10 column volumes of 50 mM Tris-HCl pH 7.8, 500 mM NaCl, 10% Glycerol, 10 mM Imidazole, and 10 mM Methionine. The protein was eluted using a step gradient with two column volumes each of the same buffer containing 50 mM, and 500 mM Imidazole, sequentially. The 6× Histidine tag was cleaved overnight using 40 units of TEV protease (Invitrogen Cat#10127017) per 1 mg of protein while dialyzing in 50 mM Tris-HCl pH 7.8, 500 mM NaCl, 10% Glycerol, 10 mM Imidazole, and 10 mM Methionine at 4° C. The 6× Histidine tag was removed by passing the sample over a Pharmacia 5 ml IMAC column (Cat#17-0409-01) charged with Nickel and equilibrated in 50 mM Tris-HCl pH 7.8, 500 mM NaCl, 10% Glycerol, 10 mM Imnidazole, and 10 mM Methionine. The cleaved protein eluted in the flow-through, whereas the uncleaved protein and the His-tag remained bound to the Ni-column. The cleaved protein fractions were combined and concentrated using spin concentrators. Further purification was done by gel filtration chromatography on an Amersham Biosciences HiLoad 16/60 Superdex 200 prep grade (Cat#17-1069-01) equilibrated in 25 mM Tris-HCl pH 7.5, 150 mM NaCl, and 5 mM DTT. The cleanest fractions were combined and concentrated to ~15 mg/ml by centrifugation in an Amicon Ultra-15 10,000 Da MWCO centrifugal filter unit (Cat#UFC901024).

Example 3

Cell Assays

MV4-11 and THP cells were maintained in Iscove's Modified Dulbecco's Medium supplemented with 10% fetal bovine serum (FBS) and penicillin/streptomycin, Ba/F3 cells were maintained in RPMI 1640 supplemented with 10% FBS, penicillin/streptomycin and 5 ng/ml recombinant mouse IL-3.

Cell Survival Assays

Compounds were tested in the following assays in duplicate.

96-well XTT assay: Cells (e.g. BaF3 315I, M351I, or E255K cells) were grown in growth media containing various concentrations of compounds (duplicates) on a 96-well plate for 72 hours at 37° C. The starting cell number was 5000-8000 cells per well and volume was 120 µl. At the end of the 72-hour incubation, 40 µl of XTT labeling mixture (50:1 solution of sodium 3'-[1-(phenylamino-carbonyl)-3,4-tetrazolium]-bis(4-methoxy-6-nitro)benzene sulfonic acid hydrate and Electron-coupling reagent: PMS (N-methyl dibenzopyrazine methyl sulfate) were added to each well of the plate. After an additional 2-6 hours of incubation at 37° C., the absorbance reading at 405 nm with background correction at 650 nm was measured with a spectrophotometer.

384-Well AlamarBlue Assay:

90 µl of cell suspension were plated onto each well of a 384-well plate preprinted with 0.5 µl of compound in DMSO or DMSO only. The starting cell number was 4000 cells per well. After a 72-hour incubation, 10 µl of AlamarBlue solution (440 µM resazurin in PBS) were then added to each well of the plate. After an additional 2-hour incubation at 37° C., fluorescence was measured using a TECAN plate reading fluorometer with excitation at 535 nm and emission at 591 nm.

BCR-ABL Phospho-ELISA Assay

The following table shows the reagents that were typically used in the BCR-ABL phospho-ELISA ("P-ELISA") assay.

TABLE 76

| BCR-ABL phospho-ELISA(p-ELISA) Typical Reagent List | | |
|---|---|---|
| Description | Vendor | Catalog # |
| RPMI 1640 | Invitrogen | 11875-135 |
| 10% Fetal Bovine Serum, characterized, heat inactivated | VWR | 16777-014 |
| Human Plasma, Anticoagulant = EDTA | Bioreclamation Inc. | HMPLEDTA |
| c-Abl (Ab-3) monoclonal antibody | VWR | 80001-286 |
| Recombinant Mouse Interleukin-3 | Chemicon | IL015 |
| Adhesive Plate Seals | | |
| 96well PP 325 µl round bottom plate w/ lid TC | Thompson Instrument Co | 932465 |
| 96well Nunc Maxisorp plate (for colorimetric assay) | Fisher Scientific | 12-565-136 |
| 96well white flat-bottom plate (for luminescent assay) | Matrix | 4923 |
| Lysis buffer components Tris-Cl pH 7.4 (20 mM) NP-40 (1%) EDTA (5 mM) Sodium pyrophosphate (NaPP; 5 mM) NaF (5 mM) NaCl (150 mM) | | |
| Protease Inhibitor Cocktail PMSF (1 mM) Sodium vanadate (NaVO$_4$; 2 mM) PBS, ice cold | Sigma | P2714 |
| Anti-Phosphotyrosine (4G10 ™), HRP conjugate or unconjugated | Upstate | 16-105 or 05-321 |

TABLE 76-continued

| BCR-ABL phospho-ELISA(p-ELISA) Typical Reagent List | | |
|---|---|---|
| Description | Vendor | Catalog # |
| Goat Anti-Mouse IgG, HRP conjugate (if unconjugated 4G10 is used) | Upstate | 12-349 |
| BD OptEIA Reagent Set B Coating Buffer (0.1M Na-carbonate, pH 9.5) Assay Diluent Wash buffer (.05% Tween/PBS) Stop Solution (2N sulfuric acid) Substrate Reagents A&B | BD Biosciences | 550534 |
| SuperSignal ELISA Pico Chemiluminescent Substrate (may be used instead of Substrate Reagents A&B) | Pierce | 37070 |

Cells (Ba/F$_3$ cells transfected with WT BCR-ABL, other kinases, or T315I, Y253F, M351T, E255K, or other mutant forms of BCR-ABL) were grown in the absence of IL-3 at least ½ week before the assay. The day before assay, the cells were fed with fresh media so that at the time of assay the cells were in log phase. Ba/F3 cells that had been grown in the absence of IL-3 for at least ½ week were resuspended in RPMI 1640 so that each well of a 96-well plate would contain approximately 200,000 cells. Cells were distributed in a 96-well plate containing serially diluted concentrations of test compounds. Cells were typically incubated with or without test compounds for 60-120 minutes at 5% $CO_2$, 37° C. The incubation was performed with or without other additives such as 10% FCS or 50% human plasma. After incubation of compounds, lysis buffer was added and incubated for 10-15 minutes; the lysate was cleared by centrifugation.

To make the ELISA plate, commercially available Anti-ABL antibodies (e.g. (Ab-3, Calbiochem OP20) were prepared at a concentration of 0.125 µg/ml in coating buffer (0.1M Na-carbonate, pH 9.5), and plated at 10 ml per plate (12.5 µl 100 µg/ml Ab/10 ml). In a high binding multi-well plate, 100 µl Ab in coating buffer were added to each well, and each plate was covered with a plate seal and incubated overnight at 4° C.

Excess antibody was removed and the ELISA plate was washed 3-4 times with 200 µl of wash buffer (0.05% Tween in PBS, pH 7.4). 150 µl of lysate (see above) were transferred to the ELISA plate. Plates were sealed and incubated 2 hours at room temperature. The detection antibody (e.g. HRP conjugated anti-pTyr or unconjugated α-p-Y 4G10, Upstate) was prepared in assay diluent. The antibody was diluted 1:1000 (stock=2 µg/µl, 200 µg in 100 µl; f.c.=2 µg/ml) in assay diluent and 10 ml of diluted antibody per plate were added. The lysate was removed from the ELISA plates, and wells were washed four times with 200 µl of wash buffer per well. 100 µl of detection antibody was added to each well; the plate was covered, and incubated 1 hr at room temperature (21° C.). Excess detection antibody was removed from the ELISA plates, and the wells were washed four times with 200 µl of wash buffer per well.

If necessary, (i.e. for unconjugated anti-pTyr antibody) secondary antibody (goat anti-rabbit HRP) was diluted 1:3000 in assay diluent (3.33 µl per 10 ml diluent) and added at 10 ml of diluted antibody per plate. Excess secondary antibody was removed from the ELISA plate, and the plate was washed four times with 200 µl per well of wash buffer.

Substrate Reagent A and Substrate Reagent B (Pierce Cat#37070 SuperSignal ELISA Pico Chemiluminescent Substrate) were added immediately before use (10 ml resultant solution per plate). 100 μl substrate were added per well, mixed for 1 minute, and chemiluminescent signal was measured with a luminometer.
Assay Results on Selected Compounds
Abl_T315I_0P_bioassay IC50
A<0.05 μM
0.05 μM<B<0.5 μM
C>0.5 μM
Abl_WT_XTT_[Ba/F3]_IC50
D<1 μM
E>1 μM
Abl_T315I_XTT_[Ba/F3]_IC50
D<1 μM
E>1 μM
| Structure | Abl T315I 0P IC50 uM | ABL1 WT XTT [Ba/F3] IC50 | ABL1 T315I XTT [Ba/F3] IC50 |
|---|---|---|---|
| 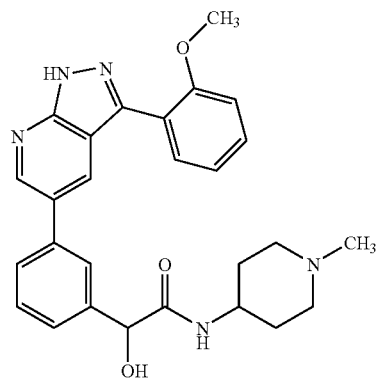 | A | E | E |
| 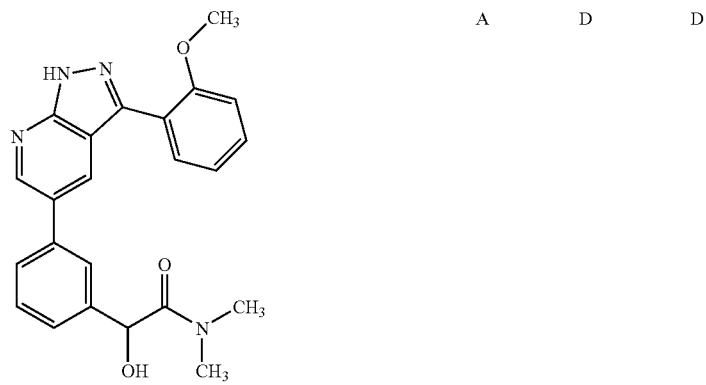 | A | D | D |
| 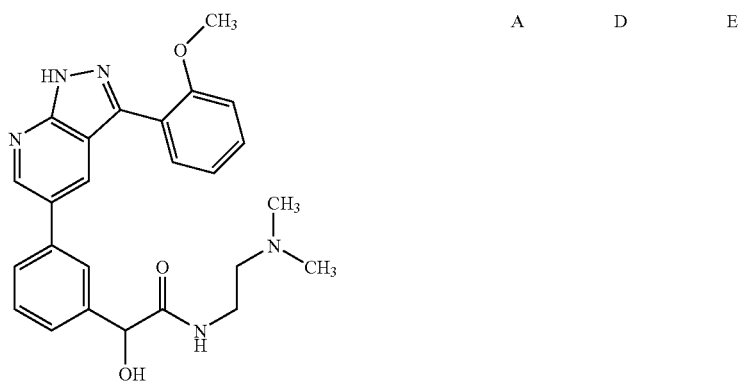 | A | D | E |

| Structure | AbI T315I 0P IC50 uM | ABL1 WT XTT [Ba/F3] IC50 | ABL1 T315I XTT [Ba/F3] IC50 |
|---|---|---|---|
| 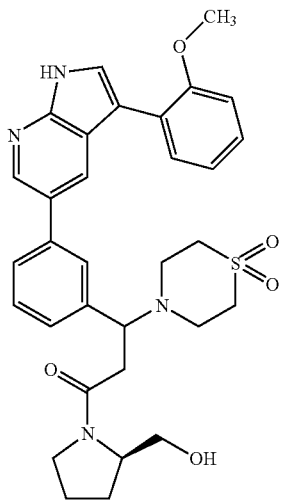 | B | E | E |
| 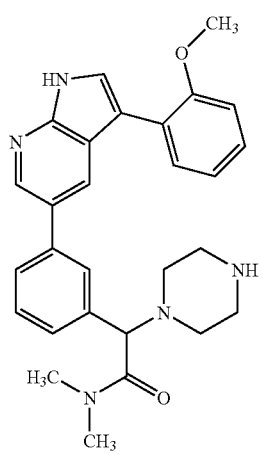 | A | E | E |
| 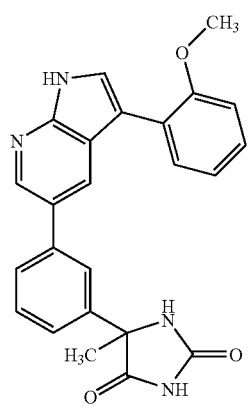 | A | D | E |

| Structure | AbI T315I OP IC50 uM | ABL1 WT XTT [Ba/F3] IC50 | ABL1 T315I XTT [Ba/F3] IC50 |
|---|---|---|---|
| 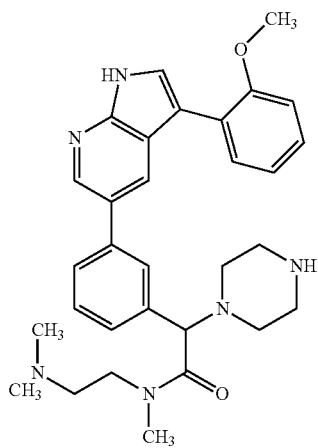 | A | E | E |
| 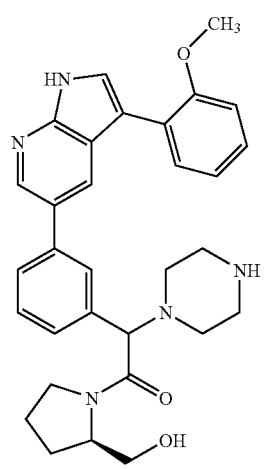 | A | E | E |
| 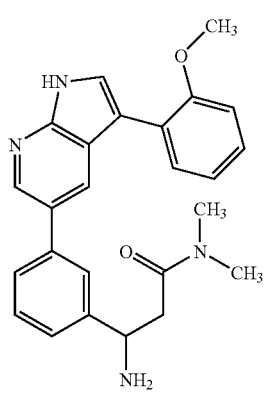 | A | E | E |

| Structure | AbI T315I 0P IC50 uM | ABL1 WT XTT [Ba/F3] IC50 | ABL1 T315I XTT [Ba/F3] IC50 |
|---|---|---|---|
| 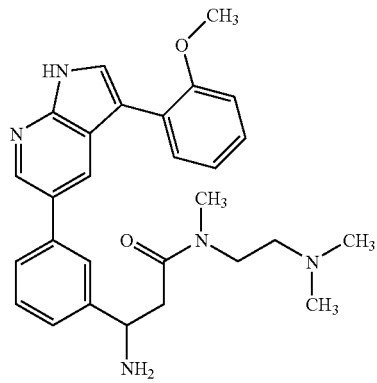 | A | E | E |
| 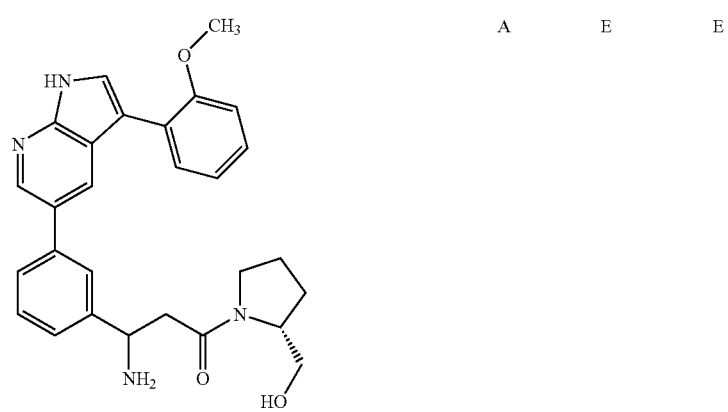 | A | E | E |
| 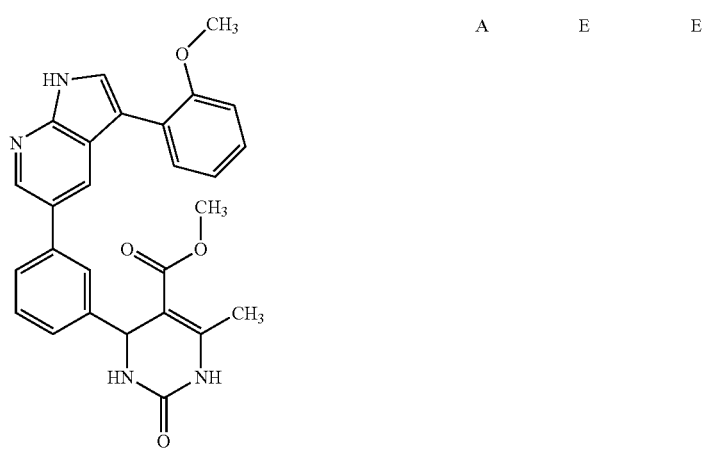 | A | E | E |

-continued
| Structure | AbI T315I 0P IC50 uM | ABL1 WT XTT [Ba/F3] IC50 | ABL1 T315I XTT [Ba/F3] IC50 |
|---|---|---|---|
| 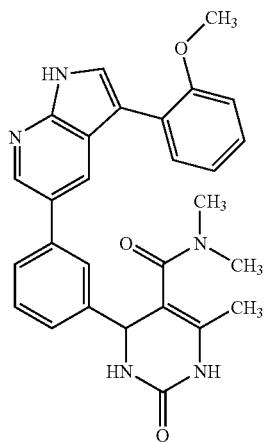 | A | E | E |
| 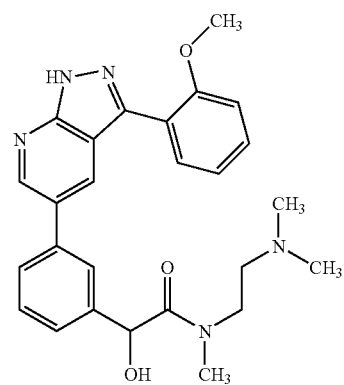 | A | D | D |
| 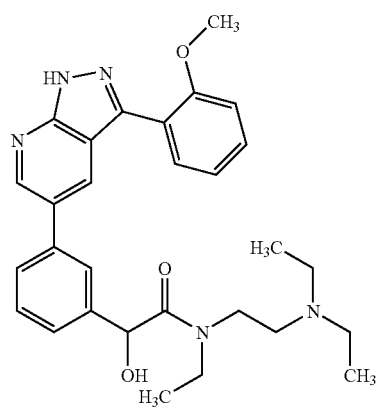 | A | D | D |

| Structure | AbI T315I 0P IC50 uM | ABL1 WT XTT [Ba/F3] IC50 | ABL1 T315I XTT [Ba/F3] IC50 |
|---|---|---|---|
| | A | E | E |
| | A | E | E |
| | A | D | D |
| | A | D | D |

| Structure | AbI T315I 0P IC50 uM | ABL1 WT XTT [Ba/F3] IC50 | ABL1 T315I XTT [Ba/F3] IC50 |
|---|---|---|---|
| 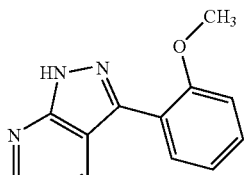 | A | D | E |
| 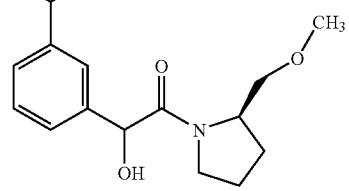 | A | D | D |
| 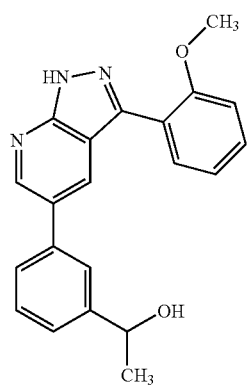 | A | D | D |
| 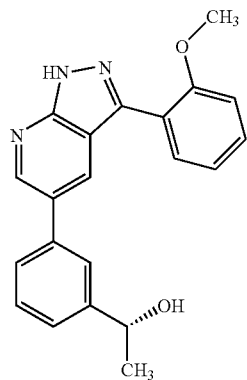 | A | E | E |

-continued
| Structure | AbI T315I OP IC50 uM | ABL1 WT XTT [Ba/F3] IC50 | ABL1 T315I XTT [Ba/F3] IC50 |
|---|---|---|---|
| 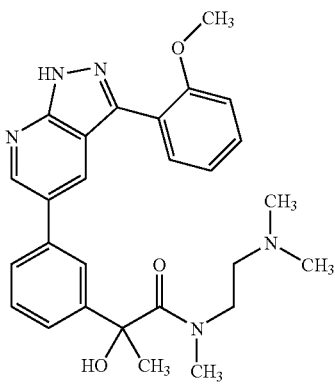 | A | E | E |
| 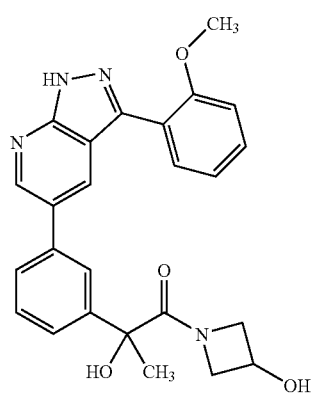 | A | E | E |
| 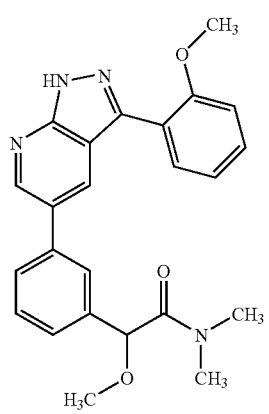 | A | D | D |

-continued

| Structure | AbI T315I OP IC50 uM | ABL1 WT XTT [Ba/F3] IC50 | ABL1 T315I XTT [Ba/F3] IC50 |
|---|---|---|---|
| | A | D | D |
| | A | ND | ND |
| | A | D | D |
| | A | E | E |

-continued

| Structure | AbI T315I OP IC50 uM | ABL1 WT XTT [Ba/F3] IC50 | ABL1 T315I XTT [Ba/F3] IC50 |
|---|---|---|---|
| | A | E | E |
| | A | E | E |
| | A | D | D |
| | A | E | E |

-continued
| Structure | AbI T315I OP IC50 uM | ABL1 WT XTT [Ba/F3] IC50 | ABL1 T315I XTT [Ba/F3] IC50 |
|---|---|---|---|
| 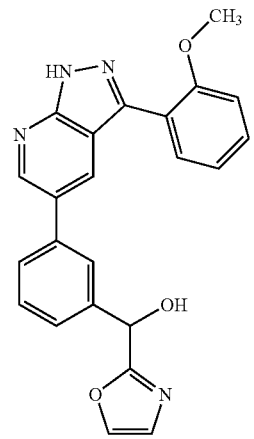 | A | D | E |
| 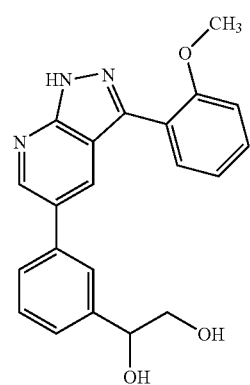 | A | D | E |
| 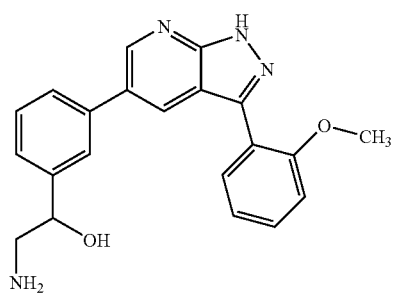 | A | ND | ND |
| 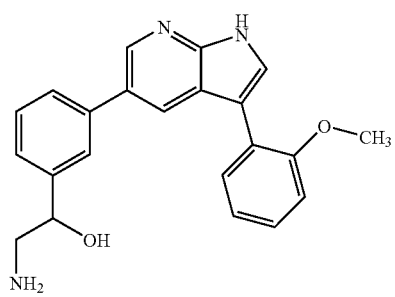 | A | E | E |

-continued

| Structure | AbI T315I OP IC50 uM | ABL1 WT XTT [Ba/F3] IC50 | ABL1 T315I XTT [Ba/F3] IC50 |
|---|---|---|---|
| (structure) | A | D | D |
| (structure) | A | E | E |
| (structure) | A | D | D |
| (structure) | A | D | D |

-continued
| Structure | AbI T315I OP IC50 uM | ABL1 WT XTT [Ba/F3] IC50 | ABL1 T315I XTT [Ba/F3] IC50 |
|---|---|---|---|
| 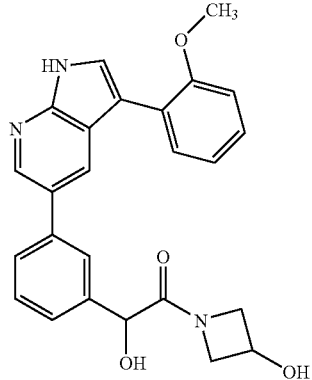 | A | D | E |
| 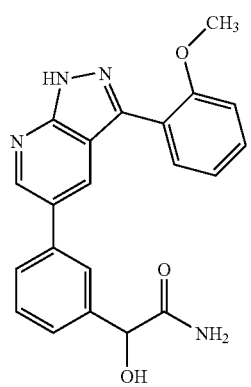 | A | D | D |
| 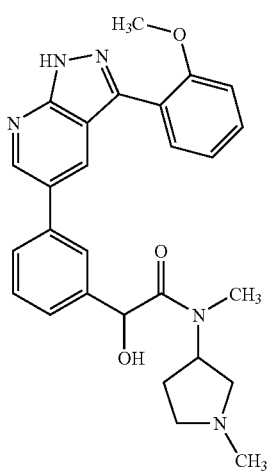 | A | D | D |

| Structure | AbI T315I OP IC50 uM | ABL1 WT XTT [Ba/F3] IC50 | ABL1 T315I XTT [Ba/F3] IC50 |
|---|---|---|---|
| 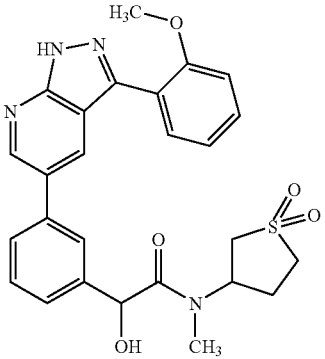 | A | D | E |
| 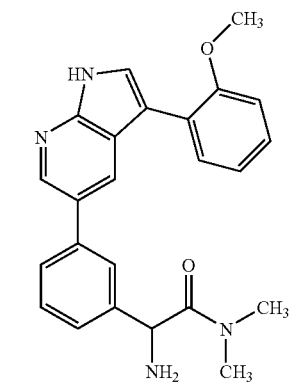 | A | D | D |
| 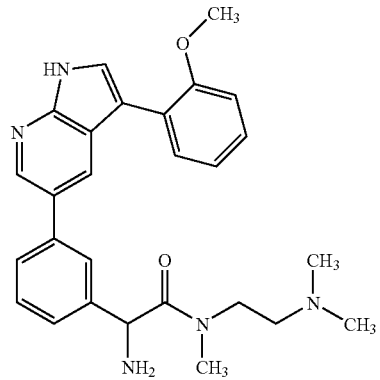 | A | E | E |
| 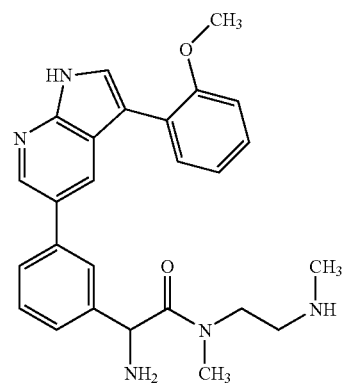 | A | E | E |

-continued
| Structure | AbI T315I OP IC50 uM | ABL1 WT XTT [Ba/F3] IC50 | ABL1 T315I XTT [Ba/F3] IC50 |
|---|---|---|---|
| 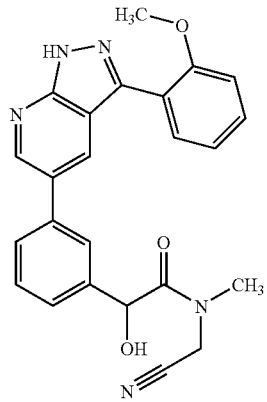 | A | D | E |
| 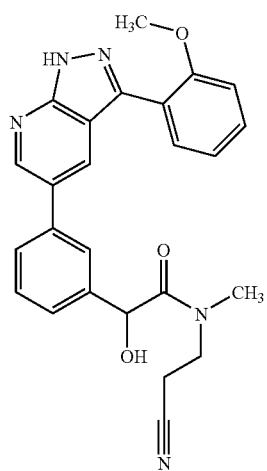 | A | D | D |
| 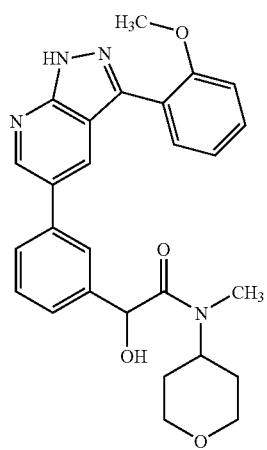 | A | D | D |

-continued
| Structure | AbI T315I OP IC50 uM | ABL1 WT XTT [Ba/F3] IC50 | ABL1 T315I XTT [Ba/F3] IC50 |
|---|---|---|---|
| 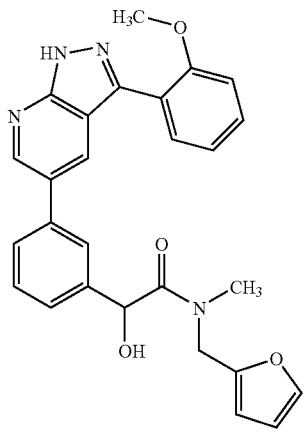 | A | E | E |
| 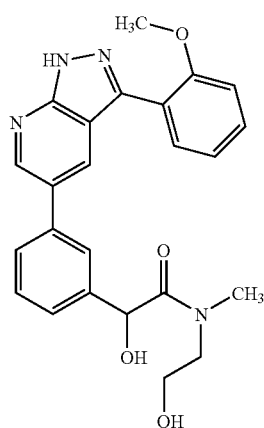 | A | D | D |
| 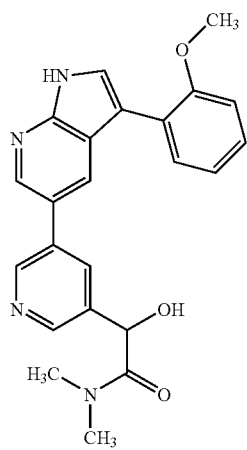 | A | D | D |

-continued
| Structure | AbI T315I OP IC50 uM | ABL1 WT XTT [Ba/F3] IC50 | ABL1 T315I XTT [Ba/F3] IC50 |
|---|---|---|---|
| 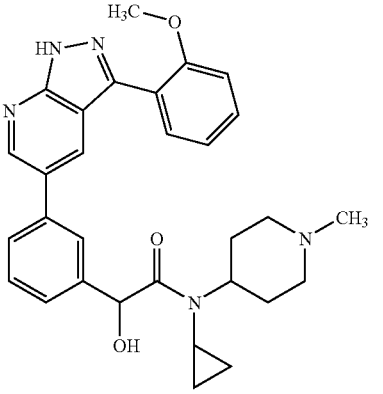 | A | D | D |
| 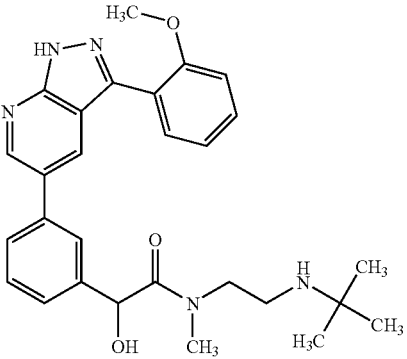 | A | D | D |
| 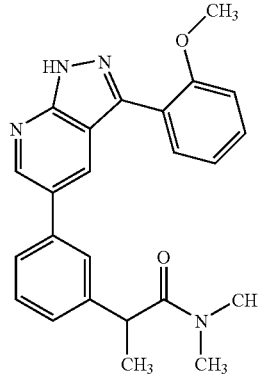 | A | E | E |
| 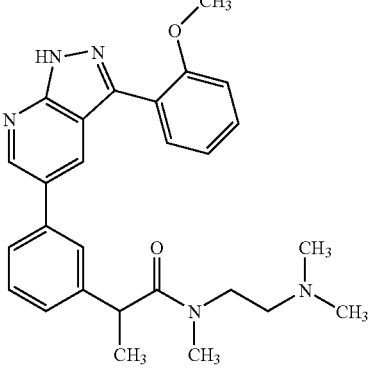 | A | E | E |

| Structure | AbI T315I OP IC50 uM | ABL1 WT XTT [Ba/F3] IC50 | ABL1 T315I XTT [Ba/F3] IC50 |
|---|---|---|---|
| | A | D | D |
| | A | D | E |
| | A | E | E |

-continued
| Structure | AbI T315I OP IC50 uM | ABL1 WT XTT [Ba/F3] IC50 | ABL1 T315I XTT [Ba/F3] IC50 |
|---|---|---|---|
| 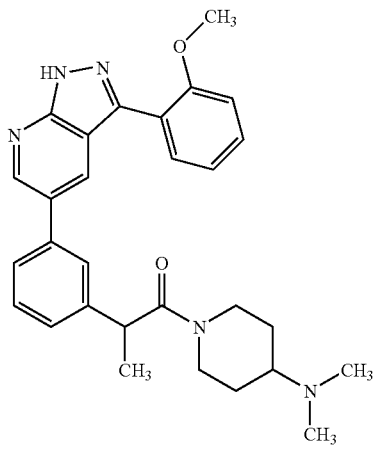 | A | D | D |
| 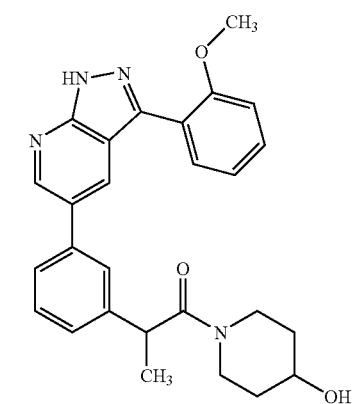 | A | D | E |
| 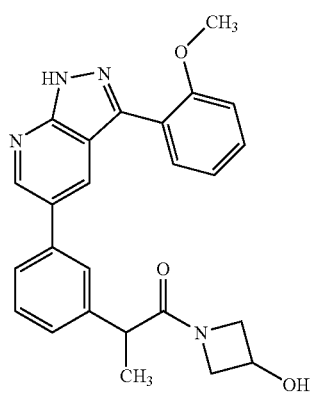 | A | E | E |

-continued
| Structure | AbI T315I 0P IC50 uM | ABL1 WT XTT [Ba/F3] IC50 | ABL1 T315I XTT [Ba/F3] IC50 |
|---|---|---|---|
| 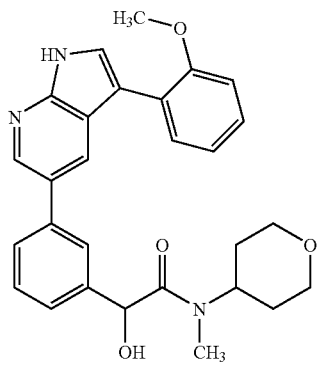 | A | D | D |
| 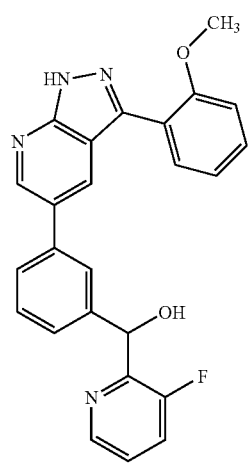 | A | D | D |
| 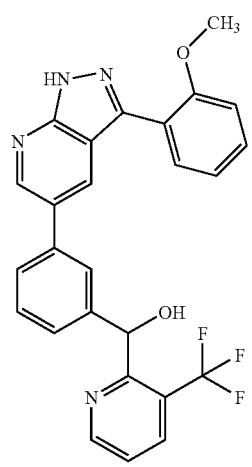 | A | E | E |

-continued
| Structure | AbI T315I OP IC50 uM | ABL1 WT XTT [Ba/F3] IC50 | ABL1 T315I XTT [Ba/F3] IC50 |
|---|---|---|---|
| 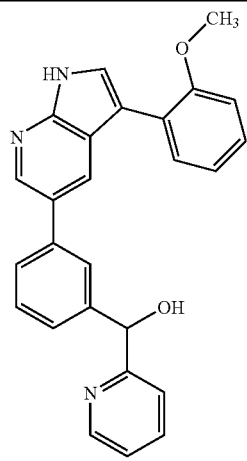 | A | D | D |
| 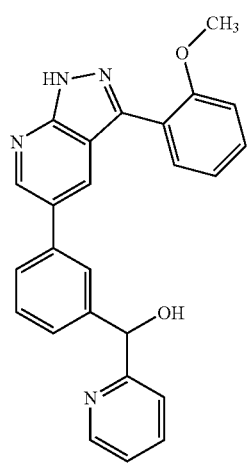 | A | D | E |
| 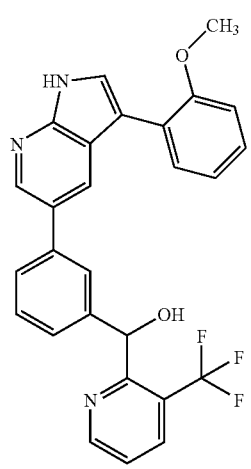 | A | E | E |

-continued
| Structure | AbI T315I OP IC50 uM | ABL1 WT XTT [Ba/F3] IC50 | ABL1 T315I XTT [Ba/F3] IC50 |
|---|---|---|---|
| 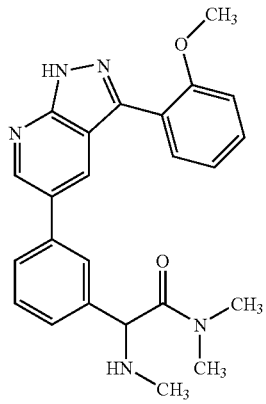 | A | E | E |
| 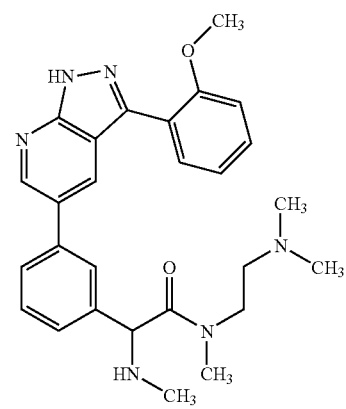 | A | E | E |
| 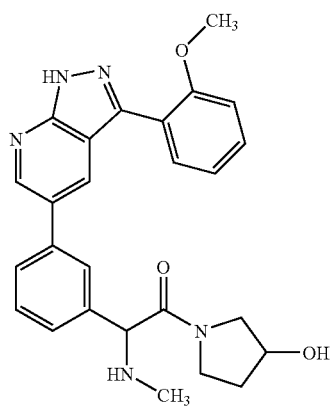 | A | ND | ND |

-continued
| Structure | AbI T315I OP IC50 uM | ABL1 WT XTT [Ba/F3] IC50 | ABL1 T315I XTT [Ba/F3] IC50 |
|---|---|---|---|
| 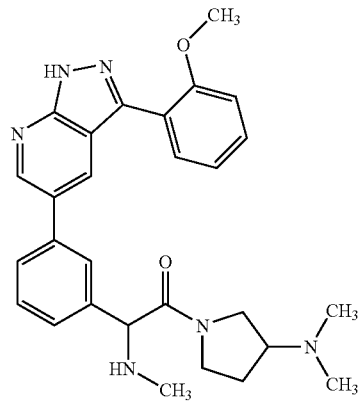 | A | E | E |
| 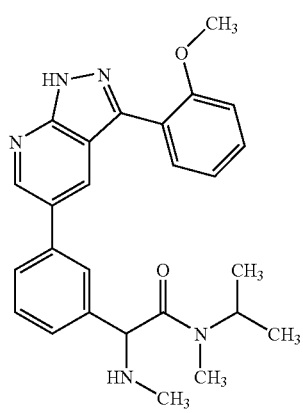 | A | E | E |
| 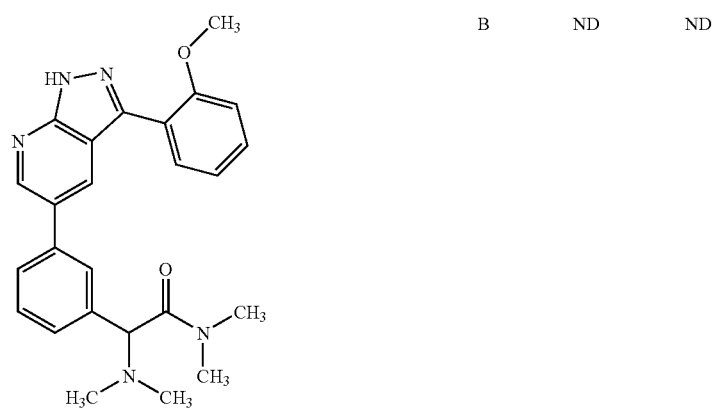 | B | ND | ND |

-continued
| Structure | AbI T315I OP IC50 uM | ABL1 WT XTT [Ba/F3] IC50 | ABL1 T315I XTT [Ba/F3] IC50 |
|---|---|---|---|
| 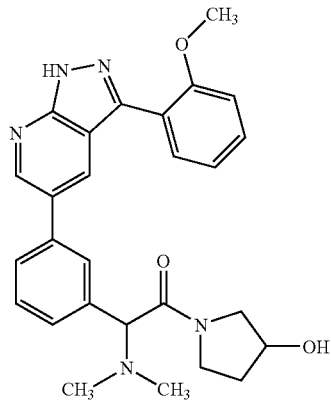 | B | ND | ND |
| 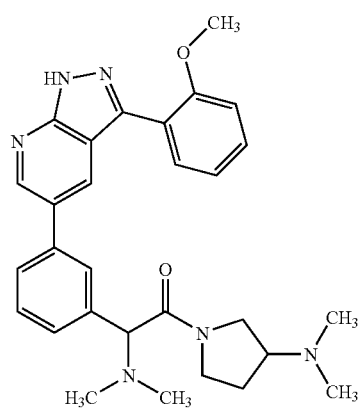 | B | E | E |
| 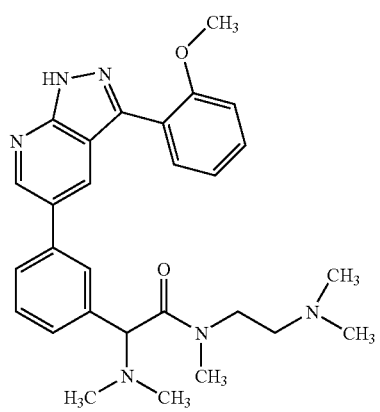 | B | E | E |

-continued
| Structure | AbI T315I OP IC50 uM | ABL1 WT XTT [Ba/F3] IC50 | ABL1 T315I XTT [Ba/F3] IC50 |
|---|---|---|---|
| 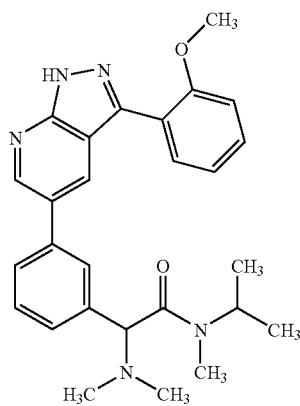 | B | ND | ND |
| 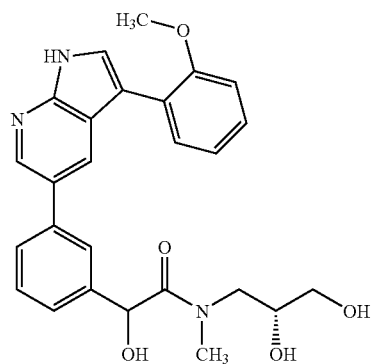 | A | D | D |
| 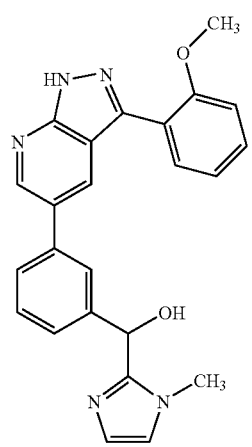 | A | D | E |

-continued
| Structure | AbI T315I OP IC50 uM | ABL1 WT XTT [Ba/F3] IC50 | ABL1 T315I XTT [Ba/F3] IC50 |
|---|---|---|---|
| 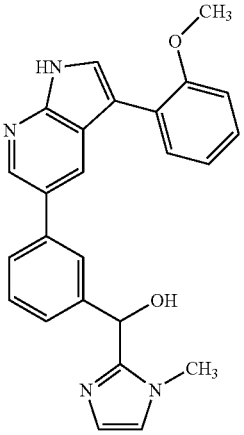 | A | D | D |
| 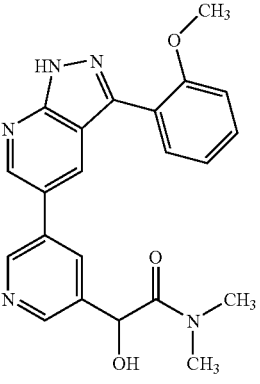 | A | D | D |
| 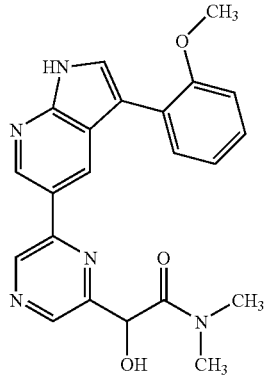 | C | ND | ND |
| 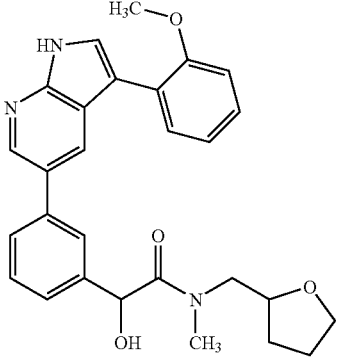 | A | D | D |

| Structure | AbI T315I OP IC50 uM | ABL1 WT XTT [Ba/F3] IC50 | ABL1 T315I XTT [Ba/F3] IC50 |
|---|---|---|---|
| 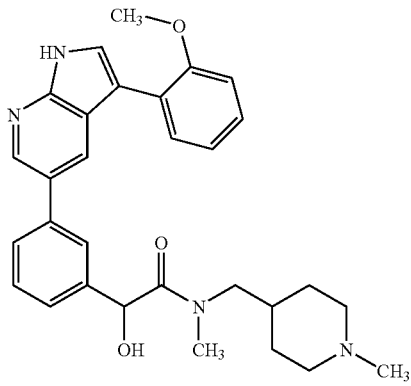 | A | D | D |
| 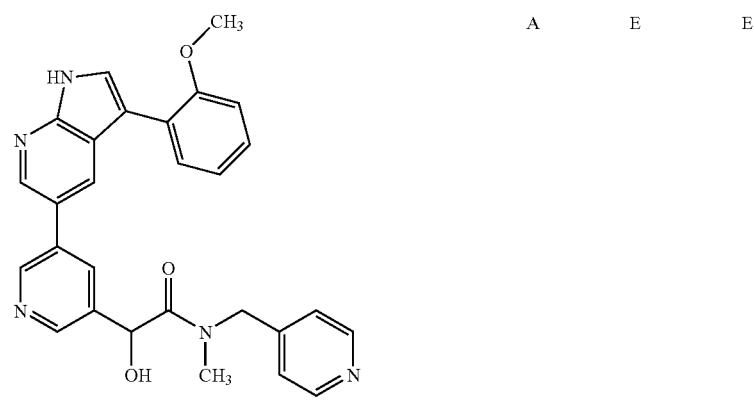 | A | E | E |
| 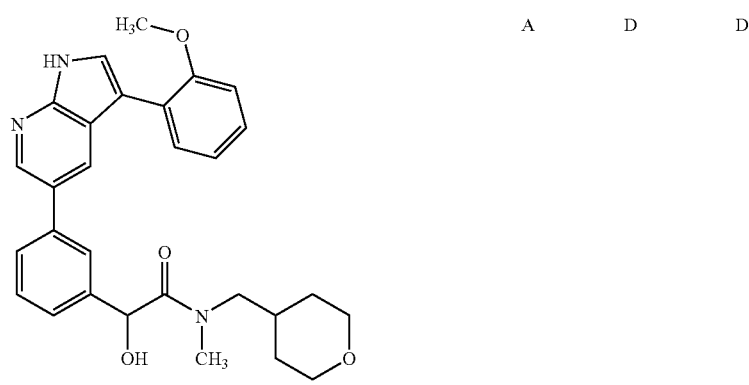 | A | D | D |

-continued
| Structure | AbI T315I OP IC50 uM | ABL1 WT XTT [Ba/F3] IC50 | ABL1 T315I XTT [Ba/F3] IC50 |
|---|---|---|---|
| 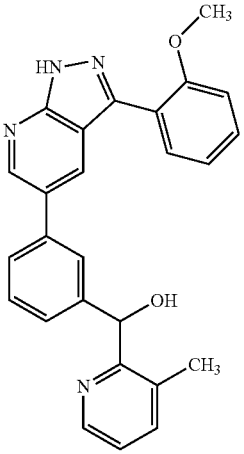 | A | D | D |
| 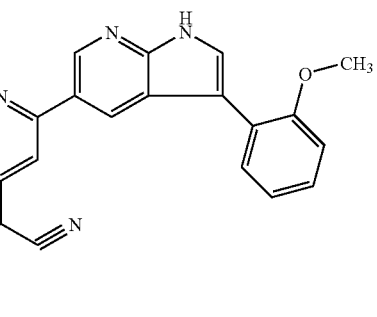 | C | E | E |
| 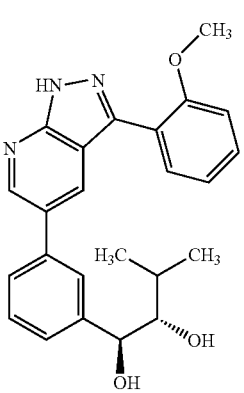 | A | D | D |
| 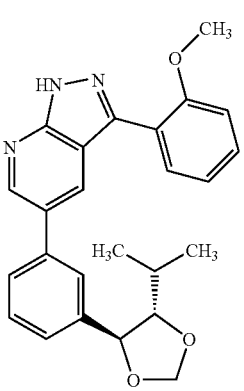 | A | ND | ND |

-continued

| Structure | AbI T315I OP IC50 uM | ABL1 WT XTT [Ba/F3] IC50 | ABL1 T315I XTT [Ba/F3] IC50 |
|---|---|---|---|
| | A | D | D |
| | A | E | E |
| | A | D | D |
| | A | E | E |

-continued

| Structure | AbI T315I OP IC50 uM | ABL1 WT XTT [Ba/F3] IC50 | ABL1 T315I XTT [Ba/F3] IC50 |
|---|---|---|---|
| | A | D | D |
| | A | E | E |
| | A | D | D |
| | A | E | E |

-continued
| Structure | AbI T315I OP IC50 uM | ABL1 WT XTT [Ba/F3] IC50 | ABL1 T315I XTT [Ba/F3] IC50 |
|---|---|---|---|
| 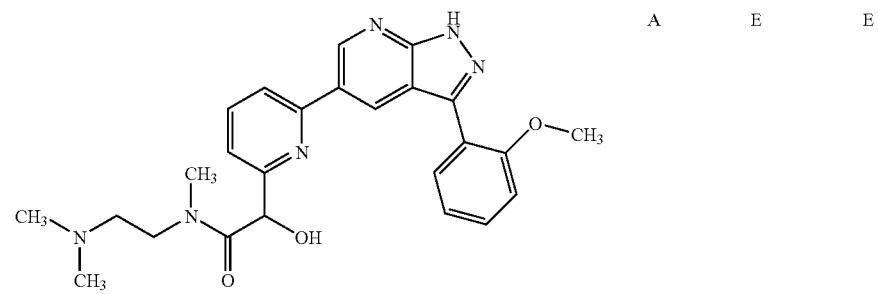 | A | E | E |
| 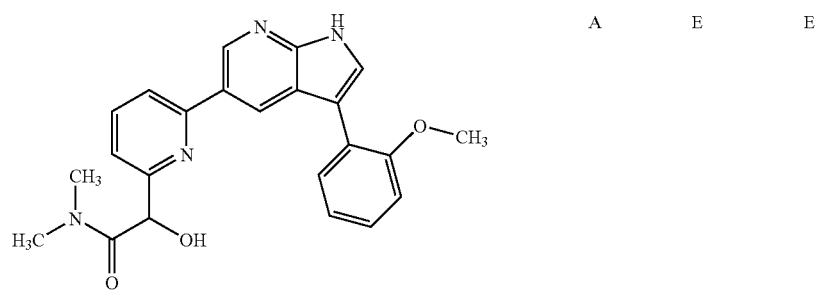 | A | E | E |
| 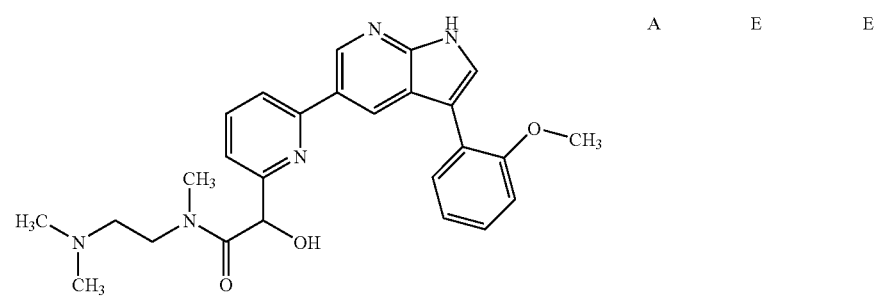 | A | E | E |
| 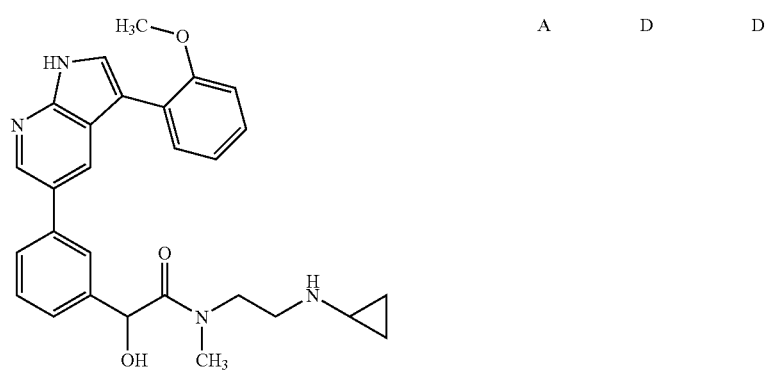 | A | D | D |

-continued

| Structure | AbI T315I OP IC50 uM | ABL1 WT XTT [Ba/F3] IC50 | ABL1 T315I XTT [Ba/F3] IC50 |
|---|---|---|---|
| (structure) | A | E | D |
| (structure) | A | D | D |
| (structure) | A | D | D |
| (structure) | B | E | E |

-continued

| Structure | AbI T315I OP IC50 uM | ABL1 WT XTT [Ba/F3] IC50 | ABL1 T315I XTT [Ba/F3] IC50 |
|---|---|---|---|
| | A | D | D |
| | A | E | E |
| | A | E | E |
| | A | E | E |

-continued
| Structure | AbI T315I OP IC50 uM | ABL1 WT XTT [Ba/F3] IC50 | ABL1 T315I XTT [Ba/F3] IC50 |
|---|---|---|---|
| 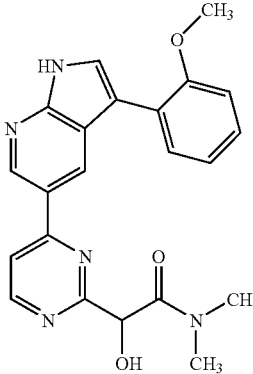 | B | E | E |
| 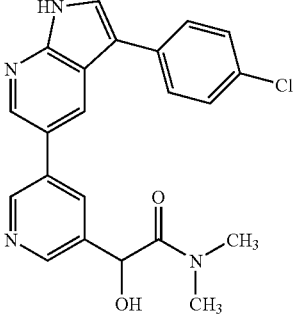 | A | D | E |
| 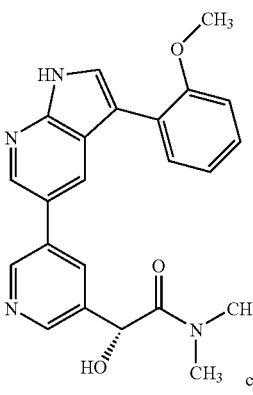 | A | D | D |
| 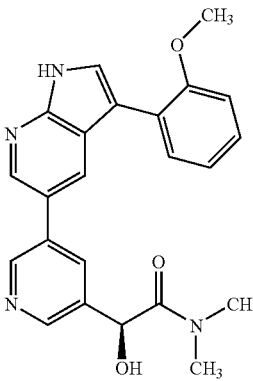 | A | D | D |

| Structure | AbI T315I OP IC50 uM | ABL1 WT XTT [Ba/F3] IC50 | ABL1 T315I XTT [Ba/F3] IC50 |
|---|---|---|---|
| 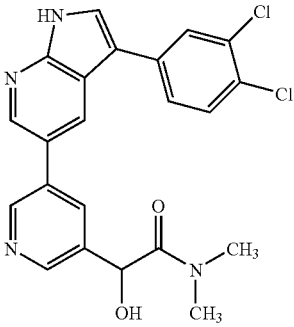 | A | E | E |
| 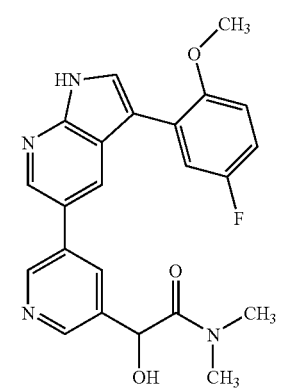 | A | D | D |
| 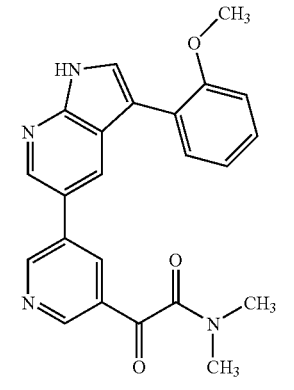 | A | D | D |
| 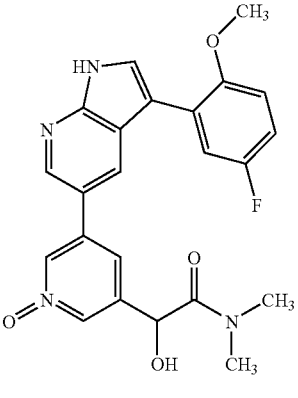 | A | E | E |

-continued
| Structure | AbI T315I OP IC50 uM | ABL1 WT XTT [Ba/F3] IC50 | ABL1 T315I XTT [Ba/F3] IC50 |
|---|---|---|---|
| 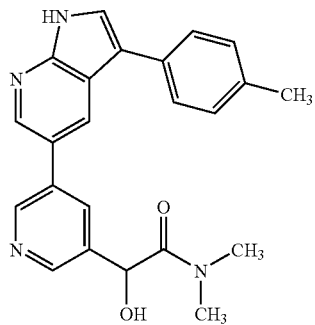 | A | E | E |
| 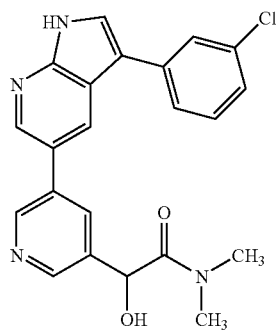 | A | D | D |
| 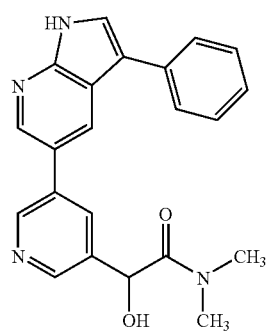 | A | D | D |
| 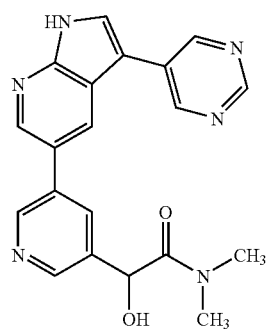 | C | E | E |

| Structure | AbI T315I OP IC50 uM | ABL1 WT XTT [Ba/F3] IC50 | ABL1 T315I XTT [Ba/F3] IC50 |
|---|---|---|---|
| 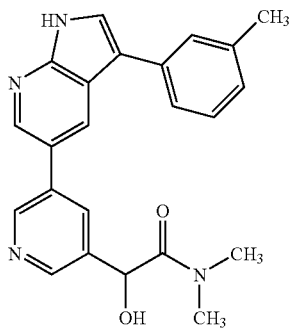 | A | D | D |
| 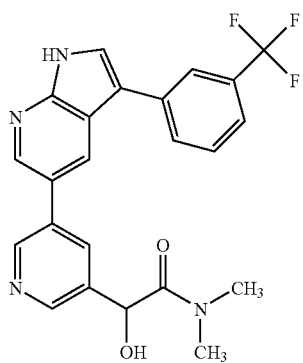 | A | E | E |
| 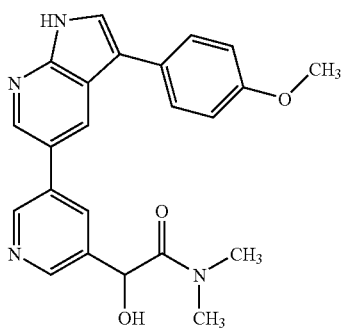 | A | E | E |
| 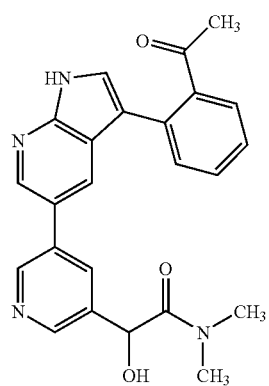 | B | E | E |

| Structure | AbI T315I OP IC50 uM | ABL1 WT XTT [Ba/F3] IC50 | ABL1 T315I XTT [Ba/F3] IC50 |
|---|---|---|---|
| 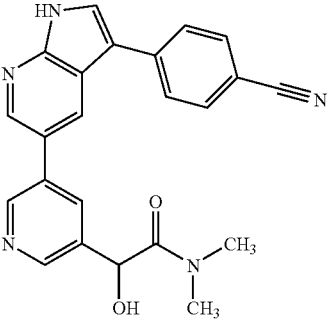 | B | E | E |
| 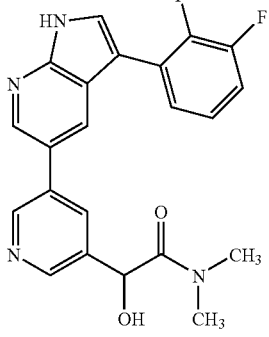 | A | D | D |
| 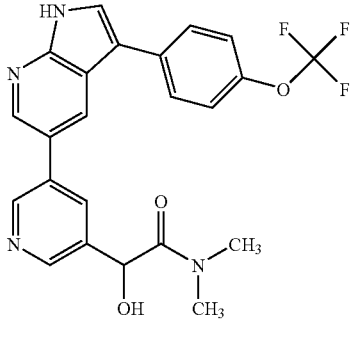 | B | E | E |
| 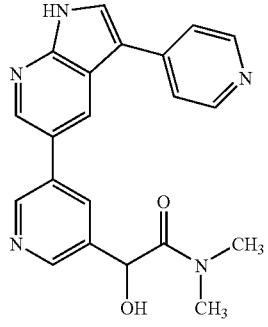 | B | E | E |

-continued
| Structure | AbI T315I OP IC50 uM | ABL1 WT XTT [Ba/F3] IC50 | ABL1 T315I XTT [Ba/F3] IC50 |
|---|---|---|---|
| 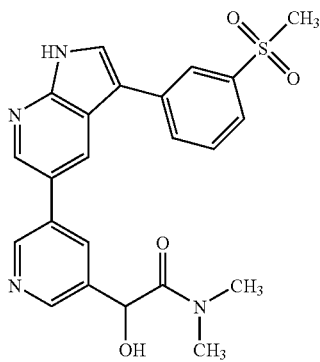 | C | E | E |
| 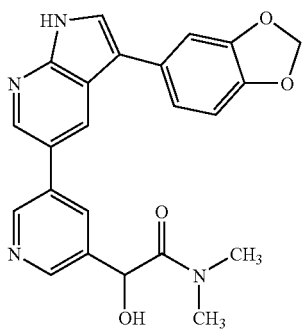 | A | D | E |
| 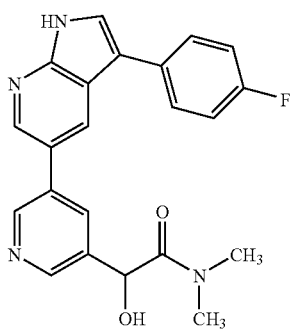 | A | E | E |
| 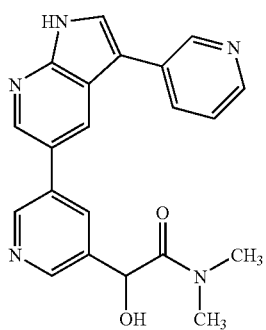 | B | E | E |

-continued

| Structure | AbI T315I OP IC50 uM | ABL1 WT XTT [Ba/F3] IC50 | ABL1 T315I XTT [Ba/F3] IC50 |
|---|---|---|---|
| | A | E | E |
| 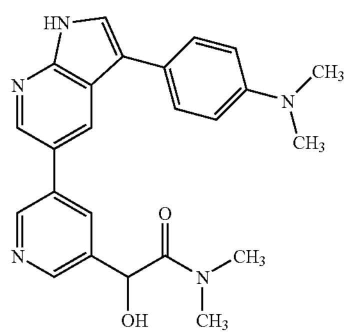 | B | E | E |
| | A | E | E |
| | A | ND | E |

-continued

| Structure | AbI T315I 0P IC50 uM | ABL1 WT XTT [Ba/F3] IC50 | ABL1 T315I XTT [Ba/F3] IC50 |
|---|---|---|---|
| (structure with 2-fluorophenyl) | A | D | D |
| (structure with 2-ethylphenyl) | A | D | D |
| (structure with 2-trifluoromethoxyphenyl) | A | D | E |
| (structure with 2-methylthiophenyl) | A | D | D |

-continued

| Structure | AbI T315I OP IC50 uM | ABL1 WT XTT [Ba/F3] IC50 | ABL1 T315I XTT [Ba/F3] IC50 |
|---|---|---|---|
| (structure: 3-(2-methoxypyridin-3-yl)-5-[5-(pyridin-3-yl with N,N-dimethyl-2-hydroxyacetamide)]-1H-pyrrolo[2,3-b]pyridine) | A | D | E |
| (structure: 3-(2-chlorophenyl)-1H-pyrrolo[2,3-b]pyridine linked to pyridine with N,N-dimethyl-2-hydroxyacetamide) | A | D | D |
| (structure: 3-(3-cyanophenyl)-1H-pyrrolo[2,3-b]pyridine linked to pyridine with N,N-dimethyl-2-hydroxyacetamide) | B | ND | ND |
| (structure: 3-[3-(dimethylamino)phenyl]-1H-pyrrolo[2,3-b]pyridine linked to pyridine with N,N-dimethyl-2-hydroxyacetamide) | A | D | E |

-continued

| Structure | AbI T315I OP IC50 uM | ABL1 WT XTT [Ba/F3] IC50 | ABL1 T315I XTT [Ba/F3] IC50 |
|---|---|---|---|
| | B | ND | ND |
| 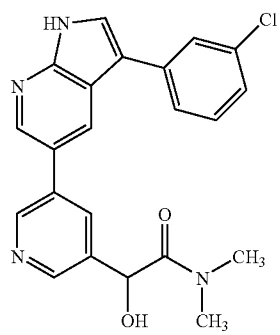 | A | D | E |
| | B | ND | ND |
| | B | ND | ND |

| Structure | AbI T315I 0P IC50 uM | ABL1 WT XTT [Ba/F3] IC50 | ABL1 T315I XTT [Ba/F3] IC50 |
|---|---|---|---|
| | A | D | E |
| | A | E | E |
| 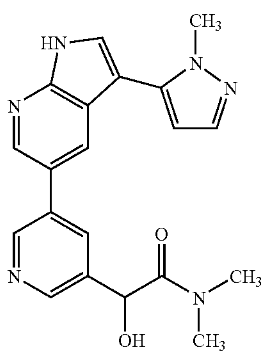 | B | E | E |
| | A | E | E |

-continued

| Structure | AbI T315I OP IC50 uM | ABL1 WT XTT [Ba/F3] IC50 | ABL1 T315I XTT [Ba/F3] IC50 |
|---|---|---|---|
| (structure) | C | E | E |
| (structure) | A | D | D |
| (structure) | A | E | E |
| (structure) | B | E | E |

-continued

| Structure | AbI T315I 0P IC50 uM | ABL1 WT XTT [Ba/F3] IC50 | ABL1 T315I XTT [Ba/F3] IC50 |
|---|---|---|---|
| (structure) | A | D | D |
| (structure) | A | D | D |
| (structure) | A | E | E |
| (structure) | A | D | D |

-continued
| Structure | AbI T315I OP IC50 uM | ABL1 WT XTT [Ba/F3] IC50 | ABL1 T315I XTT [Ba/F3] IC50 |
|---|---|---|---|
| 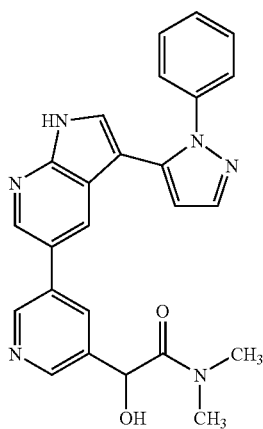 | A | D | E |
| 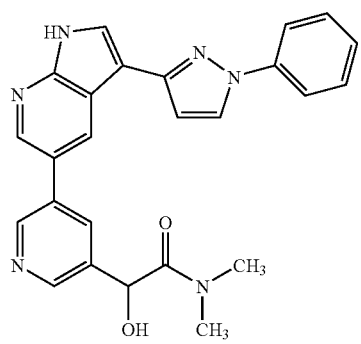 | B | ND | ND |
| 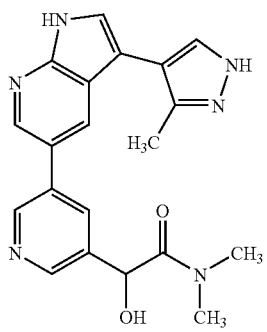 | A | E | E |
| 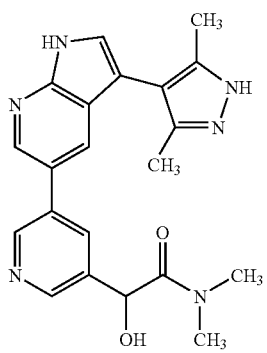 | A | E | E |

| Structure | AbI T315I OP IC50 uM | ABL1 WT XTT [Ba/F3] IC50 | ABL1 T315I XTT [Ba/F3] IC50 |
|---|---|---|---|
| 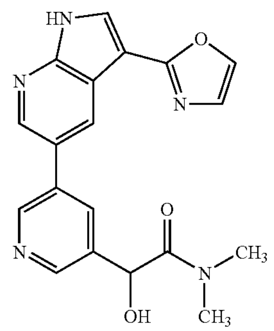 | B | ND | ND |
| 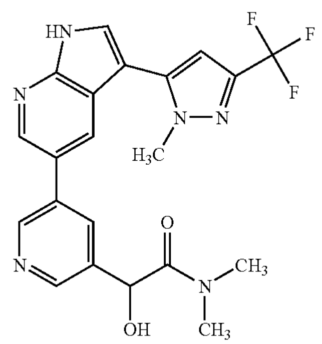 | C | ND | ND |
| | A | E | E |
| | A | D | D |

-continued
| Structure | AbI T315I 0P IC50 uM | ABL1 WT XTT [Ba/F3] IC50 | ABL1 T315I XTT [Ba/F3] IC50 |
|---|---|---|---|
| 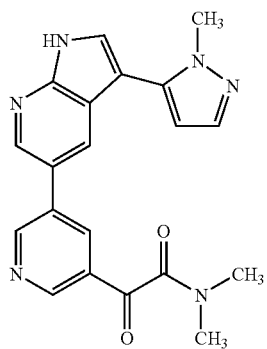 | C | ND | ND |
| 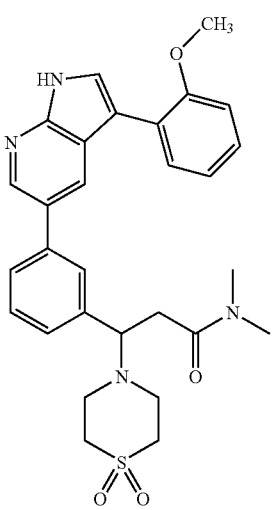 | C | ND | ND |
| 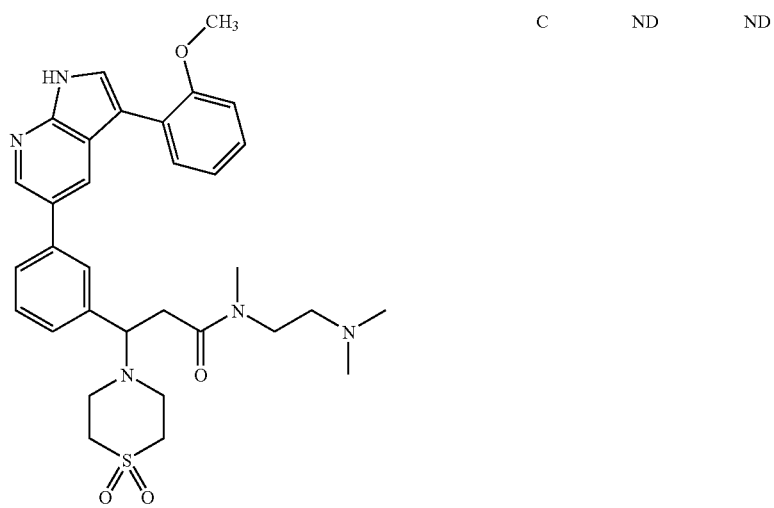 | C | ND | ND |

-continued

| Structure | AbI T315I OP IC50 uM | ABL1 WT XTT [Ba/F3] IC50 | ABL1 T315I XTT [Ba/F3] IC50 |
|---|---|---|---|
| 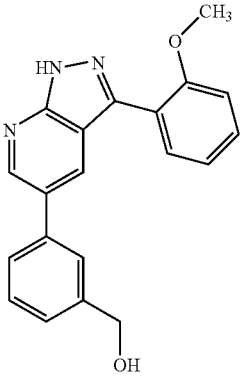 | C | D | D |
| 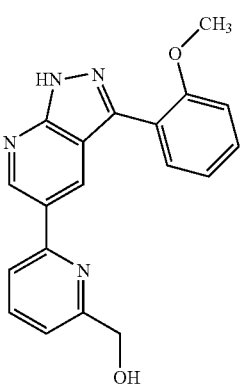 | A | D | E |

What is claimed is:

1. A compound of Formula (A), or an enantiomer, diastereomer, racemate, tautomer or pharmaceutically acceptable salt thereof:

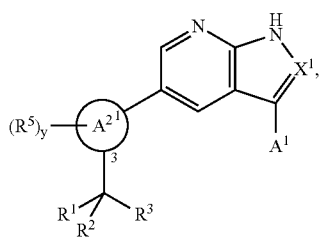

Formula (A)

wherein
- $A^1$ is substituted or unsubstituted phenyl;
- $A^2$ is a pyridinyl group;
- $X^1$ is $CR^4$; wherein
  - $R^4$ is hydrogen, halogen, cyano, nitro, haloalkyl, or substituted or unsubstituted alkyl;
- $R^1$ is hydrogen, lower alkyl or lower heteroalkyl;
- $R^2$ is hydrogen, lower alkyl, halogen, hydroxy, —$OR^8$, cyano, nitro, haloalkyl, —$NR^6R^7$;
- $R^3$ is hydrogen, substituted or unsubstituted alkyl, substituted or unsubstituted heteroalkyl, substituted or unsubstituted haloalkyl, substituted or unsubstituted heterocycloalkyl, substituted or unsubstituted aryl, substituted or unsubstituted (cycloalkyl)alkyl, substituted or unsubstituted (heterocycloalkyl)alkyl, substituted or unsubstituted arylalkyl, substituted or unsubstituted heteroaryl, substituted or unsubstituted heteroarylalkyl, —COOH, —$NR^9R^{10}$, —$CH_2NR^9R^{10}$, —$CONR^9R^{10}$, —$CH_2CONR^9R^{10}$ or —$OR^8$; or
- $R^2$ and $R^3$ together with the carbon atom to which they are attached, form a substituted or unsubstituted heterocycloalkyl, or a substituted or unsubstituted cycloalkyl;
- each $R^5$ is independently halogen, cyano, nitro, substituted or unsubstituted haloalkyl, substituted or unsubstituted alkyl, —$NR^{11}R^{12}$, —$CONR^{11}R^{12}$, —$OR^{13}$, —$C(=Z)R^{14}$, or —$S(O)R^{15}$, wherein n is independently an integer from 0 to 2;
- y is 0, 1, 2, 3 or 4;
- Z is independently O, S or $N(R^{16})$;
- $R^6$ and $R^7$, $R^9$ and $R^{10}$, and $R^{11}$ and $R^{12}$ are each independently hydrogen, substituted or unsubstituted alkyl, substituted or unsubstituted haloalkyl, substituted or unsubstituted alkyl-$NR^{17}R^{18}$, substituted or unsubstituted alkyl-$CONR^{17}R^{18}$, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted (cycloalkyl)alkyl, substituted or unsubstituted (heterocycloalkyl)alkyl, substituted or unsubstituted arylalkyl, or substituted or unsubstituted heteroarylalkyl, or
- one or more of $R^6$ and $R^7$, $R^9$ and $R^{10}$, and $R^{11}$ and $R^{12}$ are each independently joined together with the nitrogen to which they are attached, to form substituted or unsubstituted 3- to 7-membered heterocycloalkyl, or substituted or unsubstituted heteroaryl;
- $R^8$ and $R^{13}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or
- a pair of $R^{13}$, taken together with the oxygens to which they are attached, form a heterocycle;
- $R^{14}$ is independently —$OR^{13}$, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^{15}$ is independently substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein if n is 2, then $R^{15}$ is optionally —$NR^{19}R^{20}$ or —$OR^{13}$;
- $R^{16}$ is independently hydrogen, substituted or unsubstituted alkyl, substituted or unsubstituted haloalkyl, or substituted or unsubstituted heteroalkyl;
- $R^{17}$ and $R^{18}$, and $R^{19}$ and $R^{20}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted (cycloalkyl)alkyl, substituted or unsubstituted (heterocycloalkyl)alkyl, substituted or unsubstituted arylalkyl, or substituted or unsubstituted heteroarylalkyl; or one or more of $R^{17}$ and $R^{18}$ and $R^{19}$ and $R^{20}$ are each independently joined together with the nitrogen to which they are attached, to form substituted or unsubstituted heterocycloalkyl, or substituted or unsubstituted heteroaryl; and
- wherein any of the groups listed for $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ are each optionally independently substituted with 1 to 3 groups, each group independently selected from halogen, hydroxyl, amino, aminomonoalkyl, aminomonohaloalkyl, aminodihaloalkyl, aminodialkyl, cyano, nitro, haloalkyl, alkyl, —O-alkyl, O-haloalkyl, S-haloalkyl and —S-alkyl
- with the proviso that when $R^1$ and $R^2$ are both hydrogen, $R^3$ is not hydrogen, $NR^9R^{10}$, $CONR^9R^{10}$, or $CHNH_2CONR^9R^{10}$ and with the proviso that when $R^1$ and $R^3$ are both hydrogen, $R^2$ is not $NR^6R^7$.

2. The compound of claim 1, wherein $A^2$ has the formula:

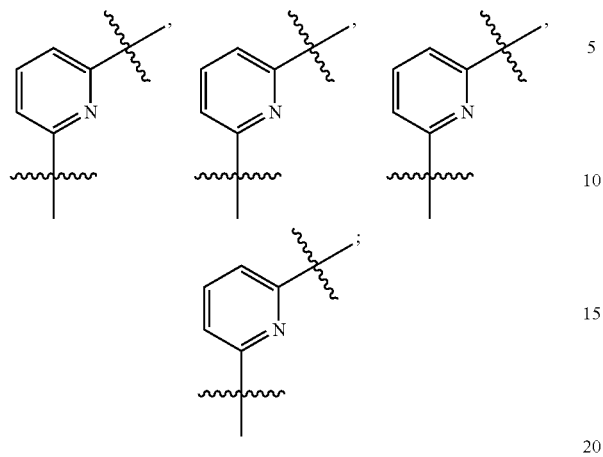

wherein any of the above groups are each independently optionally substituted with 1 to 4 $R^5$ groups.

3. The compound of claim 1, wherein $A^1$ is substituted with one or more halogen, cyano, nitro, trifluoromethyl, difluoromethyl, —$NR^{11}R^{12}$, —$N(R^{11})COR^{12}$, —$CONR^{11}R^{12}$, $OR^{13}$, —$SR^{13}$, —$C(=Z)R^{14}$, —$S(O)_nR^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or combination thereof.

4. The compound of claim 1, wherein $A^1$ is:

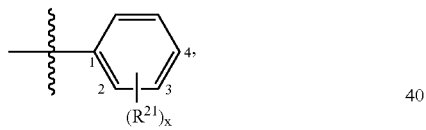

wherein x is an integer from 1 to 5; and $R^{21}$ is independently halogen, cyano, nitro, trifluoromethyl, difluoromethyl, fluoromethyl, —$NR^{11}R^{12}$, —$CONR^{11}R^{12}$, —$OR^{13}$, —$SR^{13}$, —$C(=Z)R^{14}$, —$S(O)_nR^{15}$, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or two adjacent $R^{21}$ groups together with the carbon atoms to which they are attached are combined to form a substituted or unsubstituted ring.

5. The compound of claim 1, wherein $R^1$ is hydrogen or methyl.

6. The compound of claim 5, wherein $R^2$ is hydroxy or methoxy.

7. The compound of claim 1 or claim 6, wherein $R^3$ is —$CH_2CONR^9R^{10}$ or —$CONR^9R^{10}$.

8. The compound of claim 1, wherein $A^1$ is 2-methoxyphenyl.

9. The compound of claim 1, having the formula:

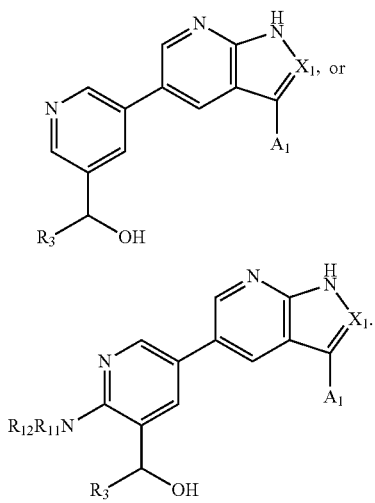

10. The compound of claim 9, wherein $R^3$ is —$CONR^{10}$.

11. The compound of claim 1, wherein $R^1$ is hydrogen;

$R^2$ is —OH, —$NH_2$, —$NHCH_3$, —$N(CH_3)_2$, —F, —CN, —$CF$, —$OCH_3$, thiomorpholinyl sulfone, or piperazinyl; and $R^3$ is

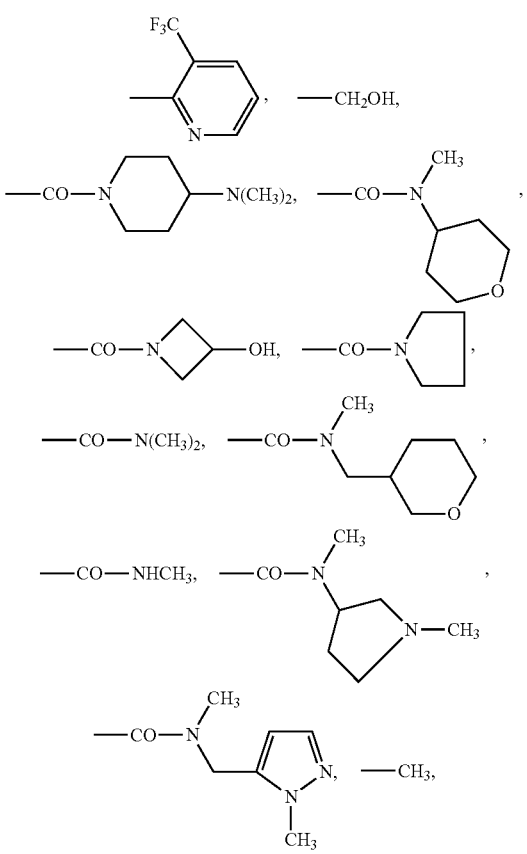

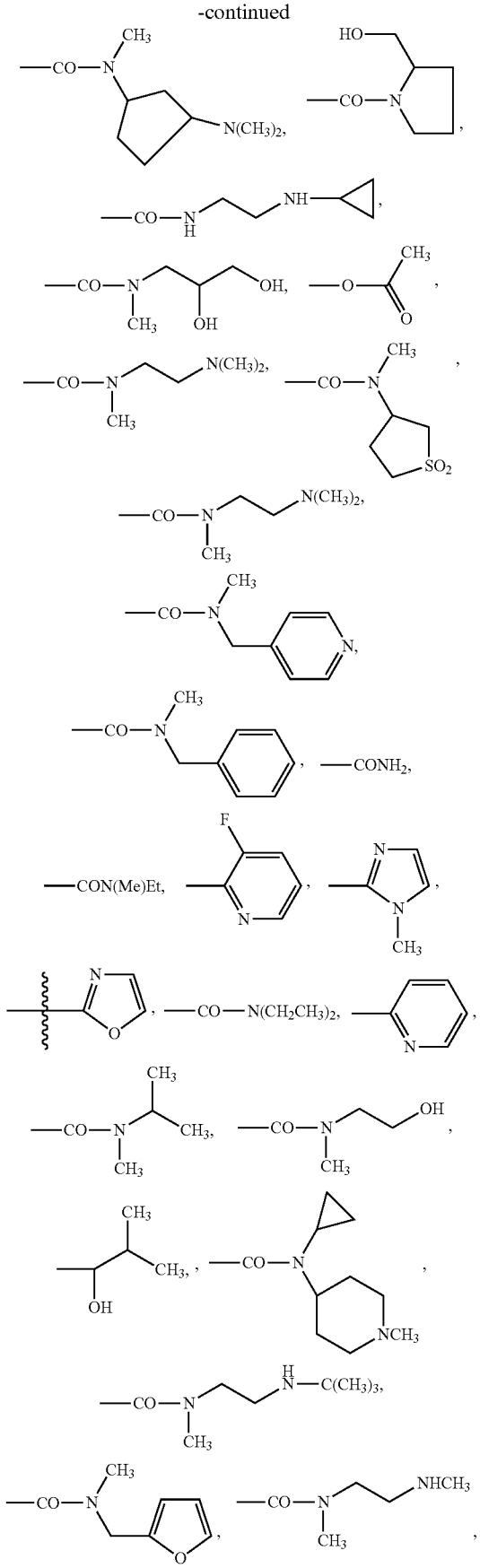
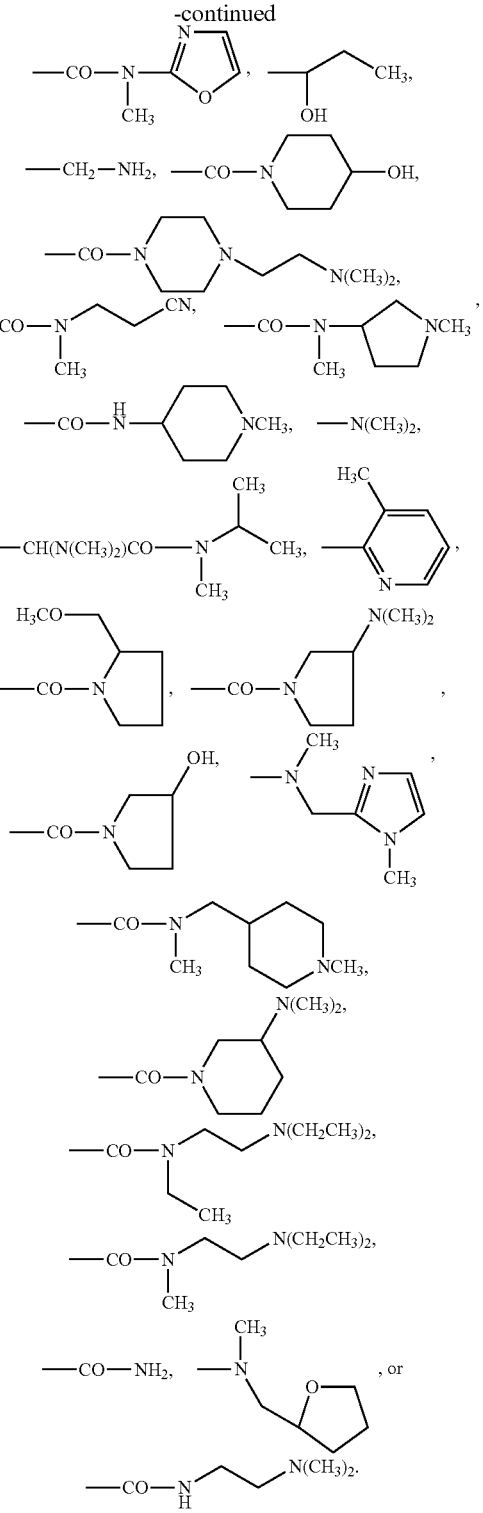
12. The compound of claim 1 wherein
 R$^1$ is hydrogen;
 R$^2$ is hydroxy; and
 R$^3$ is —CONR$^9$R$^{10}$.
13. A compound of Formula (B), or an enantiomer, diastereomer, racemate, tautomer or pharmaceutically acceptable salt thereof:

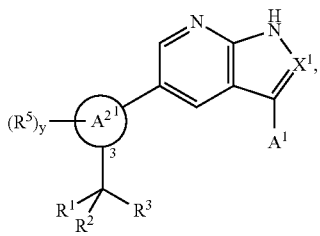

Formula (B)

wherein
A¹ is substituted or unsubstituted phenyl;
A² is a pyridinyl group;
X¹ is CR⁴; wherein
  R⁴ is hydrogen, halogen, cyano, nitro, haloalkyl, or substituted or unsubstituted alkyl;
R¹ is hydrogen, lower alkyl or lower heteroalkyl;
R² is lower alkyl, halogen, hydroxy, —OR⁸, cyano, nitro, haloalkyl, —NR⁶R⁷;
R³ is substituted or unsubstituted alkyl, substituted or unsubstituted heteroalkyl, substituted or unsubstituted haloalkyl, substituted or unsubstituted heterocycloalkyl, substituted or unsubstituted aryl, substituted or unsubstituted (cycloalkyl)alkyl, substituted or unsubstituted (heterocycloalkyl)alkyl, substituted or unsubstituted arylalkyl, substituted or unsubstituted heteroaryl, substituted or unsubstituted heteroarylalkyl, —COOH, —NR⁹R¹⁰, —CH₂NR⁹R¹⁰, —CONR⁹R¹⁰, —CH₂CONR⁹R¹⁰ or —OR⁸; or
R² and R³ together with the carbon atom to which they are attached, form a substituted or unsubstituted heterocycloalkyl, or a substituted or unsubstituted cycloalkyl; or
each R⁵ is independently halogen, cyano, nitro, substituted or unsubstituted haloalkyl, substituted or unsubstituted alkyl, —NR¹¹R¹², —CONR¹¹R¹², —OR¹³, —C(=Z)R¹⁴, or —S(O)ₙR¹⁵, wherein n is independently an integer from 0 to 2;
y is 0, 1, 2, 3 or 4;
Z is independently O, S or N(R¹⁶);
R⁶ and R⁷, R⁹ and R¹⁰, and R¹¹ and R¹² are each independently hydrogen, substituted or unsubstituted alkyl, substituted or unsubstituted haloalkyl, substituted or unsubstituted alkyl-NR¹⁷R¹⁸, substituted or unsubstituted alkyl-CONR¹⁷R¹⁸, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted (cycloalkyl)alkyl, substituted or unsubstituted (heterocycloalkyl)alkyl, substituted or unsubstituted arylalkyl, or substituted or unsubstituted heteroarylalkyl, or
one or more of R⁶ and R⁷, R⁹ and R¹⁰, and R¹¹ and R¹² are each independently joined together with the nitrogen to which they are attached, to form substituted or unsubstituted 3- to 7-membered heterocycloalkyl, or substituted or unsubstituted heteroaryl;
R⁸ and R¹³ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or
a pair of R¹³, taken together with the oxygens to which they are attached, form a heterocycle;

R¹⁴ is independently —OR¹³, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R¹⁵ is independently substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein if n is 2, then R¹⁵ is optionally —NR¹⁹R²⁰ or —OR¹³;
R¹⁶ is independently hydrogen, substituted or unsubstituted alkyl, substituted or unsubstituted haloalkyl, or substituted or unsubstituted heteroalkyl;
R¹⁷ and R¹⁸, and R¹⁹ and R²⁰ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted (cycloalkyl)alkyl, substituted or unsubstituted (heterocycloalkyl)alkyl, substituted or unsubstituted arylalkyl, or substituted or unsubstituted heteroarylalkyl; or one or more of R¹⁷ and R¹⁸ or R¹⁹ and R²⁰ are each independently joined together with the nitrogen to which they are attached, to form substituted or unsubstituted heterocycloalkyl, or substituted or unsubstituted heteroaryl; and
wherein any of the groups listed for R¹, R², R³, R⁴, R⁵, R⁶, R⁷, R⁸, R⁹, R¹⁰, R¹¹, R¹², R¹³, R¹⁴, R¹⁵, R¹⁶, R¹⁷, R¹⁸, R¹⁹, and R²⁰ are each optionally independently substituted with 1 to 3 groups, each group independently selected from halogen, hydroxyl, amino, aminomonoalkyl, aminomonohaloalkyl, aminodihaloalkyl, aminodialkyl, cyano, nitro, haloalkyl, alkyl, —O-alkyl, O-haloalkyl, S-haloalkyl and —S-alkyl.

14. The compound of claim 13, wherein
A¹ is 2-methoxyphenyl.

15. The compound of claim 13, wherein
R¹ is hydrogen;
R² is —OH, —NH₂, —NHCH₃, —N(CH₃)₂, —CH₃, —F, —CN, —OCH₃, thiomorpholinyl sulfone, or piperazinyl; and
R³ is substituted or unsubstituted alkyl, substituted or unsubstituted heteroalkyl, substituted or unsubstituted haloalkyl, substituted or unsubstituted heterocycloalkyl, substituted or unsubstituted aryl, substituted or unsubstituted heteroaryl, —COOH, —NR⁹R¹⁰, —CH₂CONR⁹R¹⁰, —CONR⁹R¹⁰, —CH₂CONR⁹R¹⁰ or —OR⁸.

16. The compound of any of claims 13 wherein R³ is

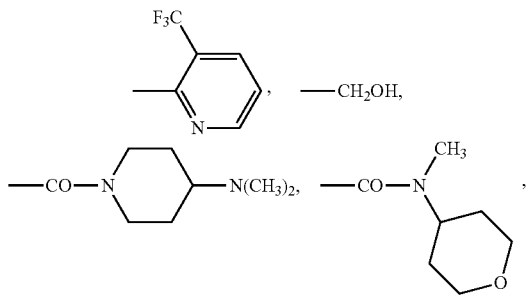

413
-continued
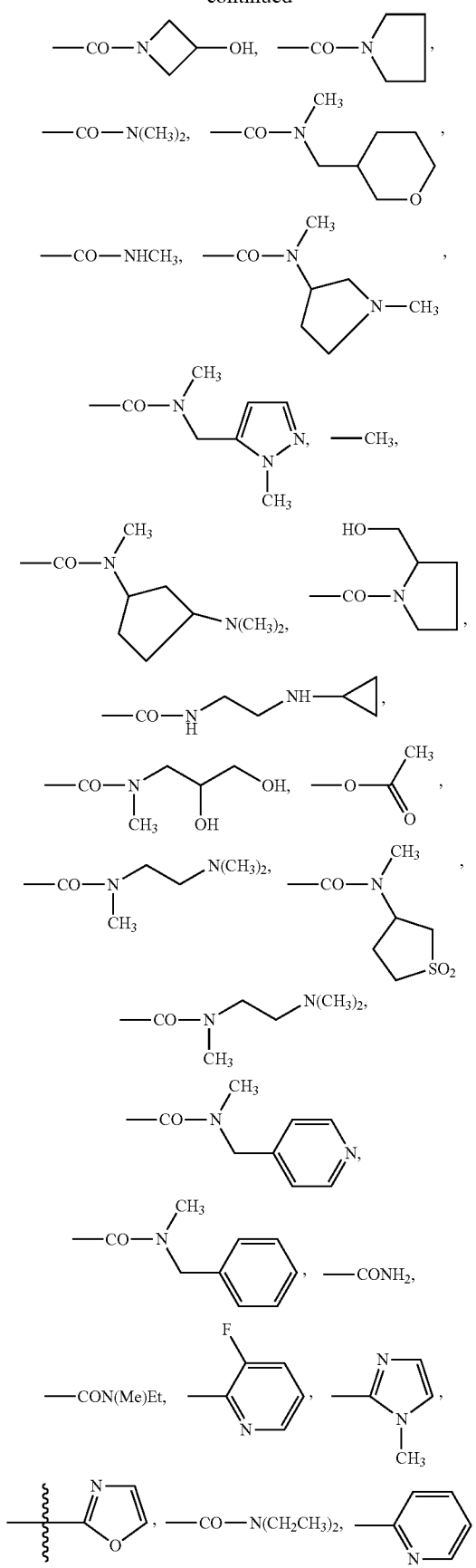
414
-continued
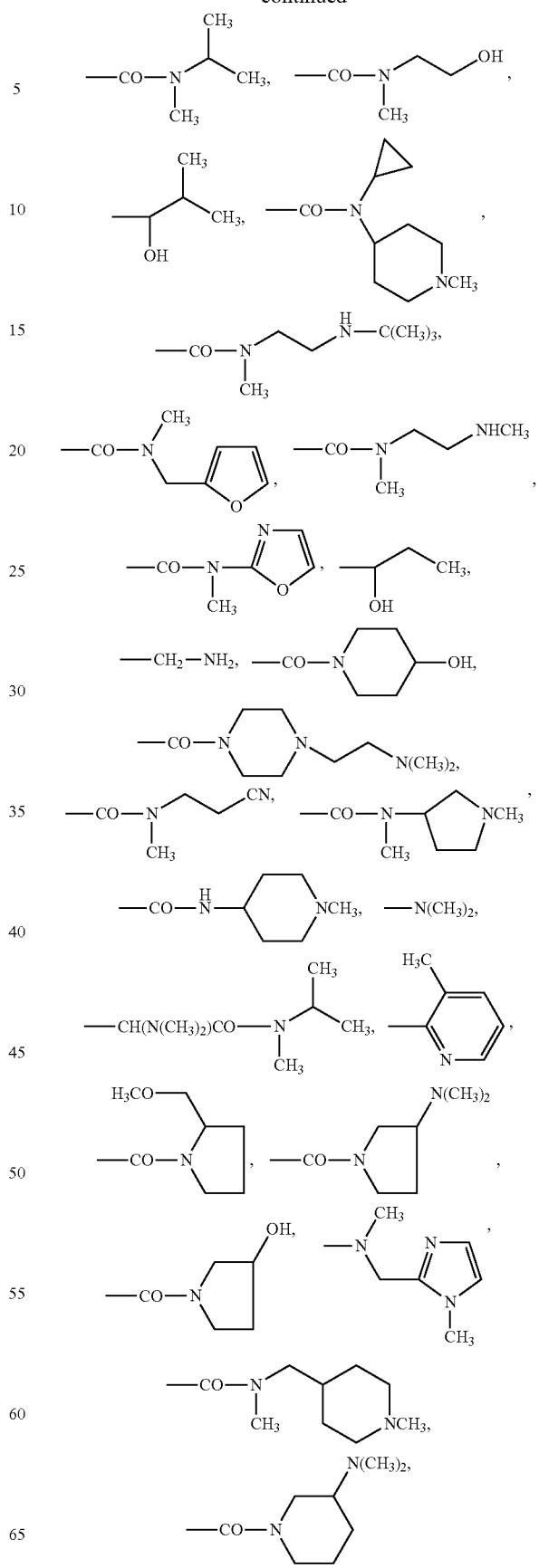

-continued

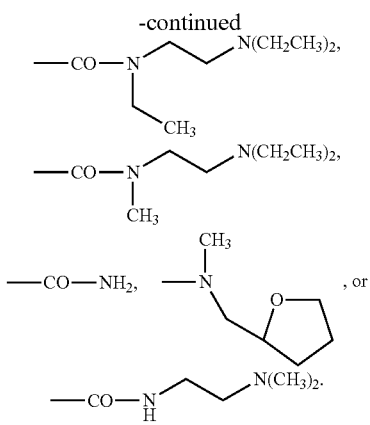

17. A compound of Formula (C), or an enantiomer, diastereomer, racemate, tautomer or pharmaceutically acceptable salt thereof:

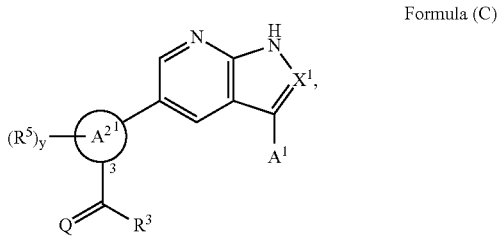

Formula (C)

wherein
A$^1$ is substituted or unsubstituted phenyl;
A$^2$ is a pyridinyl group;
X$^1$ is CR$^4$; wherein
R$^4$ is hydrogen, halogen, cyano, nitro, haloalkyl, or substituted or unsubstituted alkyl;
Q is O;
R$^3$ is substituted or unsubstituted C-attached heteroalkyl, substituted or unsubstituted C-attached heterocycloalkyl, substituted or unsubstituted aryl, substituted or unsubstituted C-attached heteroaryl, —COOR$^8$, —CH$_2$NR$^9$R$^{10}$, —CONR$^9$R$^{10}$, —CH$_2$CONR$^9$R$^{10}$;
each R$^5$ is independently halogen, cyano, nitro, substituted or unsubstituted haloalkyl, substituted or unsubstituted alkyl, —NR$^{11}$R$^{12}$, —CONR$^{11}$R$^{12}$, —OR$^{13}$, —C(=Z)R$^{14}$, or —S(O)$_n$R$^{15}$, wherein n is independently an integer from 0 to 2;
y is 0, 1, 2, 3 or 4;
Z is independently O, S or N(R$^{16}$);
R$^9$ and R$^{10}$, and R$^{11}$ and R$^{12}$ are each independently hydrogen, substituted or unsubstituted alkyl, substituted or unsubstituted haloalkyl, substituted or unsubstituted alkyl-NR$^{17}$R$^{18}$, substituted or unsubstituted alkyl-CONR$^{17}$R$^{18}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or one or more of R$^9$ and R$^{10}$, and R$^{12}$ are each independently joined together with the nitrogen to which they are attached, to form substituted or unsubstituted 3- to 7-membered heterocycloalkyl, or substituted or unsubstituted heteroaryl;
R$^8$ and R$^{13}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a pair of R$^{13}$, taken together with the oxygens to which they are attached, form a heterocycle;
R$^{14}$ is independently —OR$^{13}$, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^{15}$ is independently substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein if n is 2, then R$^{15}$ is optionally —NR$^{19}$R$^{20}$ or —OR$^{13}$;
R$^{16}$ is independently hydrogen, substituted or unsubstituted alkyl, substituted or unsubstituted haloalkyl, or substituted or unsubstituted heteroalkyl;
R$^{17}$ and R$^{18}$, and R$^{19}$ and R$^{20}$ are each independently hydrogen, substituted or unsubstituted alkyl, substituted or unsubstituted haloalkyl, substituted or unsubstituted heteroalkyl, substituted or unsubstituted cycloalkyl, substituted or =substituted heterocycloalkyl, substituted or unsubstituted aryl, or substituted or unsubstituted heteroaryl; or one or more of R$^{17}$ and R$^{18}$ or R$^{19}$ and R$^{20}$ are each independently joined together with the nitrogen to which they are attached, to form substituted or unsubstituted heterocycloalkyl, or substituted or unsubstituted heteroaryl; and
wherein any of the groups listed for R$^3$, R$^4$, R$^5$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$ and R$^{20}$ are each optionally independently substituted with 1 to 3 groups, each group independently selected from halogen, hydroxyl, amino, aminomonoalkyl, aminomonohaloalkyl, aminodihaloalkyl, aminodialkyl, cyano, nitro, haloalkyl, alkyl, —O-alkyl, O-haloalkyl, S-haloalkyl and —S-alkyl.

18. The compound of claim 17, wherein
A$^1$ is 2-methoxyphenyl.

19. The compound of claim 17, wherein
R$^3$ is —CH$_2$NR$^9$R$^{10}$, —CONR$^9$R$^{10}$, —CH$_2$CONR$^9$R$^{10}$.

20. The compound of claim 17 wherein R$^3$ is

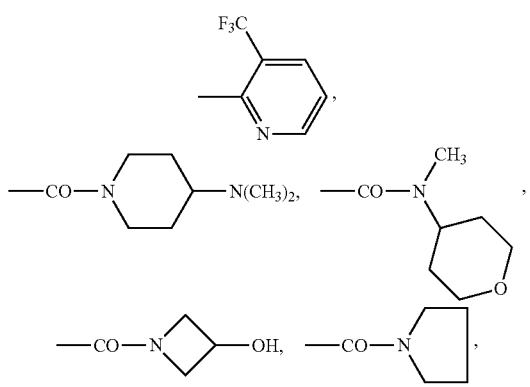

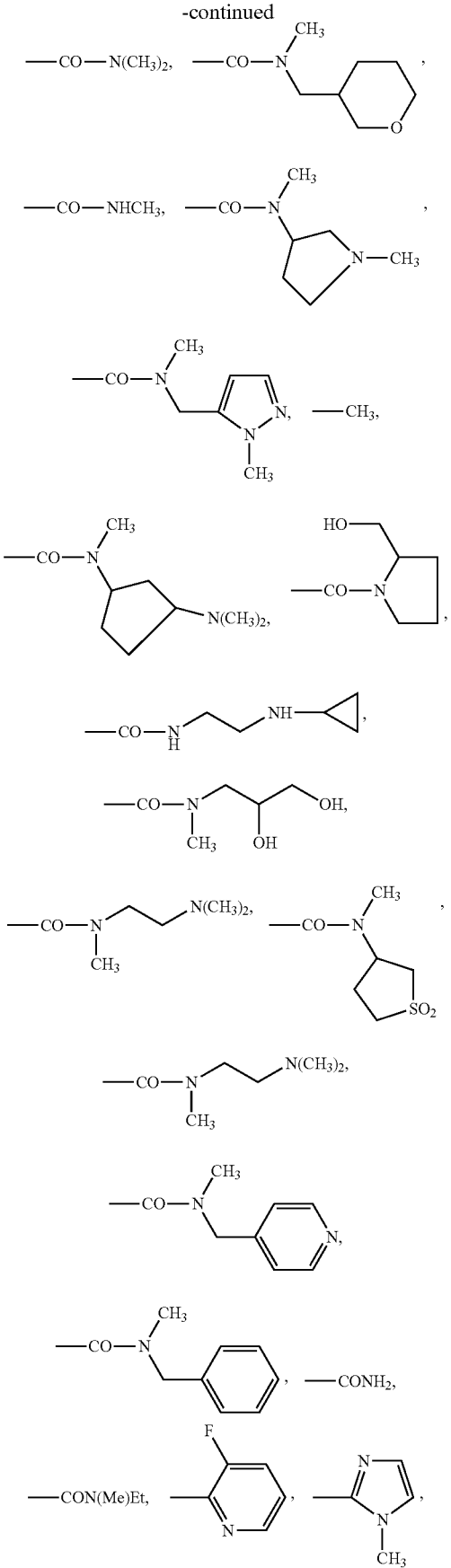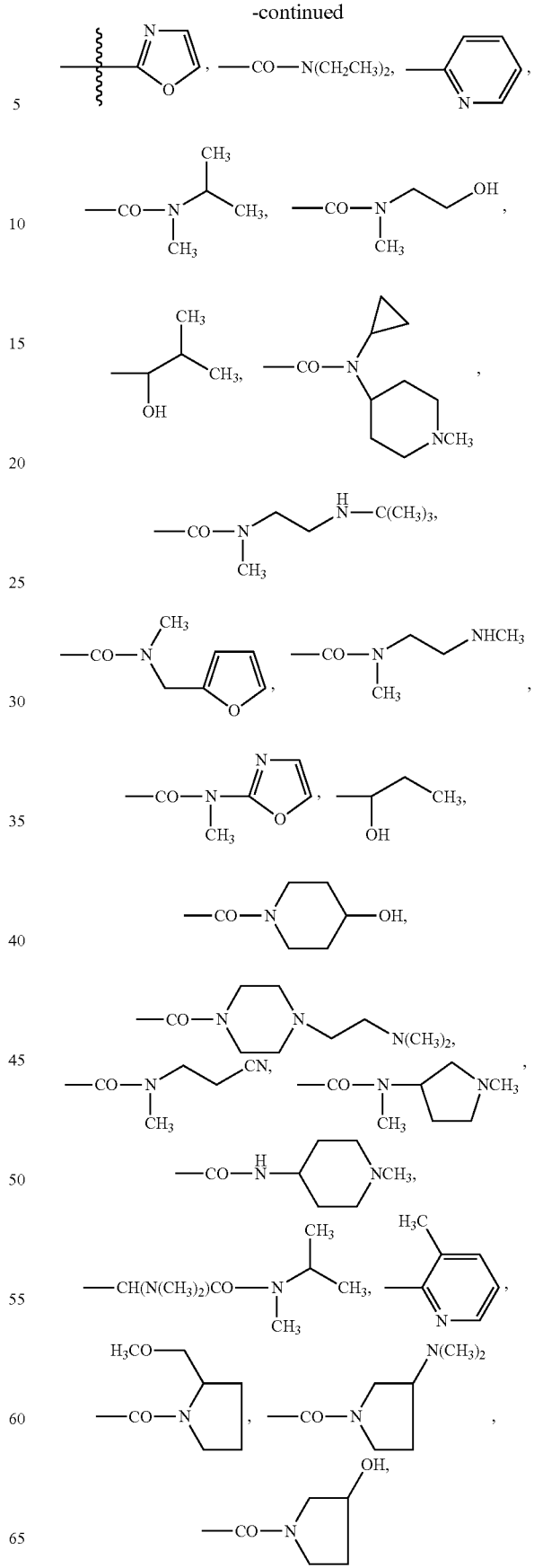

419
-continued
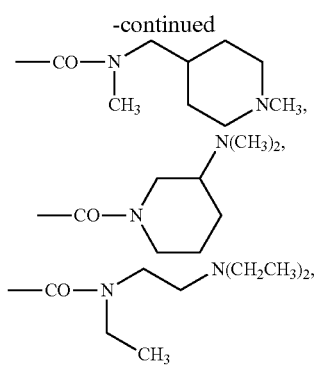
420
-continued
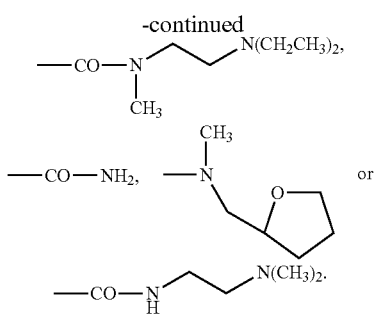
* * * * *

SEQUENCE LISTING

<160> NUMBER OF SEQ ID NOS: 23

<210> SEQ ID NO 1
<211> LENGTH: 12
<212> TYPE: PRT
<213> ORGANISM: Artificial Sequence
<220> FEATURE:
<223> OTHER INFORMATION: Synthetic construct - AB1 substrate peptide

<400> SEQUENCE: 1

Glu Ala Ile Tyr Ala Ala Pro Phe Ala Lys Lys Lys
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic construct - Kemptide peptide
      substrate

<400> SEQUENCE: 2

Leu Arg Arg Ala Ser Leu Gly
1               5

<210> SEQ ID NO 3
<211> LENGTH: 39

```
<212> TYPE: PRT
<213> ORGANISM: Artificial Sequence
<220> FEATURE:
<223> OTHER INFORMATION: Synthetic construct - PDKtide peptide
      substrate

<400> SEQUENCE: 3

Lys Thr Phe Cys Gly Thr Pro Glu Tyr Leu Ala Pro Glu Val Arg Arg
1               5                   10                  15

Glu Pro Arg Ile Leu Ser Glu Glu Glu Gln Glu Met Phe Arg Asp Phe
            20                  25                  30

Asp Tyr Ile Ala Asp Trp Cys
        35

<210> SEQ ID NO 4
<211> LENGTH: 24
<212> TYPE: DNA
<213> ORGANISM: Artificial Sequence
<220> FEATURE:
<223> OTHER INFORMATION: Forward primer

<400> SEQUENCE: 4
tcaaaaaaga ggcagtgggc tttg                                         24

<210> SEQ ID NO 5
<211> LENGTH: 21
<212> TYPE: DNA
<213> ORGANISM: Artificial Sequence
<220> FEATURE:
<223> OTHER INFORMATION: Reverse primer

<400> SEQUENCE: 5
ctgaatttgc tgtgatccag g                                            21

<210> SEQ ID NO 6
<211> LENGTH: 46
<212> TYPE: DNA
<213> ORGANISM: Artificial Sequence
<220> FEATURE:
<223> OTHER INFORMATION: Synthetic construct - sequence inserted into
      NdeI site of vector pSB2-TOPO

<400> SEQUENCE: 6
cataatgggc catcatcatc atcatcacgg tggtcatatg tccctt                 46

<210> SEQ ID NO 7
<211> LENGTH: 27
<212> TYPE: DNA
<213> ORGANISM: Artificial Sequence
<220> FEATURE:
<223> OTHER INFORMATION: Synthetic construct - sequence inserted into
      BamHI site of vector pSB2-TOPO

<400> SEQUENCE: 7 aaggggatc ctaaactgca gagatcc                                       27

<210> SEQ ID NO 8
<211> LENGTH: 60
<212> TYPE: DNA
<213> ORGANISM: Artificial Sequence
<220> FEATURE:
<223> OTHER INFORMATION: Synthetic construct - portion of resulting
      plasmid sequence upstream of ORF

<400> SEQUENCE: 8
aaggaggaga tatacataat gggccatcat catcatcatc acggtggtca tatgtccctt  60
```

```
<210> SEQ ID NO 9
<211> LENGTH: 27
<212> TYPE: DNA
<213> ORGANISM: Artificial Sequence
<220> FEATURE:
<223> OTHER INFORMATION: Synthetic construct - portion of resulting
      plasmid sequence downstream of ORF

<400> SEQUENCE: 9 aaggggatc ctaaactgca gagatcc                                          27

<210> SEQ ID NO 10
<211> LENGTH: 14
<212> TYPE: PRT
<213> ORGANISM: Artificial Sequence
<220> FEATURE:
<223> OTHER INFORMATION: Synthetic construct - amino acids added to
      N-terminus of expressed Aurora kinase

<400> SEQUENCE: 10

Met Gly His His His His His His Gly Gly His Met Ser Leu
1               5                   10

<210> SEQ ID NO 11
<211> LENGTH: 4
<212> TYPE: PRT
<213> ORGANISM: Artificial Sequence
<220> FEATURE:
<223> OTHER INFORMATION: Synthetic construct - amino acids added to C-
      terminus of expressed Aurora kinase

<400> SEQUENCE: 11

Glu Gly Gly Ser
1

<210> SEQ ID NO 12
<211> LENGTH: 51
<212> TYPE: DNA
<213> ORGANISM: Artificial Sequence
<220> FEATURE:
<223> OTHER INFORMATION: Forward primer - PPfor

<400> SEQUENCE: 12
gcagagatcc gaattcgagc tccgtcgacg gatggagtga agagatgcg c               51

<210> SEQ ID NO 13
<211> LENGTH: 55
<212> TYPE: DNA
<213> ORGANISM: Artificial Sequence
<220> FEATURE:
<223> OTHER INFORMATION: Reverse primer - PPrev

<400> SEQUENCE: 13
ggtggtggtg ctcgagtgcg gccgcaagct ttcatcatgc gccttctccc tgtac          55

<210> SEQ ID NO 14
<211> LENGTH: 19
<212> TYPE: DNA
<213> ORGANISM: Artificial Sequence
<220> FEATURE:
<223> OTHER INFORMATION: Forward primer

<400> SEQUENCE: 14
gacaagtggg aaatggagc                                                  19

<210> SEQ ID NO 15
<211> LENGTH: 19
```

```
<212> TYPE: DNA
<213> ORGANISM: Artificial Sequence
<220> FEATURE:
<223> OTHER INFORMATION: Reverse primer

<400> SEQUENCE: 15
cgcctcgttt ccccagctc                                                  19

<210> SEQ ID NO 16
<211> LENGTH: 12
<212> TYPE: DNA
<213> ORGANISM: Artificial Sequence
<220> FEATURE:
<223> OTHER INFORMATION: Synthetic construct - sequence inserted into
      NdeI site of vector pSGX3-TOPO

<400> SEQUENCE: 16
catatgtccc tt                                                         12

<210> SEQ ID NO 17
<211> LENGTH: 29
<212> TYPE: DNA
<213> ORGANISM: Artificial Sequence
<220> FEATURE:
<223> OTHER INFORMATION: Synthetic construct - sequence inserted into
      the BamHI site of vector pSGX3-TOPO

<400> SEQUENCE: 17
aagggcatca tcaccatcac cactgatcc                                       29

<210> SEQ ID NO 18
<211> LENGTH: 26
<212> TYPE: DNA
<213> ORGANISM: Artificial Sequence
<220> FEATURE:
<223> OTHER INFORMATION: Synthetic construct - portion of resulting
      plasmid sequence upstream of ORF

<400> SEQUENCE: 18
aaggaggaga tatacatatg tccctt                                          26

<210> SEQ ID NO 19
<211> LENGTH: 29
<212> TYPE: DNA
<213> ORGANISM: Artificial Sequence
<220> FEATURE:
<223> OTHER INFORMATION: Synthetic construct - portion of resulting
      plasmid sequence downstream of ORF

<400> SEQUENCE: 19
aagggcatca tcaccatcac cactgatcc                                       29

<210> SEQ ID NO 20
<211> LENGTH: 8
<212> TYPE: PRT
<213> ORGANISM: Artificial Sequence
<220> FEATURE:
<223> OTHER INFORMATION: Synthetic construct - amino acids added to
      C-terminus of expressed c-AB1

<400> SEQUENCE: 20

Glu Gly His His His His His His
1               5

<210> SEQ ID NO 21
<211> LENGTH: 39
<212> TYPE: DNA
<213> ORGANISM: Artificial Sequence
```

```
<220> FEATURE:
<223> OTHER INFORMATION: Synthetic construct - Mm05582dS4
      oligonucleotide used to modify A b1 plasmid

<400> SEQUENCE: 21
ccaccattct acataatcat tgagttcatg acctatggg                                39

<210> SEQ ID NO 22
<211> LENGTH: 39
<212> TYPE: DNA
<213> ORGANISM: Artificial Sequence
<220> FEATURE:
<223> OTHER INFORMATION: Synthetic construct - Mm05582dA4
      oligonucleotide used to modify A b1 plasmid

<400> SEQUENCE: 22
cccataggtc atgaactcaa tgattatgta gaatggtgg                                 39

<210> SEQ ID NO 23
<211> LENGTH: 1130
<212> TYPE: PRT
<213> ORGANISM: Homo sapiens

<400> SEQUENCE: 23
```

Met Leu Glu Ile Cys Leu Lys Leu Val Gly Cys Lys Ser Lys Lys Gly
1               5                   10                  15

Leu Ser Ser Ser Ser Cys Tyr Leu Glu Ala Leu Gln Arg Pro
            20                  25                  30

Val Ala Ser Asp Phe Glu Pro Gln Gly Leu Ser Glu Ala Ala Arg Trp
        35                  40                  45

Asn Ser Lys Glu Asn Leu Leu Ala Gly Pro Ser Glu Asn Asp Pro Asn
    50                  55                  60

Leu Phe Val Ala Leu Tyr Asp Phe Val Ala Ser Gly Asp Asn Thr Leu
65                  70                  75                  80

Ser Ile Thr Lys Gly Glu Lys Leu Arg Val Leu Gly Tyr Asn His Asn
                85                  90                  95

Gly Glu Trp Cys Glu Ala Gln Thr Lys Asn Gly Gln Gly Trp Val Pro
            100                 105                 110

Ser Asn Tyr Ile Thr Pro Val Asn Ser Leu Glu Lys His Ser Trp Tyr
        115                 120                 125

His Gly Pro Val Ser Arg Asn Ala Ala Glu Tyr Leu Leu Ser Ser Gly
    130                 135                 140

Ile Asn Gly Ser Phe Leu Val Arg Glu Ser Glu Ser Ser Pro Gly Gln
145                 150                 155                 160

Arg Ser Ile Ser Leu Arg Tyr Glu Gly Arg Val Tyr His Tyr Arg Ile
                165                 170                 175

Asn Thr Ala Ser Asp Gly Lys Leu Tyr Val Ser Ser Glu Ser Arg Phe
            180                 185                 190

Asn Thr Leu Ala Glu Leu Val His His Ser Thr Val Ala Asp Gly
        195                 200                 205

Leu Ile Thr Thr Leu His Tyr Pro Ala Pro Lys Arg Asn Lys Pro Thr
    210                 215                 220

Val Tyr Gly Val Ser Pro Asn Tyr Asp Lys Trp Glu Met Glu Arg Thr
225                 230                 235                 240

Asp Ile Thr Met Lys His Lys Leu Gly Gly Gly Gln Tyr Gly Glu Val
                245                 250                 255

Tyr Glu Gly Val Trp Lys Lys Tyr Ser Leu Thr Val Ala Val Lys Thr
            260                 265                 270

```
Leu Lys Glu Asp Thr Met Glu Val Glu Glu Phe Leu Lys Glu Ala Ala
        275                 280                 285

Val Met Lys Glu Ile Lys His Pro Asn Leu Val Gln Leu Leu Gly Val
290                 295                 300

Cys Thr Arg Glu Pro Pro Phe Tyr Ile Ile Thr Glu Phe Met Thr Tyr
305                 310                 315                 320

Gly Asn Leu Leu Asp Tyr Leu Arg Glu Cys Asn Arg Gln Glu Val Asn
                325                 330                 335

Ala Val Val Leu Leu Tyr Met Ala Thr Gln Ile Ser Ser Ala Met Glu
                340                 345                 350

Tyr Leu Glu Lys Lys Asn Phe Ile His Arg Asp Leu Ala Ala Arg Asn
                355                 360                 365

Cys Leu Val Gly Glu Asn His Leu Val Lys Val Ala Asp Phe Gly Leu
370                 375                 380

Ser Arg Leu Met Thr Gly Asp Thr Tyr Thr Ala His Ala Gly Ala Lys
385                 390                 395                 400

Phe Pro Ile Lys Trp Thr Ala Pro Glu Ser Leu Ala Tyr Asn Lys Phe
                405                 410                 415

Ser Ile Lys Ser Asp Val Trp Ala Phe Gly Val Leu Leu Trp Glu Ile
                420                 425                 430

Ala Thr Tyr Gly Met Ser Pro Tyr Pro Gly Ile Asp Leu Ser Gln Val
                435                 440                 445

Tyr Glu Leu Leu Glu Lys Asp Tyr Arg Met Glu Arg Pro Glu Gly Cys
                450                 455                 460

Pro Glu Lys Val Tyr Glu Leu Met Arg Ala Cys Trp Gln Trp Asn Pro
465                 470                 475                 480

Ser Asp Arg Pro Ser Phe Ala Glu Ile His Gln Ala Phe Glu Thr Met
                485                 490                 495

Phe Gln Glu Ser Ser Ile Ser Asp Glu Val Glu Lys Glu Leu Gly Lys
                500                 505                 510

Gln Gly Val Arg Gly Ala Val Ser Thr Leu Leu Gln Ala Pro Glu Leu
                515                 520                 525

Pro Thr Lys Thr Arg Thr Ser Arg Arg Ala Ala Glu His Arg Asp Thr
530                 535                 540

Thr Asp Val Pro Glu Met Pro His Ser Lys Gly Gln Gly Glu Ser Asp
545                 550                 555                 560

Pro Leu Asp His Glu Pro Ala Val Ser Pro Leu Leu Pro Arg Lys Glu
                565                 570                 575

Arg Gly Pro Pro Glu Gly Gly Leu Asn Glu Asp Glu Arg Leu Leu Pro
                580                 585                 590

Lys Asp Lys Lys Thr Asn Leu Phe Ser Ala Leu Ile Lys Lys Lys Lys
                595                 600                 605

Lys Thr Ala Pro Thr Pro Pro Lys Arg Ser Ser Ser Phe Arg Glu Met
610                 615                 620

Asp Gly Gln Pro Glu Arg Arg Gly Ala Gly Glu Glu Glu Gly Arg Asp
625                 630                 635                 640

Ile Ser Asn Gly Ala Leu Ala Phe Thr Pro Leu Asp Thr Ala Asp Pro
                645                 650                 655

Ala Lys Ser Pro Lys Pro Ser Asn Gly Ala Gly Val Pro Asn Gly Ala
                660                 665                 670

Leu Arg Glu Ser Gly Gly Ser Gly Phe Arg Ser Pro His Leu Trp Lys
                675                 680                 685

Lys Ser Ser Thr Leu Thr Ser Ser Arg Leu Ala Thr Gly Glu Glu Glu
                690                 695                 700
```

```
Gly Gly Gly Ser Ser Ser Lys Arg Phe Leu Arg Ser Cys Ser Ala Ser
705                 710                 715                 720

Cys Val Pro His Gly Ala Lys Asp Thr Glu Trp Arg Ser Val Thr Leu
            725                 730                 735

Pro Arg Asp Leu Gln Ser Thr Gly Arg Gln Phe Asp Ser Ser Thr Phe
        740                 745                 750

Gly Gly His Lys Ser Glu Lys Pro Ala Leu Pro Arg Lys Arg Ala Gly
        755                 760                 765

Glu Asn Arg Ser Asp Gln Val Thr Arg Gly Thr Val Thr Pro Pro Pro
770                 775                 780

Arg Leu Val Lys Lys Asn Glu Glu Ala Ala Asp Glu Val Phe Lys Asp
785                 790                 795                 800

Ile Met Glu Ser Ser Pro Gly Ser Pro Pro Asn Leu Thr Pro Lys
                805                 810                 815

Pro Leu Arg Arg Gln Val Thr Val Ala Pro Ala Ser Gly Leu Pro His
            820                 825                 830

Lys Glu Glu Ala Glu Lys Gly Ser Ala Leu Gly Thr Pro Ala Ala Ala
            835                 840                 845

Glu Pro Val Thr Pro Thr Ser Lys Ala Gly Ser Gly Ala Pro Gly Gly
    850                 855                 860

Thr Ser Lys Gly Pro Ala Glu Glu Ser Arg Val Arg Arg His Lys His
865                 870                 875                 880

Ser Ser Glu Ser Pro Gly Arg Asp Lys Gly Lys Leu Ser Arg Leu Lys
                885                 890                 895

Pro Ala Pro Pro Pro Pro Ala Ala Ser Ala Gly Lys Ala Gly Gly
                900                 905                 910

Lys Pro Ser Gln Ser Pro Ser Gln Glu Ala Ala Gly Glu Ala Val Leu
            915                 920                 925

Gly Ala Lys Thr Lys Ala Thr Ser Leu Val Asp Ala Val Asn Ser Asp
930                 935                 940

Ala Ala Lys Pro Ser Gln Pro Gly Glu Gly Leu Lys Lys Pro Val Leu
945                 950                 955                 960

Pro Ala Thr Pro Lys Pro Gln Ser Ala Lys Pro Ser Gly Thr Pro Ile
                965                 970                 975

Ser Pro Ala Pro Val Pro Ser Thr Leu Pro Ser Ala Ser Ser Ala Leu
            980                 985                 990

Ala Gly Asp Gln Pro Ser Ser Thr Ala Phe Ile Pro Leu Ile Ser Thr
        995                 1000                1005

Arg Val Ser Leu Arg Lys Thr Arg Gln Pro Pro Glu Arg Ile Ala
    1010                1015                1020

Ser Gly Ala Ile Thr Lys Gly Val Val Leu Asp Ser Thr Glu Ala
    1025                1030                1035

Leu Cys Leu Ala Ile Ser Arg Asn Ser Glu Gln Met Ala Ser His
    1040                1045                1050

Ser Ala Val Leu Glu Ala Gly Lys Asn Leu Tyr Thr Phe Cys Val
    1055                1060                1065

Ser Tyr Val Asp Ser Ile Gln Gln Met Arg Asn Lys Phe Ala Phe
    1070                1075                1080

Arg Glu Ala Ile Asn Lys Leu Glu Asn Asn Leu Arg Glu Leu Gln
    1085                1090                1095

Ile Cys Pro Ala Thr Ala Gly Ser Gly Pro Ala Ala Thr Gln Asp
    1100                1105                1110

Phe Ser Lys Leu Leu Ser Ser Val Lys Glu Ile Ser Asp Ile Val
```